US006828098B2

(12) United States Patent
Langmore et al.

(10) Patent No.: US 6,828,098 B2
(45) Date of Patent: Dec. 7, 2004

(54) METHOD OF PRODUCING A DNA LIBRARY USING POSITIONAL AMPLIFICATION BASED ON THE USE OF ADAPTORS AND NICK TRANSLATION

(75) Inventors: John P. Langmore, Ann Arbor, MI (US); Vladimir L. Makarov, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 9 days.

(21) Appl. No.: 09/860,738

(22) Filed: May 18, 2001

(65) Prior Publication Data

US 2003/0040620 A1 Feb. 27, 2003

Related U.S. Application Data

(60) Provisional application No. 60/206,095, filed on May 20, 2000.

(51) Int. Cl.[7] .............................. C12Q 1/68; C12P 19/34
(52) U.S. Cl. .......................... 435/6; 435/91.1; 435/91.2
(58) Field of Search ............................... 435/91.1, 91.2, 435/6

(56) References Cited

U.S. PATENT DOCUMENTS

| 4,710,465 A | 12/1987 | Weissman et al. |
| 4,942,124 A | 7/1990 | Church |

(List continued on next page.)

FOREIGN PATENT DOCUMENTS

| EP | 0684 315 A1 | 3/1995 |
| WO | WO 93/24654 | 12/1993 |
| WO | WO 98/15652 | 4/1998 |
| WO | 99/18241 | 4/1999 |
| WO | 00/18960 | 4/2000 |
| WO | 00/24929 | 5/2000 |
| WO | 00/28084 | 5/2000 |
| WO | 00/60121 | 10/2000 |

OTHER PUBLICATIONS

Guilfoyle, Richard A., et al., Ligation–mediated PCR amplification of specific fragments from a Class–II restriction endonuclease total digest, Nucleic Acids Research vol. 25, No. 9 (1997), pp. 1854–1858.

(List continued on next page.)

*Primary Examiner*—Kenneth R. Horlick
(74) *Attorney, Agent, or Firm*—Fulbright & Jaworski, LLP

(57) ABSTRACT

The disclosed invention relates to general and specific methods to use the Primer Extension/Nick Translation (PENT) reaction to create an amplifiable DNA strand, called a PENTAmer. A PENTAmers can be made for the purpose of amplifying a controlled length of DNA located at a controlled position within a DNA molecule, a process referred to as Positional Amplification by Nick Translation (PANT). In contrast to PCR, which amplifies DNA between two specific sequences, PANT can amplify DNA between two specific positions. PENTAmers can be created to amplify very large regions of DNA (up to 500,000 bp) as random mixtures (unordered positional libraries), or as molecules sorted according to position (ordered positional libraries). PANT is fast and economical, because PENTAmer preparation can be multiplexed. A single PENTAmer preparation can include very complex mixtures of DNA such as hundreds of large-insert clones, complete genomes, or cDNA libraries. Subsequent PCR amplification of the preparation using a single specific primer can positionally amplify contiguous regions along a specific clone, along a specific genomic region, or along a specific expressed sequence.

206 Claims, 114 Drawing Sheets

U.S. PATENT DOCUMENTS

| | | | |
|---|---|---|---|
| 5,149,625 | A | 9/1992 | Church et al. |
| 5,508,169 | A | 4/1996 | Deugau et al. |
| 5,518,901 | A | 5/1996 | Murtagh |
| 5,648,213 | A | 7/1997 | Reddy et al. |
| 5,695,971 | A | 12/1997 | Kadokami et al. |
| 5,714,318 | A | 2/1998 | Sagner et al. |
| 5,858,671 | A | 1/1999 | Jones |
| 6,063,604 | A | 5/2000 | Wick et al. |
| 6,117,634 | A | 9/2000 | Langmore et al. |
| 6,124,120 | A | 9/2000 | Lizardi |
| 6,197,557 | B1 | 3/2001 | Makarov et al. |
| 6,218,119 | B1 | 4/2001 | Kuiper et al. |
| 6,300,071 | B1 | 10/2001 | Vuylsteke et al. |
| 6,537,757 | B1 | 3/2003 | Langmore et al. |
| 2003/0064376 | A1 * | 4/2003 | Makarov et al. ............... 435/6 |

OTHER PUBLICATIONS

Hagiwara, Koichi and Harris, Curtis C., 'Long distance sequencer' method: a novel strategy for large DNA sequencing projects, Nucleic Acids Research, vol. 24, No. 12 (1996), pp. 2460–2461.

Makorov, Vladimir L., et al., Long G. Tails at Both Ends of Human Chromosomes Suggest a C Strand Degradation Mechanism for Telomere Shortening, Cell, vol. 88 (1997), pp. 657–666.

Rosenthal, Andre, et al., Genomic walking and sequencing by oligo–cassette mediated polymerase chain reaction, Nucleic Acids Research, vol. 18, No. 10 (1990), pp. 3095–3096.

Smith, Douglas R., Ligation–mediated PCR of Restriction Fragments from Large DNA Molecules, PCR Methods and Applications, vol. 2 (1992), pp. 21–27.

Unrau, Paul and Deugau, Kenneth V., Non–cloning amplification of specific DNA fragments from whole genomic DNA digests using DNA 'indexers', Gene, 145 (1994), pp. 163–169.

Walker, G. Terrance, et al., Isothermal in vitro amplification of DNA by a restriction enzyme/DNA polymerase system, Proc. Natl. Acad. Sci. USA vol. 89 (1992), pp. 392–396, Applied Biological Sciences.

Walker G. Terrance, et al., Strand displacement amplification—an isothermal, in vitro DNA amplification technique, Nucleic Acids Research, vol. 20, No. 7 (1992), pp. 1691–1696.

Currently Pending Claims in U.S. patent application No. 09/801,346, Filed Mar. 6, 2001, Entitled "Compositions and Methods for Analysis of Nucleic Acids".

Fu, Doug–Jing, et al., Sequencing Double–Stranded DNA by Strand Displacement, Nucleic Acids Research vol. 25, No. 3 (1997), pp. 677–679.

* cited by examiner

B Amplification using 1 kb library, primer-adaptor B and primer $P_1$ from the kernel region 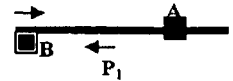

⇩

Cloning and sequencing PCR products followed by synthesis of the primer $P_2$ from the sequenced DNA region 1 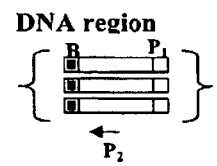

⇩

Amplification using 2 kb library, primer-adaptor B and primer $P_2$ from the sequenced region 1 

⇩

Cloning and sequencing PCR products followed by synthesis of the primer $P_3$ from the sequenced DNA region 2 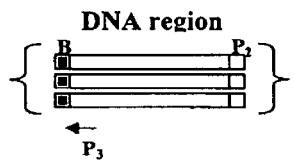

⇩

Amplification using 3 kb library, primer-adaptor B and primer $P_3$ from the sequenced region 2 

⇩

Cloning and sequencing PCR products followed by synthesis of the primer $P_4$ from the sequenced DNA region 3 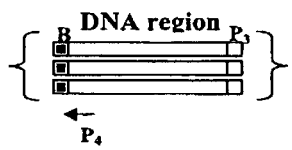

⇩

Amplification using 4 kb library, primer-adaptor B and primer $P_4$ from the sequenced region 3

Cloning and sequencing PCR products (region 4)

FIG. 12B

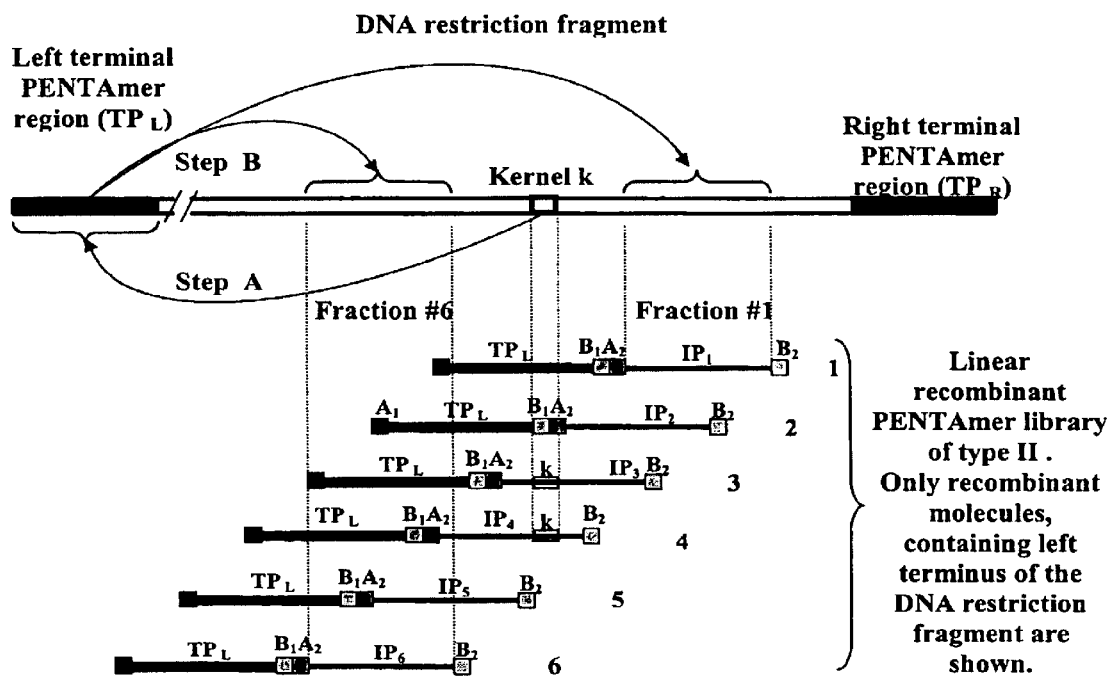
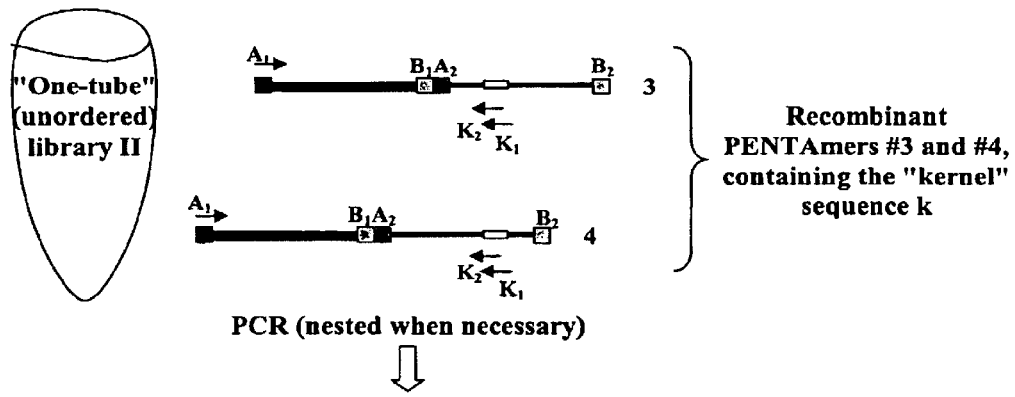
Step A. Amplification of terminal PENTAmers (TP) of a DNA restriction fragment using "One-tube" unordered library II, nested primers $K_1$ and $K_2$ from the internal "kernel" region k and adaptor-primer $A_1$ (only amplification of left terminal PENTAmer is shown)
PCR (nested when necessary)
FIG. 17A

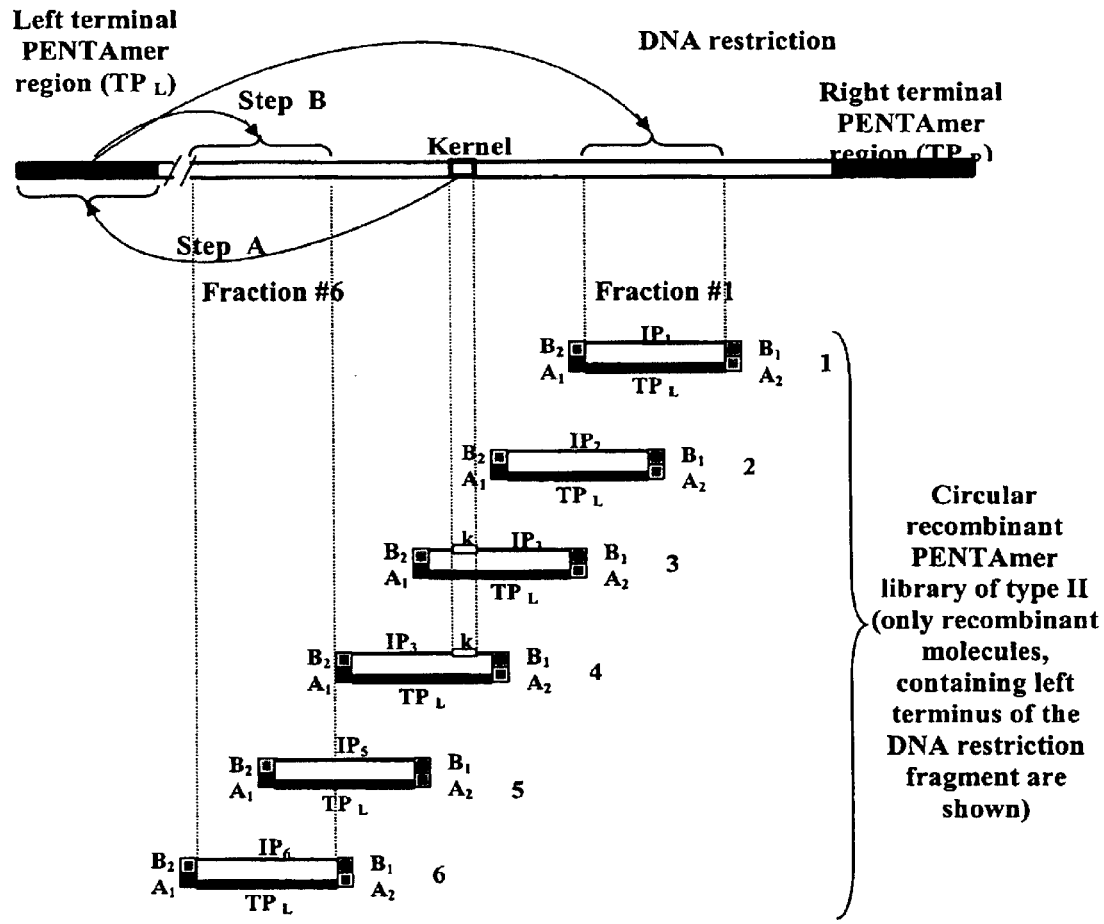
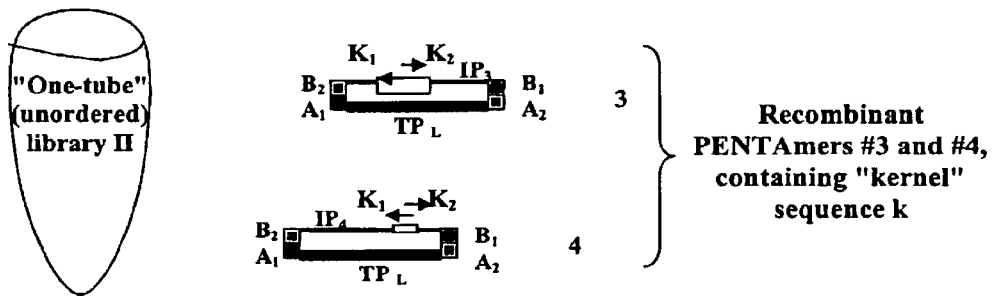
FIG. 17C

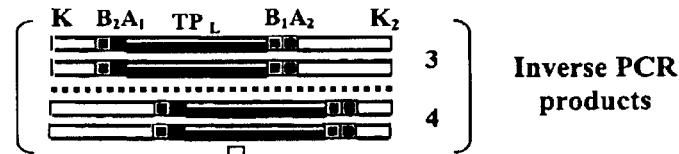
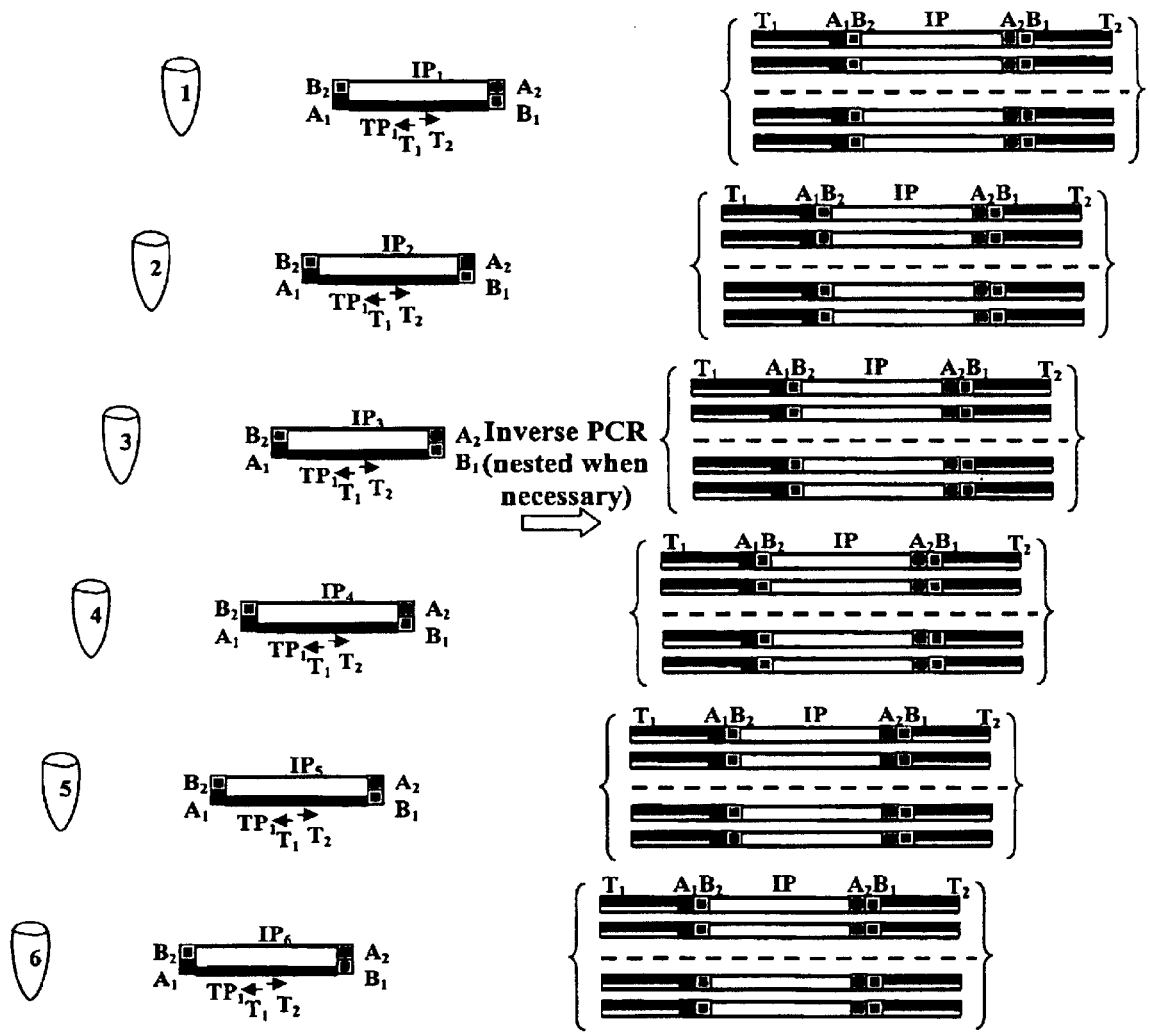
FIG. 17D

Step 1   Linear amplification of termini (TP$_L$ and TP$_R$) of all DNA restriction fragments using unordered "One-tube" SmartGenome DNA library II and adaptor-primers A$_1$ and B$_1$ (see Fig. 17A)

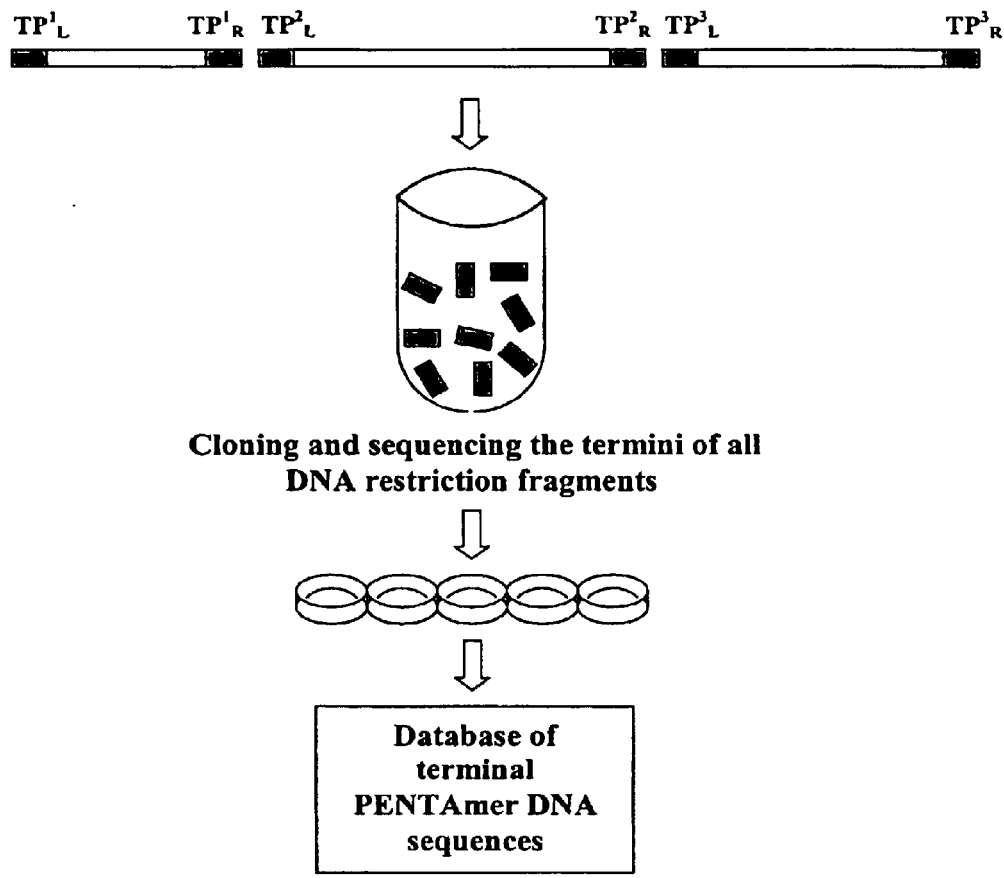

Step 2   Amplification of the ordered internal DNA fractions located within the DNA restriction fragments using ordered SmartGenome DNA library II and primers from the terminal regions

Step 3   Amplification, isolation and sequencing of the "linking" DNA fractions using ordered SmartGenome DNA library I and primers within the adjacent terminus region

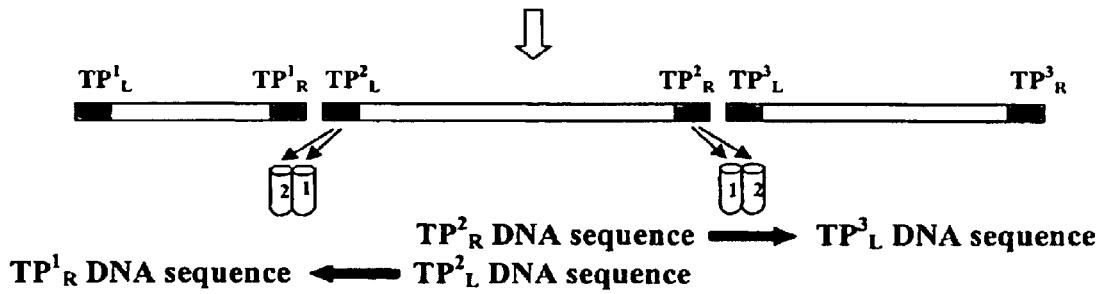

FIG. 18C

A 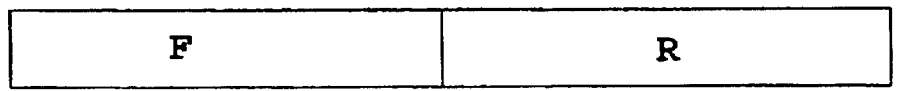
B 
FIG. 27

Examples of recombination down-stream nick-attaching adaptors
A  Up-stream terminus-attaching nick-translation recombination adaptor RA
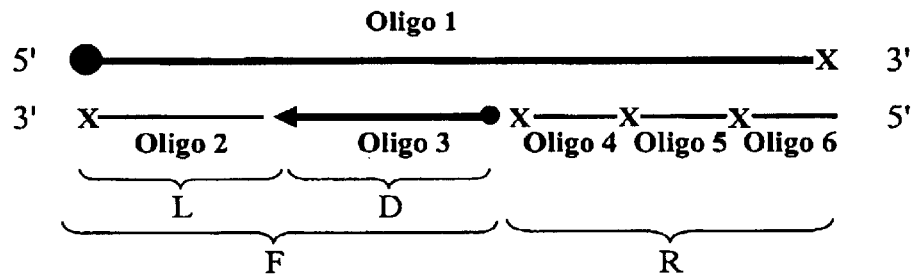
B  Down-stream nick-attaching recombination adaptor RB-3' (I) targeted to a gap by a ligation reaction
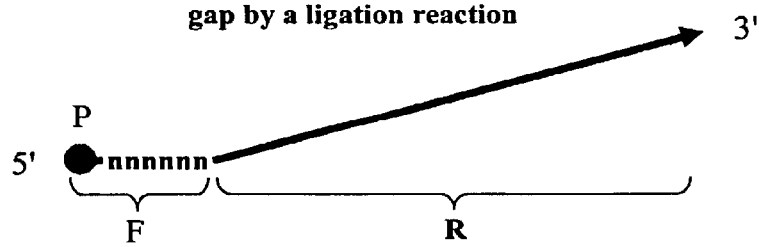
C  Down-stream nick-attaching recombination adaptor RB-3' (II) targeted to a poly-G tail by a ligation reaction
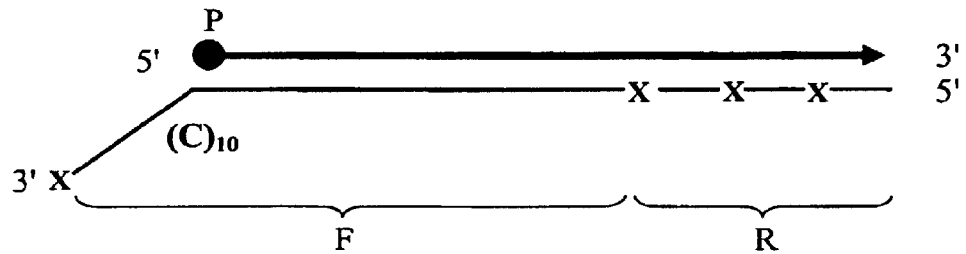
FIG. 28A D  Down-stream nick-attaching recombination adaptor RB-3' (III) targeted to a displaced 3' DNA tail by a ligation reaction

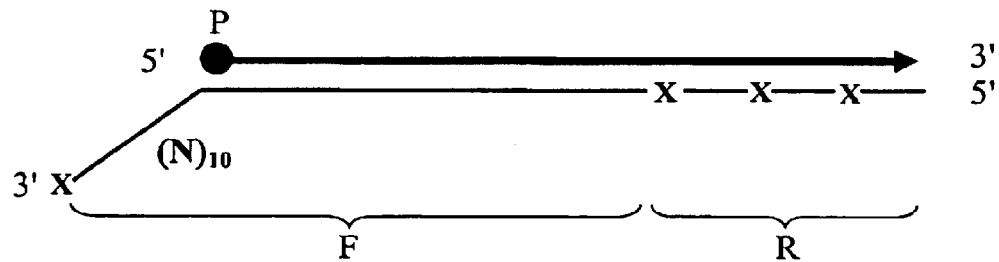

E  Down-stream nick-attaching recombination adaptor RB-3' (IV) targeted to a poly-G tail as a template for a polymerization-extension reaction

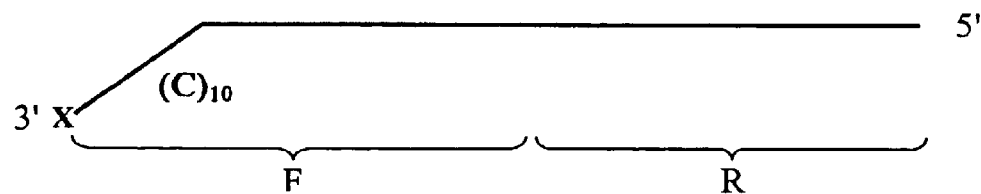

F  Down-stream nick-attaching recombination adaptor RB-3' (V) targeted to a displaced 3' DNA tail as a template for a polymerization-extension reaction

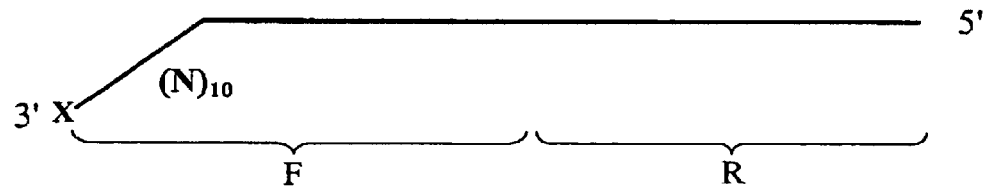

FIG. 28B

A RecAdaptors-Class I
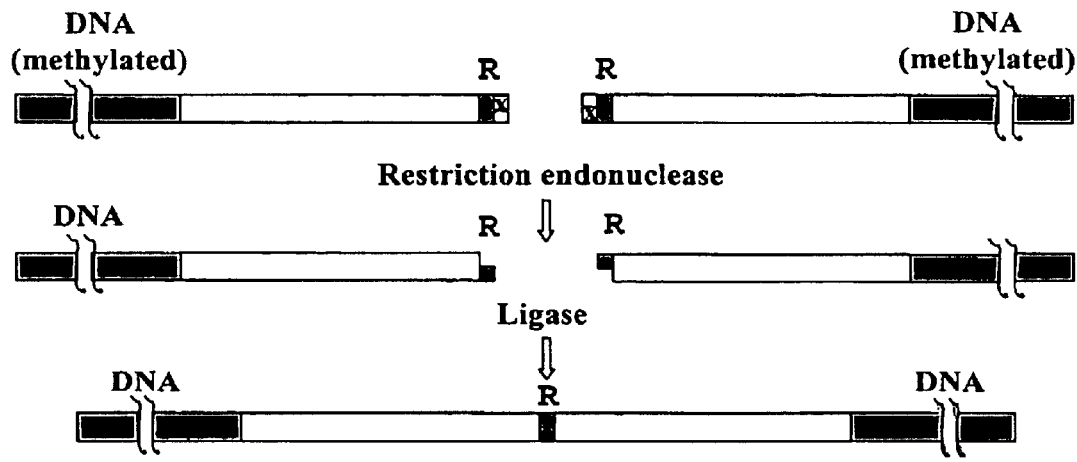
B RecAdaptors-Class II
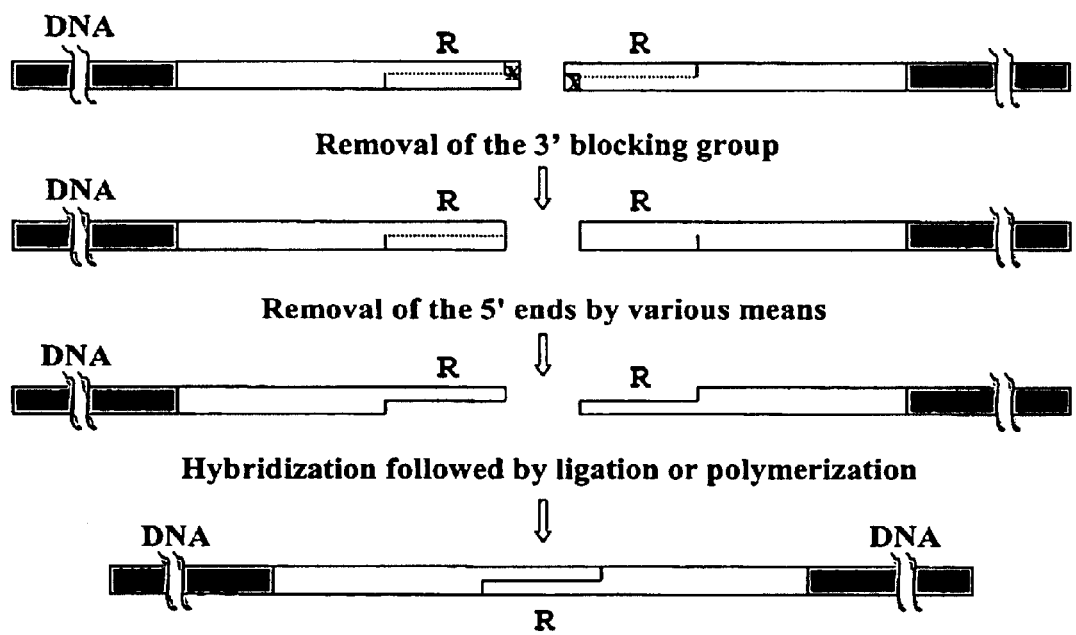
FIG. 29 or
D 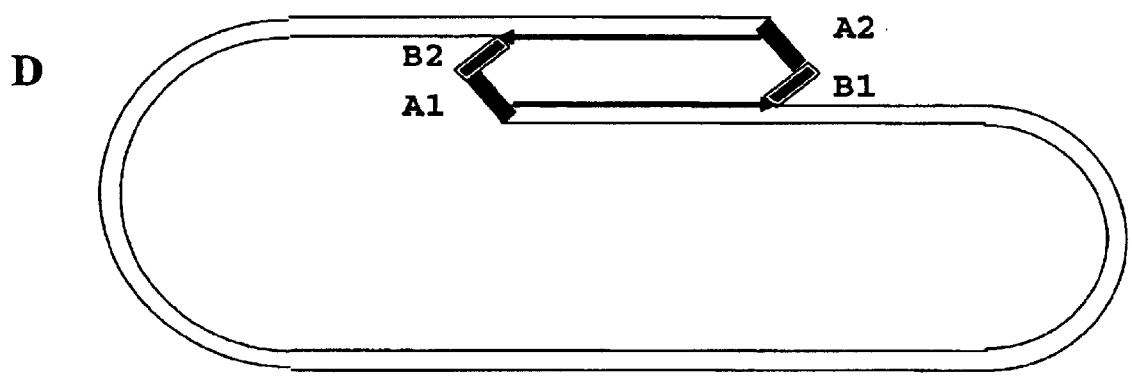
or
E 
or
F 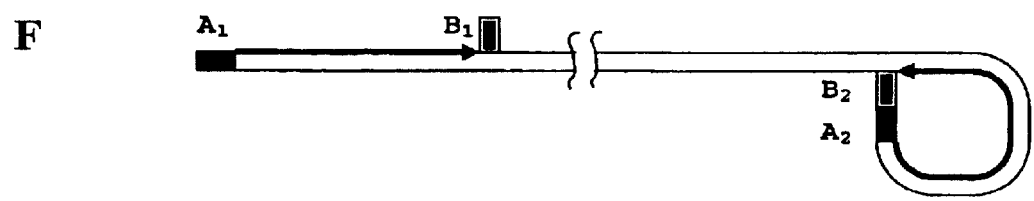
FIG. 34B

Micro-array of ordered terminal PENTAmer (TP)
DNA sequences

Up-stream, terminus-attaching, nick-translation adaptor A

5' P - GATCGCCTATACCTAGGACCATGTAAddC 3'
       3' ddCGGAUAUGGAUCCUGGUACAUUG-OH 5'

Acceptor-adaptor Ac

5' - GATCGCCTATACCTAGGACCATGTAA 3'
     3' CGGAUAUGGAUCCUGGUACAUUG-OH 5'

Recombination, nick-translation adaptor RA-(L-cos)

5' P - GATCGCCTATACCTAGGACCATGTAACGAATTCATCA 3'
       NH₂CGGAUAUGGAUCCUGGUACAUUGCTTAAGTAGTCCCGCCGCTGGA-OH 5'

Down-stream, nick-attaching adaptors B-3' (a), B-3' (b), B-3' (c) and B-3' (d)

| | |
|---|---|
| 5'-GGGAGATCTGAATTCCCCCCCCCCCddC-3'<br>3'-ddCGCCACTGGGCCCTCTAGACTTAAG - P 5' | (a) |
| 5'-GTTACATGGTCCTAGGTATAGGC GCGGTGACCCGGGAGATCTGCCCCCCCCCCC-3'<br>3'- AATGTACCAGGATCCATATCCGCGCCACTGGGCCCTCTAGAC - P 5' | (b) |
| 5'-GGGAGATTCTGAATTCAAAAAAAAddA-3'<br>3'-ddAGCCACTGGGCCCTCTAGACTTAAG - P 5' | (c) |
| 5-GTTACATGGTCCTAGGTATAGGC GCGGTGACCCGGGAGATCTGAAAAAAAAAA-3'<br>3- AATGTACCAGGATCCATATCCGCGCCACTGGGCCCTCTAGAC - P 5' | (d) |

Oligo-construct with nick    ³²P-A    nick
                                   ↓ ↙

5'-Biotin-GCGGTGACCCGGGAGATCTGAATTCA GGGCGGCGACCT-3'
3'-       CGCCACTGGGCCCTCTAGACTTAAGTCCCGCCGCTGGA - P-5' a) for a nomenclature of the adaptors A and B-3' see section 6

Fig. 40

A  RA-(L-λ cos) adaptor - Lambda DNA junction structure
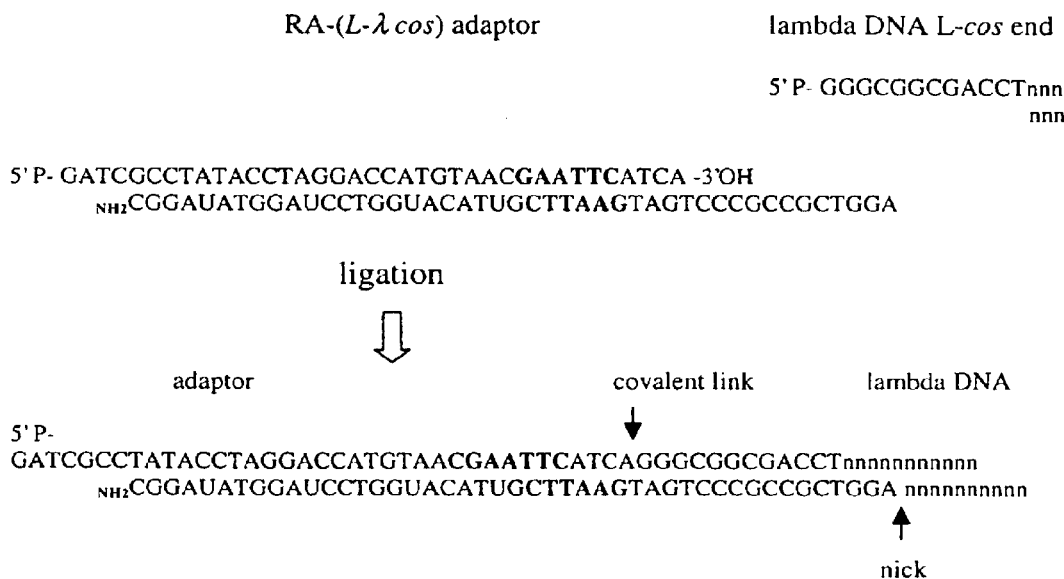
B  Recombinant junction formed by circularization
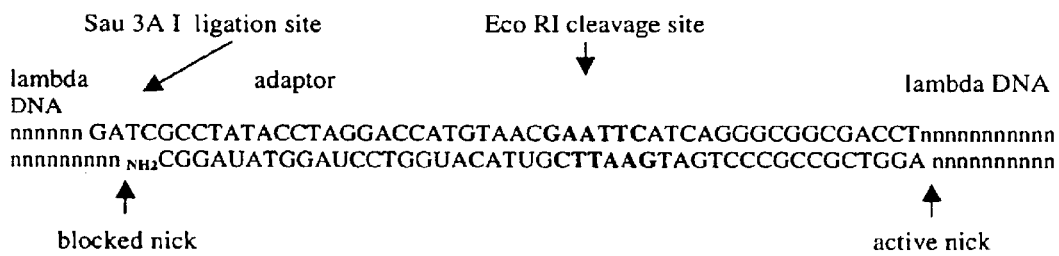
C  5'-end of the PENTamer
nnnnnnnnnctagCGGAUAUGGAUCCUGGUACAUGCUUAA - 5'
Fig. 61

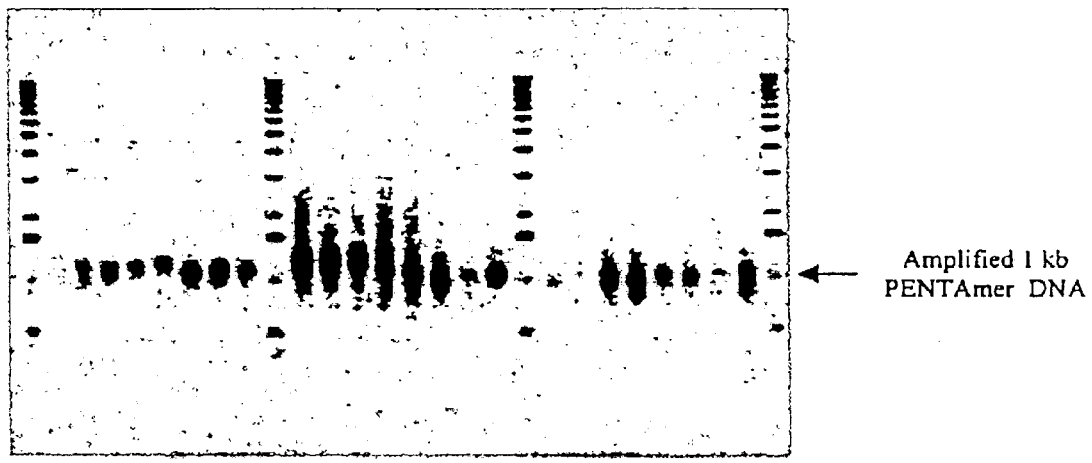
M 1 2 3 4 5 6 7 8 M 9 10 11 12 13 14 15 16 M 17 18 19 20 21 22 23 24 M
fraction number
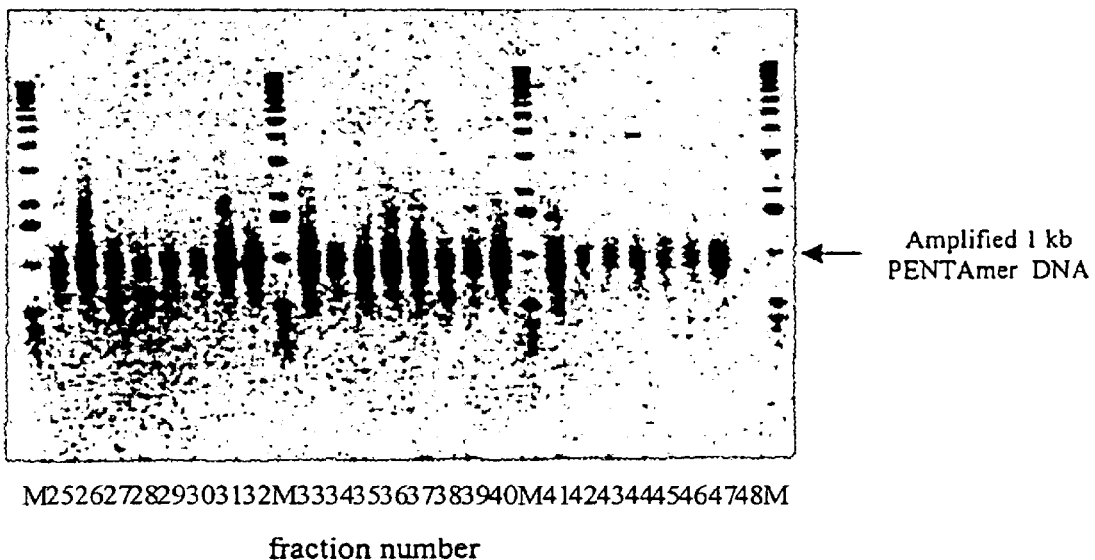
M 25 26 27 28 29 30 31 32 M 33 34 35 36 37 38 39 40 M 41 42 43 44 45 46 47 48 M
fraction number
FIG. 63

M 1 2 3 4 5 6 7 8 M 9 10 11 12 13 14 15 16 M 17 18 19 20 21 22 23 24 M
fraction number
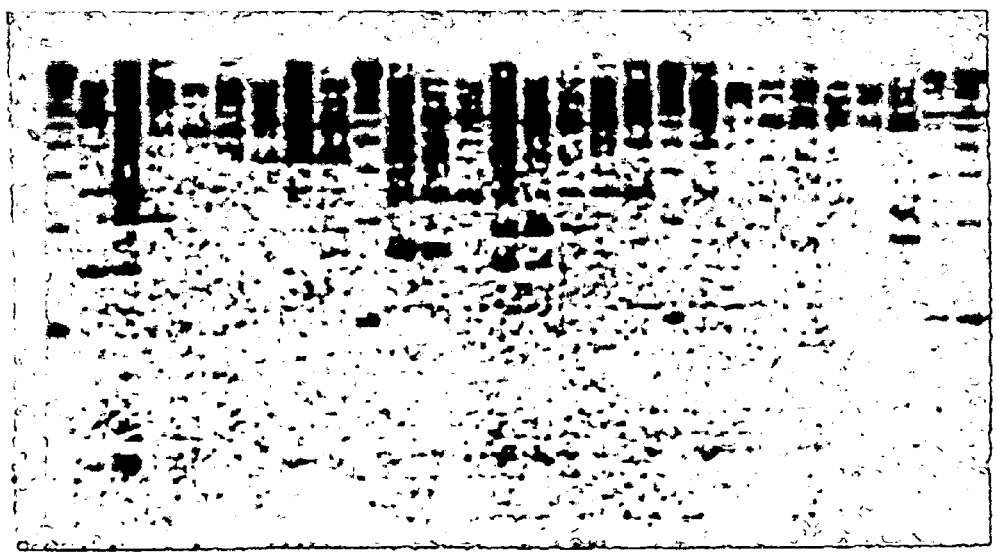
M 25 26 27 28 29 30 31 32 M 33 34 35 36 37 38 39 40 M 41 42 43 44 45 46 47 48 M
fraction number
FIG. 64

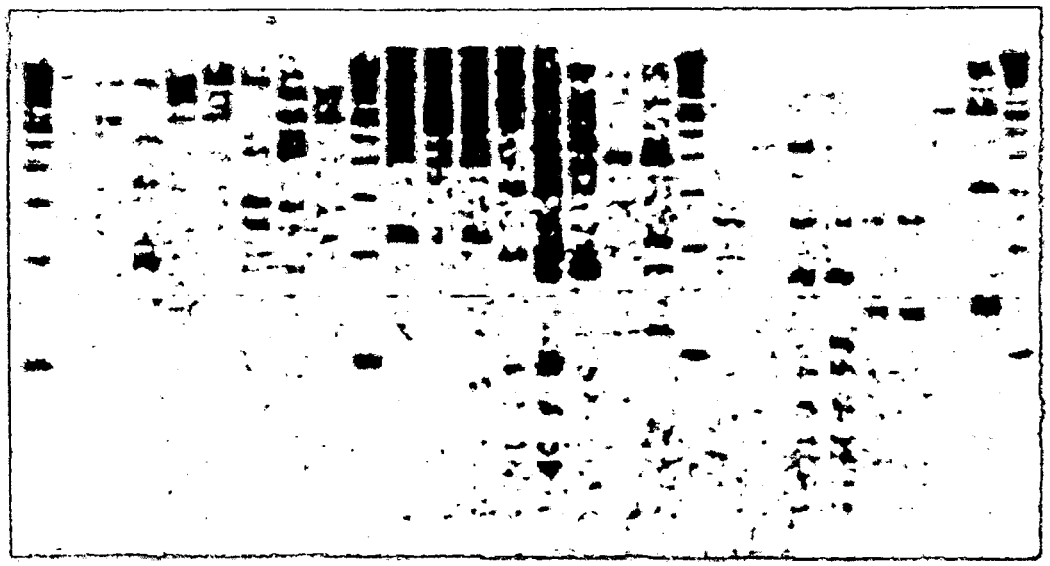
M 1 2 3 4 5 6 7 8 M 9 10 11 12 13 14 15 16 M 17 18 19 20 21 22 23 24 M
fraction number
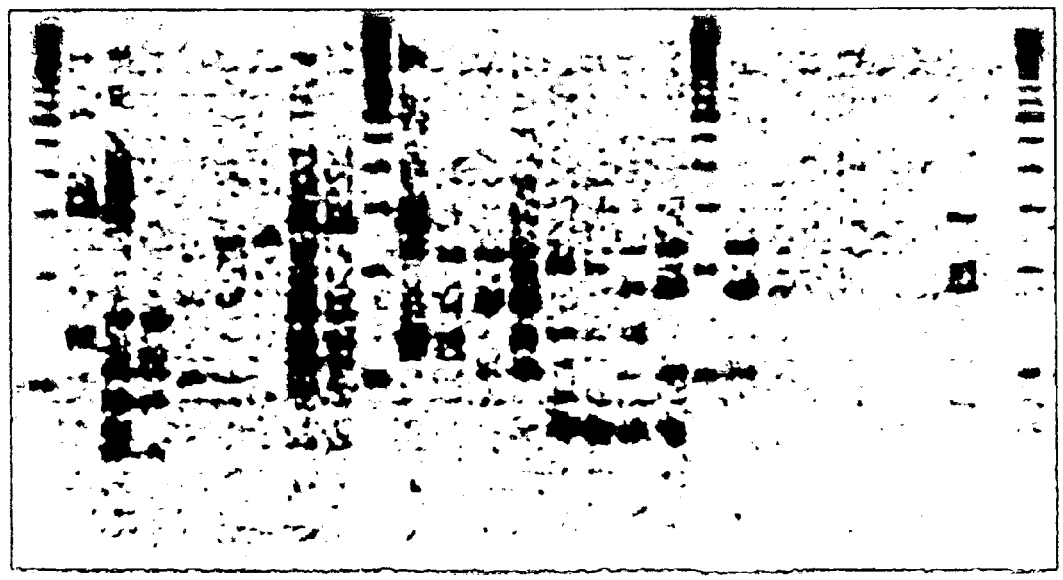
M 25 26 27 28 29 30 31 32 M 33 34 35 36 37 38 39 40 M 41 42 43 44 45 46 47 48 M
fraction number
FIG. 65

A) RA1/RA2 (Methylation Dpn-I Activation)

RA1 5'-GATCTGAGGTTGTAGAAGACTCGGACGATACACATGCACCGTCGGTCAGTCGTAATCCAGTCCGA (SEQ ID NO:69)
       AGCCACGTCAGCATTAGGTCAGGGCTCCTCTCGGATAAAACGATCGGGCACTCGTTATTGATCGCTAG-5' RA2 (SEQ ID NO:70 below)

Assembled RA1 5'-(P)- GATCTGAGGTTGTAGAAGACTCGGACGATACACATGCACCGTCGGTCAGTCGTAATCCAGTCCGATCTCAGAGCGTT\ (SEQ ID NO:71)
              B3'-ACTCCAACATCTTCTGAGCCTGCTATGTGTACGTGGCAGCCACTGCAGCATTAGGTCAGGGCTAGAGTCTCGCTT/

RA1 Component Oligos:
  RA1(A) 5'-(P)- GATCTGAGGTTGTAGAAGACTCGGACGATACACATGCACCGTCGGTCAGTCGTAATCCAGTCCCGATCTC-3' (SEQ ID NO:72)
  RA1(B) 5'-CTTCTACAACCTCA-B3' (SEQ ID NO:73)
  RA1(C) 5'-(P)-CGGTGCATGTGTATCGTCCCAGT-3' (SEQ ID NO:74)
  RA1(D) 5'-(P)-AGAGCGTTTTCGCTCGAGATCGGGACTGGATTACGACTGCACCGA-B3' (SEQ ID NO:75)

Assembled RA2 5'-(P)- GATCGCTAGTTATTGCTCACGGGCTAGCAAAATAGGCGTCTCCGGACTGATTACGACTGCACCGATCTCAGAGCG-T-T\ (SEQ ID NO:76)
              B3'-CGATCAATAACGAGTGCCCGATCGTTTATCGCGACAGGAGCCCTGACCTAATGCTGACGTGGCTAGAGTCTCGC-T-T/

RA2 Component Oligos:
  RA2(A) 5'-(P)-GATCGCTAGTTATTGCTCACGGGCTAGCAAAATAGCGCTGTCTCCGGACTGGATTACGACTGCACCGATCTC-3' (SEQ ID NO:77)
  RA2(B) 5'-GAGCAATAACTAGC-B3' (SEQ ID NO:78)
  RA2(C) 5'-(P)-GGACAGGCGCTATTTTGCTAGCCCGT-3' (SEQ ID NO:79)
  RA2(D) 5'-(P)-AGAGCGTTTTCGCTCGAGATCGGTGCAGTCGTAATCCAGTCCCGA-B3' (SEQ ID NO:80)

B) Simplified Recombinant Adapters Sra1/Sra2

Sra 1 5' P-GATCTGAGGTTGTTGAAGACTCGGACGATACACACGCTGGGTTGAGGAAGTCGTAAATA                                     (SEQ ID NO:81)
                                        TGTGCGACCCAACTCCTTCAGCATTTATTTATTGGTAGGGTTGTCGTTATTGATCGCTAG-5' P Sra 2

Sra 1A  5' P-GATCTGAGGTTGTTGAAGACTCGGACGATACACACGCTGGGTTGAGGAAGTCGTAAATA-3'           (SEQ ID NO:82)
      Sra 1B         B3'-ACTCCAACACTTC-5'                                                  (SEQ ID NO:83)
      Sra 1C         B3'-ACTCCAACACTTCTGAGCCTGCT-5'                                        (SEQ ID NO:84)
      Sra 1D             B3'-TGTGCGACCCAACTCCTTCAGCATTTATTTATTGGTAGGGTTGTCGTTATTGATCGCTAG-5' P  Sra 2A (SEQ ID NO:85)
                                                                               Sra 2B (SEQ ID NO:86)
                                                                               Sra 2C (SEQ ID NO:87)
                                                                               Sra 2D (SEQ ID NO:88)
                                                    5'-CAGCAATAACTAGC-B3'
                                                    5'-AACCATCCCAACAGCAATAACTAGC-B3'
                              5'-ACACGCTGGGTTGAGGAAGTCGTAAATA-B3'

C) Sra1' Expanded complementarity with original Sra2

5' P-GATCTGAGGTTGTTGAAGACACGCTGGGTTGAGGAAGTCGTAAATAATAATAACCATCCCAA-3' Sra 1A' (SEQ ID NO:89)
                     B3'-ACTCCAACAACTTC-5'                            Sra 1B (SEQ ID NO:82)
                                                                      Sra 1D (SEQ ID NO:84)
                                                                      Sra 1H (SEQ ID NO:90)

5' P-GATCTGAGGTTGTTGAAGACACGCTGGGTTGAGGAAGTCGTAAATAATAATAACCATCCCAA
                          TGTGCGACCCAACTCCTTCAGCATTTATTTATTGGTAGGGTTGTCGTTATTGATCGCTAG-P5'
     B3'-ACTCCAACAACTTC-5'
               B3'-TGTGCGACCCAACTCCTTCAGCATTTAT-5'
                                  B3'-TTATTGGTAGGGTT-5'

FIG. 69

```
Simplified recombinant adapter (Sra) oligos
Sra 1A       P5'-GATCTGAGGTTGTTGAAGACTCGGACGATACACACGCTGGGTTGAGGAAGTCGTAAATA-3' (SEQ
ID NO:91)

Sra 1B       5'-CTTCAACAACCTCA-B3' (SEQ ID NO:92)

Sra 1C       5'-TCGTCCGAGTCTTCAACAACCTCA-B3' (SEQ ID NO:93)
Sra 1D       5'-TATTTACGACTTCCTCAACCCAGCGTGT-B3' (SEQ ID NO:94)

Sra 2A       P5'-GATCGCTAGTTATTGCTGTTGGGATGGTTATTTATTTACGACTTCCTCAACCCAGCGTGT-3' (SEQ ID
NO:95)

Sra 2B       5'-CAGCAATAACTAGC-B3' (SEQ ID NO:96)

Sra 2C       5'-AACCATCCCAACAGCAATAACTAGC-B3' (SEQ ID NO:97)
Sra 2D       5'-ACACGCTGGGTTGAGGAAGTCGTAAATA-B3' (SEQ ID NO:98)

Sra 1A'      P5'-GATCTGAGGTTGTTGAAGACACGCTGGGTTGAGGAAGTCGTAAATAAATAACCATCCCAA-3' (SEQ ID
NO:99)

Sra 1H       5'-TTGGGATGGTTATT-B3' (SEQ ID NO:100)

Lambda recombination screening oligos
Total(+)     5'-AGGTTGTAGAAGACTCGG-3' (SEQ ID NO:101)

Total(-)     5'-GCTAGTTATTGCTCACGG-3' (SEQ ID NO:102)

Intra(+34273) 5'-GCATCGCTTGAATTGTCC-3' (SEQ ID NO:103)

Intra(-28119) 5'-TGCTCTCGGAATATCAAT-3' (SEQ ID NO:104)

Inter(+34273) 5'-GCATCGCTTGAATTGTCC-3' (SEQ ID NO:105)

Inter(-34599) 5'-ATATTCAGGCCAGTTATC-3' (SEQ ID NO:106)

E-coli recombination screening oligos
B1(RP)       5'-CTTACACCGGCGAAGTGAAAG-3' (SEQ ID NO:107)

B1(PCR)      5'-CGCTGCCGGAGCTGTTAGACAATTC-3' (SEQ ID NO:108)

B1(NEST)     5'-GCCTGCAAGCCGGTGTAGACATCAC-3' (SEQ ID NO:109)

B3(RP)       5'-CTGCAGGCCAGCGAGACAGAT-3' (SEQ ID NO:110)

B3(PCR)      5'-GTTGTGGCCTTCCAGTAAGGTCC-3' (SEQ ID NO:111)

B3(NEST)     5'-GCAAAATAGCTGGCTGGCAGGTGTAGG-3' (SEQ ID NO:112)

B5(RP)       5'-TAGGGCGGCATCAGGTAATAC-3' (SEQ ID NO:113)

B5(PCR)      5'-TGCCGCCGTTCGCATCCATACCA-3' (SEQ ID NO:114)

B5(NEST)     5'-TTCCCTGCCTGGTCGCCGTATCTGTG-3' (SEQ ID NO:115)

B8(RP)       5'-TGAAGGATACGGAAGCAGAAA-3' (SEQ ID NO:116)

B8(PCR)      5'-GCCATTGCTGATTGCCCACCGACAA-3' (SEQ ID NO:117)

B8(NEST)     5'-CTCTATCGCTCGGCCTAAGTCTTTAC-3' (SEQ ID NO:118)

B12(RP)      5'-GCGGTCGGCGTGGATAAAGTA-3' (SEQ ID NO:119)

B12(PCR)     5'-GTGAGCGGGATGAACGAACCTTA-3' (SEQ ID NO:120)

B12(NEST)    5'-CTGCGCCAGGGCTTCCAGACATTGTG-3' (SEQ ID NO:121)
```

FIG. 70

Enzymatic Release of Recombinant Pentamers T7 gene6 – S1 nuclease

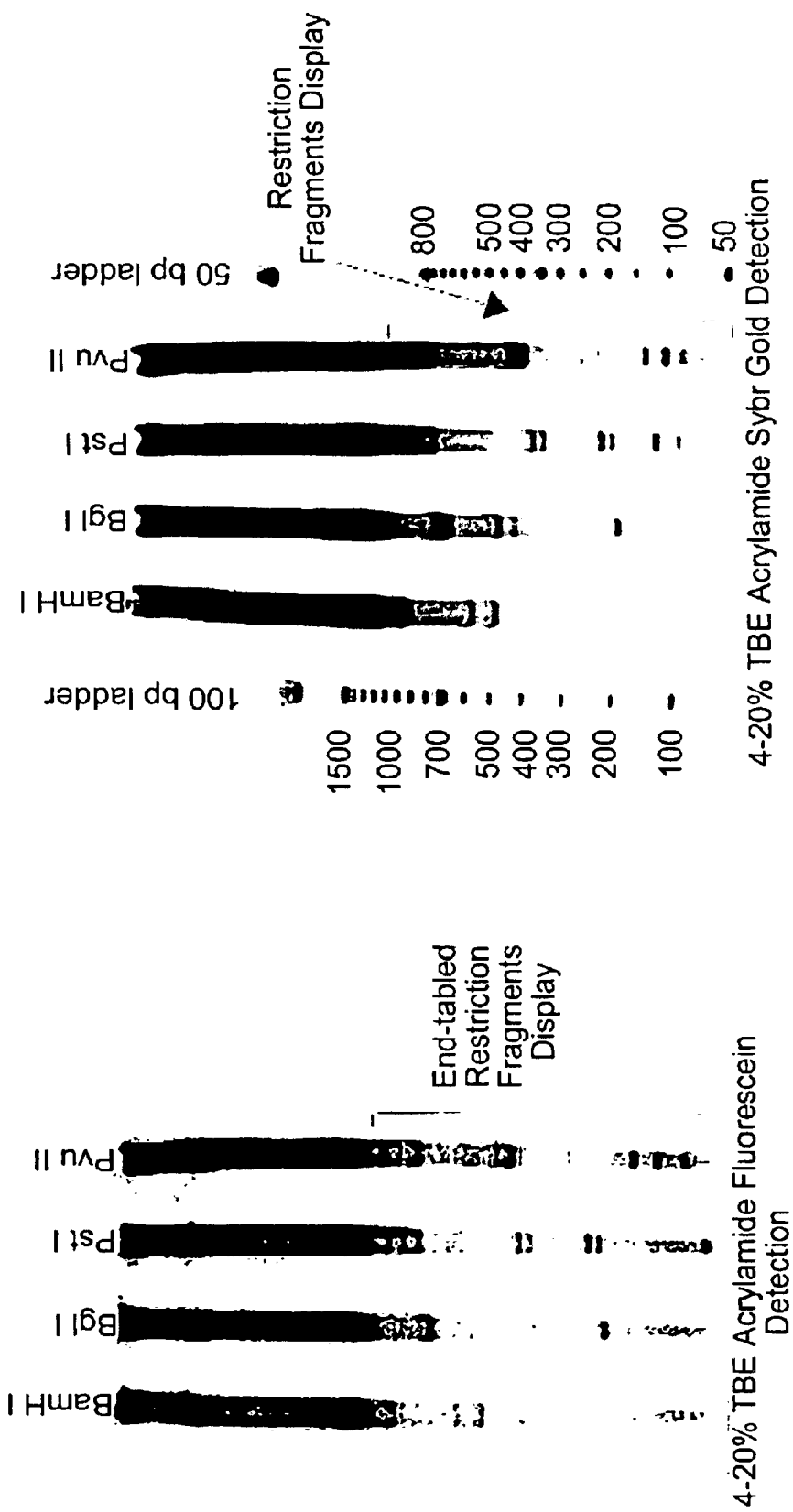

SEQUENCE LISTING

<160> NUMBER OF SEQ ID NOS: 121

<210> SEQ ID NO 1
<211> LENGTH: 24
<212> TYPE: DNA
<213> ORGANISM: Unknown
<220> FEATURE:
<223> OTHER INFORMATION: Primer

<400> SEQUENCE: 1
gatcgcctat acctaggacc atgt                                        24

<210> SEQ ID NO 2
<211> LENGTH: 22
<212> TYPE: DNA
<213> ORGANISM: Artificial Sequence
<220> FEATURE:
<223> OTHER INFORMATION: DNA/RNA Primer
<220> FEATURE:
<221> NAME/KEY: misc_feature
<222> LOCATION: (1)..(22)
<223> OTHER INFORMATION: Ribonucleotide at 7, 10 ,13, 19

<400> SEQUENCE: 2
gttacauggu ccuaggtaua gg                                          22

<210> SEQ ID NO 3
<211> LENGTH: 23
<212> TYPE: DNA
<213> ORGANISM: Unknown
<220> FEATURE:
<223> OTHER INFORMATION: Primer

<400> SEQUENCE: 3
gttacatggt cctaggtata ggc                                         23

<210> SEQ ID NO 4
<211> LENGTH: 37
<212> TYPE: DNA
<213> ORGANISM: Unknown
<220> FEATURE:
<223> OTHER INFORMATION: Primer

<400> SEQUENCE: 4
gatcgcctat acctaggacc atgtaacgaa ttcatca                          37

<210> SEQ ID NO 5
<211> LENGTH: 45
<212> TYPE: DNA
<213> ORGANISM: Unknown
<220> FEATURE:
<223> OTHER INFORMATION: DNA/RNA Primer
<220> FEATURE:
<221> NAME/KEY: misc_feature
<222> LOCATION: (1)..(45)
<223> OTHER INFORMATION: Ribonucleotide at 24, 29, 35, 41

<400> SEQUENCE: 5
aggtcgccgc cctgatgaat tcgutacaug gtccuaggta uaggc                45

<210> SEQ ID NO 6
<211> LENGTH: 12
<212> TYPE: DNA
<213> ORGANISM: Unknown
<220> FEATURE:
<223> OTHER INFORMATION: Primer

<400> SEQUENCE: 6
gggcggcgac ct                                                    12

<210> SEQ ID NO 7
<211> LENGTH: 25
<212> TYPE: DNA
<213> ORGANISM: Unknown
<220> FEATURE:
<223> OTHER INFORMATION: Primer

<400> SEQUENCE: 7
gggagatctg aattccccccc ccccc                                     25

<210> SEQ ID NO 8
<211> LENGTH: 23
<212> TYPE: DNA
<213> ORGANISM: Unknown
<220> FEATURE:
<223> OTHER INFORMATION: Primer

<400> SEQUENCE: 8
gggagatctg aattcaaaaa aaa                                        23

<210> SEQ ID NO 9
<211> LENGTH: 24
<212> TYPE: DNA
<213> ORGANISM: Unknown
<220> FEATURE:
<223> OTHER INFORMATION: Primer

<400> SEQUENCE: 9
gaattcagat ctcccgggtc accg                                       24

<210> SEQ ID NO 10
<211> LENGTH: 30
<212> TYPE: DNA
<213> ORGANISM: Unknown
<220> FEATURE:
<223> OTHER INFORMATION: Primer

<400> SEQUENCE: 10
gcggtgaccc gggagatctg cccccccccc                                 30

<210> SEQ ID NO 11
<211> LENGTH: 30

```
<212> TYPE: DNA
<213> ORGANISM: Unknown
<220> FEATURE:
<223> OTHER INFORMATION: Primer

<400> SEQUENCE: 11
gcggtgaccc gggagatctg aaaaaaaaaa                                        30

<210> SEQ ID NO 12
<211> LENGTH: 42
<212> TYPE: DNA
<213> ORGANISM: Unknown
<220> FEATURE:
<223> OTHER INFORMATION: Primer

<400> SEQUENCE: 12
cagatctccc gggtcaccgc gcctatacct aggaccatgt aa                          42

<210> SEQ ID NO 13
<211> LENGTH: 25
<212> TYPE: DNA
<213> ORGANISM: Unknown
<220> FEATURE:
<223> OTHER INFORMATION: Primer

<400> SEQUENCE: 13
gcggtgaccc gggagatctg aattc                                             25

<210> SEQ ID NO 14
<211> LENGTH: 25
<212> TYPE: DNA
<213> ORGANISM: Unknown
<220> FEATURE:
<223> OTHER INFORMATION: Primer

<400> SEQUENCE: 14
gcggtgaccc gggagatctg aattc                                             25

<210> SEQ ID NO 15
<211> LENGTH: 38
<212> TYPE: DNA
<213> ORGANISM: Unknown
<220> FEATURE:
<223> OTHER INFORMATION: Primer

<400> SEQUENCE: 15
aggtcgccgc cctgaattca gatctcccgg gtcaccgc                               38

<210> SEQ ID NO 16
<211> LENGTH: 27
<212> TYPE: DNA
<213> ORGANISM: Unknown
<220> FEATURE:
<223> OTHER INFORMATION: Primer
<220> FEATURE:
<221> NAME/KEY: misc_feature
<222> LOCATION: (27)..(27)
<223> OTHER INFORMATION: n equals ddC

<400> SEQUENCE: 16
gatcgcctat acctaggacc atgtaan                                           27

<210> SEQ ID NO 17
<211> LENGTH: 23
<212> TYPE: DNA
<213> ORGANISM: Artificial Sequence
<220> FEATURE:
```

```
<223> OTHER INFORMATION: DNA/RNA Primer
<220> FEATURE:
<221> NAME/KEY: misc_feature
<222> LOCATION: (1)..(23)
<223> OTHER INFORMATION: Ribonucletide at 7, 10, 13, 19
<220> FEATURE:
<221> NAME/KEY: misc_feature
<222> LOCATION: (23)..(23)
<223> OTHER INFORMATION: n equals ddC

<400> SEQUENCE: 17
gttacauggu ccuaggtaua ggn                                          23

<210> SEQ ID NO 18
<211> LENGTH: 26
<212> TYPE: DNA
<213> ORGANISM: Unknown
<220> FEATURE:
<223> OTHER INFORMATION: Primer

<400> SEQUENCE: 18
gatcgcctat acctaggacc atgtaa                                       26

<210> SEQ ID NO 19
<211> LENGTH: 23
<212> TYPE: DNA
<213> ORGANISM: Artificial Sequence
<220> FEATURE:
<223> OTHER INFORMATION: DNA/RNA Primer
<220> FEATURE:
<221> NAME/KEY: misc_feature
<222> LOCATION: (1)..(23)
<223> OTHER INFORMATION: Ribonucleotide at 7, 10, 13, 19

<400> SEQUENCE: 19
gttacauggu ccuaggtaua ggc                                          23

<210> SEQ ID NO 20
<211> LENGTH: 37
<212> TYPE: DNA
<213> ORGANISM: Unknown
<220> FEATURE:
<223> OTHER INFORMATION: Primer

<400> SEQUENCE: 20
gatcgcctat acctaggacc atgtaacgaa ttcatca                           37

<210> SEQ ID NO 21
<211> LENGTH: 45
<212> TYPE: DNA
<213> ORGANISM: Artificial Sequence
<220> FEATURE:
<223> OTHER INFORMATION: DNA/RNA Primer
<220> FEATURE:
<221> NAME/KEY: misc_feature
<222> LOCATION: (1)..(45)
<223> OTHER INFORMATION: Ribonucleotide at 24, 29, 35, 41

<400> SEQUENCE: 21
aggtcgccgc cctgatgaat tcgutacaug gtccuaggta uaggc                  45

<210> SEQ ID NO 22
<211> LENGTH: 26
<212> TYPE: DNA
<213> ORGANISM: Unknown
<220> FEATURE:
<223> OTHER INFORMATION: Primer
<220> FEATURE:
<221> NAME/KEY: misc_feature
```

```
<222> LOCATION: (26)..(26)
<223> OTHER INFORMATION: n equals ddC

<400> SEQUENCE: 22
gggagatctg aattcccccc ccccn                                              26

<210> SEQ ID NO 23
<211> LENGTH: 25
<212> TYPE: DNA
<213> ORGANISM: Unknown
<220> FEATURE:
<223> OTHER INFORMATION: Primer
<220> FEATURE:
<221> NAME/KEY: misc_feature
<222> LOCATION: (25)..(25)
<223> OTHER INFORMATION: n equals ddC

<400> SEQUENCE: 23
gaattcagat ctcccgggtc accgn                                              25

<210> SEQ ID NO 24
<211> LENGTH: 53
<212> TYPE: DNA
<213> ORGANISM: Unknown
<220> FEATURE:
<223> OTHER INFORMATION: Primer

<400> SEQUENCE: 24
gttacatggt cctaggtata ggcgcggtga cccgggagat ctgcccccccc ccc              53

<210> SEQ ID NO 25
<211> LENGTH: 42
<212> TYPE: DNA
<213> ORGANISM: Unknown
<220> FEATURE:
<223> OTHER INFORMATION: Primer

<400> SEQUENCE: 25
cagatctccc gggtcaccgc gcctatacct aggaccatgt aa                           42

<210> SEQ ID NO 26
<211> LENGTH: 25
<212> TYPE: DNA
<213> ORGANISM: Unknown
<220> FEATURE:
<223> OTHER INFORMATION: Primer
<220> FEATURE:
<221> NAME/KEY: misc_feature
<222> LOCATION: (25)..(25)
<223> OTHER INFORMATION: n equals ddA

<400> SEQUENCE: 26
gggagattct gaattcaaaa aaaan                                              25

<210> SEQ ID NO 27
<211> LENGTH: 25
<212> TYPE: DNA
<213> ORGANISM: Unknown
<220> FEATURE:
<223> OTHER INFORMATION: Primer
<220> FEATURE:
<221> NAME/KEY: misc_feature
<222> LOCATION: (25)..(25)
<223> OTHER INFORMATION: n equals ddA
<220> FEATURE:
<221> NAME/KEY: misc_feature
<222> LOCATION: (25)..(25)
<223> OTHER INFORMATION: n equals ddA
```

<400> SEQUENCE: 27
gaattcagat ctcccgggtc accgn                                          25

<210> SEQ ID NO 28
<211> LENGTH: 53
<212> TYPE: DNA
<213> ORGANISM: Unknown
<220> FEATURE:
<223> OTHER INFORMATION: Primer

<400> SEQUENCE: 28
gttacatggt cctaggtata ggcgcggtga cccgggagat ctgaaaaaaa aaa           53

<210> SEQ ID NO 29
<211> LENGTH: 42
<212> TYPE: DNA
<213> ORGANISM: Unknown
<220> FEATURE:
<223> OTHER INFORMATION: Primer

<400> SEQUENCE: 29
cagatctccc gggtcaccgc gcctatacct aggaccatgt aa                       42

<210> SEQ ID NO 30
<211> LENGTH: 26
<212> TYPE: DNA
<213> ORGANISM: Unknown
<220> FEATURE:
<223> OTHER INFORMATION: Primer

<400> SEQUENCE: 30
gcggtgaccc gggagatctg aattca                                         26

<210> SEQ ID NO 31
<211> LENGTH: 12
<212> TYPE: DNA
<213> ORGANISM: Unknown
<220> FEATURE:
<223> OTHER INFORMATION: Primer

<400> SEQUENCE: 31
gggcggcgac ct                                                        12

<210> SEQ ID NO 32
<211> LENGTH: 38
<212> TYPE: DNA
<213> ORGANISM: Unknown
<220> FEATURE:
<223> OTHER INFORMATION: Primer

<400> SEQUENCE: 32
aggtcgccgc cctgaattca gatctcccgg gtcaccgc                            38

<210> SEQ ID NO 33
<211> LENGTH: 70
<212> TYPE: DNA
<213> ORGANISM: Unknown
<220> FEATURE:
<223> OTHER INFORMATION: Primer

<400> SEQUENCE: 33
gatctgaggt tgtagaagac tcggacgata cacatgcacc gtcggtgcag tcgtaatcca    60
gtcccgatct                                                           70

<210> SEQ ID NO 34
<211> LENGTH: 14
<212> TYPE: DNA
<213> ORGANISM: Unknown
<220> FEATURE:
<223> OTHER INFORMATION: Primer

<400> SEQUENCE: 34
cttctacaac ctca                                                      14

<210> SEQ ID NO 35
<211> LENGTH: 23
<212> TYPE: DNA
<213> ORGANISM: Unknown
<220> FEATURE:
<223> OTHER INFORMATION: Primer

<400> SEQUENCE: 35
cggtgcatgt gtatcgtccg agt                                            23

<210> SEQ ID NO 36
<211> LENGTH: 41
<212> TYPE: DNA
<213> ORGANISM: Unknown
<220> FEATURE:
<223> OTHER INFORMATION: Primer

<400> SEQUENCE: 36
ggcctgaggt tgtagaagac tcggacgata cacatgcacc g                        41

<210> SEQ ID NO 37
<211> LENGTH: 14
<212> TYPE: DNA
<213> ORGANISM: Unknown
<220> FEATURE:
<223> OTHER INFORMATION: Primer

<400> SEQUENCE: 37
cttctacaac ctca                                                      14

<210> SEQ ID NO 38
<211> LENGTH: 23
<212> TYPE: DNA
<213> ORGANISM: Unknown
<220> FEATURE:
<223> OTHER INFORMATION: Primer

<400> SEQUENCE: 38
cggtgcatgt gtatcgtccg agt                                            23

<210> SEQ ID NO 39
<211> LENGTH: 42
<212> TYPE: DNA
<213> ORGANISM: Artificial Sequence
<220> FEATURE:
<223> OTHER INFORMATION: DNA/RNA Primer
<220> FEATURE:
<221> NAME/KEY: misc_feature
<222> LOCATION: (1)..(42)
<223> OTHER INFORMATION: Ribonucleotide at 23, 30, 36

<400> SEQUENCE: 39
gatctgaggt tgttgaagcg ttuacccaau tcgatuaggc aa                       42

<210> SEQ ID NO 40
<211> LENGTH: 14
<212> TYPE: DNA

```
<213> ORGANISM: Unknown
<220> FEATURE:
<223> OTHER INFORMATION: Primer

<400> SEQUENCE: 40
cttcaacaac ctca                                                      14

<210> SEQ ID NO 41
<211> LENGTH: 24
<212> TYPE: DNA
<213> ORGANISM: Unknown
<220> FEATURE:
<223> OTHER INFORMATION: DNA/RNA Primer
<220> FEATURE:
<221> NAME/KEY: misc_feature
<222> LOCATION: (1)..(24)
<223> OTHER INFORMATION: Ribonucleotide at 9, 14, 19

<400> SEQUENCE: 41
ttgcctaauc gaautgggua aacg                                           24

<210> SEQ ID NO 42
<211> LENGTH: 51
<212> TYPE: DNA
<213> ORGANISM: Unknown
<220> FEATURE:
<223> OTHER INFORMATION: Primer
<220> FEATURE:
<221> NAME/KEY: misc_feature
<222> LOCATION: (1)..(51)
<223> OTHER INFORMATION: n equals any base

<400> SEQUENCE: 42
aagtctgcaa gatcatcgcg gaaggtgaca aagactcgta tcgtaannnn c             51

<210> SEQ ID NO 43
<211> LENGTH: 46
<212> TYPE: DNA
<213> ORGANISM: Unknown
<220> FEATURE:
<223> OTHER INFORMATION: Primer

<400> SEQUENCE: 43
ttacgatacg agtctttgtc accttccgcg atgatcttgc agactt                   46

<210> SEQ ID NO 44
<211> LENGTH: 51
<212> TYPE: DNA
<213> ORGANISM: Unknown
<220> FEATURE:
<223> OTHER INFORMATION: Primer
<220> FEATURE:
<221> NAME/KEY: misc_feature
<222> LOCATION: (1)..(51)
<223> OTHER INFORMATION: n equals any base

<400> SEQUENCE: 44
aaatcaccat accaactcgc gtcctcctgt gcatgtcgat acgtaannnn c             51

<210> SEQ ID NO 45
<211> LENGTH: 46
<212> TYPE: DNA
<213> ORGANISM: Unknown
<220> FEATURE:
<223> OTHER INFORMATION: Primer

<400> SEQUENCE: 45
ttacgtatcg acatgcacag gaggacgcga gttggtgtgg tgattt                   46
```

```
<210> SEQ ID NO 46
<211> LENGTH: 57
<212> TYPE: DNA
<213> ORGANISM: Unknown
<220> FEATURE:
<223> OTHER INFORMATION: Primer

<400> SEQUENCE: 46
aagtctgcaa gatcatcgcg gaaggtgaca aagactcgta tcgtaacccc ccccccc        57

<210> SEQ ID NO 47
<211> LENGTH: 46
<212> TYPE: DNA
<213> ORGANISM: Unknown
<220> FEATURE:
<223> OTHER INFORMATION: Primer

<400> SEQUENCE: 47
ttacgatacg agtctttgtc accttccgcg atgatcttgc agactt                    46

<210> SEQ ID NO 48
<211> LENGTH: 23
<212> TYPE: DNA
<213> ORGANISM: Unknown
<220> FEATURE:
<223> OTHER INFORMATION: Primer

<400> SEQUENCE: 48
cggtgcatgt gtatcgtccg agt                                             23

<210> SEQ ID NO 49
<211> LENGTH: 33
<212> TYPE: DNA
<213> ORGANISM: Unknown
<220> FEATURE:
<223> OTHER INFORMATION: Primer

<400> SEQUENCE: 49
ctcctgtgca tgtcgatacg taaccccccc ccc                                  33

<210> SEQ ID NO 50
<211> LENGTH: 23
<212> TYPE: DNA
<213> ORGANISM: Unknown
<220> FEATURE:
<223> OTHER INFORMATION: Primer

<400> SEQUENCE: 50
cggtgcatgt gtatcgtccg agt                                             23

<210> SEQ ID NO 51
<211> LENGTH: 71
<212> TYPE: DNA
<213> ORGANISM: Unknown
<220> FEATURE:
<223> OTHER INFORMATION: Primer

<400> SEQUENCE: 51
gatctgaggt tgtagaagac tcggacgata cacatgcacc gtcggtgcag tcgtaatcca     60
gtcccgatct c                                                          71

<210> SEQ ID NO 52
<211> LENGTH: 14
<212> TYPE: DNA
```

```
<213> ORGANISM: Unknown
<220> FEATURE:
<223> OTHER INFORMATION: Primer

<400> SEQUENCE: 52
cttctacaac ctca                                                        14

<210> SEQ ID NO 53
<211> LENGTH: 23
<212> TYPE: DNA
<213> ORGANISM: Unknown
<220> FEATURE:
<223> OTHER INFORMATION: Primer

<400> SEQUENCE: 53
cggtgcatgt gtatcgtccg agt                                              23

<210> SEQ ID NO 54
<211> LENGTH: 41
<212> TYPE: DNA
<213> ORGANISM: Unknown
<220> FEATURE:
<223> OTHER INFORMATION: Primer

<400> SEQUENCE: 54
ggcctgaggt tgtagaagac tcggacgata cacatgcacc g                          41

<210> SEQ ID NO 55
<211> LENGTH: 23
<212> TYPE: DNA
<213> ORGANISM: Unknown
<220> FEATURE:
<223> OTHER INFORMATION: Primer

<400> SEQUENCE: 55
cggtgcatgt gtatcgtccg agt                                              23

<210> SEQ ID NO 56
<211> LENGTH: 42
<212> TYPE: DNA
<213> ORGANISM: Artificial Sequence
<220> FEATURE:
<223> OTHER INFORMATION: DNA/RNA Primer
<220> FEATURE:
<221> NAME/KEY: misc_feature
<222> LOCATION: (1)..(42)
<223> OTHER INFORMATION: Ribonucleotide at 23, 30, 36

<400> SEQUENCE: 56
gatctgaggt tgttgaagcg ttuacccaau tcgatuaggc aa                         42

<210> SEQ ID NO 57
<211> LENGTH: 24
<212> TYPE: DNA
<213> ORGANISM: Artificial Sequence
<220> FEATURE:
<223> OTHER INFORMATION: DNA/RNA Primer
<220> FEATURE:
<221> NAME/KEY: misc_feature
<222> LOCATION: (1)..(24)
<223> OTHER INFORMATION: Ribonucleotide at 9, 14, 19,

<400> SEQUENCE: 57
ttgcctaauc gaautgggua aacg                                             24

<210> SEQ ID NO 58
<211> LENGTH: 14
```

```
<212> TYPE: DNA
<213> ORGANISM: Unknown
<220> FEATURE:
<223> OTHER INFORMATION: Primer

<400> SEQUENCE: 58
cttcaacaac ctca                                                         14

<210> SEQ ID NO 59
<211> LENGTH: 24
<212> TYPE: DNA
<213> ORGANISM: Unknown
<220> FEATURE:
<223> OTHER INFORMATION: Primer

<400> SEQUENCE: 59
ttgcctaatc gaattgggta aacg                                              24

<210> SEQ ID NO 60
<211> LENGTH: 42
<212> TYPE: DNA
<213> ORGANISM: Unknown
<220> FEATURE:
<223> OTHER INFORMATION: Primer

<400> SEQUENCE: 60
ttccctaatc gaattgggta aacgcttcaa caacctcaga tc                          42

<210> SEQ ID NO 61
<211> LENGTH: 46
<212> TYPE: DNA
<213> ORGANISM: Unknown
<220> FEATURE:
<223> OTHER INFORMATION: Primer

<400> SEQUENCE: 61
ttacgatacg agtctttgtc accttccgcg atgatcttgc agactt                      46

<210> SEQ ID NO 62
<211> LENGTH: 51
<212> TYPE: DNA
<213> ORGANISM: Unknown
<220> FEATURE:
<223> OTHER INFORMATION: Primer
<220> FEATURE:
<221> NAME/KEY: misc_feature
<222> LOCATION: (1)..(51)
<223> OTHER INFORMATION: n equals any base

<400> SEQUENCE: 62
aagtctgcaa gatcatcgcg gaaggtgaca aagactcgta tcgtaannnn c                51

<210> SEQ ID NO 63
<211> LENGTH: 23
<212> TYPE: DNA
<213> ORGANISM: Unknown
<220> FEATURE:
<223> OTHER INFORMATION: Primer

<400> SEQUENCE: 63
aagtctgcaa gatcatcgcg gaa                                               23

<210> SEQ ID NO 64
<211> LENGTH: 46
<212> TYPE: DNA
<213> ORGANISM: Unknown
<220> FEATURE:
```

<223> OTHER INFORMATION: Primer
<220> FEATURE:
<221> NAME/KEY: misc_feature
<222> LOCATION: (1)..(46)
<223> OTHER INFORMATION: n equals any base

<400> SEQUENCE: 64
acgggctagc aaaatagcgc tgtccngatc tgaggttgtt gaagcg        46

<210> SEQ ID NO 65
<211> LENGTH: 25
<212> TYPE: DNA
<213> ORGANISM: Unknown
<220> FEATURE:
<223> OTHER INFORMATION: Primer

<400> SEQUENCE: 65
ggacagcgct attttgctag cccgt        25

<210> SEQ ID NO 66
<211> LENGTH: 23
<212> TYPE: DNA
<213> ORGANISM: Unknown
<220> FEATURE:
<223> OTHER INFORMATION: Primer

<400> SEQUENCE: 66
ggtgacaaag actcgtatcg taa        23

<210> SEQ ID NO 67
<211> LENGTH: 23
<212> TYPE: DNA
<213> ORGANISM: Unknown
<220> FEATURE:
<223> OTHER INFORMATION: Primer

<400> SEQUENCE: 67
ctcctgtgca tgtcgatacg taa        23

<210> SEQ ID NO 68
<211> LENGTH: 23
<212> TYPE: DNA
<213> ORGANISM: Unknown
<220> FEATURE:
<223> OTHER INFORMATION: Primer

<400> SEQUENCE: 68
aaatcaccat accaactcgc gtc        23

<210> SEQ ID NO 69
<211> LENGTH: 67
<212> TYPE: DNA
<213> ORGANISM: Unknown
<220> FEATURE:
<223> OTHER INFORMATION: Primer

<400> SEQUENCE: 69
gatctgaggt tgtagaagac tcggacgata cacatgcacc gtcggtgcag tcgtaatcca        60
gtcccga        67

<210> SEQ ID NO 70
<211> LENGTH: 69
<212> TYPE: DNA
<213> ORGANISM: Unknown
<220> FEATURE:
<223> OTHER INFORMATION: Primer

```
<400> SEQUENCE: 70
gatcgctagt tattgctcac gggctagcaa aatagcgctg tcctcgggac tggattacga      60
ctgcaccga                                                              69

<210> SEQ ID NO 71
<211> LENGTH: 156
<212> TYPE: DNA
<213> ORGANISM: Unknown
<220> FEATURE:
<223> OTHER INFORMATION: Primer

<400> SEQUENCE: 71
gatctgaggt tgtagaagac tcggacgata cacatgcacc gtcggtgcag tcgtaatcca      60
gtcccgatct cagagcgttt tcgctctgag atcggtgcag tcgtaatcca gtcccgagga     120
cagcgctatt ttgctagccc gtgagcaata actagc                               156

<210> SEQ ID NO 72
<211> LENGTH: 71
<212> TYPE: DNA
<213> ORGANISM: Unknown
<220> FEATURE:
<223> OTHER INFORMATION: Primer

<400> SEQUENCE: 72
gatctgaggt tgtagaagac tcggacgata cacatgcacc gtcggtgcag tcgtaatcca      60
gtcccgatct c                                                           71

<210> SEQ ID NO 73
<211> LENGTH: 14
<212> TYPE: DNA
<213> ORGANISM: Unknown
<220> FEATURE:
<223> OTHER INFORMATION: Primer

<400> SEQUENCE: 73
cttctacaac ctca                                                        14

<210> SEQ ID NO 74
<211> LENGTH: 23
<212> TYPE: DNA
<213> ORGANISM: Unknown
<220> FEATURE:
<223> OTHER INFORMATION: Primer

<400> SEQUENCE: 74
cggtgcatgt gtatcgtccg agt                                              23

<210> SEQ ID NO 75
<211> LENGTH: 46
<212> TYPE: DNA
<213> ORGANISM: Unknown
<220> FEATURE:
<223> OTHER INFORMATION: Primer

<400> SEQUENCE: 75
agagcgtttt cgctctgaga tcgggactgg attacgactg caccga                    46

<210> SEQ ID NO 76
<211> LENGTH: 158
<212> TYPE: DNA
<213> ORGANISM: Unknown
<220> FEATURE:
```

<223> OTHER INFORMATION: Primer

<400> SEQUENCE: 76
gatcgctagt tattgctcac gggctagcaa aatagcgctg tcctcgggac tggattacga      60
ctgcaccgat ctcagagcgt tttcgctctg agatcggtgc agtcgtaatc cagtcccgag     120
gacagcgcta ttttgctagc ccgtgagcaa taactagc                             158

<210> SEQ ID NO 77
<211> LENGTH: 73
<212> TYPE: DNA
<213> ORGANISM: Unknown
<220> FEATURE:
<223> OTHER INFORMATION: Primer

<400> SEQUENCE: 77
gatcgctagt tattgctcac gggctagcaa aatagcgctg tcctcgggac tggattacga      60
ctgcaccgat ctc                                                        73

<210> SEQ ID NO 78
<211> LENGTH: 13
<212> TYPE: DNA
<213> ORGANISM: Unknown
<220> FEATURE:
<223> OTHER INFORMATION: Primer

<400> SEQUENCE: 78
gagcaatact agc                                                        13

<210> SEQ ID NO 79
<211> LENGTH: 25
<212> TYPE: DNA
<213> ORGANISM: Unknown
<220> FEATURE:
<223> OTHER INFORMATION: Primer

<400> SEQUENCE: 79
ggacagcgct attttgctag cccgt                                           25

<210> SEQ ID NO 80
<211> LENGTH: 46
<212> TYPE: DNA
<213> ORGANISM: Unknown
<220> FEATURE:
<223> OTHER INFORMATION: Primer

<400> SEQUENCE: 80
agagcgtttt cgctctgaga tcggtgcagt cgtaatccag tcccga                    46

<210> SEQ ID NO 81
<211> LENGTH: 59
<212> TYPE: DNA
<213> ORGANISM: Unknown
<220> FEATURE:
<223> OTHER INFORMATION: Primer

<400> SEQUENCE: 81
gatctgaggt tgttgaagac tcggacgata cacacgctgg gttgaggaag tcgtaaata      59

<210> SEQ ID NO 82
<211> LENGTH: 14
<212> TYPE: DNA
<213> ORGANISM: Unknown
<220> FEATURE:
<223> OTHER INFORMATION: Primer

<400> SEQUENCE: 82
cttcaacaac ctca                                                    14

<210> SEQ ID NO 83
<211> LENGTH: 24
<212> TYPE: DNA
<213> ORGANISM: Unknown
<220> FEATURE:
<223> OTHER INFORMATION: Primer

<400> SEQUENCE: 83
tcgtccgagt cttcaacaac ctca                                         24

<210> SEQ ID NO 84
<211> LENGTH: 28
<212> TYPE: DNA
<213> ORGANISM: Unknown
<220> FEATURE:
<223> OTHER INFORMATION: Primer

<400> SEQUENCE: 84
tatttacgac ttcctcaacc cagcgtgt                                     28

<210> SEQ ID NO 85
<211> LENGTH: 60
<212> TYPE: DNA
<213> ORGANISM: Unknown
<220> FEATURE:
<223> OTHER INFORMATION: Primer

<400> SEQUENCE: 85
gatcgctagt tattgctgtt gggatggtta tttatttacg acttcctcaa cccagcgtgt  60

<210> SEQ ID NO 86
<211> LENGTH: 14
<212> TYPE: DNA
<213> ORGANISM: Unknown
<220> FEATURE:
<223> OTHER INFORMATION: Primer

<400> SEQUENCE: 86
cagcaataac tagc                                                    14

<210> SEQ ID NO 87
<211> LENGTH: 25
<212> TYPE: DNA
<213> ORGANISM: Unknown
<220> FEATURE:
<223> OTHER INFORMATION: Primer

<400> SEQUENCE: 87
aaccatccca acagcaataa ctagc                                        25

<210> SEQ ID NO 88
<211> LENGTH: 28
<212> TYPE: DNA
<213> ORGANISM: Unknown
<220> FEATURE:
<223> OTHER INFORMATION: Primer

<400> SEQUENCE: 88
acacgctggg ttgaggaagt cgtaaata                                     28

<210> SEQ ID NO 89

```
<211> LENGTH: 60
<212> TYPE: DNA
<213> ORGANISM: Unknown
<220> FEATURE:
<223> OTHER INFORMATION: Primer

<400> SEQUENCE: 89
gatctgaggt tgttgaagac acgctgggtt gaggaagtcg taaataaata accatcccaa    60

<210> SEQ ID NO 90
<211> LENGTH: 14
<212> TYPE: DNA
<213> ORGANISM: Unknown
<220> FEATURE:
<223> OTHER INFORMATION: Primer

<400> SEQUENCE: 90
ttgggatggt tatt                                                      14

<210> SEQ ID NO 91
<211> LENGTH: 59
<212> TYPE: DNA
<213> ORGANISM: Unknown
<220> FEATURE:
<223> OTHER INFORMATION: Primer

<400> SEQUENCE: 91
gatctgaggt tgttgaagac tcggacgata cacacgctgg gttgaggaag tcgtaaata     59

<210> SEQ ID NO 92
<211> LENGTH: 14
<212> TYPE: DNA
<213> ORGANISM: Unknown
<220> FEATURE:
<223> OTHER INFORMATION: Primer

<400> SEQUENCE: 92
cttcaacaac ctca                                                      14

<210> SEQ ID NO 93
<211> LENGTH: 24
<212> TYPE: DNA
<213> ORGANISM: Unknown
<220> FEATURE:
<223> OTHER INFORMATION: Primer

<400> SEQUENCE: 93
tcgtccgagt cttcaacaac ctca                                           24

<210> SEQ ID NO 94
<211> LENGTH: 28
<212> TYPE: DNA
<213> ORGANISM: Unknown
<220> FEATURE:
<223> OTHER INFORMATION: Primer

<400> SEQUENCE: 94
tatttacgac ttcctcaacc cagcgtgt                                       28

<210> SEQ ID NO 95
<211> LENGTH: 60
<212> TYPE: DNA
<213> ORGANISM: Unknown
<220> FEATURE:
<223> OTHER INFORMATION: Primer

<400> SEQUENCE: 95
```

```
gatcgctagt tattgctgtt gggatggtta tttatttacg acttcctcaa cccagcgtgt    60
```

<210> SEQ ID NO 96
<211> LENGTH: 14
<212> TYPE: DNA
<213> ORGANISM: Unknown
<220> FEATURE:
<223> OTHER INFORMATION: Primer

<400> SEQUENCE: 96

```
cagcaataac tagc                                                      14
```

<210> SEQ ID NO 97
<211> LENGTH: 25
<212> TYPE: DNA
<213> ORGANISM: Unknown
<220> FEATURE:
<223> OTHER INFORMATION: Primer

<400> SEQUENCE: 97

```
aaccatccca acagcaataa ctagc                                          25
```

<210> SEQ ID NO 98
<211> LENGTH: 28
<212> TYPE: DNA
<213> ORGANISM: Unknown
<220> FEATURE:
<223> OTHER INFORMATION: Primer

<400> SEQUENCE: 98

```
acacgctggg ttgaggaagt cgtaaata                                       28
```

<210> SEQ ID NO 99
<211> LENGTH: 60
<212> TYPE: DNA
<213> ORGANISM: Unknown
<220> FEATURE:
<223> OTHER INFORMATION: Primer

<400> SEQUENCE: 99

```
gatctgaggt tgttgaagac acgctgggtt gaggaagtcg taaataaata accatcccaa    60
```

<210> SEQ ID NO 100
<211> LENGTH: 14
<212> TYPE: DNA
<213> ORGANISM: Unknown
<220> FEATURE:
<223> OTHER INFORMATION: Primer

<400> SEQUENCE: 100

```
ttgggatggt tatt                                                      14
```

<210> SEQ ID NO 101
<211> LENGTH: 18
<212> TYPE: DNA
<213> ORGANISM: Unknown
<220> FEATURE:
<223> OTHER INFORMATION: Primer

<400> SEQUENCE: 101

```
aggttgtaga agactcgg                                                  18
```

<210> SEQ ID NO 102
<211> LENGTH: 18
<212> TYPE: DNA

```
<213> ORGANISM: Unknown
<220> FEATURE:
<223> OTHER INFORMATION: Primer

<400> SEQUENCE: 102
gctagttatt gctcacgg                                                  18

<210> SEQ ID NO 103
<211> LENGTH: 18
<212> TYPE: DNA
<213> ORGANISM: Unknown
<220> FEATURE:
<223> OTHER INFORMATION: Primer

<400> SEQUENCE: 103
gcatcgcttg aattgtcc                                                  18

<210> SEQ ID NO 104
<211> LENGTH: 18
<212> TYPE: DNA
<213> ORGANISM: Unknown
<220> FEATURE:
<223> OTHER INFORMATION: Primer

<400> SEQUENCE: 104
tgctctcgga atatcaat                                                  18

<210> SEQ ID NO 105
<211> LENGTH: 18
<212> TYPE: DNA
<213> ORGANISM: Unknown
<220> FEATURE:
<223> OTHER INFORMATION: Primer

<400> SEQUENCE: 105
gcatcgcttg aattgtcc                                                  18

<210> SEQ ID NO 106
<211> LENGTH: 18
<212> TYPE: DNA
<213> ORGANISM: Unknown
<220> FEATURE:
<223> OTHER INFORMATION: Primer

<400> SEQUENCE: 106
atattcaggc cagttatc                                                  18

<210> SEQ ID NO 107
<211> LENGTH: 21
<212> TYPE: DNA
<213> ORGANISM: Unknown
<220> FEATURE:
<223> OTHER INFORMATION: Primer

<400> SEQUENCE: 107
cttacaccgg cgaagtgaaa g                                              21

<210> SEQ ID NO 108
<211> LENGTH: 25
<212> TYPE: DNA
<213> ORGANISM: Unknown
<220> FEATURE:
<223> OTHER INFORMATION: Primer

<400> SEQUENCE: 108
cgctgccgga gctgttagac aattc                                          25
```

```
<210> SEQ ID NO 109
<211> LENGTH: 25
<212> TYPE: DNA
<213> ORGANISM: Unknown
<220> FEATURE:
<223> OTHER INFORMATION: Primer

<400> SEQUENCE: 109
gcctgcaagc cggtgtagac atcac                                              25

<210> SEQ ID NO 110
<211> LENGTH: 21
<212> TYPE: DNA
<213> ORGANISM: Unknown
<220> FEATURE:
<223> OTHER INFORMATION: Primer

<400> SEQUENCE: 110
ctgcaggcca gcgagacaga t                                                  21

<210> SEQ ID NO 111
<211> LENGTH: 23
<212> TYPE: DNA
<213> ORGANISM: Unknown
<220> FEATURE:
<223> OTHER INFORMATION: Primer

<400> SEQUENCE: 111
gttgtggcct tccagtaagg tcc                                                23

<210> SEQ ID NO 112
<211> LENGTH: 27
<212> TYPE: DNA
<213> ORGANISM: Unknown
<220> FEATURE:
<223> OTHER INFORMATION: Primer

<400> SEQUENCE: 112
gcaaaatagc tggctggcag gtgtagg                                            27

<210> SEQ ID NO 113
<211> LENGTH: 21
<212> TYPE: DNA
<213> ORGANISM: Unknown
<220> FEATURE:
<223> OTHER INFORMATION: Primer

<400> SEQUENCE: 113
tagggcggca tcaggtaata c                                                  21

<210> SEQ ID NO 114
<211> LENGTH: 23
<212> TYPE: DNA
<213> ORGANISM: Unknown
<220> FEATURE:
<223> OTHER INFORMATION: Primer

<400> SEQUENCE: 114
tgccgccgtt cgcatccata cca                                                23

<210> SEQ ID NO 115
<211> LENGTH: 26
<212> TYPE: DNA
<213> ORGANISM: Unknown
<220> FEATURE:
```

<223> OTHER INFORMATION: Primer

<400> SEQUENCE: 115
ttccctgcct ggtcgccgta tctgtg    26

<210> SEQ ID NO 116
<211> LENGTH: 21
<212> TYPE: DNA
<213> ORGANISM: Unknown
<220> FEATURE:
<223> OTHER INFORMATION: Primer

<400> SEQUENCE: 116
tgaaggatac ggaagcagaa a    21

<210> SEQ ID NO 117
<211> LENGTH: 25
<212> TYPE: DNA
<213> ORGANISM: Unknown
<220> FEATURE:
<223> OTHER INFORMATION: Primer

<400> SEQUENCE: 117
gccattgctg attgcccacc gacaa    25

<210> SEQ ID NO 118
<211> LENGTH: 26
<212> TYPE: DNA
<213> ORGANISM: Unknown
<220> FEATURE:
<223> OTHER INFORMATION: Primer

<400> SEQUENCE: 118
ctctatcgct cggcctaagt ctttac    26

<210> SEQ ID NO 119
<211> LENGTH: 21
<212> TYPE: DNA
<213> ORGANISM: Unknown
<220> FEATURE:
<223> OTHER INFORMATION: Primer

<400> SEQUENCE: 119
gcggtcggcg tggataaagt a    21

<210> SEQ ID NO 120
<211> LENGTH: 23
<212> TYPE: DNA
<213> ORGANISM: Unknown
<220> FEATURE:
<223> OTHER INFORMATION: Primer

<400> SEQUENCE: 120
gtgagcggga tgaacgaacc tta    23

<210> SEQ ID NO 121
<211> LENGTH: 26
<212> TYPE: DNA
<213> ORGANISM: Unknown
<220> FEATURE:
<223> OTHER INFORMATION: Primer

<400> SEQUENCE: 121
ctgcgccagg gcttccagac attgtg    26

METHOD OF PRODUCING A DNA LIBRARY USING POSITIONAL AMPLIFICATION BASED ON THE USE OF ADAPTORS AND NICK TRANSLATION

This application claims priority to the U.S. Provisional Application Serial No. 60/206,095 filed May 20, 2000.

The government owns rights in the present invention pursuant to grant number MCB 9514196 from the National Science Foundation.

BACKGROUND OF THE INVENTION

1. Field of the Invention

The present invention relates generally to the fields of molecular biology and biochemistry. Specifically, it concerns means for the construction of DNA libraries facilitating amplifying and analyzing DNA. More specifically, the present invention concerns positional amplification of DNA by nick translation methods.

2. Description of Related Art

A. DNA Preparation Using in Vivo and in Vitro Amplification and Multiplexed Versions thereof Because the amount of any specific DNA molecule that can be isolated from even a large number of cells is usually very small, the only practical methods to prepare enough DNA molecules for most applications involve amplification of specific DNA molecules in vivo or in vitro. There are basically six general methods important for manipulating DNA for analysis: 1) in vivo cloning of unique fragments of DNA; 2) in vitro amplification of unique fragments of DNA; 3) in vivo cloning of random libraries (mixtures) of DNA fragments; 4) in vitro preparation of random libraries of DNA fragments; 5) in vivo cloning of ordered libraries of DNA; and 6) in vitro preparation of ordered libraries of DNA. The beneficial effect of amplifying mixtures of DNA is that it facilitates analysis of large pieces of DNA (e.g., chromosomes) by creating libraries of molecule that are small enough to be analyzed by existing techniques. For example the largest molecule that can be subjected to DNA sequencing methods is less than 2000 bases long, which is many orders of magnitude shorter than single chromosomes of organisms. Although short molecules can be analyzed, considerable effort is required to assemble the information from the analysis of the short molecules into a description of the larger piece of DNA.

1. In Vivo Cloning of Unique DNA

Unique-sequence source DNA molecules can be amplified by separating them from other molecules (e.g., by electrophoresis), ligating them into an autonomously replicating genetic element (e.g., a bacterial plasmid), transfecting a host cell with the recombinant genetic element, and growing a clone of a single transfected host cell to produce many copies of the genetic element having the insert with the same unique sequence as the source DNA (Sambrook, et al., 1989).

2. In Vitro Amplification of Unique DNA

There are many methods designed to amplify DNA in vitro. Usually these methods are used to prepare unique DNA molecules from a complex mixture, e.g., genomic DNA or an artificial chromosome. Alternatively, a restricted set of molecules can be prepared as a library that represents a subset of sequences in the complex mixture. These amplification methods include PCR, rolling circle amplification, and strand displacement (Walker, et al. 1996a; Walker, et al. 1996b; U.S. Pat. No. 5,648,213; U.S. Pat. No. 6,124,120).

The polymerase chain reaction (PCR) can be used to amplify specific regions of DNA between two known sequences (U.S. Pat. No. 4,683,195, U.S. Pat. No. 4,683,202; Frohman et al., 1995). PCR involves the repetition of a cycle consisting of denaturation of the source (template) DNA, hybridization of two oligonucleotide primers to known sequences flanking the region to the amplified, primer extension using a DNA polymerase to synthesize strands complementary to the DNA region located between the two primer sites. Because the products of one cycle of amplification serve as source DNA for succeeding cycles, the amplification is exponential. PCR can synthesize large numbers of specific molecules quickly and inexpensively.

The major disadvantages of the PCR method to amplify DNA are that 1) information about two flanking sequences must be known in order to specify the sequences of the primers; 2) synthesis of primers is expensive; 3) the level of amplification achieved depends strongly on the primer sequences, source DNA sequence, and the molecular weight of the amplified DNA; and 4) the length of amplified DNA is usually limited to less than 5 kb, although "long-distance" PCR (Cheng, 1994) allows molecules as long as 20 kb to be amplified.

"One-sided PCR" techniques are able to amplify unknown DNA adjacent to one known sequence. These techniques can be divided into 4 categories: a) ligation-mediated PCR, facilitated by addition of a universal adaptor sequence to a terminus usually created by digestion with a restriction endonuclease; b) universal primer-mediated PCR, facilitated by a primer extension reaction initiated at arbitrary sites c) terminal transferase-mediated PCR, facilitated by addition of a homonucleotide "tail" to the 3' end of DNA fragments; and d) inverse PCR, facilitated by circularization of the template molecules. These techniques can be used to amplify successive regions along a large DNA template in a process sometimes called "chromosome walking."

Ligation-mediated PCR is practiced in many forms. Rosenthal et al. (1990) outlined the basic process of amplifying an unknown region of DNA immediately adjacent to a known sequence located near the end of a restriction fragment. Reiley et al. (1990) used primers that were not exactly complementary with the adaptors in order to suppress amplification of molecules that did not have a specific priming site. Jones (1993) and Siebert (1995; U.S. Pat. No. 5,565,340.) used long universal primers that formed intrastrand "panhandle" structures that suppressed PCR of molecules having two universal adaptors. Arnold (1994) used "vectorette" primers having unpaired central regions to increase the specificity of one-sided PCR. Macrae and Brenner (1994) amplified short inserts from a Fugu genomic clone library using nested primers from a specific sequence and from vector sequences. Lin et al. (1995) ligated an adaptor to restriction fragment ends that had an overhanging 5' end and employed hot-start PCR with a single universal anchor primer and nested specific-site primers to specifically amplify human sequences. Liao et al. (1997) used two specific site primers and 2 universal adaptors, one of which had a blocked 3' end to reduce non-specific background, to amplify zebrafish promoters. Devon et al. (1995) used "splinkerette-vectorette" adaptors with special secondary structure in order to decrease non-specific amplification of molecules with two universal sequences during ligation-mediated PCR. Padegimas and Reichert (1998) used phosphorothioate-blocked oligonucleotides and exoIII digestion to remove the unligated and partially ligated molecules from the reactions before performing PCR, in order to increase the specificity of amplification of maize sequences. Zhang and Gurr (2000) used ligation-mediated hot-start PCR of restriction fragments using nested primers in order to amplify up to 6 kb of a fungal genome. The large amplicons were subsequently directly sequenced using primer extension.

To increase the specificity of ligation-mediated PCR products, many methods have been used to "index" the amplification process by selection for specific sequences adjacent to one or both termini (e.g., Smith, 1992; Unrau, 1994; Guilfoyle, 1997; U.S. Pat. No. 5,508,169).

One-sided PCR can also be achieved by direct amplification using a combination of unique and non-unique primers. Harrison et al. (1997) performed one-sided PCR using a degenerate oligonucleotide primer that was complementary to an unknown sequence and three nested primers complementary to a known sequence in order to sequence transgenes in mouse cells. U.S. Pat. No. 5,994,058 specifies using a unique PCR primer and a second, partially degenerate PCR primer to achieve one-sided PCR. Weber et al. (1998) used direct PCR of genomic DNA with nested primers from a known sequence and 1–4 primers complementary to frequent restriction sites. This technique does not require restriction digestion and ligation of adaptors to the ends of restriction fragments, Terminal transferase can also be used in one-sided PCR. Cormack and Somssich (1997) were able to amplify the termini of genomic DNA fragments using a method called RAGE (rapid amplification of genome ends) by a) restricting the genome with one or more restriction enzymes; b) denaturing the restricted DNA; c) providing a 3' polythymidine tail using terminal transferase; and d) performing two rounds of PCR using nested primers complementary to a known sequence as well as the adaptor. Rudi et al. (1999) used terminal transferase to achieve chromosome walking in bacteria using a method of one-sided PCR that is independent of restriction digestion by a) denaturation of the template DNA; b) linear amplification using a primer complementary to a known sequence; c) addition of a poly C "tail" to the 3' end of the single-stranded products of linear amplification using a reaction catalyzed by terminal transferase; and d) PCR amplification of the products using a second primer within the known sequence and a poly-G primer complementary to the poly-C tail in the unknown region. The products amplified by Rudi (1999) have a very broad size distribution, probably caused by a broad distribution of lengths of the linearly-amplified DNA molecules.

RNA polymerase can also be used to achieve one-sided amplification of DNA. U.S. Pat. No. 6,027,913 shows how one-sided PCR can be combined with transcription with RNA polymerase to amplify and sequence regions of DNA with only one known sequence.

Inverse PCR (Ochman et al., 1988) is another method to amplify DNA based on knowledge of a single DNA sequence. The template for inverse PCR is a circular molecule of DNA created by a complete restriction digestion, which contains a small region of known sequence as well as adjacent regions of unknown sequence. The oligonucleotide primers are oriented such that during PCR they give rise to primer extention products that extend way from the known sequence. This "inside-out" PCR results in linear DNA products with known sequences at the termini.

The disadvantages of all "one-sided PCR" methods is that a) the length of the products are restricted by the limitation of PCR (normally about 2 kb, but with special reagents up to 50 kb); b) whenever the products are single DNA molecules longer than 1 kb they are too long to directly sequence; c) in ligation-mediated PCR the amplicon lengths are very unpredictable due to random distances between the universal priming site and the specific priming site(s), resulting in some products that are sometimes too short to walk significant distance, some which are preferentially amplified due to small size, and some that are too long to amplify and analyze; and d) in methods that use terminal transferase to add a polynucleotide tail to the end of a primer extention product, there is great heterogeneity in the length of the amplicons due to sequence-dependent differences in the rate of primer extension.

Strand displacement amplification (Walker, et al. 1996a; Walker, et al. 1996b; U.S. Pat. No. 5,648,213; U.S. Pat. No. 6,124,120) is a method to amplify one of more termini of DNA fragments using an isothermal strand displacement reaction. The method is initiated at a nick near the terminus of a double-stranded DNA molecule, usually generated by a restriction enzyme, followed by a polymerization reaction by a DNA polymerase that is able to displace the strand complementary to the template strand. Linear amplification of the complementary strand is achieved by reusing the template multiple times by nicking each product strand as it is synthesized. The products are strands with 5' ends at a unique site and 3' ends that are various distances from the 5' ends. The extent of the strand displacement reaction is not controlled and therefore the lengths of the product strands are not uniform. The polymerase used for strand displacement amplification does not have a 5' exonuclease activity.

Rolling circle amplification (U.S. Pat. No. 5,648,245) is a method to increase the effectiveness of the strand displacement reaction by using a circular template. The polymerase, which does not have a 5' exonuclease activity, makes multiple copies of the information on the circular template as it makes multiple continuous cycles around the template. The length of the product is very large—typically too large to be directly sequenced. Additional amplification is achieved if a second strand displacement primer is added to the reaction to used the first strand displacement product as a template.

3. In Vivo Cloning of DNA of Random Libraries

Libraries are collections of small DNA molecules that represent all parts of a larger DNA molecule or collection of DNA molecules (Primrose, 1998; Cantor and Smith, 1999). Libraries can be used for analytical and preparative purposes. Genomic clone libraries are the collection of bacterial clones containing fragments of genomic DNA. cDNA clone libraries are collections of clones derived from the mRNA molecules in a tissue.

Cloning of non-specific DNA is commonly used to separate and amplify DNA for analysis. DNA from an entire genome, one chromosome, a virus, or a bacterial plasmid is fragmented by a suitable method (e.g., hydrodynamic shearing or digestion with restriction enzymes), ligated into a special region of a bacterial plasmid or other cloning vector, transfected into competent cells, amplified as a part of a plasmid or chromosome during proliferation of the cells, and harvested from the cell culture. Critical to the specificity of this technique is the fact that the mixture of cells carrying different DNA inserts can be diluted and aliquoted such that some of the aliquots, whether on a surface or in a volume of solution, contain a single transfected cell containing a unique fragment of DNA. Proliferation of this single cell (in vivo cloning) amplifies this unique fragment of DNA so that it can be analyzed. This "shotgun" cloning method is used very frequently, because: 1) it is inexpensive; 2) it produces very pure sequences that are usually faithful copies of the source DNA; 3) it can be used in conjunction with clone screening techniques to create an unlimited amount of specific-sequence DNA; 4) it allows simultaneous amplification of many different sequences; 5) it can be used to amplify DNA as large as 1,000,000 bp long; and 6) the cloned DNA can be directly used for sequencing and other purposes.

a. Multiplex Cloning

Cloning is inexpensive, because many pieces of DNA can be simultaneously transfected into host cells. The general term for this process of mixing a number of different entities (e.g., electronic signals or molecules) is "multiplexing," and is a common strategy for increasing the number of signals or molecules that can be processed simultaneously and subsequently separated to recover the information about the individual signals or molecules. In the case of conventional cloning the recovery process involves diluting the bacterial culture such that an aliquot contains a single bacterium carrying a single plasmid, allowing the bacterium to multiply to create many copies of the original plasmid, and isolating the cloned DNA for further analysis.

The principle of multiplexing different molecules in the same transfection experiment is critical to the economy of the cloning method. However, after the transfection each clone must be grown separately and the DNA isolated separately for analysis. These steps, especially the DNA isolation step, are costly and time consuming. Several attempts have been made to multiplex steps after cloning, whereby hundreds of clones can be combined during the steps of DNA isolation and analysis and the characteristics of the individual DNA molecules recovered later. In one version of multiplex cloning the DNA fragments are separated into a number of pools (e.g., one hundred pools). Each pool is ligated into a different vector, possessing a nucleic acid tag with a unique sequence, and transfected into the bacteria. One clone from each transfection pool is combined with one clone from each of the other transfection pools in order to create a mixture of bacteria having a mixture of inserted sequences, where each specific inserted sequence is tagged with a unique vector sequence, and therefore can be identified by hybridization to the nucleic acid tag. This mixture of cloned DNA molecules can be subsequently separated and subjected to any enzymatic, chemical, or physical processes for analysis such as treatment with polymerase or size separation by electrophoresis. The information about individual molecules can be recovered by detection of the nucleic acid tag sequences by hybridization, PCR amplification, or DNA sequencing. Church has shown methods and compositions to use multiplex cloning to sequence DNA molecules by pooling clones tagged with different labels during the steps of DNA isolation, sequencing reactions, and electrophoretic separation of denatured DNA strands (U.S. Pat. Nos. 4,942,124 and 5,149,625). The tags are added to the DNA as parts of the vector DNA sequences. The tags used can be detected using oligonucleotides labeled with radioactivity, fluorescent groups, or volatile mass labels (Cantor and Smith, 1999; U.S. Pat. Nos. 4,942,124; 5,149,625; and 5,112,736; Richterich and Church, (1993)). A later patent was directed to a technique whereby the tag sequences are ligated to the DNA fragments before cloning using a universal vector (U.S. Pat. No. 5,714,318). Another patent specifies method whereby the tag sequences added before transfection are amplified using PCR after electrophoretic separation of the denatured DNA (PCT WO 98/15644).

b. Disadvantages

The disadvantage of preparing DNA by amplifying random fragments of DNA is that considerable effort is necessary to assemble the information within the short fragments into a description of the original, source DNA molecule. Nevertheless, amplified short DNA fragments are commonly used for many applications, including sequencing by the technique called "shotgun sequencing." Shotgun sequencing involves sequencing one or both ends of small DNA fragments that have been cloned from randomly-fragmented large pieces of DNA. During the sequencing of many such random fragments of DNA, overlapping sequences are identified from those clones that by chance contain redundant sequence information. As more and more fragments are sequenced more overlaps can be found from contiguous regions (contigs), and the regions that are not represented become smaller and less frequent. However, even after sequencing enough fragments that the average region has been sequenced 5–10 times, there will still be gaps between contigs due to statistical sampling effects and to systematic under-representation of some sequences during cloning or PCR amplification (ref). Thus the disadvantage of sequencing random fragments of DNA is that 1) a 5–10 fold excess of DNA must be isolated, subjected to sequencing reactions, and analyzed before having large contiguous sequenced regions; and 2) there are still numerous gaps in the sequence that must be filled by expensive and time-consuming steps.

4. In Vitro Preparation of DNA as Random Libraries

DNA libraries can be formed in vitro and subjected to various selection steps to recover information about specific sequences. In vitro libraries are rarely used in genomics, because the methods that exist for creating such libraries do not offer advantages over cloned libraries. In particular, the methods used to amplify the in vitro libraries are not able to amplify all the DNA in an unbiased manner, because of the size and sequence dependence of amplification efficiency. PCT WO 00/18960 describes how different methods of DNA amplification can be used to create a library of DNA molecules representing a specific subset of the sequences within the genome for purposes of detecting genetic polymorphisms. "Random-prime PCR" (U.S. Pat. No. 5,043,272; U.S. Pat. No. 5,487,985) "random-prime strand displacement" (U.S. Pat. No. 6,124,120) and "AFLP" (U.S. Pat. No. 6,045,994) are three examples of methods to create libraries that represent subsets of complex mixtures of DNA molecules.

Single-molecule PCR can be used to amplify individual randomly-fragmented DNA molecules (Lukyanov et al., 1996). In one method, the source DNA is first fragmented into molecules usually less than 10,000 bp in size, ligated to adaptor oligonucleotides, and extensively diluted and aliquoted into separate fractions such that the fractions often contain only a single molecule. PCR amplification of a fraction containing a single molecule creates a very large number of molecules identical to one of the original fragments. If the molecules are randomly fragmented, the amplified fractions represent DNA from random positions within the source DNA.

WO0015779A2 describes how a specific sequence can be amplified from a library of circular molecules with random genomic inserts using rolling circle amplification.

5. Direct in Vivo Cloning of Ordered Libraries of DNA

Directed cloning is a procedure to clone DNA from different parts of a larger piece of DNA, usually for the purpose of sequencing DNA from a different positions along the source DNA. Methods to clone DNA with "nested deletions" have been used to make "ordered libraries" of clones that have DNA starting at different regions along a long piece of source DNA. In one version, one end of the source DNA is digested with one or more exonuclease activities to delete part of the sequence (McCombie et al., 1991; U.S. Pat. No. 4,843,003). By controlling the extent of exonuclease digestion, the average amount of the deletion can be controlled. The DNA molecules are subsequently separated based on size and cloned. By cloning molecules with different molecular weights, many copies of identical DNA plasmids are produced that have inserts ending at controlled positions within the source DNA. Transposon insertion (Berg et al. 1994) is also used to clone different regions of source DNA by facilitating priming or cleavage at random positions in the plasmids. The size separation and recloning steps make both of these methods labor intensive and slow. They are generally limited to covering regions less than 10 kb in size and cannot be used directly on genomic DNA but rather cloned DNA molecules. No in vivo methods are known are known to directly create ordered libraries of genomic DNA.

6. Direct In Vitro Preparation of Ordered Libraries of DNA

Ordered libraries have not been frequently created in vitro. Hagiwara (1996) used one-sided PCR to create an ordered library of PCR products that was used to sequence about 14 kb of a cosmid. The cosmids were first digested with multiple restriction enzymes, followed by ligation of vectorette adaptors to the products, PCR amplification of the products using primers complementary to a unique sequence in the cosmid and to the adaptor, size separation of the amplified DNA to establish the order of the restriction sites, and sequencing of the ordered PCR products. Because the non-uniform spacing of the restriction sites, 2 kb of the 16 kb region were not sequenced. This method required substantial effort to produce and order the PCR products for the job of sequencing cloned DNA. No in vitro methods are known to directly create ordered genomic libraries of DNA.

B. DNA Physical Mapping to Assemble Ordered Clones

Because of the great difficulty in direct production of ordered DNA libraries, there is a need to reorganize libraries of randomly cloned DNA molecules into ordered libraries where the clones are arranged according to position in the genome (Primrose, 1998; Cantor and Smith, 1999). Some of the purposes for creating an ordered library are 1) to compare overlapping clones to detect defects (e.g., deletions) in some of the clones; 2) to decide which clones should be used to determine the underlying DNA sequence with the least redundancy in sequencing effort; 3) to localize genetic features within the genome; 4) to access different regions of the genome on the basis of their relationship to the genetic map or proximity to another region; and 5) to compare the structure of the genomes of different individuals and different species. There are four basic methods for creating ordered libraries of clones: 1) hybridization to determine sequence homology among different clones; 2) fluorescent in situ hybridization (FISH); 3) restriction analysis; and 4) STS mapping.

1. Mapping by Hybridization

The first method usually involves hybridization of one clone or other identifiable sequence to all other clones in a library. Those clones that hybridize contain overlapping sequences. This method is useful for locating clones that overlap a common site (e.g., a specific gene) in the genome, but is too laborious to create an ordered library of an entire genome. In addition many organisms have large amounts of repetitive DNA that can give false indications of overlap between two regions. The resolution of the hybridization techniques is only as good as the distance between known sequences of DNA.

2. Mapping by FISH

The FISH method allows a particular sequence or limited set of sequences to be localized along a chromosome by hybridization of a fluorescently-labeled probe with a spread of intact chromosomes, followed by light-microscopic localization of the fluorescence. This technique is also only of use to locate a specific sequence or small number of sequences, rather than to create a physical map of the entire genome or an ordered library representing the entire genome. The resolution of the light microscope limits the resolution of FISH to about 1,000,000 bp. To map a single-copy sequence, the FISH probe usually needs to be about 10,000 long.

3. Mapping by Restriction Digestion

Mapping by restriction digestion is frequently used to determine overlaps between clones, thereby allowing ordered libraries of clones to be constructed. It involves assembly of a number of large clones into a contiguous region (contig) by analyzing the overlaps in the restriction patterns of related clones. This method is insensitive to the presence of repetitive DNA. The products of a complete or partial restriction digestion of every clone are size separated by electrophoresis and the molecular weights of the fragments analyzed by computer to find correlated sequences in different clones. The information from the restriction patterns produced by five or more restriction enzymes is usually adequate to determine not only which clones overlap, but also the extent of overlap and whether some of the clones have deletions, additions, rearrangements, etc. Physical mapping of restriction sites is a very tedious process, because of the very large numbers of clones that have to be evaluated. For example, >300,000 BAC clones of 100,000 bp length need to be analyzed to map the human genome. Using conventional techniques mapping two restriction sites would require at least 300,000 bacterial cultures and DNA isolations, as well as 600,000 restriction digestions and size separations.

4. Mapping by STS Amplification

Sequence tagged sites are sequences, often from the 3' untranslated portions of mRNA, that can be uniquely amplified in the genome. High-throughput methods employing sophisticated equipment have been devised to screen for the presence of tens of thousands of STSs in tens of thousands of clones. Two clones overlap to the extent that they share common STSs.

C. DNA Sequencing Reactions

DNA sequencing is the most important analytical tool for understanding the genetic basis of living systems. The process involves determining the positions of each of the four major nucleotide bases, adenine (A), cytosine (C), guanine (G), and thymine (T) along the DNA molecule(s) of an organism. Short sequences of DNA are usually determined by creating a nested set of DNA fragments that begin at a unique site and terminate at a plurality of positions comprised of a specific base. The fragments terminated at each of the four natural nucleic acid bases (A, T, G and C) are then separated according to molecular size in order to determine the positions of each of the four bases relative to the unique site. The pattern of fragment lengths caused by strands that terminate at a specific base is called a "sequencing ladder." The interpretation of base positions as the result of one experiment on a DNA molecule is called a "read." There are different methods of creating and separating the nested sets of terminated DNA molecules (Adams et al., 1994; Primrose, 1998; Cantor and Smith, 1999).

1. Maxim-Gilbert Method

The Maxim-Gilbert method involves degrading DNA at a specific base using chemical reagents. The DNA strands terminating at a particular base are denatured and electrophoresed to determine the positions of the particular base. The Maxim-Gilbert method involves dangerous chemicals, and is time- and labor-intensive. It is no longer used for most applications.

2. Sanger Method

The Sanger sequencing method is currently the most popular format for sequencing. It employs single-stranded DNA (ssDNA) created using special viruses like M13 or by denaturing double-stranded DNA (dsDNA). An oligonucleotide sequencing primer is hybridized to a unique site of the ssDNA and a DNA polymerase is used to synthesize a new strand complementary to the original strand using all four deoxyribonucleotide triphosphates (dATP, dCTP, dGTP, and dTTP) and small amounts of one or more dideoxyribonucleotide triphosphates (ddATP, ddCTP, ddGTP, and/or ddTTP), which cause termination of synthesis. The DNA is denatured and electrophoresed into a "ladder" of bands representing the distance of the termination site from the 5' end of the primer. If only one ddNTP (e.g., ddGTP) is used only those molecules that end with guanine will be detected in the ladder. By using ddNTPs with four different labels all four ddNTPs can be incorporated in the same polymerization reaction and the molecules ending with each of the four bases can be separately detected after electrophoresis in order to read the base sequence.

Sequencing DNA that is flanked by vector or PCR primer DNA of known sequence, can undergo Sanger termination reactions initiated from one end using a primer complementary to those known sequences. These sequencing primers are inexpensive, because the same primers can be used for DNA cloned into the same vector or PCR amplified using primers with common terminal sequences. Commonly-used electrophoretic techniques for separating the dideoxyribonucleotide-terminated DNA molecules are limited to resolving sequencing ladders shorter than 500–1000 bases. Therefore only the first 500–1000 nucleic acid bases can be "read" by this or any other method of sequencing the DNA. Sequencing DNA beyond the first 500–1000 bases requires special techniques.

3. Other Base-Specific Termination Methods

Other termination reactions have been proposed. One group of proposals involves substituting thiolated or boronated base analogs that resist exonuclease activity. After incorporation reactions very similar to Sanger reactions a 3' to 5' exonuclease is used to resect the synthesized strand to the point of the last base analog. These methods have no substantial advantage over the Sanger method.

Methods have been proposed to reduce the number of electrophoretic separations required to sequence large amounts of DNA. These include multiplex sequencing of large numbers of different molecules on the same electrophoretic device, by attaching unique tags to different molecules so that they can be separately detected. Commonly, different fluorescent dyes are used to multiplex up to 4 different types of DNA molecules in a single electrophoretic lane or capillary (U.S. Pat. No. 4,942,124). Less commonly, the DNA is tagged with large number of different nucleic acid sequences during cloning or PCR amplification, and detected by hybridization (U.S. Pat. No. 4,942,124) or by mass spectrometry (U.S. Pat. No. 4,942,124).

In principle, the sequence of a short fragment can be read by hybridizing different oligonucleotides with the unknown sequence and deciphering the information to reconstruct the sequence. This "sequencing by hybridization" is limited to fragments of DNA <50 bp in length. It is difficult to amplify such short pieces of DNA for sequencing. However, even if sequencing many random 50 bp pieces were possible, assembling the short, sometimes overlapping sequences into the complete sequence of a large piece of DNA would be impossible. The use of sequencing by hybridization is currently limited to resequencing, that is testing the sequence of regions that have already been sequenced.

D. Preparing DNA for Determining Long Sequences

Because it is currently very difficult to separate DNA molecules longer than 1000 bases with single-base resolution, special methods have been devised to sequence DNA regions within larger DNA molecules. The "primer walking" method initiates the Sanger reaction at sequence-specific sites within long DNA. However, most emphasis is on methods to amplify DNA in such a way that one of the ends originates from a specific position within the long DNA molecule.

1. Primer Walking

Once part of a sequence has been determined (e.g., the terminal 500 bases), a custom sequencing primer can be made that is complementary to the known part of the sequence, and used to prime a Sanger dideoxyribonucleotide termination reaction that extends further into the unknown region of the DNA. This procedure is called "primer walking." The requirement to synthesize a new oligonucleotide every 400–1000 bp makes this method expensive. The method is slow, because each step is done in series rather than in parallel. In addition, each new primer has a significant failure rate until optimum conditions are determined. Primer walking is primarily used to fill gaps in the sequence that have not been read after shotgun sequencing or to complete the sequencing of small DNA fragments <5,000 bp in length. However, WO 00/60121 addresses this problem using a single synthetic primer for PCR to genome walk to unknown sequences from a known sequence. The 5'-blocked primer anneals to the denatured template and is extended, followed by coupling to the extended product of a 3'-blocked oligonucleotide of known sequence, thereby creating a single stranded molecule having had only a single region of known target DNA sequence. By sequencing an amplified product from the extended product having the coupled 3'-blocked oligonucleotide, the process can be applied reiteratively to elucidate consecutive adjacent unknown sequences.

2. PCR Amplification

PCR can be used to amplify a specific region within a large DNA molecule. Because the PCR primers must be complementary to the DNA flanking the specific region, this method is usually used only to prepare DNA to "resequence" a region of DNA.

3. Nested Deletion and Transposon Insertion

As described above, cloning or PCR amplification of long DNA with nested deletions brought about by nuclease cleavage or transposon insertion enables ordered libraries of DNA to be created. When exonuclease is used to progressively digest one end of the DNA there is some control over the position of one end of the molecule. However the exonuclease activity cannot be controlled to give a narrow distribution in molecular weights, so typically the exonuclease-treated DNA is separated by electrophoresis to better select the position of the end of the DNA samples before cloning. Because transposon insertion is nearly random, clones containing inserted elements have to be screened before choosing which clones have the insertion at a specific internal site. The labor-intense steps of clone screening make these methods impractical except for DNA less than about 10 kb long.

4. Junction-Fragment DNA Probes for Preparing Ordered DNA Clones

Collins and Weissman have proposed to use "junction-fragment DNA probes and probe clusters" (U.S. Pat. No. 4,710,465) to fractionate large regions of chromosomes into ordered libraries of clones. That patent proposes to size fractionate genomic DNA fragments after partial restriction digestion, circularize the fragments in each size-fraction to form junctions between sequences separated by different physical distances in the genome, and then clone the junctions in each size fraction. By screening all the clones derived from each size-fraction using a hybridization probe from a known sequence, ordered libraries of clones could be created having sequences located different distances from the known sequence. Although this method was designed to walk along megabase distances along chromosomes, it was never put into practical use because of the necessity to maintain and screen hundreds of thousands of clones from each size fraction. In addition, cross hybridization would be expected to yield a large fraction of false positive clones.

5. Shotgun Cloning

The only practical method for preparing DNA longer than 5–20 kb for sequencing is subcloning the source DNA as random fragments small enough to be sequenced. The large source DNA molecule is fragmented by sonication or hydrodynamic shearing, fractionated to select the optimum fragment size, and then subcloned into a bacterial plasmid or virus genome (Adams et al., 1994; Primrose, 1998; Cantor and Smith, 1999). The individual subclones can be subjected to Sanger or other sequencing reactions in order to determine sequences within the source DNA. If many overlapping subclones are sequenced, the entire sequence for the large source DNA can be determined. The advantages of shotgun cloning over the other techniques are: 1) the fragments are small and uniform in size so that they can be cloned with high efficiency independent of sequence; 2) the fragments can be short enough that both strands can be sequenced using the Sanger reaction; 3) transformation and growth of many clones is rapid and inexpensive; and 4) clones are very stable E. Genomic Sequencing Current techniques to sequence genomes (as well as any DNA larger than about 5 kb) depend upon shotgun cloning of small random fragments from the entire DNA. Bacteria and other very small genomes can be directly shotgun cloned and sequenced. This is called "pure shotgun sequencing." Larger genomes are usually first cloned as large pieces and each clone is shotgun sequenced. This is called "directed shotgun sequencing."

1. Pure Shotgun Sequencing

Genomes up to several millions or billions of base pairs in length can be randomly fragmented and subcloned as small fragments (Adams et al., 1994; Primrose, 1998; Cantor and Smith, 1999). However, in the process of fragmentation all information about the relative positions of the fragment sequences in the native genome is lost. This information can be recovered by sequencing with 5–10-fold redundancy (i.e., the number of bases sequenced in different reactions add up to 5 to 10 times as many bases in the genome) so as to generate sufficiently numerous overlaps between the sequences of different fragments that a computer program can assemble the sequences from the subclones into large contiguous sequences (contigs). However, due to some regions being more difficult to clone than others and due to incomplete statistical sampling, there will still be some regions within the genome that are not sequenced even after highly redundant sequencing. These unknown regions are called "gaps." After assembly of the shotgun sequences into contigs, the sequencing is "finished" by filling in the gaps. Finishing must be done by additional sequencing of the subclones, by primer walking beginning at the edge of a contig, or by sequencing PCR products made using primers from the edges of adjacent contigs.

There are several disadvantages to the pure shotgun strategy: 1) as the size of the region to be sequenced increases, the effort of assembling a contiguous sequence from shotgun reads increases faster than $N \ln N$, where $N$ is the number of reads; 2) repetitive DNA and sequencing errors can cause ambiguities in sequence assembly; and 3) because subclones from the entire genome are sequenced at the same time and significant redundancy of sequencing is necessary to get contigs of moderate size, about 50% of the sequencing has to be finished before the sequence accuracy and the contig sizes are sufficient to get substantial information about the genome. Focusing the sequencing effort on one region is impossible.

2. Directed Shotgun Sequencing

The directed shotgun strategy, adopted by the Human Genome Project, reduces the difficulty of sequence assembly by limiting the analysis to one large clone at a time. This "clone-by-clone" approach requires four steps 1) large-insert cloning, comprised of a) random fragmentation of the genome into segments 100,000–300,000 bp in size, b) cloning of the large segments, and c) isolation, selection and mapping of the clones; 2) random fragmentation and subcloning of each clone as thousands of short subclones; 3) sequencing random subclones and assembly of the overlapping sequences into contiguous regions; and 4) "finishing" the sequence by filling the gaps between contiguous regions and resolving inaccuracies. The positions of the sequences of the large clones within the genome are determined by the mapping steps, and the positions of the sequences of the subclones are determined by redundant sequencing of the subclones and computer assembly of the sequences of individual large clones. Substantial initial investment of resources and time are required for the first two steps before sequencing begins. This inhibits sequencing DNA from different species or individuals. Sequencing random subclones is highly inefficient, because significant gaps exist until the subclones have been sequenced to about 7× redundancy. Finishing requires "smart" workers and effort equivalent to an additional ~3× sequencing redundancy.

The directed shotgun sequencing method is more likely to finish a large genome than is pure shotgun sequencing. For the human genome, for example, the computer effort for directed shotgun sequencing is more than 20 times less than that required for pure shotgun sequencing.

There is an even greater need to simplify the sequencing and finishing steps of genomic sequencing. In principle, this can be done by creating ordered libraries of DNA, giving uniform (rather than random) coverage, which would allow accurate sequencing with only about 3 fold redundancy and eliminate the finishing phase of projects. Current methods to produce ordered libraries are impractical, because they can cover only short regions (~5,000 bp) and are labor-intensive.

F. Resequencing of DNA

The presence of a known DNA sequence or variation of a known sequence can be detected using a variety of techniques that are more rapid and less expensive than de novo sequencing. These "resequencing" techniques are important for health applications, where determination of which allele or alleles are present has prognostic and diagnostic value.

1. Microarray Detection of Specific DNA Sequences

The DNA from an individual human or animal is amplified, usually by PCR, labeled with a detectable tag, and hybridized to spots of DNA with known sequences bound to a surface (Primrose, 1998; Cantor and Smith, 1999). If the individual's DNA contains sequences that are complementary to those on one or more spots on the DNA array, the tagged molecules are physically detected. If the individual's amplified DNA is not complementary to the probe DNA in a spot, the tagged molecules are not detected. Microarrays of different design have different sensitivities to the amount of tested DNA and the extact amount of sequence complementarity that is required for a positive result. The advantage of the microarray resequencing technique is that many regions of an individual's DNA can be simultaneously amplified using multiplex PCR, and the mixture of amplified genetic elements hybridized simultaneously to a microarray having thousands of different probe spots, such that variations at many different sites can be simultaneously detected.

One disadvantage to using PCR to amplify the DNA is that only one genetic element can be amplified in each reaction, unless multiplex PCR is employed, in which case only as many as 10–50 loci can be simultaneously amplified. For certain applications, such as SNP (single nucleotide polymorphism) screening, it would be advantageous to simultaneously amplify 1,000–100,000 elements and detect the amplified sequences simultaneously. A second disadvantage to PCR is that only a limited number of DNA bases can be amplified from each element (usually <2000 bp). Many applications require resequencing entire genes, which can be up to 200,000 bp in length.

2. Other Methods of Resequencing

Other methods such as mass spectrometry, secondary structure conformation polymorphism, ligation amplification, primer extension, and target-dependent cleavage can be used to detect sequence polymorphisms. All these methods either require initial amplification of one or more specific genetic elements by PCR or incorporate other forms of amplification that have the same deficiencies of PCR, because they can amplify only a very limited region of the genome at one time.

WO 00/28084 is directed to isothermal amplification of a target nucleic acid sequence utilizing serial generation of double-stranded DNA engineered to contain terminal nicking sites, nicking at least one of those sites, and extending it by strand displacement with a polymerase that lacks 5' to 3' exonuclease activity. The nick is generated by restriction endonuclease digestion of a site formed by hybridization of amplification primers to a target nucleic acid, wherein the site is hemi-modified through polymerization in the presence of modified nucleotides.

WO 99/18241 concerns methods for amplification of nucleic acid sequences of interest utilizing multiple strand displacement amplifications with two sets of multiple primers situated to amplify the sequence of interest. Following hybridization of the primers distally to the sequence of interest, amplification proceeds by replication initiated at each primer and continuing through the nucleic acid sequence of interest. In the course of polymerization from the primers in a continuous isothermal reaction, the intervening primers are displaced. Once the nucleic acid strands elongated from the right set of primers reaches the region of the nucleic acid molecule to which the left set of primers hybridizes, and vice versa, another round of priming and replication occurs, allowing multiple copies of a nested set of the target nucleic acid sequence to be synthesized quickly. In specific embodiments the methods concern amplification of whole genomes or concatenated DNA.

WO 00/60121 regards amplification methods of unknown sequences of interest using PCR genome walking with synthetic primers. Specifically, a sequence which is 3' to a known sequence is amplified. A 5' oligonucleotide blocked at its 5' end is annealed to the known sequence in a denatured sample of DNA and extended by polymerization. The strands of the resulting dsDNA molecule are melted, and a 3' oligonucleotide blocked at its 3' end is coupled to the polymerized strand. A primer complementary in sequence to the 3'-blocked oligonucleotide is used to generate a double-stranded template for subsequence cycles of PCR.

WO 00/24929 is directed to linear amplification mediated PCR, whereby an unknown DNA or RNA sequence which is adjacent to a known DNA or RNA region is identified and/or sequenced. The region is first subjected to one or more linear PCR steps using one or more primers, and a ds DNA molecule is generated from the resultant ss DNA of the first step. The ds DNA is digested with restriction enzymes to generate blunt and/or cohesive ends, and an oligonucleotide of known sequence is added to the digested ends, and the ds DNA is then subjected to propagation and detection.

U.S. Pat. No. 6,063,604 is directed to amplification of a target nucleic acid sequence within a single- or double-stranded polynucleotide, wherein the method comprises providing a reaction mixture containing a 5' primer and a 3' primer each having a recognition sequence for a restriction endonuclease capable of nicking one strand of a double-stranded hemi-modiifed recognition site. The 5' primer is first annealed to a single stranded target sequence and extended in the presence of deoxyribonucleoside triphosphates wherein at least one is modified. The resultant ds DNA product having one original target strand and a modified polynucleotide extension product is enzymatically separated, and a second amplification primer anneals to the modified polynucleotide extension product and is extended in the presence of deoxyribonucleoside triphosphates wherein at least one is modified to generate a double-stranded polynucleotide comprising the two resultant modified polynucleotide extension products. The resultant hemi-modified recognition sites are subjected to nicking of one strand, and the 3' end produced by the nick is extended, preferably with a polymerase which displaces the strand.

U.S. Pat. No. 6,117,634, incorporated by reference herein in its entirety, regards sequencing whereby the nucleic acid molecule to be sequenced is double stranded and undenatured, which is an improvement for sequencing regions having intramolecular and/or intermolecular secondary structure. In one embodiment, the double strand is nicked and is followed by strand replacement. The nick is generated by, for example, restriction digestion wherein only one strand is hydrolyzed, random nicking by an enzyme such as DNAase I, nicking by fl gene product II or homologous enzymes from other filamentous bacteriophage, or chemical nicking of the template directed by triple-helix formation. Alternatively, the nick is generated by adapters having a gap or nick generated by, for example, restriction enzyme digestion. The polymerase preferably has 5' to 3' exonuclease activity. However, the resultant polymerized strand is the sequencing substrate, and no further modifications or manipulations to the polymerized strand occur.

Similarly, U.S. Pat. No. 6,197,557 and Makarov et al. (1997) regard methods to prepare a DNA molecule by ligating or hybridizing an adaptor to the end of a template double-stranded DNA molecule, thereby introducing a nick, following with nick translation using a DNA polymerase having 5' to 3' exonuclease activity. The reaction proceeds for a specific time and is then terminated. The resultant product may be amplified through linear amplification, such as by primer extension, or alternatively by PCR. However, this reference fails to teach specific modifications or manipulations prior to the amplification of the nick translation-extended strand to facilitate the amplification.

SUMMARY OF THE INVENTION

The instant invention seeks to overcome the noted deficiencies in the art by providing methods and compositions for use in positionally amplifying a specific sequence within a polynucleotide molecule. Positional Amplification by Nick Translation (PANT) is designed to amplify internal regions of DNA molecules, including restriction fragments, cloned DNA, and intact chromosomes, as molecules of controllable length. Positional Amplification of sequences near the terminus of a DNA molecule involves three essential steps: 1) a Primer Extension/Nick Translation (PENT) reaction; 2) appending a second primer sequence to the 3' end of the PENT product, forming a PENT amplifiable strand (PENTAmer); and 3) an amplification reaction using one or both priming sequences. In contrast to PCR, which amplifies DNA between two specific sequences, PANT can amplify DNA between two specific positions, or a specified position relative to a specific sequence. PENTAmers can be created to amplify very large regions of DNA (up to 500,000 bp) as random mixtures (unordered positional libraries) or as molecules sorted according to position (ordered positional libraries). PANT is fast and economical, because PENTAmer preparation can be multiplexed. A single PENTAmer preparation can include very complex mixtures of DNA such as hundreds of large-insert clones, complete genomes, or cDNA libraries. Subsequent PCR amplification of the preparation using a single specific primer can positionally amplify contiguous regions along a specific clone, along a specific genomic region, or along a specific expressed sequence. A schematic diagram of how locus specific amplification of DNA can be achieved using PCR, cloning, and three examples of positional amplification of nick-translate libraries are shown in FIG. 1.

Positional Amplification at large distances from the terminus of a DNA molecule also requires size separation and recombination of the template DNA. This disclosure describes the core technology for preparing PENTAmers, as well as specific implementations that produce PENTAmers suitable for amplifying short templates up to 10 kb long, and "recombinant" PENTAmers (formed by recombination between internal and terminal sites on templates) suitable for amplifying large-insert clones such as BACs and up to 500 kb regions of genomic DNA. In both cases the PENTAmers may be prepared in microwell plates, such that successive wells contain PENTAmers from a large number (e.g. 96) successive positions within the template. Novel reagents and methods are disclosed for: 1) efficient initiation of PENT reactions at specific sites using novel oligonucleotides; 2) termination of PENT reactions at controllable distances from initiation; 3) novel nick-processing reactions to append priming sequences to the 3' ends of PENTAmers; 4) novel recombination reactions; 5) novel ways to separate PENTAmers that are located different distances from a DNA terminus; 6) novel ways to prepare hundreds or thousands of PENTAmers simultaneously by multiplexing; 7) novel ways to make and use libraries of PENTAmers; and 8) novel ways to analyze the sequence information in genomes.

PANT allows the amplification of a specific position within a large clone or genome as a PENTAmer of constant length, between 10 and 5,000 bp. The most important applications of PANT involve: 1) creation of mixtures of PENTAmers covering a large region of DNA between 500 and 500,000 bp (an unordered positional library); 2) creation of ordered mixtures of PENTAmers that cover successive slightly overlapping regions along a large region of DNA between 500 and 500,000 bp (an ordered positional library); and 3) creation of mixtures of PENTAmers that cover multiple small regions of DNA dispersed throughout the genome (a sampled positional library). Unordered libraries can be used for purposes such as creating FISH probes and identifying cDNA clones complementary to specific regions of the genome, as well as shotgun sequencing of cDNA, large-insert clones and genomes. Ordered libraries can be used for directed sequencing of cDNA, large-insert clone and genomes, as well as for comparative genomics. Sampled libraries can be used to sequence or resequence informative sequences spread throughout the genome to identify point variations and rearrangements within one genome, or to identify the presence of specific genomes or genetic elements within a population of genomes. PANT can be commercialized as services (e.g., sequence ready ordered PENTAmers for directed sequencing of BACs in high-throughput sequencing centers), as kits (e.g., kits to allow large and small laboratories to create ordered positional libraries for sequence analysis of specific regions of the human genome), or as diagnostic products (e.g., PENTAmer arrays for hybridization analysis of patients' blood to determine chromosomal mutations).

The following definitions are provided to assist in understanding the nature of the invention:

Up-stream (terminus-attaching) adaptor molecules: short artificial DNA molecules that are ligated to the ends of DNA fragments. Their design has a minimum of two domains: 1) a domain that facilitates ligation to the ends of template DNA molecules; and 2) a domain that facilitates initiation of a nick-translation reaction. In addition, up-stream adaptors may comprise additional domains that facilitate manipulation of the DNA strand, including, for example, recombination, amplification, detection, affinity capture, and inhibition of self-ligation.

Down-stream (nick-attaching) adaptor molecules: partially double-stranded or completely single-stranded DNA molecules that can be linked to 3' or 5' DNA termini at a nick within double-stranded DNA molecule. Their design has a minimum of two domains: 1) a domain that facilitates ligation to the 3' or 5' DNA termini within the nick or a domain that facilitates priming of the polymerization reaction which results in the extension of the 3' terminus near the nick; 2) a domain that facilitates amplification. In addition, down-stream adaptors may comprise additional domains that facilitate manipulation of the DNA strand, including, for example, recombination, amplification, detection, affinity capture, and inhibition of self-ligation.

Internal adaptor molecules: Short artificial DNA molecules that are ligated to the ends of DNA fragments that have been exposed by a second cleavage event, usually restriction endonuclease cleavage of an internal site within the source DNA molecules. Their design has a minimum of two domains: 1) a domain that facilitates ligation to the ends of template DNA molecules, and 2) a domain that facilitates initiation of a nick-translation reaction. In addition, internal adaptors may comprise additional domains that facilitate manipulation of the DNA strand, including, for example, recombination, amplification, detection, affinity capture, and inhibition of self-ligation.

Nick translate molecules: DNA molecules produced by coordinated 5'→3' DNA polymerase activity and 5'→3' exonuclease activity. The two activities can be present within one enzyme molecule (as in the case of Taq DNA polymerase or DNA polymerase I) or two enzymes. The synthesis of nick translate molecules is usually initiated at a nick site within an up-stream adaptor at the ends of a DNA fragment or within a down-stream adaptor within a DNA fragment, or within an internal adaptor.

Adaptor attached nick translate molecules: nick translate molecules with up-stream and down-stream adaptor sequences at the 5' and 3' termini. Adaptor attached nick translate molecules are usually created by covalent attachment of the down-stream adaptor to the 3' end of the nick translate molecule.

Nick translation initiation site: a free 3'OH-containing terminus at a nick or a small gap within an adaptor molecule. Where the nick site is contained within an adaptor, the nick translation initiation site can be: 1) a part of the adaptor before attachment to DNA, 2) created by annealing a priming oligonucleotide to the distal primer binding region of the adaptor before or after the first nick translation reaction, or, 3) created by recombination of two different adaptors.

DNA library: a collection of DNA molecules that represent all or a specified fraction of the sequences within a template DNA. DNA libraries can be formed from whole genome, cDNA, cloned, or PCR amplified templates, whereby the template DNA has been reduced in size, recombined, or otherwise processed to become more useful than the original template DNA. Individual members of the library, complementary to sequences within the template DNA, can be selected and/or amplified by in vivo cloning or in vitro amplification.

Unordered DNA library: a DNA library with a pooled collection of molecules comprised of sequences complementary to unknown positions within a region of the template DNA.

Ordered DNA library: a DNA library separated into sublibraries comprised of molecules complementary to specified positions within a region of the template DNA.

Sampled DNA library: a DNA library with a pooled collection of molecules comprised of sequences complementary to multiple non-contiguous specific regions of the template DNA.

Nick-translate DNA library: a DNA library comprised of adaptor attached DNA molecules that have been created by one or more nick translation reactions.

Unordered nick-translate DNA library: a pooled collection of all adaptor attached nick-translate molecules that are complementary to random positions within a region of the template DNA.

Sampled nick-translate DNA library: a DNA library with a pooled collection of Adaptor-attached nick-translate molecules that are complementary to multiple non-contiguous specific regions of the template DNA.

Ordered nick-translate DNA library: an adaptor attached nick-translate library separated into sublibraries of molecules that are complementary to specified positions within a region of the template DNA.

Adaptor mediated recombination: a biochemical process that involves transient or stable non-covalent association of two adaptor attached DNA regions followed by covalent stabilization using DNA ligase or DNA polymerase enzymes.

Nick site: a discontinuity in one of the strands within double stranded DNA. A nick site created enzymatically by the nick translation reaction is characterized by a free, phosphorylated 5' end a 3' hydroxyl group.

Nick translation: a coupled polymerization/degradation process that is characterized by a coordinated 5' to 3' DNA polymerase activity and 5' to 3' exonuclease activity. The two activities are usually present within one enzyme molecule (as in the case of Taq DNA polymerase or DNA polymerase I), however nick translation may also be achieved by simultaneous activity multiple enzymes exhibiting polymerase and exonuclease activity.

Partial cleavage: the cleavage by an endonuclease of a controlled fraction of the available sites within a DNA template. The extent of partial cleavage can be controlled by, for example, limiting the reaction time, the amount of enzyme, and/or reaction conditions.

Kernel: a known sequence of DNA that is used to select the amplified region within the template DNA.

The invention is a means of preparing a DNA molecule having an amplifiable region. In a preferred embodiment, DNA is prepared by a method comprising obtaining a DNA sample including DNA molecules and attaching upstream adaptor molecules to 5' termini of DNA molecules of the sample to provide a nick translation initiation site. The DNA is subjected to nick translation using a DNA polymerase having 5'–3' exonuclease activity. This reaction produces nick translate molecules. Downstream adaptor molecules are attached to the 3' termini of the nick translate molecules to produce adaptor attached DNA molecules.

It is contemplated that a variety of starting materials may be employed in the context of the instant invention. Therefore, it is contemplated that the DNA will often need to be prepared prior to adaptor attachment. The 5' termini of the DNA sample may be produced prior to the attachment of the upstream adaptor molecule. It is contemplated that the termini may be produced by restriction digestion by one or more restriction enzymes, by digestion with a nuclease, by mechanical shearing, or by any other means known by those of skill in the art to modify DNA such that an appropriate adaptor may be attached. Where a DNA molecule is restriction digested, a person of ordinary skill would be aware of a wide variety of restriction enzymes that could be employed in the context of the instant invention. Particularly, a person of ordinary skill would be aware that particular application would necessitate the use of a frequently cutting restriction enzyme while other applications would necessitate the use of an infrequent cutter. It would further be clear to a person of ordinary skill, in the context of the contemplated application what would distinguish a frequent from an infrequent cutter. It is further contemplated that the enzymes used to digest may be manipulated to perform either a partial or full digest. A person of ordinary skill would be aware of specific modifications to reaction conditions that would facilitate a partial digest. By means of example: salt conditions could be modified or time of digest could be shortened. A person of ordinary skill would also be aware of methods of modifying chemical or mechanical cleaving processes to achieve a full or partial digest of a DNA sample.

Following attachment of the adaptors to the nick translate product, it is envisioned that the DNA may be denatured. For the purpose of the instant invention, denatured DNA is DNA in which the hydrogen bonds between base pairs in the double-stranded nucleic acid molecules are disrupted to produce single-stranded polynucleotides. Following denaturation, the DNA may be separated. Separation of the denatured DNA may facilitate the separation of a single stranded nick translation product from the DNA sample template strand.

In a preferred embodiment of the invention, DNA is subjected to nick translation for a specified period of time. As the number of bases polymerized by a given DNA polymerase in a specific time T may be definitively calculated, product length may be extrapolated from reaction time. Consequently, the products of a timed reaction will be of a predictable length.

In a further embodiment, upstream and down stream adaptors include functional sites. It is envisioned that the adaptors are specifically engineered to comprise sites that facilitate the further manipulation of the DNA molecule. In preferred embodiments, the upstream adaptors may be engineered to include at least one of the following: a nick translation initiation site, a primer binding region and/or further sites a person of ordinary skill would envision as useful in the modification of the DNA sample. Downstream adaptor may be similarly constructed to include a primer binding region, a nick translation initiation site and/or further sites a person of ordinary skill would envision as useful in the modification of the DNA sample in the context of the invention.

The invention facilitates the manipulation of a both a homogeneous and heterogeneous DNA sample. It is contemplated that to facilitate the differentiation of alternate DNA species, more than one adaptor construct may be attached to DNA molecules within a DNA sample. In an embodiment of the invention, the upstream adaptor attached to the DNA sample consists of a mixture of more than one upstream adaptor molecule constructs. It is envisioned that the alternate constructs may have different primer binding regions. It is further envisioned that the downstream adaptor may comprise more than one downstream adaptor molecule constructs. These constructs may be also be distinguishable by the inclusion of different primer binding regions.

It is envisioned that following adaptor attachment and nick translation that the modified DNA molecules may be amplified. Following amplification, the amplified DNA may be cloned, sequenced or separated.

In a preferred embodiment of the claimed invention, it is envisioned that the adaptor attached DNA, either prior to or subsequent to amplification may be used in the creation of a DNA library. It is envisioned that the DNA library may be either an unordered or an ordered DNA library.

The ordered DNA library may be created with steps involving DNA recombination or by performing nick translation for a specific period of time. The ordered library may further constitute an ordered genomic library. In a preferred embodiment, an ordered library is subjected to sequence scanning.

In a further embodiment of the invention, Applicant's envision that amplification of the adaptor attached DNA may be carried out with primers complementary to the upstream adaptor molecule and the downstream adaptor molecule. In an alternate embodiment, the adaptor attached DNA may be amplified with a first primer specific to the upstream adaptor and a second primer specific to an internal sequence of the DNA molecule. In a further embodiment, the adaptor attached DNA may be amplified with a first primer specific to the downstream adaptor molecule and a second primer specific to an internal sequence of the DNA molecule.

It is envisioned that the primers used for amplification of the adaptor attached DNA may be labeled. In an additional embodiment of the invention, use of these labeled probes facilitates the creation of hybridization probes.

In a further embodiment of the claimed invention, the adaptor attached DNA molecules may be subjected to recombination. It is envisioned that the recombination may be carried out by: 1) joining an upstream adaptor molecule attached to a first adaptor attached DNA molecule and a downstream adaptor molecule attached to the same adaptor attached DNA molecule; 2) joining an upstream adaptor molecule attached to a first adaptor attached DNA molecule and an internal adaptor molecule attached at an internal site within the same adaptor attached DNA molecule; 3) joining a downstream adaptor molecule attached to a first adaptor attached DNA molecule and an internal adaptor molecule attached at an internal site within the same adaptor attached DNA molecule; 4) joining an upstream adaptor molecule attached to a first adaptor attached DNA molecule and an internal adaptor molecule attached at an internal site within the same adaptor attached DNA molecule and further joining a downstream adaptor molecule attached to a first adaptor attached DNA molecule and an internal adaptor molecule attached at an internal site within the same adaptor attached DNA molecule; or 5) joining an upstream adaptor molecule attached to a first adaptor attached DNA molecule and a downstream adaptor molecule attached to a second adaptor attached DNA molecule.

In another embodiment, it is envisioned that the sample DNA molecules may be between 0.5 and 500 kb in length. In a preferred embodiment, the DNA sample comprises short template molecules of 1–20 kB. It is further envisioned that the sample DNA is cDNA, genomic DNA, or cloned DNA. The cloned DNA may further be classified as originating from a BAC, a YAC, a cosmid, or a large insert clone.

Once the sample DNA is converted to adaptor attached DNA molecules, it is envisioned that the DNA may be separated. In a preferred embodiment, separation of the adaptor attached DNA is based upon size. Nevertheless, a person of ordinary skill would be aware of a variety of means of separating the DNA constructs of the instant invention.

In a further embodiment of the claimed invention, diagnostic mutation analysis is performed. In a preferred embodiment, diagnostic mutation analysis involves the steps of: preparing a DNA library in accordance with the disclosed methods and then screening the DNA library for single or multiple nucleotide polymorphisms. The disclosed DNA library facilitates the shotgun sequencing of the DNA by sequencing the library using primers specific for known loci to derive the sequence of adjacent unknown regions.

In an additional embodiment of the claimed invention, the adaptor attached DNA is recombined after adaptor attachment, size separated and then amplified. It is further envisioned that the size separated DNA is distributed into the wells of a multi-well plate. In a preferred embodiment, the amplified DNA is subsequently mapped, sequenced, resequenced, and/or cloned into a vector.

In a further embodiment of the claimed invention, the adaptor attached DNA is recombined after adaptor attachment, PCR amplified using locus specific primers and subsequently PCR amplified using one locus specific primer and one adaptor specific primer. This amplified DNA may be subsequently sequenced or cloned into a vector.

In a particular embodiment of the claimed invention, the adaptor attached DNA is recombined after adaptor attachment. In a preferred embodiment, the DNA is amplified after adaptor attachment, hybridized to a microarray and the hybridization patterns subsequently analyzed.

It is further envisioned that the DNA sample to be nick translated is modified. This modification is, for example, methylation. In another embodiment, modification of DNA occurs during the nick translation reaction. In this context, the nucleotides integrated by the reaction are modified. In a preferred embodiment, the modified nucleotides are exonuclease resistant. In this context, it is contemplated that the presence of exonuclease resistant nucleotides facilitates the differentiation or isolation of the nick translate product from the template strand.

It is specifically envisioned that the adaptor attached DNA molecules of the instant invention may be further modified or manipulated after the initial reaction. In a preferred embodiment of the claimed invention, the adaptor attached DNA molecules are modified by initiating a second nick translation reaction at the upstream adaptor with a DNA polymerase having 5'–3' exonuclease activity. A second downstream adaptor molecules is then attached to the 5' end of the molecules to produce adaptor attached nick translate molecules.

In a further embodiment, the adaptor attached DNA molecules are denatured to produce single stranded DNA. The denatured DNA is then replicated to form a double stranded product. This product is subjected to nick translation using a DNA polymerase having 5'–3' exonuclease activity, to produce nick translate molecules. Downstream adaptor molecules are then attached to the nick translation initiation site of the nick translate molecules to produce adaptor attached nick translate molecules.

Modification of the DNA molecules of the instant invention may be to facilitate more efficient manipulation of the nick translate product. It is specifically envisioned that the DNA is modified to facilitate efficient isolation or separation of different DNA molecules. In a preferred embodiment, isolation or purification is facilitated by the attachment to the DNA of an affinity adaptor.

In preferred embodiments of the invention, DNA molecules are subjected to recombination. A person of ordinary skill would recognize that a variety of methods exist to carry out recombination of DNA molecules. In a preferred embodiment, recombination is carried out by attaching the upstream adaptor molecule to both the proximal and distal ends of a DNA molecules to create a circular product. Several alternate means of recombination are specifically contemplated within the scope of the instant invention. In a first embodiment, the adaptor attached, nick translate product is recombined by incubating the product with a linker oligonucleotide to form a nick site. The ends of the product are then ligated with a DNA ligase. While a person of ordinary skill would recognize that a broad range of oligonucleotide sizes and properties would function in the context of this embodiment, it is contemplated in the context of this embodiment that the linker oligonucleotide is between 20–200 bp long and further that the linker oligonucleotide includes a region complementary to the upstream adaptor and a region complementary to the downstream adaptor.

In a second embodiment, recombination is carried out by restricting the DNA molecules of the DNA sample with one or more restriction enzymes. Restriction generally is carried out with a frequent cutter, and in specific embodiments, it is contemplated that the digestion is only a partial digest. Further, each end of the DNA molecule may be created with a different restriction enzyme. Upstream adaptor molecules are then attached at both ends of the restricted DNA molecules and nick translation carried out from both upstream adaptors. Once this is done, the ends of the DNA molecules are recombined. Once recombination has been carried out, the recombined molecules may be separated according to size.

In a third embodiment, recombination is carried out by restricting the DNA molecules of the DNA sample with one or more infrequent cutting restriction enzymes. Upstream adaptor molecules are then attached at ends of the restricted DNA molecules and nick translation is carried out from the upstream adaptors. Following nick translation, the nick translate molecules are partially restricted with a frequent cutter and internal adaptor molecules attached at ends of the restricted DNA molecules. Another nick translation reaction is then carried out from the internal adaptors, with the ends of the DNA molecules subsequently being recombined.

Additional methods for recombination are included within various aspects of the claimed invention. In a preferred embodiment, recombination is carried out in a dilute solution and is characterized as: cleaving the DNA molecules with a first sequence-specific endonuclease, ligating an adaptor to the sequence-specific termini of the DNA molecule, cleaving the DNA molecules with a second sequence-specific endonuclease, incubating the DNA molecules at low concentration with an excess of T4 DNA ligase for 16–36 h and then concentrating the DNA molecules. In an alternate embodiment, recombination is carried out in a dilute solution by methylating the DNA molecules, attaching a first and second adaptor with an activatable region to the ends of the DNA molecules, activating the adaptors by incubation with a restriction endonuclease thereby removing distal portion of the adaptors and creating sticky ends, incubating the DNA molecules at low concentration with an excess of T4 DNA ligase for 16–36 h; and then concentrating the DNA molecules.

In a further embodiment, recombination is carried out in a dilute solution by hybridizing the ends of adaptor attached template molecules in dilute solution, concentrating the molecules and ligating the ends of the molecules. In a still further embodiment, recombination is carried out in a dilute solution by hybridizing the ends of adaptor attached template molecules and subjecting the DNA molecule to a nick-translation reaction to form the covalent intramolecular junction.

Various alternate embodiments and modifications of the basic methods of producing adaptor attached nick translate molecules are specifically contemplated. In one embodiment, a DNA molecule having an amplifiable region is produced by obtaining a DNA sample comprising DNA molecules having regions to be amplified and attaching upstream adaptor molecules to the proximal end of DNA molecules to provide a nick translation initiation site. The DNA molecules are then subjected to a nick translation reaction comprising DNA polymerization and 5'–3' exonuclease activity, for a specific time T. Downstream adaptor molecules are then attached to the 5' end of the degraded template strand to produce adaptor attached nick translate molecules. The product of this method may then be amplified, sequenced, cloned or otherwise manipulated. In embodiments in which the DNA sample contains a plurality of alternate DNA molecules, the different DNA molecules may be reacted for different times T.

Once a circular product is achieved through recombination, the existence of a nick translation site facilitates the initiation of a nick translation reaction. The positioning of the nick site on the intramolecular junction facilitates nick translation through the region. Proper placement of the nick site allows nick translation to proceed either through the proximal or distal end of the recombined molecule. Coverage of the molecule can be increased by exposing different internal regions of the nick translate molecules as distal ends. It is further contemplated that the adaptors used in recombination comprise single stranded tails.

Where an adaptor is ligated to a DNA molecule in the context of the instant invention, it is specifically contemplated that the adaptor added to a DNA sample consists of a single adaptor construct or multiple adaptor constructs. Thus, embodiments of the invention comprise a DNA sample with a plurality of upstream adaptors in a single tube and a DNA sample with a plurality of downstream adaptors in a single tube.

The instant invention is of particular use in producing DNA to be sequenced or amplified with specific regions for which the sequence is not known. It is specifically contemplated that the instant invention will facilitate the determination of unknown sequences. In a preferred embodiment of the instant invention, the unknown sequence to be determined will abut a known sequence. In this and other contexts, it is specifically contemplated that the nick translation reaction proceed through a known sequence on the DNA molecule. Further, because the sequence of the region is known, sequencing and PCR primers may be constructed to hybridize to such regions within the context of the invention. In particular embodiments of the instant invention, PCR is carried out using a primer or primers specific for the known sequence and a primer or primers specific for the attached adaptors.

In an alternate embodiment of the basic method, an amplifiable region is prepared by obtaining a DNA sample comprising DNA molecules having regions to be amplified followed by attaching upstream adaptor molecules to the proximal end of the DNA molecules of the sample to provide a nick translation initiation site. The adaptor attached molecules are subjected to a first nick translation comprising DNA polymerization and 5'–3' exonuclease activity, for a specific time T. A first downstream adaptor is then attached to the 3' end of the nick translate product to produce adaptor attached nick translate molecules. The adaptor attached molecules are then subjected to a second nick translation initiated from the upstream adaptor for a specific time T and then a second downstream adaptor molecule is attached to the 5' end of the degraded nick translate product. The product of this method may then be amplified, sequenced, cloned, separated or otherwise manipulated. In embodiments in which the DNA sample contains a plurality of alternate DNA molecules, the different DNA molecules may be reacted for a different time T for either of the nick translation reactions performed.

In a further embodiment of the basic method, an amplifiable region is prepared by obtaining a DNA sample comprising DNA molecules having regions to be amplified followed by attaching upstream adaptor molecules to the proximal end of the DNA molecules of the sample to provide a nick translation initiation site. The adaptor attached molecules are then subjected to a first nick translation comprising DNA polymerization and 5'–3' exonuclease activity, for a specific time T. A first downstream adaptor molecules is then attached to the 3' end of the nick translate product and the nick translate product separated from the template molecule. The nick translate product is then replicated by primer extension with the product of this step then subjected to a second nick translation comprising DNA polymerization and 5'–3' exonuclease activity, for a specific time T. Following this step, a second downstream adaptor molecule is attached to the 3' end of the product. The product of this method may then be amplified, separated, sequenced, cloned or otherwise manipulated. In embodiments in which the DNA sample contains a plurality of alternate DNA molecules, the different DNA molecules may be reacted for different times T for either of the nick translation reactions performed.

In a still further embodiment of the basic method, an amplifiable region is prepared by obtaining a DNA sample comprising DNA molecules having regions to be amplified followed by attaching an affinity adaptor to the proximal ends of the DNA molecules. The affinity adaptor attached molecules are subjected to partial cleavage and then separated. Upstream adaptor molecules are attached to the ends of the affinity adaptor attached molecules to provide a nick translation initiation site and the molecules are then subjected to nick translation comprising DNA polymerization and 5'–3' exonuclease. Following this step, downstream adaptor molecules are then attached to the nick translate molecules to produce adaptor attached nick translate molecules. The product of this method may then be amplified, sequenced, separated, cloned or otherwise manipulated. In embodiments in which the DNA sample contains a plurality of alternate DNA molecules, the different DNA molecules may be reacted for different times T for either of the nick translation reactions performed. In an additional embodiment, polymerization may involve the incorporation of modified nucleotides, with specific embodiments making the nick translate molecule exonuclease resistant.

In a further modification of the basic nick translation method, an amplifiable region is prepared by obtaining a DNA sample comprising DNA molecules having regions to be amplified followed by attaching the first end of a recombination adaptor to one end of the DNA molecules and attaching the second end of the recombination adaptor to the opposite end of the DNA molecules. The circularized molecule is then subjected to nick translation involving DNA polymerization and 5'–3' exonuclease activity. A downstream adaptor molecule is attached to the nick translate molecules to produce adaptor attached nick translate molecules. The product of this method may then be amplified, sequenced, separated, cloned or otherwise manipulated. In embodiments in which the DNA sample contains a plurality of alternate DNA molecules, the different DNA molecules may be reacted for different times T for either of the nick translation reactions performed.

In an additional modification of the basic nick translation method, an amplifiable region is prepared by obtaining a DNA sample comprising DNA molecules having regions to be amplified followed by attaching the first end of a recombination adaptor to the proximal end of said DNA molecules. Following adaptor attachment, the DNA is partially cleaved to produce cleavage products having a plurality of lengths. The second end of the recombination adaptor is then attached to the distal ends produced by the partial cleavage. These molecules are subjected to nick translation comprising DNA polymerization and 5'–3' exonuclease activity, followed by attaching downstream adaptor molecules to the nick translate molecules to produce adaptor attached nick translate molecules. These molecules may then be separated, for example, by size.

In a still further embodiment based upon the basic nick translation method, a first DNA template is obtained and a first upstream adaptor molecule attached to the template to provide a nick translation initiation site. A second DNA template is obtained and a second upstream adaptor molecule attached to the template to provide a nick translation initiation site. The templates are then mixed and subjected to nick translation initiated from the upstream adaptor for a specific time T. Subsequently, a downstream adaptor molecule is attached to the nick translate molecules to produce adaptor attached nick translate molecules. These molecules may be subsequently amplified and differentiated based upon the use of alternate primers specific for the alternate upstream adaptors.

The methods of the instant application are specifically applicable to the construction of a genomic library. In a preferred embodiment, a genomic library is constructed by obtaining genomic DNA and fragmenting it to a desired size. Upstream adaptor molecules are attached to ends of the fragmented genomic DNA molecules of the sample to provide a nick translation initiation site and the molecules subjected to nick translation comprising DNA polymerization and 5'–3' exonuclease activity. Following this reaction, downstream adaptor molecules are attached to the nick translate molecules to produce adaptor attached nick translate molecules. These products may be recombined, amplified, sequenced, separated, cloned, inserted into a vector or otherwise manipulated. Separation of the library into sublibraries of molecules of different size is contemplated to create an ordered DNA library. It is further contemplated that samples may be chosen based upon the presence of a known kernel sequence within the molecule. Where such a sequence is present, it is contemplated to be useful for the construction of primers for the amplification of the molecule. Amplification in this context will generally comprise sequences adjacent to the kernel sequence. It is contemplated that recombination may be facilitated through the presence of a 5' phosphate group on the upstream adaptor or the use of a DNA ligase employing a linking oligonucleotide. This method may be further modified by incubating the linking oligonucleotide with the adaptor attached nick translate molecule to form a nick and then ligating the adaptor attached nick translate molecule with a DNA ligase. In a preferred embodiment, a thermostable ligase will be used. In a further embodiment, the sample will be diluted and performed at a low concentration prior to recombination.

In addition to the basic method set forth above, alternate methods of constructing genomic libraries are specifically contemplated in the context of the instant invention. In a preferred embodiment, the library is constructed by obtaining a genomic DNA and fragmenting it. Upstream adaptor molecules are then attached to the ends of the fragmented genomic DNA molecules of the sample to provide a nick translation initiation site. The sample is then subdivided into a plurality of reaction vessels and subjected to nick translation comprising DNA polymerization and 5'–3' exonuclease activity, for a specific time T. Following nick translation, downstream adaptor molecules are attached to the nick translate molecules to produce adaptor attached nick translate molecules. These products may be recombined, amplified, sequenced, separated, cloned, inserted into a vector or otherwise manipulated. It is further contemplated that samples may be chosen based upon the presence of a known kernel sequence within the molecule. Where such a sequence is present, it is contemplated to be useful for the construction of primers for the amplification of the molecule. Amplification in this context will generally comprise sequences adjacent to the kernel sequence. Where the molecule is recombined, it is contemplate that it may be carried out by ligating the upstream adaptor to the downstream adaptor. In a further embodiment, these molecules may be recombined employing a DNA ligase and a linking oligonucleotide. This method may be further modified by incubating the linking oligonucleotide with the adaptor attached nick; and translate molecule to form a nick and then ligating the adaptor attached nick translate molecule with a DNA ligase. In a preferred embodiment, a thermostable ligase will be used. In a further embodiment, the sample will be diluted and performed at a low concentration prior to recombination. Because this method may be run in alternate reaction vessels, it is contemplated that various times T of reaction may be applied to the different reaction vessels.

DNA libraries produced in the context of the instant invention may be ordered or unordered. In a preferred embodiment, an unordered DNA library is produced by obtaining a DNA sample comprising DNA molecules, cleaving the DNA molecules and attaching adaptors to termini of the cleaved DNA molecules. The molecules are then subjected to nick translation comprising DNA polymerization and 5'–3' exonuclease activity, to produce nick translate molecules wherein the nick translation is initiated from both ends of the cleaved DNA molecules. The ends of this product are then recombined. These products may be amplified, sequenced, separated, cloned, inserted into a vector or otherwise manipulated. It is further contemplated that samples may be chosen based upon the presence of a known kernel sequence within the molecule. Where such a sequence is present, it is contemplated to be useful for the construction of primers for the amplification of the molecule. Amplification in this context will generally comprise sequences adjacent to the kernel sequence.

In a further embodiment, an ordered DNA library is produced by obtaining a DNA sample comprising DNA molecules, cleaving the DNA molecules and attaching adaptors to termini of the cleaved DNA molecules. The cleaved molecules are then partially cleaved and adaptors attached to the termini of the DNA molecules. These DNA molecules are subjected to nick translation comprising DNA polymerization and 5'–3' exonuclease activity, to produce nick translate molecules wherein said nick translation is initiated from both ends of the DNA molecules. These products may be recombined, amplified, sequenced, separated, cloned, inserted into a vector or otherwise manipulated. It is further contemplated that samples may be chosen based upon the presence of a known kernel sequence within the molecule. Where such a sequence is present, it is contemplated to be useful for the construction of primers for the amplification of the molecule. Amplification in this context will generally comprise sequences adjacent to the kernel sequence. In a further embodiment, nucleotide analogs are integrated during amplification. In an additional embodiment, the time of primer extension is limited. In the context of recombining the molecules, it is specifically contemplated that the sample will be diluted prior to recombination and that recombination results in a covalent bond. In a preferred embodiment, the sample may be diluted to a point where the sample comprises substantially a single DNA molecule. Where the product is sequenced, sequencing may be carried out by cycle sequencing. Where cycle sequencing is performed it is specifically contemplated that the cycle sequencing employs a primer complementary to an adaptor and at least one or two base pairs adjacent to the adaptor.

In an alternate aspect of the instant invention, the basic methods set forth herein are applied to the construction of a DNA library. In a preferred embodiment, the DNA library is constructed by obtaining a DNA sample comprising DNA molecules and cleaving the DNA molecules with an infrequently-cutting restriction enzyme. Upstream adaptor molecules are then attached to the ends of the cleaved DNA molecules of the sample to provide a nick translation initiation site. The DNA molecules are then subjected to nick translation comprising DNA polymerization and 5'–3' exonuclease activity and downstream adaptor molecules subsequently attached to the nick translate molecules to produce adaptor attached nick translate molecules. These molecules are then partially cleaved with a frequently cutting restriction enzyme; and upstream adaptor molecules attached to the ends of the adaptor attached nick translate molecules produced by said partial digestion. The DNA molecules are then again subjected to nick translation comprising DNA polymerization and 5'–3' exonuclease activity and downstream adaptor molecules attached to the nick translate molecules to produce adaptor attached nick translate molecules. These products may be subsequently recombined, amplified or separated. Where the recombined molecule is amplified it is contemplated that a primer specific for an adaptor and or a primer specific for a kernel sequence within the molecule may be used.

In an additional embodiment based upon the basic method, a DNA sample comprising DNA molecules having regions to be amplified is obtained. At least a first upstream adaptor and at least a second upstream adaptor are then attached to the DNA molecules which are then subjected to recombination at low DNA concentrations. The recombined molecules are subjected to nick translation comprising DNA polymerization and 5'–3' exonuclease activity and downstream adaptor molecules attached to the nick translate molecules to produce adaptor attached nick translate molecules. The products of this reaction may be subsequently amplified, sequenced, separated, cloned or otherwise manipulated.

In an alternate embodiment, the instant invention provides methods for sequencing large DNA molecules. In a preferred embodiment, a BAC clone is sequenced by cleaving the BAC clone at a cos site with lambda terminase and ligating an upstream adaptor to the 5' overhangs. The DNA is partially cleaved with a frequently cutting enzyme and the ends of the fragments recombined. A nick-translation reaction is performed from both ends of the fragments. A poly-G tail is added to the 3' end of the recombined nick-translate product with terminal transferase. An adaptor having a poly-C 3' single-strand overhang and a unique double strand sequence is ligated at the end to the poly-G tail. The strands are then size separated and distributed into the wells of a microplate. The DNA is amplified with primers complementary to adaptor sequences such that products are formed which proceed in either a clockwise or counterclockwise direction around the recombined molecule. The molecules are then ligated into a cloning vector and subsequently sequenced.

It is further contemplated that the reagents necessary to carry out the invention may be combined in a kit. In a preferred embodiment, kits may include DNA for use in the context of the instant invention. Where DNA is included in a kit, it is specifically contemplated that the DNA may be genomic DNA. It is further contemplated that the DNA may be prokaryotic or eukaryotic; from a plant or an animal. Where the DNA is from a plant or animal, a person of ordinary skill would recognize a wide variety of species to which this method would be particularly applicable. Animal DNA of particular relevance may include human, feline, canine, bovine, equine, porcine, caprine, murine, lupine, ranine, piscine and simian. Plant species of interest include both monocots and dicots. Species of particular relevance include species of agricultural relevance, for example, tobacco, tomato, potato, sugar beet, pea, carrot, cauliflower, broccoli, soybean, canola, sunflower, alfalfa, cotton, Arabidopsis, wheat, maize, rye, rice, turfgrass, oat, barley, sorghum, millet, and sugarcane.

A variety of different adaptor constructs are important to the methods of the instant inventions. Upstream adaptors, downstream adaptors and recombination adaptors all have specific functions in various embodiments of the invention. In a preferred embodiment of the invention, an upstream adaptor construct may be characterized as a first domain comprising nucleotides that facilitate ligation of the construct to a nucleic acid and a second domain proximal to the first domain, comprising a site which facilitates the initiation of a nick translation reaction and a site that facilitates recombination. When this adaptor is ligated to a polynucleotide molecule it results in the only free 3' OH group capable of initiating a nick translation reaction within the second domain of the adaptor.

An alternate upstream adaptor construct useful in the context of the invention is characterized as comprising: a first oligonucleotide comprising a phosphate group at the 5' end and a blocking nucleotide at the 3' end; a second oligonucleotide comprising a blocked 3' end, a non-phosphorylated 5' end, and a nucleotide sequence complementary to the 5' element of the first oligonucleotide; and a third oligonucleotide comprising a 3' hydroxyl group, a non-phosphorylated 5' end, and a nucleotide sequence complementary to the 3' element of said first oligonucleotide. The oligonucleotides of this adaptor may be a variety of lengths, nevertheless, in preferred embodiments the first oligonucleotide is from 10 to 200 bases and the second and third oligonucleotide are from 5 to 195 bases. The first oligonucleotide may be further characterized as comprising an additional 3' tail, a 3' end protected from exonuclease activity, and/or one or more nuclease resistant nucleotide analogs. The third oligonucleotide may be further characterized as comprising a 3' end capable of initiating a nick translation reaction.

An additional upstream adaptor construct useful in the context of the invention is characterized as comprising: a first oligonucleotide including a 5' phosphate and a 3' nucleotide blocked to prevent ligation or extension by a polymerase; a second oligonucleotide comprising a domain which facilitates ligation to the template strand and a nucleotide sequence complementary to the 5' element of the first oligonucleotide; a third oligonucleotide comprising an initiation site for nick-translation and a nucleotide sequence complementary to a region of the first oligonucleotide; and a fourth, fifth and sixth oligonucleotide which comprise a nucleotide sequence complementary to a region of said first oligonucleotide and may be readily removed to expose the 3' terminus of the adaptor. In a particular embodiment of this construct, the removal of the fourth, fifth and sixth oligonucleotides creates a site that facilitates recombination.

Another adaptor construct envisioned to be useful in the context of the instant invention comprises a first domain comprising nucleotides that facilitate ligation of the construct to a nucleic acid, a second domain proximal to the first domain comprising a site which facilitates the initiation of a nick translation reaction, and a third domain proximal to the first domain, comprising a second site which facilitates the initiation of a nick translation reaction. This adaptor may be further characterized as a site that facilitates recombination. When this adaptor is ligated to a polynucleotide molecule, it results in the only free 3' OH groups capable of initiating a nick translation reaction within said second and said third domains.

The adaptor construct may further comprise a variety of features that would facilitate the manipulation of the attached DNA molecule. The adaptors may be further characterized as including a primer binding site, a nucleotide overhang, a domain that inhibits self ligation, a single ligatable terminus, a single free 3' OH group capable of initiating a nick translation reaction, one or more nuclease resistant analogs and/or at least one degradable base. Where the adaptor includes a degradable base, it may be used for the creation of a free 3' OH and may be deoxyribouracil. The site for initiation of a nick translation reaction may be further characterized as a single stranded region in an otherwise essentially double stranded molecule.

An additional adaptor construct is characterized as a first oligonucleotide comprising a phosphate group at the 5' end and a blocking nucleotide at the 3' end. A second oligonucleotide comprises a blocked 3' end, a non-phosphorylated 5' end, and a nucleotide sequence complementary to the 5' element of the first oligonucleotide. A third oligonucleotide comprises a 3' hydroxyl group, a non-phosphorylated 5' end, and a nucleotide sequence complementary to the 3' element of the first oligonucleotide. And, a fourth oligonucleotide comprises a 3' hydroxyl group, a non-phosphorylated 5' end, and a nucleotide sequence complementary to the 3' element of said first oligonucleotide. In additional embodiments, the length of the first oligonucleotide is from 10 to 200 bases while the second, third and fourth oligonucleotides may be from 5 to 195 bases. In alternate embodiments, the first oligonucleotide may be further characterized as comprising an additional 3' tail, a 3' end protected from exonuclease activity and/or one or more nuclease resistant nucleotide analogs. The third oligonucleotide may be further characterized as comprising a 3' end capable of initiating a nick translation reaction.

A further adaptor construct is characterized as comprising a first oligonucleotide comprising a 5' region comprising a 5' phosphate group and homopolymeric tract of 8–20 bases and a 3' region comprising a 12–100 base primer binding domain and a second oligonucleotide complementary to the 3' region of the first oligonucleotide. In an additional embodiment, the adaptor construct may be further characterized as comprising a recombination site.

A further adaptor construct is characterized as comprising a first oligonucleotide of 12–100 bases, wherein the 5' end of said oligonucleotide comprises a free phosphate group and a second oligonucleotide comprising a homopolymeric tract of 8–20, a 3' blocking nucleotide and wherein the 5' region of said second oligonucleotide is complementary to the first oligonucleotide. In an additional embodiment, the adaptor construct may be further characterized as comprising a recombination site.

A further adaptor construct is characterized as comprising a first oligonucleotide comprising a 5' region comprising a 12–100 base primer binding domain and a 3' region comprising a homopolymeric tract of 8–20 bases and a second oligonucleotide comprising a blocked 3' end and a 3' region complementary to the 5' region of the first oligonucleotide. In an additional embodiment, the adaptor construct may be further characterized as comprising a recombination site.

A further adaptor construct is characterized as comprising a first oligonucleotide comprising a 5' region comprising a 12–100 base primer binding domain and a second oligonucleotide comprising a homopolymeric tract of 4–12 bases at the 5' end, a blocking nucleotide at the 3' end, and a 3' region complementary to said first oligonucleotide. In an additional embodiment, the adaptor construct may be further characterized as comprising a recombination site.

In a further embodiment of the instant invention, an amplifiable region may be prepared by obtaining a DNA sample comprising DNA molecules having regions to be amplified and attaching upstream adaptor molecules to the ends of the DNA molecules of the sample to provide a nick translation initiation site. The molecules are then subjected to nick translation comprising DNA polymerization, to produce nick translate molecules. Downstream adaptor molecules are then attached to the nick translate molecules to produce adaptor attached nick translate molecules. These products may be recombined, amplified, sequenced, separated, cloned, inserted into a vector or otherwise manipulated. In a preferred embodiment, the product may be organized as a DNA library.

A preferred embodiment of the instant invention consists of a kit with alternate adaptor constructs combined with components necessary to carry out a nick translation reaction, including, for example, a DNA polymerase and nucleotide triphosphates.

In a preferred embodiment of the instant invention, the adaptor attached nick translate molecules are assembled as a microarray or an ordered microarray and which is capable of being probed for complementary sequences. In a preferred embodiment, the microarray is assembled on a DNA chip. In an embodiment involving the use of a DNA chip, the DNA chip may be used in a variety of applications, for example the analysis of patients' blood to determine chromosomal mutations or to facilitate diagnostic mutation analysis.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 12A and 12B: Positional amplification using primary "walking" PENTAmer library (after complete restriction digestion)

FIGS. 17A, 17B, 17C and 17D: Positional amplification of the large restriction DNA fragments using linear and circular genomic recombinant PENTAmer libraries of type II (two-step positional amplification)

FIGS. 18A, 18B, and 18C: Different strategies for positional amplification and sequencing of large genomes FIGS. 28A and 28B: Examples of recombination downstream nick-attaching adaptors FIG. 29: Classes of recombination adaptors FIGS. 34A and 34B: Different forms of nascent recombinant PENTAmers formed after the synthesis of PENTAmers at both ends of the DNA fragment.

FIG. 40: Adaptor constructs FIG. 61: Compositions of the recombinant lambda DNA PENTAmer junctions FIG. 63: PCR amplification of the ordered lambda DNA PENTAmer library ("positional amplification").

FIG. 64: Mbo I restriction fingerprint analysis of the ordered lambda DNA PENTAmer library.

FIG. 65: Msp I restriction fingerprint analysis of the ordered lambda DNA PENTAmer library.

FIG. 69: Sra oligos and extended regions of complementarity of Sra' paired with original Sra2.

FIG. 70: Sra oligonucleotides, lambda recombinant screening oligonucleotides, and E. coli recombinant screening oligonucleotides.

FIGS. 86A and 86B: Restriction enzyme fingerprint display of end-labeled E. coli genomic Not I PENTAmer library.

DESCRIPTION OF ILLUSTRATIVE EMBODIMENTS

Figure 1:
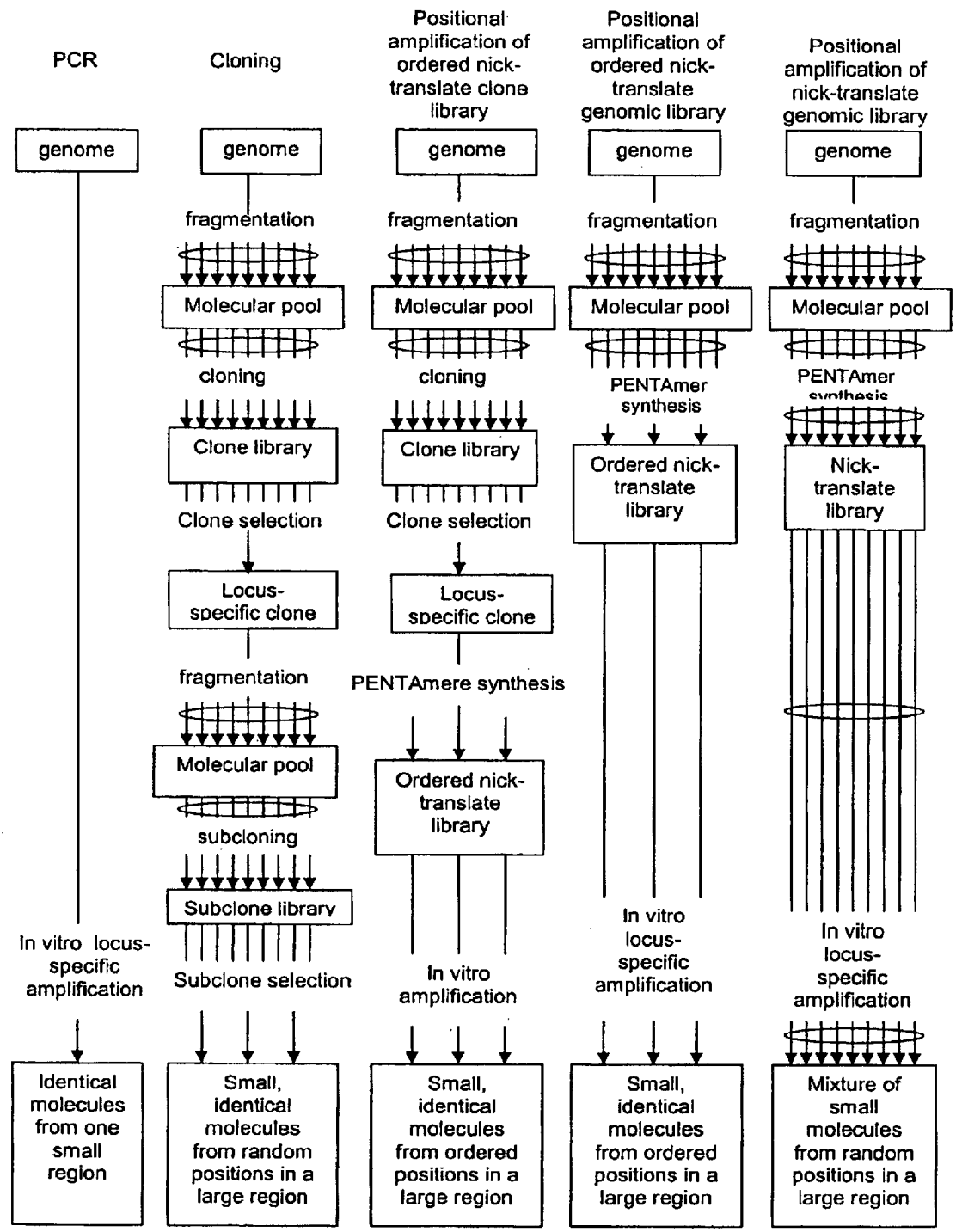
FIG. 1: Comparison of positional amplification and conventional cloning/PCR techniques with respect to DNA preparation for sequence analysis

As used herein the specification, "a" or "an" may mean one or more. As used herein in the claim(s), when used in conjunction with the word "comprising", the words "a" or "an" may mean one or more than one. As used herein "another" may mean at least a second or more.

This application incorporates by reference herein in its entirety U.S. Patent Application Serial No. 60/288,205, filed May 2, 2001 and entitled "Genome Walking by Selective Amplification of Nick-Translate DNA Library and Amplification from Complex Mixtures of Templates."

The method for creating an adaptor attached nick translate molecule (designated a PENTAmer) provides a powerful tool useful in overcoming many of the difficulties currently faced in large scale DNA manipulation, particularly genomic sequncing. This core technology can be implemented alone or in combination with other steps in order to achieve position-specific polymerization of the internal regions of small or large DNA molecules. The basic reactions for forming a primary PENTAmer are the core technology for all the applications are shown herein. Moreover, the uniqueness and advantage of the PENTAmer technology over other technologies, e.g., direct PCR amplification or ligation-mediated PCR are evident from these basic reactions.

In the simplest implementation, as set forth in FIG. 2, a PENTAmer is created and amplified by:

1) Ligating a nick-translation adaptor A to the proximal end of the source DNA (the template);
2) Initiating a nick translation reaction at the nick site of said adaptor using a DNA polymerase having 5'-3' exonuclease activity;
3) Elongating the PENT product a specific time; and
4) Appending nick-ligation adaptor B to the distal, 3' end of the PENT product to form a PENTAmer-template hybrid ("nascent PENTAmer").

While this basic technique sets forth the primary methodology envisioned by the inventors to create a PENTAmer product, it would be clear to one of ordinary skill that changes could be made in the basic application in order to achieve an analogous outcome. While the basic method is envisioned by the inventors to be a simple and efficient means of constructing a PENTAmer molecule, it is contemplated that alternate methods may facilitate carrying out the instant invention.

The PENT reaction is initiated, continued, and terminated on a largely double-stranded template, which gives the PENTAmer amplification important advantages for creating DNA for sequence analysis. An advantage of using PENTAmers to amplify different regions of the template is the fact that in most applications PENTAmers having different internal sequences have the same terminal sequences. These advantages are important for creating PENTAmers that are most useful as intermediates for in vitro or in vivo amplification. Amplification of these intermediates is more useful than direct amplification of DNA by cloning or PCR.

Initiation of the PENT reaction at the end of dsDNA molecules makes the reaction specific to terminal sites, independent of sequence. Internal sites cannot be mistakenly synthesized, e.g., by sequence-dependent mispriming during a PCR reaction. Conversely, any terminus can be made to initiate a PENT reaction, independent of sequence.

The specificity of the PENT reaction can be preserved during later steps in vitro or in vivo by incorporating distinguishable nucleotides during the reaction. For example, incorporation of exonuclease resistant nucleotides (e.g., phosphorothioates or phosphoroboronates) allows the PENT products to be stabilized during a nuclease digestion of the entire template molecule. Alternatively, an affinity label (e.g., biotinylated bases) can be added during PENT synthesis. After destruction of the template DNA or affinity isolation of the PENT products, the PENTAmers can be amplified in vitro or in vivo, without any background from non-specific amplification of the template.

Continuation of the PENT reaction on a dsDNA template allows the rate of synthesis of the strand to be independent of sequence. This allows the length of the PENTAmer to be controlled by time of the PENT reaction, independent of sequence. Such uniformity of synthesis is not possible on a single-strand template, for example, due to formation of secondary structure that can interfere with polymerization. The uniform molecular weight of the PENTAmers make them easier to amplify by cloning or PCR, which vary in efficiency for different molecular weights. The uniform molecular weight also make it possible for each PENTAmer to carry a similar amount of sequence information.

Another advantage of the uniform size of PENTAmers of different sequence, created by a single PENT reaction, is that they can be easily separated from the template DNA on the basis of molecular weight. This separation decreases the background (increases the specificity) during subsequent PCR or cloning steps.

In every replication reaction there is chance for misincorporation of the wrong nucleotide. The frequency of misincorporation is expected to be increased on a single-strand template, because the template strand can "slip" especially in repetitive DNA tracts and the polymerase can "stall" and "jump" when encountering secondary structure in the template. Replication of DNA in cells achieves high fidelity, in part because a largely double-strand template is used. Thus, the PENT reaction could have increased fidelity of base incorporation over primer extension on single-strand DNA.

Termination of the PENT reaction on a largely double-strand DNA molecule allows the PENTAmer to be separated according to the molecular weight of the parent template after the PENT. This property allows all steps creating PENTAmers to be performed on a mixture of templates of different molecular weights, which can be later fractionated by molecular weight. In many applications this allows for extensive multiplexing of the reactions to save time and effort.

The initiation site for a PENT reaction (as distinct from an oligonucleotide primer) can be introduced by any method that results in a free 3' OH group on one side of a nick or gap in otherwise double-stranded DNA, including, but not limited to such groups introduced by: a) digestion by a restriction enzyme under conditions that only one strand of the double-stranded DNA template is hydrolyzed; b) random nicking by a chemical agent or an endonuclease such as DNAase I; c) nicking by f1 gene product II or homologous enzymes from other filamentous bacteriophage (Meyer and Geider, 1979); and/or d) chemical nicking of the template directed by triple-helix formation (Grant and Dervan, 1996).

However, for PENTAmer synthesis, the primary means of initiation is through the ligation of an oligonucleotide primer onto the target nucleic acid. This very powerful and general method to introduce an initiation site for strand replacement synthesis employs a panel of special double-stranded oligonucleotide adapters designed specifically to be ligated to the termini produced by restriction enzymes. Each of these adapters is designed such that the 3' end of the restriction fragment to be sequenced can be covalently joined (ligated) to the adaptor, but the 5' end cannot. Thus the 3' end of the adaptor remains as a free 3' OH at a 1 nucleotide gap in the DNA, which can serve as an initiation site for the strand-replacement sequencing of the restriction fragment. Because the number of different 3' and 5' overhanging sequences that can be produced by all restriction enzymes is finite, and the design of each adaptor will follow the same simple strategy, above, the design of every one of the possible adapters can be foreseen, even for restriction enzymes that have not yet been identified. To facilitate sequencing, a set of such adapters for strand replacement initiation can be synthesized with labels (radioactive, fluorescent, or chemical) and incorporated into the dideoxyribonucleotide-terminated strands to facilitate the detection of the bands on sequencing gels.

More specifically, adapters with 5' and 3' extensions can be used in combination with restriction enzymes generating 2-base, 3-base and 4-base (or more) overhangs. The sense strand (the upper strand shown in Table 1 below) of the adaptor has a 5' phosphate group that can be efficiently ligated to the restriction fragment to be sequenced. The anti-sense strand (bottom, underlined) is not phosphorylated at the 5' end and is missing one base at the 3' end, effectively preventing ligation between adapters. This gap does not interfere with the covalent joining of the sense strand to the restriction fragment, and leaves a free 3' OH site in the anti-sense strand for initiation of strand replacement synthesis.

Polymerization may be terminated specific distances from the priming site by inhibiting the polymerase a specific time after initiation. For example, under specific conditions Taq DNA polymerase is capable of strand replacement at the rate of 250 bases/min, so that arrest of the polymerase after 10 min occurs about 2500 bases from the initiation site. This strategy allows for pieces of DNA to be isolated from different locations in the genome.

PENT reactions may also be terminated by incorporation of a dideoxyribonucleotide instead of the homologous naturally-occurring nucleotide. This terminates growth of the new DNA strand at one of the positions that was formerly occupied by dA, dT, dG, or dC by incorporating ddA, ddT, ddG, or ddC. In principle, the reaction can be terminated using any suitable nucleotide analogs that prevent continuation of DNA synthesis at that site. For specific mapping applications, such as the determination of the length of telomeres, the polymerization reaction can be terminated when the polymerase cannot insert a particular nucleotide, because it is missing from the reaction mixture.

The next sections provide a brief overview of materials and techniques that a person of ordinary skill would deem important to the practice of the invention. These sections are followed by a more detailed description of the various embodiments of the invention.

A. Nucleic Acids

Genes are sequences of DNA in an organism's genome encoding information that is converted into various products making up a whole cell. They are expressed by the process of transcription, which involves copying the sequence of DNA into RNA. Most genes encode information to make proteins, but some encode RNAs involved in other processes. If a gene encodes a protein, its transcription product is called mRNA ("messenger" RNA). After transcription in the nucleus (where DNA is located), the mRNA must be transported into the cytoplasm for the process of translation, which converts the code of the mRNA into a sequence of amino acids to form protein. In order to direct transport into the cytoplasm, the 3' ends of mRNA molecules are post-transcriptionally modified by addition of several adenylate residues to form the "polyA" tail. This characteristic modification distinguishes gene expression products destined to make protein from other molecules in the cell, and thereby provides one means for detecting and monitoring the gene expression activities of a cell.

The term "nucleic acid" will generally refer to at least one molecule or strand of DNA, RNA or a derivative or mimic thereof, comprising at least one nucleobase, such as, for example, a naturally occurring purine or pyrimidine base found in DNA (e.g. adenine "A," guanine "G," thymine "T" and cytosine "C") or RNA (e.g. A, G, uracil "U" and C). The term "nucleic acid" encompass the terms "oligonucleotide" and "polynucleotide." The term "oligonucleotide" refers to at least one molecule of between about 3 and about 100 nucleobases in length. The term "polynucleotide" refers to at least one molecule of greater than about 100 nucleobases in length. These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule. As used herein, a single stranded nucleic acid may be denoted by the prefix "ss", a double stranded nucleic acid by the prefix "ds", and a triple stranded nucleic acid by the prefix "ts."

Nucleic acid(s) that are "complementary" or "complement(s)" are those that are capable of base-pairing according to the standard Watson-Crick, Hoogsteen or reverse Hoogsteen binding complementarity rules. As used herein, the term "complementary" or "complement(s)" also refers to nucleic acid(s) that are substantially complementary, as may be assessed by the same nucleotide comparison set forth above. The term "substantially complementary" refers to a nucleic acid comprising at least one sequence of consecutive nucleobases, or semiconsecutive nucleobases if one or more nucleobase moieties are not present in the molecule, are capable of hybridizing to at least one nucleic acid strand or duplex even if less than all nucleobases do not base pair with a counterpart nucleobase. In certain embodiments, a "substantially complementary" nucleic acid contains at least one sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range therein, of the nucleobase sequence is capable of base-pairing with at least one single or double stranded nucleic acid molecule during hybridization. In certain embodiments, the term "substantially complementary" refers to at least one nucleic acid that may hybridize to at least one nucleic acid strand or duplex in stringent conditions. In certain embodiments, a "partly complementary" nucleic acid comprises at least one sequence that may hybridize in low stringency conditions to at least one single or double stranded nucleic acid, or contains at least one sequence in which less than about 70% of the nucleobase sequence is capable of base-pairing with at least one single or double stranded nucleic acid molecule during hybridization.

As used herein, "hybridization", "hybridizes" or "capable of hybridizing" is understood to mean the forming of a double or triple stranded molecule or a molecule with partial double or triple stranded nature. The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating at least one nucleic acid, such as a gene or nucleic acid segment thereof, or detecting at least one specific mRNA transcript or nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence of formamide, tetramethylammonium chloride or other solvent (s) in the hybridization mixture. It is generally appreciated that conditions may be rendered more stringent, such as, for example, the addition of increasing amounts of formamide.

It is also understood that these ranges, compositions and conditions for hybridization are mentioned by way of non-limiting example only, and that the desired stringency for a particular hybridization reaction is often determined empirically by comparison to one or more positive or negative controls. Depending on the application envisioned it is preferred to employ varying conditions of hybridization to achieve varying degrees of selectivity of the nucleic acid(s) towards target sequence(s). In a non-limiting example, identification or isolation of related target nucleic acid(s) that do not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

As used herein a "nucleobase" refers to a naturally occurring heterocyclic base, such as A, T, G, C or U ("naturally occurring nucleobase(s)"), found in at least one naturally occurring nucleic acid (i.e. DNA and RNA), and their naturally or non-naturally occurring derivatives and mimics. Non-limiting examples of nucleobases include purines and pyrimidines, as well as derivatives and mimics thereof, which generally can form one or more hydrogen bonds ("anneal" or "hybridize") with at least one naturally occurring nucleobase in manner that may substitute for naturally occurring nucleobase pairing (e.g. the hydrogen bonding between A and T, G and C, and A and U).

As used herein, a "nucleotide" refers to a nucleoside further comprising a "backbone moiety" generally used for the covalent attachment of one or more nucleotides to another molecule or to each other to form one or more nucleic acids. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when the nucleotide comprises derivatives or mimics of a naturally occurring 5-carbon sugar or phosphorus moiety, and non-limiting examples are described herein.

B. Restriction Enzymes

Restriction-enzymes recognize specific short DNA sequences four to eight nucleotides long (see Table 1), and cleave the DNA at a site within this sequence. In the context of the present invention, restriction enzymes are used to cleave DNA molecules at sites corresponding to various restriction-enzyme recognition sites. The site may be specifically modified to allow for the initiation of the PENT reaction. In another embodiment, if the sequence of the recognition site is known primers can be designed comprising nucleotides corresponding to the recognition sequences. These primers, further comprising PENT initiation sites may be ligated to the digested DNA.

Restriction-enzymes recognize specific short DNA sequences four to eight nucleotides long (see Table 1), and cleave the DNA at a site within this sequence. In the context of the present invention, restriction enzymes are used to cleave cDNA molecules at sites corresponding to various restriction-enzyme recognition sites. Frequently cutting enzymes, such as the four-base cutter enzymes, are preferred as this yields DNA fragments that are in the right size range for subsequent amplification reactions. Some of the preferred four-base cutters are NlaIII, DpnII, Sau3AI, Hsp92II, MboI, NdeI, Bspl431, Tsp509 I, HhaI, HinPlI, HpaII, MspI, Taq alphaI, MaeII or K2091.

As the sequence of the recognition site is known (see list below), primers can be designed comprising nucleotides corresponding to the recognition sequences. If the primer sets have in addition to the restriction recognition sequence, degenerate sequences corresponding to different combinations of nucleotide sequences, one can use the primer set to amplify DNA fragments that have been cleaved by the particular restriction enzyme. The list below exemplifies the currently known restriction enzymes that may be used in the invention.

TABLE 1

RESTRICTION ENZYMES

| Enzyme Name | Recognition Sequence |
|---|---|
| AatII | GACGTC |
| Acc65 I | GGTACC |
| Acc I | GTMKAC |
| Aci I | CCGC |
| Acl I | AACGTT |
| Afe I | AGCGCT |
| Afl II | CTTAAG |
| Afl III | ACRYGT |
| Age I | ACCGGT |
| Ahd I | GACNNNNNGTC |
| Alu I | AGCT |
| Alw I | GGATC |
| AlwN I | CAGNNNCTG |
| Apa I | GGGCCC |
| ApaL I | GTGCAC |
| Apo I | RAATTY |
| Asc I | GGCGCGCC |
| Ase I | ATTAAT |
| Ava I | CYCGRG |
| Ava II | GGWCC |
| Avr II | CCTAGG |
| Bae I | NACNNNNGTAPyCN |
| BamH I | GGATCC |
| Ban I | GGYRCC |
| Ban II | GRGCYC |
| Bbs I | GAAGAC |
| Bbv I | GCAGC |
| BbvC I | CCTCAGC |
| Bcg I | CGANNNNNNTGC |
| BciV I | GTATCC |
| Bcl I | TGATCA |
| Bfa I | CTAG |
| Bgl I | GCCNNNNNGGC |
| Bgl II | AGATCT |
| Blp I | GCTNAGC |
| Bmr I | ACTGGG |
| Bpm I | CTGGAG |
| BsaA I | YACGTR |
| BsaB I | GATNNNNATC |
| BsaH I | GRCGYC |
| Bsa I | GGTCTC |
| BsaJ I | CCNNGG |
| BsaW I | WCCGGW |
| BseR I | GAGGAG |
| Bsg I | GTGCAG |
| BsiE I | CGRYCG |
| BsiHKA I | GWGCWC |
| BsiW I | CGTACG |
| Bsl I | CCNNNNNNNGG |
| BsmA I | GTCTC |
| BsmB I | CGTCTC |
| BsmF I | GGGAC |
| Bsm I | GAATGC |
| BsoB I | CYCGRG |
| Bsp1286 I | GDGCHC |
| BspD I | ATCGAT |
| BspE I | TCCGGA |
| BspH I | TCATGA |
| BspM I | ACCTGC |
| BsrB I | CCGCTC |
| BsrD I | GCAATG |
| BsrF I | RCCGGY |
| BsrG I | TGTACA |
| Bsr I | ACTGG |
| BssH II | GCGCGC |
| BssK I | CCNGG |
| Bst4C I | ACNGT |
| BssS I | CACGAG |
| BstAP I | GCANNNNNTGC |
| BstB I | TTCGAA |
| BstE II | GGTNACC |
| BstF5 I | GGATGNN |
| BstN I | CCWGG |
| BstU I | CGCG |
| BstX I | CCANNNNNNTGG |

TABLE 1-continued

RESTRICTION ENZYMES

| Enzyme Name | Recognition Sequence |
|---|---|
| BstY I | RGATCY |
| BstZ17 I | GTATAC |
| Bsu36 I | CCTNAGG |
| Btg I | CCPuPyGG |
| Btr I | CACGTG |
| Cac8 I | GCNNGC |
| Cla I | ATCGAT |
| Dde I | CTNAG |
| Dpn I | GATC |
| Dpn II | GATC |
| Dra I | TTTAAA |
| Dra III | CACNNNGTG |
| Drd I | GACNNNNNNGTC |
| Eae I | YGGCCR |
| Eag I | CGGCCG |
| Ear I | CTCTTC |
| Eci I | GGCGGA |
| EcoN I | CCTNNNNNAGG |
| EcoO109 I | RGGNCCY |
| EcoR I | GAATTC |
| EcoR V | GATATC |
| Fau I | CCCGCNNNN |
| Fnu4H I | GCNGC |
| Fok I | GGATG |
| Fse I | GGCCGGCC |
| Fsp I | TGCGCA |
| Hae II | RGCGCY |
| Hae III | GGCC |
| Hga I | GACGC |
| Hha I | GCGC |
| Hinc II | GTYRAC |
| Hind III | AAGCTT |
| Hinf I | GANTC |
| HinP1 I | GCGC |
| Hpa I | GTTAAC |
| Hpa II | CCGG |
| Hph I | GGTGA |
| Kas I | GGCGCC |
| Kpn I | GGTACC |
| Mbo I | GATC |
| Mbo II | GAAGA |
| Mfe I | CAATTG |
| Mlu I | ACGCGT |
| Mly I | GAGTCNNNNN |
| Mnl I | CCTC |
| Msc I | TGGCCA |
| Mse I | TTAA |
| Msl I | CAYNNNNRTG |
| MspA1 I | CMGCKG |
| Msp I | CCGG |
| Mwo I | GCNNNNNNNGC |
| Nae I | GCCGGC |
| Nar I | GGCGCC |
| Nci I | CCSGG |
| Nco I | CCATGG |
| Nde I | CATATG |
| NgoMI V | GCCGGC |
| Nhe I | GCTAGC |
| Nla III | CATG |
| Nla IV | GGNNCC |
| Not I | GCGGCCGC |
| Nru I | TCGCGA |
| Nsi I | ATGCAT |
| Nsp I | RCATGY |
| Pac I | TTAATTAA |
| PaeR7 I | CTCGAG |
| Pci I | ACATGT |
| PflF I | GACNNNGTC |
| PflM I | CCANNNNNTGG |
| Ple I | GAGTC |
| Pme I | GTTTAAAC |
| Pml I | CACGTG |
| PpuM I | RGGWCCY |
| PshA I | GACNNNNGTC |
| Psi I | TTATAA |

TABLE 1-continued

RESTRICTION ENZYMES

| Enzyme Name | Recognition Sequence |
|---|---|
| PspG I | CCWGG |
| PspOM I | GGGCCC |
| Pst I | CTGCAG |
| Pvu I | CGATCG |
| Pvu II | CAGCTG |
| Rsa I | GTAC |
| Rsr II | CGGWCCG |
| Sac I | GAGCTC |
| Sac II | CCGCGG |
| Sal I | GTCGAC |
| Sap I | GCTCTTC |
| Sau3A I | GATC |
| Sau96 I | GGNCC |
| Sbf I | CCTGCAGG |
| Sca I | AGTACT |
| ScrF I | CCNGG |
| SexA I | ACCWGGT |
| SfaN I | GCATC |
| Sfc I | CTRYAG |
| Sfi I | GGCCNNNNNGGCC |
| Sfo I | GGCGCC |
| SgrA I | CRCCGGYG |
| Sma I | CCCGGG |
| Sml I | CTYRAG |
| SnaB I | TACGTA |
| Spe I | ACTAGT |
| Sph I | GCATGC |
| Ssp I | AATATT |
| Stu I | AGGCCT |
| Sty I | CCWWGG |
| Swa I | ATTTAAAT |
| Taq I | TCGA |
| Tfi I | GAWTC |
| Tli I | CTCGAG |
| Tse I | GCWGC |
| Tsp45 I | GTSAC |
| Tsp509 I | AATT |
| TspR I | CAGTG |
| Tth111 I | GACNNNGTC |
| Xba I | TCTAGA |
| Xcm I | CCANNNNNNNNNTGG |
| Xho I | CTCGAG |
| Xma I | CCCGGG |
| Xmn I | GAANNNNTTC |

Other Enzymes

Other enzymes that may be used in conjunction with the invention include nucleic acid modifying enzymes listed in the following tables.

TABLE 2

POLYMERASES AND REVERSE TRANSCRIPTASES

Thermostable DNA Polymerases:

OmniBase ™ Sequencing Enzyme
Pfu DNA Polymerase
Taq DNA Polymerase
Taq DNA Polymerase, Sequencing Grade
TaqBead ™ Hot Start Polymerase
AmpliTaq Gold
Tfl DNA Polymerase
Tli DNA Polymerase
Tth DNA Polymerase
DNA Polymerases:

DNA Polymerase I, Klenow Fragment, Exonuclease Minus
DNA Polymerase I
DNA Polymerase I Large (Klenow) Fragment
Terminal Deoxynucleotidyl Transferase
T4 DNA Polymerase

TABLE 2-continued

POLYMERASES AND REVERSE TRANSCRIPTASES

Reverse Transcriptases:

AMV Reverse Transcriptase
M-MLV Reverse Transcriptase

TABLE 3

DNA/RNA MODIFYING ENZYMES

Ligases:

T4 DNA Ligase
Kinases

T4 Polynucleotide Kinase

C. DNA Polymerases

In the context of the present invention it is generally contemplated that the DNA polymerase will retain 5'–3' exonuclease activity. Nevertheless, it is envisioned that the methods of the invention could be carried out with one or more enzymes where multiple enzymes combine to carry out the function of a single DNA polymerase molecule retaining 5'–3' exonuclease activity. Effective polymerases which retain 5'–3' exonuclease activity include, for example, *E. coli* DNA polymerase I, Taq DNA polymerase, *S. pneumoniae* DNA polymerase I, Tfl DNA polymerase, *D. radiodurans* DNA polymerase I, Tth DNA polymerase, Tth XL DNA polymerase, *M. tuberculosis* DNA polymerase I, *M. thermoautotrophicum* DNA polymerase I, Herpes simplex-1 DNA polymerase, *E. coli* DNA polymerase I Klenow fragment, vent DNA polymerase, thermosequenase and wild-type or modified T7 DNA polymerases. In preferred embodiments, the effective polymerase will be *E. coli* DNA polymerase I, *M. tuberculosis* DNA polymerase I or Taq DNA polymerase.

Where the break in the substantially double stranded nucleic acid template is a gap of at least a base or nucleotide in length that comprises, or is reacted to comprise, a 3' hydroxyl group, the range of effective polymerases that may be used is even broader. In such aspects, the effective polymerase may be, for example, *E. coli* DNA polymerase I, Taq DNA polymerase, *S. pneumoniae* DNA polymerase I, Tfl DNA polymerase, *D. radiodurans* DNA polymerase I, Tth DNA polymerase, Tth XL DNA polymerase, *M. tuberculosis* DNA polymerase I, *M. thermoautotrophicum* DNA polymerase I, Herpes simplex-1 DNA polymerase, *E. coli* DNA polymerase I Klenow fragment, T4 DNA polymerase, vent DNA polymerase, thermosequenase or a wild-type or modified T7 DNA polymerase. In preferred aspects, the effective polymerase will be *E. coli* DNA polymerase I, *M. tuberculosis* DNA polymerase I, Taq DNA polymerase or T4 DNA polymerase.

D. Hybridization

PENTAmer synthesis requires the use of primers which hybridize to specific sequences. Further, PENT and PANT reaction products may be useful as probes in hybridization analysis. The use of a probe or primer of between 13 and 100 nucleotides, preferably between 17 and 100 nucleotides in length, or in some aspects of the invention up to 1–2 kb or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Depending on the application envisioned, one would desire to employ varying conditions of hybridization to achieve varying degrees of selectivity of the probe or primers for the target sequence. For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

E. Amplification of Nucleic Acids

Nucleic acids useful as templates for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in their entirety. Briefly, two synthetic oligonucleotide primers, which are complementary to two regions of the template DNA (one for each strand) to be amplified, are added to the template DNA (that need not be pure), in the presence of excess deoxynucleotides (dNTP's) and a thermostable polymerase, such as, for example, Taq (*Thermus aquaticus*) DNA polymerase. In a series (typically 30–35) of temperature cycles, the target DNA is repeatedly denatured (around 90° C.), annealed to the primers (typically at 50–60° C.) and a daughter strand extended from the primers (72° C.). As the daughter strands are created they act as templates in subsequent cycles. Thus the template region between the two primers is amplified exponentially, rather than linearly.

A reverse transcriptase PCR™ amplification procedure may be performed to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

1. LCR

Another method for amplification is the ligase chain reaction ("LCR"), disclosed in European Patent Application No. 320,308, incorporated herein by reference. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference, describes a method similar to LCR for binding probe pairs to a target sequence.

2. Qbeta Replicase

Qbeta Replicase, described in PCT Patent Application No. PCT/US87/00880, also may be used as still another amplification method in the present invention. In this method, a replicative sequence of RNA which has a region complementary to that of a target is added to a sample in the presence of an RNA polymerase. The polymerase will copy the replicative sequence which can then be detected.

3. Isothermal Amplification

An isothermal amplification method, in which restriction endonucleases and ligases are used to achieve the amplification of target molecules that contain nucleotide 5'-[α-thio]-triphosphates in one strand of a restriction site also may be useful in the amplification of nucleic acids in the present invention. Such an amplification method is described by Walker et al. 1992, incorporated herein by reference.

4. Strand Displacement Amplification

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA.

5. Cyclic Probe Reaction

Target specific sequences can also be detected using a cyclic probe reaction (CPR). In CPR, a probe having 3' and 5' sequences of non-specific DNA and a middle sequence of specific RNA is hybridized to DNA which is present in a sample. Upon hybridization, the reaction is treated with RNase H, and the products of the probe identified as distinctive products which are released after digestion. The original template is annealed to another cycling probe and the reaction is repeated.

6. Transcription-Based Amplification

Other nucleic acid amplification procedures include transcription-based amplification systems (TAS), including nucleic acid sequence based amplification (NASBA) and 3SR, Kwoh et al., 1989; PCT Patent Application WO 88/10315 et al., 1989, each incorporated herein by reference).

In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once against with a polymerase such as T7 or SP6. The resulting products, whether truncated or complete, indicate target specific sequences.

7. Other Amplification Methods

Other amplification methods, as described in British Patent Application No. GB 2,202,328, and in PCT Patent Application No. PCT/US89/01025, each incorporated herein by reference, may be used in accordance with the present invention. In the former application, "modified" primers are used in a PCR™ like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Miller et a., PCT Patent Application WO 89/06700 (incorporated herein by reference) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts.

Other suitable amplification methods include "race" and "one-sided PCR™" (Frohman, 1990; Ohara et al., 1989, each herein incorporated by reference). Methods based on ligation of two (or more) oligonucleotides in the presence of nucleic acid having the sequence of the resulting "di-oligonucleotide", thereby amplifying the di-oligonucleotide, also may be used in the amplification step of the present invention, Wu et al., 1989, incorporated herein by reference).

F. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art. See Sambrook et al., 1989. One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

G. Separation and Quantitation Methods

Following amplification, it may be desirable to separate the amplification products of several different lengths from each other and from the template and the excess primer for the purpose analysis or more specifically for determining whether specific amplification has occurred.

1. Gel Electrophoresis

In one embodiment, amplification products are separated by agarose, agarose-acrylamide or polyacrylamide gel electrophoresis using standard methods (Sambrook et al., 1989).

Separation by electrophoresis is based upon the differential migration through a gel according to the size and ionic charge of the molecules in an electrical field. High resolution techniques normally use a gel support for the fluid phase. Examples of gels used are starch, acrylamide, agarose or mixtures of acrylamide and agarose. Frictional resistance produced by the support causes size, rather than charge alone, to become the major determinant of separation. Smaller molecules with a more negative charge will travel faster and further through the gel toward the anode of an electrophoretic cell when high voltage is applied. Similar molecules will group on the gel. They may be visualized by staining and quantitated, in relative terms, using densitometers which continuously monitor the photometric density of the resulting stain. The electrolyte may be continuous (a single buffer) or discontinuous, where a sample is stacked by means of a buffer discontinuity, before it enters the running gel/running buffer. The gel may be a single concentration or gradient in which pore size decreases with migration distance. In SDS gel electrophoresis of proteins or electrophoresis of polynucleotides, mobility depends primarily on size and is used to determined molecular weight. In pulse field electrophoresis, two fields are applied alternately at right angles to each other to minimize diffusion mediated spread of large linear polymers.

Agarose gel electrophoresis facilitates the separation of DNA or RNA based upon size in a matrix composed of a highly purified form of agar. Nucleic acids tend to become oriented in an end on position in the presence of an electric field. Migration through the gel matrices occurs at a rate inversely proportional to the $\log_{10}$ of the number of base pairs (Sambrook et al., 1989).

Polyacrylamide gel electrophoresis (PAGE) is an analytical and separative technique in which molecules, particularly proteins, are separated by their different electrophoretic mobilities in a hydrated gel. The gel suppresses convective mixing of the fluid phase through which the electrophoresis takes place and contributes molecular sieving. Commonly carried out in the presence of the anionic detergent sodium dodecylsulphate (SDS). SDS denatures proteins so that noncovalently associating sub unit polypeptides migrate independently and by binding to the proteins confers a net negative charge roughly proportional to the chain weight.

2. Chromatographic Techniques

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982). In yet another alternative, labeled cDNA products, such as biotin or antigen can be captured with beads bearing avidin or antibody, respectively.

3. Microfluidic Techniques

Microfluidic techniques include separation on a platform such as microcapillaries, designed by ACLARA BioSciences Inc., or the LabChip™ "liquid integrated circuits" made by Caliper Technologies Inc. These microfluidic platforms require only nanoliter volumes of sample, in contrast to the microliter volumes required by other separation technologies. Miniaturizing some of the processes involved in genetic analysis has been achieved using microfluidic devices. For example, published PCT Application No. WO 94/05414, to Northrup and White, incorporated herein by reference, reports an integrated micro-PCR™ apparatus for collection and amplification of nucleic acids from a specimen. U.S. Pat. Nos. 5,304,487 and 5,296,375, discuss devices for collection and analysis of cell containing samples and are incorporated herein by reference. U.S. Pat. No. 5,856,174 describes an apparatus which combines the various processing and analytical operations involved in nucleic acid analysis and is incorporated herein by reference.

4. Capillary Electrophoresis

In some embodiments, it may be desirable to provide an additional, or alternative means for analyzing the amplified genes. In these embodiment, micro capillary arrays are contemplated to be used for the analysis.

Microcapillary array electrophoresis generally involves the use of a thin capillary or channel which may or may not be filled with a particular separation medium. Electrophoresis of a sample through the capillary provides a size based separation profile for the sample. The use of microcapillary electrophoresis in size separation of nucleic acids has been reported in, for example, Woolley and Mathies, 1994. Microcapillary array electrophoresis generally provides a rapid method for size-based sequencing, PCR™ product analysis and restriction fragment sizing. The high surface to volume ratio of these capillaries allows for the application of higher electric fields across the capillary without substantial thermal variation across the capillary, consequently allowing for more rapid separations. Furthermore, when combined with confocal imaging methods, these methods provide sensitivity in the range of attomoles, which is comparable to the sensitivity of radioactive sequencing methods. Microfabrication of microfluidic devices including microcapillary electrophoretic devices has been discussed in detail in, for example, Jacobsen et al, 1994; Effenhauser et al., 1994; Harrison et al., 1993; Effenhauser et al., 1993; Manz et al., 1992; and U.S. Pat. No. 5,904,824, here incorporated by reference. Typically, these methods comprise photolithographic etching of micron scale channels on a silica, silicon or other crystalline substrate or chip, and can be readily adapted for use in the present invention. In some embodiments, the capillary arrays may be fabricated from the same polymeric materials described for the fabrication of the body of the device, using the injection molding techniques described herein.

Tsuda et al., 1990, describes rectangular capillaries, an alternative to the cylindrical capillary glass tubes. Some advantages of these systems are their efficient heat dissipation due to the large height-to-width ratio and, hence, their high surface-to-volume ratio and their high detection sensitivity for optical on-column detection modes. These flat separation channels have the ability to perform two-dimensional separations, with one force being applied across the separation channel, and with the sample zones detected by the use of a multi-channel array detector.

In many capillary electrophoresis methods, the capillaries, e.g., fused silica capillaries or channels etched, machined or molded into planar substrates, are filled with an appropriate separation/sieving matrix. Typically, a variety of sieving matrices are known in the art may be used in the microcapillary arrays. Examples of such matrices include, e.g., hydroxyethyl cellulose, polyacrylamide, agarose and the like. Generally, the specific gel matrix, running buffers and running conditions are selected to maximize the separation characteristics of the particular application, e.g., the size of the nucleic acid fragments, the required resolution, and the presence of native or undenatured nucleic acid molecules. For example, running buffers may include denaturants, chaotropic agents such as urea or the like, to denature nucleic acids in the sample.

5. Mass Spectroscopy

Mass spectrometry provides a means of "weighing" individual molecules by ionizing the molecules in vacuo and making them "fly" by volatilization. Under the influence of combinations of electric and magnetic fields, the ions follow trajectories depending on their individual mass (m) and charge (z). For low molecular weight molecules, mass spectrometry has been part of the routine physical-organic repertoire for analysis and characterization of organic molecules by the determination of the mass of the parent molecular ion. In addition, by arranging collisions of this parent molecular ion with other particles (e.g., argon atoms), the molecular ion is fragmented forming secondary ions by the so-called collision induced dissociation (CID). The fragmentation pattern/pathway very often allows the derivation of detailed structural information. Other applications of mass spectrometric methods in the known in the art can be found summarized in Methods in Enzymology, Vol. 193: "Mass Spectrometry" (McCloskey, editor), 1990, Academic Press, New York.

Due to the apparent analytical advantages of mass spectrometry in providing high detection sensitivity, accuracy of mass measurements, detailed structural information by CID in conjunction with an MS/MS configuration and speed, as well as on-line data transfer to a computer, there has been considerable interest in the use of mass spectrometry for the structural analysis of nucleic acids. Reviews summarizing this field include Schram, 1990 and Crain, 1990 here incorporated by reference. The biggest hurdle to applying mass spectrometry to nucleic acids is the difficulty of volatilizing these very polar biopolymers. Therefore, "sequencing" had been limited to low molecular weight synthetic oligonucleotides by determining the mass of the parent molecular ion and through this, confirming the already known sequence, or alternatively, confirming the known sequence through the generation of secondary ions (fragment ions) via CID in an MS/MS configuration utilizing, in particular, for the ionization and volatilization, the method of fast atomic bombardment (FAB mass spectrometry) or plasma desorption (PD mass spectrometry). As an example, the application of FAB to the analysis of protected dimeric blocks for chemical synthesis of oligodeoxynucleotides has been described (Koster et al. 1987).

Two ionization/desorption techniques are electrospray/ ionspray (ES) and matrix-assisted laser desorption/ ionization (MALDI). ES mass spectrometry was introduced by Fenn, 1984; PCT Application No. WO 90/14148 and its applications are summarized in review articles, for example, Smith 1990 and Ardrey, 1992. As a mass analyzer, a quadrupole is most frequently used. The determination of molecular weights in femtomole amounts of sample is very accurate due to the presence of multiple ion peaks which all could be used for the mass calculation.

MALDI mass spectrometry, in contrast, can be particularly attractive when a time-of-flight (TOF) configuration is used as a mass analyzer. The MALDI-TOF mass spectrometry has been introduced by Hillenkamp 1990. Since, in most cases, no multiple molecular ion peaks are produced with this technique, the mass spectra, in principle, look simpler compared to ES mass spectrometry. DNA molecules up to a molecular weight of 410,000 daltons could be desorbed and volatilized (Williams, 1989). More recently, this the use of infra red lasers (IR) in this technique (as opposed to UV-lasers) has been shown to provide mass spectra of larger nucleic acids such as, synthetic DNA, restriction enzyme fragments of plasmid DNA, and RNA transcripts upto a size of 2180 nucleotides (Berkenkamp, 1998). Berkenkamp also describe how DNA and RNA samples can be analyzed by limited sample purification using MALDI-TOF IR.

In Japanese Patent No. 59-131909, an instrument is described which detects nucleic acid fragments separated either by electrophoresis, liquid chromatography or high speed gel filtration. Mass spectrometric detection is achieved by incorporating into the nucleic acids atoms which normally do not occur in DNA such as S, Br, I or Ag, Au, Pt, Os, Hg.

6. Energy Transfer

Labeling hybridization oligonucleotide probes with fluorescent labels is a well known technique in the art and is a sensitive, nonradioactive method for facilitating detection of probe hybridization. More recently developed detection methods employ the process of fluorescence energy transfer (FET) rather than direct detection of fluorescence intensity for detection of probe hybridization. FET occurs between a donor fluorophore and an acceptor dye (which may or may not be a fluorophore) when the absorption spectrum of one (the acceptor) overlaps the emission spectrum of the other (the donor) and the two dyes are in close proximity. Dyes with these properties are referred to as donor/acceptor dye pairs or energy transfer dye pairs. The excited-state energy of the donor fluorophore is transferred by a resonance dipole-induced dipole interaction to the neighboring acceptor. This results in quenching of donor fluorescence. In some cases, if the acceptor is also a fluorophore, the intensity of its fluorescence may be enhanced. The efficiency of energy transfer is highly dependent on the distance between the donor and acceptor, and equations predicting these relationships have been developed by Forster, 1948. The distance between donor and acceptor dyes at which energy transfer efficiency is 50% is referred to as the Forster distance ($R_o$). Other mechanisms of fluorescence quenching are also known including, for example, charge transfer and collisional quenching.

Energy transfer and other mechanisms which rely on the interaction of two dyes in close proximity to produce quenching are an attractive means for detecting or identifying nucleotide sequences, as such assays may be conducted in homogeneous formats. Homogeneous assay formats are simpler than conventional probe hybridization assays which rely on detection of the fluorescence of a single fluorophore label, as heterogeneous assays generally require additional steps to separate hybridized label from free label. Several formats for FET hybridization assays are reviewed in Nonisotopic DNA Probe Techniques (1992. Academic Press, Inc., pgs. 311–352).

Homogeneous methods employing energy transfer or other mechanisms of fluorescence quenching for detection of nucleic acid amplification have also been described. Higuchi (1992), discloses methods for detecting DNA amplification in real-time by monitoring increased fluorescence of ethidium bromide as it binds to double-stranded DNA. The sensitivity of this method is limited because binding of the ethidium bromide is not target specific and background amplification products are also detected. Lee, 1993, discloses a real-time detection method in which a doubly-labeled detector probe is cleaved in a target amplification-specific manner during PCR™. The detector probe is hybridized downstream of the amplification primer so that the 5'–3' exonuclease activity of Taq polymerase digests the detector probe, separating two fluorescent dyes which form an energy transfer pair. Fluorescence intensity increases as the probe is cleaved. Published PCT application WO 96/21144 discloses continuous fluorometric assays in which enzyme-mediated cleavage of nucleic acids results in increased fluorescence. Fluorescence energy transfer is suggested for use in the methods, but only in the context of a method employing a single fluorescent label which is quenched by hybridization to the target.

Signal primers or detector probes which hybridize to the target sequence downstream of the hybridization site of the amplification primers have been described for use in detection of nucleic acid amplification (U.S. Pat. No. 5,547,861). The signal primer is extended by the polymerase in a manner similar to extension of the amplification primers. Extension of the amplification primer displaces the extension product of the signal primer in a target amplification-dependent manner, producing a double-stranded secondary amplification product which may be detected as an indication of target amplification. The secondary amplification products generated from signal primers may be detected by means of a variety of labels and reporter groups, restriction sites in the signal primer which are cleaved to produce fragments of a characteristic size, capture groups, and structural features such as triple helices and recognition sites for double-stranded DNA binding proteins.

Many donor/acceptor dye pairs known in the art and may be used in the present invention. These include, for example, fluorescein isothiocyanate (FITC)/tetramethylrhodamine isothiocyanate (TRITC), FITC/Texas Red.™. (Molecular Probes), FITC/N-hydroxysuccinimidyl 1-pyrenebutyrate (PYB), FITC/eosin isothiocyanate (EITC), N-hydroxysuccinimidyl 1-pyrenesulfonate (PYS)/FITC, FITC/Rhodamine X, FITC/tetramethylrhodamine (TAMRA), and others. The selection of a particular donor/acceptor fluorophore pair is not critical. For energy transfer quenching mechanisms it is only necessary that the emission wavelengths of the donor fluorophore overlap the excitation wavelengths of the acceptor, i.e., there must be sufficient spectral overlap between the two dyes to allow efficient energy transfer, charge transfer or fluorescence quenching. P-(dimethyl aminophenylazo) benzoic acid (DABCYL) is a non-fluorescent acceptor dye which effectively quenches fluorescence from an adjacent fluorophore, e.g., fluorescein or 5-(2'-aminoethyl) aminonaphthalene (EDANS). Any dye pair which produces fluorescence quenching in the detector nucleic acids of the invention are suitable for use in the methods of the invention, regardless of the mechanism by which quenching occurs. Terminal and internal labeling methods are both known in the art and maybe routinely used to link the donor and acceptor dyes at their respective sites in the detector nucleic acid.

7. Chip Technologies

DNA arrays and gene chip technology provides a means of rapidly screening a large number of DNA samples for their ability to hybridize to a variety of single stranded DNA probes immobilized on a solid substrate. Specifically contemplated are chip-based DNA technologies such as those described by Hacia et al., (1996) and Shoemaker et al. (1996). These techniques involve quantitative methods for analyzing large numbers of genes rapidly and accurately The technology capitalizes on the complementary binding properties of single stranded DNA to screen DNA samples by hybridization. Pease et al., 1994; Fodor et al., 1991. Basically, a DNA array or gene chip consists of a solid substrate upon which an array of single stranded DNA molecules have been attached. For screening, the chip or array is contacted with a single stranded DNA sample which is allowed to hybridize under stringent conditions. The chip or array is then scanned to determine which probes have hybridized. In the context of this embodiment, such probes could include synthesized oligonucleotides, cDNA, genomic DNA, yeast artificial chromosomes (YACs), bacterial artificial chromosomes (BACs), chromosomal markers or other constructs a person of ordinary skill would recognize as adequate to demonstrate a genetic change.

A variety of gene chip or DNA array formats are described in the art, for example U.S. Pat. Nos. 5,861,242 and 5,578,832 which are expressly incorporated herein by reference. A means for applying the disclosed methods to the construction of such a chip or array would be clear to one of ordinary skill in the art. In brief, the basic structure of a gene chip or array comprises: (1) an excitation source; (2) an array of probes; (3) a sampling element; (4) a detector; and (5) a signal amplification/treatment system. A chip may also include a support for immobilizing the probe.

In particular embodiments, a target nucleic acid may be tagged or labeled with a substance that emits a detectable signal; for example, luminescence. The target nucleic acid may be immobilized onto the integrated microchip that also supports a phototransducer and related detection circuitry. Alternatively, a gene probe may be immobilized onto a membrane or filter which is then attached to the microchip or to the detector surface itself. In a further embodiment, the immobilized probe may be tagged or labeled with a substance that emits a detectable or altered signal when combined with the target nucleic acid. The tagged or labeled species may be fluorescent, phosphorescent, or otherwise luminescent, or it may emit Raman energy or it may absorb energy. When the probes selectively bind to a targeted species, a signal is generated that is detected by the chip. The signal may then be processed in several ways, depending on the nature of the signal.

The DNA probes may be directly or indirectly immobilized onto a transducer detection surface to ensure optimal contact and maximum detection. The ability to directly synthesize on or attach polynucleotide probes to solid substrates is well known in the art. See U.S. Pat. Nos. 5,837,832 and 5,837,860 both of which are expressly incorporated by reference. A variety of methods have been utilized to either permanently or removably attach the probes to the substrate. Exemplary methods include: the immobilization of biotinylated nucleic acid molecules to avidin/streptavidin coated supports (Holmstrom, 1993), the direct covalent attachment of short, 5'-phosphorylated primers to chemically modified polystyrene plates (Rasmussen, et al., 1991), or the precoating of the polystyrene or glass solid phases with poly-L-Lys or poly L-Lys, Phe, followed by the covalent attachment of either amino- or sulfhydryl-modified oligonucleotides using bi-functional crosslinking reagents. (Running, et al., 1990); Newton, et al. (1993)). When immobilized onto a substrate, the probes are stabilized and therefore may be used repeatedly. In general terms, hybridization is performed on an immobilized nucleic acid target or a probe molecule is attached to a solid surface such as nitrocellulose, nylon membrane or glass. Numerous other matrix materials may be used, including reinforced nitrocellulose membrane, activated quartz, activated glass, polyvinylidene difluoride (PVDF) membrane, polystyrene substrates, polyacrylamide-based substrate, other polymers such as poly(vinyl chloride), poly(methyl methacrylate), poly(dimethyl siloxane), photopolymers (which contain photoreactive species such as nitrenes, carbenes and ketyl radicals capable of forming covalent links with target molecules.

Binding of the probe to a selected support may be accomplished by any of several means. For example, DNA is commonly bound to glass by first silanizing the glass surface, then activating with carbodimide or glutaraldehyde. Alternative procedures may use reagents such as 3-glycidoxypropyltrimethoxysilane (GOP) or aminopropyltrimethoxysilane (APTS) with DNA linked via amino linkers incorporated either at the 3' or 5' end of the molecule during DNA synthesis. DNA may be bound directly to membranes using ultraviolet radiation. With nitrocellous membranes, the DNA probes are spotted onto the membranes. A UV light source (Stratalinker, from Stratagene, La Jolla, Calif.) is used to irradiate DNA spots and induce cross-linking. An alternative method for cross-linking involves baking the spotted membranes at 80° C. for two hours in vacuum.

Specific DNA probes may first be immobilized onto a membrane and then attached to a membrane in contact with a transducer detection surface. This method avoids binding the probe onto the transducer and may be desirable for large-scale production. Membranes particularly suitable for this application include nitrocellulose membrane (e.g., from BioRad, Hercules, Calif.) or polyvinylidene difluoride (PVDF) (BioRad, Hercules, Calif.) or nylon membrane (Zeta-Probe, BioRad) or polystyrene base substrates (DNA.BIND™ Costar, Cambridge, Mass.).

G. Identification Methods

Amplification products must be visualized in order to confirm amplification of the target-gene(s) sequences. One typical visualization method involves staining of a gel with for example, a flourescent dye, such as ethidium bromide or Vista Green and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly, using a nucleic acid probe. Following separation of amplification products, a labeled, nucleic acid probe is brought into contact with the amplified gene(s) sequence. The probe preferably is conjugated to a chromophore but may be radiolabeled. In another embodiment, the probe is conjugated to a binding partner, such as an antibody or biotin, where the other member of the binding pair carries a detectable moiety. In other embodiments, the probe incorporates a fluorescent dye or label. In yet other embodiments, the probe has a mass label that can be used to detect the molecule amplified. Other embodiments also contemplate the use of Taqman™ and Molecular Beacon™ probes. In still other embodiments, solid-phase capture methods combined with a standard probe may be used as well.

The type of label incorporated in PCR™ products is dictated by the method used for analysis. When using capillary electrophoresis, microfluidic electrophoresis, HPLC, or LC separations, either incorporated or intercalated fluorescent dyes are used to label and detect the PCR™ products. Samples are detected dynamically, in that fluorescence is quantitated as a labeled species moves past the detector. If any electrophoretic method, HPLC, or LC is used for separation, products can be detected by absorption of UV light, a property inherent to DNA and therefore not requiring addition of a label. If polyacrylamide gel or slab gel electrophoresis is used, primers for the PCR™ can be labeled with a fluorophore, a chromophore or a radioisotope, or by associated enzymatic reaction. Enzymatic detection involves binding an enzyme to primer, e.g., via a biotin:avidin interaction, following separation of PCR™ products on a gel, then detection by chemical reaction, such as chemiluminescence generated with luminol. A fluorescent signal can be monitored dynamically. Detection with a radioisotope or enzymatic reaction requires an initial separation by gel electrophoresis, followed by transfer of DNA molecules to a solid support (blot) prior to analysis. If blots are made, they can be analyzed more than once by probing, stripping the blot, and then reprobing. If PCR™ products are separated using a mass spectrometer no label is required because nucleic acids are detected directly.

A number of the above separation platforms can be coupled to achieve separations based on two different properties. For example, some of the PCR™ primers can be coupled with a moiety that allows affinity capture, and some primers remain unmodified. Modifications can include a sugar (for binding to a lectin column), a hydrophobic group (for binding to a reverse-phase column), biotin (for binding to a streptavidin column), or an antigen (for binding to an antibody column). Samples are run through an affinity chromatography column. The flow-through fraction is collected, and the bound fraction eluted (by chemical cleavage, salt elution, etc.). Each sample is then further fractionated based on a property, such as mass, to identify individual components.

H. Sequencing

It is envisioned that amplified product will commonly be sequenced for further identification. Sanger dideoxy-termination sequencing is the means commonly employed to determine nucleotide sequence. The Sanger method employs a short oligonucleotide or primer that is annealed to a single-stranded template containing the DNA to be sequenced. The primer provides a 3' hydroxyl group which allows the polymerization of a chain of DNA when a polymerase enzyme and dNTPs are provided. The Sanger method is an enzymatic reaction that utilizes chain-terminating dideoxynucleotides (ddNTPs). ddNTPs are chain-terminating because they lack a 3'-hydroxyl residue which prevents formation of a phosphodiester bond with a succeeding deoxyribonucleotide (dNTP). A small amount of one ddNTP is included with the four conventional dNTPs in a polymerization reaction. Polymerization or DNA synthesis is catalyzed by a DNA polymerase. There is competition between extension of the chain by incorporation of the conventional dNTPs and termination of the chain by incorporation of a ddNTP.

Although a variety of polymerases may be used, the use of a modified T7 DNA polymerase (Sequenase™) was a significant improvement over the original Sanger method (Sambrook et al., 1988; Hunkapiller, 1991). T7 DNA polymerase does not have any inherent 5'–3' exonuclease activity and has a reduced selectivity against incorporation of ddNTP. However, the 3'–5' exonuclease activity leads to degradation of some of the oligonucleotide primers. Sequenase™ is a chemically-modified T7 DNA polymerase that has reduced 3' to 5' exonuclease activity (Tabor et al., 1987). Sequenase™ version 2.0 is a genetically engineered form of the T7 polymerase which completely lacks 3' to 5' exonuclease activity. Sequenase™ has a very high processivity and high rate of polymerization. It can efficiently incorporate nucleotide analogs such as dITP and 7-deaza-dGTP which are used to resolve regions of compression in sequencing gels. In regions of DNA containing a high G+C content, Hoogsteen bond formation can occur which leads to compressions in the DNA. These compressions result in aberrant migration patterns of oligonucleotide strands on sequencing gels. Because these base analogs pair weakly with conventional nucleotides, intrastrand secondary structures during electrophoresis are alleviated. In contrast, Klenow does not incorporate these analogs as efficiently.

The use of Taq DNA polymerase and mutants thereof is a more recent addition to the improvements of the Sanger method (U.S. Pat. No. 5,075,216). Taq polymerase is a thermostable enzyme which works efficiently at 70–75° C. The ability to catalyze DNA synthesis at elevated temperature makes Taq polymerase useful for sequencing templates which have extensive secondary structures at 37° C. (the standard temperature used for Klenow and Sequenase™ reactions). Taq polymerase, like Sequenase™, has a high degree of processivity and like Sequenase 2.0, it lacks 3' to 5' nuclease activity. The thermal stability of Taq and related enzymes (such as Tth and Thermosequenase™) provides an advantage over T7 polymerase (and all mutants thereof) in that these thermally stable enzymes can be used for cycle sequencing which amplifies the DNA during the sequencing reaction, thus allowing sequencing to be performed on smaller amounts of DNA. Optimization of the use of Taq in the standard Sanger Method has focused on modifying Taq to eliminate the intrinsic 5'–3' exonuclease activity and to increase its ability to incorporate ddNTPs to reduce incorrect termination due to secondary structure in the single-stranded template DNA (EP 0 655 506 B1). The introduction of fluorescently labeled nucleotides has further allowed the introduction of automated sequencing which further increases processivity.

I. DNA Immobilization

Immobilization of the DNA may be achieved by a variety of methods involving either non-covalent or covalent interactions between the immobilized DNA comprising an anchorable moiety and an anchor. In a preferred embodiment of the invention, immobilization consists of the non-covalent coating of a solid phase with streptavidin or avidin and the subsequent immobilization of a biotinylated polynucleotide (Holmstrom, 1993). It is further envisioned that immobilization may occur by precoating a polystyrene or glass solid phase with poly-L-Lys or poly L-Lys, Phe, followed by the covalent attachment of either amino- or sulfhydryl-modified polynucleotides using bifunctional crosslinking reagents (Running, 1990 and Newton, 1993).

Immobilization may also take place by the direct covalent attachment of short, 5'-phosphorylated primers to chemically modified polystyrene plates ("Covalink" plates, Nunc) Rasmussen, (1991). The covalent bond between the modified oligonucleotide and the solid phase surface is introduced by condensation with a water-soluble carbodiimide. This method facilitates a predominantly 5'-attachment of the oligonucleotides via their 5'-phosphates.

Nikiforov et al. (U.S. Pat. No. 5,610,287 incorporated herein by reference) describes a method of non-covalently immobilizing nucleic acid molecules in the presence of a salt or cationic detergent on a hydrophilic polystyrene solid support containing a hydrophilic moiety or on a glass solid support. The support is contacted with a solution having a pH of about 6 to about 8 containing the synthetic nucleic acid and a cationic detergent or salt. The support containing the immobilized nucleic acid may be washed with an aqueous solution containing a non-ionic detergent without removing the attached molecules.

Another commercially available method envisioned by the inventors to facilitate immobilization is the "Reacti-Bind.TM. DNA Coating Solutions" (see "Instructions—Reacti-Bind.TM. DNA Coating Solution" January 1997). This product comprises a solution that is mixed with DNA and applied to surfaces such as polystyrene or polypropylene. After overnight incubation, the solution is removed, the surface washed with buffer and dried, after which it is ready for hybridization. It is envisioned that similar products, i.e. Costar "DNA-BINDTM" or. Immobilon-AV Affinity Membrane (IAV, Millipore, Bedford, Mass.) are equally applicable to immobilize the respective fragment.

J. Analysis of Data

Gathering data from the various analysis operations will typically be carried out using methods known in the art. For example, microcapillary arrays may be scanned using lasers to excite fluorescently labeled targets that have hybridized to regions of probe arrays, which can then be imaged using charged coupled devices ("CCDs") for a wide field scanning of the array. Alternatively, another particularly useful method for gathering data from the arrays is through the use of laser confocal microscopy which combines the ease and speed of a readily automated process with high resolution detection. Scanning devices of this kind are described in U.S. Pat. Nos. 5,143,854 and 5,424,186.

Following the data gathering operation, the data will typically be reported to a data analysis operation. To facilitate the sample analysis operation, the data obtained by a reader from the device will typically be analyzed using a digital computer. Typically, the computer will be appropriately programmed for receipt and storage of the data from the device, as well as for analysis and reporting of the data gathered, i.e., interpreting fluorescence data to determine the sequence of hybridizing probes, normalization of background and single base mismatch hybridizations, ordering of sequence data in SBH applications, and the like, as described in, e.g., U.S. Pat. Nos. 4,683,194, 5,599,668 and 5,843,651 incorporated herein by reference.

K. Kits

The materials and reagents required for performing the PENT reactions and producing PENTAmeres from a biological sample may be assembled together in a kit. The kits of the invention also will generally comprise one or more preselected primer sets and/or probes that may be specifically designed for the amplification to be performed. Preferably, the kits will comprise, in suitable container means, one or more nucleic acid primer sets, the necessary reagents for amplification and isolation and potentially a means for detecting nucleic acid products. In certain embodiments, such as in kits for use in amplification reactions, the means for detecting the nucleic acids may be a label, such as a fluorophore, a radiolabel, an enzyme tag, etc., that is linked to the nucleic acid primer or the nucleotides themselves. It is envisioned that kits may contain DNA samples for standardization.

Preferred kits are those suitable for use in PCR™. In PCR™ kits, two primers will preferably be provided that have sequences from, and that hybridize to, specific adaptor sequences. Also included in PCR™ kits may be enzymes suitable for amplifying nucleic acids, including various polymerases (RT, Taq, etc.), deoxynucleotides and buffers to provide the necessary reaction mixture for amplification.

In each case, the kits will preferably comprise distinct containers for each individual reagent and enzyme, as well as for each probe or primer pair. Each biological agent will generally be suitable aliquoted in their respective containers. The container means of the kits will generally include at least one vial or test tube. Flasks, bottles and other container means into which the reagents are placed and aliquoted are also possible. The individual containers of the kit will preferably be maintained in close confinement for commercial sale. Suitable larger containers may include injection or blow-molded plastic containers into which the desired vials are retained. Instructions may be provided with the kit.

L. Plants

The term "plant," as used herein, refers to any type of plant. The inventors have provided below an exemplary description of some plants that may be used with the invention. However, the list is not in any way limiting, as other types of plants will be known to those of skill in the art and could be used with the invention.

A common class of plants exploited in agriculture are vegetable crops, including artichokes, kohlrabi, arugula, leeks, asparagus, lettuce (e.g., head, leaf, romaine), bok choy, malanga, broccoli, melons (e.g., muskmelon, watermelon, crenshaw, honeydew, cantaloupe), brussels sprouts, cabbage, cardoni, carrots, napa, cauliflower, okra, onions, celery, parsley, chick peas, parsnips, chicory, chinese cabbage, peppers, collards, potatoes, cucumber plants (marrows, cucumbers), pumpkins, cucurbits, radishes, dry bulb onions, rutabaga, eggplant, salsify, escarole, shallots, endive, garlic, spinach, green onions, squash, greens, beet (sugar beet and fodder beet), sweet potatoes, swiss chard, horseradish, tomatoes, kale, turnips, and spices.

Other types of plants frequently finding commercial use include fruit and vine crops such as apples, apricots, cherries, nectarines, peaches, pears, plums, prunes, quince almonds, chestnuts, filberts, pecans, pistachios, walnuts, citrus, blueberries, boysenberries, cranberries, currants, loganberries, raspberries, strawberries, blackberries, grapes, avocados, bananas, kiwi, persimmons, pomegranate, pineapple, tropical fruits, pomes, melon, mango, papaya, and lychee.

Many of the most widely grown plants are field crop plants such as evening primrose, meadow foam, corn (field, sweet, popcorn), hops, jojoba, peanuts, rice, safflower, small grains (barley, oats, rye, wheat, etc.), sorghum, tobacco, kapok, leguminous plants (beans, lentils, peas, soybeans), oil plants (rape, mustard, poppy, olives, sunflowers, coconut, castor oil plants, cocoa beans, groundnuts), fibre plants (cotton, flax, hemp, jute), lauraceae (cinnamon, camphor), or plants such as coffee, sugarcane, tea, and natural rubber plants.

Still other examples of plants include bedding plants such as flowers, cactus, succulents and ornamental plants, as well as trees such as forest (broad-leaved trees and evergreens, such as conifers), fruit, ornamental, and nut-bearing trees, as well as shrubs and other nursery stock.

M. Animals

The term "animal," as used herein, refers to any type of animal. The inventors have provided below an exemplary description of some animals that may be used with the invention. However, the list is not in any way limiting, as other types of animals will be known to those of skill in the art and could be used with the invention.

For the purpose of the instant invention, the term animal is expressly construed to include humans.

In addition to humans, other animals of importance in the context of the instant invention are those animals deemed of commercial relevance. Animals of commercial relevance specifically include domesticated species including companion and agricultural species.

The following sections provide a detailed description of specific embodiments and applications of the instant invention.

N. Principles of Creating PENTAmers to Amplify the Terminal and Internal Regions of a Single DNA Template Using specific methods and compositions, a terminal or internal region of a DNA template can be synthesized as an amplifiable DNA strand (a PENTAmer). The methods comprise nick-translation reactions that are initiated and terminated at controlled positions within the template and methods to separate and recombine the products of the nick translation reactions. The compositions comprise oligonucleotide adaptor molecules that become attached to the 3' and 5' ends of the nick translated strands that are specifically designed to initiate the nick-translation reaction and serve as priming sites during PENTAmer amplification. Additional compositions comprise oligonucleotides designed to direct intramolecular recombination reactions involving the PENTAmers.

1. Primary PENTAmers

The basic reactions forming a primary PENTAmer is the core technology for most of the applications shown in this disclosure. Moreover, the uniqueness and advantage of the PENTAmer technology over other technologies, e.g., direct PCR amplification or ligation-mediated PCR are evident from these basic reactions.

a. Creation of a Primary PENTAmer

Figure 2A:
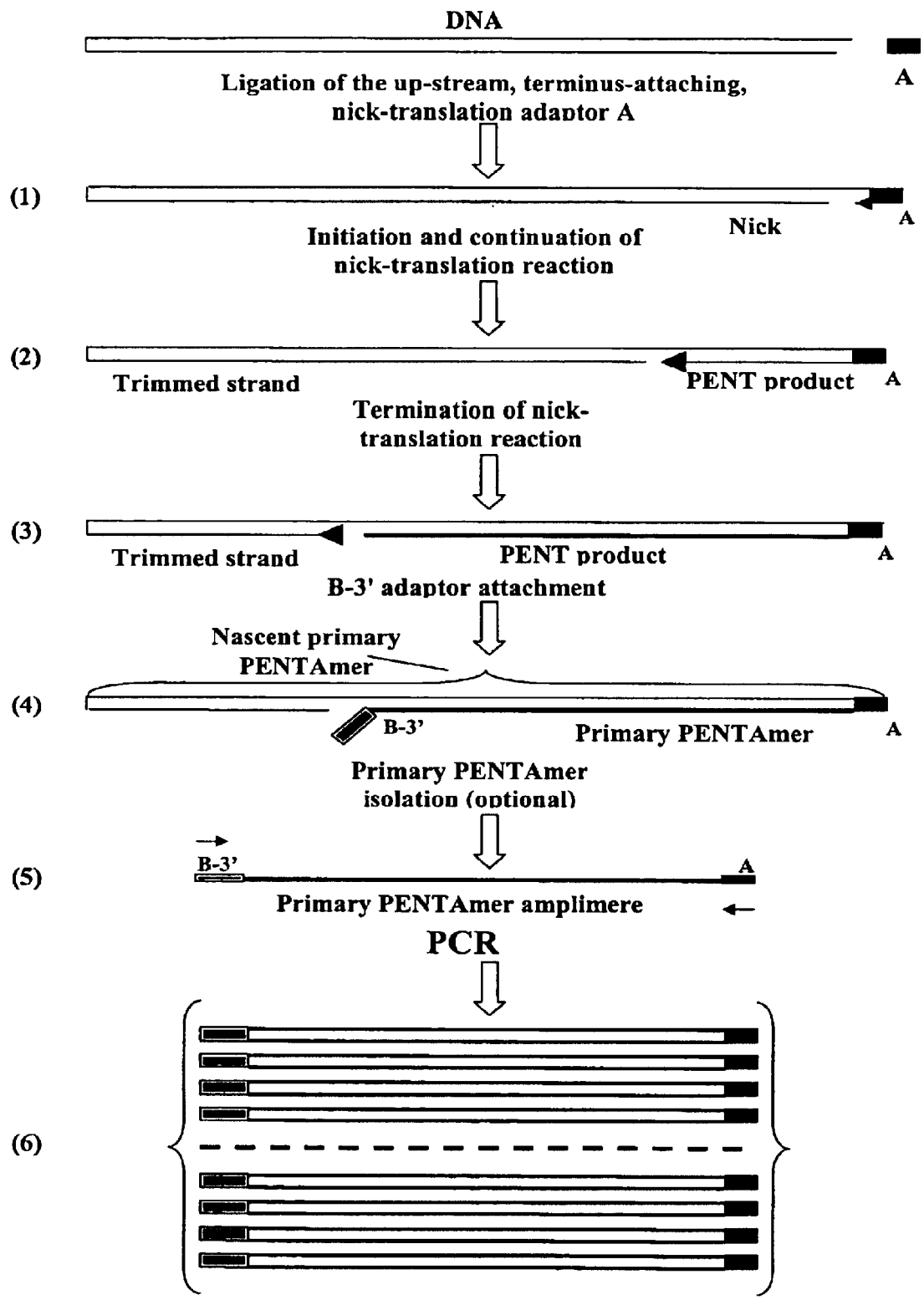
FIGS. 2A and 2B: Synthesis of primary and complement PENTAmers

In the simplest implementation, shown in FIG. 2A, the primary PENTAmer is created by:

Ligating an up-stream, terminus-attaching, nick-translation adaptor A to the proximal end of the template DNA;

Initiating a PENT reaction at the proximal end of the template using adaptor A, a DNA polymerase with 5'–3' exonuclease activity, and nucleotide triphosphates;

Continuing the nick-translation reaction a specified time to create a nick-translation product of a specified length;

Appending a down-stream, nick-attaching adaptor B-3' to the distal, 3' end of the PENT product to form a PENTAmer, comprising a covalently intact strand containing adaptor A, the nick-translation product strand, and adaptor B-3'.

Nick-translation has created the PENTAmer as a single strand, hydrogen bonded to the template. This double-stranded PENTAmer-template hybrid is called a "nascent primary PENTAmer." The PENTAmer can undergo subsequent preparative and analytical steps as the double-stranded nascent PENTAmer or as a single-stranded molecule, after separation from the template by denaturation (e.g., heating or alkaline treatment), or destruction of the template.

Specific designs for the adaptors and methods for attaching the adaptors to the terminus and nick used in steps 1 and 4 are described below.

2. Creation of a Primary PENTAmer with Modified Nucleotides

For purposes of distinguishing the synthetic PENTAmer strand from template strands, modified nucleotides can be incorporated during the nick-translation reaction and/or in the adaptors. Subsequent steps can separate the PENTAmer strand from the template strands. For example, affinity chromatography can be used to isolate the molecules containing the modified nucleotides from those that do not. Alternatively, chemical or enzymatic treatment can be used to destroy the template strands. For example, incorporation of exonuclease-resistant nucleotides (e.g., phosphorothioates or phosphoroboronates) allows the PENT products to be stabilized during a nuclease digestion of the entire template molecule. After destruction of the template DNA or affinity isolation of the PENT products, the PENTAmers can be amplified in vitro or in vivo, without any background from non-specific amplification of the template.

3. Unique Features of the PENT Reaction and Primary PENTAmers a. Specificity and Efficiency of Initiation of Nick-Translation Reaction on a Double Strand Template The nick-translation reaction is specific to the end of the double-strand template to which the upstream terminus-attaching adaptor has been ligated. In this simplest example of the nick-translation reaction at a single end of the template, the adaptor can be specifically targeted to the desired end by employing an asymmetric template, i.e., with one terminus cleaved with a first restriction enzyme and second terminus cleaved using a different agent such as a second endonuclease, a chemical, or hydrodynamic force, which creates a non-complementary structure at the distal end. Initiation of the PENT reaction at the end of double-stranded DNA molecules makes the reaction specific to terminal sites, independent of sequence. Internal sites cannot be mistakenly synthesized, e.g., by sequence-dependent mispriming on an internal sequence.

b. Control of the Length of the Nick-Translation Product

Continuation of the PENT reaction on a dsDNA template allows the rate of synthesis of the strand to be nearly independent of sequence. This allows the length of the primary PENTAmer to be controlled to within narrow limits by adjusting time of the PENT reaction, independent of sequence. Such uniformity of synthesis is not possible on a single-strand template, for example, due to formation of secondary structure that can interfere with polymerization. The uniform molecular weight of the primary PENTAmers make them easier to amplify by cloning or PCR, which vary in efficiency for different molecular weights. The uniform molecular weight also makes it possible for each PENTAmer to carry a similar amount of sequence information. For these purposes it is important that the template DNA not have an excessive number of nicks or gaps, because a nick or gap on the template strand will lead to termination of nick translation of the opposite strand. This is fundamentally different than conditions used for uncontrolled nick-translation reactions, e.g., those used to radioactively label DNA. These labeling reactions create molecules of random length that start at random sites within the native template and are often terminated at random nicks within the template strand.

Another advantage of the uniform size of primary PENTAmers of different sequence, created by a single PENT reaction, is that they can be easily separated from the template DNA on the basis of molecular weight. This separation decreases the background (increases the specificity) during subsequent PCR or cloning steps.

c. Unique Position of the 5' end of the PENTAmer and Variable Position of the 3' End of the PENTAmer The 5' terminus and sequences adjacent to the 5' terminus of the primary PENTAmer are unique by virtue of the unique initiation site for nick translation. In contrast, the 3' terminus of the PENTAmer has a unique adaptor sequence but a variable sequence adjacent to the adaptor, because the nick translation reaction does not proceed an exact number of bases from the initiation site. There is a continuous distribution of lengths of the nick-translation products, and thus of the PENTAmer. Experimental results (e.g., Makarov et al., 1997) show that the uncertainty in PENTAmer length is about 10% of the average length.

d. High Fidelity of Replication of a Double-Strand Template

In every replication reaction there is chance for misincorporation of the wrong nucleotide. The frequency of misincorporation is expected to be higher on a single-strand template because the template strand can "slip," especially in repetitive DNA tracts, and the polymerase can "stall" and "jump" when encountering secondary structure in the template. Replication of DNA in cells achieves high fidelity, in part because a largely double-strand template is used. The PENT reaction is expected to have increased fidelity of base incorporation than primer extension on single-strand DNA.

e. Nascent Primary PENTAmer Remains a Part of Double-Strand Template

Time-controlled termination of the PENT reaction on a largely double-strand DNA template allows the primary PENTAmer to be separated according to the molecular weight of the parent template after synthesis of the PENTAmer.

4. Amplification of a PENTAmer or Nascent PENTAmer

A PENTAmer can be amplified in vitro or in vivo using specific sequences on one or both adaptors. For example, a PENTAmer can be linearly amplified using primers complementary to adaptor B-3' or adaptor A, or exponentially amplified by PCR using primer sequence A and primer sequence B-3'. A nascent PENTAmer can be amplified by any means possible for double-stranded templates, such as transcription by an RNA polymerase, strand displacement amplification, etc. The specificity and efficiency of amplification can be increased, if necessary, using any of the common techniques available for those purposes including, but not limited to 1) using nested PCR primers; 2) using different temperatures, times, and conditions; and/or 3) using different combinations of polymerases. After conversion into a double-stranded molecule by primer extension or by PCR amplification, a PENTAmer can be cloned into any of a number of bacterial or viral vectors.

5. Sequencing of PENTAmers

PENTAmers can be subjected to any sequencing reactions, including the Sanger dideoxyribonucleotide termination reactions and cycle sequencing reactions using, for example, primers complementary to sequences on the upstream terminus-attaching adaptor A.

PENTAmers from a single template terminate at sequences that are complementary to different positions within the template, because the nick-translation reaction has terminated at different positions on different copies of the template molecule. Therefore the 3' ends of the PENTAmers have heterogeneous sequence and the 3' end of the sequencing primer cannot be complementary to adaptor B-3'.

PENTAmers with unique 3' ends can be prepared for sequencing by two methods:

First, the PENTAmers with heterogeneous 3' ends can be cloned into a bacterial or viral vector. Each PENTAmer clone will have unique sequence and can be sequenced from either terminus.

Second, uncloned PENTAmers with heterogeneous sequences adjacent to the downstream adaptor can be amplified or sequenced as unique molecules using a "selection" primer with 5' terminus complementary to the downstream nick-attaching adaptor B-3' and 3' terminus complementary to a specific sequence present at the 3' end of the nick-translation product. In one embodiment, downstream primers with different 3' termini are tested by trial and error and the primer that is specific that is complementary to a PENTAmer with unique sequence used for the amplification or sequencing reaction.

PENTAmer amplification of the termini of a template is distinct from direct amplification of DNA fragments using random-prime PCR, which amplifies random internal regions. PENTAmer amplification is distinct from direct amplification of DNA termini using conventional techniques of one-sided PCR and strand-displacement amplification, which result in amplimers of heterogeneous size. PENTAmers are amplified as molecules of uniform size.

6. Construction of Ordered Primary PENTAmers

Figure 4:
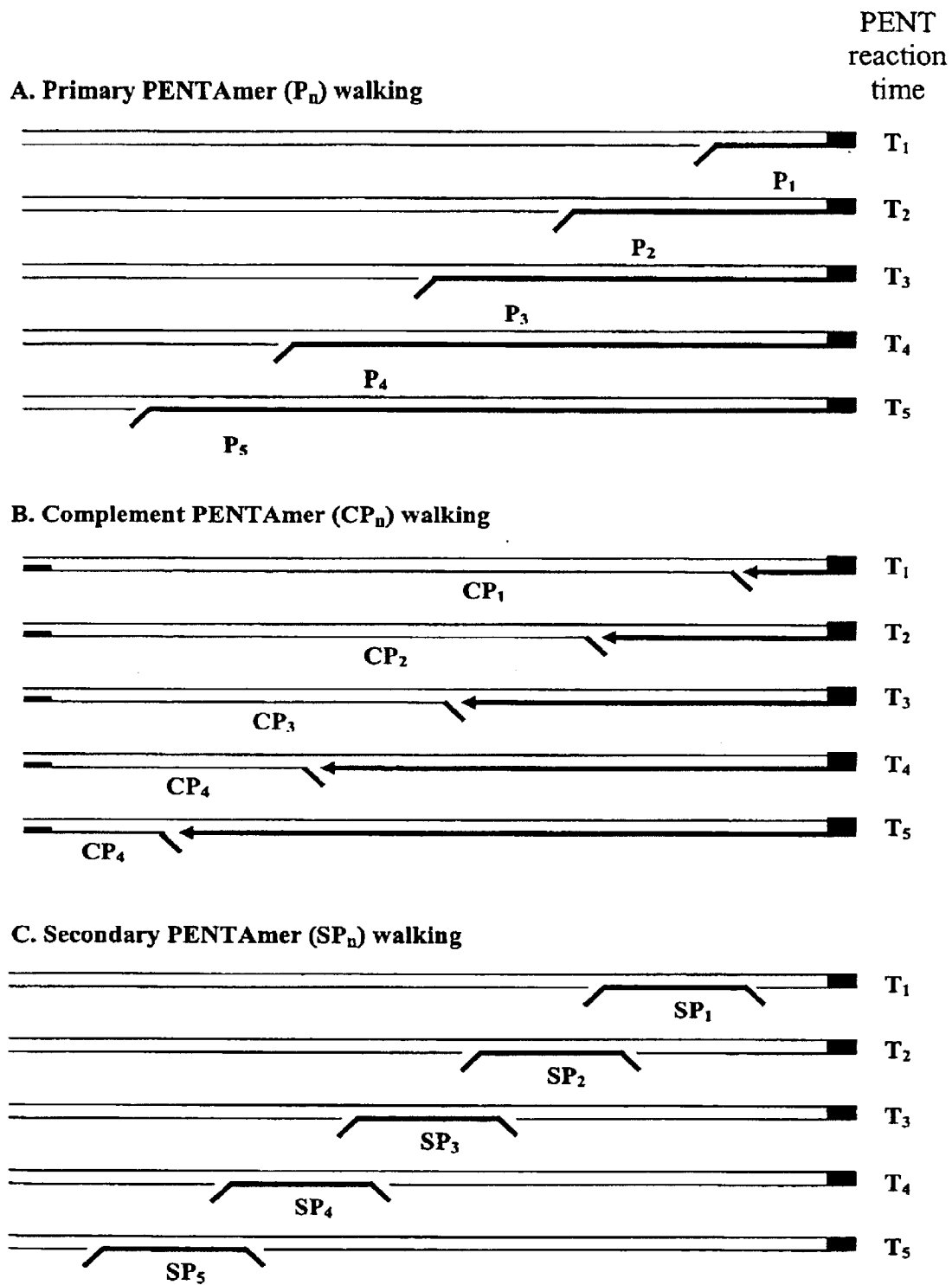
FIG. 4: Time-controlled PENTAmer-mediated walking

Different times of PENT reaction produce primary PENTAmers of different lengths having 3' ends different distances from the end of the template (FIG. 4A). The 3' end of the primary PENTAmer can be 10 kb or more from the end of the template. PENTAmer molecules created by different reaction times can be organized into a library of ordered PENTAmers that can be amplified in vitro as an ordered library of amplified DNA molecules or in vivo as ordered clones. PENTAmers from different internal regions of the template can also be pooled into a mixture of amplimers or clones from a large region.

Primary PENTAmers created by different times of the PENT reaction can be used as template for polymerization reactions localized to the 3' ends of the primary PENTAmers using conventional techniques, such as a) ligation-mediated PCR; b) strand displacement amplification; or c) RNA transcription. Alternatively, a second PENT reaction can be initiated from the 3' end of the primary PENTAmer, as described in subsection 8, below.

7. Complement PENTAmers

Synthesis of the PENT product is coordinated with unidirectional degradation of one of the template DNA strands by the 5' exonuclease activity of the polymerase used for nick-translation. Appending a nick-attaching adaptor to the 5' terminus of the degraded DNA strand results in a creation of a new type of amplimer, which is termed herein a complement PENTAmer.

a. Creation of a Complement PENTAmer

Figure 2B:
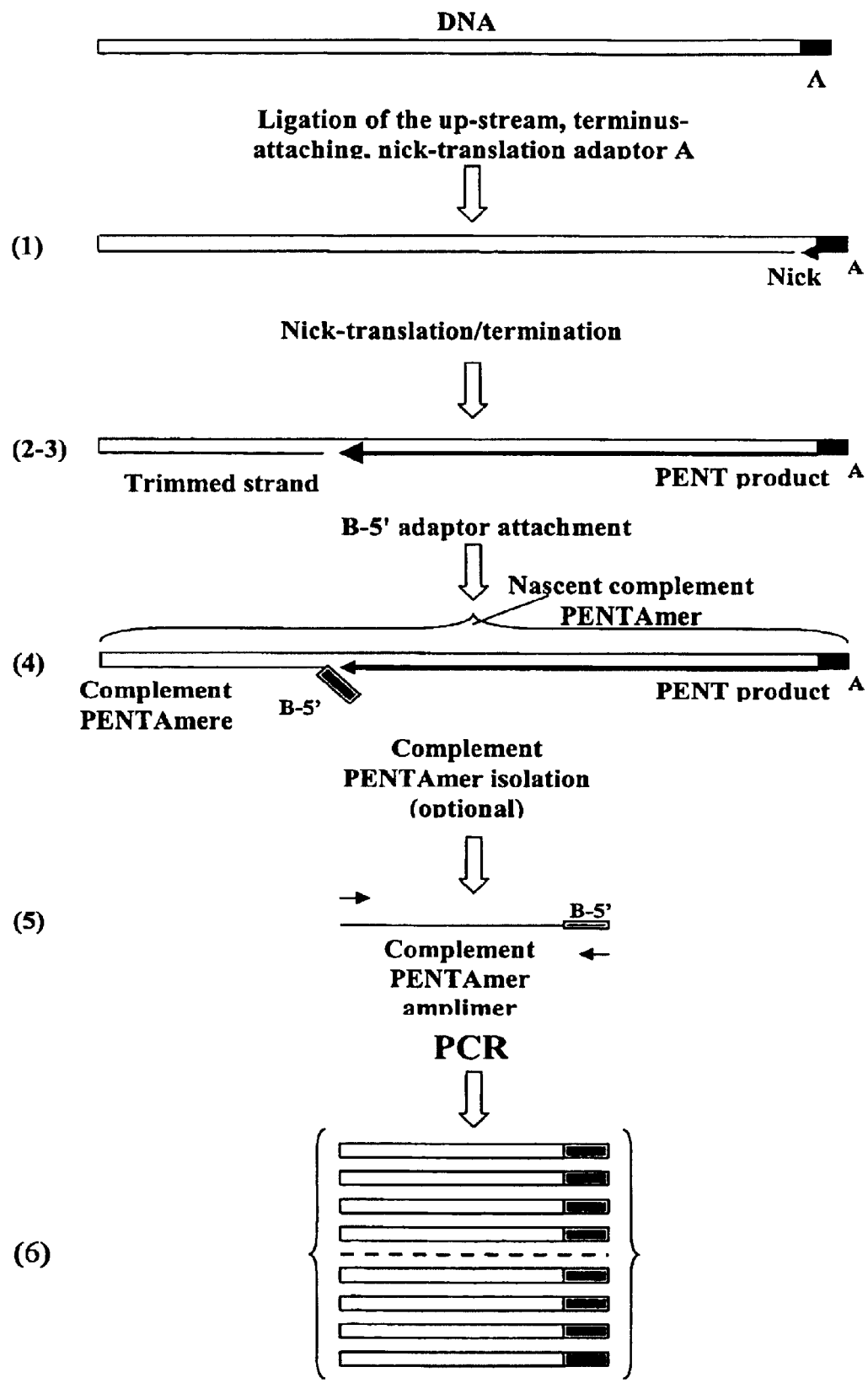

In the simplest implementation, shown in FIG. 2B, the complement PENTAmer is created and amplified by:

Ligating an up-stream, terminus-attaching, nick-translation adaptor A to the proximal end of the template DNA;

Initiating a PENT reaction at the proximal end of the template using adaptor A;

Elongating the PENT product a specific time, T;

Appending an up-stream nick-attaching adaptor B-5' to the 5' end of the degraded template DNA strand to form a complement PENTAmer-template hybrid ("nascent complement PENTAmer"); and (Optionally) separating the single-stranded complement PENTAmer from the template (e.g., by denaturation).

b. Amplification of a Complement PENTAmer

A complement PENTAmer can be amplified in vitro or in vivo by the same means used to amplify primary PENTAmers, except initiating syntheses at adaptor sequence A and/or adaptor sequence B-5'.

c. Construction of an Ordered Complement PENTAmers

Different times of PENT reaction produce complement PENTAmers of different lengths having 5' ends different distances from the end of the template (FIG. 4B). The 5' end of the complement PENTAmer can be 10 kb or more from the end of the template. Complement PENTAmers created by different nick-translation reaction times can be organized into a ordered complement PENTAmers that can be amplified in vitro as an ordered set of amplified DNA molecules or in vivo as an ordered set of clones. Complement PENTAmers from different internal regions of the template can also be pooled into a mixture of amplimers from a large region or unordered clones.

d. Unique Features of the Complement PENTAmer

The sum of the lengths of the primary PENTAmer and the complement PENTAmers is constant and equal to the length of the original template DNA strand. The complement PENTAmer has all unique features of the primary PENTAmer, however increasing times of the PENT reaction result in shorter complement PENTAmers.

8. Secondary PENTAmers a. Creation of Secondary PENTAmers

Secondary PENTAmers are created by two nick-translation reactions. The length of the first PENT reaction determines the distance of one end of the secondary PENTAmer from the initiation position, whereas the second (shorter) PENT reaction determines the length of the secondary PENTAmer. The advantage of secondary PENTAmers is that the position of the PENTAmer within the template DNA and the length of the PENTAmer are independently controlled.

There are two methods to synthesize a secondary PENTAmer.

Figure 3A:
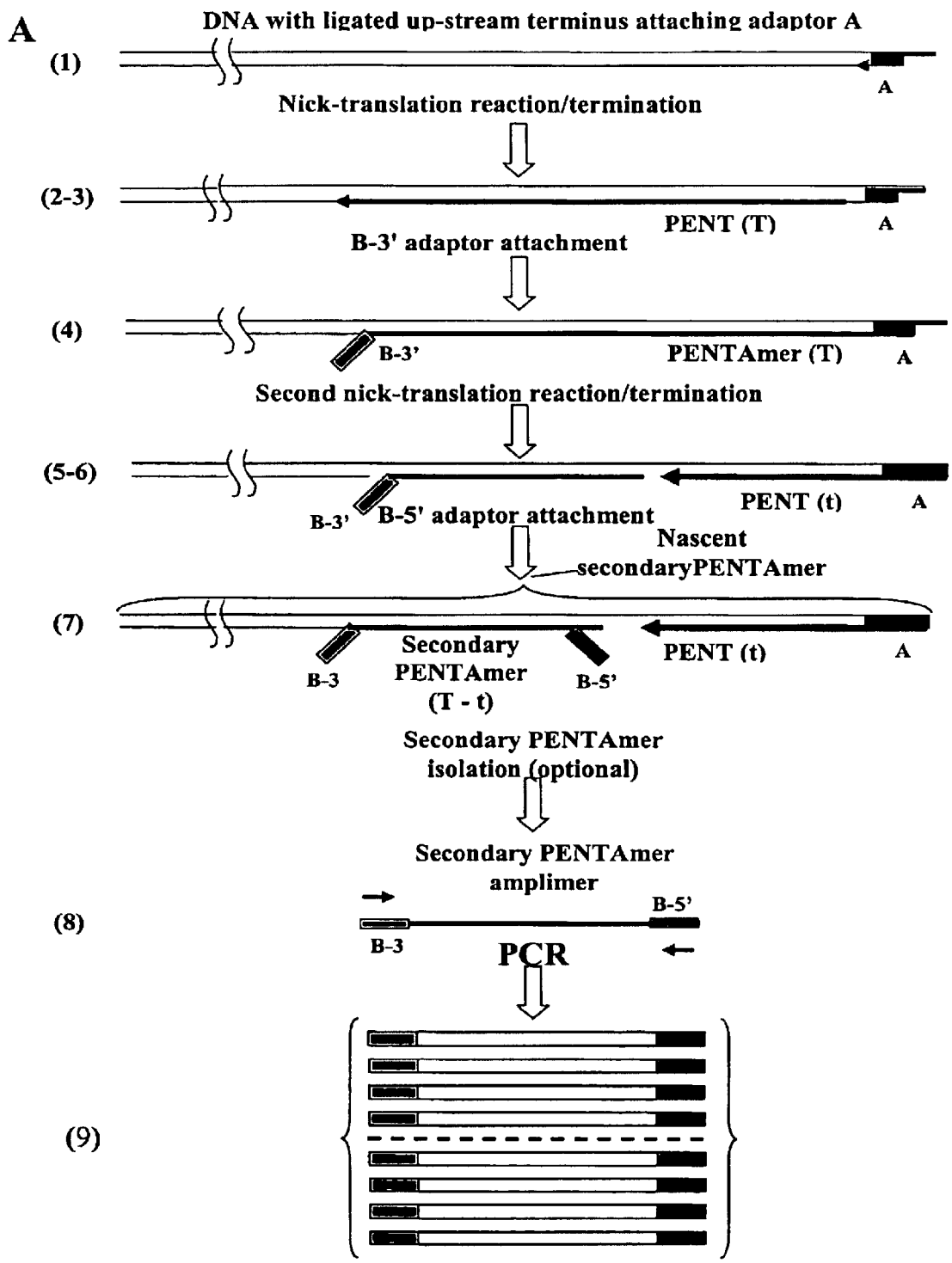
FIGS. 3A and 3B: Synthesis of secondary PENTAmers

In the first method (FIG. 3A) a secondary PENTAmer is created and amplified by:

Ligating an up-stream, terminus-attaching, nick translation adaptor A to the proximal end of the template DNA molecule;

Initiating a first PENT reaction at the proximal end of the source DNA molecule using up-stream adaptor A;

Elongating the first PENT product a specific time T;

Appending a first, down-stream nick-attaching adaptor B-3' to the distal, 3' end of the first PENT product;

Initiating a second PENT reaction at the same proximal end of the source DNA molecule using the up-stream adaptor A;

Elongating the second PENT product a specific time t;

Appending a second, up-stream nick-attaching adaptor B-5' to the 5' end of the degraded first PENT product;

(Optionally) separating the single-stranded secondary PENTAmer of length from the template (e.g., by denaturation);

A secondary PENTAmer of the first type can be amplified in vitro or in vivo using the same methods used to amplify a primary PENTAmer, except polymerization reactions begin at adaptor sequence B-3' and/or adaptor sequence B-5'.

In the second method (FIG. 3B) a secondary PENTAmer is created by:

Ligating an up-stream, terminus-attaching, nick translation adaptor A to the proximal end of the template DNA molecule;

Initiating a first PENT reaction at the proximal end of the source DNA molecule using adaptor A;

Elongating the PENT product a specific time T;

Appending a first down-stream, nick-attaching adaptor B-3' (I) to the distal, 3' end of the PENT product;

Separating the single-stranded primary PENTAmer from the template

Figure 3B:
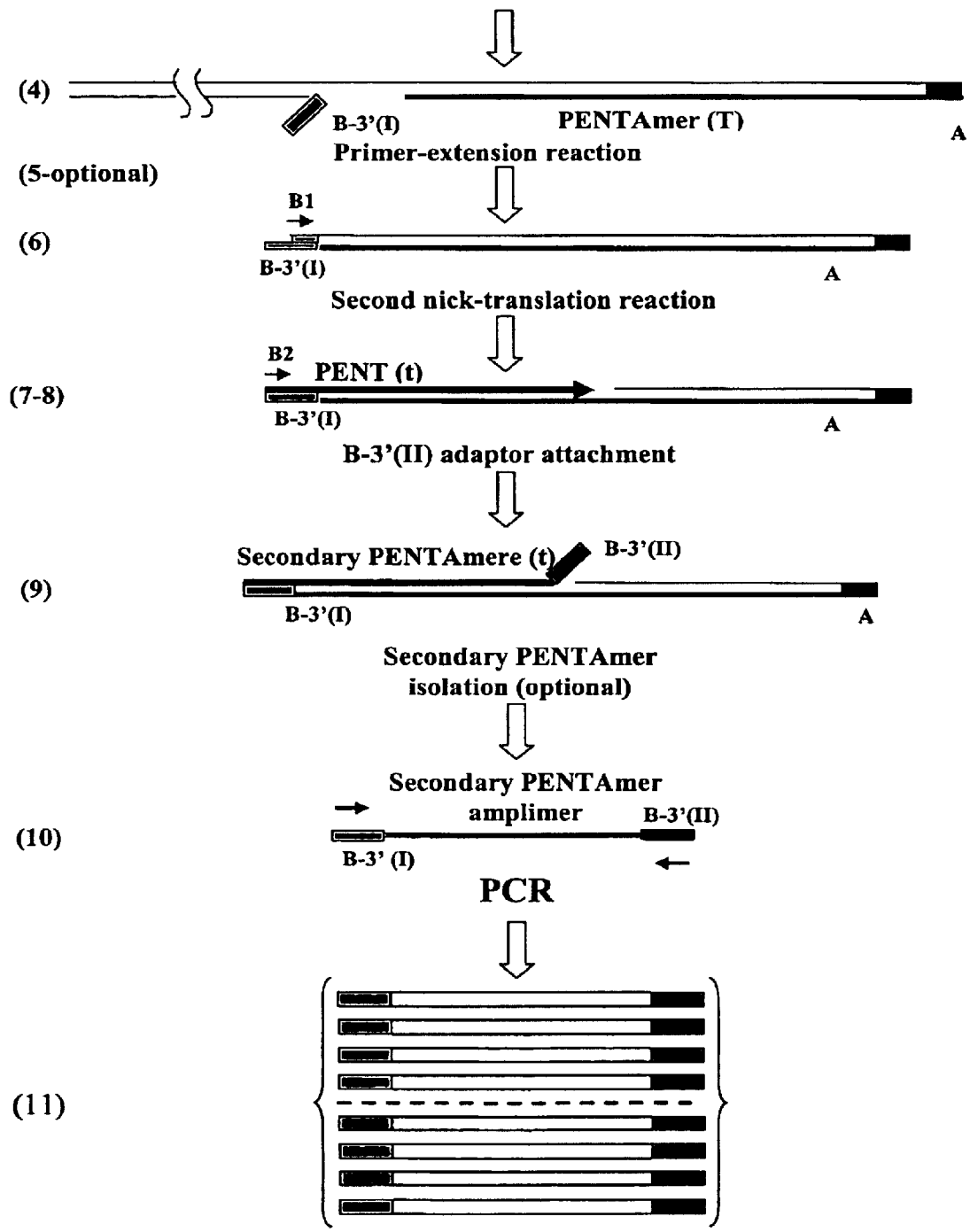

Replicating the second strand of the primary PENTAmer using primer extension from primer sequence B1 (as indicated in FIG. 3B);

Initiating a second PENT reaction at the upstream end of the secondary PENTAmer using primer sequence B2 (as indicated in FIG. 3B);

Elongating the secondary PENT product a specific time t;

Appending a second, down-stream, nick-attaching adaptor B-3' (II) to the 3' end of the secondary PENT product; and (Optionally) separating the single-stranded secondary PENTAmer from the template.

A secondary PENTAmer of the second type can be amplified in vitro or in vivo using the same methods used to amplify a primary PENTAmer, except polymerization reactions begin at adaptor sequence B-3' (I) and/or adaptor sequence B-3' (II).

b. Construction of Ordered Secondary PENTAmers

Different times (T) of the primary PENT reaction produce secondary PENTAmers with one end a controllable distance from the start of the primary PENT reaction (FIG. 4C). Different times (t) of the secondary PENT reaction produce secondary PENTAmers of different length. To positionally amplify regions of DNA increasing distances from the initiation site on the template, the same template should be reacted for increasing nick translation times, e.g., T1<T2<T3, < . . . <Tn. By using longer times t1<t2<t3, . . . <tn for the secondary PENT reactions in the first method, or constant time t for the secondary PENT reactions in the second method the PENTAmers from different positions within the template can all be designed to have about the same length. Secondary PENTAmers located different distances from the terminus of the template DNA can be collected into an ordered set of PENTAmers of similar length. Because all the amplimers are of similar length and have the same adaptor sequences on both ends, the efficiencies of amplification of different members of the set are independent of distance of the member from the terminus of the template. The ordered PENTAmers can be amplified in vitro or in vivo, or pooled into unordered sets as described earlier.

9. Synthesis of Primary PENTAmers Large Distances from the Terminus of a Template The methods disclosed above are limited to creating and amplifying regions up to 10–20 kb from the terminus of the template. PENTAmers synthesized with longer times of the nick-translation reaction would form products with increasing positional uncertainty. This section describes methods to synthesize PENTAmers large, specified distances from a terminus of a template.

a. Synthesis of a Primary PENTAmer a Large Distance from the Terminus of a Template The simplest method to make a PENTAmer a large distance from a specified end of a template is to make a primary PENTAmer on the opposite end. For example, if the template is 100 kb long, a 1 kb-long primary PENTAmer created using an adaptor ligated to the right end of the template will be complementary to a region that is not only 0–1 kb from the right end of the template, but is also 99–100 kb from the left end of the template. If the length of the template is initially unknown, then the distance of the PENTAmer from the left end will become known by determining the length of the template by any means available, e.g., gel electrophoresis, column chromatography, or centrifugation. The determination of the length of the template can be done before or after synthesizing the nascent primary PENTAmer, because the nascent primary PENTAmer has nearly the same molecular weight and structure as the unreacted template and therefore should be separated by electrophoresis or other methods nearly the same as the unreacted template.

b. Synthesis of Ordered PENTAmers Complementary to Different Distances within a Large Template Molecule Primary PENTAmers can be synthesized on a nested set of double-stranded DNA molecules (e.g., created by a partial restriction digestion), creating a nested set of nascent PENTAmers having one common terminus and a set of termini different distances from the common terminus. Separation of the nascent PENTAmers by electrophoresis or other means creates an ordered set of PENTAmers complementary to different regions within the template. Creation of nested sets of nascent primary PENTAmers is a critical step in the most important applications of PENTAmers to genomics.

Figure 5:
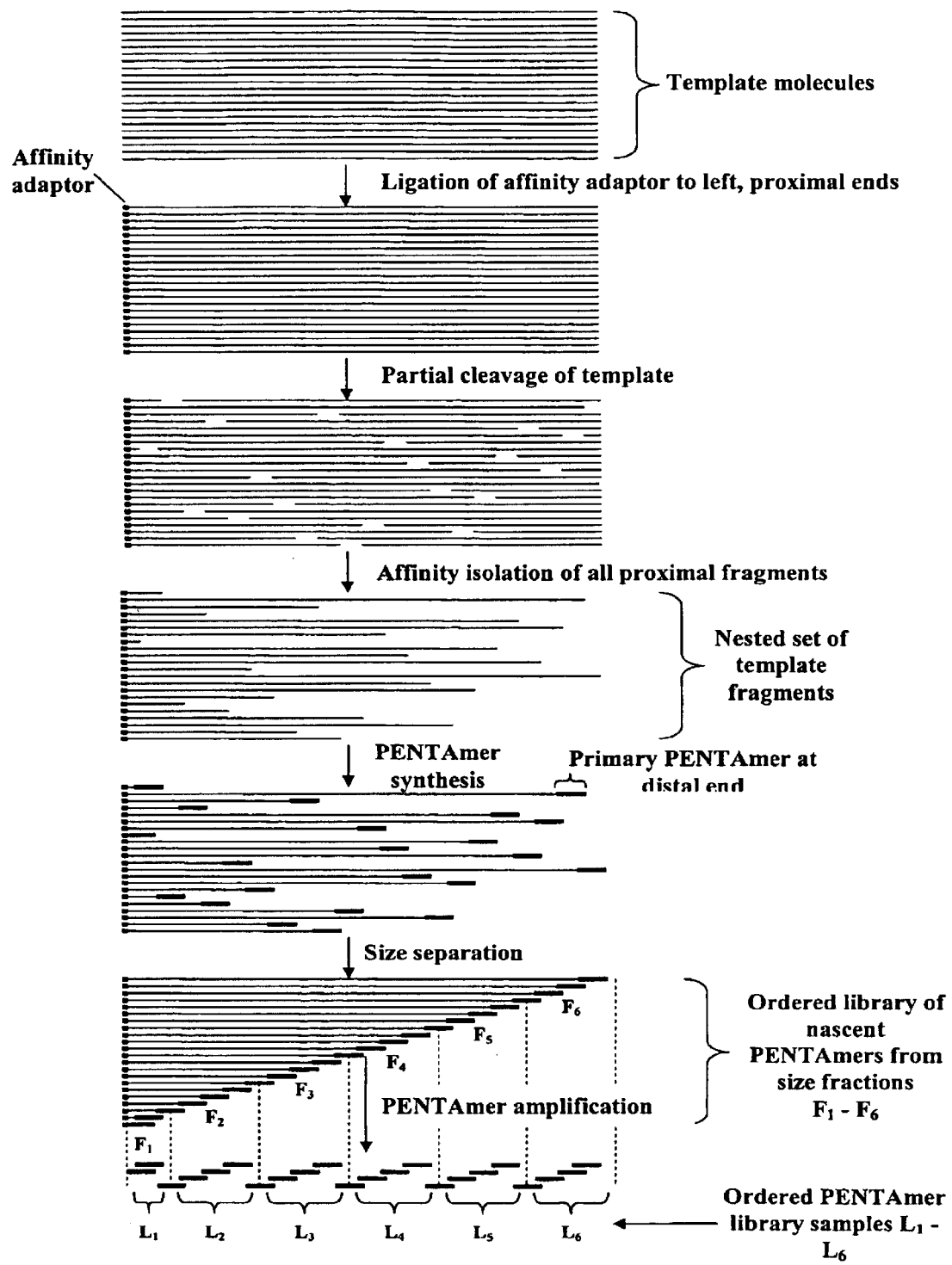
FIG. 5: Creation of ordered libraries of PENTAmers from a single template molecule

FIG. 5 schematically shows how primary PENTAmers can be used to organize distal regions of a template DNA molecule into ordered sets of overlapping nascent PENTAmers and PENTAmers. The basic steps of creating a non-recombinant ordered set of primary PENTAmers on a large template are:

1) Ligation of an affinity adaptor (e.g., a double-stranded oligonucleotide with biotinylated bases) to the proximal ends of the template molecules;
2) Exposure of different internal regions of the template DNA as distal ends (e.g., partial cleavage with a restriction endonuclease, non-specific endonuclease, or chemical cleavage,);
3) Separation of all fragments having the proximal ends (e.g., by immobilization on and subsequent release from a streptavidin-coated surface), creating a nested set of template molecules with distal ends different distances from the proximal ends;
4) Creation of a primary PENTAmer at all distal ends (ligation of up-stream, terminus-attaching, nick-translation adaptor A, controlled PENT reaction, and appending of down-stream, nick-attaching adaptor B to the end of the PENT products); and
5) Size fractionation.

These steps can be done in any order that follows the logic of 3 after 1 and 2; 4 after 2; 5 after 1 and 2.

Amplification of the primary PENTAmers in individual size fractions creates an ordered set of PENTAmers that can be amplified by the methods discussed previously.

The template is made with one end compatible for ligation to the immobilization template. This can be achieved by using a template with incompatible restriction sites at the two ends, or by creating the template ends using a sequence-specific endonuclease, such as lambda terminase, that cleaves at non-palindromic sequences.

The PENT reaction at the distal ends is necessary to create primary PENTAmers that contain sequences from different internal positions. The sequence independence of the PENT reaction rate makes this practical to do for a mixture of molecules with different distal sequences.

Size separation of the nested set of DNA is critical to the construction of the ordered PENTAmers. In the schematic procedure shown in FIG. 5, the nascent primary PENTAmers are separated according to size. The number of different fragments in each size fraction depends upon the density of partial cleavage sites and the range of fragment sizes included in the set of PENTAmers. In the example shown in FIG. 5, each size fraction contains a plurality of PENTAmers that are complementary to partially overlapping regions of the template, because many cleavage sites exist within the range of molecular weights in each size fraction. It is expected that PENTAmers will behave very similarly to the intact template molecules during the procedures now used for molecular weight separation of DNA. The only difference between a template and the nascent primary PENTAmer made from that template is 1) a nick or a small gap located near the end of the molecule; and 2) a short extension to the end of the PENT product. Neither of these differences should alter the charge, hydrodynamic properties, molecular weight, or spectroscopic properties of the molecule. While in principle the templates could be separated by size before creating the primary PENTAmer, it is more efficient to complete as many steps as possible before size fractionation. Separation of the nascent primary PENTAmers yields maximal efficiency.

Cleavage-resistant nucleotide analogs can be incorporated into the terminus-attaching and nick-attaching adaptors, as described earlier, in order to allow destruction of all template strands before amplification so that there is an increase in the specificity of amplification.

c. Creation of Ordered PCR Products from Nested Sets of DNA Molecules Using Ligation-Mediated PCR In principle, ligation-mediated PCR could be used to create and amplify ordered amplimers. Ligation-mediated PCR is able to amplify the termini of DNA fragments using the following steps:

1) Ligation of an affinity adaptor (e.g., a double-stranded oligonucleotide with biotinylated bases) to the proximal ends of the template molecules;
2) Exposure of different internal regions of the template DNA as distal ends (e.g., partial cleavage with a restriction endonuclease, non-specific endonuclease, or chemical cleavage,);
3) Ligation of a PCR adaptor to all restricted ends;
4) Separation of all fragments having the proximal ends (e.g., by immobilization on and subsequent release from a streptavidin-coated surface), creating a nested set of template molecules with distal ends different distances from the proximal ends;
5) Size fractionation of the proximal fragments;
6) Complete restriction with a frequently-cutting restriction endonuclease, and ligation of a second PCR adaptor to the completely-restricted termini;
7) PCR amplification of each size fraction using primers complementary to the two conventional adaptors to create an ordered set of PCR products.

Ordered PCR products would have less-attractive characteristics than the ordered PENTAmers. Because ligation-mediated PCR depends upon a second restriction site to determine the internal priming site, the PCR products would have very heterogeneous size. Some ends might have internal priming sites so close to the end that insufficient DNA would be amplified to represent the region. Other ends might have internal priming sites so far from the ends that PCR would be inefficient. In addition, special methods would be required to reduce the amplification of non-terminal DNA sequences due to pairs of non-terminal restriction sites. One of these special methods is called "suppression PCR," used to suppress PCR of fragments with the same priming sequences on both ends.

d. Creation of Ordered Sets of RNA Molecules from Nested Sets of DNA Molecules Using RNA Polymerase In principle, ligation-mediated RNA synthesis could be used to create ordered sets of single-stranded RNA molecules. Ligation-mediated RNA synthesis is able to amplify the termini of DNA fragments using the following steps:

1) Ligation of an affinity adaptor (e.g., a double-stranded oligonucleotide with biotinylated bases) to the proximal ends of the template molecules;
2) Exposure of different internal regions of the template DNA as distal ends (e.g., partial cleavage with a restriction endonuclease, non-specific endonuclease, or chemical cleavage,);
3) Ligation of a conventional adaptor containing an RNA polymerase promotor to the ends left by partial cleavage;
4) Separation of all fragments having the proximal ends (e.g., by immobilization on and subsequent release from a streptavidin-coated surface), creating a nested set of template molecules with distal ends different distances from the proximal ends;
5) Size fractionation of the nested DNA molecules;
6) Amplification of each size fraction using RNA polymerase to make an ordered set of RNA molecules.

Ordered RNA molecules would have less-attractive characteristics than ordered PENTAmers, because 1) The RNA molecules will be of variable length; 2) RNA is less stable than DNA; and 3) RNA polymerase linearly amplifies the sequence rather than exponentially, as in PCR.

10. Recombinant PENTAmers and Ordered Recombinant PENTAmers from Single Template Molecules The difficulty of using very long PENTAmers to amplify or analyze sequences long distances from termini may be overcome by bringing together sequences from both the proximal and distal ends of long templates to create a short recombinant PENTAmer having two sequences far apart.

a. Synthesis of a Recombinant PENTAmer from a Single Template

Figure 6:
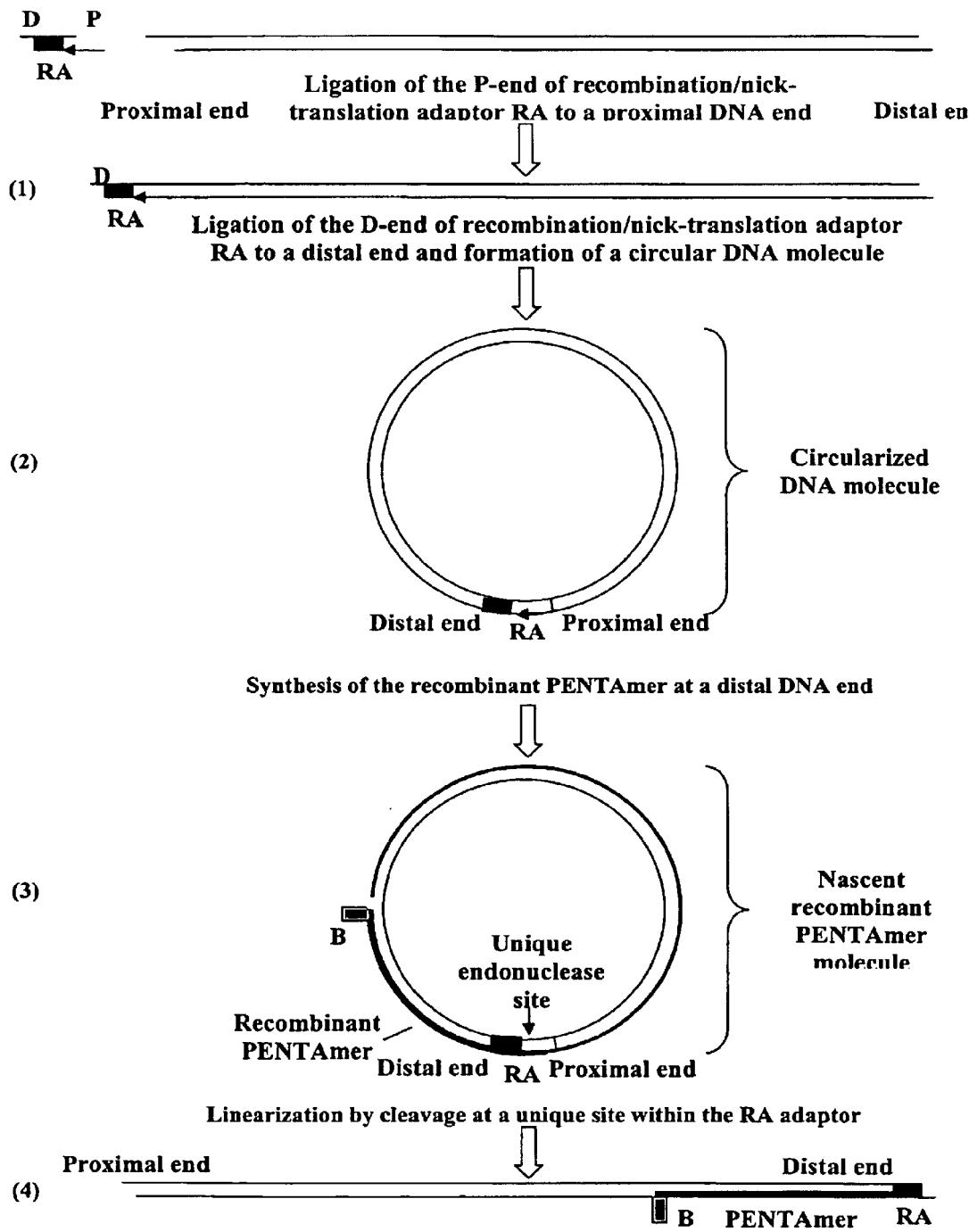
FIG. 6: Creation of the recombinant PENTAmer on a single DNA molecule

FIG. 6 shows how a recombinant PENTAmer can be made on a single template molecule, having different structures at the left (proximal, P) and right (distal, D) ends.

1) The first end of recombination adaptor RA is attached to the left, proximal end of the template;
2) The second end of recombination adaptor RA is attached to the right, distal end, to form a circular molecule; and
3) The initiation domain of adaptor RA is used to synthesize a PENTAmer containing the distal template sequences.

PENTAmers will only be created on those fragments that have been ligated to both ends of the recombination adaptor RA. Thus the recombination step replaces the affinity immobilization step previously described. Specific designs and use of recombination adaptors are described elsewhere in this application. One embodiment uses an adaptor RA comprising a first ligation domain complementary to the proximal terminus of the template, an activatable second ligation domain complementary to the distal terminus, and a nick-translation initiation domain capable of translating the nick from the distal end toward the center of the template. In the case of a recombination adaptor of that specific design, the template would be made resistant to cleavage by the activation restriction enzyme by methylation at the restriction recognition sites, and the second step would be executed in the following way: 1) removal of unligated adaptor RA from solution, 2) activation of adaptor RA by restriction digestion of the unmethylated site within the adaptor, 3) dilution of the template, 4) ligation of the second ligation domain to the distal end of the template, and 5) concentration of the circularized molecules. Step 3 is executed by the same methods used to create a primary PENTAmer, however the nick-translation initiates at the initiation domain of an RA adaptor.

The PENTAmer formed can be amplified by any of the methods described earlier, e.g., by PCR using primers complementary to sequences in adaptors RA and B-3'.

b. Synthesis of an Ordered Set of Recombinant PENTAmers Complementary to Different Regions within a Single Template Recombinant PENTAmers can be synthesized on a nested set of double-stranded DNA molecules (e.g., created by a partial restriction digestion), to create a nested set of nascent PENTAmers having common proximal termini and a set of distal termini different distances from the common termini. Separation of the nascent PENTAmers by electrophoresis or other means creates an ordered set of recombinant PENTAmers complementary to different regions within the template.

Figure 7:
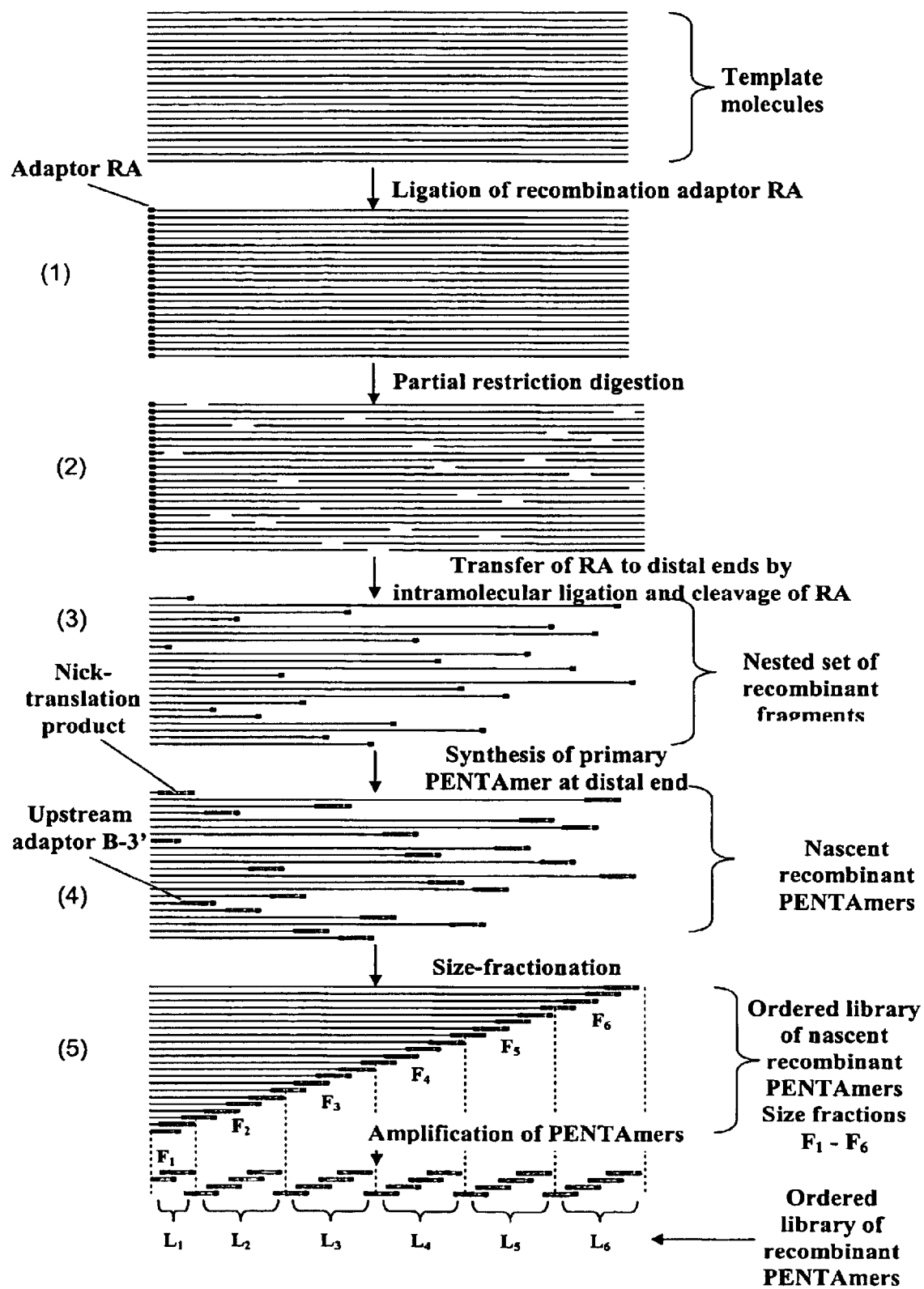
FIG. 7: Positional amplification using ordered positional libraries of recombinant PENTAmers from a single template molecule

FIG. 7 schematically shows how recombinant PENTAmers can be used to amplify distal regions of DNA as an ordered set of overlapping PENTAmers. The number of different fragments in each set depends upon the density of partial cleavage sites and the range of fragment sizes included in the set. In the example shown in FIG. 7, each size fraction contains a plurality of PENTAmers that are complementary to partially overlapping regions of the template, because many cleavage sites exist within the range of molecular weights in each size fraction.

The basic steps of creating recombinant ordered PENTAmers on a large template are:

1) The first end of recombination adaptor RA is attached to the left, proximal end of the template;
2) Different internal regions of the template DNA are exposed as distal ends;
3) The second end of recombination adaptor RA is attached to the right, distal ends of the fragments, to form a nested set of circular molecules;
4) Synthesis of a nascent PENTAmer or PENTAmers containing the distal template sequences of each member of the nested set of fragments; and
5) Size fractionation of the nested set of nascent recombinant PENTAmers.

Steps 1 and 3 are achieved using the oligonucleotide adaptors and methods described herein. Step 2 is achieved by partial cleavage with a restriction endonuclease, non-specific endonuclease, or chemical cleavage. To facilitate recombination, the distal ends can be attached to a second type of recombination adaptor before the recombination step. PENTAmer synthesis (step 4) uses the methods detailed elsewhere beginning at the initiation domain(s) of adaptor RA (i.e., initiating of the nick-translation reaction, terminating the nick-translation reaction at a specified time, and appending a down-stream, nick-attaching adaptor B-3' to the nick). Size-separation can be performed on the nested set of circular molecules, or on linear molecules produced after linearization of the template by cleavage of a restriction site within adaptor RA. Alternative order of the five steps is possible, including steps 2 and 3 before step 1, and step 5 any time after step 2. The order shown is usually optimal, because all samples are processed simultaneously in the same tube and size-selected at the last step.

Amplification of the ordered nascent recombinant PENTAmers creates ordered PENTAmers that can be amplified by the methods discussed previously.

The PENT reaction at the distal ends is necessary to create primary PENTAmers that contain sequences from different internal positions. The sequence independence of the PENT reaction rate makes this practical do for a mixture of distal sequences. If a single PENTAmer is synthesized on each template molecule, the nick-translation reaction must proceed from the distal template end toward the center of the molecule. If the RA adaptor is designed to create two PENTAmers they will be in opposite directions and will result in two down-stream nick-attaching adaptors, capable of numerous recombination reactions.

Size separation of the nested set of DNA is critical to the construction of the ordered PENTAmers. It is expected that PENTAmers will behave very similarly to the intact template fragments during the procedures now used for molecular weight separation of DNA. The only difference between a template fragment and the nascent primary PENTAmer made from that fragment is 1) a nick or a small gap located near the end of the molecule; and 2) a short extension to the 3' and 5' ends of the PENT product. Neither of these differences are expected to alter the molecular weight, charge, or hydrodynamic properties of the molecule. While in principle the templates could be separated by size before creating the primary PENTAmer, it is more efficient to complete as many steps as possible before size fractionation. Separation of the pool of nascent primary PENTAmers yields maximal efficiency.

Separation of the PENTAmers from the template molecules before amplification on the basis of molecular weight and/or incorporation of affinity-tagged or nuclease-resistant nucleotides during the PENT reaction will increase the specificity of the amplification reaction. This can be done by incorporating cleavage-resistant nucleotide analogs during the nick-translation reaction and/or into the adaptors, as described earlier. In the case of high molecular weight templates, this can be done by denaturation of the molecules and size separation of the smaller PENTAmers from the larger, template fragments.

O. Multiplexing of PENTAmer Synthesis and Amplification

Reaction-specific adaptors can be incorporated during PENTAmer synthesis and subsequently used for amplification of specific PENTAmers. This process allows PENTAmers from multiple templates or from multiple regions within templates to be pooled during one or more preparative steps. The processing of the pools of molecules saves time, effort and cost of those steps. At the end of the processing, the PENTAmers from a specific template or region within a template can be recovered from the pool and be specifically amplified with a primer or primers specific for the reaction-specific adaptors.

1. Multiplexing PENTAmer Synthesis from Different Templates

The synthesis of PENTAmers from a single template molecule is described above. In this section it is demonstrated that a plurality of different templates can be synthesized as PENTAmers by using adaptors with template-specific sequences. PENTAmers from individual templates can be subsequently recovered using template-specific amplification primers (e.g., thermal cycling primer extension, strand displacement amplification, PCR, or RNA transcription), and/or subsequent to amplification using methods to distinguish among the reaction-specific adaptor sequences, such as Sanger cycle sequencing, or hybridization to DNA microarrays.

Multiplex cloning methods described in U.S. Pat. No. 4,942,124 are directed to multiplexed clones combined during a Sanger sequencing reaction followed by analytical electrophoresis and recovery of the sequences of individual molecules during analysis of the sequencing ladders. However, the multiplexing disclosed herein is distinct from that of U.S. Pat. No. 4,942,124, because the multiplexing occurs during molecule preparation rather than sequencing analysis. The sequences that facilitate multiplexing are incorporated into template-specific adaptors that are used to initiate or terminate a nick-translation synthesis of a new molecular species, the PENTAmer. Recovery of information about individual templates is done during the preparative step of PENTAmer amplification or during sequencing or hybridization array analysis.

The method to multiplex preparation of a primary PENTAmer on two templates is as follows:
1) Upstream terminus-attaching adaptor A1 is ligated to template 1;
2) Upstream terminus-attaching adaptor A2 is ligated to template 2;
3) Adapted templates 1 and 2 are mixed into a single tube; and
4) PENTAmer synthesis is completed on templates 1 and 2 in said tube.

PENTAmers on both templates are elongated under identical conditions (e.g., time, temperature, enzyme concentration, etc.) and attaching the same downstream adaptor B-3' to each template.

To recover PENTAmers complementary to template 1, amplification is done including a primer that is specific for sequences within adaptor A1. For example, the PENTAmers from template 1 can be PCR amplified using a primer specific for sequences within template-specific adaptor A1 and universal adaptor B-3'. Likewise, to recover PENTAmers complementary to template 2, amplification is done including a primer that is specific for sequences within adaptor A2, e.g., a primer complementary to adaptor A2 and a primer complementary to adaptor B-3'.

In cases where templates 1 and 2 have identical termini that are to be attached to the adaptors, steps 1 and 2 above will be performed in separate tubes. If templates 1 and 2 have termini of different structure, adaptors A1 and A2 will have different terminal structure and can be attached to templates 1 and 2 within the same tube.

In addition, if the template-specific adaptors have an outer region with universal sequence and an inner region with unique sequence, then amplification can be performed with primers complementary to the universal sequences and analysis performed with primers complementary to the inner unique sequences, e.g., by Sanger sequencing reaction, pyrosequencing, or DNA microarray hybridization.

Multiplexing can be achieved with two or more template molecules. In principle, thousands of templates can be prepared with thousands of template-specific upstream terminus-attaching adaptors, mixed into a single tube, and prepared as a pool of PENTAmers. PENTAmers containing sequences from a specified template can subsequently be amplified and/or analyzed using at least one primer complementary to the template-specific upstream terminus-attaching adaptor.

In principle templates can also be multiplexed using template-specific downstream nick-attaching adaptors. However in this case PENTAmers can only be mixed after completion of PENTAmer synthesis.

Figure 8:
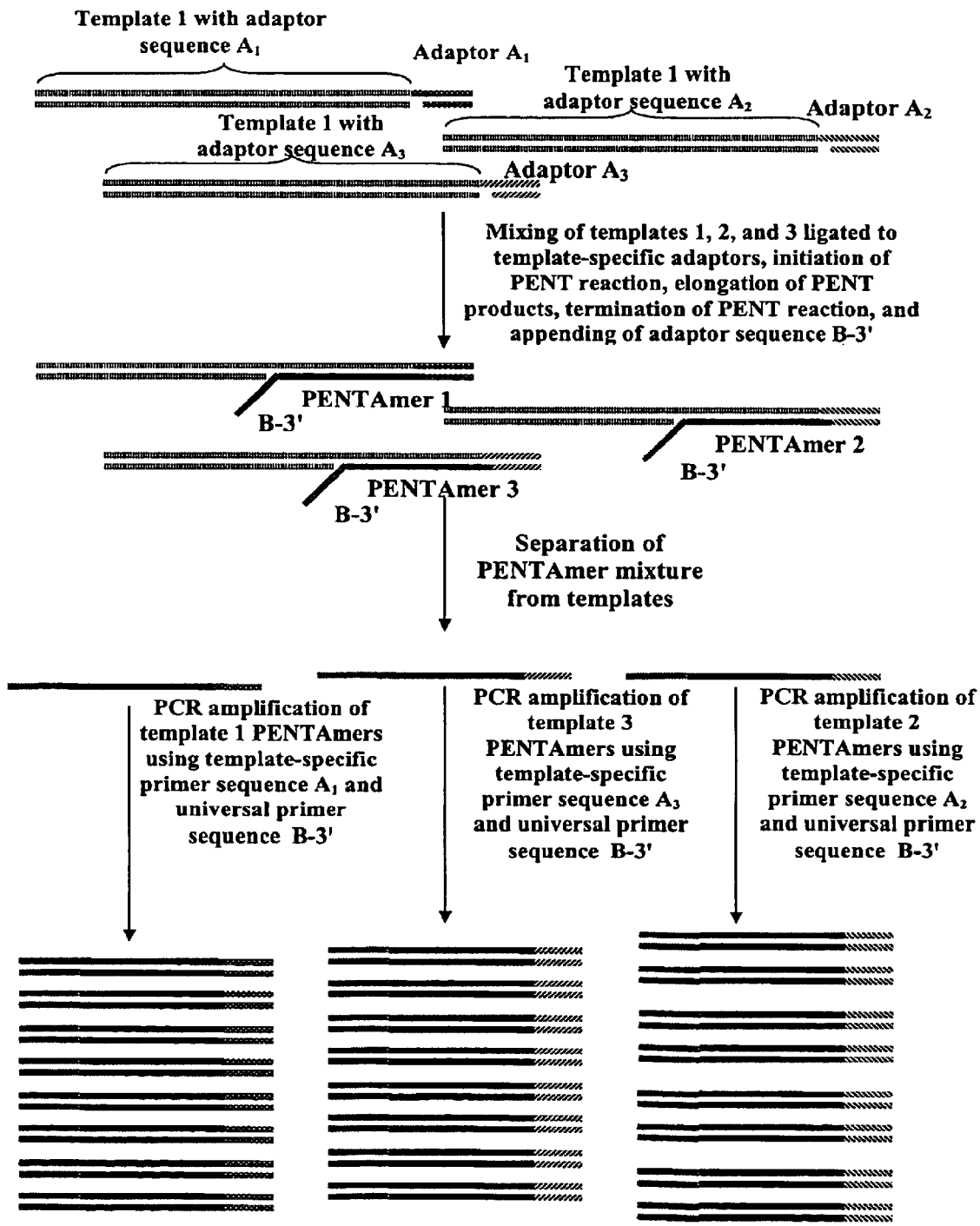
FIG. 8: Multiplexed primary PENTAmers

FIG. 8 is a schematic diagram of multiplexed PENTAmer creation and amplification.

Complement PENTAmers from different templates can be multiplexed by attaching different adaptor A' sequences A'1, A'2, A'3, . . . A'n) to n different templates.

Secondary PENTAmers prepared by the first method can be multiplexed by attaching template-specific adaptors B-3' and/or B-5'. Secondary PENTAmers prepared by the second method can be multiplexed by attaching template-specific adaptors B-3'(I) or B-3'(II). The purpose of this multiplexing is to combine secondary PENTAmers complementary to different templates. Recovery of information from specified templates or regions within templates is subsequently done using template-specific amplification primers.

2. Multiplexing PENTAmer Synthesis from Different Regions within One or More Templates Recombinant PENTAmers from multiple templates or from multiple regions within templates can be prepared using template-specific or template-fragment-length-specific adaptors. Secondary PENTAmers prepared by the first method can be multiplexed by attaching template-specific, time T-specific or time t-specific adaptors B-3' or B-5'. Secondary PENTAmers prepared by the second method can be multiplexed by attaching template-specific, time T-specific or time t-specific adaptors B-3'(I) or B-3'(II) adaptors. The purpose of this multiplexing is to combine secondary PENTAmers complementary to different templates and/or different regions within the same template. The templates to be amplified or analyzed by multiplexing must exist in separate reaction volumes in order to attach different adaptors. The separated volumes can comprise DNA from different individual organisms, different species of bacteria, animals or plants, different size fractions, different restriction digestions of the same starting DNA, etc. Recovery of information from specified templates or regions within templates is subsequently done using template- or region-specific amplification primers.

P. PENTAmer Library Synthesis on Complex Mixtures of Templates Such as Genomes and cDNA Preparations Current strategies for preparing genomic libraries include random DNA fragmentation, size fractionation, and DNA-end repair, followed by in vivo cloning. The clones can be randomly selected for analysis or screened by hybridization or PCR in order to select locus-specific clones for analysis.

PENTAmers can be used to form in vitro genomic libraries. The controllable, narrow size distribution of PENTAmers make them an ideal resource to prepare useful genomic libraries. Amplification of PENTAmer libraries using template-specific primers is used to select locus-specific PENTAmers for analysis.

PENTAmer libraries may be made from complex mixtures of templates such as genomes and subsequently amplified using locus-specific priming sites within the template. Consistent with usage of the term library in genomics a PENTAmer library is herein defined as PENTAmers representing the sequences present in the mixture of template molecules. PENTAmer libraries can be unordered or ordered. PENTAmer libraries can represent all sequences within the template or subsets of sequences. PENTAmer libraries can be amplified or unamplified.

Complex templates can be prepared by different methods before PENTAmer synthesis, however the methods to synthesize and separate PENTAmers are the same as those used for single templates. The locus-specific primers are used to selectively amplify specified positions within the genome or specified expressed sequences within the cDNA preparation. These applications are different from those previously described, because the amplification primer(s) used to create libraries include one or more primers complementary to sequences within the template, rather than sequences in the adaptors.

1. Primary PENTAmer Library Synthesis and Amplification from Complex Mixtures of Templates When primary PENTAmers are made from complex template mixtures all sequences within the mixtures are represented in the PENTAmer library. Amplification of the library with a locus-specific primer or primers is used to isolate the PENTAmers that contain the locus.

The amplification of primary PENTAmer libraries is analogous to amplifying a locus of an intact genome or large-insert clone using PCR primers complementary to sequences adjacent to the locus. However, PCR employs priming sites flanking both ends of the locus, whereas PENTAmer amplification requires a single priming site to one side of the locus.

The amplification of primary PENTAmer libraries is also analogous to amplification of "GeneWalker" Libraries (Clontech), which are fragments prepared by complete restriction digestion of a genome and ligation of universal adaptors to both ends. These libraries are commercial versions of molecular intermediates used in one-sided PCR. Locus-specific amplification is performed using one locus-specific primer and one universal primer complementary to the terminal adaptor. In this case, the lengths of the PCR products are determined by the distance between a restriction site and the locus-specific site. Because the restriction sites are sometimes too close to the locus-specific priming site or sometimes too far from the locus-specific priming site, many combinations of restriction enzyme and genomic priming site are unsuccessful in amplifying an appreciable length of the genome. To compensate for this problem, multiple GeneWalker Libraries are made using different restriction enzymes, and the amplification of a specific region is performed on each library in order to find a library capable of forming a PCR product of the desired size.

In contrast to the GeneWalker Libraries, PENTAmer libraries are synthetic strands of uniform length made from templates consisting of partially-digested genomic DNA. In contrast to GeneWalker amplification, primary PENTAmer amplification results in amplimers that are a range of sizes, up to a maximum size, set by the size of the PENTAmer. In addition, before amplification PENTAmers can be separated from the template strands, which reduces background during amplification.

a. Synthesis and Amplification of Genomic Primary PENTAmer Libraries Made from Template Molecules Comprised of a Partial Restriction Digest of Genomic DNA.

Primary PENTAmer libraries from a genome (or other complex template) is synthesized as follows:

1) The genome is fragmented into molecules of desired size; and
2) Primary PENTAmers are synthesized at fragment termini.

After synthesis of the library, a locus-specific molecule can be amplified using PCR or other amplification method. If the locus is to be sequenced, molecules having regions of identical sequence are selected by cloning, PCR, or other or other in vitro or in vivo amplification method and subjected to a dideoxyribonucleotide termination or other suitable reaction.

Figure 9A:
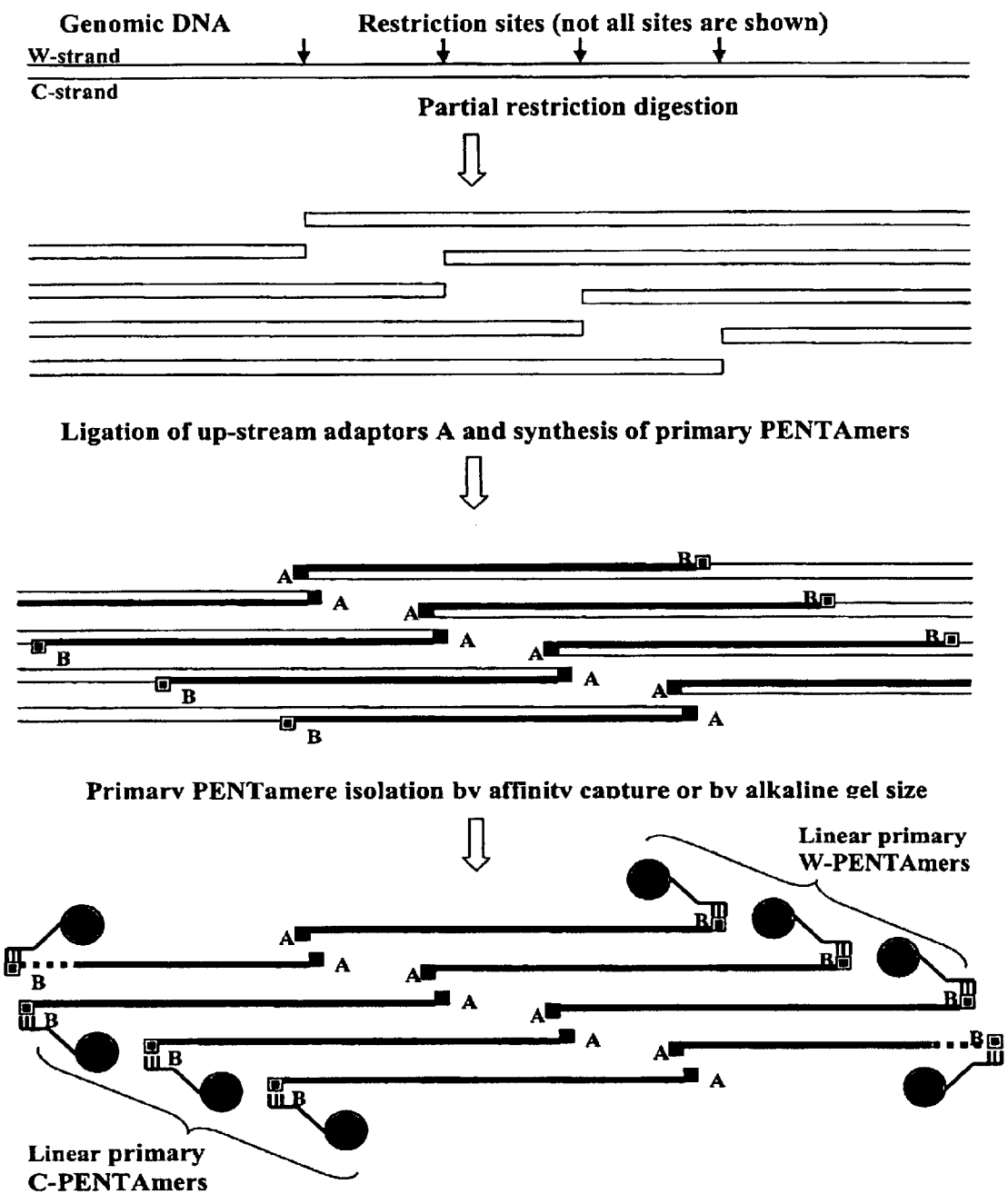
FIGS. 9A and 9B: Genomic primary PENTAmer libraries (after partial digestion with frequently-cutting restriction enzyme)

FIG. 9A shows an example of generation of linear primary PENTAmer libraries. The genome or other complex template is fragmented to a specified size (e.g., 1–10 kb) by partial cleavage using a frequently-cutting restriction enzyme (e.g., Sau 3A I or CvJ, which on average cleave random sequences every 256 or 64 bp, respectively). Alternatively, DNase I, or very gentle sonication, nebulization, or gradient shearing can be used for cleavage. These template fragments are ligated to the up-stream terminus-attaching nick-translation adaptor A. (Sheared or DNase I cleaved DNA should be end-repaired by T4 DNA polymerase/exonuclease III mixture before blunt-end ligation.) Terminal PENTAmers of a specified size are synthesized at all DNA ends by time-controlled nick-translation synthesis and by appending a down-stream nick-attaching adaptor B-3'. Upper (W) and lower (C) strands of the template DNA result in W- and C-PENTAmers. The PENTAmers can be separated from the template DNA by affinity capture or by size fractionation under denaturing conditions. Both sets of PENTAmers constitute a primary linear PENTAmer library, which redundantly represents the whole genome.

Locus-specific members of the linear PENTAmer library can be amplified by: 1) PCR; 2) cloning; or 3) circularization followed by PCR. Single members of the library are selected by gel electrophoresis.

i. Positional Amplification and Selection of Locus-Specific Sequences from Primary Linear PENTAmer Libraries A subset of PENTAmers in the library will overlap a specified sequence (the kernel, K) in the genome. If the specified sequence is unique to the genome, a nested set of PENTAmers overlapping the unique locus can be amplified. If the specified sequence appears multiple times in the genome, multiple nested sets representing all of loci with the kernel sequences can be amplified.

Figure 10:
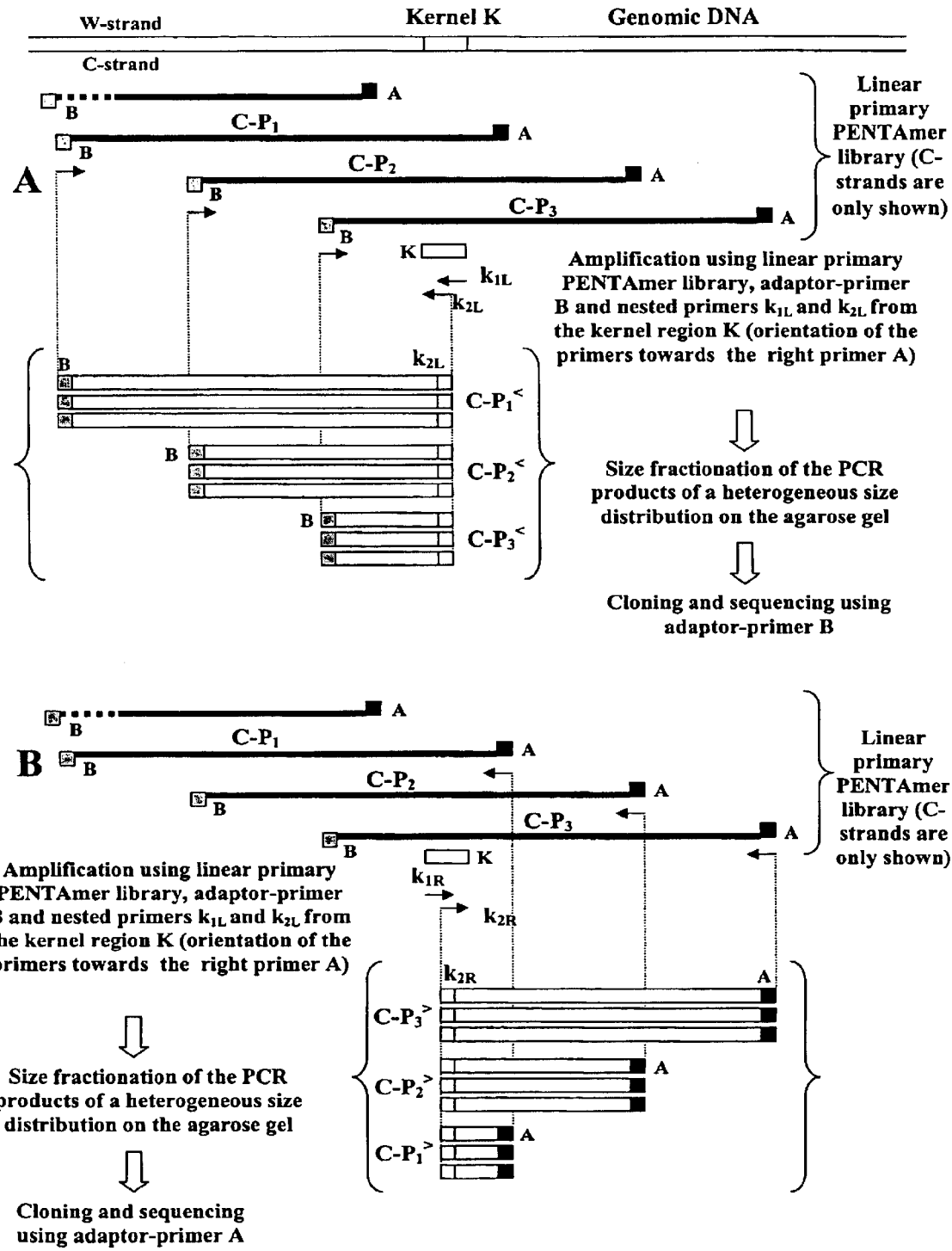
FIG. 10: Positional amplification using primary linear PENTAmer library

FIG. 10 illustrates how the C-strands in the linear primary PENTAmer library (comprised of molecules $C-P_1$, $C-P_2$, $C-P_3$, etc., where $C-P_n$ denotes the nth C-strand PENTAmer) that overlap the kernel are amplified using PCR. A one step (or nested, two step) PCR reaction in the presence of primary PENTAmer molecules, primer complementary to adaptor B and primer $k_{2L}$ (or $k_{1L}$ and $k_{2L}$) oriented toward adaptor B-3' results in a nested set of DNA fragments $C-P_1<$, $C-P_2<$, $C-P_3<$, etc. (FIG. 10A). These fragments have one common terminal sequence, within the kernel, and one variable terminal sequence (left end in FIG. 10A), determined by the length of the PENTAmer and the initiation site nick-translation adjacent to the cleavage sites. The amplified DNA fragments are size-separated on an agarose gel. The length of each amplified fragment is determined by where the cleavage site occurred relative to the kernel sequence. The electrophoretic band from PENTAmers terminated at each cleavage site is slightly diffuse, because of intrinsic uncertainty in the distance of nick-translation.

A PCR reaction using a primer complementary to adaptor A and primer $k_{2R}$ (or $k_{1R}$ and $k_{2R}$) oriented towards the primer A would result in another nested set of DNA fragments, C-P1>, C-P2>, C-P3>(FIG. 10B). Contrary to the previous case, the electrophoretic bands are sharp, because adaptor A is always adjacent to the restriction sites.

Using different combinations of primers, e.g., kL and A, or kR and B would result in amplification of PENTAmers from the opposite strand (W-PENTAmers).

The amplification of W- or C-strand PENTAmers is positional amplification, because the positions of the sequences at the termini of the amplimers (relative to the kernel) is known from the size of the amplimers.

Kernel-specific PENTAmer amplimers that terminate at restriction sites contain unique sequences discrete distances from the kernel. Whenever amplimers of different length can be distinguished, they can be directly subjected to cycle sequencing, PCR amplified and sequenced, or cloned and sequenced Because amplimers can be selected from specific distances in each direction from the kernel, the sequence of a large region surrounding the kernel can be assembled from minimally redundant sequencing.

Figure 9B:
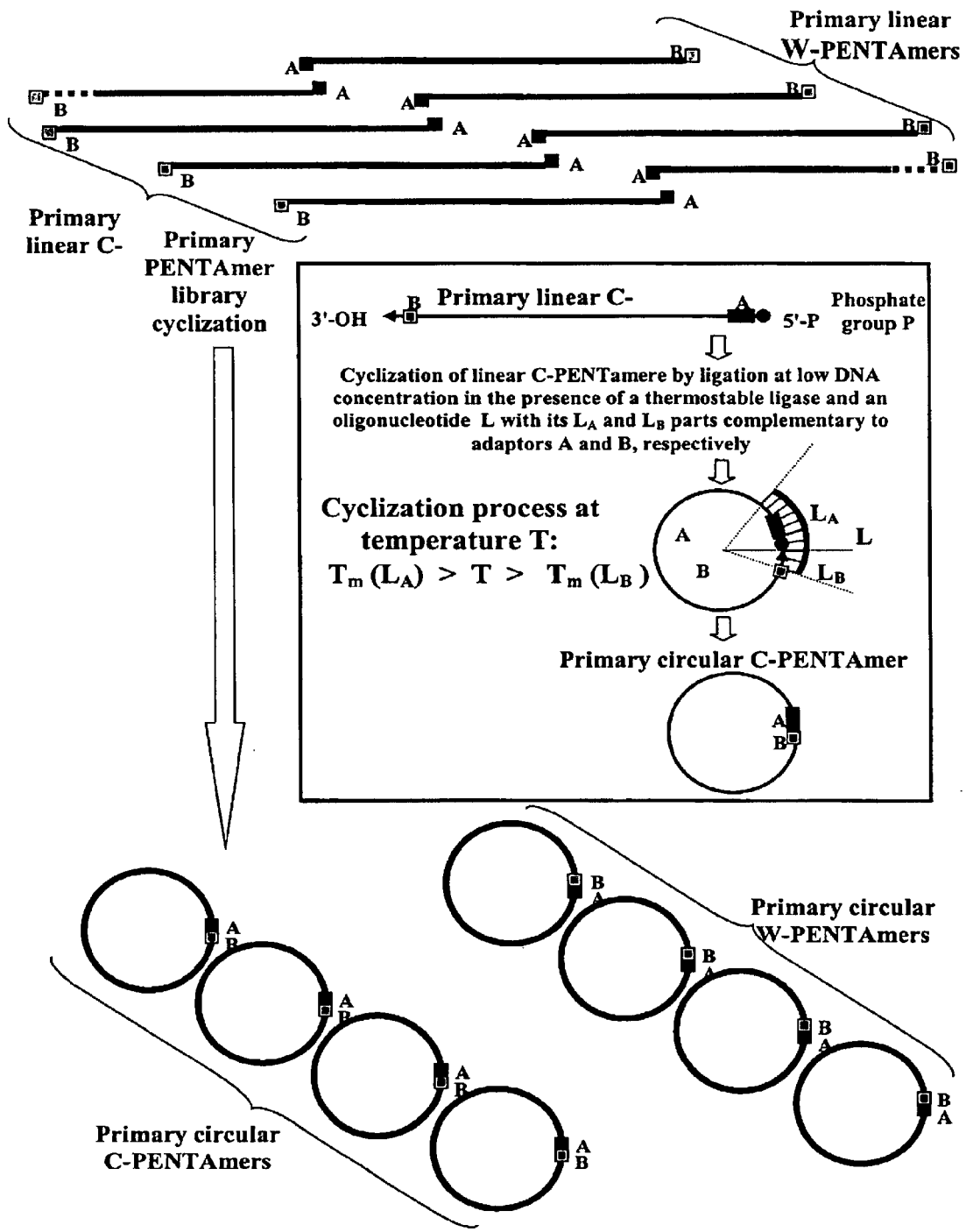

Kernel-specific PENTAmer amplimers that terminate at heterogeneous ends (i.e., including the downstream nick-attaching adaptor sequences) contain sequences different distances from the kernel. These amplimers of heterogeneous length can be amplified by selection PCR, dilution PCR, or cloned to create large numbers of unique sequence templates for sequencing. Because amplimers can be selected from specific distances in each direction from the kernel, the sequence of a large region surrounding the kernel can be assembled from sequences of minimally redundant in vivo or in vitro amplified PENTAmers.

ii. Positional Amplification and Selection of Locus-Specific Sequences from Circularized Primary PENTAmer Libraries Linear primary PENTAmers have common adaptor sequences at their 5' and 3' ends. Therefore, they can be circularized by ligation. To be circularized, the upstream, terminus attaching adaptor A needs to be synthesized with a 5' phosphate group. Although circularization is possible using ligase specific for single-stranded DNA ends (e.g., RNA ligase), it is more rapid and efficient using a DNA ligase employing a "linking" oligonucleotide (shown in FIG. 9B).

Circularization is performed using the following steps:
1) A linking oligonucleotide is incubated under optimized conditions to the ends of the PENTAmer together to form a nick; and
2) The PENTAmer ends are ligated using a DNA enzyme, such as a ligase.

The linking oligonucleotide (shown as L in FIG. 9B) is 20–200 bp long and has a 5' arm complementary to the 3' PENTAmer end and 3' arm complementary to the 5' PENTAmer end. The lengths and sequences of the arms form a more stable duplex with one PENTAmer end compared to the other. In the example shown in FIG. 9B, this is achieved by having a greater number of nucleotides at the 5' arm (LA) that are complementary to the PENTAmer than the number of complementary nucleotides on the 3' arm (LB). Alternatively, arms of the same length, but different GC content can be used.

The reaction is performed at low PENTAmer concentration to facilitate intra- versus inter-ligation processes. The criteria for selection of DNA concentration is simple: The concentration of PENTAmer termini should be much lower then their "local" molecular concentration. The last concentration is much higher for single stranded then for double stranded DNA because of big difference in a persistence length between the two types of molecules.

The ligation reaction is performed with thermostable ligase at 50–70 C° to reduce effect of secondary structure and intermolecular interactions. The reaction temperature should be lower than the melting temperature of a duplex formed between oligonucleotide L and one of PENTAmer ends (duplex between adaptor sequence A and LA portion of the oligo L in FIG. 9B) but slightly higher then the melting temperature of a duplex formed by oligo L with the other PENTAmer end. At this temperature oligonucleotide L will be stably bound to only one end of the single-stranded PENTAmer and form transient secondary structure with another end, providing a template for the ligase. This approach overcomes the need to precisely adjust the stoichiometric ratio of PENTAmers to linking oligonucleotides. The reaction can take place at much higher linking oligonucleotide concentration, increasing the rate and efficiency of ligation.

The library of circularized PENTAmers is a mixture of circular C-PENTAmers and W-PENTAmers.

FIG. 11 shows an example of how a circular primary PENTAmer library is used to amplify sequences adjacent to the kernel, K.

Figure 11A:
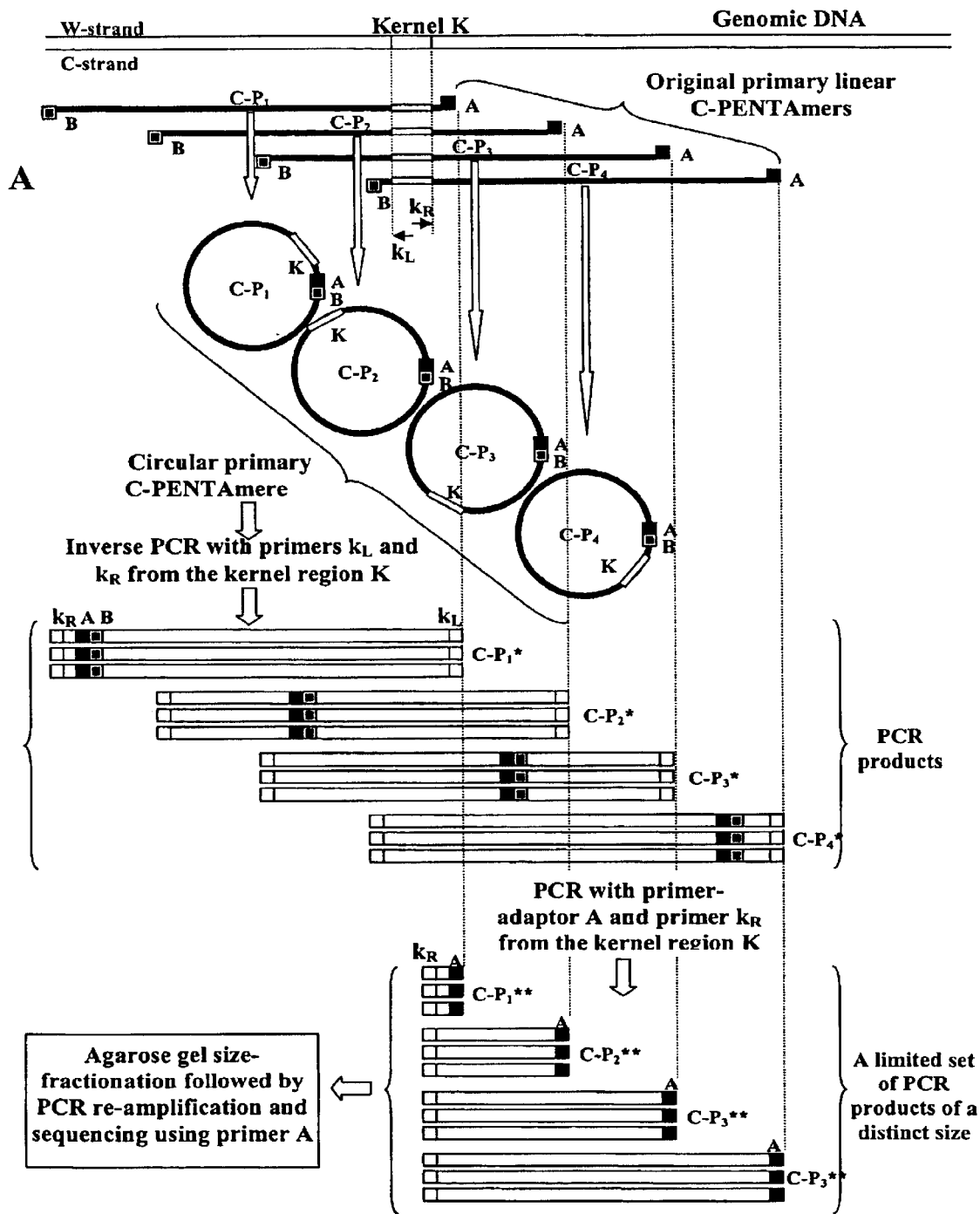
FIGS. 11A and 11B: Positional amplification using primary circular PENTAmer library
Figure 11B:
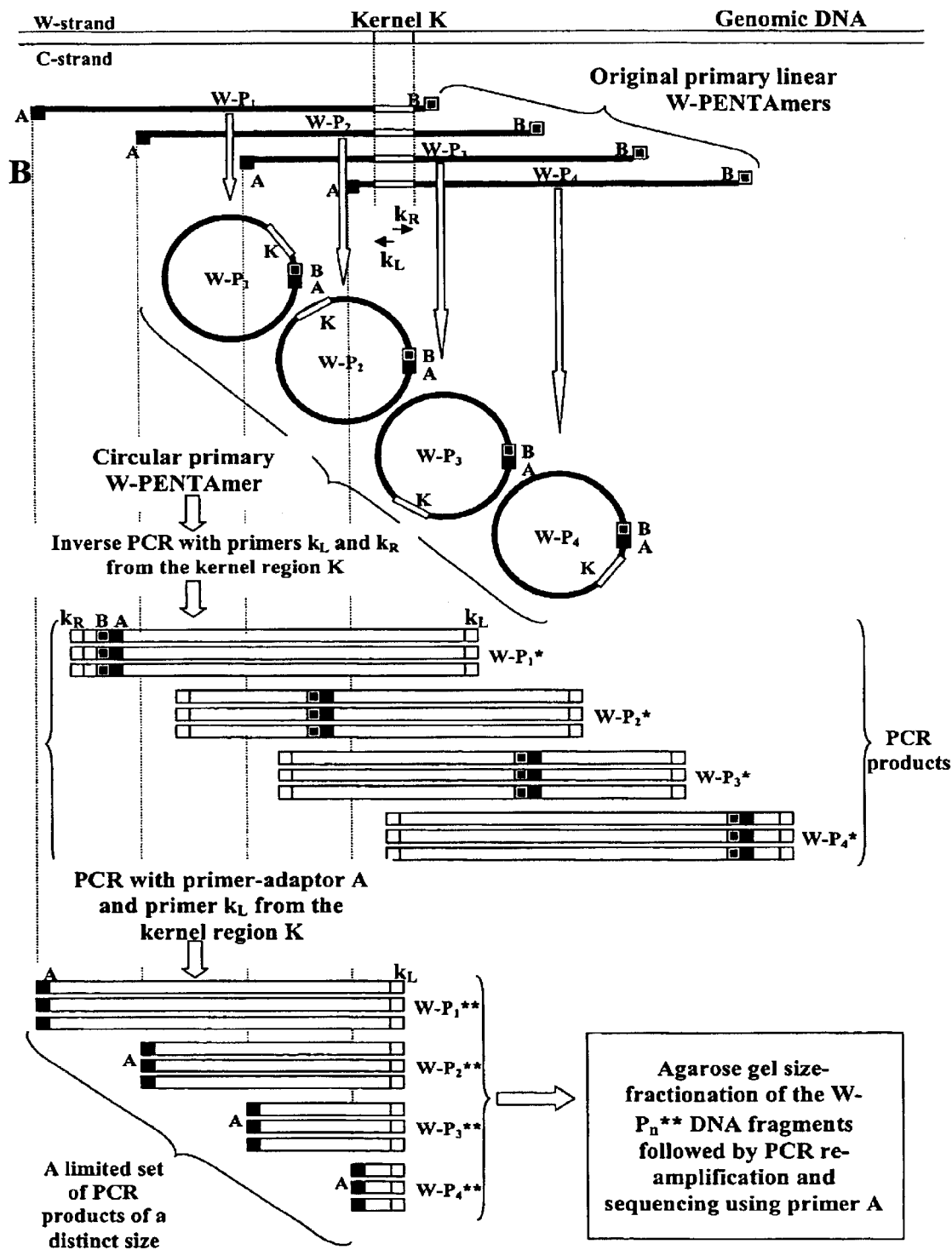

The first step is an inverse PCR reaction of all members of the library. FIG. 11A shows amplification of circular C-strand PENTAmers $C-P_1$, $C-P_2$, $C-P_3$, and $C-P_4$ and FIG. 11B shows amplification of circular W-strand PENTAmers $W-P_1$, $W-P_2$, $W-P_3$, and $W-P_4$. Primers $k_L$ and $k_R$ oriented towards the boundaries of the kernel results in amplification of the mixture of DNA fragments $C-P_1^*$, $C-P_2^*$, $C-P_3^*$, $C-P_4^*$, and $W-P_1^*$, $W-P_2^*$, $W-P_3^*$, $W-P_4^*$. These molecules have the same size and common junction element AB with different orientation and at different distances from the end for different DNA fragments (FIGS. 11A, B). The amplimers contain sequences on both sides of the kernel.

The second step is PCR amplification of the products of the first amplification (diluted 100–1000 times) using a primer complementary to adaptor A and a kernel primer. Amplification with $k_R$ results in a nested set of amplimers $C-P_1^{}$, $C-P_2^{}$, $C-P_3^{}$, and $C-P_4^{}$ complementary to the region to the right of the kernel (FIG. 11A). Amplification with $k_L$ results in a nested set of amplimers $W-P_1^{}$, $W-P_2^{}$, $W-P_3^{}$, and $W-P_4^{}$, complementary to the region to the left of the kernel. Amplimers $C-P_1^{}$, $C-P_2^{}$, $C-P_3^{}$, and $C-P_4^{}$ and/or $W-P_1^{}$, $W-P_2^{}$, $W-P_3^{}$, and $W-P_4^{}$ are size separated by electrophoresis. Their lengths reflect the distances between the kernel and the restriction sites. The electrophoretic bands are sharp, because of the distinct positions of the adaptor A sequences with respect to the restriction sites.

The amplification of circularized W- or C-strand PENTAmers is positional amplification, because the positions of the sequences at the termini of the amplimers (relative to the kernel) is known from the size of the amplimers.

Amplicons from the second amplifications are separated (by human or robot selection), further amplified (if necessary) and cycle sequenced using a primer complementary to adaptor A. The sequence assembly can be performed with minimal redundancy at both sides of the kernel.

Circular primary PENTAmer libraries are amplified and selected more efficiently than linear PENTAmer libraries, because:
1) The reaction is more specific because it involves inverse PCR using only kernel-specific primers at the first, most critical amplification step;
2) Both sequences to the right and left of the kernel are amplified in one step;
3) All amplimers are of equal size during the first amplification step;
4) Cloning is not obligatory because the electrophoretic bands are sharp and individual fragments can be isolated and sequenced.

b. Synthesis and Amplification of Genomic "Walking" PENTAmer Libraries Made from Template Molecules Comprised of a Complete Restriction Digest of Genomic DNA.

A walking PENTAmer library is produced by the following steps:
1) Complete digestion of genomic DNA with a restriction enzyme; and
2) Synthesis of primary PENTAmers of different specified lengths.

The optimal size of restriction fragments is 8–10 kb. The primary PENTAmers are created to be different lengths in different tubes, up to ~10 kb long.

FIG. 12 shows an example of creating a walking library for four different lengths of PENTAmers prepared in different tubes by controlling nick-translation times. Each reaction results in a library of W- and C-strand PENTAmers, originating from the two ends of each restriction fragment. If necessary, PENTAmers can be separated from template DNA by affinity capture or by denaturation and size fractionation.

Figure 12A:
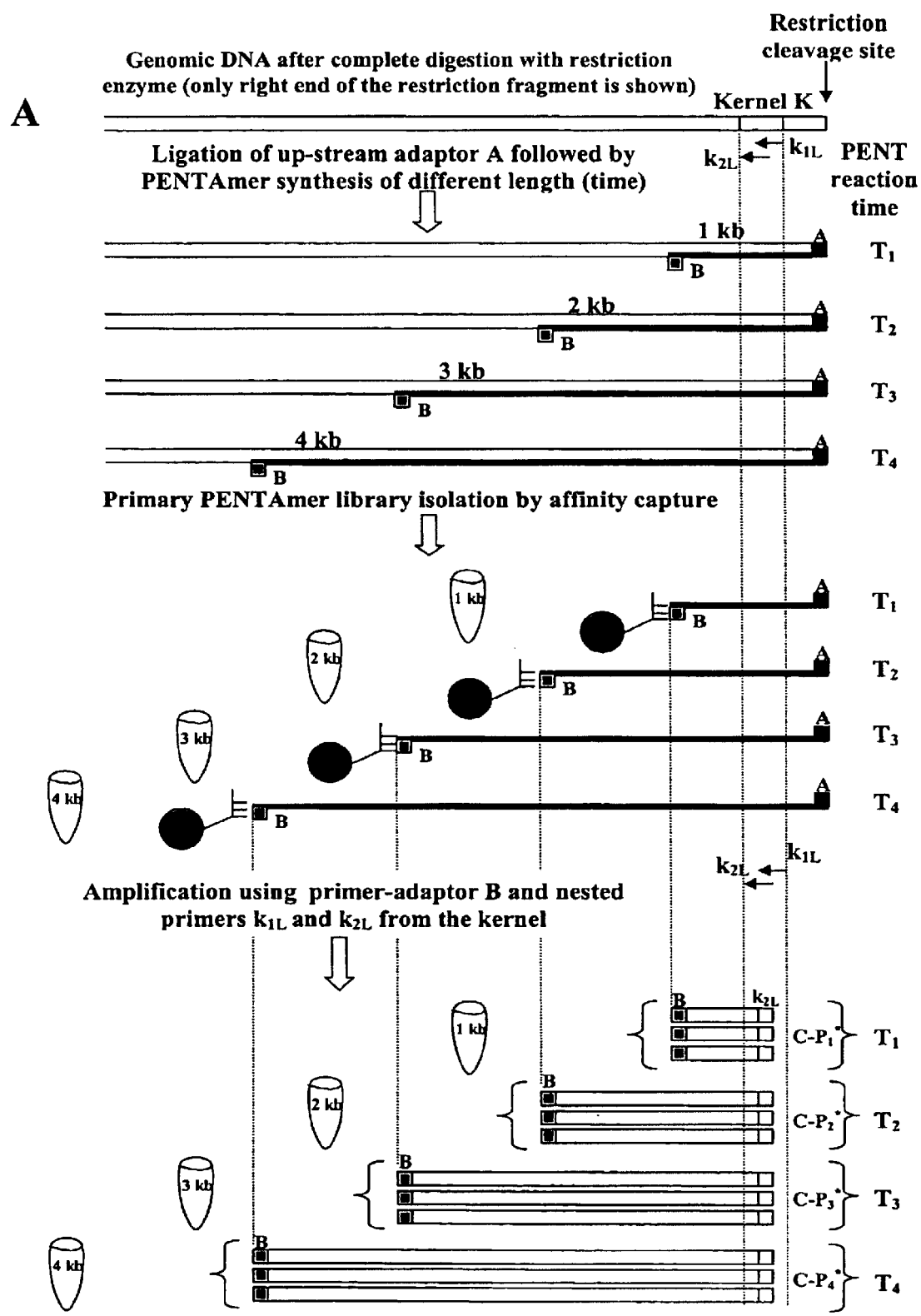

FIG. 12A is an example of "parallel" positional amplification to the left of a kernel using walking PENTAmer libraries of 1, 2, 3, and 4 kb. One step (or nested, two step) PCR amplification of each library using a primer complementary to adaptor B and primer $k_{2L}$ (or $k_{1L}$ and $k_{2L}$)

oriented towards primer B produces amplimers C-P$_1$*, C-P$_2$*, C-P$_3$*, C-P$_4$*. These amplimers have one common end within the kernel and a variable end specified by the length of PENTAmer. The amplimers from each tube can be cloned and directly sequenced. Walking libraries give access to sequences located within ~10 kb of restriction sites. To apply positional amplification to the entire genome several walking libraries should be prepared by digestion with different restriction endonucleases, e.g., Eco RI, Hind III, and Bam HI, Pvu II. PCR screening of the 1 and 2 kb restriction-enzyme-specific walking libraries using primers specific to adaptor A and the kernel is used to identify which restriction-enzyme-specific walking library should be used to amplify the locus adjacent to the specified kernel.

A parallel positional amplification to the right of the kernel shown in FIG. 12A requires amplification of the walking library using primers complementary to the opposite strands of adaptor B and the kernel.

FIG. 12B is an example of "serial" positional amplification to the left of a kernel using walking PENTAmer libraries. In this case DNA sequence information generated at one amplification/sequencing step is used for the design of a primer to amplify and sequence the next, more distal DNA region.

2. Secondary PENTAmer Library Synthesis and Amplification from Complex Mixtures of Templates Secondary PENTAmer walking libraries can be made from complex templates such as genomes. Synthesis of secondary PENTAmers different distances from the ends of restriction fragments will give rise to linear or circular PENTAmer libraries that can be used for serial positional amplification to either side of a kernel using obvious extension of the methods used to amplify primary PENTAmer libraries.

3. Recombinant PENTAmer Library Synthesis and Amplification from Complex Template Mixtures Recombinant PENTAmer libraries can be made by the same techniques used to synthesize recombinant PENTAmers on single template molecules. After synthesis the PENTAmers representative of one locus are amplified using one or more primers complementary to a kernel region within the genome or other complex template mixture, and (optionally) one or more primers complementary to a recombination adaptor. Genomic PENTAmer libraries are made from either DNA fragments produced from a partial restriction digestion of a genome with a frequently-cutting restriction enzyme (type I library), or fragments from a partial restriction with a frequently-cutting restriction enzyme and complete digestion with an infrequently-cutting enzyme (type II library). The genomic libraries either represent a mixture of nascent PENTAmers of all lengths (unordered libraries) or nascent PENTAmers of different lengths (ordered PENTAmers). Amplification of unordered libraries using at least one primer complementary to a kernel sequence produces a random mixture of amplified PENTAmers complementary to a large region to one side of the kernel. Amplification of ordered libraries using at least one primer complementary to a kernel sequence produces an ordered set of amplified PENTAmers complementary to ordered regions different distances from the kernel on one side of the kernel.

The fundamental steps of preparing an unordered library are:

1) Restriction with one or more restriction enzymes;
2) Attachment of one or more types of recombination adaptors to fragment termini;
3) Synthesis of primary PENTAmers at both ends of the fragments; and
4) Intramolecular recombination between the ends of the fragments.

The fundamental steps of preparing an ordered library are:

1) Restriction with one or more restriction enzymes;
2) Attachment of one or more types of recombination adaptors to fragment termini;
3) Synthesis of primary PENTAmers at both ends of the fragments;
4) Intramolecular recombination between the ends of the fragments; and
5) Separation of the nascent PENTAmers according to size.

Depending upon the type of library to be formed, the design of the adaptors, and methods of recombination, size separation, and amplification, the details and order of these steps can be different.

PENTAmer libraries are amplified using the same methods used for PENTAmers made from single template molecules, however inclusion of one or more kernel-specific primers selects and amplifies only those PENTAmers that contain the kernel sequence (in the specified orientation).

Convenient genomic kernels are ESTs, STSs, and anonymous sequences known to be within the genome. Kernels can also be discovered by random or systematic sequencing of small fragments of a genome. For special applications, kernels can be genetic elements that have been inserted into the genome by natural (e.g., viral) or artificial (e.g., bioballistics) means. Kernels can be known by exact sequence, or by sequence analogy with known sequences in related organisms. Specifically, primers complementary to a kernel in one species can be tested and optimized for efficiency of amplification of the analogous locus in a related species, by the same process that PCR primers for one species can be optimized or modified to amplify an analogous locus in a different species. Most applications are best developed using kernels that are unique to the genome, however some applications can also be developed that use kernels that could occur multiple times in the genome, such as transposable elements, microsatellites, etc., in order to create libraries of DNA sequences that are adjacent to those multi-copy sequences. Convenient cDNA kernels are 3' ESTs.

The topological construction and the applications of the recombinant PENTAmers are similar to the "junction-fragment DNA probes and probe clusters" (U.S. Pat. No. 4,710,465). That patent proposes to size fractionate genomic DNA fragments after partial restriction digestion, circularize the fragments in each size-fraction to form junctions between sequences separated by different physical distances in the genome, and then clone the junctions in each size fraction. By screening all the clones derived from each size-fraction for using a hybridization probe from a known sequence, ordered libraries of clones could be created having sequences located different distances from the known sequence.

Figure 13:
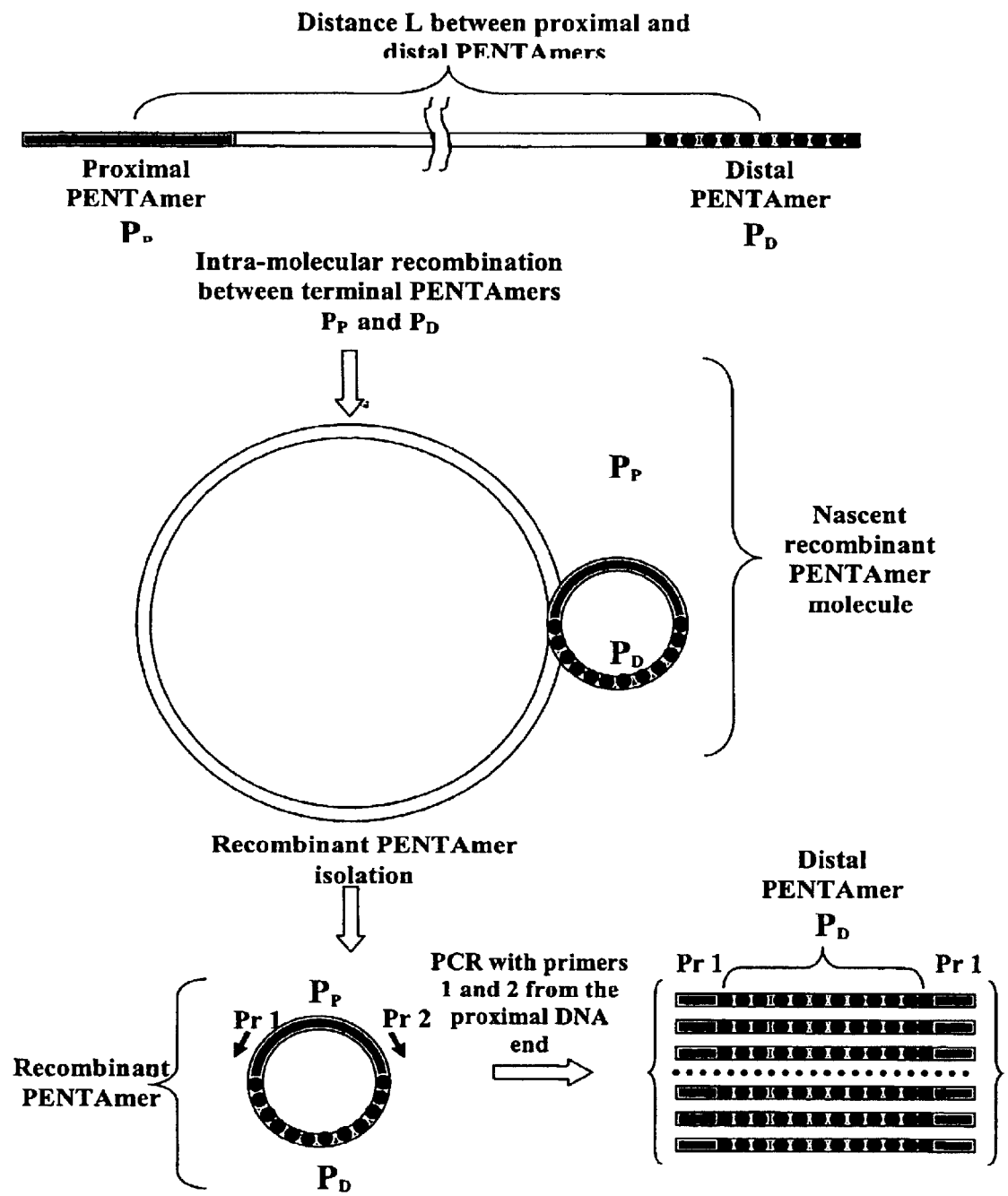
FIG. 13: General principle for creation and amplification of a recombinant PENTAmer molecule

In contrast to the methods described by Collins and Weissman, the methods described herein use specially-designed multi-functional adaptors and nick translation reactions to synthesize an in vitro amplifiable strand of controlled length. The locus specificity of in vitro amplification is determined by a primer complementary to a natural sequence in the genome (see FIG. 13).

4. Type I Recombinant PENTAmer Library

A type I recombinant PENTAmer ordered library is created from a complex template such as a genome that has been partially fragmented using a frequently-cutting restriction enzyme or randomly cleaved. In this example, it is assumed that a genome has been partially restricted.

a. Synthesis of a type I Genomic Recombinant PENTAmer Ordered Library

FIG. 14 shows an example of creating a type I genomic PENTAmer ordered library.

Figure 14A:
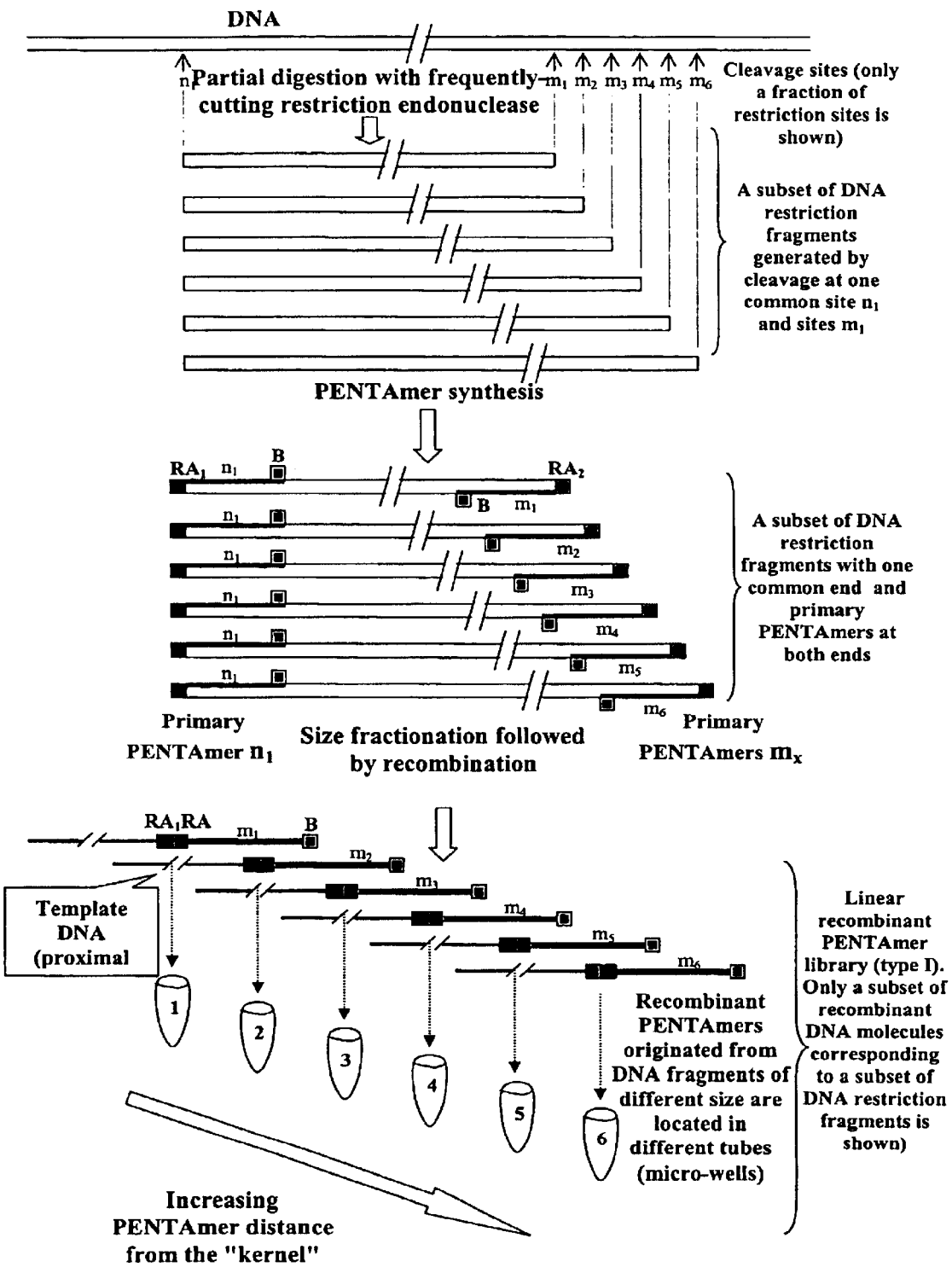
FIGS. 14A and 14B: Recombinant genomic PENTAmer library I preparation using partial digestion with frequently-cutting restriction enzyme (SmartGenome DNA I)
Figure 14B:
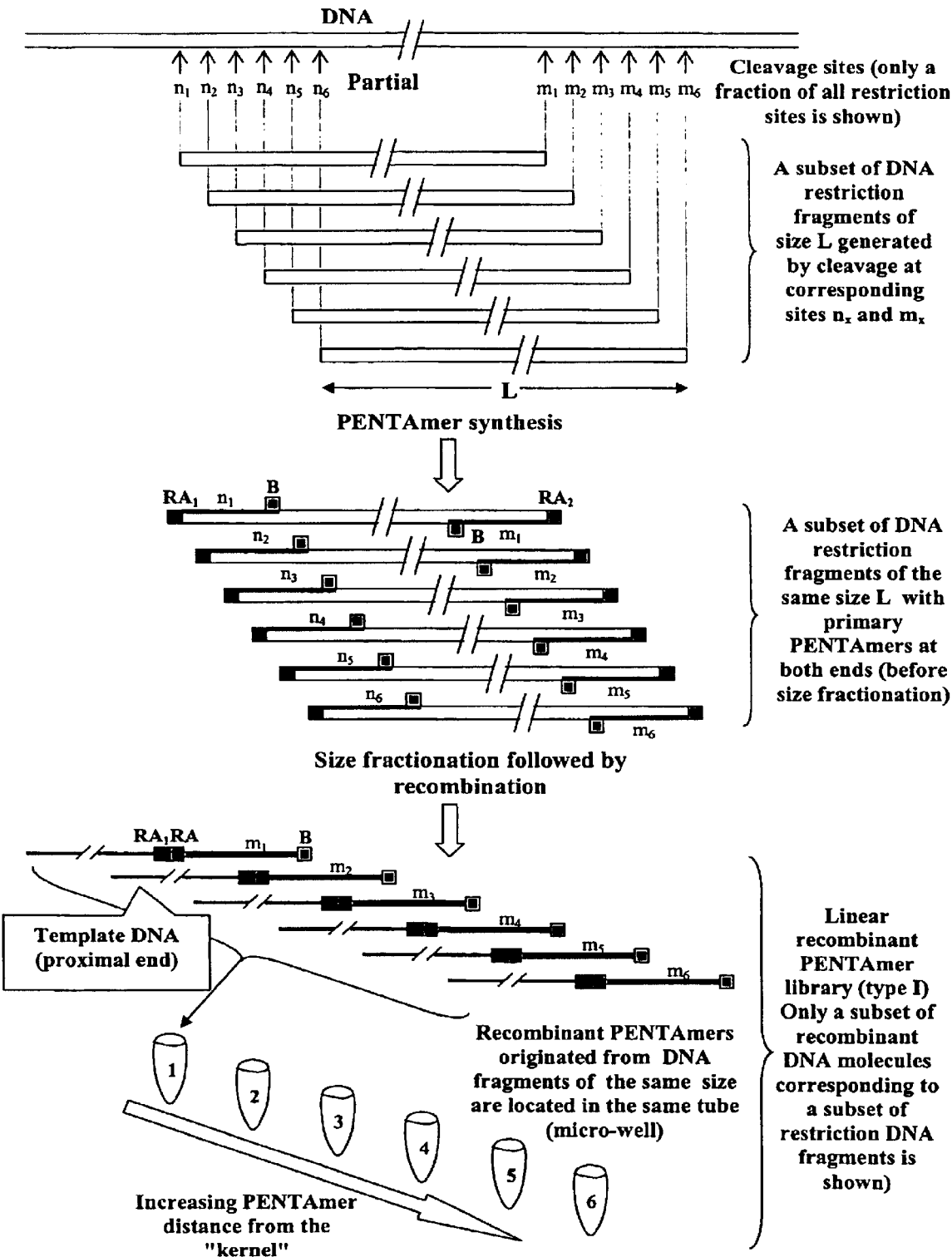

First the genome is restricted using a frequently-cutting restriction enzyme. The nested set of fragments terminating at a specific, proximal restriction site n1 is shown in FIG. 14A. The members of this set have distal ends at different restriction sites, m1, m2, m3, . . . The set of fragments of uniform size terminating at distal restriction sites m1, m2, m3, . . . is shown in FIG. 14B.

Second, nascent primary PENTAmers are synthesized at the ends of the restriction fragments (i.e., ligation of an upstream terminus-attaching recombination adaptor to each end, initiation and termination of a controlled nick-translation reaction, and attachment of a down-stream nick-attaching adaptor B).

Third, the nascent PENTAmers are fractionated by size using gel electrophoresis, pulse-field gel electrophoresis, centrifugation, or another appropriate method. Individual size fractions are placed into different tubes. The nascent PENTAmers from increasing size fractions contain distal PENTAmers increasing distances from the proximal PENTAmers. These nascent PENTAmers form a component of the genomic ordered PENTAmer library.

Fourth, the nascent PENTAmers are circularized by one of the recombination methods described in a later section. The FIG. shows the RA1–RA2 adaptor junctions formed by recombination of the distal PENTAmer strand with the proximal template strand. In this example, both adaptors can have the same sequence and structure. The structure of these recombinant PENTAmers is shown to be linear in this example, however the recombinant PENTAmers made using other recombination procedures could have different structure, including circular. The essential feature of these recombinant PENTAmers is that they join the proximal and distal ends of template fragments of different length.

Using appropriately designed adaptors, recombination can be performed before PENTAmer synthesis or before size separation. Whenever recombination is done before size fractionation, the nascent PENTAmers are separated as circular molecules.

b. Positional Amplification of a Type I Genomic Recombinant PENTAmer Ordered Library Recombinant PENTAmers can be amplified in a locus-independent or locus-specific manner.

Locus-independent amplification of all or most all of the members of a recombinant PENTAmer library is useful to increase the number and fraction of molecules that can later be subjected to locus-specific amplification. The molecules produced can incorporate nucleotide analogs during nick-translation or as a part of the primer, and subsequently isolated by affinity of a matrix or surface for the nucleotide analog, e.g., a biotinylated nucleotide. Alternatively, the complexity of the library can be decreased by incorporating nucleotide analogs into the PENTAmer strands that are resistant to chemical or enzymatic degradation. Subsequent degradation of the natural genomic DNA will enrich the library for PENTAmers. Locus-independent amplification can be done using multiple cycles of a primer-extension reaction using a primer complementary to the nick attaching adaptor B, or a single cycle of primer extension followed by transcription of the double-stranded product using RNA polymerase and a promotor domain within adaptor B.

Figure 16:
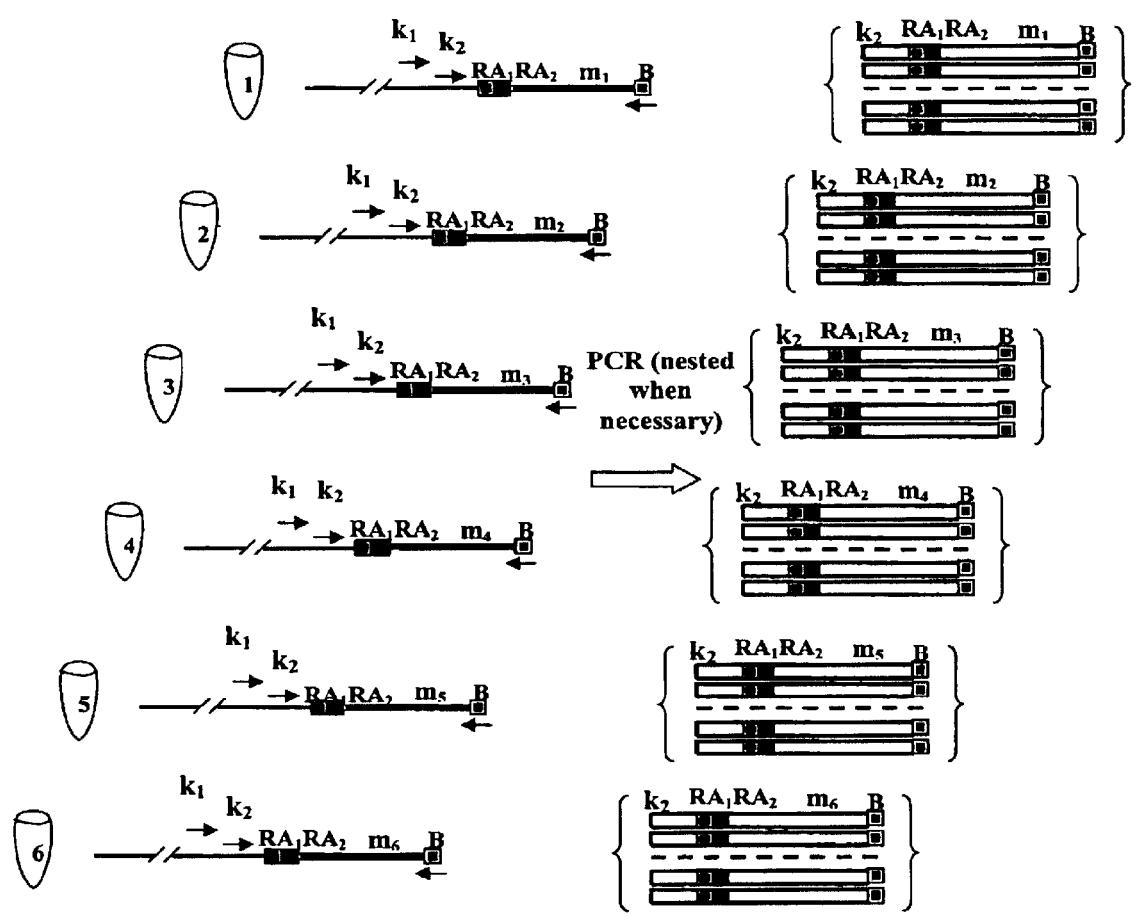
FIG. 16: Positional amplification of large DNA regions using recombinant genomic PENTAmer libraries of type I

To amplify a specific locus in a genome as an ordered amplified library, those members of the recombinant PENTAmer library containing a specified, kernel sequence are amplified. The specificity of this amplification is highest when conventional or nested PCR is used. However, any other method that employs kernels-specific primers can also be used. FIG. 16 shows an example of how the recombinant PENTAmers containing kernel sequences are amplified using a nested PCR reaction with primers complementary to the kernel sequences k1 and k2. Sequences complementary to regions increasingly distant from the genomic kernel are amplified in successive size fractions as amplimers of uniform size. Of course, depending upon the length difference between successive nascent PENTAmer size fractions and upon the length of the nick-translation products, the PENTAmer sequences in adjacent tubes will overlap by different amounts or not overlap at all.

Figure 34A:
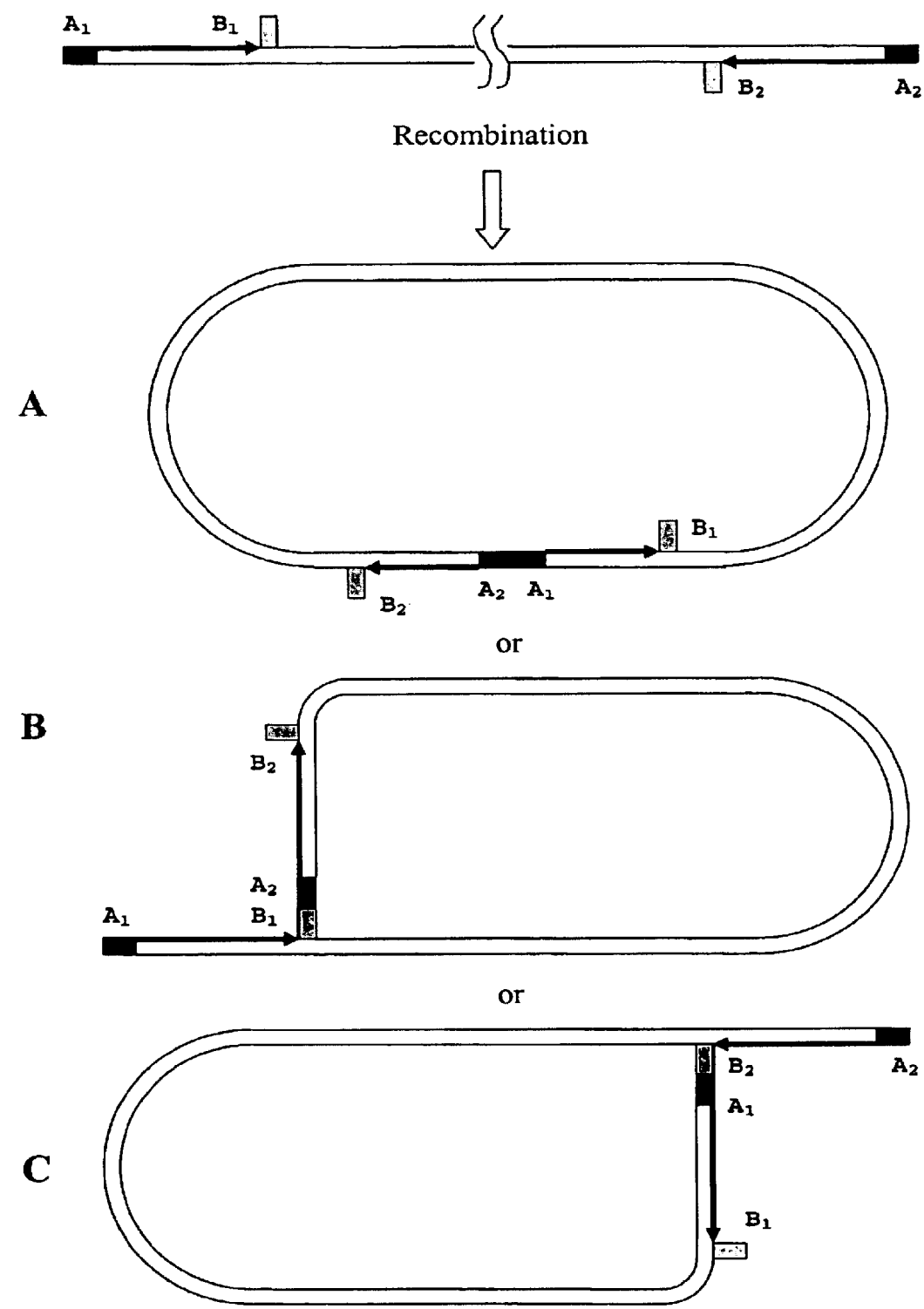

Fragments with identical proximal ends (as shown in FIG. 14A) will have kernel regions unique distances from the junctions. Fragments with all possible proximal ends (as shown in FIG. 14B) will have kernel regions different distances from the junctions. The distance between the kernel and the junction can be limited to a narrow distribution by doing one of the following:

1) Limiting the time of primer extension during linear or exponential amplification;
2) Separating the amplified strands by size; or
3) Designing the adaptors and recombination reactions to covalently join the proximal and distal PENTAmer strands, as shown in FIGS. 34A, B, and D, in which cases the time of the nick-translation reactions limit the distance of the kernel from the junction.

After locus-specific amplification of each tube from the ordered library using kernel-specific primers, the distal PENTAmers can be amplified using a primer complementary to a site within one of the recombination adaptors and the downstream adaptor B. This will produce amplimers that are smaller and more uniform in size, which are more appropriate for in vivo or in vitro cloning as molecules with unique sequence.

C. Selection of Unique Members of a Type I Genomic Recombinant PENTAmer Ordered Library The molecules amplified in a single tube of a type I genomic recombinant PENTAmer ordered library will have a distribution of sequences, because the upstream adaptor RA2 has been attached to a number of different restriction sites, and the nick-translation reaction will have terminated at a large number of sites within the genome. Although a distribution of sequences can be "read" by certain sequencing methods, including sequencing by hybridization and mass spectrometry, a distribution of sequences cannot be read using a conventional sequencing apparatus, which requires that most strands have a unique 5' end, and a 3' end that terminates at a specific nucleotide base.

To prepare samples from a PENTAmer library for sequencing, the amplified molecules should have unique sequences at one or both ends of the template-complementary region. This can be achieved by one of the following techniques:

1) PCR amplification of samples that have been diluted to the extent that usually only one DNA molecule is contained by the reaction mixture;
2) PCR amplification of samples using one primer complementary to the nick-attaching adaptor and a second primer with 5' end complementary to the terminus-attaching primer and a 3' end with one or more bases complementary to one or two specific template bases adjacent to the terminus-attaching primer. Only molecules with template sequences complementary to the selection primers will be amplified;

3) Cycle sequencing reactions that employ a selection primer with 3' end complementary to one or two bases of the template adjacent to the upstream terminus attaching adaptor; or 4) Cloning of the amplified fragments in a bacterial or viral vector and selecting individual clones for sequencing.

Figure 18A:
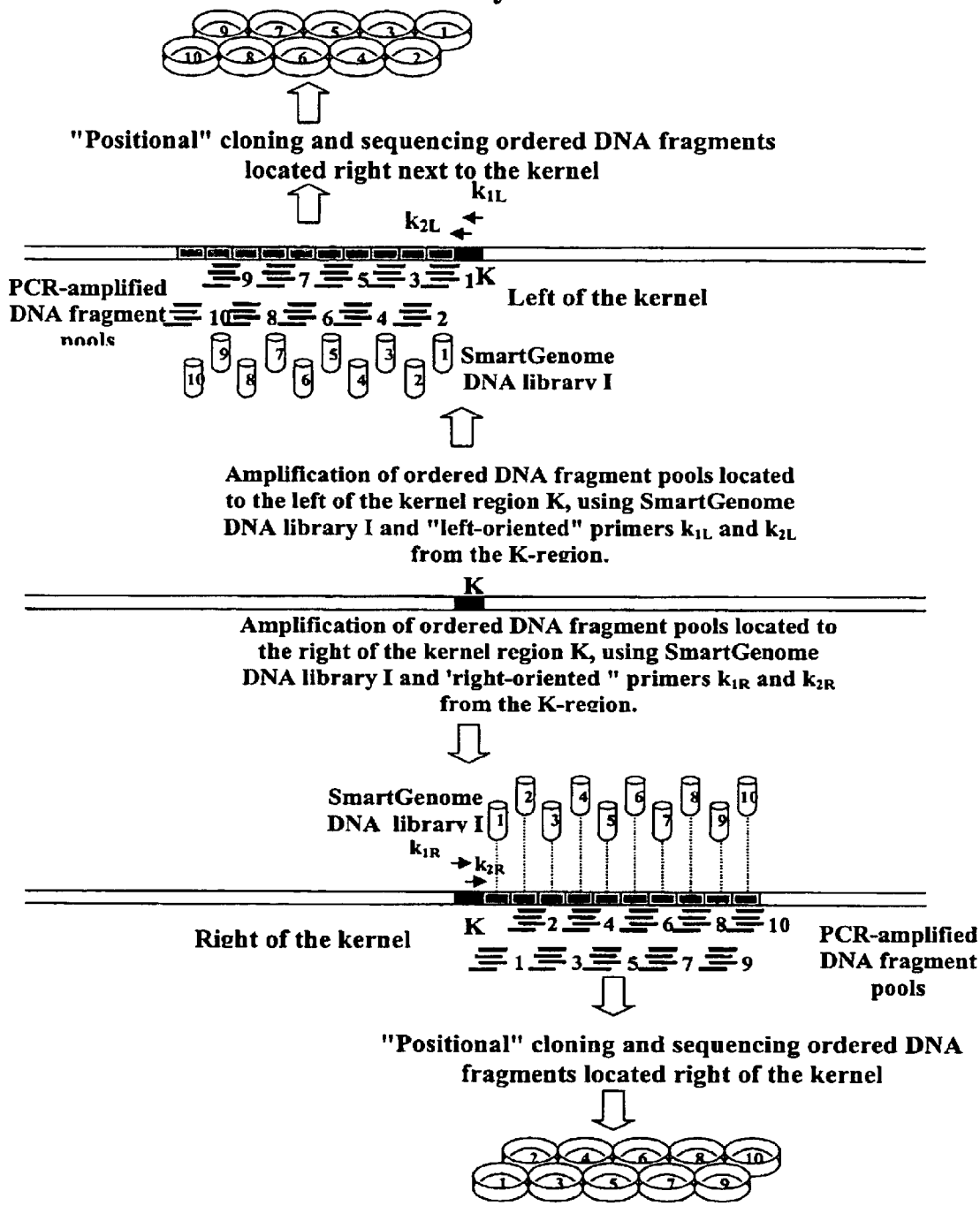

The advantage of the last method is that the cloned DNA has unique sequences at both ends of the template region and can be sequenced using sequencing reactions in both directions. The in vivo cloning approach is illustrated in FIG. 18A.

d. Type I Recombinant PENTAmer Unordered Libraries

Omission of the size fractionation produces a single tube with nascent PENTAmers of all sizes. When this mixture is amplified using primers complementary to the kernel and the adaptors, all template sequences covering a large region to the right or left of the kernel are amplified as a mixture. The sequence of this mixture can be used for many preparative and analytic purposes. Because the size of the region amplified is limited only by the physical stability of the fragments produced by enzymatic, physical, or chemical cleavage, a region of the genome as large as ~500,000 bp can be amplified in a single tube using one set of PCR primers or transcription initiation site. This mixture of fragments can resequenced using DNA microarrays, or cloned and shotgun sequenced. This mixture can be used to map the positions of genetic markers using PCR or hybridization, or to map loci on chromosomes using FISH.

e. Multiplexed Type I Recombinant PENTAmer Libraries

Using adaptors with different sequences during creation of different PENTAmer ordered or unordered libraries allows different libraries to be combined during subsequent processing steps, and the members of individual libraries later recovered by amplification using library-specific primers. For example, different bacterial genomes can be separately attached to upstream (and/or downstream) adaptors having distinguishable sequences, and subsequently combined to form a mixed library. Additionally, genomic DNA from different individual animals and plants can be separately attached to upstream (and/or downstream) adaptors having distinguishable sequences, and subsequently combined to form a mixed library. The ordered library produced could be amplified using locus-specific primers and adaptor-specific primers to amplify DNA strands from a specified position in a specified genome. Multiplexed adaptors can be distinguished during amplification, as above, as the result of reading the sequence, by hybridization, by direct labeling of the adaptors using fluorescence or mass tags, or other means. Multiplexing is an efficient method to combine the steps of processing, amplification, and detection of DNA molecules to decrease the time and cost of analysis.

5. Type II Recombinant PENTAmer Libraries

Ordered and unordered libraries can also be made from complex templates that have been cleaved twice—a complete restriction digestion with an infrequently cutting restriction enzyme and a partial digestion with a frequently-cutting agent such as a frequently-cutting restriction enzyme. The kernel sequences are chosen to be adjacent to the infrequently-cut sites. These "asymmetric" fragments have many advantages over the "symmetric" fragments restricted with a single enzyme. First, all kernel sequences are close enough to the terminus that they can be used for amplification. Second, the fraction of fragments that contain a specified kernel close to the terminus is greatly increased. Third, because the fragments containing kernels have ends created by different restriction digestions, the PENTAmers created at the two ends can have different lengths as well as different upstream and downstream adaptor sequences. Fourth, this approach makes it easy to systematically choose kernel sequences to sequence entire chromosomes. Fifth, the kernel sequences developed for amplification can also be used to detect genome instabilities.

a. Synthesis of Type II Recombinant PENTAmer Ordered Libraries

FIG. 15 shows an example of synthesis of a type II recombinant PENTAmer ordered library.

The steps are as follows:

1) Complete restriction with an infrequently-cutting restriction endonuclease to produce R1 ends;

2) Synthesis of primary PENTAmers at R1 ends (terminal PENTAmers);

3) Partial cleavage using a frequently-cutting restriction endonuclease to produce R2 ends;

4) Synthesis of primary PENTAmers at R2 ends (internal PENTAmers);

5) Recombination between the R1 and R2 ends; and

6) Size fractionation of the nascent PENTAmers.

Synthesis of the primary PENTAmers is achieved by the means described earlier. Each PENTAmer is made by attaching an upstream adaptor A, performing a controlled nick-translation reaction, and attaching a downstream adaptor B. The upstream and downstream adaptors are appropriate for specifically recombining the terminal and internal PENTAmers on the same DNA fragments. It is this joining of a proximal PENTAmer to a distal PENTAmer that creates a recombinant PENTAmer that is able to be amplified using locus-specific kernel primers.

Figure 15A:
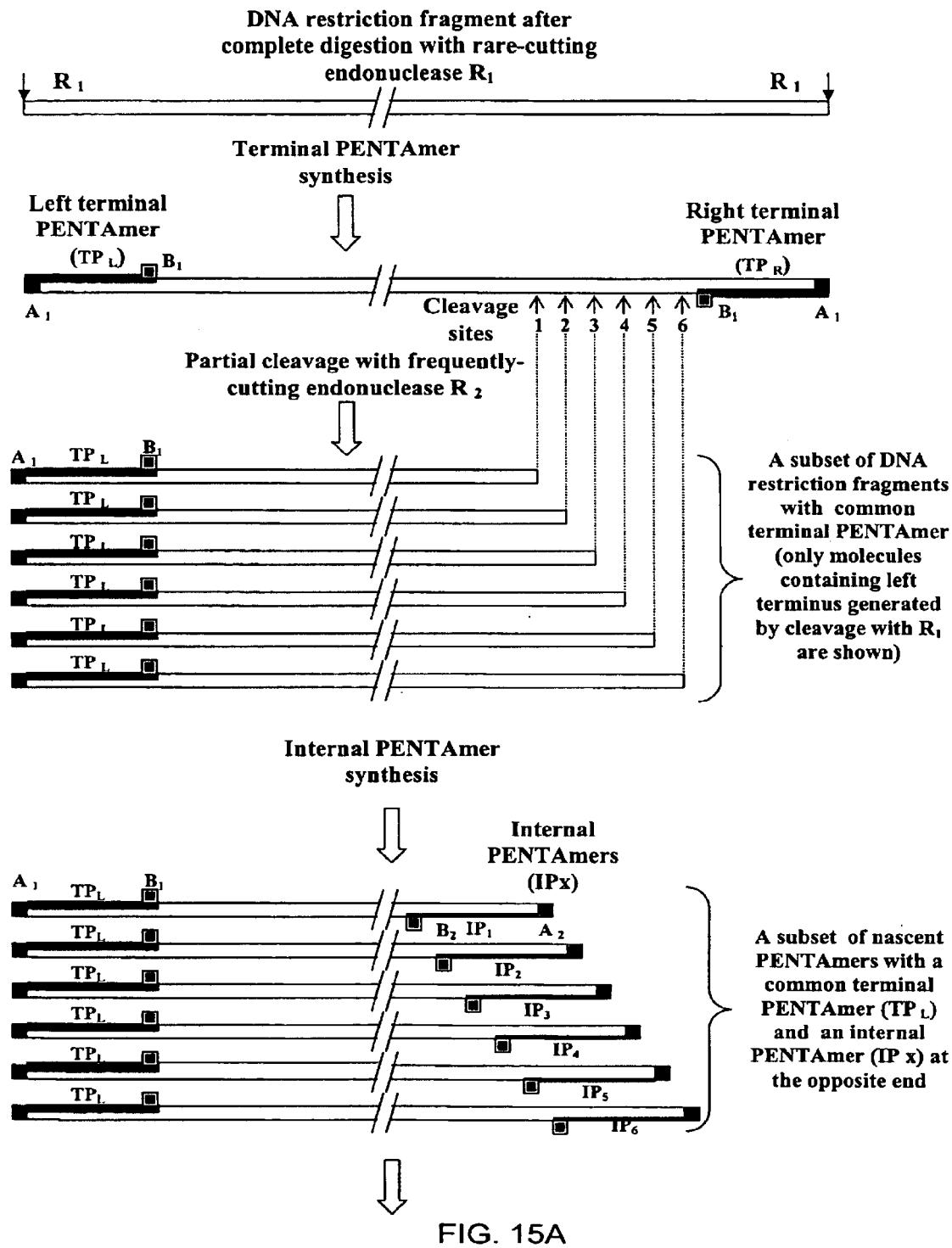
FIGS. 15A and 15B: Recombinant genomic PENTAmer library II preparation using complete digestion with rare-cutting enzyme and partial digestion (SmartGenome DNA II)

The terminal PENTAmer is shown in FIG. 15A as being synthesized prior to partial restriction, followed by synthesis of the internal PENTAmers. This stepwise process allows the upstream and downstream adaptors and the length of the PENTAmers to be different on the proximal (terminal) and distal (internal) ends of the fragments. Fragments with two $R_2$ ends will not recombine. The order of the partial and complete restriction digestions is arbitrary. For many applications, it is more advantageous to digest with the frequently-cutting restriction enzyme first. Because the R1 and R2 sites can be made to have non-complementary structure, it is also possible to synthesized the PENTAmers after both restriction digestions.

The recombination reaction is carried out with highly diluted template fragments to reduce dramatically the frequency of intermolecular recombination.

Figure 15B:
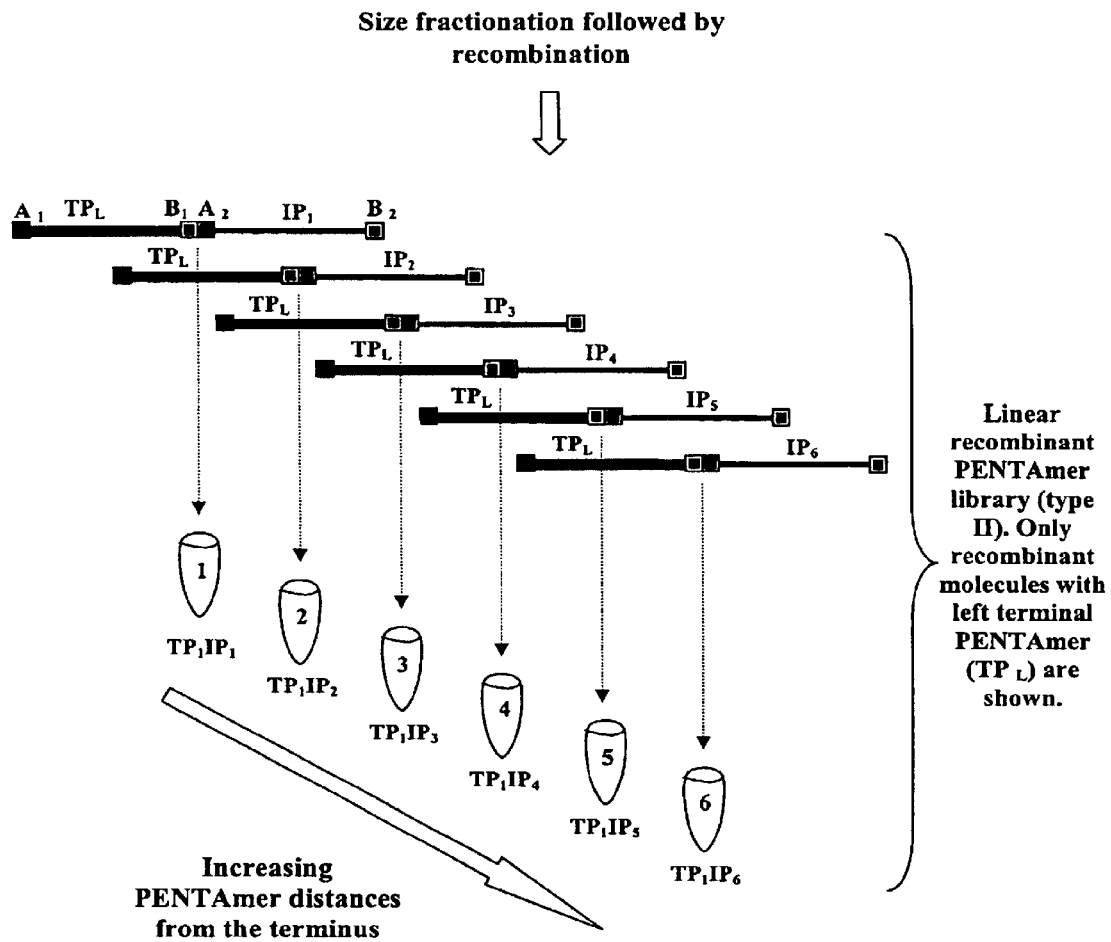

FIG. 15B shows one linear recombinant PENTAmer, made by joining a recombinant upstream adaptor $RA_2$ (shown in diagram as $A_2$) and a downstream recombinant adaptor $RB_1$ (shown in diagram as $B_1$), to produce a recombinant PENTAmer with two strands synthesized by nick-translation.

Other examples of recombinant adaptors, recombination reactions, and recombinant structures are described in later sections. Of particular interest are the circular recombinant PENTAmers.

As the result of size fractionation of the nascent recombinant PENTAmers, different tubes of the ordered library contain nascent PENTAmers of different lengths, having terminal and internal PENTAmers complementary to regions different distances apart in the genome.

b. Synthesis of Type II Recombinant PENTAmer Unordered Libraries

A type II recombinant PENTAmer unordered library is synthesized by performing all steps as in synthesizing a type II recombinant PENTAmer ordered libraries, without size separation of the nascent PENTAmers.

C. Amplification of Type II Recombinant PENTAmer Libraries

Type II recombinant PENTAmer libraries can be PCR amplified in a non-locus-specific fashion using primers complementary to the adaptors (e.g., $A_1$ and $B_2$, as shown in FIG. 15B). Such amplification amplifies the entire library.

Linear type II recombinant PENTAmer libraries can be PCR amplified in a locus-specific fashion using one or more primers complementary to a kernel region within a terminal PENTAmer and one or more primers complementary to the upstream adaptor at the distal (internal) R1 ends of the fragments.

d. Two-Step Locus-Specific Amplification of Type II Recombinant PENTAmer Unordered and Ordered Libraries In many applications, a known kernel sequence is not adjacent to an infrequently-cut restriction site and therefore cannot be used for locus-specific amplification. In this very important case, an initial amplification (step A) of a type II recombinant PENTAmer unordered library can be used to sequence a terminal kernel site and that terminal kernel used in a second step (step B) to amplify a large region adjacent to the R1 terminus as an unordered or ordered library.

FIGS. 17A through 17D show an example of using linear type II recombinant PENTAmer libraries in a two-step process. An unordered library is used in the first step and an ordered or unordered library used in the second step. Both libraries have been made with the same infrequently-cutting restriction enzyme. The frequently-cutting restriction enzymes may be identical or different. In step A, the unordered library is amplified using one or more primers complementary to a known, internal kernel sequence and one or more primers complementary to the upstream adaptor RA1 (shown as A1). The recombinant PENTAmers containing the kernel sequence will be amplified, including a region within the internal PENTAmers and the entire terminal PENTAmer. The sequence of the terminal PENTAmer can be determined using a Sanger sequencing reaction primed by an oligonucleotide complementary to the upstream adaptor A1. The sequence of the terminal PENTAmer is examined to determine one or more sites that can be used as terminal kernels, e.g., T1 and T2. Primers complementary to the terminal kernel(s) and complementary to an adaptor of the internal PENTAmer (shown in FIG. 17A as downstream adaptor B2) will amplify different internal PENTAmer sequences, IPx. If an ordered library is used in the second step, ordered fragments will be produced in different tubes. If an unordered library is used in the second step, random fragments from throughout a large region between two infrequently-cut restriction sites will be amplified.

Figure 17B:
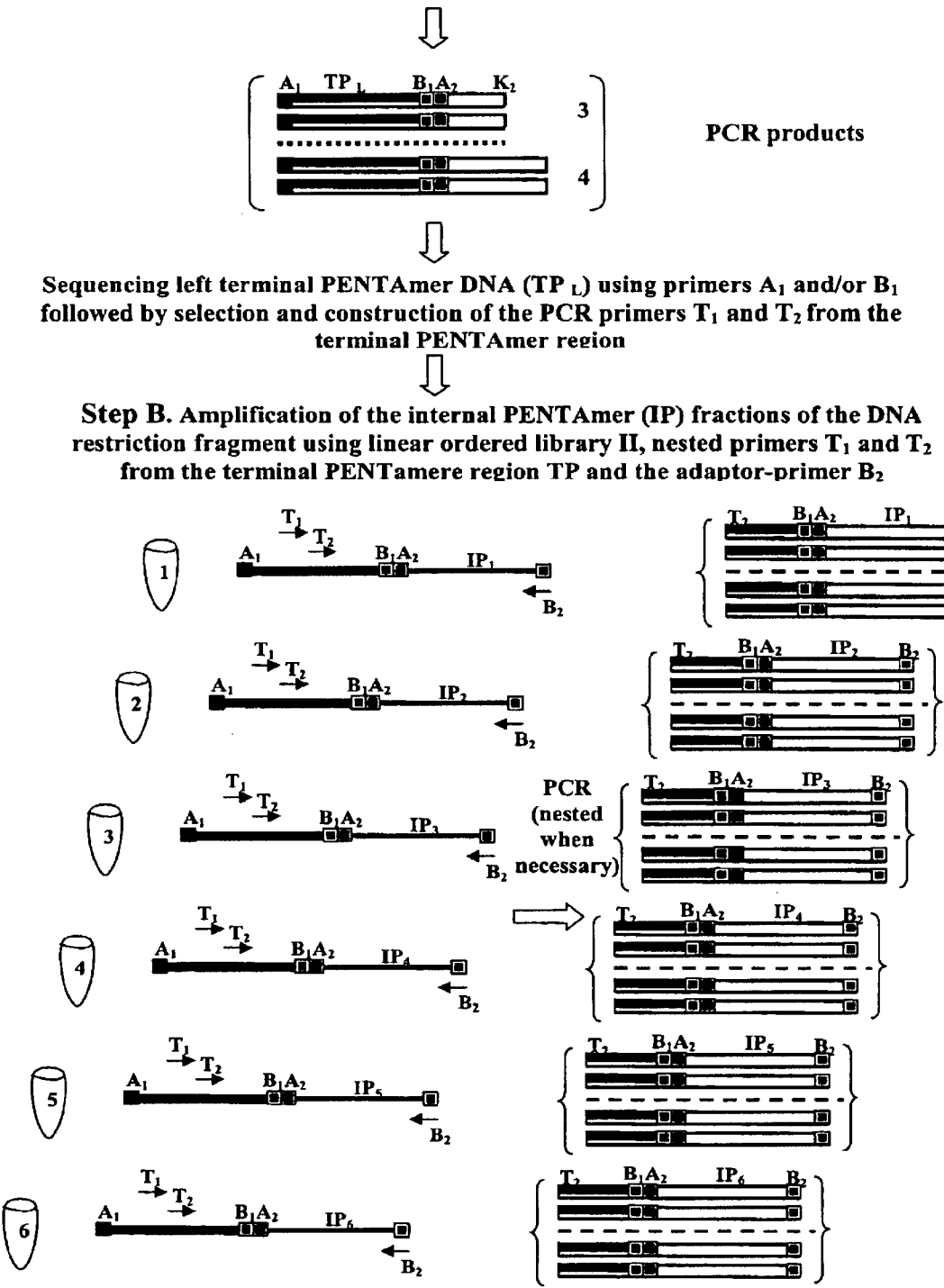

The choice of priming sites for amplification depends upon the sequences of the adaptors used and the method used to achieve recombination. For example, FIG. 17B shows the two step process of positional amplification beginning with an internal kernel mediated by circular recombinant PENTAmers. This example shows a first amplification of an unordered circular library using inverse PCR with two internal kernel-specific primers and a second step of inverse PCR using two terminal kernel primers.

e. Use of Type II PENTAmer Libraries for Genome Sequencing

Figure 18B:
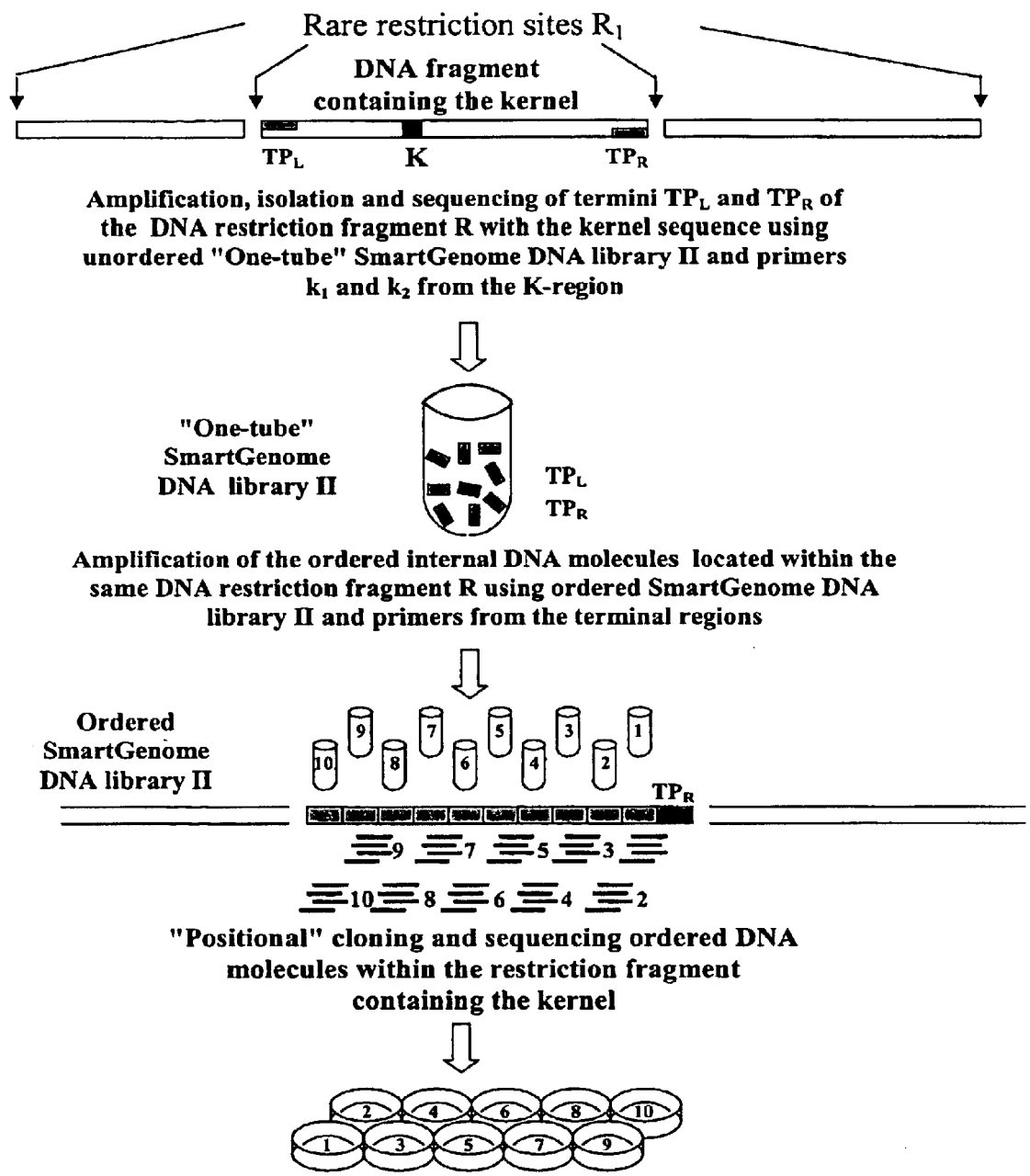

FIGS. 18B and C illustrate the strategies for using type II libraries for genomic sequencing. FIG. 18B shows how a known internal kernel can be used to first determine the terminal sequences of one region flanked by two rare restriction sites, and then the terminal sequences used to amplify all the internal PENTAmers, followed by selection of unique fragments by in vivo or in vitro cloning and sequencing.

FIG. 18C shows a strategy to sequence an entire genome without prior identification of kernels. In step 1 primary PENTAmers are synthesized at all termini created by the rare restriction enzyme. These terminal PENTAmers are sequenced and the sequences assembled into a database of terminal sequences. In step 2 the internal PENTAmers are amplified and sequenced, using kernels in the database of terminal sequences. In step 3 a type I ordered or unordered library is used to link the terminal sequences from one large restriction fragment with the sequences of the adjacent large restriction fragment.

Q. Specialized Adaptors for PENTAmer Synthesis

To promote synthesis of the primary PENTAmers and facilitate creation of the complement PENTAmers and secondary PENTAmers, several new adaptors and methods for their creation described herein. Depending on the location of the attachment site along double-stranded DNA molecule the adaptors can be divided into two classes: terminus-attaching and nick-attaching adaptors. A terminus-attaching adaptor is designed to be ligated to a DNA end created by enzymatic, chemical or physical DNA cleavage. A nick-attaching adaptor is designed to be covalently linked to a free 3'-OH or 5'-P group located at an internal nick or gap within a primarily double-stranded DNA molecule. Depending on the position within the DNA strand the adaptors can be also divided into two groups: up-stream and down-stream adaptors. Up-stream adaptors are adaptors located at the 5' end of the DNA strand, down-stream adaptors are adaptors located at the 3' end. Adaptors can have multiple domains with different functions, for instance, specific domains for hybridization or ligation to a ends of template DNA molecules, efficient initiation of a PENT reaction, detection, amplification, and recombination. Adaptors can be single or double stranded DNA molecules. A functional domain can be a fraction of the nucleotides of a DNA molecule, the entirety of a DNA molecule, or multiple DNA molecules connected via non-covalent linkages.

1. Up-Stream Terminus-Attaching Nick-Translation Adaptors: Composition and Attachment to DNA.

Up-stream terminus-attaching nick-translation adaptors are short artificial DNA molecules that are directly ligated to the ends of DNA fragments generated, for example, by digestion with restriction enzyme(s). Their design has a minimum of two domains: 1) a domain optimized for efficient ligation to the ends of template DNA molecules, and 2) a domain optimized for efficient initiation of the nick-translation reaction towards the middle of the template DNA fragments. In addition, other functional domains can be present, such as domains for optimal amplification or detection and/or domains that inhibit self-ligation of the adaptors.

A preferred design of an up-stream nick-translation adaptor is formed by annealing 3 oligonucleotides (or more): oligonucleotide 1, oligonucleotide 2 and oligonucleotide 3 (FIG. 19A). The left ends of these adaptors are designed to be ligated to double-stranded ends of template DNA molecules and used to initiate nick-translation reactions. Oligonucleotide 1 has a phosphate group (P) at the 5' end and a blocking nucleotide (X) at the 3' end, a non-specified nucleotide composition and length from 10 to 200 bases. Oligonucleotide 2 has a blocked 3' end (X), a non-phosphorylated 5' end, a nucleotide sequence complementary to the 5' part of oligonucleotide 1 and length from 5 to 195 bases. When hybridized together, oligonucleotides 1 and 2 form a double-stranded end designed to be ligated to the 3' strand at the end of a template molecule. To be compatible with a ligation reaction to the end of a DNA restriction fragment, an up-stream nick-translation adaptor can have blunt, 5'-protruding (as shown by example in FIG. 19A) or 3'-protruding end. Oligonucleotide 3 has a 3' hydroxyl group, a non-phosphorylated 5' end, a nucleotide sequence complementary to the 3' part of oligonucleotide 1, and length from 5 to 195 bases. When hybridized to oligonucleotide 1, oligonucleotides 2 and 3 form a nick or a few base gap within the lower strand of the adaptor. Oligonucleotide 3 can serve as a primer for initiation of the nick-translation reaction.

Figure 19:
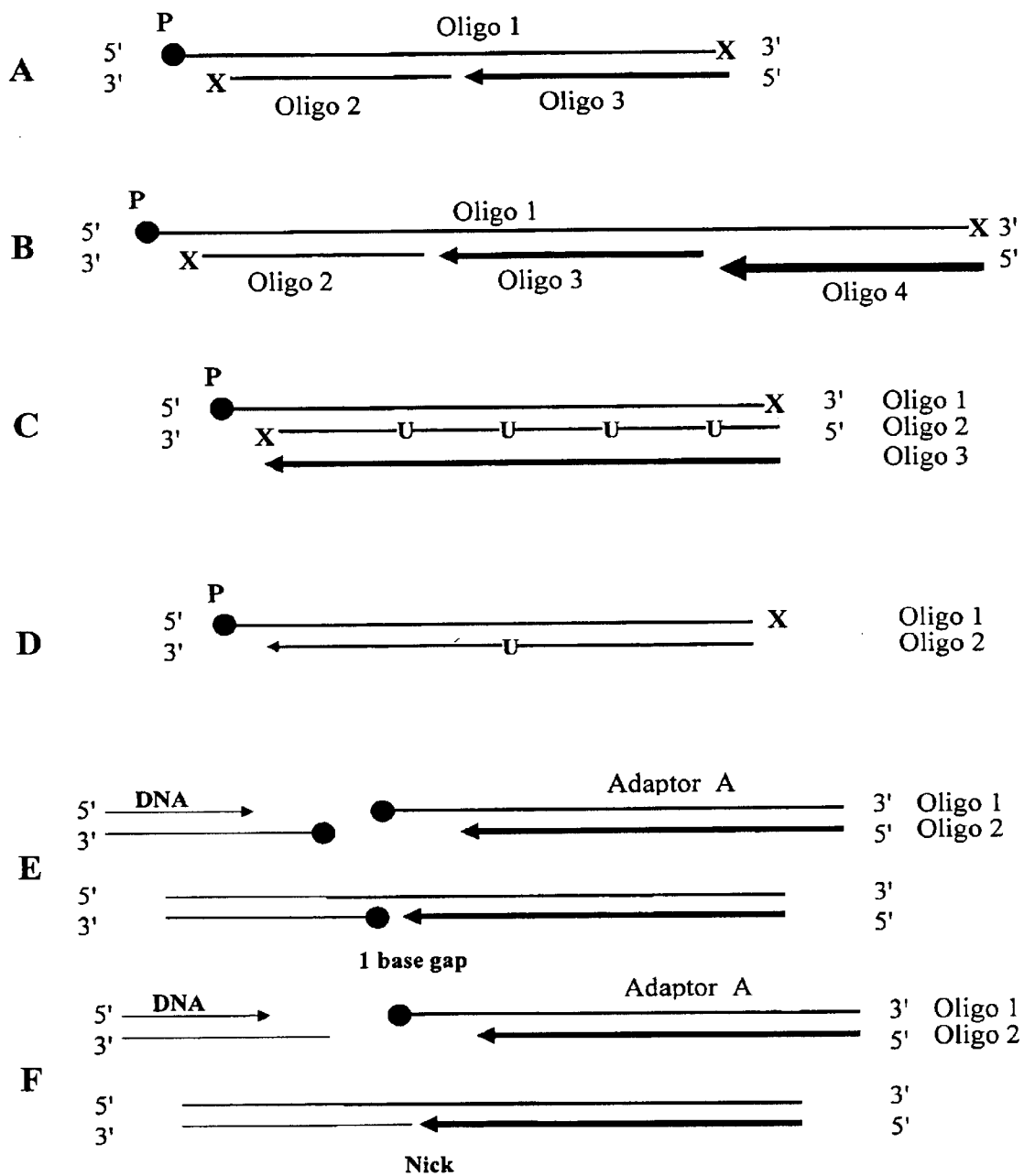
FIG. 19: Up-stream terminus attaching nick-translation adaptors

Blocking nucleotides at the 3' ends can be any dideoxynucleotide, amino-modified nucleotide or any other nucleotide analog that prevents ligation of the 3' ends to another strand or extension of the oligonucleotide by a polymerase such as Taq polymerase or terminal deoxynucleotidyl transferase (TdT). The 5' ends of all oligonucleotides in FIG. 19 are not phosphorylated, and therefore blocked from ligation reactions, unless where indicated wherein phosphorylation competent 5' ends are shown as dark circles.

The functions of oligonucleotide 1 are to be ligated to the end of a template DNA molecule, and to hybridize to additional, complementary oligonucleotides that have additional functions. Oligonucleotide 2 hydrogen bonds to complementary sequences adjacent to the 5' end of oligonucleotide 1 to make a double-stranded terminus that is compatible (i.e., can be ligated to) the end of a template DNA molecule. Oligonucleotide 3 hydrogen bonds to complementary sequences adjacent to the 3' end of oligonucleotide 1, has a 3' end that can prime (i.e., initiate) a nick-translation reaction, and a 5' end incapable of being ligated to another strand.

Less preferred embodiments of the upstream terminus-attaching nick-translation adaptors can be made to achieve the same purposes. For example, a gap between the 5' end of oligonucleotide 2 and 3' end of oligonucleotide 3 would achieve the same goal of preventing ligation of oligonucleotide 2 to oligonucleotide 3.

When it is necessary to perform a second nick-translation reaction to create a secondary PENTAmer molecule, oligonucleotide 1 is designed to have an extended 3' tail for binding the second oligonucleotide primer 4 (FIG. 19B).

An up-stream nick-translation adaptor has only one ligation-competent terminus—the phosphorylated 5' end of oligonucleotide 1. This novel feature prevents ligase from dimerizing the adaptors. As a result, the adaptor concentration remains high during the ligation reaction with T4 DNA ligase, and the adaptor can be efficiently ligated to the 3' ends of DNA molecules even when present at a low adaptor/DNA terminus ratio.

After an upstream terminus-attaching nick-translation adaptor is ligated to template DNA there is only one free 3' OH group available for a DNA polymerase reaction. This novel feature is critical for the production of a PENTAmer, because it allows 1) efficient initiation of a nick-translation reaction from the ends of the template DNA fragments by extending oligonucleotide 3 in the presence of DNA polymerase with 5' exonuclease activity, and 2) appends a known sequence to the 3' end of the nick-translation product that can later be used in amplification reactions.

In addition to the critical functions of the upstream terminus-attaching nick-translation adaptor listed above, there are two optional features that can be designed into the adaptor. First, for those applications where an 3' exonuclease is used to convert the nick-translation nick to a gap, the adaptor should be designed so as to protect the 3' end of oligonucleotide 1 from exonucleolytic activity. This can be done by incorporation of a nuclease-resistant nucleotide analog (e.g., α-thioated (Nakayame et al., 1988) or α-boronated nucleotides (WO 98.1112)) into the adaptor. Second, for those applications involving recombination of the upstream end of the adaptor, the sequence and structure of the adaptor can be optimized to promote recombination. These more sophisticated nick-translation recombination adaptors are referred to as RA adaptors and are discussed later.

According to the nomenclature utilized herein, up-stream terminus-attaching nick-translation adaptors are labeled with the capital letter A. Subscript symbols are used to differentiate adaptors attached to two different ends of a template DNA fragment, if they are produced by two different biochemical, chemical or physical procedures and have different structure.

An additional design (FIG. 19C) has oligonucleotide 1 of the same design as above, and complementary oligonucleotide 2 that hydrogen bonds to all or part of oligonucleotide 1. Although not always necessary, oligonucleotide 2 can have a blocking nucleotides at the 3' and 5' ends to prevent ligation to other adaptors. To facilitate creation of an initiation site for the nick-translation reaction, several nucleotide positions have deoxyribouracil or other degradable bases. After ligation to the adaptor end of a template molecule, the degradable bases can be degraded (e.g., using dU glycosylase and endonuclease IV or V, fragmenting a region of oligonucleotide into short molecules that dissociate from oligonucleotide 1, so as to expose a single-stranded region of oligonucleotide 1. Oligonucleotide 3 can subsequently be hybridized to the 3' single strand region on oligonucleotide 1. Oligonucleotide 3 should have a 3' end capable of being extended to initiate the nick-translation reaction. The 5' end of oligonucleotide 3 can be blocked or unblocked.

An additional design (FIG. 19D) has oligonucleotide 1 with 5' phosphate group and blocked 3' end. Oligonucleotide 2 has a single degradable base, such as a deoxyribouracil, and a 3' end that is blocked or has a 3' hydroxyl that can be covalently joined to the template. After ligation of this adaptor to the template DNA the degradable base is degraded to expose a 3' hydroxyl group that can be extended in a nick-translation reaction using a polymerase.

An additional design (FIG. 19E) has an oligonucleotide 1 with a 5' phosphate, and an oligonucleotide 2 that is complementary to oligonucleotide 1 and a 3' end with a 3' hydroxyl group, capable of being extended by a polymerase. This forms a double-stranded DNA molecules that can ligate to the 3' strand of the template DNA, but forms a gap between the 5' end of the template and the 3' end of the adaptor that prevents ligation of the 5' end of even a phosphorylated template to the adaptor. This gap has the function of protecting this 3' end of the adaptor from ligation to the template, while still serving as an efficient initiation site for the nick-translation reaction. This initiation oligonucleotide could be designed to be ligated to a template with either a 3' or 5' overhang, but not a blunt end. This adaptor would be protected against dimerization.

FIG. 19F shows an example of an adaptor that has the left end that is compatible with the restricted end of the template and is ligated to the template without a gap. This simple adaptor design can be used on template molecules that have been dephosphorylated before ligation of the adaptor. This adaptor design has the disadvantage that it will form adaptor dimers in addition to being ligated to the template.

2. Nick-Attaching Adaptors

Nick-attaching adaptors are partially double-stranded or completely single-stranded short DNA molecules that can be covalently linked to 3' or 5' DNA termini within the nick produced by a nick-translation reaction. Addition of these adaptors to the products of the nick-translation reaction is necessary to add the specific sequences used in the amplification of PENTAmers.

a. Nick Modifications.

Because DNA termini within the nick have very low ligation efficiency, additional enzymatic procedures that specifically modify the nick are necessary for efficient attachment of the down-stream adaptor. These procedures either convert the nick into a small gap, add a limited number of nucleotides to the 3' terminus, or displace a small length of the 5' end.

A nick can be converted into a small gap by a limited treatment of DNA with: (i) 5'-exonuclease (e.g., gene 6 exonuclease from bacteriophage T7, α-exonuclease), or (ii) 3' exonuclease (e.g., exonuclease III, Klenow fragment of the DNA polymerase I, T4 DNA polymerase). In the last case, the control of the DNA trimming in the 3'→5' direction can be facilitated by incorporation of a nuclease-resistant α-thioated or α-boronated nucleotide derivatives at the end of the nick-translation reaction.

A 3' hydroxyl group within the nick can be extended with a homopolymeric tail by DNA incubation with terminal deoxynucleotidyl transferase (TdT) and one of the triphosphates (dATP, dTTP, dCTP or dGTP). The dGTP is a preferred nucleotide, because G-tails of a limited length (15–20 guanines) can be efficiently added to the ends of DNA, and to DNA templates with a nick (See Examples 8, 9, 11, 12, 13, and 21).

DNA templates with nick can be subjected to a limited strand-displacement DNA synthesis in the presence of such polymerases as Klenow fragment, DNA polymerase I (exo⁻), Bst DNA polymerase, Vent (exo⁻) and Deep Vent (exo⁻). These polymerases have strand-displacement activity but lack 3'→5' and 5'→3' exonucleolytic activities. As a result of such treatment, a small (10–20 base) 5' portion of the DNA strand beyond the nick (trimmed strand) will be displaced by additionally synthesized DNA. At elevated temperature the displaced phosphorylated 5' tail would transiently re-associate with DNA and displace the 3' portion of the newly synthesized strand.

b. Down-Stream Nick-Attaching Adaptors: Composition and Attachment to DNA.

Down-stream nick-attaching adaptors are partially double-stranded or completely single-stranded short DNA molecules that can be covalently linked to the 3' hydroxyl group of the nick-translation DNA product. Nick-translation DNA product can be a single-stranded molecule isolated from its DNA template or the nick-translation product still hybridized to the template DNA. Down-stream nick-attaching adaptors are designed to complete the synthesis of the 3' end of PENTAmers. The label B-3' denotes all types of down-stream nick-attaching adaptors.

Below, it is proposed five types of down-stream nick-attaching adaptors that can be linked to the gapped or tailed nicks within double-stranded DNA to create a covalent link between the adaptor and the 3' end of the nick-translation product.

i. Down-Stream Nick-Attaching Adaptor B-3' (I) Targeted to a Gap by a Ligation Reaction.

Figure 20:
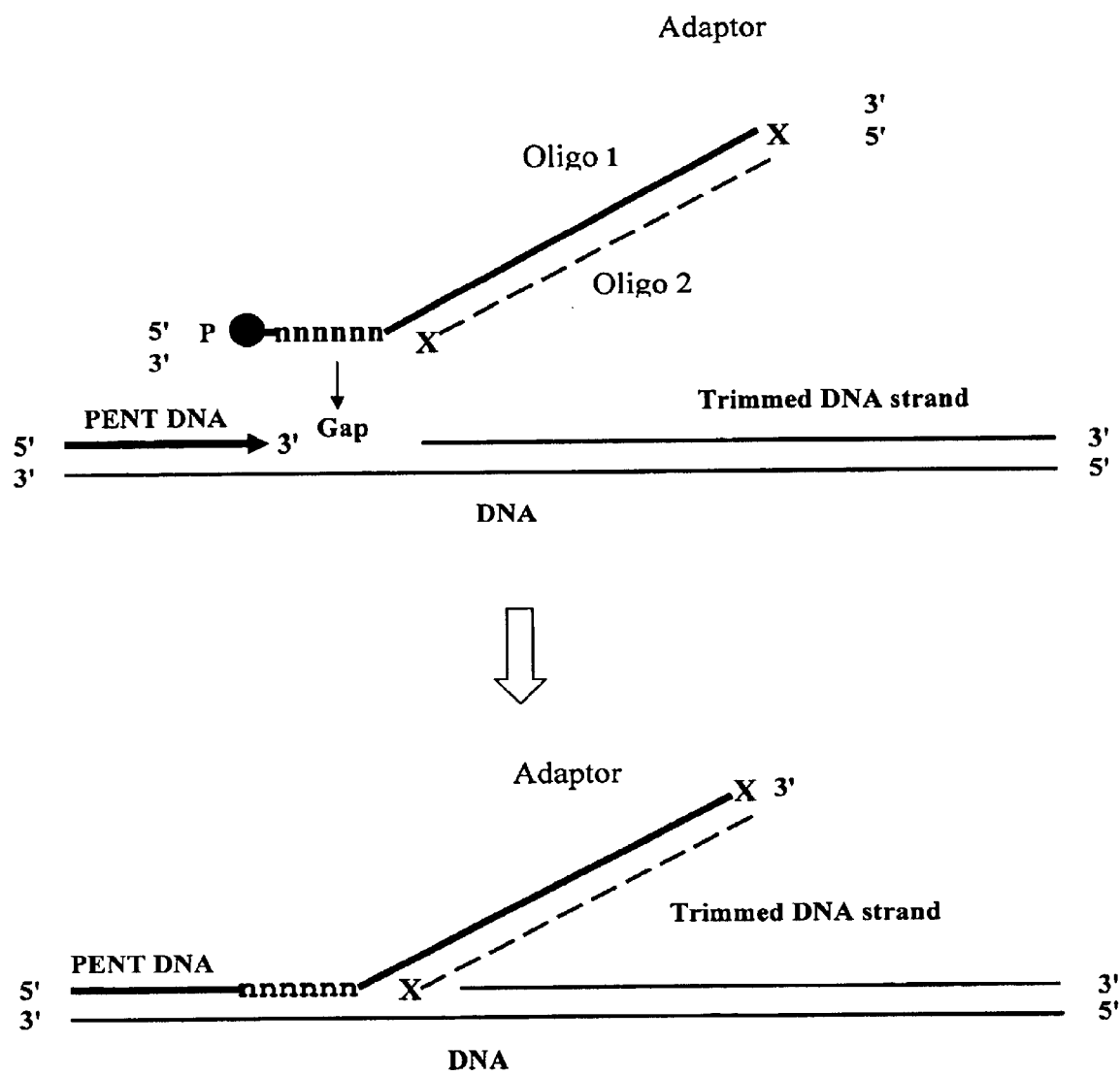
FIG. 20: Down stream nick attaching adaptor B-3' (I) targeted to a gap by a ligation reaction

Down-stream adaptor B-3' (I) is a completely or partially single-stranded oligonucleotide construct. It consists of oligonucleotide 1 and optional complementary oligonucleotide 2 (FIG. 20). Oligonucleotide 1 has a short 5' region (n)N with a random base composition and a length from 4 to 10 bases, and a long 3' region with a unique but non-specified nucleotide composition and length from 12 to 100 bases. At the 5' and 3' ends it has a phosphate group P and a blocking nucleotide X, respectively. Oligonucleotide 2 has a blocking nucleotide X at the 3' end. It hybridizes to the unique 3' region of the oligonucleotide 1 to reduce the non-specific interaction of the adaptor with DNA.

Down-stream nick-attaching adaptor B-3' (I) can be ligated by its 5' phosphate group P to the 3' end of the nick-translation product when it transiently hybridizes to the single-stranded DNA within a gap (FIG. 20). Different ligases can be used to ligate the down-stream nick-attaching adaptor, including T4 DNA ligase.

ii. Down-Stream Nick-Attaching Adaptor B-3' (II) Targeted to the Terminal Deoxynucleotidyl Transferase-Synthesized Homopolymeric Tail by a Ligation Reaction.

Figure 21:
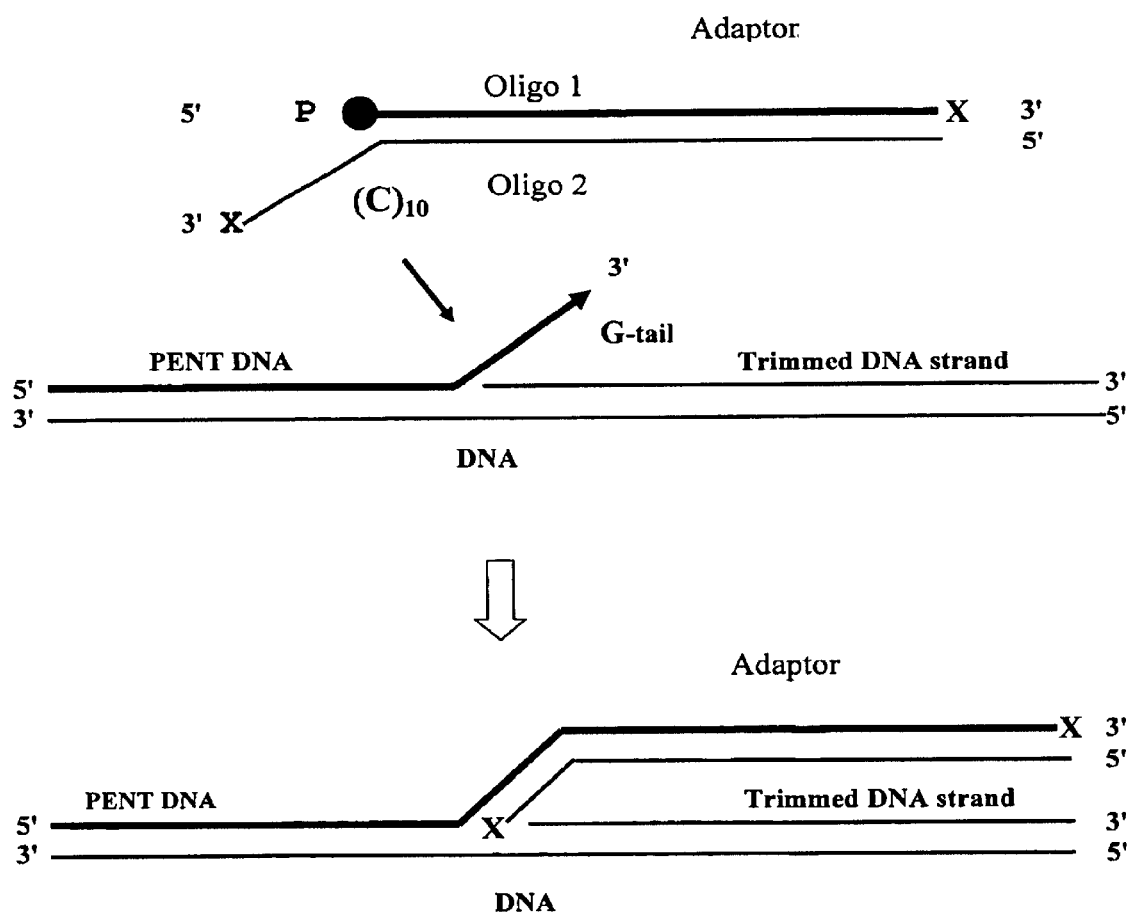
FIG. 21: Down stream nick attaching adaptor B-3' (II) targeted to a homopolymeric DNA tail by a ligation reaction

Down-stream adaptor B-3'(II) is a partially single-stranded molecule. It is formed by annealing two mostly complementary oligonucleotides 1 and 2 (FIG. 21). Oligonucleotide 1 has a unique sequence with a non-specified nucleotide composition and a length from 12 to 100 bases and a phosphate group P at the 5' end. Oligonucleotide 2 has a homopolymeric tract of 8–20 bases (poly A, poly T, poly C or poly G), a blocking nucleotide X at the 3' end, and a 5' region complementary to the oligonucleotide 1 of the same length (12–100 bases).

Down-stream adaptor B-3' (II) is ligated by its 5' phosphate group P to the 3' end of the homopolymeric tail at the end of the nick-translation product when it transiently or stably hybridizes to it (FIG. 21). Different ligases can be used to ligate the down-stream nick-attaching adaptor including T4 DNA ligase, E. coli DNA ligase, Taq DNA ligase (New England BioLabs), or Ampligase (Epicentre).

iii. Down-Stream Nick-Attaching Adaptor B-3' (III) Targeted to a Partially Displaced 3' Terminus of the Nick-Translation Product by a Ligation Reaction.

Figure 22:
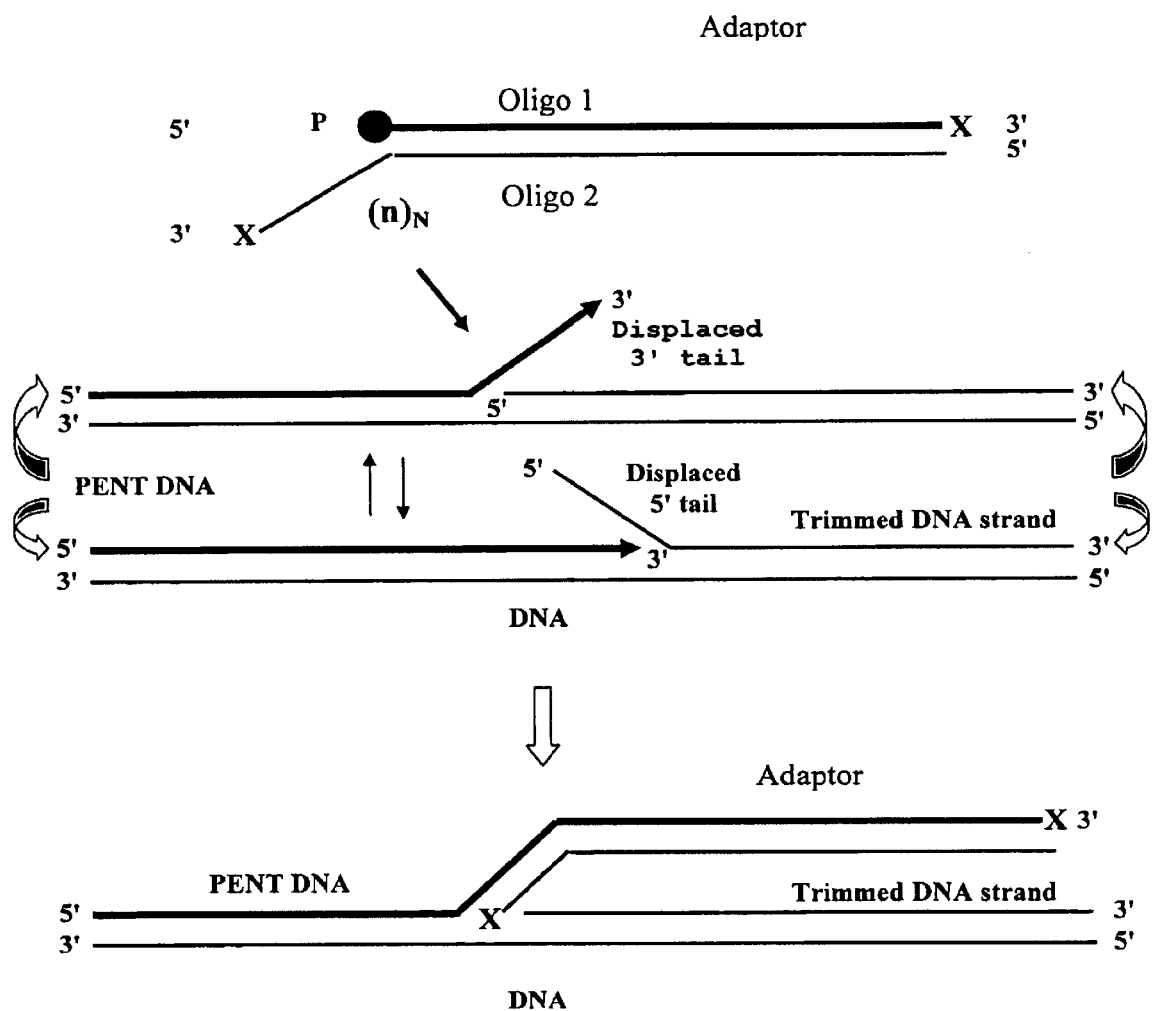
FIG. 22: Down stream nick attaching adaptor B-3' (III) targeted to a displaced 3' DNA tail by a ligation reaction

Down-stream adaptor B-3' (III) is a partially single-stranded oligonucleotide construct. It is formed by annealing two mostly complementary oligonucleotides 1 and 2 (FIG. 22). Oligonucleotide 1 has a unique sequence with a non-specified nucleotide composition and a length from 12 to 100 bases and a phosphate group P at the 5' end. Oligonucleotide 2 has a short random tract of N bases preferably 4–12 bases), a blocking nucleotide X at the 3' end, and a 5' region complementary to the oligonucleotide 1 of the same length (12–100 bases).

Figure 23:
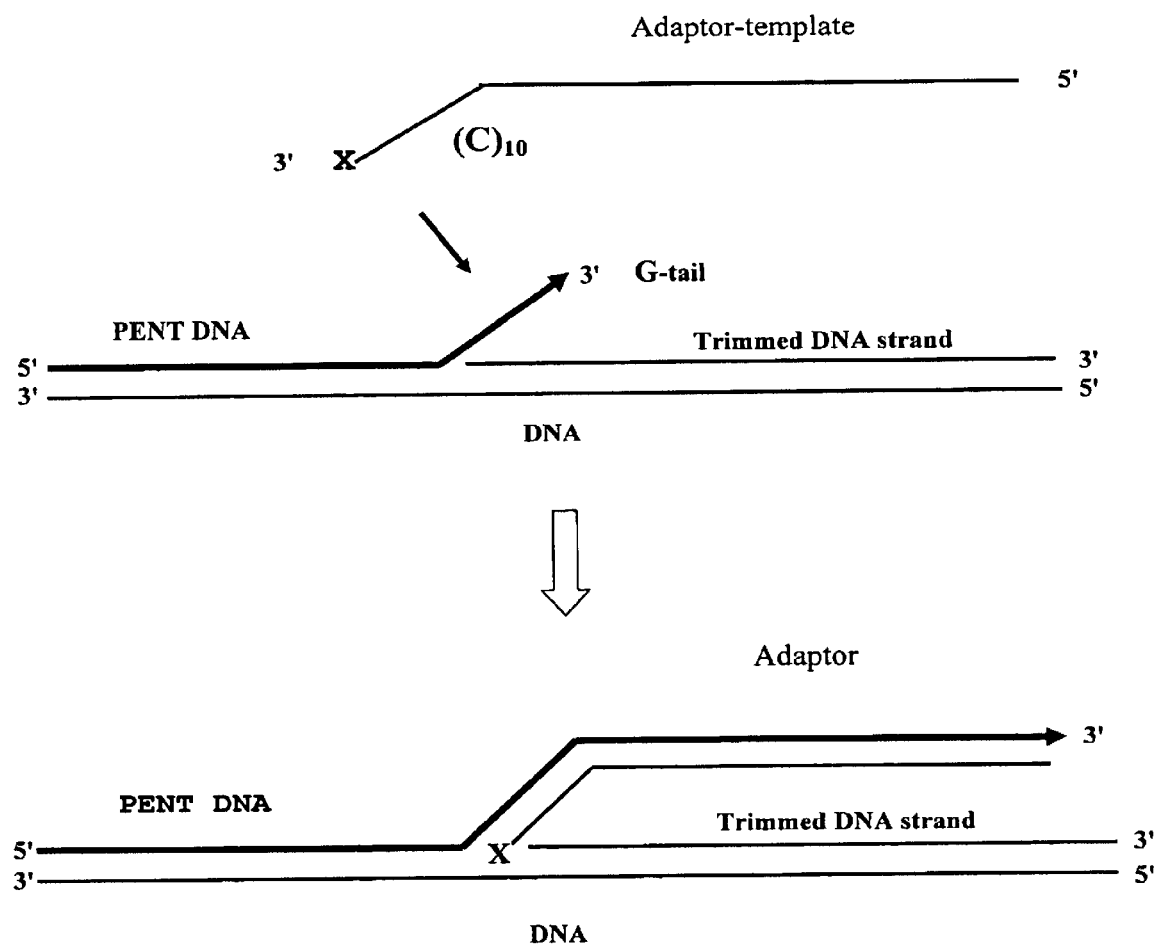
FIG. 23: Down stream nick attaching adaptor B-3' (IV) targeted to a homopolymeric DNA tail as a template for a polymerization-extension reaction
Figure 24:
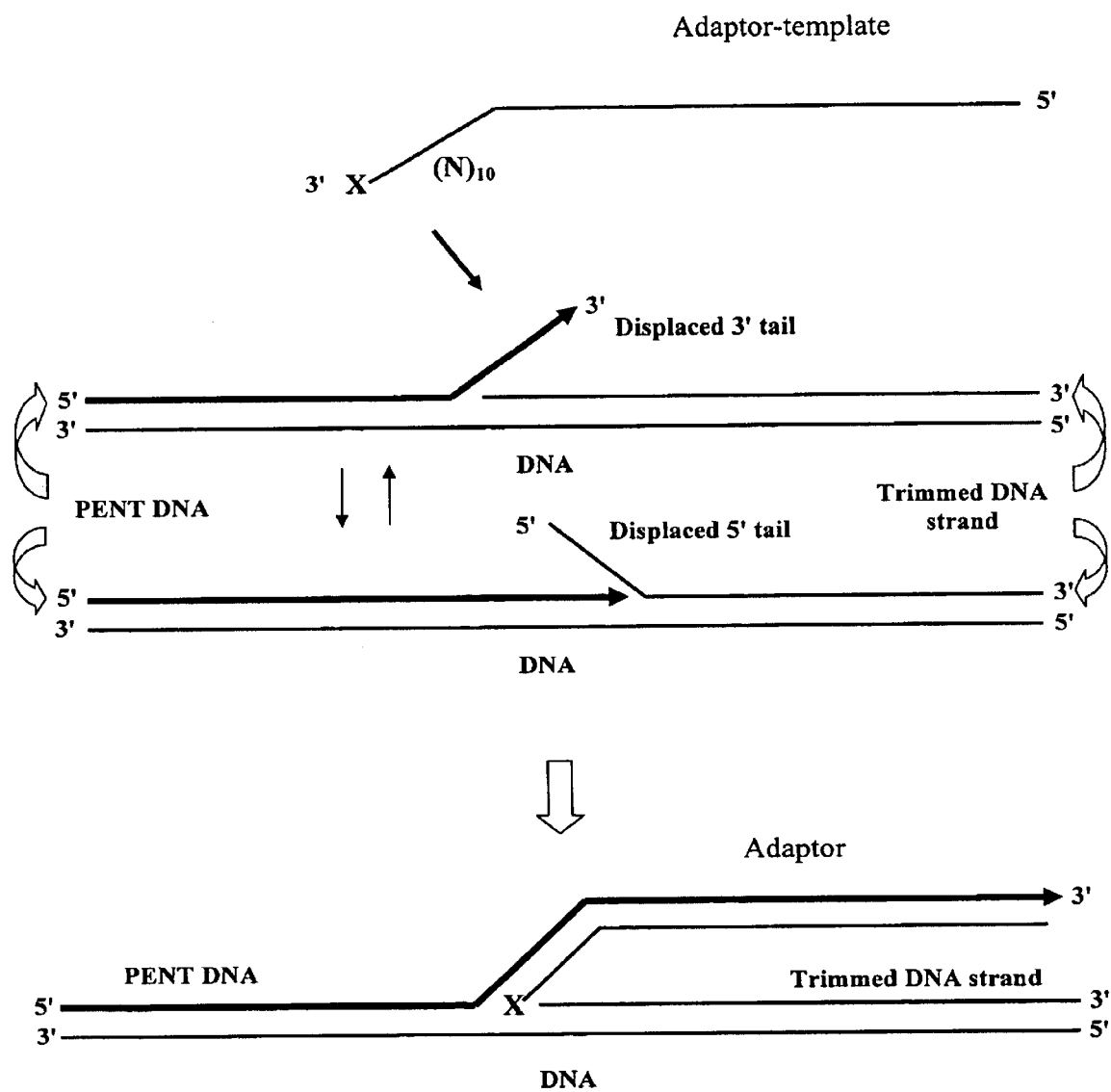
FIG. 24: Down stream nick attaching adaptor B-3' (V) targeted to a displaced 3' DNA tail as a template for a polymerization-extension reaction

Down-stream nick-attaching adaptor B-3' (III) is ligated by its 5' phosphate group P to the 3' end of the displaced DNA tail at the end of the nick-translation product by transiently or stably hybridizing it to the displaced 3' tail (FIG. 22). Different ligases can be used to ligate the down-stream nick-attaching adaptor including T4 DNA ligase, E. coli DNA ligase, Taq DNA ligase (New England BioLabs), Ampligase (Epicentre).

iv. Down-Stream Nick-Attaching Adaptor B-3' (IV) Targeted to the TdT-Synthesized Homopolymeric Tail by a Primer-Extension Reaction Down-stream nick-attaching adaptor B-3' (IV) is a single-stranded oligonucleotide (FIG. 23). The oligonucleotide has a homopolymeric tract of 8–20 bases (poly A, poly T, poly C or poly G) and a blocking nucleotide X at the 3' end, a unique sequence with a non-specified nucleotide composition at the 5' end and length from 12 to 100 bases. In the example shown in FIG. 23, the homopolymer tail of the extended product is poly G. This adaptor is hybridized transiently or stably to the 3' end of the nick-translation product and subjected to a primer extension reaction that uses the sequences of the adaptor as the template to complete synthesis of the PENTAmer. Different DNA polymerases can be used for the polymerization reaction.

v. Down-Stream Nick-Attaching Adaptor B-3' (V) Targeted to a Partially Displaced 3' Termini of the Nick-Translation Products by a Primer-Extension Reaction Down-stream adaptor B-3' (V) is a single-stranded oligonucleotide (FIG. 24). The oligonucleotide has a short random tract of 4–12 bases, a blocking nucleotide X at the 3' end, and a unique sequence with a non-specified nucleotide composition at the 5' end and length from 12 to 100 bases.

Down-stream nick-attaching adaptor B-3' (V) is used as a template for the primer-extension reaction by transiently or stably hybridizing it to the displaced 3' tail at the end of the nick-translation product. Different DNA polymerases can be used for the polymerization reaction.

C. Up-Stream Nick-Attaching Adaptors: Composition and Attachment to DNA.

Up-stream nick-attaching adaptors are partially double-stranded or completely single-stranded short DNA molecules that can be covalently linked to the 5' phosphate group of the trimmed DNA strand located down-stream of a nick-translation DNA product. Up-stream nick-attaching adaptors B-5' are designed to create amplifiable DNA units compromising the trimmed DNA strand (PENTAmer complement) or fraction of the primary PENTAmer if a second nick-translation synthesis was initiated and performed from the same DNA end for a shorter period of time (secondary PENTAmer).

It is propose herein two types of the up-stream nick-attaching adaptors that can be attached to the gapped or tailed nicks within a double-stranded DNA to create a covalent bond between the adaptor and the 5' end of degraded original or nascent DNA strand.

i. Up-Stream Nick-Attaching Adaptor B-5' (I) Targeted to a Gap by a Ligation Reaction.

Figure 25:
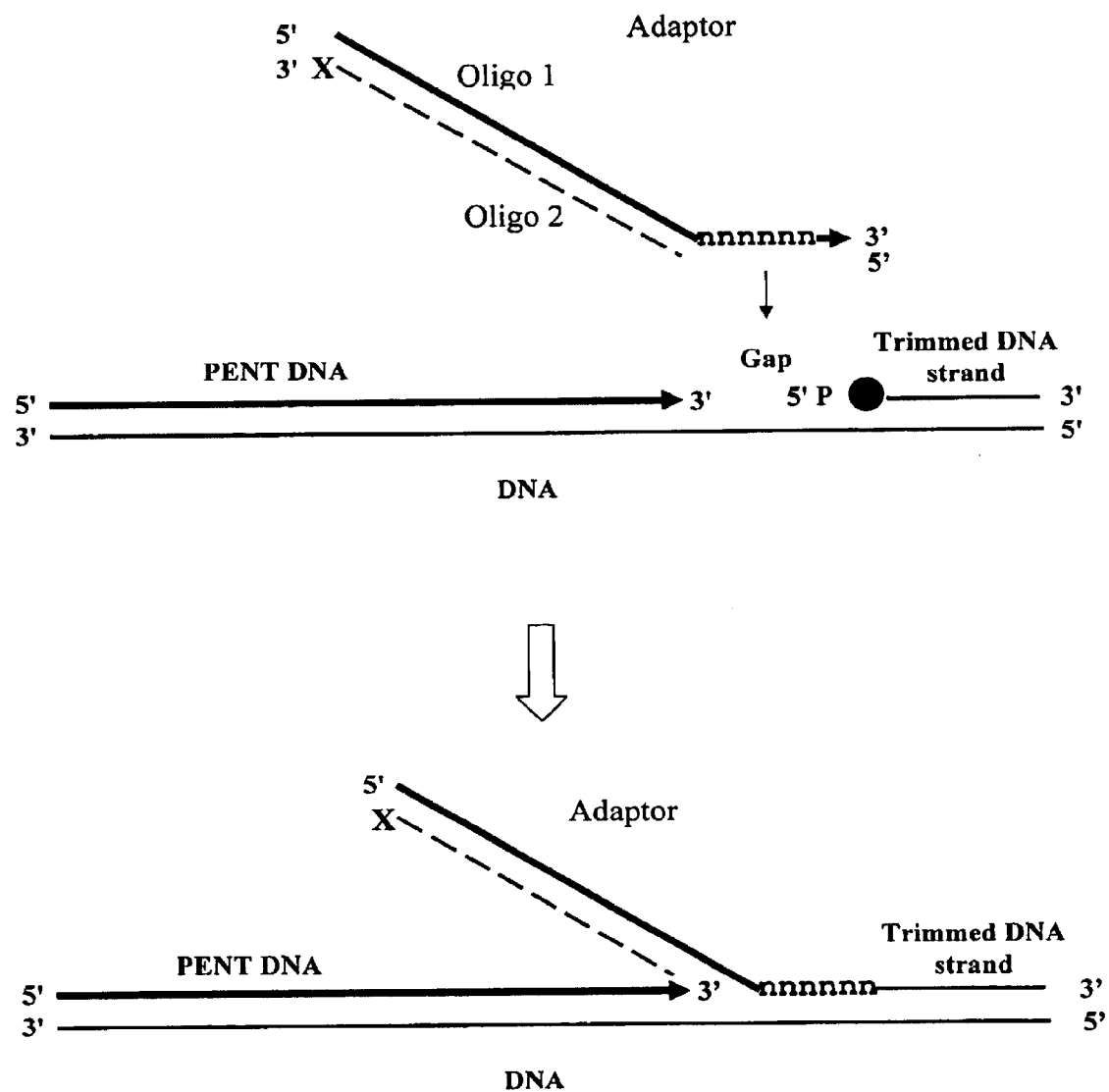
FIG. 25: Upstream nick-attaching adaptor B-5 (I) targeted to a gap by a ligation reaction

Up-stream adaptor B-5' (I) is a completely or partially single-stranded oligonucleotide construct. It consists of oligonucleotide 1 and optional oligonucleotide 2 (FIG. 25). Oligonucleotide 1 has a unique 5' region with a non-specified nucleotide composition and length from 12 to 100 bases, and short random 3'-region (n)N where N=4–10 bases. Oligonucleotide 2 has a blocking nucleotide X at the 3' end, and, when present, is hybridized to oligonucleotide 1 to reduce its non-specific interaction with DNA.

Up-stream nick-attaching adaptor B-5' (I) is ligated by its non-blocked 3' end to the 5' phosphate group of the trimmed DNA strand by transiently or stably hybridizing it to a single-stranded DNA within a gap and performing a ligation reaction (FIG. 25). Different ligases can be used to ligate the adaptor B-5' (I) including T4 DNA ligase, E. coli DNA ligase, Taq DNA ligase (New England BioLabs), and Ampligase (Epicentre).

ii. Up-Stream Nick-Attaching Adaptor B-5' (II) Targeted to a Partially-Displaced 5' Tail Near the Nick by a Ligation Reaction.

Figure 26:
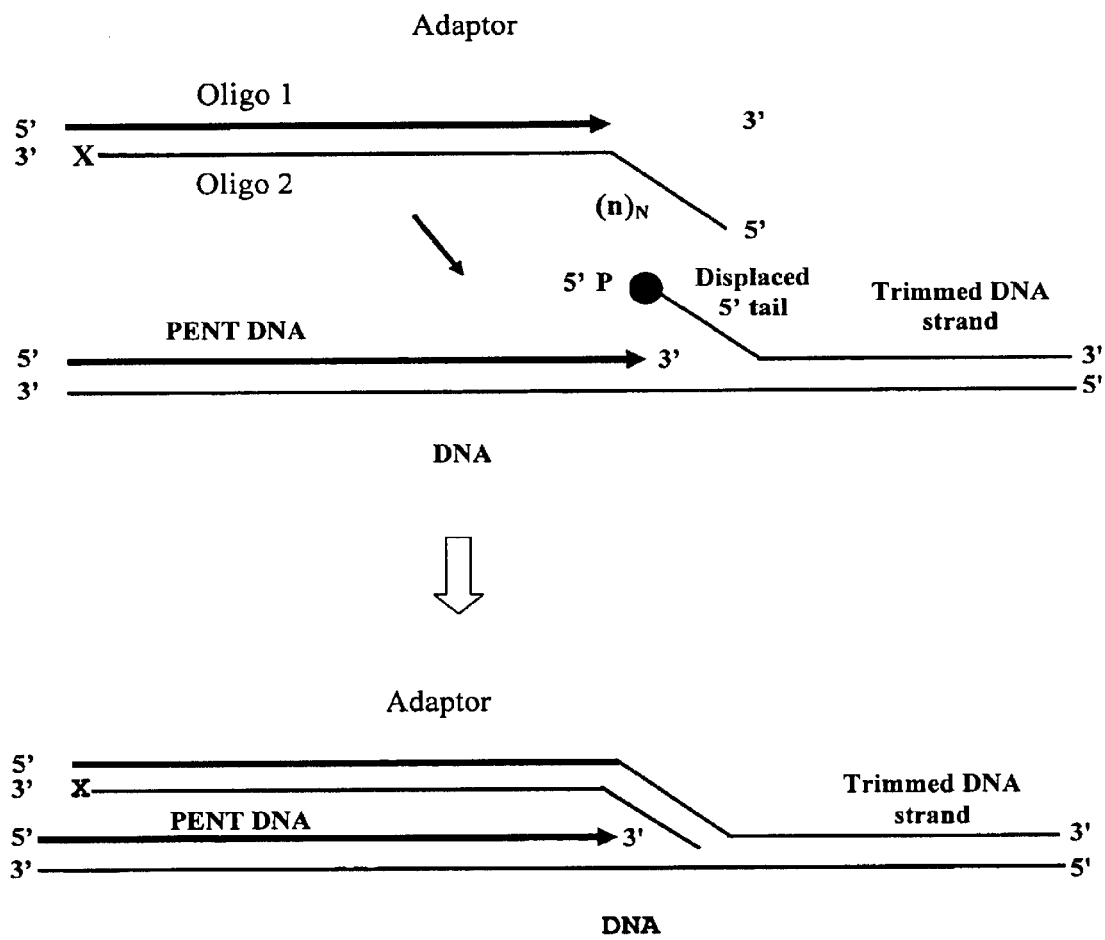
FIG. 26: Upstream nick-attaching adaptor B-5 (II) targeted to a displaced 5' tail of the trimmed DNA strand by a ligation reaction FIG. 27 General structure of the recombination adaptor

Up-stream nick-attaching adaptor B-5' (II) is a partially single-stranded oligonucleotide construct. It is formed by two mostly complementary oligonucleotides 1 and 2 (FIG. 26). Oligonucleotide 1 has a unique sequence with a non-specified nucleotide composition and a length from 12 to 100 bases. Oligonucleotide 2 has a short random tract of 4–12 bases at the 5' end, a blocking nucleotide X at the 3' end, and a 3' region complementary to the oligonucleotide 1.

Oligonucleotide 1 is ligated by its 3' hydroxyl to the phosphate group of the displaced 5' tail near the nick by transiently or stably hybridizing it to the displaced DNA (FIG. 26). Different ligases can be used to ligate the up-stream nick-attaching adaptor including T4 DNA ligase, E. coli DNA ligase, Taq DNA ligase (New England BioLabs), and Ampligase (Epicentre).

R. Recombination Adaptors

Recombination adaptors (RA or RB adaptors) are oligonucleotide constructs attached to the ends or to the internal regions of a double-stranded DNA to promote intramolecular interactions and facilitate creation of recombinant DNA molecules, specifically recombinant PENTAmers. In many applications, recombination adaptors are designed to have at least one additional function. For example, they can also function as up-stream terminus-attaching nick-translation adaptors or down-stream nick-attaching adaptors.

1. General Structure of the Recombination Adaptor.

Recombination adaptors have two major domains F and R, FIG. 27A. The proximal, F domain comprises all of the functional domains that are not directly involved in the recombination reactions, and the distal, R domain is specific for the specificity and efficiency of recombination. The part of the F domain at the terminus of the recombination adaptor is responsible for adaptor attachment to termini or nicks in DNA and has similar composition and function as the terminus-attaching or nick-attaching adaptors (see FIG. 19–FIG. 26). Internal regions within the F domain are responsible for optional functions, such as initiation of the nick-translation reactions, amplification (e.g., PCR priming sites, RNA polymerase promotor sites), affinity capture (e.g., on magnetic beads), and/or detection (e.g., on filters, microarrays, or in solution. FIG. 27B schematically shows an adaptor with ligation domain (L), nick-translation initiation domain (D), and recombination domain (R). The distal domain R is essential for the recombination processes that are used to make recombinant PENTAmers, which are the focus of this section.

a. Examples of Recombination Adaptors with Multiple Functions.

As example, FIG. 28A shows the structure of the up-stream terminus-attaching nick-translation recombination adaptor RA, which has a dual-function F domain (described previously in FIG. 19A) attached to a specific recombination domain. This adaptor has oligonucleotide 1 with 5' phosphate and 3' end blocked with dideoxyribonucleotide or other nucleotide unable to be ligated by ligase or extended by polymerase. Oligonucleotide 2 assists in directing the adaptor to the ligation site on the template molecule. Oligonucleotide 3 is the specific priming site for a nick-translation reaction. Oligonucleotides 4, 5, and 6 are short strands that can be easily removed by mild heating or other reaction to expose a recombinogenic 3' terminus of the adaptor.

FIGS. 28B and C shows examples of different down-stream nick-attaching recombination adaptors RB-3' (for recombination adaptors, the nomenclature described previously in 4.1 and 4.2 is used, but R is added to indicate the recombination nature of the adaptor). The upper strand of the adaptors shown on FIG. 28A is formed by the long oligonucleotide (20 to 100 b), and the lower strand is composed of multiple oligonucleotides complementary to different regions of the long oligonucleotide. In all cases, the left proximal part of the adaptor represents a non-recombinogenic functional domain F, and the right distal part of the adaptor represents a recombination domain R.

b. Forms and Classes of Recombination Adaptors

The molecular basis for recombination of the RA and RB adaptors is the complementarity of the sequences of distal single-stranded regions of adaptors on two DNA ends. The simplest designs of RA adaptors are single-stranded (examples of single-stranded down-stream nick attaching RB-3' adaptors are shown in FIGS. 28B, E, F). The functional domains that target RA and RB adaptors to the ends or internal nicks of the template DNA molecules are the same as for the A and B adaptors described for making primary and secondary PENTAmers.

In many situations it is preferable to use double-stranded recombination adaptors with two possible states, "inactive" and "active". In the "inactive" form, recombination adaptors are unable to interact by their distal recombination domains. For many reasons it is preferable to maintain this condition during DNA processing and "activate" adaptors just before the initiation of recombination. In the "active" form the adaptors become recombinogenic. The transition into the active form can be carried out by chemical, biochemical, and/or physical process, which affects the structure of the distal terminus of the recombination domain. This process is illustrated by FIG. 29 using up-stream terminus-attaching nick-translation recombination adaptor RA (FIG. 28A) as an example.

In a simple case (recombination adaptors of class I, shown in FIG. 29A) the inactive recombination adaptors have termini blocked from ligation using a blocking nucleotide X such as a dideoxynucleotide. Activation is done by cleaving the recombination domain with a restriction endonuclease. Such cleavage removes the blocking 3' group X and exposes a 3' or 5' single-stranded overhang with the phosphate group at the distal 5' terminus.

To prevent cleavage of the genomic DNA, either the endonuclease chosen should be an extremely rare-cutting enzyme (such as homing endonucleases Ceu I, Sce I, PI-Psp I, etc.), or the genomic DNA should be methylated (as shown in FIG. 29A) with a methylase before attaching the recombination adaptor, such that the methylated genomic DNA cannot be cleaved by the restriction enzyme used.

In a more sophisticated but preferable case (recombination adaptors of class II FIG. 29 B) the R domain has a structure similar to that shown in FIGS. 28B, C, which have one or more small oligonucleotides hydrogen bonded to the region protecting the end of the adaptor from unwanted reactions. Activation of the R domain involves two steps: (1) removal of the blocking 3' group X at the distal end of oligonucleotide 1 using some chemical, photochemical, biochemical or physical reaction; and (2) exposure of a long (10–100 b) single-stranded tail.

Removal of the 3' blocking group X from oligonucleotide 1 is achieved by cleavage of the terminal base(s) using a restriction endonuclease, or chemical removal of a labile base, for example removal of a ribonucleotide using high pH.

Exposure of the long 3' single strand tail is achieved by removal of the bases complementary to that tail. For the adaptor shown in FIG. 28A, activation is achieved by dissociation of the distal short (10–15 bp long) oligonucleotides 4–6 bound to oligonucleotide 1. This can be done by mild heating to dissociate the short oligonucleotides, but leave oligonucleotides 2 and 3 bound to oligonucleotide 1. Alternatively, the short oligonucleotide(s) can be designed with labile nucleotides such as deoxyuridine or ribonucleotides, that can be degraded using dU-glycosylase or RNase, respectively. Alternatively, the 5' end of the oligonucleotide(s) bound to oligonucleotide 1 can be degraded by a 5' exonuclease (e.g., exonuclease T7, gene 6). This exonuclease degradation can be terminated at a specific location by incorporating resistant bases (e.g., $\alpha$S-nucleotides) at desired distances from the 5' end of the adaptor.

S. Methods of Recombination

Three different molecular processes are proposed for creation of recombinant PENTAmers. In the first process, intramolecular recombination is effected by ligating complementary ends of the adapted template molecule in dilute solution. In the second process, intramolecular recombination is effected by stably hybridizing the ends of the adapted template molecules in dilute solution, followed by concentration of the molecules and ligation in the concentrated state. In the third process, recombination is effected by hybridizing the ends of the adapted template molecules, followed by a nick-translation reaction to form the covalent intramolecular junction.

1. Direct Intra-Molecular Ligation and Nick-Translation

Recombination by direct ligation and nick-translation can be applied to molecules with short or long complementary termini (adaptors of class I and II, respectively). To minimize intermolecular interactions and maximize the yield of the intramolecular products the ligation reaction should be performed at a very low concentration of termini and high concentration of ligase.

a. One Adaptor Approach

Figure 30A:
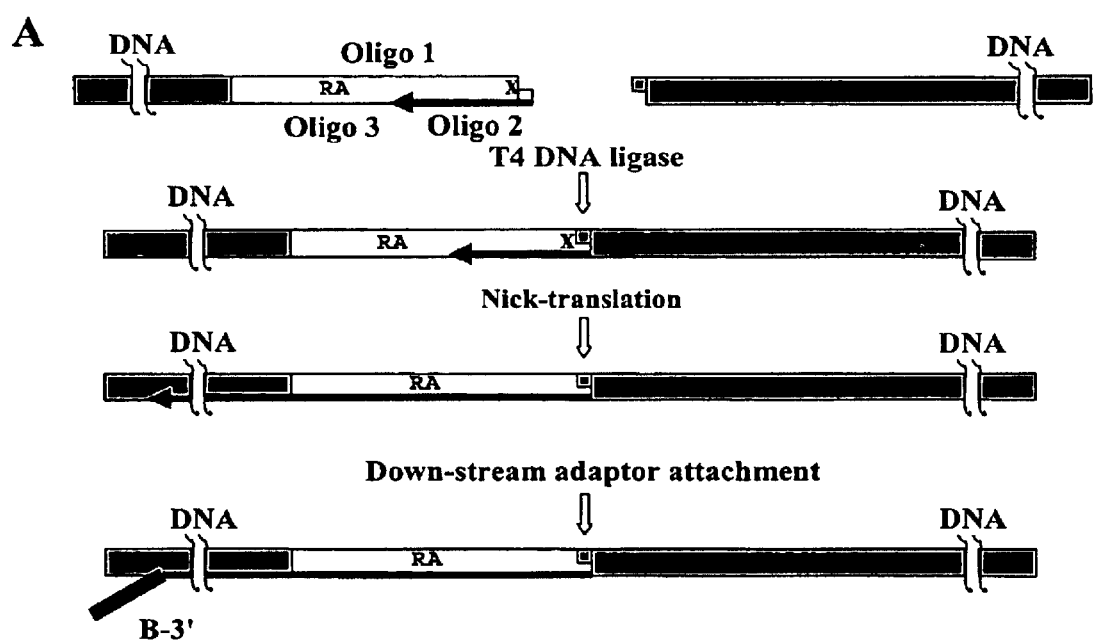
FIGS. 30A, 30B, 30C, 30D and 30E: Recombination by direct ligation

In simple cases (shown in FIGS. 30A, B) recombination by direct ligation uses adaptor RA ligated to only one end of the template DNA molecule ("one-adaptor" approach). This is appropriate when DNA ends are produced by cleavage of the template DNA with two different restriction enzymes. The designs of the ligation and initiation domains of the adaptor are similar to the design of up-stream end-attaching, nick-translation A adaptors shown in FIG. 19 with the ligation domain compatible with the DNA end produced by a first endonuclease, a nick-translation initiation domain, and a recombination domain compatible with the end produced by a second endonuclease. Unlike the designs shown in FIG. 19, oligonucleotide 1, which initiates the nick-translation reaction must be phosphorylated at the 5' end in order to be covalently joined to the template. Unlike many of the other applications, the adaptor is not activated by removal of the 3' blocking group. In the example shown in FIG. 30A, the nick-translation primer (shown in bold) is located on the lower-strand and oriented towards the attached template terminus. In the example shown in FIG. 30B, the nick-translation initiation oligonucleotides is located on the upper strand and oriented in the opposite orientation, away from the unique template end and toward the recombination site. Because of the inverse orientation of the nick-translation primer it is obligatory to perform the nick-translation reaction in the second case only after the intra-molecular ligation. The one adaptor approach achieves recombination using the following steps:

1) A first sequence-specific endonuclease is used to digest the template DNA into smaller molecules;
2) Both strands of the RA adaptor are ligated to the sequence-specific termini of the template molecules;
3) The template molecules are digested (partially, in most cases) with the second sequence-specific endonuclease;
4) The adapted template molecules are incubated at low concentration with a large amount of T4 DNA ligase for 16–36 h to achieve the intramolecular recombination reaction (FIGS. 30A, B), and then concentrated using a microfiltration device or by ethanol precipitation;
5) A nick-translation reaction is initiated and allowed to proceed a controlled time to create a PENT product of specified length (FIGS. 30A, B);

6) A down-stream nick-attaching adaptor B-3' is added to the 3' end of the PENT product to create a recombinant PENTAmer.

Because of low yield of circularized DNA molecules with blunt or one- or two-base single strand termini, it is expected that the "one-adaptor" direct ligation approach will have a reasonable efficiency only if the second sequence-specific endonuclease produces DNA ends with three- or four-base 5' or 3' overhangs.

b. Two Adaptor Approach

In order to increase the circularization efficiency using restriction enzymes that produce short 3' or 5' overhangs or blunt ends, a "two-adaptor" direct ligation approach is described herein, which employs an adaptor activation step. For example, FIG. 30C shows the recombination by direct ligation between two adaptors $RA_1$ and $RA_2$ (class I) that have been ligated to the two ends of a template DNA molecule. Their design is similar to the design of up-stream adaptors $A_1$ and $A_2$ (FIG. 19) with the only difference that both adaptors have a recombination domain and a site specifically for restriction endonuclease at their distal part. FIG. 30C shows the steps to making a recombinant PENTAmer at Eco RI sites.

1) Template DNA molecules are methylated using Eco RI methylase;
2) Adaptors RA1 and RA2 (each having a proximal terminus with: a) an Eco RI-compatible end that has a sequence that cannot form an Eco RI recognition sequence; b) a single nick-translation initiation site; and c) a single Eco RI restriction recognition sequence within the recombination domain) are ligated to both strands at the termini of the template molecules;
3) The adaptors are activated by incubation with restriction endonuclease Eco RI which removes the 3'-blocked distal portion of the adaptors and creates sticky ends with four-base 5' overhangs without affecting the integrity of the nascent PENTAmers;
4) The adapted template fragments are incubated at low concentration with large amount of T4 DNA ligase for 16–36 h to circularize the template molecules, and then concentrated using a microfiltration device or by ethanol precipitation;
5) The circularized template molecules are subjected to a nick-translation reaction to which is followed by addition of down-stream nick-attaching adaptors B-3'.

PCR using primers complementary to B-3' and a known sequence either on the left or right end of the template junction will amplify the DNA in the unknown region, thus achieving amplification of a distal, unknown sequence, using a primer that is specific for a known, proximal sequence.

Figure 30B:
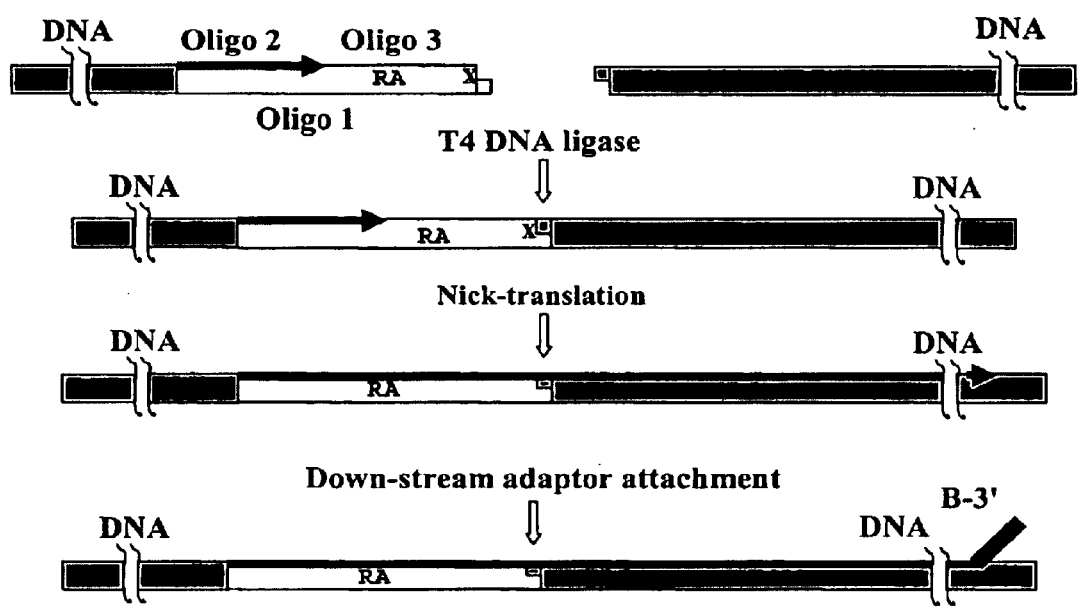
Figure 30C:
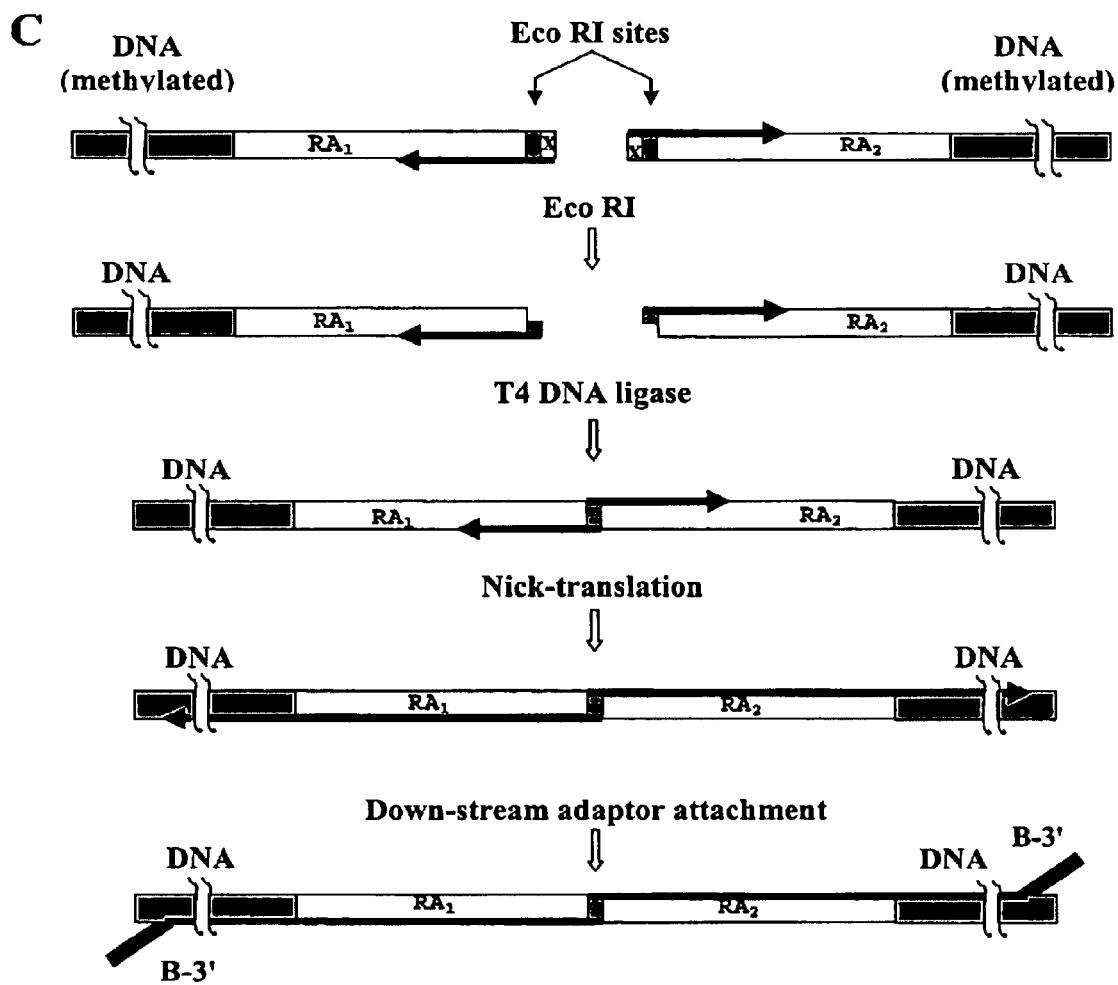
Figure 30D:
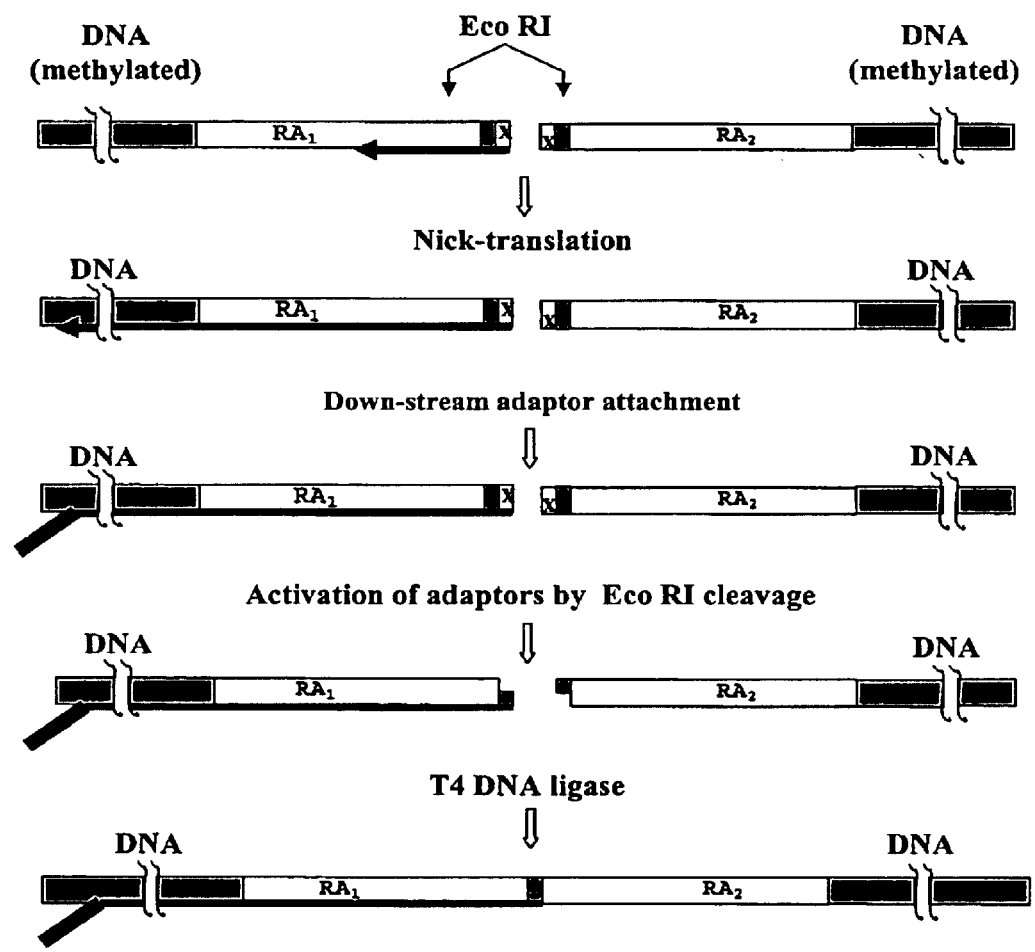
Figure 30E:
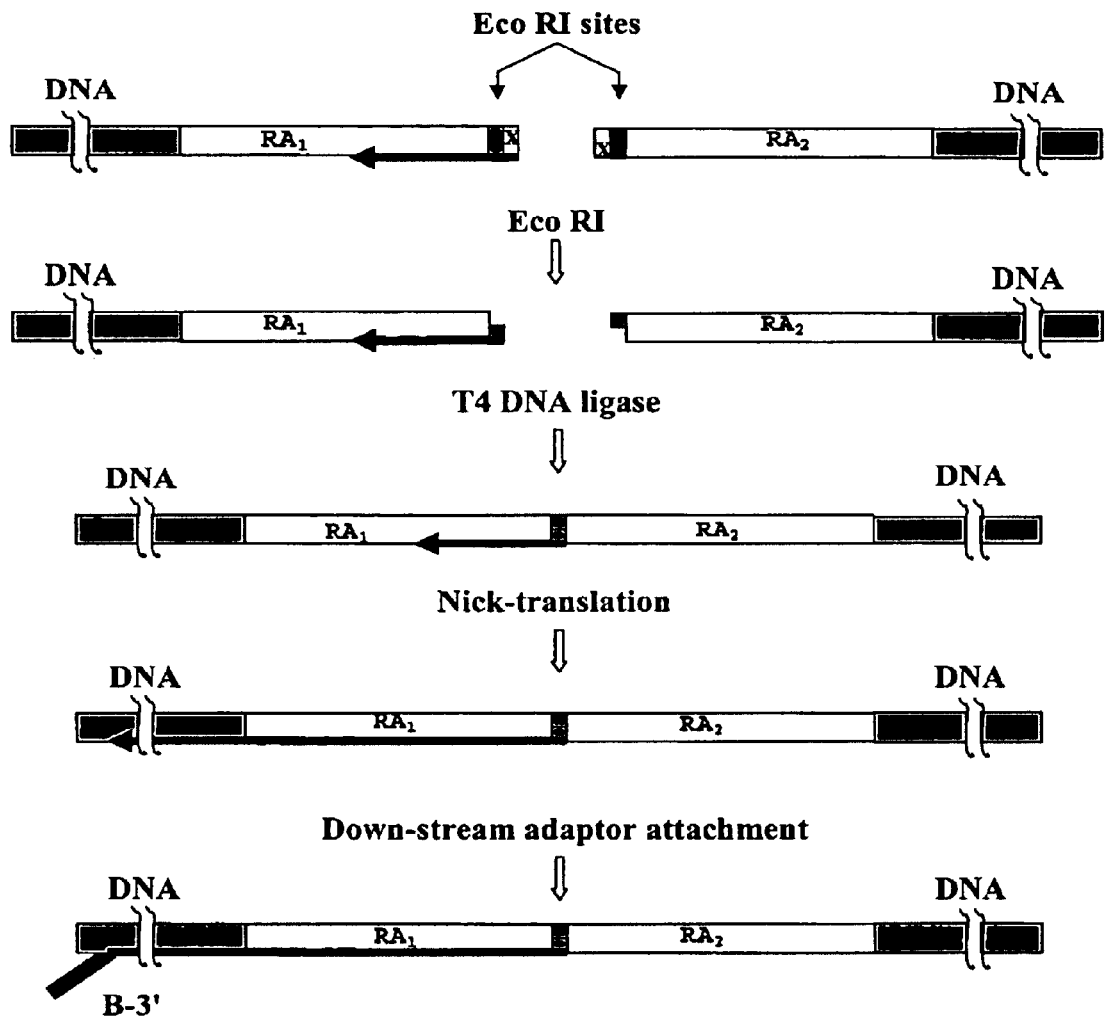

In many applications, the nick-translation reaction will be done before the ends of the RA adaptors are activated and recombined (e.g., FIG. 30D). In other applications, the PENTAmers are created after recombination (FIGS. 30A, B, C, E). Depending on the design of the adaptors $RA_1$ and $RA_2$, the reactions would result in one (unidirectional nick-translation reaction, FIGS. 30D, E) or two (bidirectional nick-translation reaction (FIG. 30C) recombinant PENTAmer molecules.

The method of recombination shown in FIG. 30B was used to circularize template DNA molecules with >70% efficiency in Example 19 and to create PENTAmers from circularized template DNA in Example 21.

2. Intra-Molecular Hybridization Followed by a Ligation Reaction.

Recombination by direct ligation described above requires large amounts of DNA ligase because of the large reaction volume necessary to reduce the fraction of non-desirable intermolecular products.

To address this problem, new methods of recombination between DNA ends by a "hybridization-ligation" process using recombination adaptors with long 3' tails (class II) are described herein. FIGS. 31A–D illustrates several examples of recombination by hybridization-ligation between two adaptors $RA_1$ and $RA_2$.

Figure 31A:
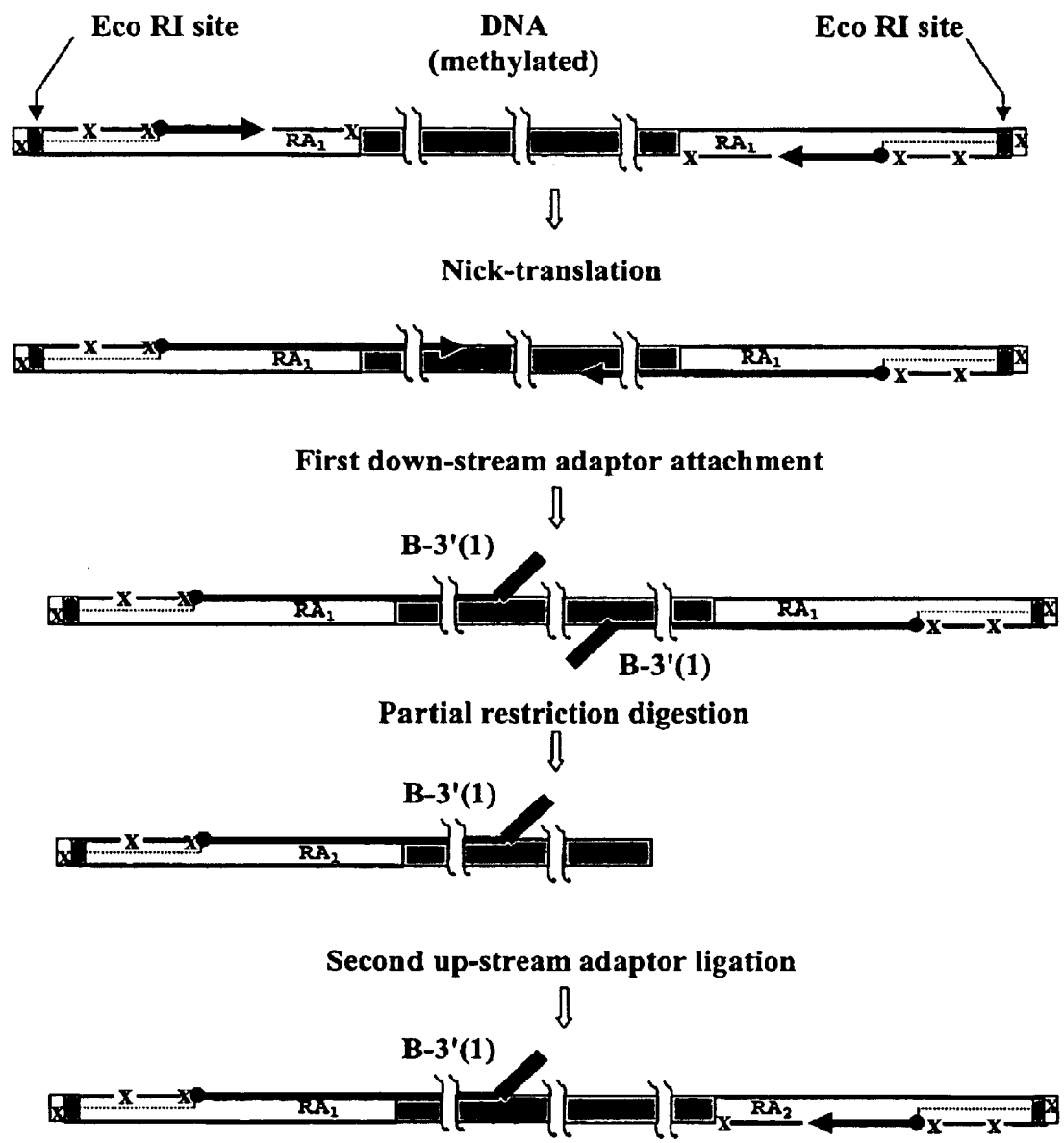
FIGS. 31A, 31B, 31C, 31D and 31E: Recombination by hybridization followed by ligation

FIG. 31A shows the case of upstream adaptors designed as shown in FIG. 28A and used as shown in FIG. 29B. FIG. 31A illustrates the most sophisticated protocol for creation of recombinant PENTAmer molecules by the hybridization-ligation method. In this protocol, ligation of adaptor $RA_1$ and synthesis of PENTAmers at the DNA ends created by the first restriction endonuclease (e.g., rare cutting) is followed by second digestion with a second endonuclease (for example, partial digestion with frequently cutting restriction enzyme), ligation of adaptor $RA_2$ and synthesis of PENTAmers at newly created DNA ends. Because the two PENTAmer synthesis reactions are separated in time, this method allows control of the individual size of both PENT products and to append different down-stream sequences B-3'(1) and B-3'(2) to the 3' ends of PENTAmers.

Figure 31B:
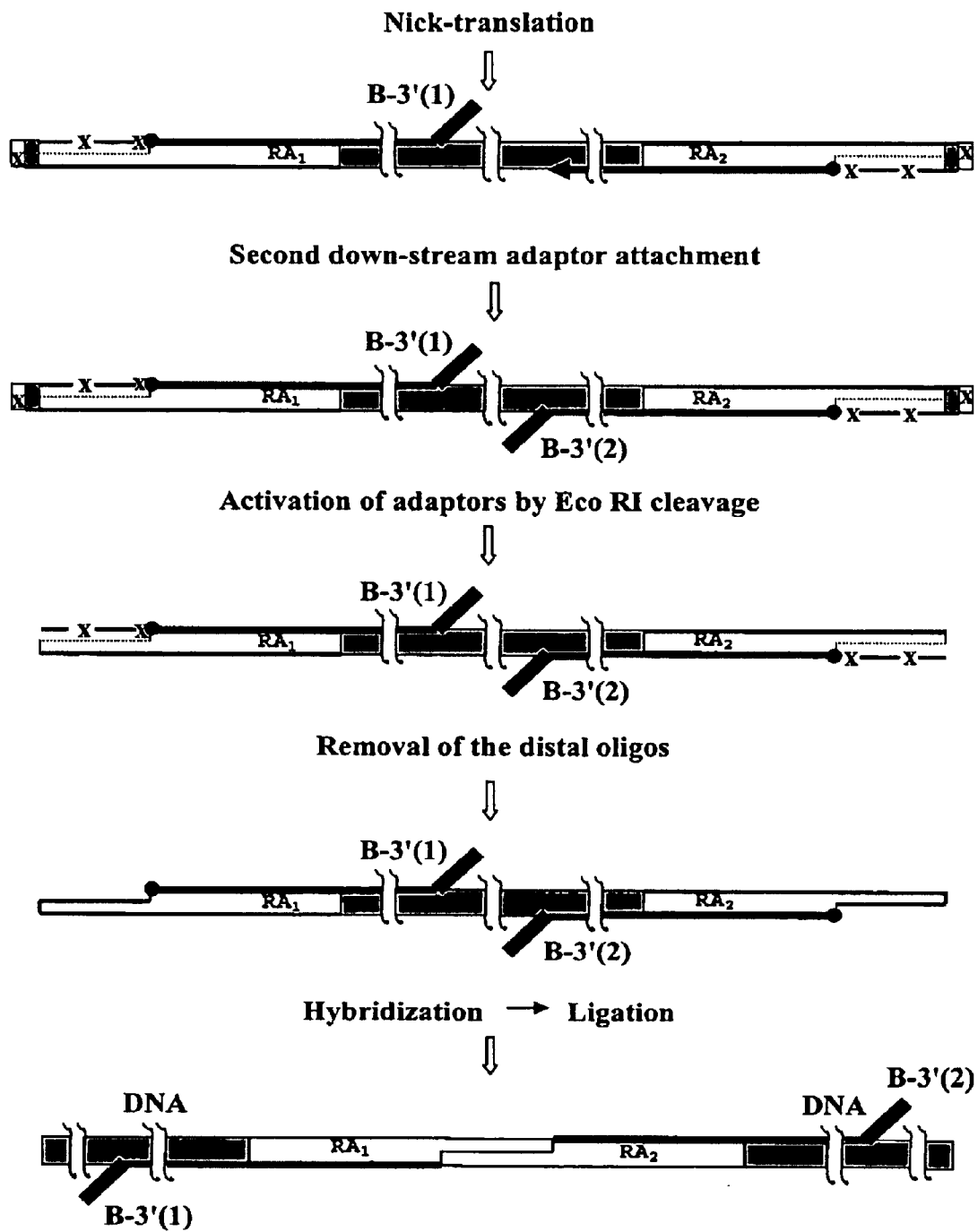

FIG. 31B illustrates the case when ligation of adaptors $RA_1$ and $RA_2$ occurs simultaneously and is followed by a bi-directional nick-translation reaction and appending of the same nick-attaching adaptor B-3' to both PENT products.

Figure 31C:
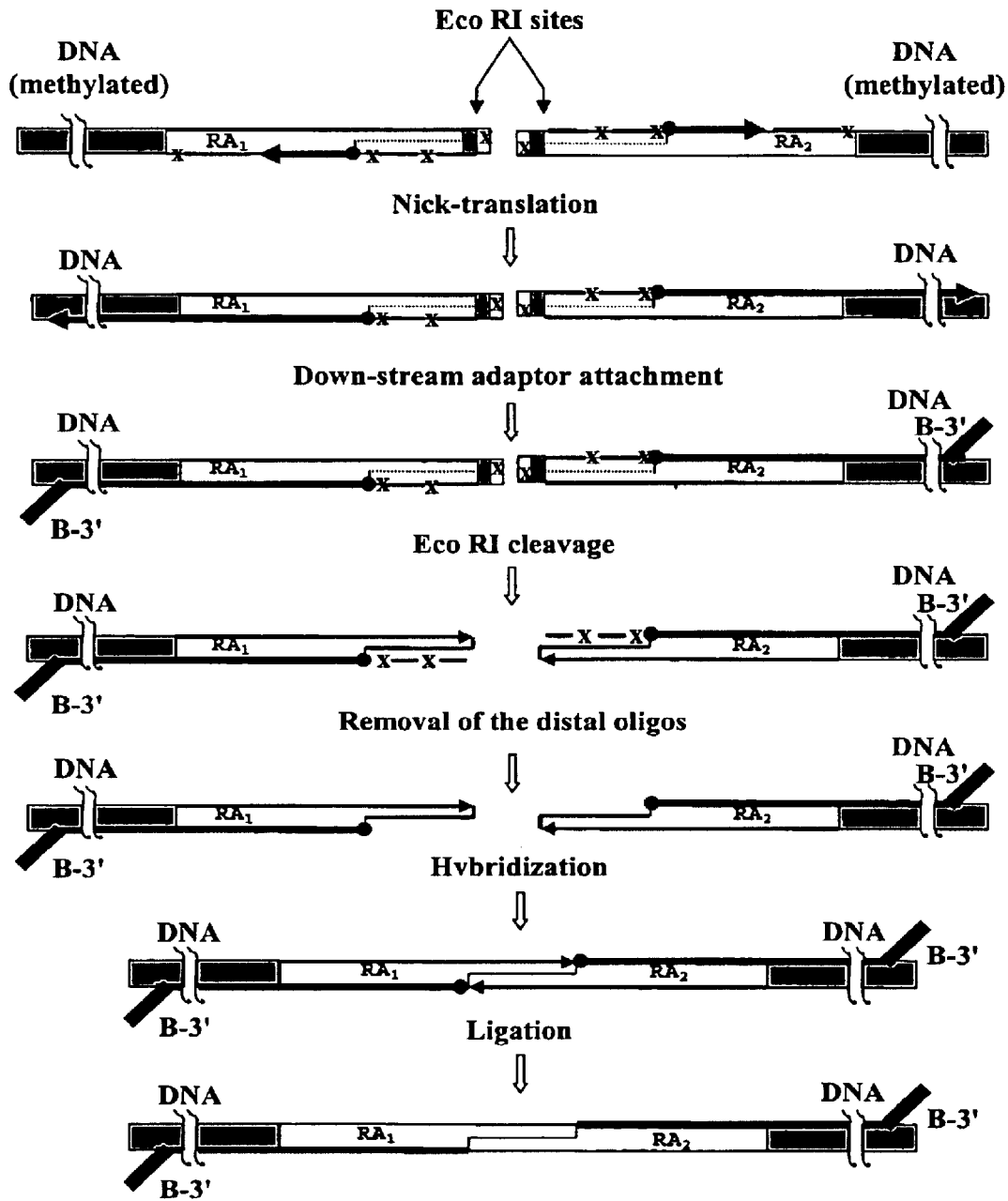

FIG. 31C illustrates the case which is similar to the previous one except that the nick-translation reaction is performed in only one direction, owing to only one adaptor having a nick-translation initiation domain.

Figure 31D:
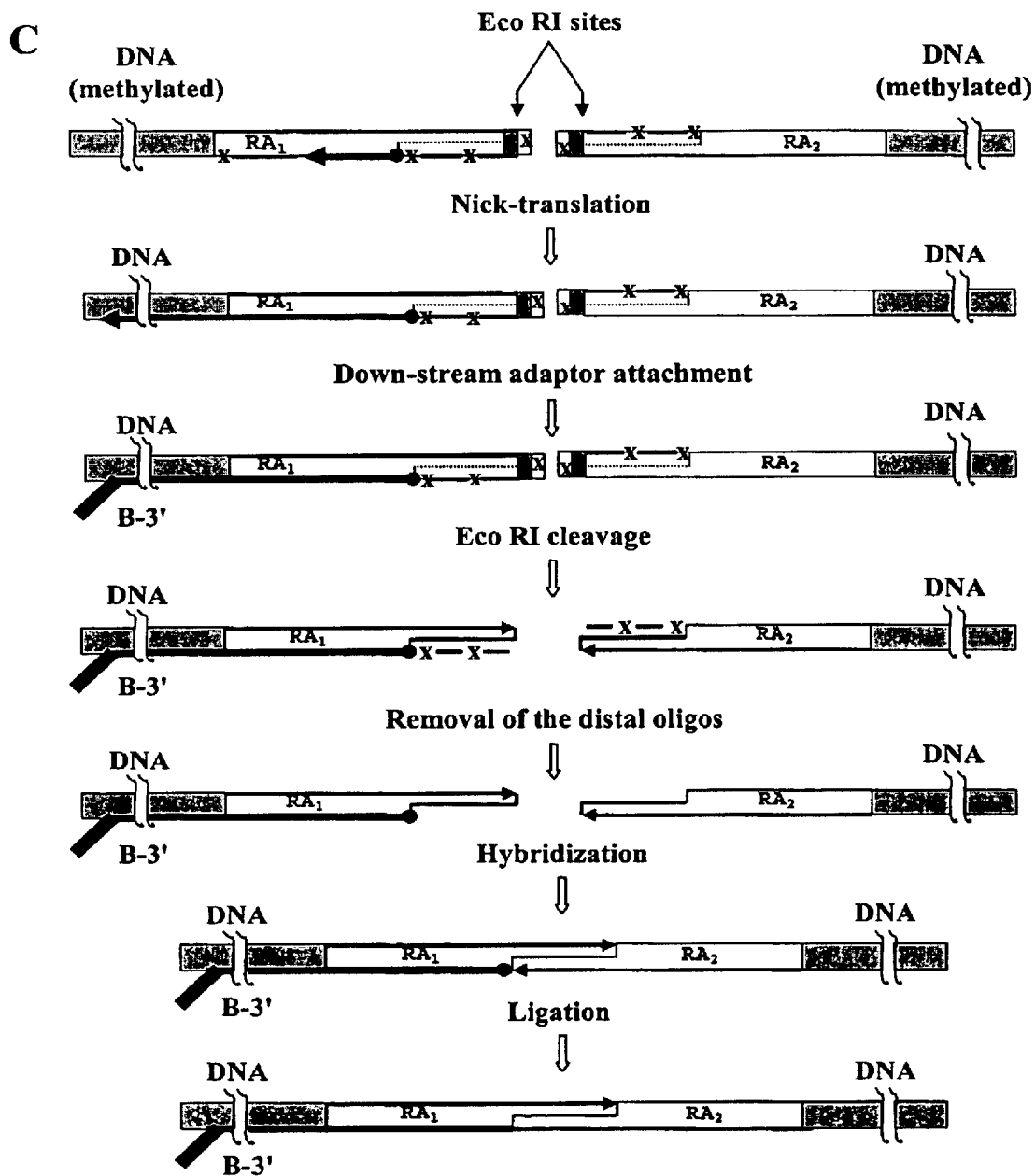
Figure 31E:
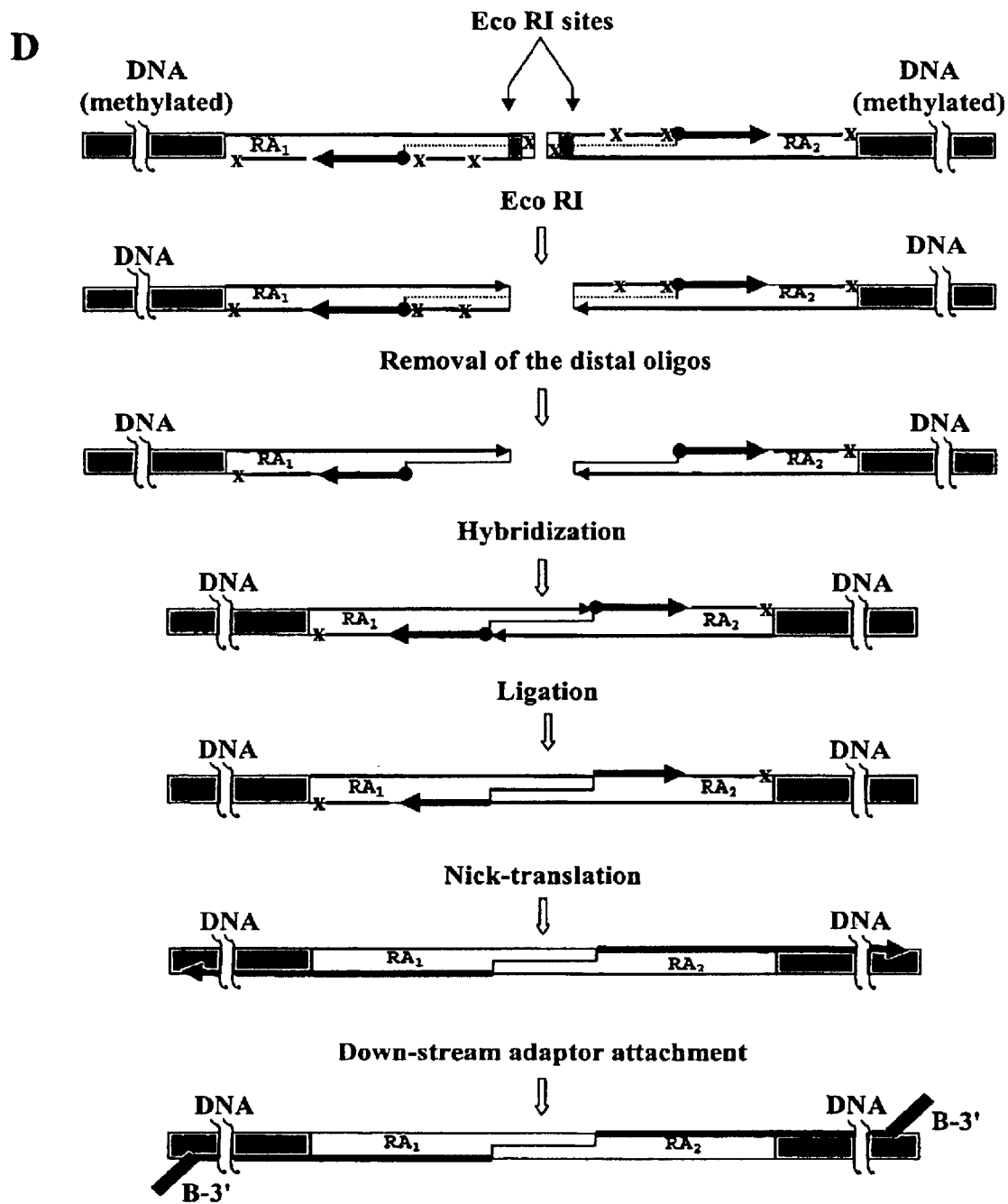

FIG. 31D illustrates the case when activation of the adaptors, hybridization and ligation steps are performed first. After the ligation reaction, the DNA molecules are subjected to a PENT reaction and PENTAmers are created by the usual protocols.

After completion of the PENTAmer synthesis in protocols presented in FIG. 31A-C the adaptors are activated by the incubation with Eco RI to remove blocking groups at the 3' end of the two adaptors. Subsequent cleavage with dU-glycosylase at 37° C. and incubation at 50–60° C. releases the short oligonucleotides adjacent to the termini to form the long single-strand tails necessary for recombination.

Hybridization of the two ends is then done in a large volume for sufficient time to approach completion. If necessary, the unreacted termini can be subsequently blocked by adding excess amounts of the blocked short oligonucleotides complementary to the tails. Finally, all DNA molecules are concentrated by a microfiltration device or ethanol precipitation and then ligated in a small volume with a DNA ligase. The ligase will covalently close circular molecules with hybridized tails but will not be able to ligate ends that have not hybridized at low concentration. Because very large hybridization volumes can be used for the hybridization reactions, very high ratios of intra- versus intermolecular recombination can be achieved with this method, even for very long DNA molecules. However, because the intramolecular ligation reaction can be carried out in a small volume, only small amounts of ligase and reaction time are necessary to achieve a high efficiency of ligation.

3. Intra-Molecular Hybridization Followed by a Polymerization (Nick-Translation) Reaction.

Class II recombination adaptors can also be used to create PENTAmers without using ligase to covalently attach the two ends of the template molecules. Hybridization of the two ends of DNA molecules with class II recombination adaptors creates templates for two nick-translation reactions, which stabilizes the circular form that can be further processed to form the recombinant PENTAmer. In this case, a polymerase rather then a ligase is used to create the recombinant PENTAmer molecule.

Figure 32:
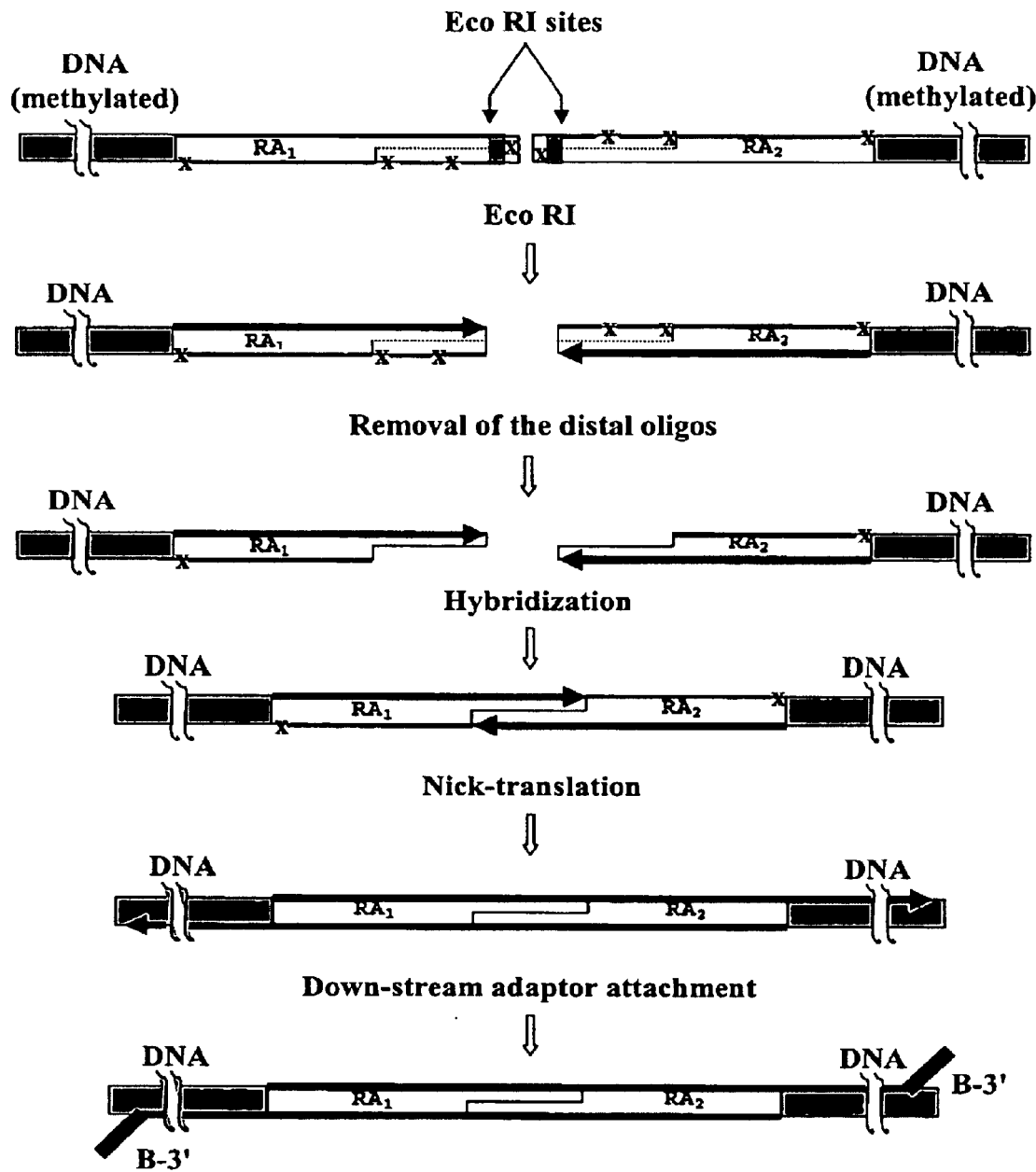
FIG. 32: Recombination by hybridization followed by nick-translation reaction

As an example, FIG. 32 shows the recombination between two adaptors $RA_1$ and $RA_2$ using hybridization-polymerization to effect recombination. These adaptors are similar to those described in the previous cases, except the adaptors are designed to propagate the nick through the intermolecular junction, rather than away from the intramolecular junction. The adaptor termini are activated by restriction enzyme cleavage, the protecting oligonucleotides removed, the resulting complementary single-strand tails hybridized, and a bidirectional PENT reaction performed to create the recombinant PENTAmer.

Hybridization of the two ends is done in a large volume for sufficient time to approach completion. If necessary, the unreacted termini are blocked after the hybridization reaction by adding excess amounts of the short blocking oligonucleotides. Finally, all DNA molecules are concentrated by the microfiltration device or by ethanol precipitation. As a result of the nick-translation reaction, the 3' termini of the adaptors are extended, creating the recombinant PENTAmer and stabilizing its association with the template. The polymerization reaction stabilizes the circularized molecules, but not the linear molecules, with ends that have not hybridized at low concentration. Because very large hybridization volumes can be used for the hybridization reactions, very high ratios of intra- versus inter-molecular recombination can be achieved with this method, even for very long DNA molecules. However, because the polymerization reaction can be carried out in a small volume, only small amounts of polymerase and time are necessary to achieve a high efficiency of nick-translation.

T. Composition of Recombinant PENTAmers

Limitations of the time-controlled PENTAmer-mediated walking technique are overcome by creating recombinant PENTAmers, which bring together sequences from both the proximal and distal ends of templates. Different forms of recombinant PENTAmers can be created, depending on when the recombination process occurs, before or after the PENTAmer synthesis. The term "nascent recombinant PENTAmer" is used herein to describe a double stranded DNA molecule with PENTAmers produced by the intra-molecular adaptor-mediated recombination. The term "recombinant PENTAmer" is used herein to describe a recombinant single-stranded DNA molecule that is formed by fusion of two primary PENTAmers or a single primary PENTAmer and a distal DNA strand. The name of the resultant recombinant form is determined by the names of recombination adaptors involved in the process of recombination. For example, the recombinant PENTAmer form is termed $B_2A_1$ if it is formed by interaction between recombination adaptors $RB_2$ and $RA_1$.

1. Recombinant PENTAmer Formed when Recombination Occurs Before PENTAmer Synthesis.

Figure 33:
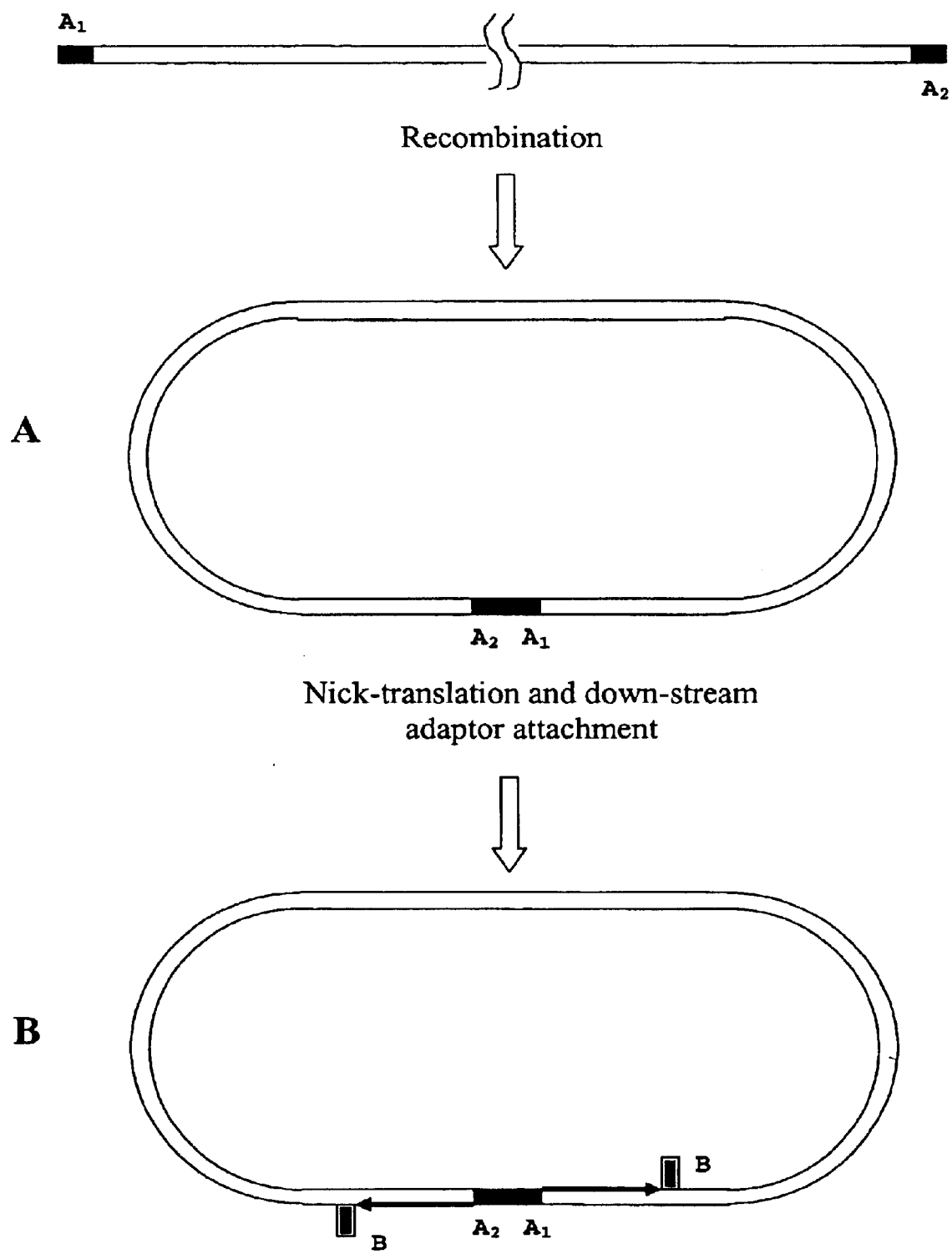
FIG. 33: Forms of recombinant DNA and nascent recombinant PENTAmer formed when recombination occurs before the synthesis of PENTAmers

This is a very simple case, because only two up-stream recombination adaptors $RA_1$ and $RA_2$ can be involved in the recombination process. Consequently, only one form of the nascent recombinant PENTAmer can be formed ($A_1A_2$). The process involves three major steps, shown in FIG. 33:

1) Ligation of up-stream recombination adaptors A1 and A2;
2) Intramolecular recombination at low DNA concentration;
3) PENTAmer synthesis.

a. PENTAmer Recombinant Form $T_1A_1A_2P_2B$ ($T_1A_1A_2P_2B$)

Figure 36:
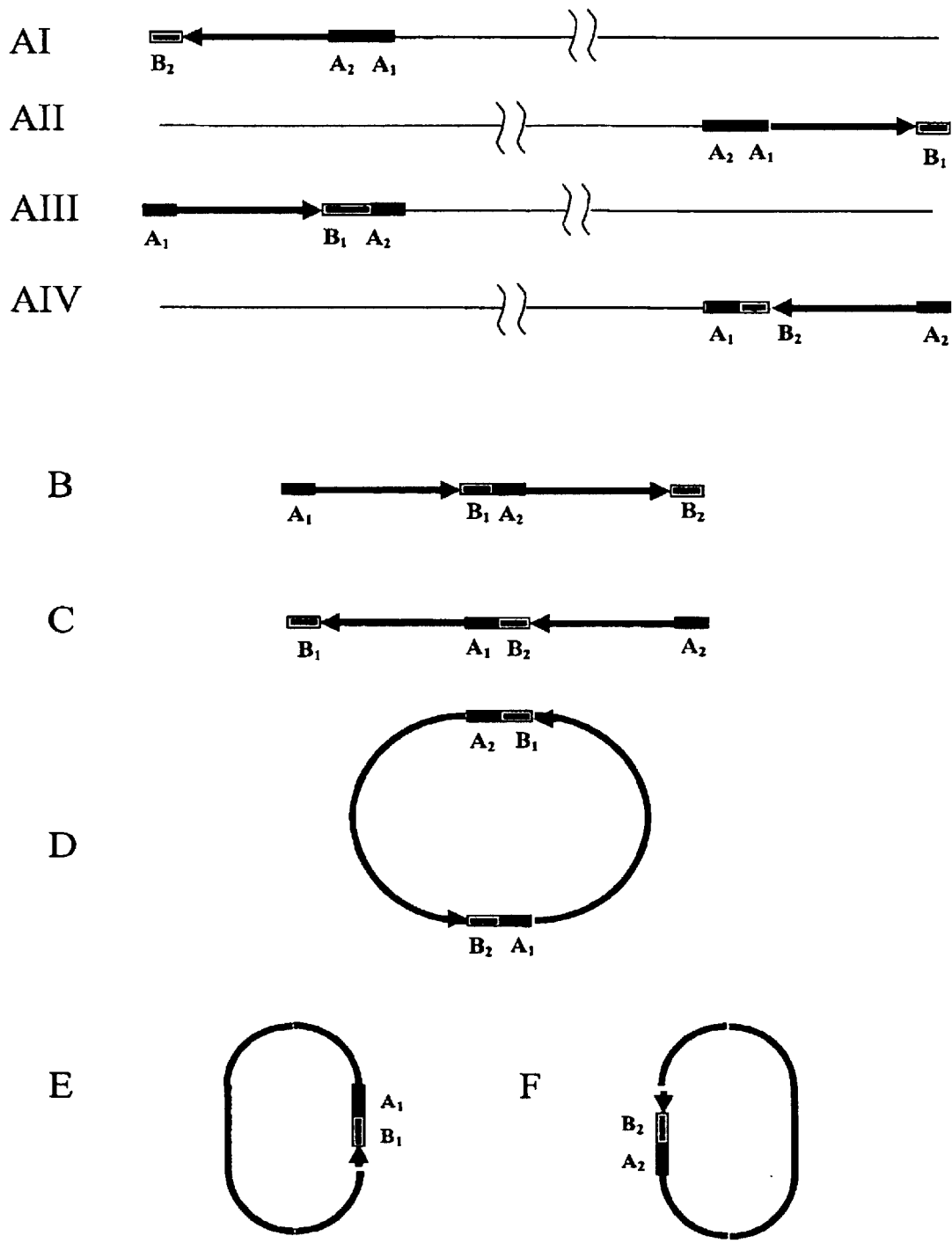
FIG. 36: Different forms of single-stranded recombinant PENTAmers

The resultant recombinant nascent PENTAmer structure is a circular double-stranded DNA molecule with two internally attached adaptors B (FIG. 33B). The recombinant PENTAmers are long single-stranded DNA molecules formed by covalent junctions between the 5' end of synthesized PENTAmers and the 3' end of non-modified DNA strand at the opposite end of the DNA fragment, with the $A_1A_2$ junction in the middle (FIG. 36, AI, AII). These recombinant PENTAmers are denoted $T_1A_1A_2P_2B$, explicitly showing the order of recombined elements within the recombinant PENTAmer molecule: $T_1$ (the template DNA strand ligated to the adaptor $A_1$); $A_1A_2$ (the fused adaptors); $P_2$ (the PENT product initiated at the adaptor $A_2$); and B (the nick-attaching adaptor).

It is preferable that adaptors $RA_1$ and $RA_2$ have different sequences. Recombination between two identical adaptors would result in a palindrome sequence, which might cause some problems during PENTAmer amplification.

Ligation of two different adaptors $RA_1$ and $RA_2$ is straightforward when templates are produced by two enzymes: a complete digestion with a first, rarely-cutting restriction enzyme, and a partial digestion with a second, frequently-cutting restriction enzyme. In this case, stepwise ligation of the adaptors $RA_1$ and $RA_2$ can be achieved in two separate cleavage-ligation reactions:

complete cleavage→$RA_1$ adaptor ligation→partial cleavage→$RA_2$ adaptor ligation, or partial cleavage→$RA_2$ adaptor ligation→complete cleavage→$RA_1$ adaptor ligation.

When templates are produced by partial digestion with only a frequently-cutting restriction enzyme, the ligation of different adaptors RA1 and RA2 to the ends of the same DNA molecule can be achieved by having both adaptors in the ligation reaction at an equimolar ratio. In this case, 50% of DNA molecules are expected to have different adaptors at their ends, while 50% have identical adaptors. By choosing class II recombination adaptors, it is possible to promote recombination only between ends with adaptors $RA_1$ and $RA_2$ using the recombination-ligation or recombination-polymerization methods. Alternatively, if class I adaptors are used, both the homotypic junctions ($A_1A_1$ and $A_2A_2$) and heterotypic junctions (A1A2 and A2A1) junctions will be produced. The molecules with heterotypic junctions can be purified by affinity capture. After addition of adaptors to both ends, the template molecules will form non-covalently closed circles due to intramolecular hybridization of the complementary sequences at the 3' ends of the adaptors.

When the hybridization-ligation method is used, the covalent recombinant junctions are formed by incubation with ligase, and converted to recombinant PENTAmers by unidirectional or bidirectional nick-translation reactions initiated at nick(s) within adaptor(s) $RA_1$ and/or $RA_2$. When the hybridization-polymerization method is used, the recombinant PENTAmers are formed by direct unidirectional or bidirectional nick-translation reaction using 3' end(s) of $RA_1$ or/and $RA_2$ adaptors as primers.

Synthesis of the recombinant PENTAmer(s) is completed after appending the adaptor sequence B at the internal nick(s).

The described preparation of the recombinant molecules when recombination precedes the PENTAmer synthesis might be especially useful for very large DNA molecules (100–1000 kb). In this case, DNA is prepared in agarose plugs or micro-beads, digested in-gel with one or two restriction enzymes, ligated to adaptors and size fractionated by pulse-field agarose gel electrophoresis. Gently melted agarose slices containing very large DNA fragments are incubated with agarase, diluted, and DNA fragments are circularized by hybridization. After concentration, the PENTAmer synthesis is performed as described before.

2. Recombinant PENTAmers Produced by Recombination After the PENTAmer Synthesis.

This is the most interesting case because four elements, namely, adaptors $RA_1$, $RA_2$, $RB_1$ and $RB_2$ can be involved in recombination. Consequently, forms of recombinant PENTAmers with different adaptor junctions can be created:

1) linear forms $T_1A_1A_2P_2B_2$ or $T_2A_2A_1P_1B_1$, with $A_1A_2$ or $A_2A_1$ junctions;
2) linear forms $A_1P_1B_1A_2P_2B_2$ or $A_2P_2B_2A_1P_1B_1$, with $B_1A_2$ or $B_2A_1$ junctions;
3) cyclic form $cA_1P_1B_1A_2P_2B_2$ with the both $B_1A_2$ and $B_2A_1$ junctions;
4) cyclic forms $cA_1P_1B_1$ or $cA_2P_2B_2$; with the $B_1A_1$ or $B_2A_2$ junctions;

All seven recombinant PENTAmer forms are shown on the FIG. 34 and FIG. 36 (AI,AII, B–F) and described below.

a. Recombinant PENTAmers $T_1A_1A_2P_2B_2$ and $T_2A_2A_1P_1B_1$

This form of recombinant PENTAmer is similar to the previously analyzed form. The recombination reaction can be achieved by a direct ligation or by hybridization-ligation method bringing together distal and proximal ends of the adapted DNA fragments (FIG. 34A).

The nascent recombinant PENTAmer structure is a circular double-stranded DNA molecule with two attached down-stream adaptors $B_1$ and $B_2$. The recombinant PENTAmers are long single-stranded DNA molecules formed by a covalent junction between the 5' end of the synthesized PENTAmers and the 3' end of the displaced and trimmed DNA strand at the opposite end of the DNA fragment, with the $A_1A_2$ or $A_2A_1$ junction in the middle (FIG. 36, AI, AII).

It is preferable that adaptors $RA_1$ and $RA_2$ have different sequence composition. It is important that they are mutually recombinogenic. Adaptors $B_1$ and $B_2$ can have similar or different sequence, which differentiates this case from the previously analyzed.

In this case, two different restriction enzymes should be used to produce proximal and distal ends of the template and the two PENTAmers should be synthesized in separate reactions.

b. Recombinant PENTAmer $A_1P_1B_1A_2P_2B_2$

This recombinant PENTAmer structure can only be formed after synthesis of both PENTAmers. The recombination reaction can be achieved by a direct ligation or by a hybridization-ligation method bringing together up-stream and down-stream adaptors $RA_2$ and $RB_1$ of distal and proximal PENTAmers (FIG. 34B).

The recombinant nascent PENTAmer structure is a double-stranded DNA molecule with one large loop region, and two linear branches: one formed by double-stranded DNA containing PENTAmer $A_1P_1B_1$ (1–2 kb in size), another by the down-stream adaptor $B_2$.

The recombinant PENTAmer is a single-stranded DNA molecule formed by a covalent junction between the 3' end of the PENTAmer $A_1P_1B_1$ and the 5' end of the PENTAmer $A_2P_2B_2$ with the $B_1A_2$ junction in the middle (FIG. 34B and FIG. 36B).

It is critical that the up-stream adaptor $RA_2$ is mutually recombinogenic with the down-stream adaptor $RB_1$ but not with the adaptor $B_2$. Consequently, the sequences $RB_1$ and $RB_2$ should be different to avoid simultaneous production of non-desirable cyclic form $cA_2P_2B_2$. This is possible if: (i) two different restriction enzymes are used to produce the proximal and distal ends of the template, (ii) the PENTAmers $A_1P_1B_1$ and $A_2P_2B_2$ are synthesized in different reactions.

C. Recombinant PENTAmer $A_2P_2B_2A_1P_1B_1$.

The form is produced by recombination of the second pair of up-stream and down-stream adaptors $RA_1$ and $RB_2$, (FIG. 34C and FIG. 36C).

d. Cyclic Recombinant PENTAmer $cA_1P_1B_1A_2P_2B_2$ with both $B_1A_2$ and $B_2A_1$ Junctions.

This recombinant PENTAmer can be only formed after synthesis of PENTAmers at both ends of the template. Recombination can be achieved by direct ligation or by hybridization-ligation, bringing together up-stream adaptor $RA_1$ with down-stream adaptor $RB_2$, and up-stream adaptor $RA_2$ with down-stream adaptor $RB_1$ (FIG. 34D).

The nascent recombinant PENTAmer structure is a theta-shaped double-stranded DNA molecule with a small loop (2–4 kb) formed by PENTAmers $A_1P_1B_1$ and $A_2P_2B_2$, and a large loop formed by the rest of the template (FIG. 34D). The recombinant PENTAmer is a single-stranded circular DNA molecule, formed by a covalent junction between the 5' end of PENTAmer $A_1P_1B_1$ and the 3' end of PENTAmer $A_2P_2B_2$, and the 5' end of the PENTAmer $A_2P_2B_2$ and the 3' end of the PENTAmer $A_1P_1B_1$, with the both $A_2B_1$ and $B_2A_1$ junctions in the middle, (FIG. 36D).

Adaptor $RA_1$ is mutually recombinogenic with adaptor $RB_2$ but not with adaptor $RB_1$. Adaptor $RA_2$ is mutually recombinogenic with adaptor $RB_1$ but not with adaptor $RB_2$. Consequently, the adaptor sequences $B_1$ and $B_2$ are different to avoid simultaneous synthesis of non-desirable cyclic forms $cA_1P_1B_1$ and $cA_2P_2B_2$. The desired conditions are possible if: (i) two different restriction enzymes are used to produce the proximal and distal ends of DNA template, and (ii) PENTAmers $A_1P_1B_1$ and $A_2P_2B_2$ are synthesized in two different reactions.

e. Cyclic Recombinant PENTAmer $cA_1P_1B_1$ with $B_1A_1$ Junction

This is a special recombinant structure that can be formed after PENTAmer synthesis. It is expected as a side product during synthesis of the linear recombinant form $A_2P_2B_2A_1P_1B_1$ when down-stream adaptors $B_1$ and $B_2$ have the same sequence composition (FIG. 34E).

The recombinant nascent PENTAmer structure is a predominantly linear double-stranded DNA molecule with a small loop (1–2 kb in size) at one end (FIG. 34E). The recombinant PENTAmer is a single-stranded circular DNA molecule formed by covalent junction between 3' and 5' ends of the PENTAmer $A_1P_1B_1$ (FIG. 36E). Note that sequences from the proximal and distal ends of the template have not been recombined.

f. Cyclic Recombinant PENTAmer $cA_2P_2B_2$ with $B_2A_2$ Junction

This form of recombinant structure is similar to the form $cA_1P_1B_1$ and is produced by recombination between another pair of up-stream and down-stream adaptors $RA_2$ and $RB_2$ (FIG. 34F and FIG. 36F). Note that sequences from the proximal and distal ends of the template have not been recombined.

Figure 35:
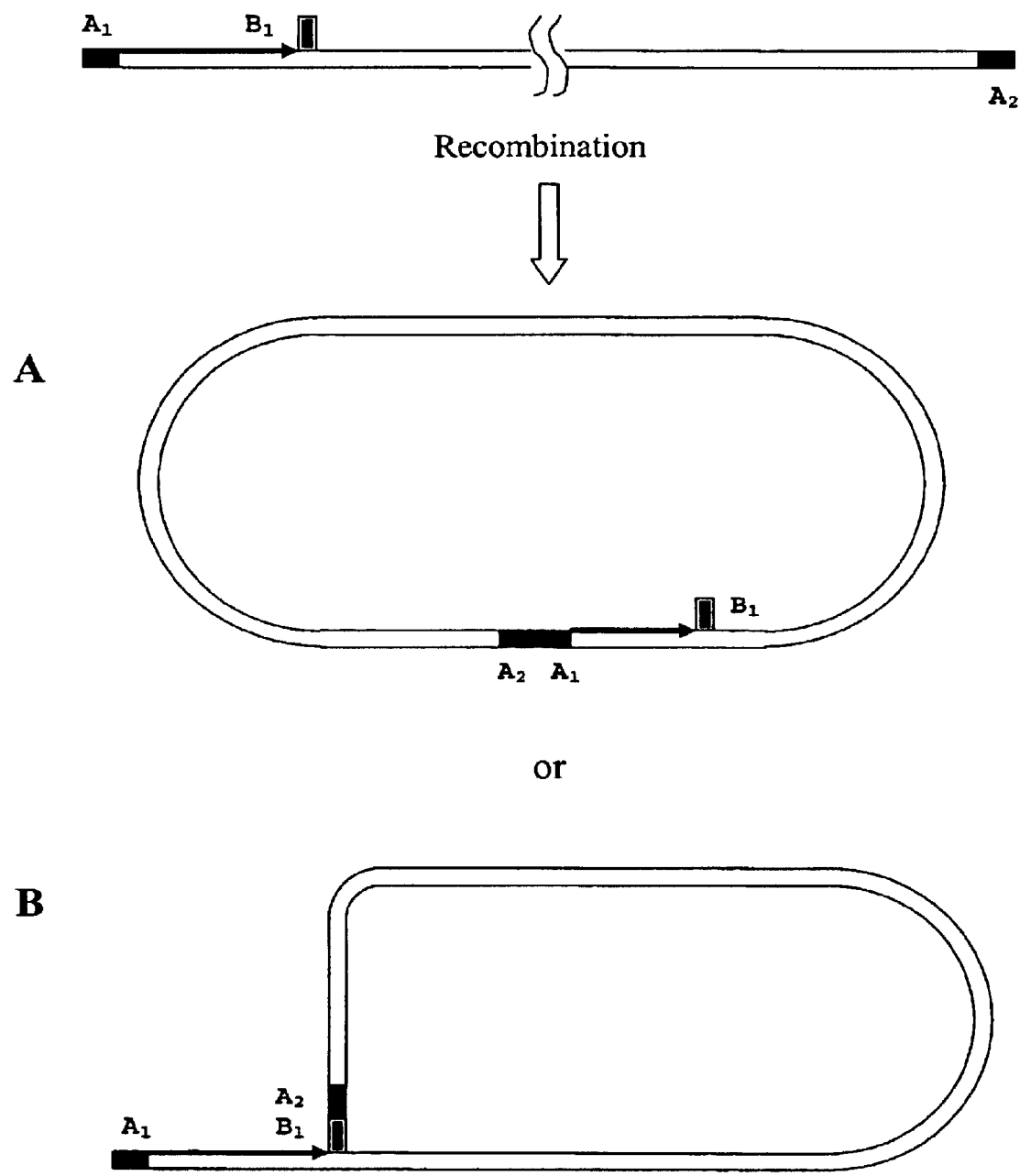
FIG. 35: Different forms of nascent recombinant PENTAmers formed after the synthesis of PENTAmer at one end of the DNA fragment

3. Recombinant PENTAmers Produced when Recombination Occurs After the Synthesis of Only One PENTAmer This is only possible if two different restriction enzymes are involved in the generation of the template DNA. There are four different possible nascent recombinant forms:

$T_2A_1B_1$ (FIG. 35A) and $T_1A_1A_2B_2$ (not shown), and $A_1P_1B_1A_2T_2$ (FIG. 35B) and A2P2B2A1T1 (not shown). The nascent recombinant PENTAmer structures (FIGS. 35A, B) and corresponding recombinant single-stranded PENTAmer molecules (FIG. 36, AI–AIV) are similar to structures previously described.

U. Applications of Positional Amplification Using PENTAmers

Like PCR, Positional Amplification using PENTAmers is a general method to select and amplify DNA in vitro. To demonstrate the utility of Positional Amplification obvious applications of the method to create DNA molecules for sequencing and hybridization analysis of genomic DNA and cDNA are herein described.

1. Sequencing Internal Regions of Short Templates Using Primary PENTAmers

Primary PENTAmers can be used to sequence internal regions of DNA molecules approximately 1–20 kb in size.

Primary PENTAmers that terminate at specific positions within the DNA strand are created by different times of controlled PENT reaction from one or both ends of the DNA molecule. PENTAmers that terminate at a designated position are cloned into a suitable vector (or PCR amplified) and the downstream end of the PENTAmer insert sequenced using a conventional technique.

The entire length of the DNA molecule can be sequenced by producing an ordered set of PENTAmers created by synthesizing primary PENTAmers of different lengths (determined by the time of PENT reaction), cloning or otherwise amplifying the molecules in each size class, and sequencing the downstream ends of the PENTAmers by conventional techniques. If, for example, successive PENTAmer preparations differ by 500 bp, sequencing of the downstream ends of all the PENTAmers with read lengths of 600 bp should produce overlapping sequence information covering the entire source DNA fragment. Sequence information from one strand is produced using PENTAmers created from one end of the template, and sequence information from the opposite strand is produced from PENTAmers created from the opposite end of the template.

2. Sequencing Internal Regions of Short Templates Using Secondary PENTAmers

Secondary PENTAmers can be used to sequence internal regions of DNA molecules approximately 1–20 kb in size.

Secondary PENTAmers that terminate at specific positions within the DNA strand are created by different times of controlled PENT reaction from one or both ends of the DNA molecule. PENTAmers that terminate at a designated position are cloned into a suitable vector (or PCR amplified) and the downstream end of the PENTAmer insert sequenced using a conventional technique. Because the PENTAmers have two ends internal to the template DNA, both strands can be sequenced using PENTAmers initiated from one end of the template.

The entire length of the DNA molecule can be sequenced by producing an ordered set of PENTAmers created by synthesizing secondary PENTAmers of the same length (determined by the protocol used) located different distances from the initiation site for the PENT reaction (determined by the time of the initial PENT reaction), cloning or otherwise amplifying the molecules in each size class, and sequencing the upstream and/or downstream ends of the PENTAmers by conventional techniques. If, for example, the position of the internal ends of the PENT products designed to be separated by 800 bp, and the size of the secondary PENTAmers is designed to be 1000, sequencing the downstream and upstream ends of the secondary PENTAmers with a read length of ~600 bases should produce overlapping sequence information covering the entire source DNA fragment.

3. Sequencing Internal Regions of Short Templates Using Complement PENTAmers

Complement PENTAmers can be used to sequence internal regions of DNA molecules approximately 1–20 kb in size.

Complement PENTAmers that terminate at specific positions within the DNA strand are created by different times of controlled PENT reaction from one or both ends of the DNA molecule. PENTAmers that terminate at a designated position are cloned into a suitable vector (or PCR amplified) and the internal end of the PENTAmer insert sequenced using a conventional technique.

The entire length of the DNA molecule can be sequenced by producing an ordered set of PENTAmers created by synthesizing complement PENTAmers of different lengths (determined by the time of PENT reaction), cloning or otherwise amplifying the molecules in each size class, and sequencing the internal ends of the PENTAmers by conventional techniques. If successive complement PENTAmer preparations differ by 500 bp, sequencing of the ends of all the PENTAmers with read lengths of 600 bp should produce overlapping sequence information covering the entire source DNA fragment. Sequence information from one strand is produced using PENTAmers created from one end of the template, and sequence information from the opposite strand is produced from PENTAmers created from the opposite end of the template.

4. Sequencing Large-Insert Clones Using Ordered Positional Libraries of PENTAmers Sequencing of a single 100 kb BAC using PENTAmers would be done using ordered positional libraries as described above. The procedure would be very similar to the 50 kb lambda positional amplification experiment provided in the Examples, and could involve:

1) Cleavage of the BAC at the cos site with lambda terminase
2) Ligation of a different nick-translation adaptor to each of the 5' overhangs. The design of these adaptors is critical to the preparation, because they must be very specific for ligation to individual cos overhangs but not self-ligating, specific for initiating PENT reactions and specific for subsequent ligation to restriction sites such as Sau 3A ends.
3) Removal of the unligated adaptors
4) Partial restriction of the mixture with a frequently cutting enzyme such as Sau 3A to create a nested set of template molecules having proximal ends at the cos sites and distal ends at the restriction sites, as well as other molecules having two cos ends or two restricted ends
5) Dilution of the DNA and intermolecular circularization of the DNA molecules
6) Concentration of the DNA
7) Initiation of an approximately 3 minute PENT reaction by addition of Taq and dNTPs to create approximately 700–1000 bp PENT products (note that molecules having two cos ends or two restricted ends will not undergo PENT reactions
8) Removal of Taq
9) Addition of a polyG tail to the 3' end of the PENT product using terminal transferase.
10) Ligation of a nick-ligation adaptor having a poly-C 3' single-strand overhang and a unique double strand sequence at the other end to form a nascent PENTAmer 11) Concentration of the nascent PENTAmers
12) Size-separation of the nascent PENTAmers by pulse-field electrophoresis into fractions each covering about a 1 kb interval (this can be done with the circular nascent PENTAmers or after linearization of the nascent PENTAmers by specific cleavage of the adaptor). The size fractions can be automatically eluted from the gel, such as by using a Bio-Rad (Hercules, Calif.) electrophoretic elution device.
13) Each of 48 size fractions are placed in duplicate wells of one 96-well microplate.
14) The first 48 wells of one plate are PCR amplified using a primer complementary to the nick-ligation adaptor and a primer complementary to the nick-translation adaptor that was ligated to the left side of the cos site. The other half of the plate is PCR amplified with the same common primer and the specific primer complementary to the nick-translation adaptor ligated to the right side of the cos site. This creates two ordered libraries of PENTAmers, one extending clockwise into the BAC and one counterclockwise into the BAC. Amplification is preferably done using a polymerase with high fidelity.
15) Cloning vector is added to each microwell, ligated to the amplified PENTAmers and used to transform bacteria using a 96-well electroporation device
16) Colonies from each clone library are selected, isolated, and sequenced using conventional technology.

Because each library contains clones with DNA from only one region within the BAC, all regions will be equally represented rather than statistically represented as in shotgun cloning. This directed sequencing strategy is expected to yield high quality sequences with minimal redundancy (3–4x). Assembly of the sequences of individual clones into contigs will be extremely easy even in regions containing repetitive sequences, because the position of each sequence is known within the BAC. If gaps or sequence ambiguities exist after the initial sequencing run, the positions of those deficiencies will be known and specific libraries targeted for additional sequencing. Even if specific regions have not been cloned due to failure to amplify or failure to clone the PENTAmers from that region, the gap formed will be between contigs of known sequence and orientation so that primer walking or PCR can be used to directly sequence DNA from that position in the BAC.

To make this process more efficient for sequencing many large-insert clones, PENTAmer preparation can be completely multiplexed between steps 2 and 13, above. For steps 1 and 2 a large number of BACs (e.g., 100) can be processed separately, ligating a different set of nick-translation adaptors to each BAC. All of these "tagged" BACs can be mixed together and processed as one pool for steps 3–12. At step 13 all 48 samples can be first linearly amplified using a primer complementary to the common nick-ligation adaptor, aliquoted into 100 microwell plates and separately handled during steps 14–16. PENTAmers from specific BACs will be amplified in specific wells using primers complementary to the template-specific "tags" on the nick-translation adaptors. This multiplex preparation greatly reduces the labor involved in preparing OPL-DNA for BAC sequencing.

5. Genomic Sequencing Using Type I and Type II Recombinant PENTAmer Ordered Libraries Recombinant PENTAmer ordered libraries contain all the recombinant DNA necessary to amplify any locus in a specific genome. The recombinant PENTAmers will have been purified from template DNA to reduce non-specific background and linearly amplified using locus-independent adaptor sequences so that one electrophoretic fraction can be diluted to fill a specified well in hundreds or thousands of multiwell plates. These amplified ordered libraries will be aliquoted into 48 or 96-microwell plates and diluted. Successive wells will be capable of amplifying sequences complementary to regions different distances from the kernel sequences used for locus-specific amplification.

To amplify locus-specific PENTAmers for sequencing, kernel primers are synthesized and tested to determine the specificity of amplification using PENTAmers from a single size-fraction. If the kernel primers initially chosen are not specific, the amplification conditions or primer sequences will be altered to achieve high specificity.

In order to efficiently use the Ordered Positional Library ("OPL")-DNA for sequencing, molecules with unique sequences need to be generated. Usually Positional Amplification produces a number of different molecules in each well. Only a limited number of possibilities exist for the sequences at the upstream end of the PENTAmers, corresponding to the position of restriction sites. The downstream ends of the PENTAmers will have a large number of different sequences due to different exact positions of termination of the PENT reaction. Separation of unique-sequence fragments for sequencing can be done in three ways: 1) cloning the locus-specific PENTAmers in each microwell and choosing individual clones for sequencing; 2) diluting each sample of locus-specific PENTAmers in each microwell into many subwells such that at least one well contains a single DNA molecule that can be amplified by PCR; or 3) selectively amplifying specific PENTAmers using primers that are complementary to the adaptors but having 3' ends that include 1, 2, or 3 additional bases that will selectively amplify PENTAmers that have template DNA terminating with a specific sequence.

6. Using Ordered PENTAmers to Determine Gene Position

PENTAmers amplified different distances from the end of the clone or from the kernel sequence are spotted as an ordered array onto a membrane. To determine which positions code for proteins the membrane is hybridized to a DNA probe that is complementary to coding sequences (e.g., a cDNA clone or pool of cDNA molecules). Those spots that hybridize to the probe contain coding sequences. To determine non-coding regions, the membrane is hybridized with a probe containing non-coding sequences, isolated using subtractive hybridization or complementary to repetitive DNA. Information gained by these simple hybridization experiments can be used to determine which members of the ordered libraries should be sequenced to focus effort on the coding sequences. This approach is expected to be especially useful to study corn and other plant genes, because the genes are small with large regions consisting of repetitive retrotransposon sequences located in the "spacer" regions. In a specific embodiment, spacer regions identified by hybridization do not necessarily need to be sequenced.

7. Using Unordered Positional Libraries for Sequencing and Resequencing

Because Positional Amplification can amplify a very large region adjacent to the kernel sequence, it can be used as a general tool to create unordered DNA molecules for analysis. Unordered PENTAmers are created when the nascent PENTAmers are not separated according to size before amplification. This results in a large region of the genome being amplified as molecules of uniform size in a single tube. If recombinant PENTAmer libraries are created in this way, their locus-specific amplification produces a pool of molecules covering a region as large as 500 kb. These molecules can be shotgun sequenced or used for non-sequencing applications. The inherent advantages over PCR in these applications are 1) only a single priming site rather than two priming sites is necessary; 2) the amplimers are of short, uniform length, which is ideal for labeling and hybridization; and 3) the amplimers cover larger regions. Example applications are:

1) Diagnostic mutation analysis—PCR is currently used to amplify patient DNA for mutation detection using microarray hybridization, heteroduplex analysis, and other methods. Positional Amplification can amplify DNA to diagnose mutations over much larger distances than is possible with PCR alone. Now that the human genome has been sequenced, these point mutation chips are powerful tools in the discovery and analysis of the alleles responsible for inherited and acquired diseases, propensity for disease, and/or pharmacogenomic response to treatment.
2) Automated instruments for diagnostic mutation analysis—In order to perform rapid, inexpensive diagnostics, dedicated instrumentation for PENTAmer preparation, hybridization, and detection are envisioned. Conventional bioprocessing principles and/or microdevices are adequate to develop such instrumentation.
3) Shotgun sequencing of a region of the genome without cloning—A region as large as about 100–500 kb can be amplified by locus-specific PENTAmer amplification, cloned as a library of random fragments representing a large region of a genome, and subsequently sequenced using a conventional "shotgun" strategy. This is useful for sequencing regions of a genome that cannot be cloned (such as the 11 gaps remaining in the sequence of human chromosome 22) and to sequence the same locus in related species or individuals without cloning.
4) Single-tube kits for shotgun sequencing of a region without cloning—Unamplified PENTAmers are made for different genomes and sold as kits. Addition of locus-specific primers and amplification by PCR or other techniques amplify the regions adjacent to the kernels.
5) Hybridization probes for FISH—Conventional PCR probes are too short to detect single-copy genes. Rubicon SmartDNA amplimers can cover about 100–500 kb, which is easily detected by FISH. In this application, the primers used for Positional Amplification can be labeled with fluorescent dyes and incorporated into the DNA during linear or exponential amplification of the PENTAmers. Alternatively, fluorescently-labeled nucleotides or nucleotides that can be fluorescently or otherwise labeled in vitro can be incorporated along the entire length of the PENTAmers during Positional Amplification.
6) FISH Positional Amplification kits—Unamplified PENTAmers in individual tubes can be sold for purposes of making visible FISH probes. All components except the locus specific primers could be provided.

8. cDNA Sequencing Using Type I Recombinant PENTAmers Made from cDNA Preparations Unamplified cDNA preparations can be prepared as recombinant PENTAmers. Briefly, the cDNA molecules are partially restricted and prepared as ordered PENTAmer libraries using methods similar to those used for genomic DNA.

The cDNA is less complex than genomic DNA and can be prepared as size fractions up to only about 20 kb and organized into 24 or 48 wells of a microwell plate. The poly A 3' tails can be used to create the proximal ends of the recombinant PENTAmers. Ideal kernel sequences would be in the 3' UTRs, which are often found in EST databases. After amplifying the PENTAmers from a specific gene, the microwell plates that have been amplified (e.g., 5 or 10 for a 5 kb transcript) can be cloned as ordered libraries and sequenced by the same method used for directed sequencing of large-insert clones or genomic DNA discussed above.

During the process of PCR amplification of the PENTAmers, underrepresented sequences from rare transcripts and 5' ends regions will be amplified. For example, even if only 1% of the cDNA molecules in the cDNA preparation extends all the way to a 5' end that is 18 kb away from the 3' end of the expressed sequence, the recombinant PENTAmers from that sequence will be present in the "18 kb" microwell and be amplifiable without competition from the much more abundant cDNA sequences from near the 3' end, which will be in different wells.

By using OPL-cDNA kits from the entire mixture of cDNA molecules, there is no need to first isolate clones having a specific cDNA sequences, and then sequence the longest clones. The investigator can go directly to the full length cDNA sequence.

9. Use of Terminal PENTAmers for Diagnosis of Chromosomal Rearrangements

Nascent PENTAmers from a complete restriction digest of a genome can be size separated, amplified in a sequence-independent manner, and hybridized to a DNA microarray in order to diagnose rearrangements of genomic DNA between different individuals or between different tissues samples in the same individual. The types of rearrangements diagnosable include: 1) deletions; 2) amplifications; 3) translocations; 4) inversions; and 5) complex combinations of the individual rearrangements. DNA microarray hybridization with PENTAmers could replace karyotyping as the major method to diagnose chromosomal aberrations, because it could be 1) more sensitive; 2) less labor-intensive; 3) faster; and/or 4) less expensive. The examples given below relate to human diagnostics, however, it is understood that similar methods can be used for animal and plant genome diagnostics.

a. Representation of a Genome by Terminal Sequences of Restriction Fragments

Figure 37:
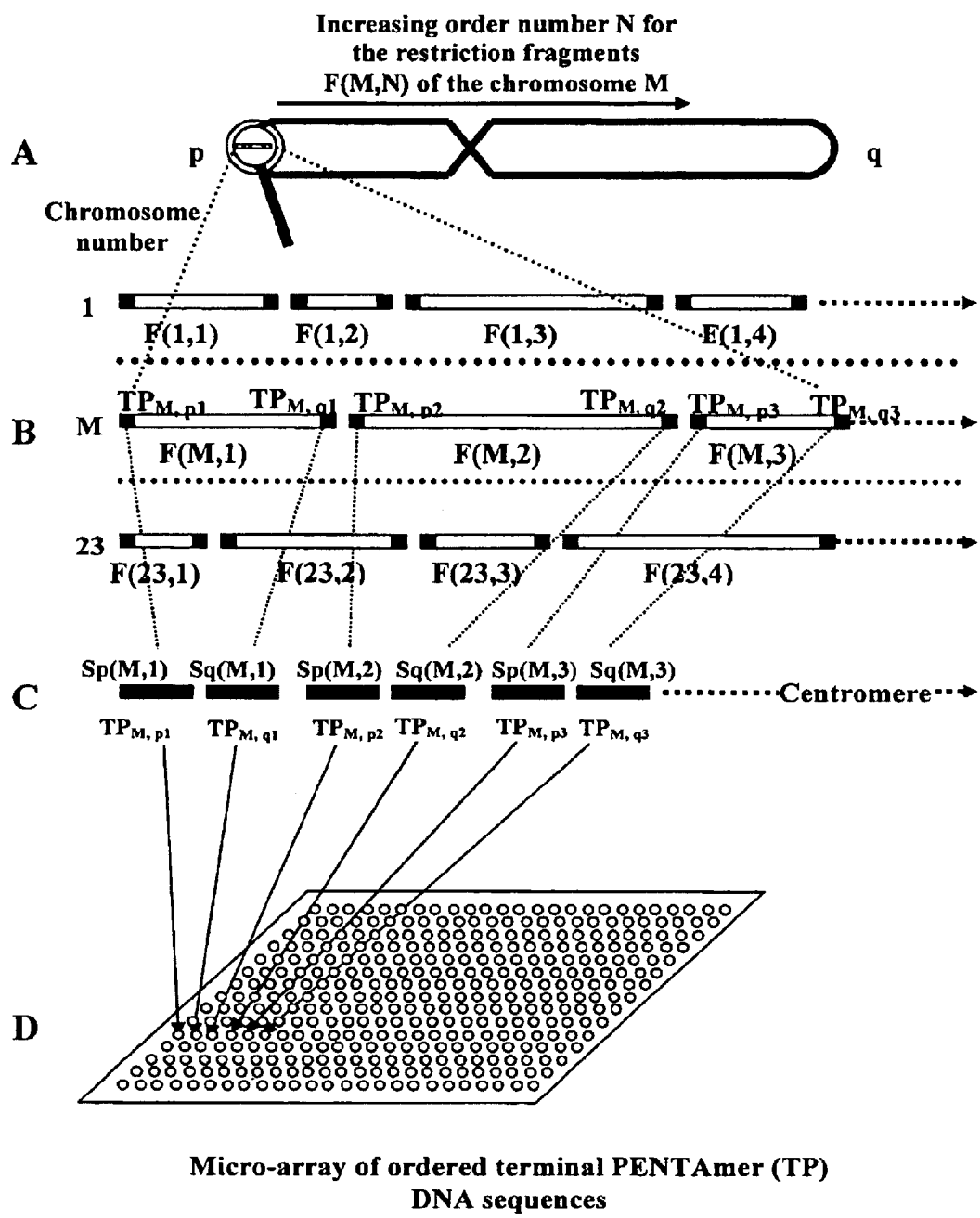
FIG. 37: Terminal PENTAmer micro-arrays for chromosome mutation analysis

A genome can be described, in part, as an ordered set of restriction recognition sites and restriction fragments, FIGS. 37A, B. For example, chromosome 1 can be partially described as an ordered set of restriction recognition fragments; starting from one end of the chromosome (e.g., the tip of the "p" arm) these fragments can be given successive numerical labels, e.g., $F(1,1)$, $F(1,2)$, $F(1,3)$ . . . Chromosome M would be described by the set of fragments, $F(M,1)$, $F(M,2)$, $F(M,3)$ . . . The fragments can also be described by the DNA sequences at the ends of each fragment, e.g., the sequences at the "p" and "q" ends of fragment 1 of chromosome 1 would be $Sp(1,1)$ and $Sq(1,1)$, respectively. The two sequences for the Nth fragment of the Mth chromosome would be $Sp(M,N)$ and $Sq(M,N)$. If the average length of the restriction fragments is 50,000, there should be approximately 60,000 fragments in the human genome, and therefore 120,000 terminal sequences. Each of those 120,000 sequences is prepared as a cloned terminal PENTAmer or represented by a unique complementary oligonucleotide. The terminal PENTAmers (TP) for the Nth restriction fragment of the Mth chromosome (or their oligonucleotide representatives) are denoted $TP(M,pN)$ and $TP(M,qN)$ (with sequences $Sp(M,N)$ and $Sq(M,N)$, respectively (FIGS. 37B, C).

To prepare a diagnostic DNA microarray, each of the TP terminal PENTAmers or oligonucleotides are placed or synthesized as different spots in a DNA microarray (FIGS. 37C, D). Each spot in the microarray is used to detect the presence of one of the terminal sequences in a test sample of DNA by hybridizing labeled test DNA to the microarray. A microarray containing 500 bp TP clones represents ~2% of the human genome. A microarray containing unique 20-mer TP oligonucleotides represents 0.1% of the human genome.

b. Determination of Deletions Using Unfractionated PENTAmers

Figure 38:
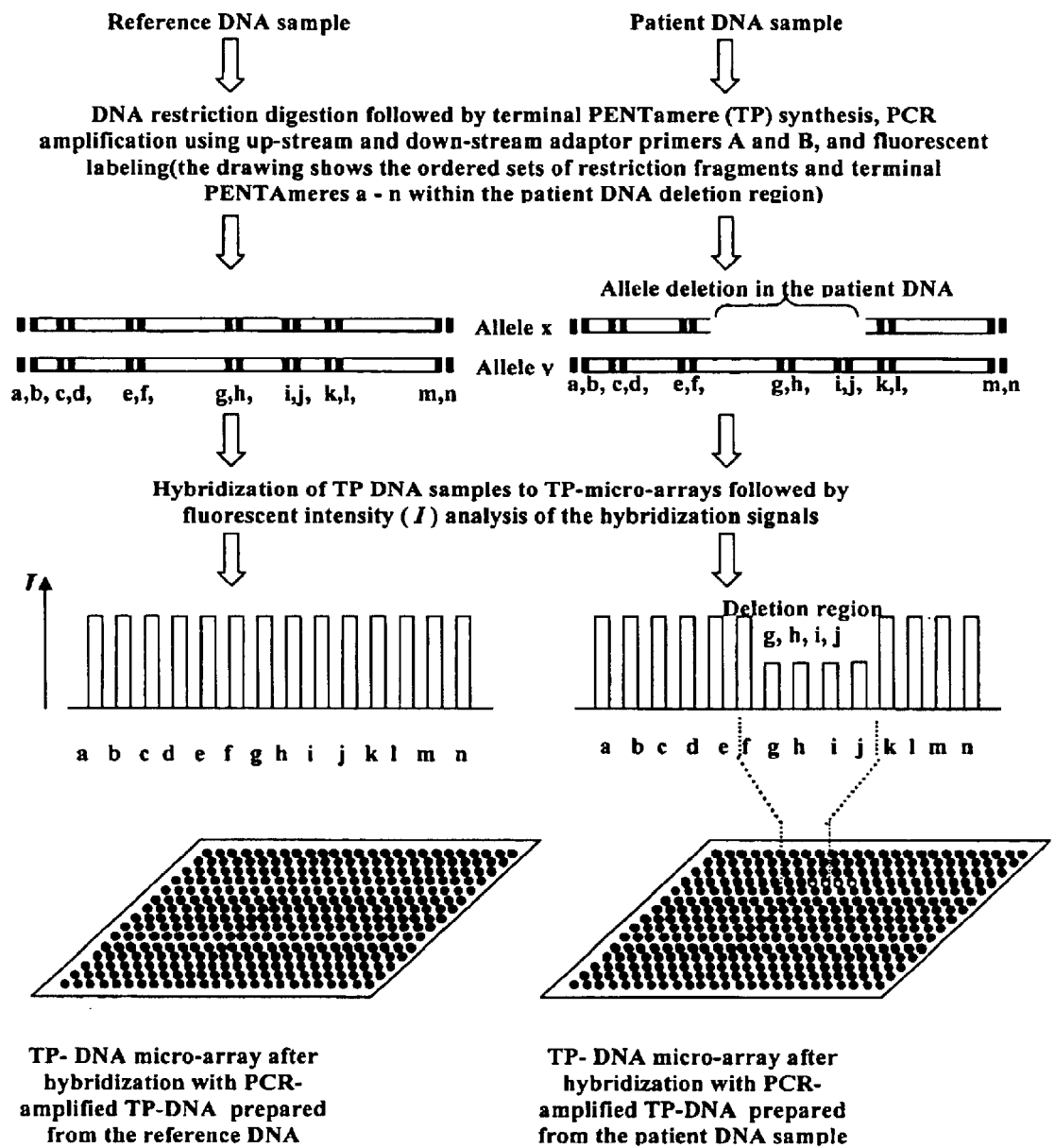
FIG. 38: Whole-genome chromosome deletion analysis using terminal PENTAmer micro-array technology

A TP microarray is produced to represent a single "reference" individual. This array will have each of the terminal sequences characteristic of that reference individual. If DNA from the same reference individual is restricted with the same restriction enzyme, used to synthesize terminal PENTAmers, amplified and labeled using PCR, and hybridized to the microarray of reference terminal fragments, every terminal PENTAmer will be present in the hybridization mixture and every spot on the microarray will hybridize to the PENTAmer DNA and have a fluorescent signal, FIG. 38 (left panels). However, if the DNA from a "test" individual is restricted, terminally amplified, labeled as PENTAmer DNA, and hybridized to the microarray, deletions of terminal sequences in one allele (FIG. 38, right panel)) will cause a 2× decrease of the hybridization intensity of specific spots in the microarray. For example a 100 kb deletion would be expected to delete on average 2 restriction sites (assuming an average restriction fragment length of 50 kb) and therefore deletion of 4 terminal sequences. By recording which spots have 2× reduced hybridization intensity, the chromosomal position of the deletion is determined. To reduce the effect of variations in the amount of reference terminal sequences present in every microarray spot and differences in rate of hybridization of different PENTAmers to different spots, the hybridization reactions is best carried out simultaneously with a means to differentiate between PENTAmers from the reference genome, and the PENTAmers from the test genome, such as by labeling with nonidentical fluorescent dyes. To quantify the abundance of a particular PENTAmer in the experimental genome, a ratio of intensities from the dyes used to label the test and reference genomes is detected.

The sensitivity of this technique is limited by the size of the restriction fragments and complexity of the terminal PENTAmers. The advantage of using PENTAmers to detect deletions is that the PENTAmers can be amplified en masse to increase the concentration of the labeled sequences. Conventional strategies of hybridizing unamplified DNA or randomly-amplified DNA would produce a lower molar concentration and a higher complexity of the hybridizing sequences, increasing the time required for efficient hybridization and increasing the background from hybridization of non-specific sequences. The disadvantage of using this method to detect deletions is that sequence polymorphisms (estimated to be 1 bp out of every 1,000 bp) will prevent some of the expected sequences from being produced as PENTAmers. Assuming an 8-base restriction recognition sequence, about 1% of the expected terminal sequences will not be found due to polymorphism. This problem can be reduced by referring to the database of known polymorphisms to anticipate which sequences might be polymorphic in the population, and therefore unreliable for deletion detection. In addition, loss of several consecutive terminal sequences will rarely occur due to polymorphisms.

It is also envisioned that arrays are made to represent populations of individuals. Population microarrays will contain terminal sequences of all common TP polymorphisms in the population. Population microarrays would genotype individuals in terms of known and novel restriction site polymorphisms and rearrangements.

C. Determination of Chromosomal Amplification Using Unfractionated PENTAmers

Using the same protocol utilized to detect deletions of DNA, amplification of loci can also be detected. If a specific locus in the experimental individual's DNA has been amplified, e.g., in the course of tumorigenesis, the copy number of specific sequences will be increased. This will lead to an increase in the strength of the hybridization signal on specific spots of the DNA microarray. Identification of adjacent sequences that more strongly hybridize than expected reveals the position and size of the amplified region. This leads immediately to information about which gene or genes might have been amplified. In case of differences in the amount of DNA in different spots of the microarray, PENTAmers from the reference genome can be labeled differentially from PENTAmers from the experimental genome, such as by labeling with different fluorescent dyes. In this case, the intensity of both fluorophores will be measured at every spot after hybridization, and the ratio of signals used to determine the copy number of specific terminal sequences.

d. Determination of Chromosome Rearrangements Using Size-Fractionated Restriction Fragments In this section, it is shown that measurement of the sizes of the restriction fragments make it possible to determine small deletions and rearrangements of a test genome relative to a reference genome. Each reference restriction fragment is characterized by a length, L(M,N). The lengths of every reference fragment can be predicted from the complete sequence of the genome, or experimentally determined by size separation. To determine the sizes experimentally, the reference genome is digested to completion with the restriction enzyme, nascent primary PENTAmers created at both ends of each restriction fragment, and the nascent PENTAmer restriction fragments separated by size, e.g., by electrophoresis. When the nascent PENTAmers from a specific size fraction (e.g., 80 kb) are amplified in a sequence-independent way using PCR primers complementary to the two universal adaptors, all the sequences at the termini of 80 kb restriction fragments will be amplified. If these "80 kb" reference PENTAmers are labeled and hybridized to a reference DNA microarray, only those spots containing sequences from 80 kb restriction fragments will be labeled. Because every restriction fragment has two ends, the microarray spots will be labeled in pairs, e.g., if spot Sq(2,350) is labeled, so will spot Sp(2,350), and the labeling of both of these spots indicates that restriction fragment F(2,350) has a length of about 80 kb. When all of the size fractions from the reference genome have been hybridized to the reference microarray, the sizes of all restriction fragments will be known.

Figure 39A:
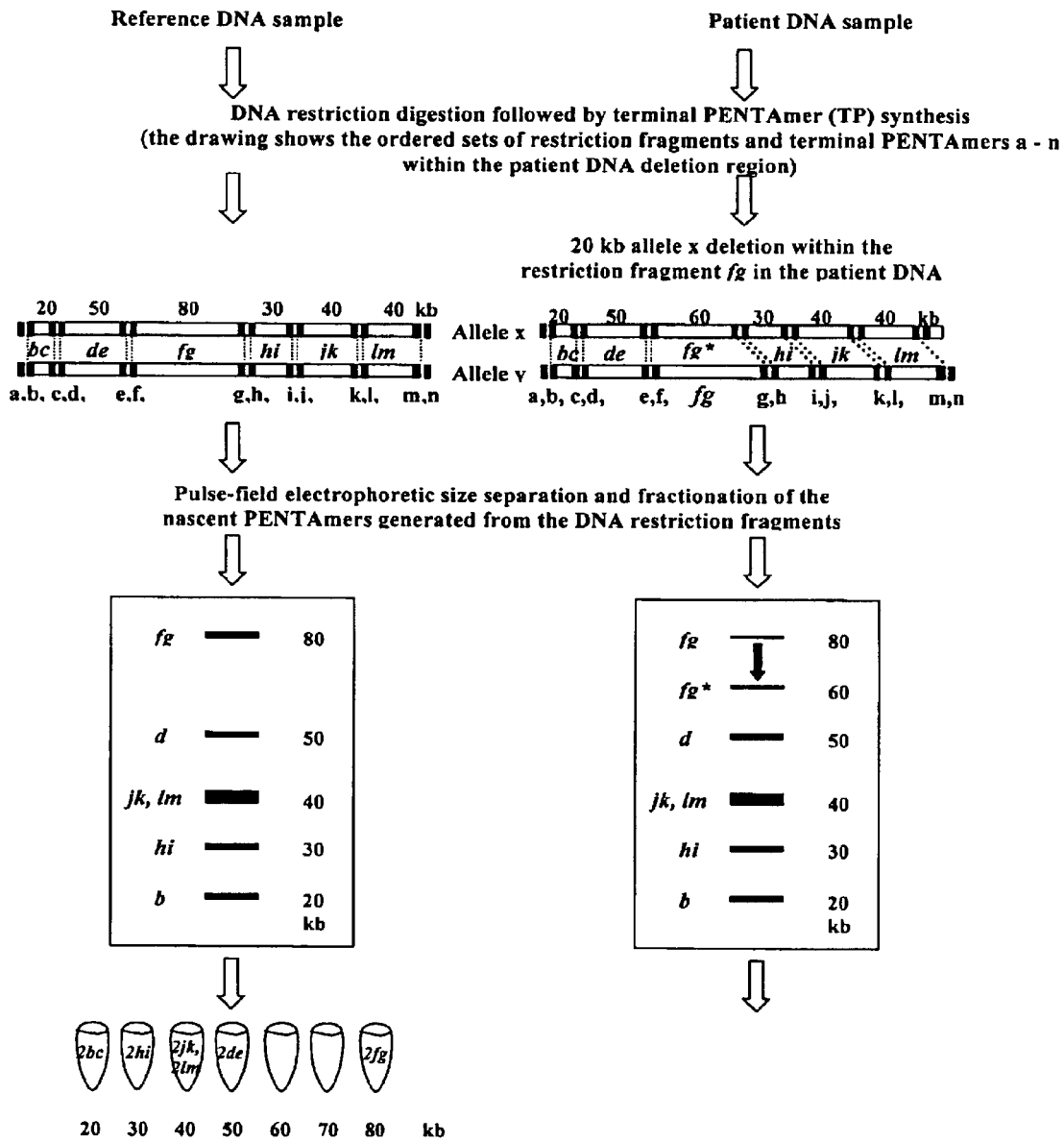
FIGS. 39A and 39B: High-resolution whole-genome chromosome deletion analysis using terminal PENTAmer micro-array technology and DNA size separation
Figure 39B:
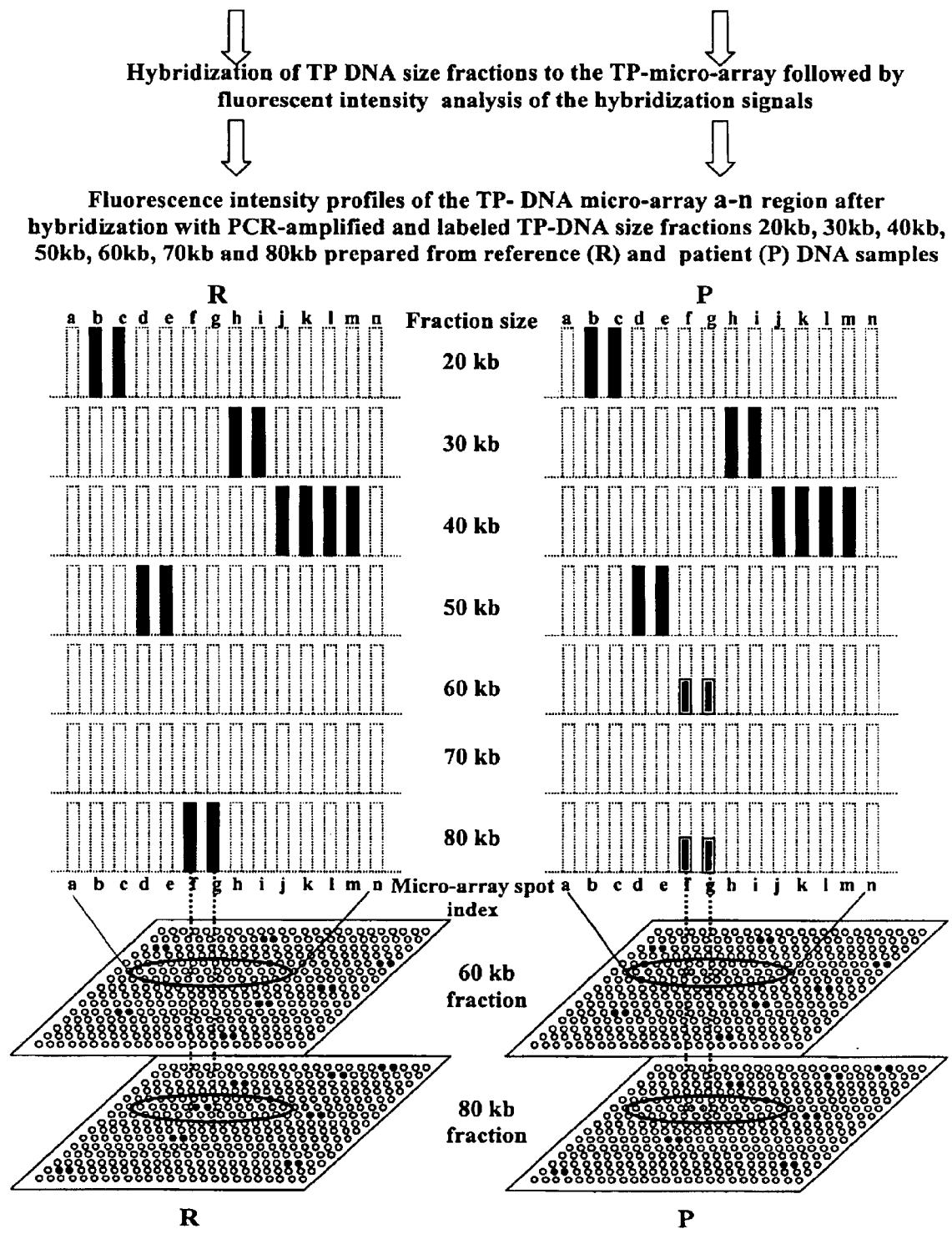

To analyze a test genome, the genome is restricted, terminal PENTAmers synthesized, the nascent PENTAmers separated according to size, and each size fraction hybridized to the reference DNA microarray (FIGS. 39A and 39B). If each test size fraction has the same sequences present as the reference size fractions, then all the restriction fragment lengths are the same in the reference and test genomes. If two test sequences, Sp(M,N) (shown as f in FIG. 39), and Sq(M,N) (shown as g in FIG. 39) are found in a different size fraction in the reference and test samples, then the length of that particular restriction fragment is different in the two genomes. For example, if both sequences are found in the 80 kb fraction of the reference sample (i.e., the length of F(M,N) (shown as fg in FIG. 39) is 80 kb, but in the 60 kb fraction of the test sample (i.e., the length of the test fragment, F*(M,N) (shown as fg* in FIG. 39) is 60 kb in one of alleles, a deletion of 20 kb would have been detected within fragment F(M,N) of one of alleles (allele x in FIG. 39).

If the test genome has a chromosomal translocation (genetic exchange between two chromosomes) then a new situation arises. The outcome of a specific translocation is predictable. For example, if the test genome has a reciprocal translocation between the DNA in fragment F(5,360) and fragment F(20,502), then two new restriction fragments are present in the test DNA, one fragment F*(5,360) containing Sq(5,360) and Sp(20,502), and a second fragment F*'(20, 502) containing Sq(20,502) and Sp(5,360). The sum of the lengths of the two new fragments will be the same as the sum of the fragment lengths from the two reference fragments. However, because the break point for the translocation can be anywhere within the two reference fragments, the sizes of the test fragments will not be the same as the reference fragments. The result is that when the size fractions from the test PENTAmers are hybridized to the reference DNA microarray, sequences Sq(5,360) and Sp(20,502) will be found in a new size fraction corresponding to the new restriction fragment F*(5,360), and sequences Sq(20,502) and Sp(5,360) will be found in a new size fraction corresponding to the new restriction fragment F*(20,502). A different outcome is predicted for an inversion of genetic information within a chromosome. Therefore, to analyze a test genome for these rearrangements, the nascent PENTAmer size fractions from the test individual are hybridized to the reference DNA microarray and the sizes of the restriction fragments containing each of the terminal sequences are determined. Analysis of those sequences that appear in unexpected size fractions can determine the nature and position of chromosomal rearrangements.

It is also envisioned that the arrays made to represent populations of individuals will be used to determine translocations, inversions, deletions, and amplifications of individuals using size-fractionated nascent PENTAmers. Population microarrays will contain terminal sequences of all common TP polymorphisms in the population. Population microarrays would genotype individuals in terms of known and novel restriction site polymorphisms and rearrangements.

10. Use of Sampled PENTAmer Libraries Comprising Terminal PENTAmers for Detection and Identification of Organisms and Variants of Organisms Complete or partial digestion of a single genome or genomes from a mixture of organisms with a first restriction enzyme, followed by synthesis of primary PENTamers at the ends of the restriction fragments, creates a sampled PENTAmer library of amplifiable DNA molecules that represent a specific, restricted fraction of the entire genome. This sampled genome is amplified and analyzed in vitro. Amplification is achieved by PCR or other amplification method using the two primers complementary to adaptor A and B sequences. Analysis is done by restriction fragment fingerprinting or hybridization, in specific embodiments. Fragment fingerprinting can be achieved by cutting to completion the sampled PENTAmer library with one or more other restriction enzymes in order to produce a spectrum of fragments of different length which contain the adaptor A sequence. Those fragments are separated by size using electrophoresis or other method and visualized directly in the electrophoretic gel or transferred to a membrane for detection. The size-separated fragments are visualized by means of a fluorescent, radioactive, chemiluminescent, or other label incorporated within adaptor A, or by detecting the adaptor A sequence indirectly by hybridizing labeled DNA probes to the size-separated DNA. Example 31 shows the fingerprint patterns from a Not I digest of E. coli DNA. The fingerprint patterns from a series of digestions with second restriction enzymes in a specific embodiment are compared to a reference fingerprint of different bacteria in order to determine the specie(s) of bacteria present in a sample, or to determine the type or subtype of a bacterium present in the sample. The presence or absence of specific fragment lengths after digestion with a specific second restriction enzyme is diagnostic for the presence or absence of an expected specific sequence in the sample, as well as the presence of unexpected sequences from unexpected restriction sites in known or unknown genomes.

Hybridization analysis of the sampled PENTAmer library identifies, in specific embodiments, the presence or absence of known sequences in the sample. For example, after a Not I digestion of a culture of bacteria or mixture of bacteria, primary PENTAmers are created from the terminus of every restriction fragment, the PENTAmers amplified using primers complementary to adaptors A and B, and the amplified sampled PENTAmer library hybridized to a DNA microarray containing all or a fraction of all the Not I terminal sequences from one or more reference cultures of bacteria. During amplification, labeled primers or labeled bases are used to label the amplified PENTAmers. If a particular species, type, or subtype of bacterium is present in the sampled PENTAmer library, those microarray spots that contain DNA from the reference bacteria are labeled. In principle, oligonucleotides complementary to restriction termini from hundreds of different bacteria are placed on a single microarray and used to detect the presence of hundreds of different bacteria simultaneously from a mixture of many bacteria.

For large quantities of source DNA, analysis by fingerprinting or hybridization is done by direct labeling of the unamplified PENTAmers using labeled adaptors or by incorporation of a label during the nick-translation reaction.

Applications for a sampled PENTAmer library of bacteria include: a) identification of different bacterial species, types, or subtypes present in a mixture; b) identification of deletion of specific sequences from or insertion of known sequences into a bacterium that, in a specific embodiment, is relevant for surveillance or diagnostic purposes.

11. Use of Sampled PENTAmer Libraries Comprised of Terminal PENTAmers to Amplify Specific Subsets of Genomes Complete restriction digestion of a single genome or genomes from a mixture of organisms with a restriction enzyme, followed by synthesis of primary PENTAmers at the ends of the fragments, is a method to produce an amplifiable library of fragments that represent a specific subset of the genome.

For example, if a human genome is digested with a restriction enzyme that cleaves on average every 100,000 bp, the PENTAmer library made from all 35,000 restriction fragments would comprise about 70,000 specific sequences in the human genome. The molecules in the library could be made to have an average length of 1 kb by controlling the time of the nick-translation reaction. The PENTAmers in a specific embodiment are separated from the remainder of the genome (e.g., by size separation, or by using a biotinylated adaptor). The sampled library in another specific embodiment is labeled during amplification using primers complementary to adaptors A and B (e.g., using a fluorescent primer(s)). The advantage of the sampled PENTAmer library over other proposals to amplify a subset of the genome (e.g., WO 099/18241, WO 00/18960A2) is that the amplimers are of uniform, controllable length and are specific to the termini of restriction fragments. Therefore, the PENTAmer library is used for single-tube amplification of a specific subpopulation of the sequences of a complex genome with minimal non-specific amplification of non-terminal sequences and substantially equal representation of all restriction termini.

12. Use of Oversampled PENTAmer Libraries Comprised of Terminal PENTAmers to Amplify Complete Genomes Partial restriction digestion of a single genome or genomes from a mixture of organisms with a frequently-cutting restriction enzyme, followed by synthesis of primary PENTAmers at the ends of the fragments is a method to produce an amplifiable library of fragments that represent an entire genome.

For example, if a human genome is partially digested with a restriction enzyme that cleaves on average every 64 bp to produce DNA fragments with an average size of 5 kb, templates will be formed to make an overlapping PENTAmer library of the genome. Primary PENTAmers of specified length are synthesized from all restriction fragments. In a specific embodiment, the PENTAmers are separated from the remainder of the genome (e.g., by size separation, or by using a biotinylated adaptor). The sampled library are labeled during amplification using primers complementary to adaptors A and B (e.g., using a fluorescent primer(s)). The resulting mixture of PENTAmers represents the entire human genome. Amplification of the PENTAmer library achieves amplification of the entire genome. The advantage of the oversampled PENTAmer library over the proposal to amplify an entire genome using strand displacement amplification with random primers (WO 99/18241) is that the amplimers are of uniform, controllable length and are specific to the termini of restriction fragments. Therefore the oversampled PENTAmer library can be used for single-tube amplification of all sequences of a complex genome with substantially equal representation of all sequences.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1
Preparation of PENT Adaptors.

This example describes the preparation of several types of adaptors used in different examples for terminal and internal tagging of the double-stranded DNA molecules. Oligonucleotide sequences are shown in Table 4.

Up-stream, terminus-attaching nick-translation adaptor A (FIG. 40) is prepared by annealing 100 pmol of oligonucleotide 5608 I and 100 pmol of the oligonucleotide 5602 I by cooling from 70° C. to room temperature at least 2 h in 20 µl of TE-0.1 (10 mM Tris-HCl pH 8.0, 0.1 mM EDTA). The annealed oligonucleotides are incubated with 5 U of Klenow enzyme (exo⁻) in 40 µl of 50 mM Tris-HCl, pH 7.5, 10 mM $MgCl_2$, 1 mM DTT, 50 µg/ml BSA, and in the presence of 100 mM dATP and 1 mM ddCTP at 37° C. for 1 h.

Acceptor-adaptor (AC) (FIG. 40) is prepared by dephosphorylation of 10 pmol of oligonucleotide 5608 I in 10 µl of 50 mM Tris-HCl, pH 8.5, 5 mM $MgCl_2$ using 2 U of shrimp alkaline phosphatase, SAP (Boehringer Mannheim; Indianapolis, Ind.) for 1 h at 37° C., followed by heat inactivation of SAP at 68° C. for 15 min, mixing with 1 µl of 10 mM oligonucleotide 5603 I and annealing at room temperature for at least 2 h.

Recombination, nick translation adaptor RA-(L-cos) (FIG. 40) is prepared by annealing 100 pmol of 5'-phosphorylated oligonucleotide 5686 I and 100 pmol of 3'-blocked oligonucleotide 5689 I (cooled from 70° C. to room temperature over at least 2 h) in 30 µl volume of TE-0.1.

Down-stream, nick attaching Adaptor B-3'(a) (FIG. 40) is prepared by annealing (as above) 100 pmol of oligonucleotide 5607 I and 100 pmol of oligonucleotide 5604 I in 40 µl of TE-0.1, followed by incubation for 1 h at 37° C. in 60 µl of 100 mM potassium cacodylate, pH 7.2, 2 mM $CoCl_2$, 0.2 mM DTT in the presence of 333 µM ddCTP and 20 U of terminal deoxynucleotidyl transferase (Gibco BRL).

TABLE 4

Oligonucleotides[a]

| Code | Sequence (5'-3') | Length (b) | Applications |
|---|---|---|---|
| 5608 I | P-GATCGCCTATACCTAGGACCATGT (SEQ ID NO.1) | 24[b] | A adaptor |
| 5602 I | GTTACAUGGUCCUAGGTAUAGG (SEQ ID NO.2) | 22 | A adaptor |
| 5603 I | GTTACATGGTCCTAGGTATAGGC (SEQ ID NO.3) | 23 | PENT, PCR primer |
| 5686 I | P-GATCGCCTATACCTAGGACCATGT (SEQ ID NO.4) AACGAATTCATCA | 37[b] | RA-(L-cos) adaptor |
| 5689 I | AGGTCGCCGCCCTGATGAATTCGUTACAUG (SEQ ID NO.5) GTCCUAGGTAUAGGCNH₂ | 45[c] | RA-(L-cos) adaptor |
| 5687 I | GGGCGGCGACCT (SEQ ID NO.6) | 12 | R-cos blocker |
| 5604 I | GGGAGATCTGAATTCCCCCCCCCCC (SEQ ID NO.7) | 25 | B-3' adaptor (a) |
| 5605 I | GGGAGATCTGAATTCAAAAAAAA (SEQ ID NO.8) | 23 | B-3' adaptor (c) |
| 5607 I | P-GAATTCAGATCTCCCGGGTCACCG (SEQ ID NO.9) | 24[b] | B-3' adaptor (a,c) |
| 7422 I | GCGGTGACCCGGGAGATCTGCCCCCCCCCC (SEQ ID NO.10) | 30 | B-3' adaptor (b) |
| 7421 I | GCGGTGACCCGGGAGATCTGAAAAAAA (SEQ ID NO.11) AAA | 30 | B-3' adaptor (d) |
| 7424 I | P-CAGATCTCCCGGGTCACCGCGCCTAT (SEQ ID NO.12) ACCTAGGACCATGTAA | 42[b] | B-3' adaptor (b,d) |

TABLE 4-continued

Oligonuclcotides[a]

| Code | Sequence (5'-3') | Length (b) | Applications |
|---|---|---|---|
| 5776 I | GCGGTGACCCGGGAGATCTGAATTC (SEQ ID NO.13) | 25 | PCR primer |
| 2498 D | Biotin-GCGGTGACCCGGGAGATCTGAATTC (SEQ ID NO.14) | 25[d] | Oligo-construct with nick |
| 464108 P- | AGGTCGCCGCCCTGAATTCAGATCT (SEQ ID NO.15) CCCGGGTCACCGC | 38[b] | Oligo-construct with nick |

[a] all oligonucleotides except 464108 are synthesized at the U of M DNA Synthesis Core; oligonucleotide 464108 is synthesized by Gibco BRL Customer Service.
[b] oligonucleotides 5608 I, 5686 I, 5607 I, and 464108 are synthesized with 5' phosphate group P
[c] oligonucleotide 5689 I is synthesized with 3' blocking amino group NH
[d] oligonucleotide 2498 D is synthesized with 5' biotin molecule Down-stream, nick-attaching adaptor B-3'(b) (FIG. 40) is prepared by phosphorylation of 800 pmol of oligonucleotide 7424 I in 20 µl of 50 mM Tris-HCl, pH 8.2, 10 mM MgCl$_2$, 0.1 mM EDTA, 5 mM DTT, 0.1 mM spermidine in the presence of 1 mM dATP and 10 U of polynucleotide kinase, PNK (Boehringer Mannheim, Indianapolis, Ind.) at 37° C. for 1 h, followed by heat inactivation of PNK, adding 800 pmol of the oligonucleotide 5603 I and 800 pmol of oligonucleotide 7422 I, and annealing from 80° C. to room temperature for at least 2 h in 20 µl 25 mM Tris-HCl, 0.05 mM EDTA, pH 8.0.

Down-stream, nick-attaching adaptor B-3'(c) (FIG. 40) is prepared by annealing (as above) 100 pmol of oligonucleotide 5607 I and 100 pmol of oligonucleotide 5605 I, in 40 µl TE-0.1, followed by incubation for 1 h at 37° C. in 60 µl of 100 mM potassium cacodylate, pH 7.2, 2 mM CoCl$_2$, 0.2 mM DTT in the presence of 333 µM ddATP and 20 U of terminal deoxynucleotidyl transferase (Gibco BRL).

Down-stream, nick-attaching adaptor B-3'(d) (FIG. 40) is prepared by phosphorylation of 800 pmol of oligonucleotide 7424 I in 20 µl of 50 mM Tris-HCl, pH 8.2, 10 mM MgCl$_2$, 0.1 mM EDTA, 5 mM DTT, 0.1 mM spermidine in the presence of 1 mM dATP and 10 U of polynucleotide kinase (Boehringer Mannheim, Indianapolis, Ind.) at 37° C. for 1 h, followed by heat inactivation of PNK, addition of 800 pmol of oligonucleotide 5603 I and 800 pmol of oligonucleotide 7421 I, and annealing from 80° C. to room temperature for at least 2 h in 20 µl 25 mM Tris-HCl, 0.05 mM EDTA, pH 8.0.

Adaptors B-3'(a), B-3'(b), B-3'(c) and B-3'(d) are equivalent to a down-stream, nick-attaching adaptor B-3'(II) shown in FIG. 28 and discussed above.

Example 2
Efficient Ligation of Blocked PENT-Adaptors.

Ligation of specialized nick-translation adaptors to the ends of DNA molecules is an important step towards the creation of a PENTAmer. This example describes the efficiency of ligation of a specialized 3'-end-blocked recombination nick-translation adaptor RA-(L-cos)(donor-adaptor Dn) with 5'phosphorylated 4-base GATC terminus to the recipient molecule (acceptor-adaptor AC) with complementary 5' termini (Example 1).

Five reaction mixtures which contain 0, 200, 400, 800 and 800 nM adaptor RA-(L-cos) (donor Dn), 200 nM acceptor-adaptor (AC) in the first four tubes (no acceptor-adaptor in tube 5), 66 mM Tris-HCl, pH 7.5, 5 mM MgCl$_2$, 1 mM DTT, 1 mM ATP and 1 U of T4 DNA ligase (Boehringer Mannheim, Indianapolis, Ind.) in 10 µl are incubated for 2 h at 20° C. Tubes 6 and 7 contain ligase-deficient controls with 200 nM adaptor-acceptor and 800 nM adaptor-acceptor, respectively. The products of the ligation reactions are analyzed on a 15% polyacrylamide, 1×TBE gel, stained with ethidium bromide (FIG. 41).

Figure 41:
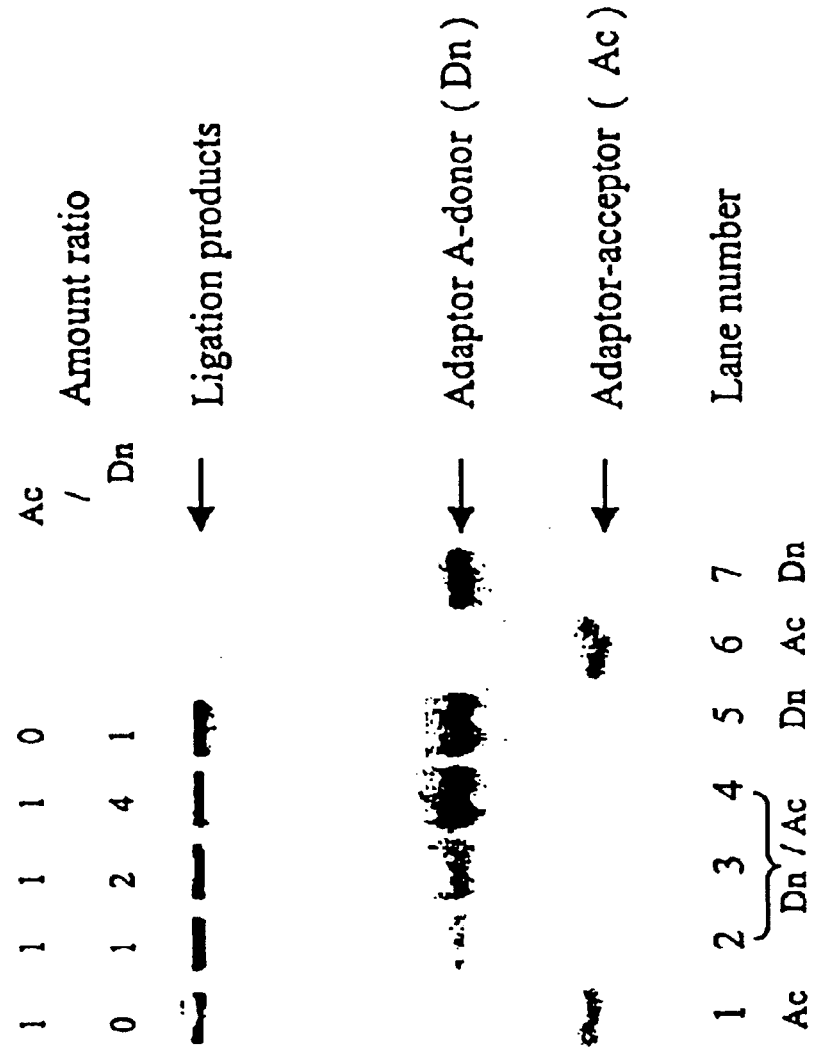
FIG. 41: Efficient ligation of the 3'-end blocked up-stream nick-translation adaptor A

FIG. 41 shows the results of ligation. The bands at the top of the gel represent ligation products. The bands of lower molecular weight are from the monomeric species. Lane 6 shows adaptor-acceptor in the absence of ligase. Lane 7 shows adaptor-donor in the absence of ligase. The ratio of monomers to dimers is determined from the relative intensities of fluorescence from the monomer and dimer bands. In the reaction with adaptor-acceptors alone, about 30% of the molecules form dimers as a result of self-ligation of not completely dephosphorylated adaptor A (lane 1). Addition to the ligation mixture oif the adaptor-donor (Dn) leads to formation of the donor-acceptor dimers (Ac-Dn) and disappearance of the monomer acceptor band Ac, even with only a 1:1 ratio of the two adaptors (lanes 2–4). The 3'-end blocked adaptor RA-(L-cos)(donor-adaptor Dn) shows minor formation of self-ligation products at 800 nM concentration (lane 5) when compared with control 800 nM donor-adaptor sample without ligation (lane 7). This gel shows that self-ligation can be inhibited.

Example 3
Preparation of the "PENT-Ready" Lambda DNA Bam HI Templates.

This example describes the preparation of lambda DNA/ Bam HI restriction fragments with upstream nick-translation adaptors A, which are used in Examples 4–7, and 9–14.

Following the incubation of 5 µg of lambda DNA with 20 U Bam HI (Boehringer Mannheim, Indianapolis, Ind.) in 25 µl of 10 mM Tris-HCl, pH 8.0, 5 mM MgCl$_2$, 100 mM NaCl, 1 mM 2-mercaptoethanol for 2 h at 37° C., the mixture is supplemented with 3 µl of shrimp alkaline phosphatase (SAP) buffer (Boehringer Mannheim) and 2 U of SAP (Boehringer Mannheim), and incubated for 30 min at 37° C. After heat inactivation of SAP at 68° C. for 15 min the DNA is precipitated with ethanol, washed with 70% ethanol, dried and dissolved in 31 µl TE (10 mM Tris-HCl pH 8.0, 1 mM EDTA) with a final molar concentration of Bam HI ends equal to 50 nM. Then, 5 µl of SAP treated Bam HI lambda DNA restriction fragments (250 fmol ends) are ligated with 1 pmol of nick-translation adaptor A (type C) or recombination nick-translation adaptor RA-(L-cos) in 10 µl of 66 mM Tris-HCl, pH 7.5, 5 mM MgCl$_2$, 1 mM DTT, 1 mM ATP and 1 U T4 DNA ligase (Boehringer Mannheim, Indianapolis, Ind.) at room temperature for 4 h. The reaction is terminated by adding 1.5 µl 50 mM EDTA and heating at 68° C. for 15 min, followed by adding 1 U dU-glycosylase (Boehringer Mannheim, Indianapolis, Ind.) and incubation for 1 h at 37° C. to destabilize the binding of the 3'-blocked oligonucleotide 5602 I (adaptor A) or 5689 I (RA-(L-cos) adaptor).

Example 4
T4 DNA Polymerase-Mediated Repair of the Blocked 3'-ends of PENT-Adaptors.

The PENT adaptors that are used in this example contain blocked 3' ends. To initiate PENT reaction it is necessary to have a primer with 3'-OH group. This example describes a first method to activate the nick-translation primer within PENT-adaptors.

Figure 42:
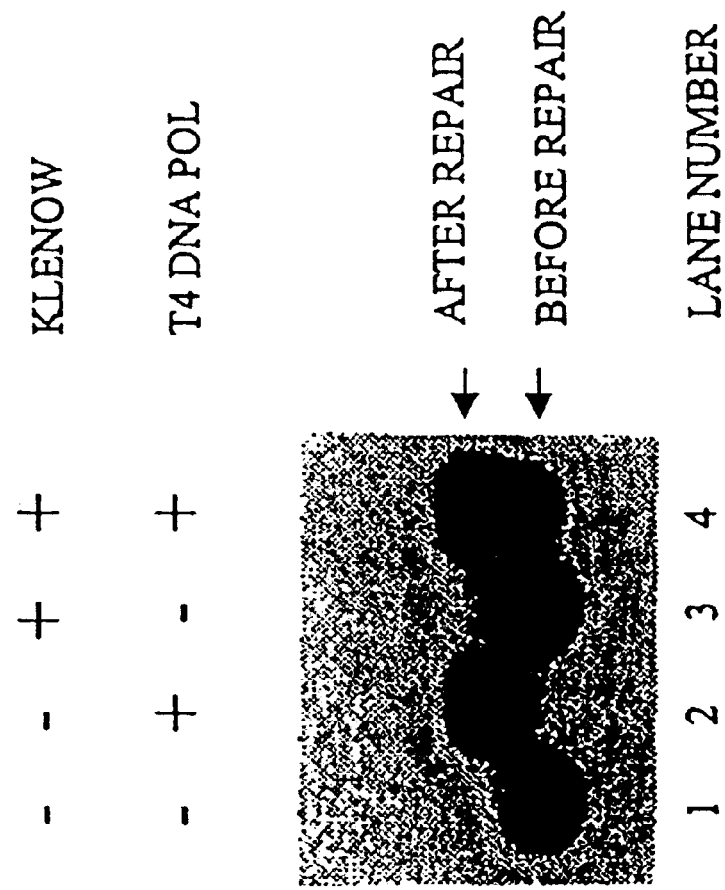
FIG. 42: T4 DNA polymerase-mediated repair of blocked 3'-ends of the nick-translation adaptor A

1 pmol of the 3'-end blocked oligonucleotide 5689 I labeled with [$\gamma$-$^{32}$P]ATP (using T4 kinase) is hybridized with 2 pmol of oligonucleotide 5686 I (FIG. 40) in 20 $\mu$l of 100 mM KCl, 50 mM Tris-HCl, pH 7.5 to form a RA-(L-cos) adaptor at a concentration of 50 nM. Four repair reaction mixtures are prepared. Each tube has a final volume of 25 $\mu$l containing 50 fmol $^{32}$P-labeled adaptor RA-(L-cos) and 100 $\mu$M dNTP (i.e., 100 $\mu$M dATP, 100 $\mu$M dCTP, 100 $\mu$M dGTP, and 100 $\mu$M dTTP). Tube 1 contains no polymerase. Tube 2 contains 1 U T4 DNA polymerase (Boehringer Mannheim). Tube 3 contains 2 U Klenow fragment (Gibco BRL). Tube 4 contains 1 U of T4 DNA polymerase and 2 U Klenow fragment. Tubes 1, 2 and 4 are brought to final volume with 50 mM Tris-HCl, pH 8.8, 15 mM (NH$_4$)$_2$SO$_4$, 7 mM MgCl$_2$, 0.1 mM EDTA, 10 mM 2-mercaptoethanol, 20 $\mu$g/ml BSA. Tube 3 is brought to final volume with 50 mM Tris-HCl, pH 7.5, 10 mM MgCl$_2$, 1 mM DTT, 50 $\mu$g/ml BSA. After adjusting the volumes with buffer, the tubes are incubated for 1 h at 16° C. Products of the repair reactions are separated on 12% polyacrylamide/7 M urea denaturing gel at 60° C. After electrophoresis, the gel is dried and analyzed using a Molecular Dynamics, (Sunnyvale, Calif.) 400A PhosphorImager and ImageQuant software (Makarov et al., 1997) (FIG. 42).

Repair of the blocked oligonucleotide 5689 I should be evidenced by increase of the molecular weight of the labeled oligonucleotide from 45 b to 49 b. The repair is efficient with T4 DNA polymerase (compare lanes 1 and 2) but not with Klenow fragment (compare lanes 1 and 3). Mixture of T4 DNA polymerase and Klenow fragment (lane 4) results in only partial repair probably due to competitive binding of Klenow fragment.

Example 5
Primer-Displacement Activation of the PENT Reaction.

This example describes a method to initiate the PENT reaction, which utilizes the reduced binding of the 3' blocked primer after dU-glycosylase treatment of the adapted DNA fragments.

0.8 $\mu$g "PENT-ready" lambda DNA Bam HI templates prepared as described in Example 3 (250 fmol adapted ends) are mixed with 500 fmol of $^{32}$P-labeled PENT primer 5603 I in 13.5 $\mu$l volume, heated to 70° C. and allowed to cool slowly to room temperature for more than 2 h. The concentration of the ends is adjusted to 1 fmol/$\mu$l with TE buffer.

Figure 43:
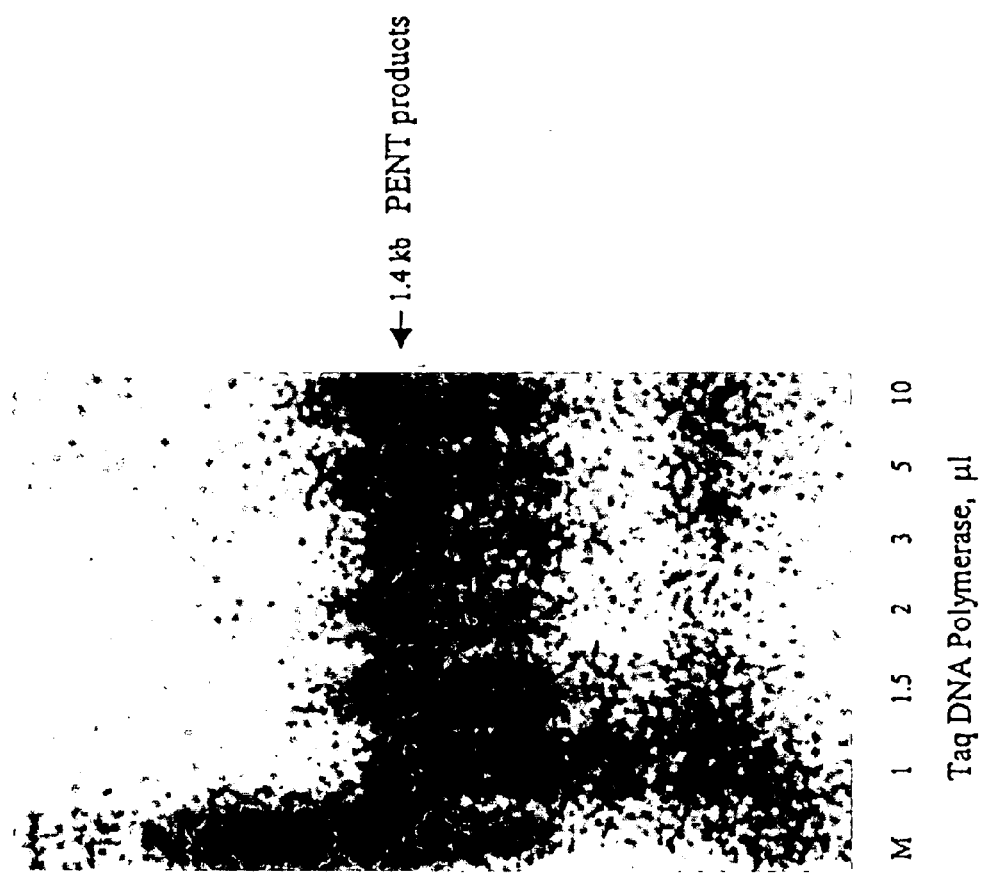
FIG. 43: Primer-displacement activation of PENT reaction

Primer-extension nick-translation reaction (PENT) is performed with wild type Taq DNA polymerase as described before (Makarov et al., 1997). In all examples described, wild type Taq stock at 60 U/$\mu$l was provided by Dr. David Engelke of the University of Michigan. It was always diluted 30× with Taq buffer (20 mM Tris-HCl pH 8.3, 50 mM KCl, 2 mM Mg Cl$_2$) before use. To conduct PENT reactions at different Taq DNA polymerase concentrations, six mixtures containing 5 $\mu$l of lambda DNA/Bam HI restriction fragments with ligated and activated nick-translation adaptor A (as described above), 5 $\mu$l of 10×PCR™ buffer (100 mM Tris-HCl, pH 8.3, 50 mM KCl), 4 $\mu$l 25 mM MgCl$_2$, and 1, 1.5, 2, 3, 5 or 10 $\mu$l of Taq DNA polymerase (30 times diluted with 1×Taq buffer from stock at 60 U/$\mu$l) and H$_2$O to make a final volume of 49 $\mu$l are prepared in six 0.5 ml PCR™ tubes. Samples are preheated at 50° C. for 5 min, and the PENT reactions are initiated by adding 1 $\mu$l of 2.5 mM dNTP (i.e., 2.5 mM dATP, 2.5 mM dTTP, 2.5 mM dGTP, and 2.5 mM dCTP) solution to each tube. After 7 min of incubation at 50° C., the reactions are terminated by adding 1 $\mu$l 0.5 M EDTA and precipitated with ethanol. PENT reaction products are separated on an alkaline (40 mM NaOH, 1 mM EDTA) 1% agarose gel. After electrophoresis, the gel is neutralized, electro-blotted onto ZetaProbe membrane (BioRad) and analyzed with a Molecular Dynamics (Sunnyvale, Calif.) 400A PhosphorImager and ImageQuant software (Makarov et al., 1997) (FIG. 43).

PENT products are detected as a 1.4 kb band from 3 U to 20 U of Taq DNA polymerase (lanes 2–6), which suggest the PENT reaction initiates synchronously and proceeds at about 200 bp/min at 50° C.

Example 6
Effect of MgCl$_2$ Concentration on the Rate of PENT Reaction

This example shows that the PENT reaction can be performed by wild type Taq DNA polymerase over a broad range of Mg ion concentration.

To carry out the PENT reactions at different MgCl$_2$ concentrations, five mixtures containing 5 $\mu$l of lambda DNA/Bam HI restriction fragments with ligated and activated nick-translation adaptor A (as described in Example 5), 5 $\mu$l of 10×PCR™ buffer (100 mM Tris-HCl, pH 8.3, 50 mM KCl), 2, 4, 8, 10 or 14 $\mu$l 25 mM MgCl$_2$, 2 $\mu$l of Taq DNA polymerase (30 times diluted with 1×Taq buffer from stock at 60 U/$\mu$l) and an amount of H$_2$O to attain a final volume of 49 $\mu$l are prepared in five 0.5 ml PCR™ tubes. Samples are preheated at 50° C. for 5 min, and the PENT reactions are initiated by adding 1 $\mu$l of 2.5 mM dNTP solution to each tube. After 7 min of incubation at 50° C., reactions are terminated by adding 1 $\mu$l 0.5 M EDTA and EtOH precipitated.

Figure 44:
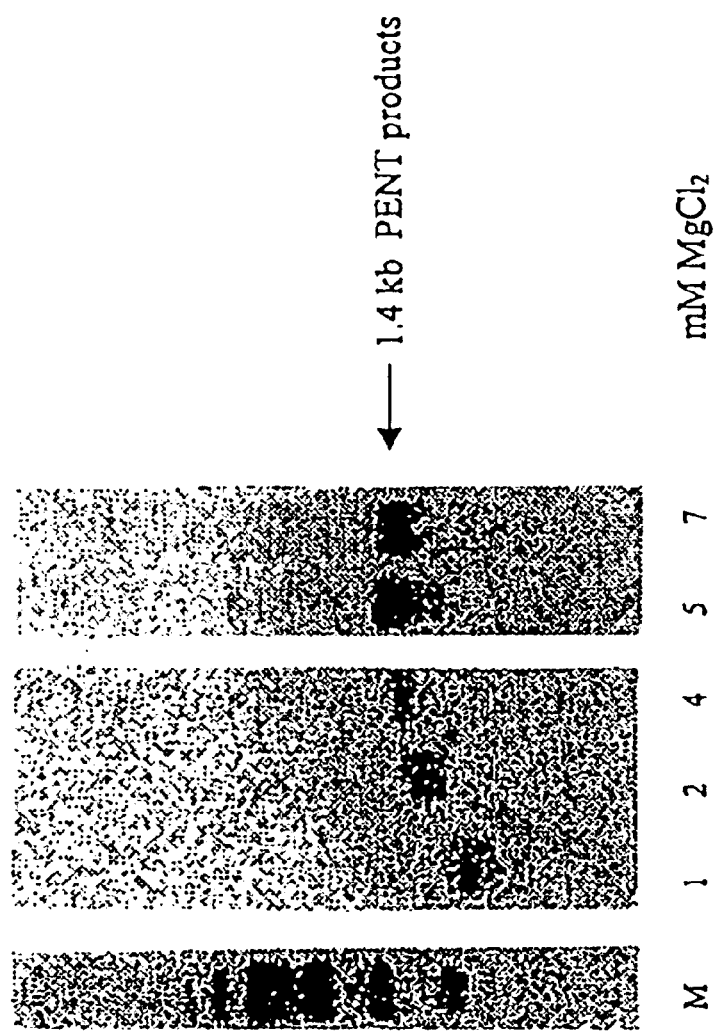
FIG. 44: Effect of $MgCl_2$ concentration on the rate of PENT reaction

PENT reaction products are separated on an alkaline (40 mM NaOH, 1 mM EDTA) 1% agarose gel. After electrophoresis, the gel is neutralized, electro-blotted onto ZetaProbe membrane (BioRad; Hercules, Calif.) and analyzed with a Molecular Dynamics (Sunnyvale, Calif.) 400A PhosphorImager and ImageQuant software (Makarov et al., 1997) (FIG. 44).

PENT products are detected as 1.2–1.4 kb bands with PENT reaction rate changing from 170 to 200 bp/min when MgCl$_2$ concentration rises from 1 to 4 mM. No further increase of the PENT reaction rate is found in the range of 4 to 7 MM MgCl$_2$. The efficiency of initiation is fairly independent of Mg concentration.

Example 7
Control of the Length of PENT Products by Control of the Duration of the PENT Reaction.

It was shown before for human telomeres and model plasmid construct that the size of newly synthesized strand during PENT is strictly proportional to the time of reaction, suggesting a simple and reproducible method of time-controlled DNA synthesis (Makarov et al., 1997). This example describes time-controlled DNA synthesis on a mixture of 10 different DNA templates.

Three mixtures are prepared in three 0.5 ml PCR™ tubes which contain 10 ml of lambda DNA/Bam HI restriction fragments with ligated and activated nick-translation adaptor A (as described in Example 5), 5 $\mu$l of 10×PCR™buffer (100 mM Tris-HCl, pH 8.3, 50 mM KCl), 4 $\mu$l 25 mM MgCl$_2$, 2 $\mu$l of Taq DNA polymerase (30 times diluted with 1×Taq buffer from stock at 60 U/$\mu$l) and H$_2$O in final volume 49 µl. Samples are preheated at 50° C. for 5 min, and the PENT reactions are initiated by adding 1 µl of 2.5 mM dNTP solution to each tube. The reactions are continued at 50° C. and terminated by adding 1 µl 0.5 M EDTA after 2 min (tube 1), after 4 min (tube 2), and after 6 min (tube 3). The contents of all tubes were EtOH precipitated.

Figure 45:
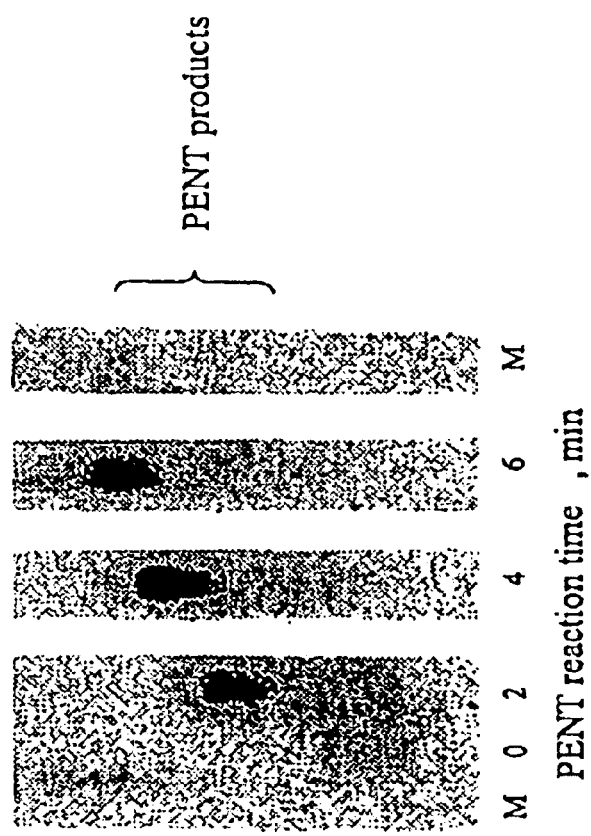
FIG. 45: Time-controlled synthesis of PENT products

PENT reaction products are separated on an alkaline (40 mM NaOH, 1 mM EDTA) 1% agarose gel. Molecular weight markers were also loaded onto the gel. After electrophoresis, the gel is neutralized, electro-blotted onto ZetaProbe membrane (BioRad; Hercules, Calif.) and analyzed with a Molecular Dynamics (Sunnyvale, Calif.) 400A PhosphorImager and ImageQuant software (Makarov et al., 1997) (FIG. 45).

PENT products from tubes 1, 2, and 3 are detected as 0.4, 0.8 and 1.2 kb bands, respectively. The average rate of PENT reaction is estimated to be 200 bases/min at 50° C. Because the bands are narrow, it is concluded that the PENT products from the 10 template ends had similar lengths.

Example 8
Terminal Deoxynucleotidyl Transferase (TdT) Tailing at the Nick in a Model Oligonucleotide Construct This example describes the addition of long homopolymeric tails to the 3'-OH within a nick of a model double-stranded oligonucleotide using TdT.

Model oligonucleotide construct with a nick (FIG. 40) is prepared by: a) mixing 1 nmol oligonucleotide 2498 D with 1 nmol oligonucleotide 464108 in 20 µl TE buffer; b) heating and annealing as described in Example 1; c) $^{32}$P-labeling of the 3'-end of oligonucleotide 2498 D by incubating 5 pmol of the oligo 2498 D/oligo 464108 hybrid in 10 µl reaction mixture containing 50 mM Tris-HCl, pH 7.5, 10 mM MgCl$_2$, 1 mM DTT, 50 µg/ml BSA, 0.33 mM [α-$^{32}$p] dATP and 5 U Klenow fragment (exo-) (Ambion) for 30 min at 20° C.; d) inhibiting with 0.5 µl 0.5 M EDTA and hybridizing 5 pmol of the oligonucleotide lambda R-cos to 5' end of the oligo 2498 D/oligo 464108 hybrid at 37° C. in 20 µl TE to form a structure with nick; e) diluting to 50 nM.

Four 20 µl TdT reaction mixtures containing 50 fmol [α-$^{32}$P]-labeled oligo-construct (see above), 100 mM potassium cacodylate, pH 7.2, 2 mM CoCl$_2$, 0.2 mM DTT, 15 U TdT (Gibco BRL), and 1 µM, 3 µM, 10 µM and 30 µM dGTP are incubated at 37° C. for 40 min. Reactions are terminated by adding 1 µl 200 mM EDTA and 20 µl 2×formamide loading buffer (10×TBE, 90% deionized formamide, 0.5% Bromphenol Blue).

Figure 46:
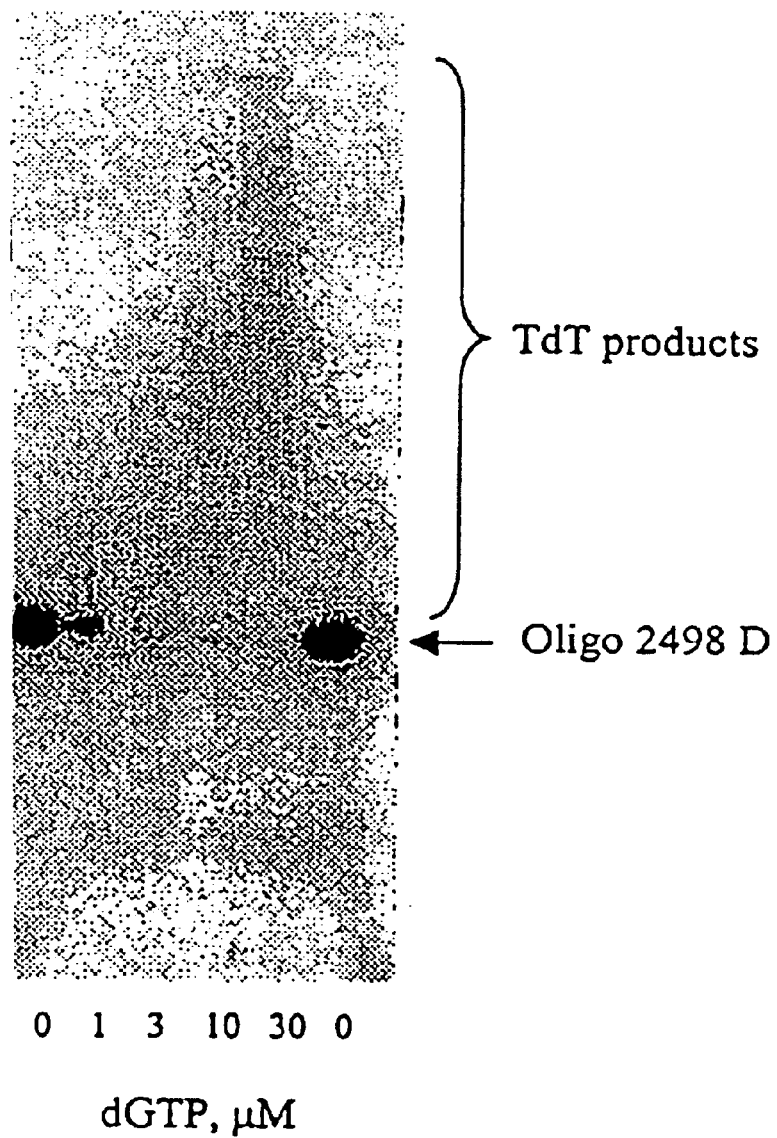
FIG. 46: Poly-G TdT-mediated tailing at nick: model oligonucleotide construct

Products of the reactions are separated on 12% polyacrylamide/7M urea denaturing gel at 60° C. After electrophoresis, gel is dried and analyzed with a Molecular Dynamics (Sunnyvale, Calif.) 400A PhosphorImager and ImageQuant software (Makarov et al., 1997) (FIG. 46). Products of TdT-mediated tailing are detected as broad smeared bands with a size larger than 26 bp. Tubes with increasing concentrations of dGTP contained labeled molecules with longer homopolymeric tails. Even at low concentrations of nucleotide, the majority of nicks were extended.

Example 9
Terminal Deoxynucleotidyl Transferase (TdT) Tailing of PENT Products: Inhibitor Effect of Taq DNA Polymerase.

This example describes prerequisites for efficient homopolymeric tailing by TdT at the internal 3'-ends (nicks) of PENT products. The addition of homopolymer tails using TdT and non-purified templates directly after PENT reaction are not preferred. In fact, phenol/chloroform purification of DNA after incubation with Taq polymerase followed by ethanol precipitation is preferred for TdT-mediated reaction.

PENT reaction is performed as described in Examples 5–7. Specifically, four mixtures are prepared in four 0.5 ml PCR™ tubes which contain 5 µl of lambda DNA/Bam HI restriction fragments with ligated and activated nick-translation adaptor A (as described in the Example 5), 5 µl of 10×PCR™ buffer (100 mM Tris-HCl, pH 8.3, 50 mM KCl), 4 µl 25 mM MgCl$_2$, 2 µl of Taq DNA polymerase (30 times diluted with 1×Taq buffer from stock at 60 U/µl) and H$_2$O in final volume 49 µl. Samples are preheated at 50° C. for 5 min, and the PENT reactions are initiated by adding 1 µl of 2.5 mM dNTP solution to each tube. After 5 minutes of incubation at 50° C., the reactions are terminated by adding 1 µl 200 mM EDTA. The PENT DNA samples from tubes 1 and 2 are precipitated with ethanol in the presence of 1 µl glycogen (Boehringer Mannheim; Indianapolis, Ind.). The PENT DNA from tube 3 is extracted with phenol/chloroform and precipitated as described above. The PENT DNA from tube 4 is washed 3× with 0.5 ml of TE-0.1 in a Microcon 100 centrifugal filter device (Amicon) by spinning at 300 g for 20 min at room temperature and recovered in 26 µl volume. The PENT DNA samples from tubes 1, 2 and 3 are pelleted, washed 3× with 70% EtOH, dried, and dissolved in 20 µl TE.

Four TdT tailing reactions and four control reactions are performed. Tubes 1A (experimental) and 1B (control) contain 10 µl DNA from tube 1 (above), 100 mM potassium cacodylate, pH 7.2, 2 mM CoCl$_2$, and 0.2 mM DTT. 1 µl 1 mM dTTP and 15 U TdT (Gibco BRL) are added to tube 1A. Tubes 2A (experimental) and 2B (control) contain 10 µl DNA from tube 2, 100 mM potassium cacodylate, pH 7.2, 2 mM CoCl$_2$, and 0.2 mM DTT. 0.5 µl 1 mM dGTP and 15 U TdT (Gibco BRL) are added to tube 2B. Tubes 3A (experimental) and 3B (control) contain 10 µl DNA from tube 3, 100 mM potassium cacodylate, pH 7.2, 2 mM CoCl$_2$, and 0.2 mM DTT. 1 µl 1 mM dTTP and 15 U TdT (Gibco BRL) are added to tube 3A. Tubes 4A (experimental) and 4B (control) contain 10 µl DNA from tube 4, 100 mM potassium cacodylate, pH 7.2, 2 mM CoCl$_2$, and 0.2 mM DTT. 1 µl 1 mM dTTP and 15 U TdT (Gibco BRL) are added to tube 4A. Tubes are adjusted to 20 µl with H$_2$O.

Figure 47:
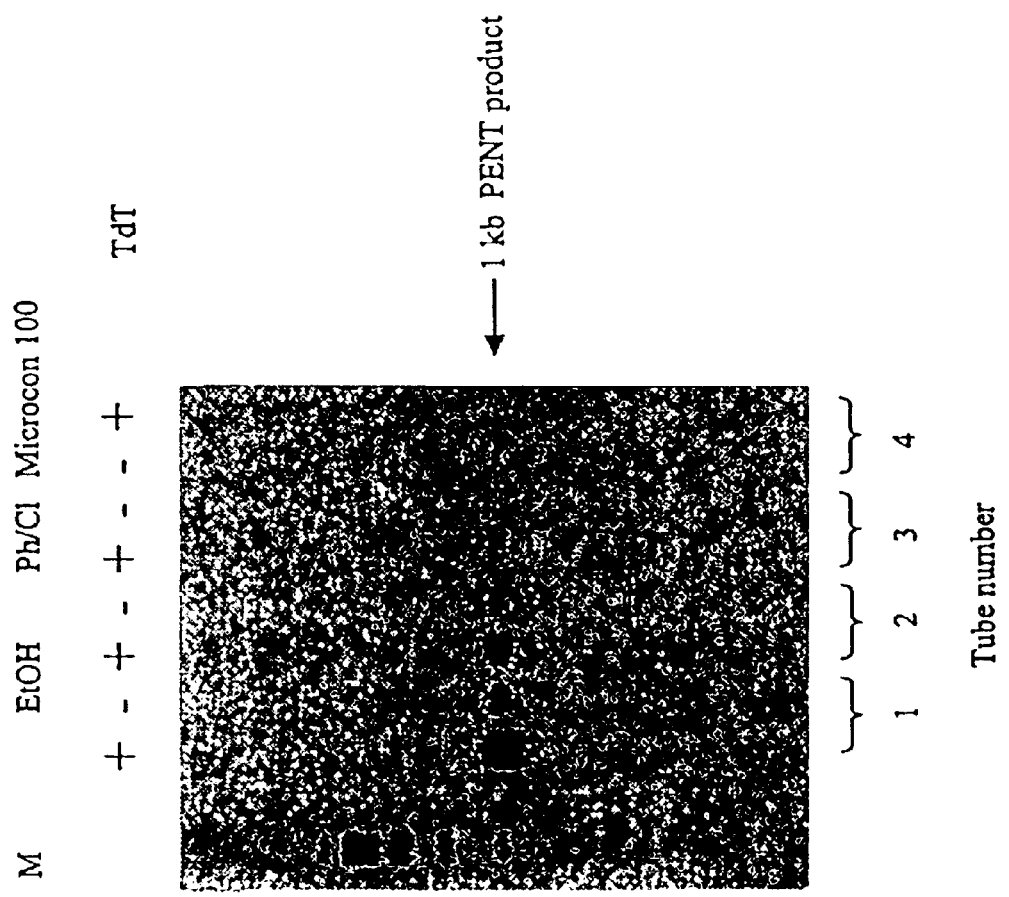
FIG. 47: TdT tailing of PENT products: inhibitory effect of Taq DNA polymerase

All 8 tubes are incubated at 37° C. for 40 min, ethanol precipitated, dissolved, loaded and separated on an alkaline (40 mM NaOH, 1 mM EDTA) 1% agarose gel. After electrophoresis, gel is neutralized, electro-blotted onto ZetaProbe membrane (BioRad; Hercules, Calif.). and analyzed with a Molecular Dynamics (Sunnyvale, Colo.) 400A PhosphorImager and ImageQuant software (Makarov et al., 1997) (FIG. 47).

TdT-tailed PENT products are detected as broadened DNA bands with increased molecular weight relative to the controls. Only those DNA samples that are extracted with phenol/chloroform or washed with Amicon filters have noticable lengths of homopolymeric DNA. These results indicate that removal of Taq polymerase after the PENT reaction is necessary to allow the TdT to use the PENT product as a substrate.

Example 10
Terminal Deoxynucleotidyl Transferase (TdT) Tailing of PENT Products: Effect of Carrier.

Frequently, in manipulations of small amounts of DNA it is necessary to use a carrier molecule for efficient DNA recovery. This example describes the observation that tRNA as a carrier has no inhibitory effect on the PENT tailing capacity of the terminal deoxynucleotidyl transferase, while glycogen inhibits the reaction.

PENT reaction is performed as described in Examples 5–7. Specifically, four mixtures are prepared in four 0.5 ml PCR™ tubes which contain 5 µl of lambda DNA/Bam HI restriction fragments with ligated and activated nick-translation adaptor A (as described in the Example 5), 5 µl of 10×PCR™ buffer (100 mM Tris-HCl, pH 8.3, 50 mM KCl), 4 µl 25 MM MgCl$_2$, 2 µl of Taq DNA polymerase (30 times diluted with 1×Taq buffer from stock at 60 U/µl) and H$_2$O in final volume 49 µl. Samples are preheated at 50° C. for 5 min, and the PENT reactions are initiated by adding 1 µl of 2.5 mM dNTP solution to each tube. After 5 min incubation at 50° C. the reactions are terminated by adding 1 µl 500 mM EDTA. DNA samples in all 4 tubes are extracted with phenol/chloroform and precipitated with ethanol in the presence of 1 µl glycogen (tubes 1 and 3), 3 µl tRNA in tube 2, and 1 µl tRNA (tube 4). After overnight precipitation, the DNA samples in tubes 1–4 are washed 3 times with 75% ethanol, dried and dissolved in 20 µl H$_2$O.

Figure 48:
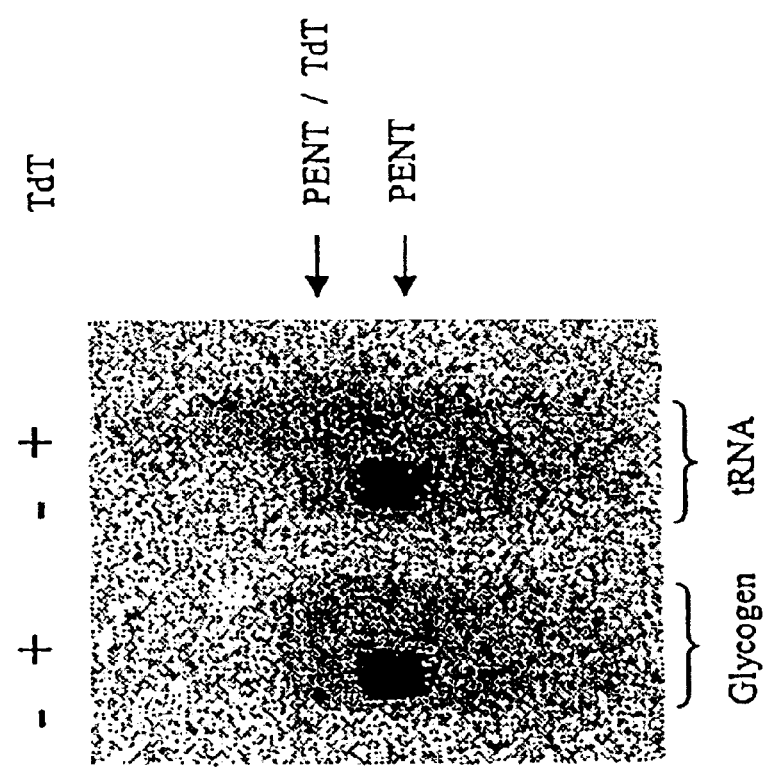
FIG. 48: TdT-mediated tailing of PENT products: effect of carrier

Four TdT tailing reactions are performed as described below. Tube A, B, C and D contain 10 µl DNA from tube 1, 2, 3, and 4, respectively, and all four tubes contain 100 mM potassium cacodylate, pH 7.2, 2 mM CoCl$_2$, 0.2 mM DTT, 1 µl 1 mM dTTP, and 15 U TdT (Gibco BRL) in 20 µl volume. All 4 reaction mixtures are incubated at 37° C. for 70 min, terminated by adding 1 µl 200 mM EDTA, ethanol precipitated, dissolved, loaded and separated on the alkaline (40 mM NaOH, 1 mM EDTA) % agarose gel. After electrophoresis, gel is neutralized, electro-blotted onto ZetaProbe membrane (BioRad; Hercules, Calif.), and analyzed with a Molecular Dynamics (Sunnyvale, Calif.) 400A PhosphorImager and ImageQuant software (Makarov et al., 1997) (FIG. 48).

TdT-tailed PENT products are detected as broadened DNA bands with increased molecular weight relative to the controls. DNA samples precipitated with tRNA show more prominent increase of the molecular weight then DNA precipitated with glycogen, indicating that glycogen inhibits TdT. In contrast, tRNA can be used to increase precipitation efficiency without inhibiting TdT activity.

Example 11
TdT-Mediated Synthesis and PCR™ Amplification of Model PENTAmers.

This example describes the preparation of model PENTAmers and their amplification using PCR™.

First, six different DNA molecules are synthesized using PENT primer (oligo 5603 I, Table 4) as a template and terminal deoxynucleotidyl transferase homopolymeric tailing activity in the presence of 3, 10 and 30 µM dTTP, and 3, 10 and 30 µM dGTP. Second, 3'-ends of these tailed-DNA molecules are ligated to down-stream adaptors B-3'(a) and B-3'(b) to form model PENTAmers. Third, the model PENTAmers are diluted, amplified by PCR™ and analyzed on agarose gel.

Figure 49:
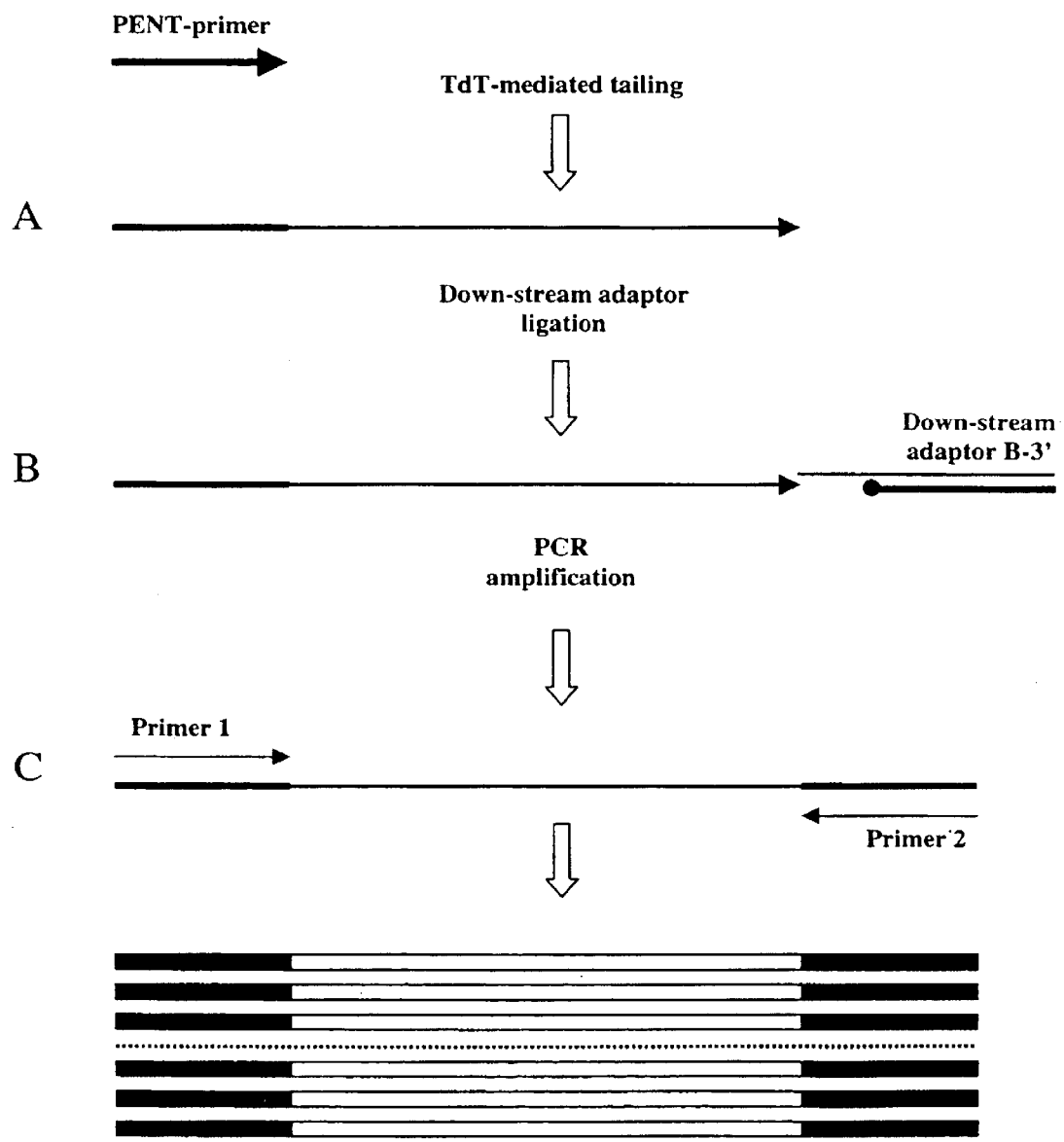
FIG. 49: Model PENTAmer construct

TdT tailing reactions (schematically shown in FIG. 49A): Six 10 µl mixtures are prepared in six 0.5 ml tubes which contain 100 nM PENT primer (oligo 5603 I), 100 mM potassium cacodylate, pH 7.2, 2 mM CoCl$_2$, 0.2 mM DTT, 7.5 U TdT (Gibco BRL) and 3, 10, 30 µM dTTP in tailing reaction tubes 1, 2, 3, respectively, and 3, 10, 30 µM dGTP in tailing reaction tubes 4, 5, 6, respectively. Mixtures are incubated at 37° C. for 30 min, then heated at 70° C. for 15 min.

Down-stream adaptor B-3' ligation reactions (schematically shown in FIG. 49B): Eight mixtures are prepared in eight 0.5 ml tubes which contain 66 mM Tris-HCl, pH 7.5, 5 mM MgCl$_2$, 1 mM DTT, 1 mM ATP, 0.5 U T4 DNA ligase (Boehringer Mannheim; Indianapolis, Ind.). Ligation reaction tubes 1, 2, and 3 are supplemented with 3 µl of the TdT reaction products from tailing reaction tubes 1, 2, 3, and 3 µl 1 µM adaptor B-3'(c). Ligation reaction tubes 4, 5, and 6 are supplemented with 3 µl of the TdT reaction products from tailing reaction tubes 4, 5, 6, and 3 µl 1 µM down-stream adaptor B-3'(a). Ligation reaction tubes 7 and 8 (controls) are supplemented with 300 fmol PENT primer (oligo 5603 I without TdT tail) and 3 µl down-stream adaptors B-3'(c) and B-3'(a), respectively. All volumes are adjusted to 20 µl with H$_2$O. Ligation reactions in tubes 1, 2, 3, and 7 are performed at room temperature for 1 h; ligation reactions in tubes 4, 5, 6, and 8 are performed at 37° C. for 1 h. Reactions are terminated by adding 0.5 µl 500 mM EDTA and 280 µl H$_2$O. Aliquots of the samples are also diluted 10× and 100× with TE and placed into separate sets of tubes.

Figure 50:
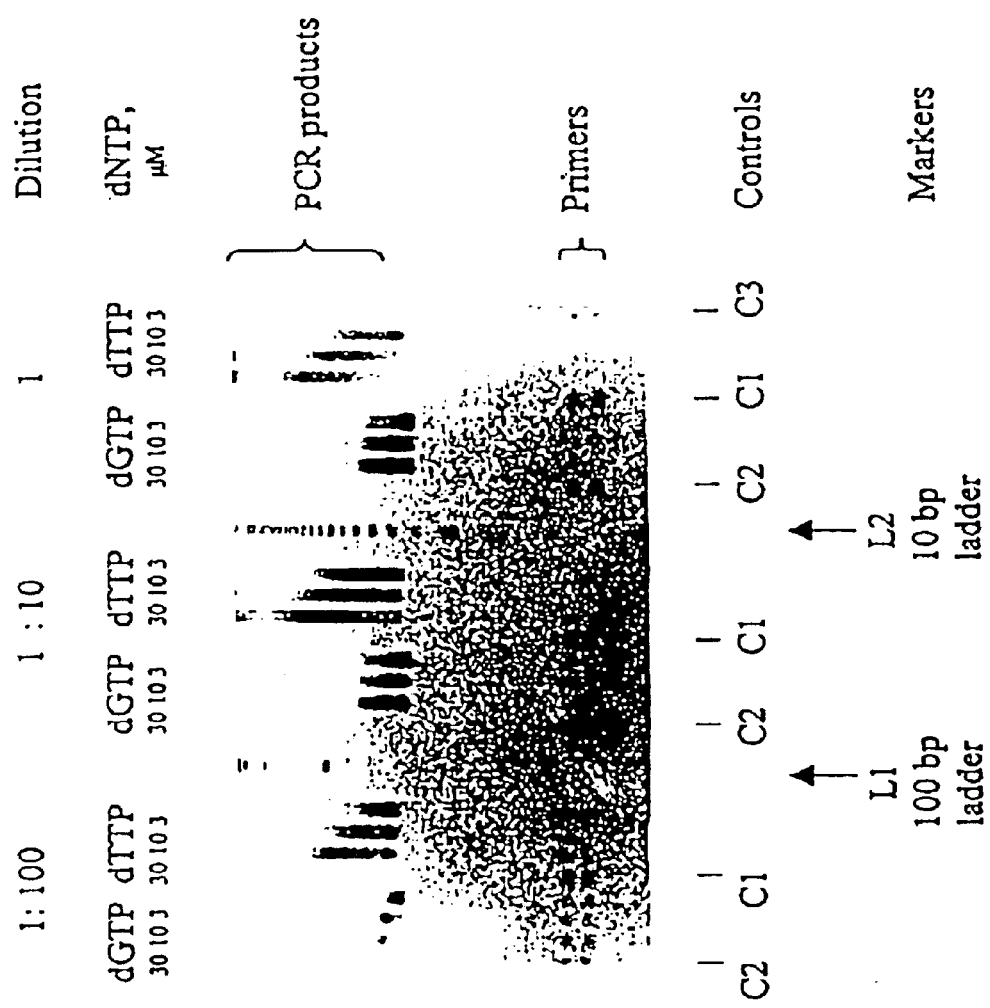
FIG. 50: TdT-mediated synthesis and PCR amplification of model PENTAmer molecules

PCR amplification (schematically shown in FIG. 49C): 25 mixtures are prepared in 25 thin-wall 0.5 ml PCR™ tubes which contain 10 mM Tris-HCl, pH 8.3, 50 mM KCl, 2 mM MgCl$_2$, 100 µM dNTP, 200 nM PENTAmer PCR™ primer 1 (oligo 5602 I), 200 nM PENTAmer PCR™ primer 2 (oligo 5776 I), 2 ml Taq polymerase (30 times diluted with 1×Taq buffer from stock at 60 U/µl). Tubes 1–8 are supplemented with 1 µl DNA from non-diluted ligation reaction tubes 1–8. Tubes 9–16 are supplemented with 1 µl DNA from 10× diluted ligation reaction tubes 1–8. Tubes 17–24 are supplemented with 1 µl DNA from 100× diluted ligation reaction tubes 1–8. No DNA is added to tube 25 (primer-dimer control). Volumes of all tubes are adjusted to 50 µl with H$_2$O. 21 cycles of PCR™ amplification were performed in a DNA Thermal Cycler 480 (Perkin-Elmer) using the following PCR™ cycling conditions: 94° C. for 30 sec, 58° C. for 30 sec, 72° C. for 30 sec. PCR™ products are analyzed on 10% polyacrylamide/1×TBE gel (FIG. 50).

PCR™ amplified PENTAmers (created by tailing with poly T and ligation of the adaptor) are detected as broadened DNA bands with increased molecular weight relative to 48 b size of the putative primer-dimer formed by PENTAmer primers 1 and 2 (oligonucleotides 5603 I and 5776 I). No amplification is detected for control DNA samples C1 and C2 where TdT tailing reaction is omitted (tubes 8 and 7, respectively, and for control C3 in the absence of any DNA (primer-dimer control). TdT-mediated tailing with dGTP results in a limited addition of only 15–20 guanine bases while the reaction with dTTP produces more than 100 b homopolymeric tails. Both nucleotides are efficiently incorporated by terminal deoxynucleotidyl transferase at 3–10 µM concentration.

Example 12
Synthesis and PCR™ Amplification of PENTAmers at the Ends of Lambda DNA/Bam HI Restriction Fragments This example describes the complete process of PENTAmer synthesis and amplification. The process includes: a) upstream nick-translation adaptor A ligation; b) adaptor A activation; c) PENT reaction; d) internal TdT tailing of PENT products; e) internal down-stream nick-attaching adaptor B-3' ligation; and f) PENTAmer amplification.

Steps (a) and (b) are performed exactly as described in Examples 3 and 5, respectively. Step (c) is performed as described in Example 10.

Step (d): Four tailing mixtures are prepared in four 0.5 ml tailing reaction tubes 1, 2, 3, 4 which contain 2 µl PENT DNA from tube 2 from Example 10, 100 mM potassium cacodylate, pH 7.2, 2 mM CoCl$_2$, 0.2 mM DTT, 7.5 U TdT (Gibco BRL), 10 and 30 µM dTTP in tubes 1 and 2, respectively, and 10 and 30 µM dGTP in tubes 3 and 4, respectively. After incubation at 37° C. for 30 min, the tailing reaction tubes are supplemented with 0.5 µl 50 mM EDTA and heated at 70° C. for 15 min.

Step (e): Four ligation mixtures are prepared in four 0.5 ml ligation reaction tubes 1, 2, 3, and 4 which contain 66 mM Tris-HCl, pH 7.5, 5 mM MgCl$_2$, 1 mM DTT, 1 mM ATP, 0.5 U T4 DNA ligase (Boehringer Mannheim; Indianapolis, Ind.), 3 µl DNA from tailing reaction tubes 1, 2, 3, 4, respectively. 3 µl of 1 mM adaptor B-3'(c) and H$_2$O are added to ligation reaction tubes 1 and 2 to final volume 20 µl and the mixtures are incubated at 20° C. for 1 h, then at 37° C. for 15 min. 3 µl of 1 mM adaptor B-3'(c) and H$_2$O are added to ligation reaction tubes 3 and 4 to final volume 20 µl and the mixtures are incubated at 37° C. for 1 h, then at 42° C. for 15 min. Reactions are terminated by adding 2.5 µl 50 mM EDTA and heating at 70° C. for 10 min and diluted 10 times with H$_2$O. The incubation temperatures were different for the two PENTAmer adaptors due to their different melting temperatures on the tailed PENT products.

Figure 51:
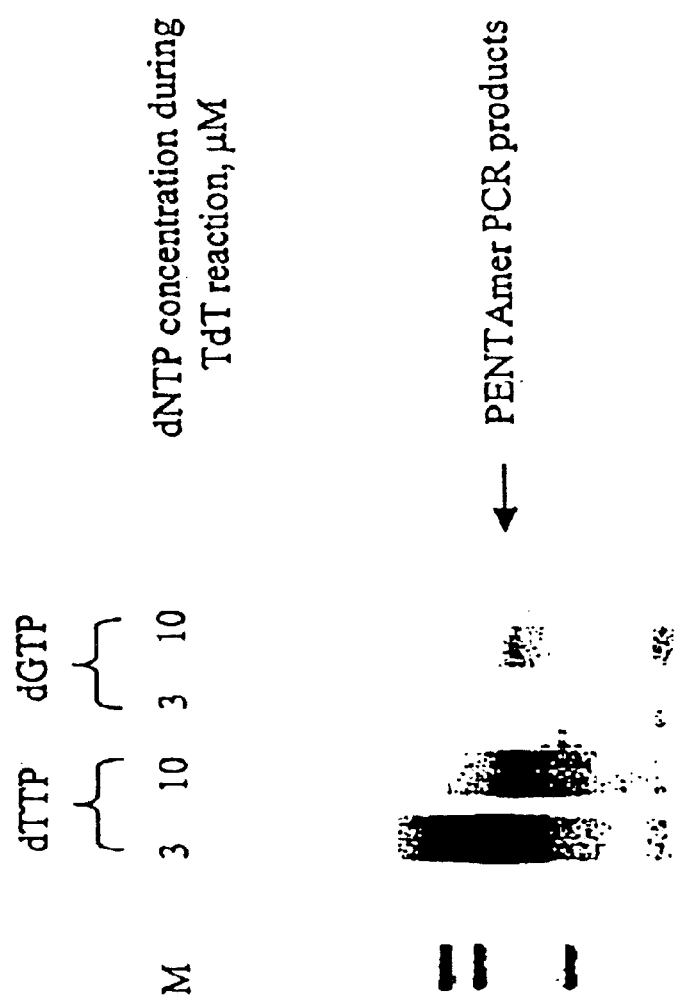
FIG. 51: PCR amplification of PENTAmers

Step (f): Four mixtures are prepared in four thin-wall 0.5 ml PCR™ tubes which contain 1 µl 10× diluted DNA from ligation reaction tubes 1, 2, 3, and 4, 2.5 µl 10×Advantage cDNA PCR™ Reaction Buffer (Clontech), 200 nM PENTAmer PCR™ primer 1 (oligo 5603 I), 200 nM PENTAmer PCR™ primer 2 (oligo 5776 I), 200 nM dNTP and 0.5 µl Advantage cDNA Polymerase Mix in 25 µl volume. 31 cycles of PCR™ were performed in a DNA Engine Thermal Cycler PTC-200 (MJ Research, Inc.) using the cycling conditions: 10 sec at 94° C., 15 sec at 58° C., 1 min at 68° C. 5 µl DNA from each PCR™ tube was mixed with 0.5 µl 10×electrophoretic loading buffer (20% Ficoll 400, 0.1 M EDTA, pH 8.0, 1% SDS, 0.025% Bromphenol Blue, 0.025% Xylene Cyanol), loaded and analyzed on the 1% agarose gel (FIG. 51).

PCR™ amplified PENTAmers are detected as bands of about 1 kb. Examples 8–12 demonstrate methods by which reaction conditions (e.g., nucleotide, enzyme, and salt concentrations, temperature, and time) can be optimized to most efficiently create and amplify PENTAmers.

Figure 52:
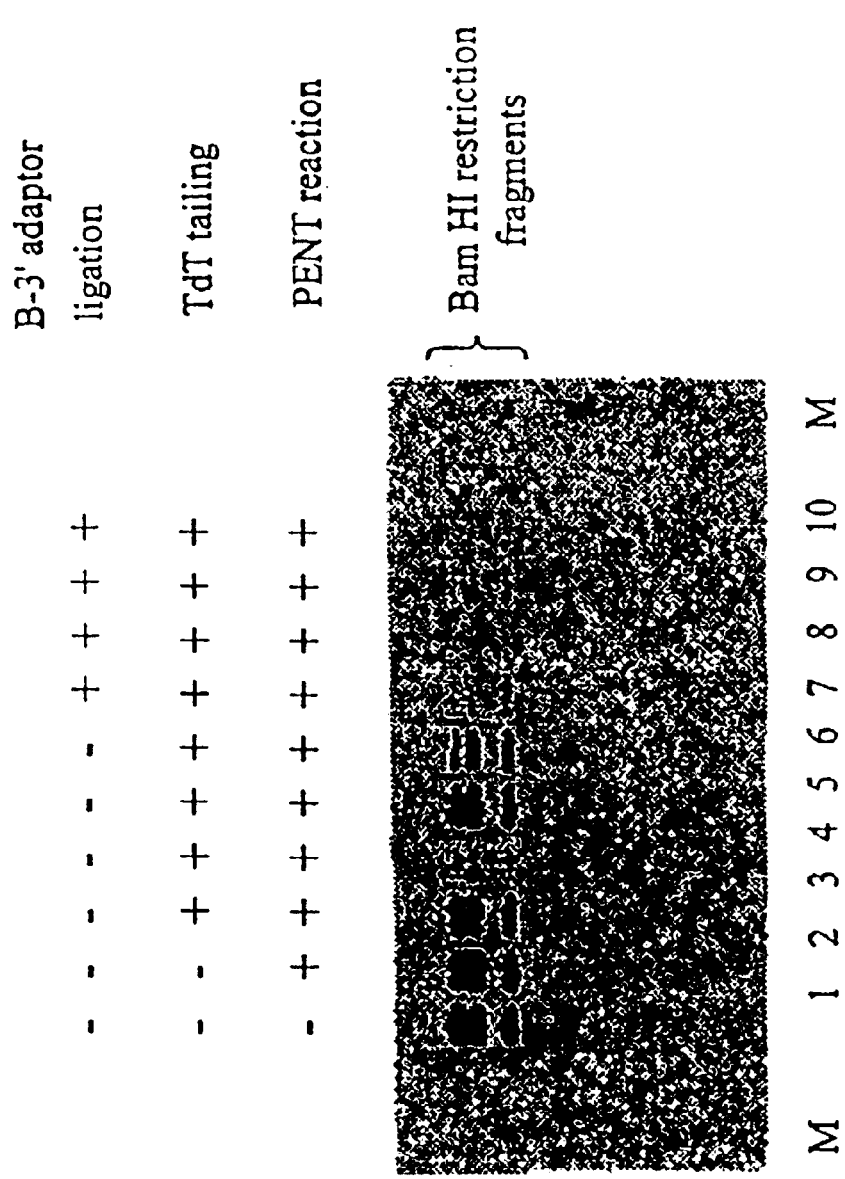
FIG. 52: PENTAmer synthesis doess not affect the mobility of ds DNA fragments

Example 13
PENTAmer Synthesis Does not Affect the Mobility of Double-Stranded DNA Fragments This example describes the electrophoretic analysis of double-stranded lambda DNA/Bam HI restriction fragments at different stages of PENTAmer synthesis: a) DNA after primer-displacement activation as described in Example 3 (FIG. 52, lane 1); b) DNA after PENT reaction as described in Example 10 (FIG. 52, lane 2); c) DNA after TdT-mediated internal tailing DNA from (b) in the presence of 3 and 30 µM dTTP (FIG. 52, lanes 3 and 4) and 3 and 30 µM dGTP (FIG. 52, lanes 5 and 6); d) DNA samples after ligation of down-stream nick-attaching adaptors B-3'(c) (FIG. 52, lanes 7 and 8) and B-3'(a) pC I (FIG. 52, lanes 9 and 10). Samples are loaded and run on 0.6% SeaKem Gold agarose/1×TAE gel, electroblotted onto ZetaProbe filter (BioRad; Hercules, Calif.) and analyzed with a Molecular Dynamics 400A PhosphorImager and ImageQuant software (Makarov et al, 1997).

Data presented on FIG. 52 show that enzymatic steps involved in the process of PENTAmer synthesis such as PENT reaction (lane 2), TdT-mediated internal tailing (lanes 3–6), and internal ligation of PENTAmer adaptors (lanes 7–10) do not affect the mobility of three resolved bands generated by cleavage of lambda DNA with Bam HI (lane 1). Bands of higher molecular weight are not shown. This example demonstrates that the nascent PENTAmers can be size-fractionated by electrophoresis, with mobilities very similar to those of double-stranded DNA restriction fragments.

Example 14
Two-Dimensional Electrophoretic Analysis of Multiple PENT Products Shows Similar Rate of Taq Polymerase-Mediated Primer-Extension/Nick-Translation Reaction at Different Ends of Lambda DNA/Bam HI Restriction Fragments This example describes the results of a single PENT reaction performed on a mixture of the 5 lambda DNA/Bam HI restriction fragments. The PENT products were analyzed on a two-dimensional neutral/alkaline gel electrophoretic system (Makarov et al., 1997).

Figure 53:
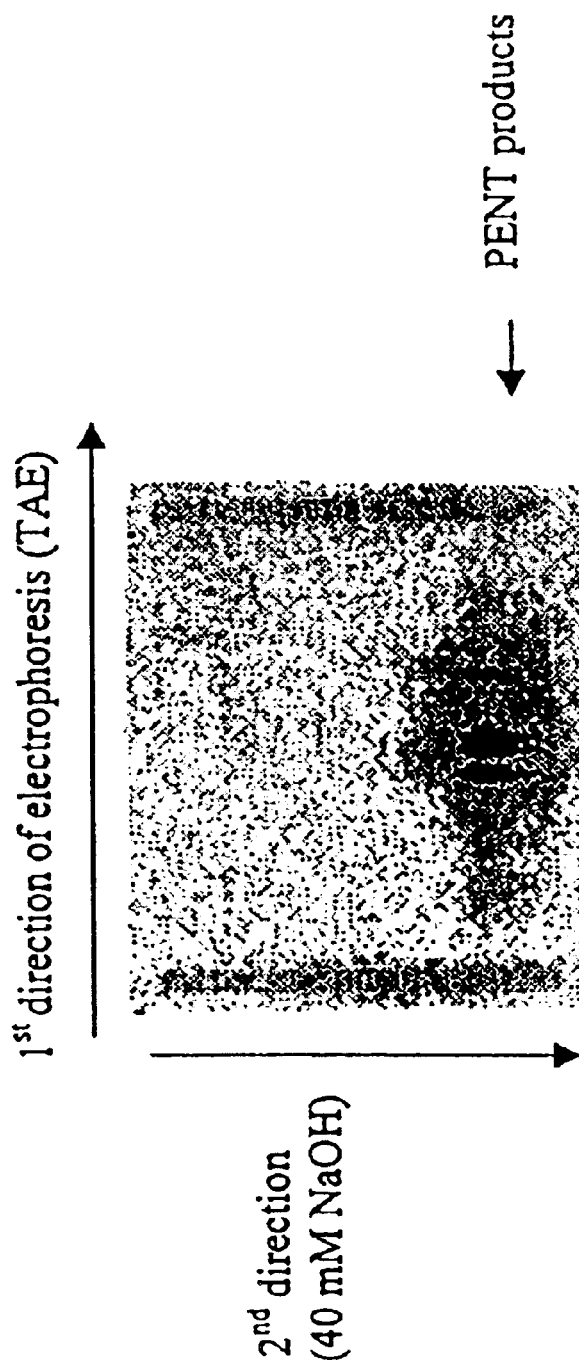
FIG. 53: 2D-electrophoretic analysis of multiple PENT products shows similar rate of Taq polymerase-mediated nick-translation reaction at different ends of lambda DNA/Bam HI restriction fragments

The PENT DNA sample is prepared as in Example 10 using lambda DNA/Bam HI restriction fragments with ligated and activated nick-translation adaptor A as described in the Example 5. First, the sample is loaded and run on 0.6% SeaKem Gold/1×TAE gel to separate restriction fragments of different size. Then the gel is soaked twice in 40 mM NaOH, 1 mM EDTA solution and run under alkaline conditions in the second direction which is orthogonal to the first one. After electrophoresis, the gel is neutralized, electro-blotted onto ZetaProbe membrane (BioRad; Hercules, Calif.) and analyzed with a Molecular Dynamics (Sunnyvale, Calif.) 400A PhosphorImager and ImageQuant software (Makarov et al., 1997) (FIG. 53).

This 2-D gel experiment shows that size distributions of radioactively labeled PENT products synthesized at the ends the lambda DNA/Bam HI restriction fragments are very similar and suggests that the rate of PENT reaction is not sensitive to the DNA base composition or size of the double stranded DNA template.

Example 15
Lambda DNA Methylation Protection/Recombination Nick-Translation Adaptor RA-(L-cos)

This example describes a complete cleavage and a complete resistance to Eco RI restriction endonuclease cleavage by the nick-translation adaptor RA-(L-cos) (FIG. 40) and methylated lambda DNA, respectively. Both reactions are important for linearization of circular recombinant intermediates in the process of preparing DNA for positional amplification (Example 21, step 7).

Methylation protection reaction: A mixture containing 1 µg lambda DNA, 50 mM NaCl, 50 mM Tris-HCl, pH 8.0, 10 mM EDTA, 80 µM S-adenosylmethionine and 10 U of Eco RI methylase (New England BioLabs) in 20 µl volume is incubated for 3 h at 37° C., following by heat inactivation at 68° C. for 20 min.

Figure 54:
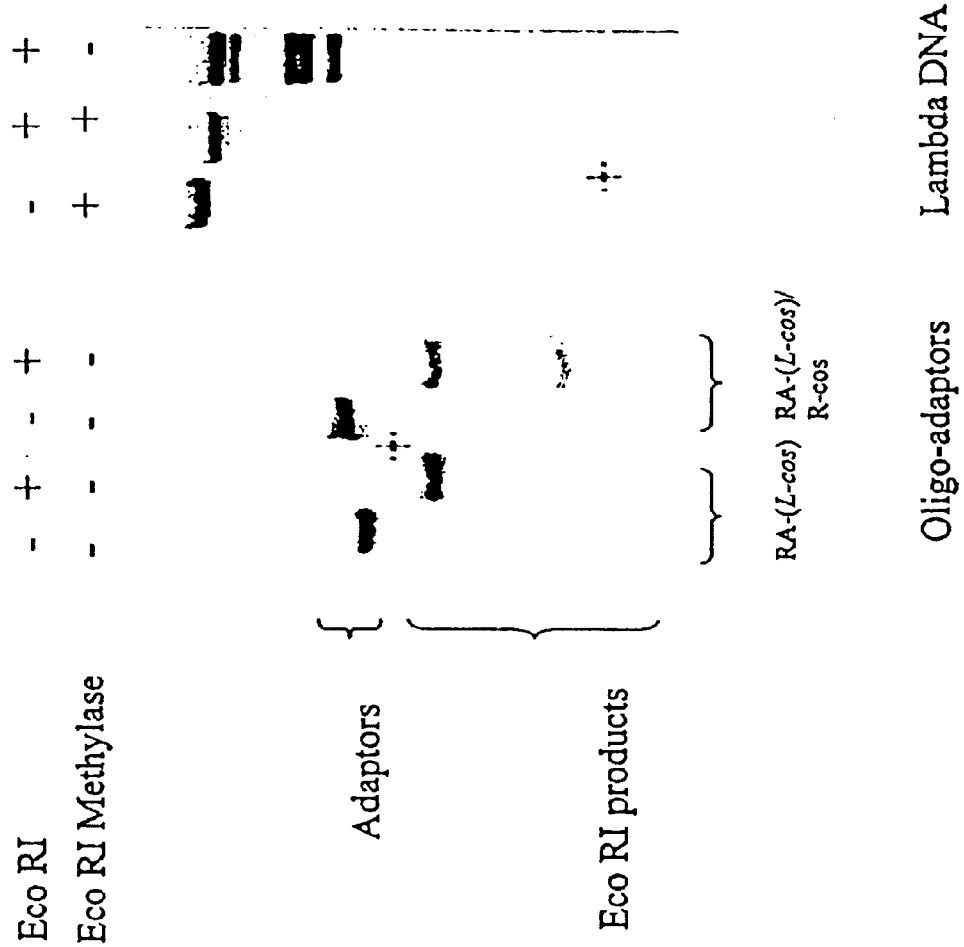
FIG. 54: λ-DNA Methylation protection/RA-(L-cos) adaptor cleavage

Eco RI cleavage: Tubes 1–4 contain 20 µl of 50 mM Tris-HCl, pH 7.5, 100 mM NaCl, 10 mM MgCl$_2$, 1 mM DTE (dithioerythrotol), 10 U Eco RI (Boehringer Mannheim). Tube 1 also contains 2.5 pmol adaptor RA-(L-cos). Tube 2 also contains 2.5 pmol adaptor RA-(L-cos) hybridized to an equimolar amount of the R-cos oligonucleotide 5687I. Tube 3 also contains 250 ng methylated lambda DNA. Tube 4 also contains 250 ng lambda DNA. Tubes 1–4 are incubated at 37° C. for 3 h and the restriction digestions terminated by addition of 2.5 µl 10×electrophoretic DNA loading buffer. Samples from tubes 1 and 2 as well as non-digested adaptors are analyzed on 15% polyacrylamide/ 1×TBE gel. (FIG. 54, left panel). Samples from tubes 3 and 4 are analyzed on 0.8% agarose/1×TAE gel (FIG. 54, right panel).

The results presented on FIG. 54 show that lambda DNA can be completely protected from Eco RI cleavage by Eco RI methylase (right panel), and that the recombination nick-translation adaptor RA-(L-cos) can be completely cleaved by Eco RI restriction endonuclease whether it is hybridized or not with the R-cos oligonucleotide 5687 I which has the same sequence as single stranded 12 base L-cos end of lambda DNA (left panel).

Example 16
Efficiency of Ligation of the Recombination Nick-Translation Adaptor RA-(L-cos) to Lambda DNA L-cos Site This example describes the efficiency of a two-step ligation process presented in detail in Example 21, step 2. To perform this, lambda DNA with and without RA-(L-cos) adaptor are digested with Bgl II restriction endonuclease, radioactively labeled, and analyzed electrophoretically. Bgl II has a restriction site located at 415 bp from the lambda L-cos end (adaptor site), so the ligation of the 45 bp adaptor should result in a new band located at 460 bp.

Specifically, two tubes containing 50 mM Tris-HCl pH 7.9, 100 mM NaCl, 10 mM $MgCl_2$, 1 mM DTT and 3 U Bgl II (New England BioLabs), and either 1 µl (100 ng) lambda DNA after ligation (Example 21, step 2) (tube 1) or 100 ng non-ligated lambda DNA (tube 2) are incubated at 37° C. for 4 h. The reactions in tubes 1 and 2 are terminated by adding 1 µl 200 mM EDTA and both DNA samples were ethanol precipitated and recovered. Tube 3 contains DNA marker (1 µg 1 kb DNA ladder, Gibco BRL). The three tubes are labeled with [$\alpha$-$^{32}$P]dATP by adding 50 mM Tris-HCl, pH 7.5, 10 mM $MgCl_2$, 1 mM DTT, 50 µg/ml BSA, 12.5 µM dTTP, 12.5 µM dCTP, 12.5 µM dGTP, 40 nM [$\alpha$-$^{32}$P] dATP and 5 U Klenow fragment (exo$^-$) (Ambion) and incubating in final 50 µl volumes at 20° C. for 1 h. The DNA samples in the three tubes are precipitated and washed with 70% ethanol, dried, and dissolved in 1×electrophoretic DNA loading buffer. The DNA samples are separated on 5% polyacrylamide/1×TBE gel, dried, and analyzed with a Molecular Dynamics (Sunnyvale, Calif.) 400A PhosphorImager and ImageQuant software (Makarov et al., 1997) (FIG. 55).

Figure 55:
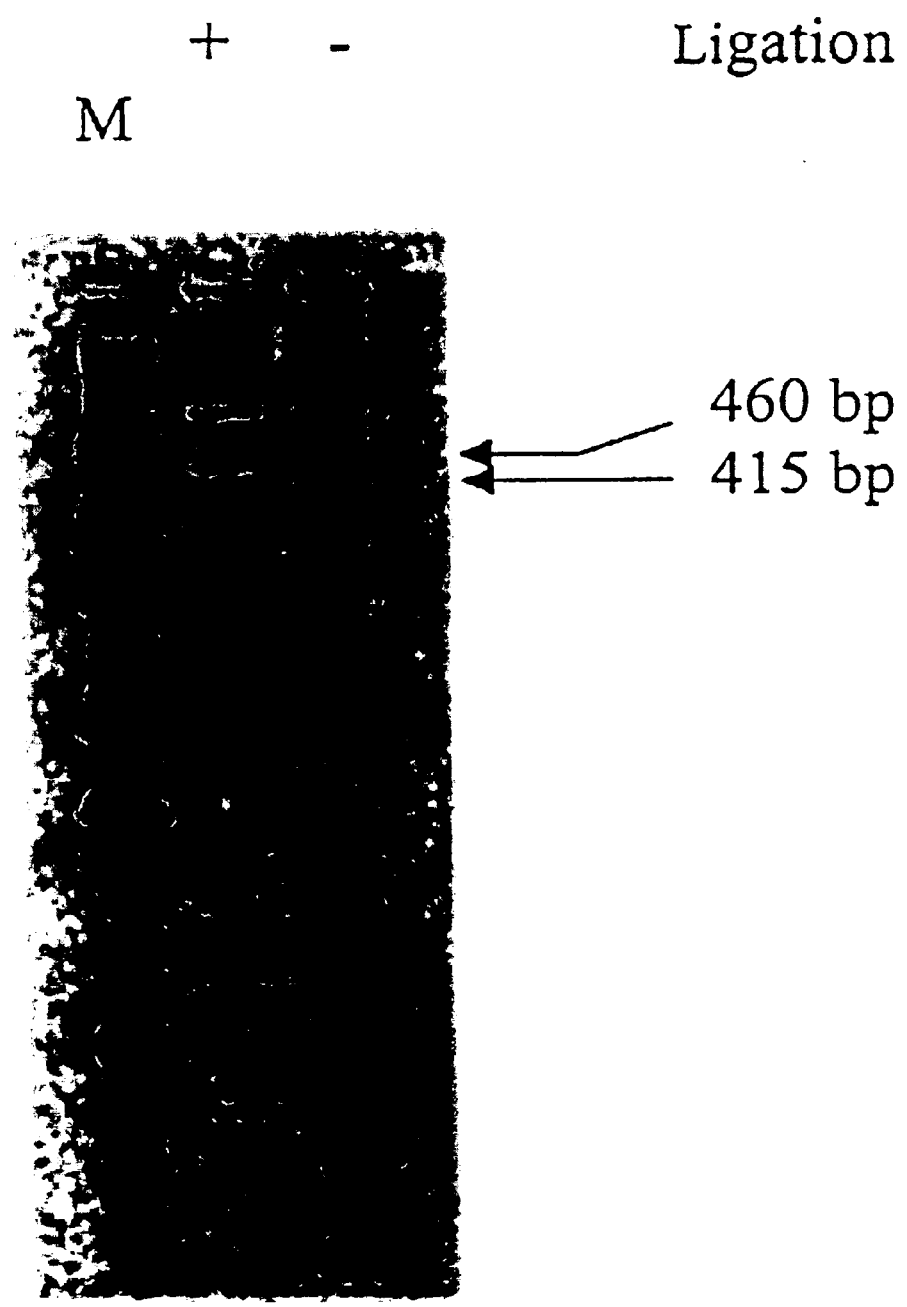
FIG. 55: RA-(L-cos) adaptor ligation to lambda DNA L-cos site

The data presented on FIG. 55 show that after ligation with RA-(L-cos) adaptor the 415 bp band corresponding to the terminal restriction fragment with L-cos end is shifted to the 460 bp position as expected if the ligation efficiency is close to 100%. No shift is observed for internal restriction fragments produced by cleavage of lambda DNA with Bgl II

Example 17
Sau 3A I Partial Digestion of Lambda and Human DNA

This example describes a serial dilution method to accurately and reproducibly control the partial digestion of genomic DNA with a restriction enzyme.

Two mixtures containing 5.5 µg lambda and human leukocyte DNA, respectively, 33 mM Tris-Acetate, pH 7.9, 66 mM K Acetate, 10 mM Mg Acetate and 0.5 mM DTT in a total volume of 110 µl are prepared at 4° C. and divided into two sets of 5×1.5 ml Eppendorf tubes such that tube 1 contains 30 µl, tubes 2 to 4 contain 20 µl, and tube 5 contains 10 µl of the lambda or human DNA mixture. Tubes are kept on ice. 2 µl of 20 times diluted Sau 3A I (Boehringer Mannheim; stock concentration 4U/µl) are then added to tube 1 and mixed. 10 µl from tube 1 is transferred into tube 2 and mixed. The serial dilution process is continued by successively pipetting 10 µl from tube 2 to 3, 3 to 4, and 4 to 5. When finished, all five tubes contain 20 µl. All five tubes are incubated for 15 min at 37° C. and the reactions are stopped by adding 1.1 µl 200 mM EDTA followed by thermal inactivation at 68° C. for 20 mm.

Figure 56:
FIG. 56: San 3A I partial digestion of lambda and human DNA

To end-label the restriction fragments produced by partial digestion of lambda and human DNA with Sau 3A I, 5 µl of each restricted DNA sample is incubated in 10 µl volume with 2.5 U of Klenow (exo$^{31}$) enzyme in the presence of 50 mM Tris-HCl, pH 7.5, 10 mM $MgCl_2$, 1 mM DTT, 50 µg/ml BSA, 25 µM dTTP, 25 µM dCTP, 25 µM dGTP, and 80 nM [$\alpha$-$^{32}$p] dATP at 20° C. for 1 h. Labeled DNA samples are precipitated with ethanol, washed, dried, dissolved in 1×electrophoretic DNA loading buffer, separated on 0.4% SeaKem Gold agarose gel (FMC Bioproducts) together with an end-labeled 1 kb DNA ladder (see Example 16) and analyzed with a Molecular Dynamics (Sunnyvale, Calif.) 400A PhosphorImager and ImageQuant software (FIG. 56). Because DNA molecules are end-labeled, the images on FIG. 56 represent molar size distributions of the restriction fragments generated by partial digestion with Sau 3A I restriction endonuclease.

Comparison of the molecular weight distributions of the fragments after different extents of restriction digestion is required to optimize the fragment lengths for short-range or long-range positional amplification. By adjusting the extent of digestion the molecular weight distribution of the fragments can be controlled. Data presented on FIG. 56 shows that, once optimized with lambda DNA, the serial dilution protocol can be efficiently and reproducibly used to produce the desired extent of partial restriction digestion of DNA from other species.

Example 18
Frequency of Sau 3A I Sites in the Human Genome

This example shows a molar size distribution of DNA restriction fragments generated after complete digestion of human leukocyte DNA with Sau 3A I restriction endonuclease. This test is used to determine the probability of PENTAmer synthesis within a region of DNA of a specified length.

Figure 57:
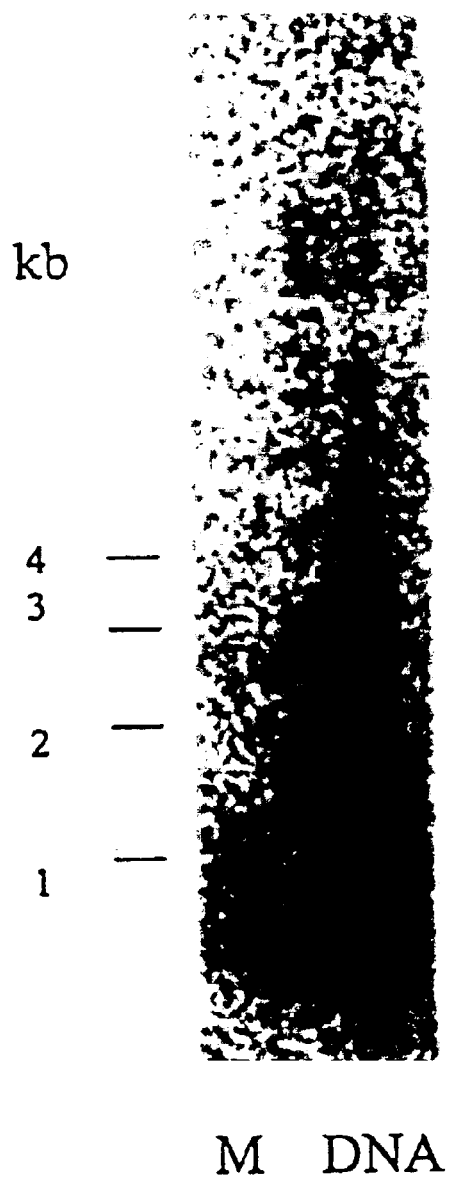
FIG. 57: Frequency of San 3A I sites in human genome

1 µg human leukocyte DNA is digested in 23 µl volume with 5 U Sau 3A I in the presence of 33 mM Tris-Acetate, pH 7.9, 66 mM K Acetate, 10 mM Mg Acetate and 0.5 mM DTT at 37° C. for 5 h. The reaction is terminated by adding 1.5 µl 200 mM EDTA and heating at 68° C. for 20 min. To end-label DNA restriction fragments 5 µl of Sau 3A I-digested DNA is incubated in 10 µl volume with 2.5 U of Klenow (exo$^-$) enzyme in the presence of 50 mM Tris-HCl, pH 7.5, 10 mM $MgCl_2$, 1 mM DTT, 50 µg/ml BSA, 25 µM dTTP, 25 µM dCTP, 25 µM dGTP, and 80 nM [$\alpha$-$^{32}$P] dATP at 20° C. for 1 h. Labeled DNA is precipitated with ethanol, washed, dried and dissolved in 1×electrophoretic DNA loading buffer. End-labeled human DNA, digested completely by Sau 3A I, and 1 kb DNA ladder are separated on 0.8% SeaKem Gold agarose gel (FMC Bioproducts) and analyzed with a Molecular Dynamics (Sunnyvale, Calif.) 400A PhosphorImager and ImageQuant software (FIG. 57). Because DNA molecules are end-labeled, the pattern on FIG. 57 represents molar size distribution of the restriction fragments generated by complete digestion with Sau 3A I restriction endonuclease.

Quantitation of the molecular weight distribution using ImageQuant software reveals the probabilities of having no Sau 3A I restriction site within 3 kb, 2 kb and 1 kb intervals as less than 1%, 3% and 18%, respectively. These probabilities are considerably larger than predicted for random-sequence DNA, showing the necessity to test each restriction enzyme before using it to prepare PENTAmers from a specific genome.

Example 19
Efficiency of Circularization Reaction with Recombination Nick-Translation Adaptor RA-(L-cos)

This example describes the efficiency of ligation-mediated circularization of lambda DNA molecules with recombination nick-translation adaptor RA-(L-cos) at one end and a Bam HI generated opposite end (Sau 3A I compatible end).

Figure 58:
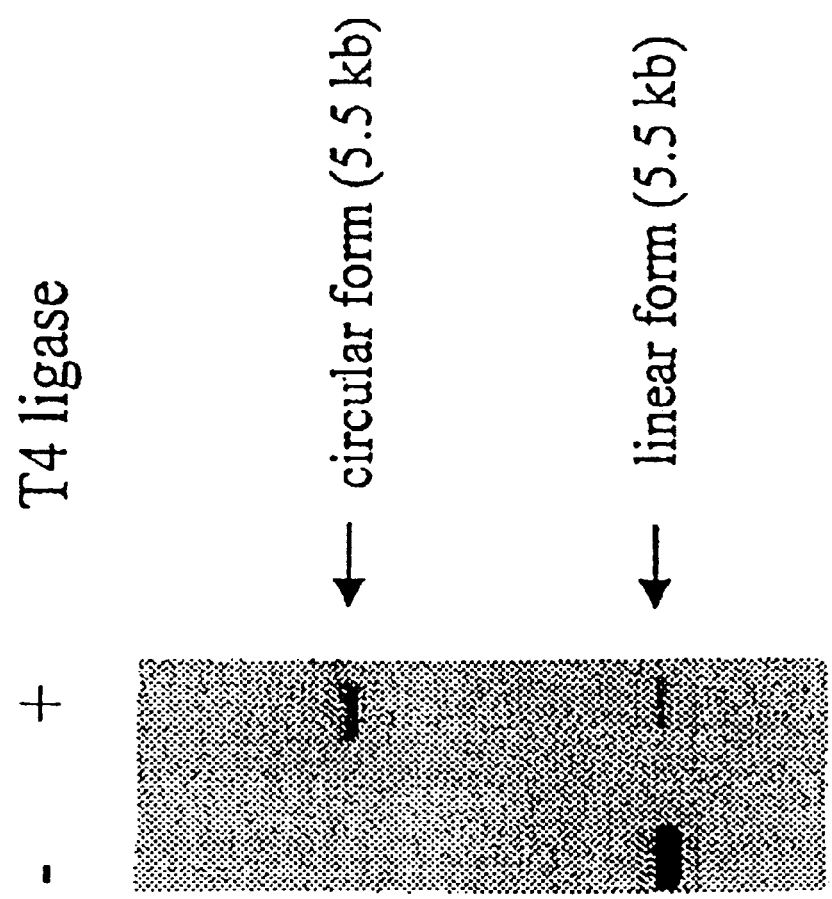
FIG. 58: Efficiency of the recombination-circularization reaction

3 μl of lambda DNA ligated to the adaptor RA-(L-cos) (after step 2.2, Example 21) is incubated with 5 U Bam HI in the presence of 10 mM Tris-HCl, pH 8.0, 100 mM NaCl, 5 mM MgCl$_2$, 1 mM 2-mercaptoethanol in 20 μl volume at 37° C. for 1 h. The reaction is terminated with 1 μl 0.5 M EDTA. DNA is extracted with phenol/chloroform, precipitated with ethanol, washed, dried and dissolved in 30 μl TE-0.1 to a concentration of 10 ng/μl. 50 ng of this Bam HI restricted DNA is incubated with 10 U T4 DNA ligase (Boehringer Mannheim, Indianapolis, Ind.) in 200 μl volume in the presence of 66 mM Tris-HCl, pH 7.5, 5 mM MgCl$_2$, 1 mM DTT and 1 mM ATP at 15° C. for 18 h. In a control experiment, 50 ng Bam HI restricted DNA is incubated at the same conditions (buffer, temperature, time) without ligase. After incubation both samples are precipitated with ethanol, washed with 70% ethanol, dissolved in 1×electrophoretic DNA loading buffer and separated on 1% agarose/0.5 TBE gel at a high voltage (7 V/cm). After electrophoresis, the gel is electroblotted onto a ZetaProbe membrane (BioRad; Hercules, Calif.) and hybridized overnight with $^{32}$P-labeled PENT-primer (prepared as described in Example 5). The washed and dried membrane is analyzed with a Molecular Dynamics (Sunnyvale, Calif.) 400A PhosphorImager and ImageQuant software (FIG. 58).

Quantitation of intensities of circular (IC) and linear (IL) DNA forms using ImageQuant software allows estimation of the efficiency of the circularization reaction E=IC/(IC+IL)= 77%. This type of test is preferred to determine the success of the circularization reaction.

Example 20
Rate of PENT Reaction is Independent of the DNA Sequence and the Number of Different DNA Molecules Participating in the Reaction: 2D Electrophoretic Approach This example determines the size distribution of PENT reaction products from a complex mixture of nested lambda DNA fragments created by partial digestion with Sau 3A I.

Methylated lambda DNA is ligated to adaptor RA-(L-cos), partially digested with Sau 3A I, incubated with Taq DNA polymerase, TdT (in the presence of 10 μM dGTP) and Eco RI as described in detail (Example 21, steps 1–7) and analyzed on the two-dimensional neutral/alkaline gel electrophoretic system (Makarov et al., 1997). Specifically, 100 ng of the processed lambda DNA is separated on 0.4% SeaKem Gold/1×TAE agarose gel (FMC Bioproducts) at 0.4 V/cm for 30 h. The gel lane with separated DNA molecules is excised and embedded in a 1% agarose gel. After soaking twice in 40 mM NaOH, 1 mM EDTA, the DNA samples are separated in the orthogonal direction in the same alkaline buffer at 1.5 V/cm for 15 h. The gel is neutralized with 1×TBE and electroblotted onto ZetaProbe membrane (BioRad; Hercules, Calif.). The membrane is hybridized overnight with $^{32}$P-labeled oligonucleotide 5608 I, complementary to the PENT-primer. Washed and dried membranes are analyzed with a Molecular Dynamics (Sunnyvale, Calif.) 400A PhosphorImager and ImageQuant software (FIG. 59).

Figure 59:
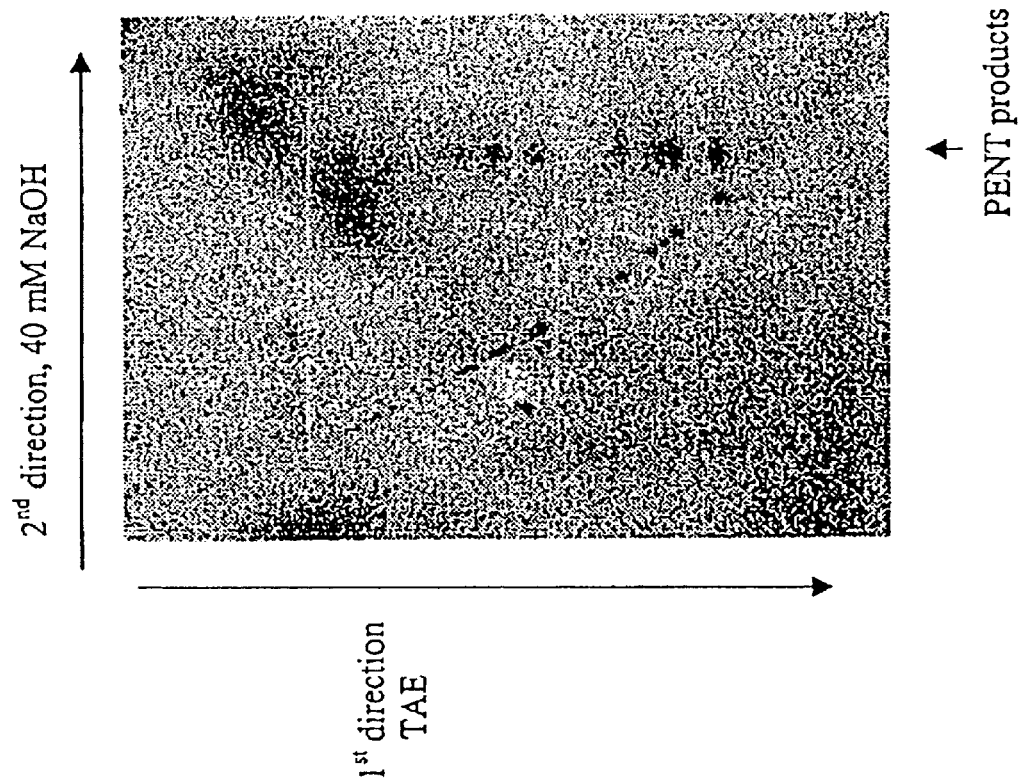
FIG. 59: Rate of PENT reaction initiated at different Sau 3A I/lambda DNA sites is sequence independent: 2D method

As can be seen from FIG. 59, PENT products (vertical spots, shown by arrow) originating from different internal lambda DNA sites produced by partial digestion with Sau 3A I endonuclease (diagonal spots) have similar mobility on the NaOH agarose gel (second direction). As in Example 14, it is concluded that the rate of PENT reaction does not depend on the DNA sequence.

Figure 60:
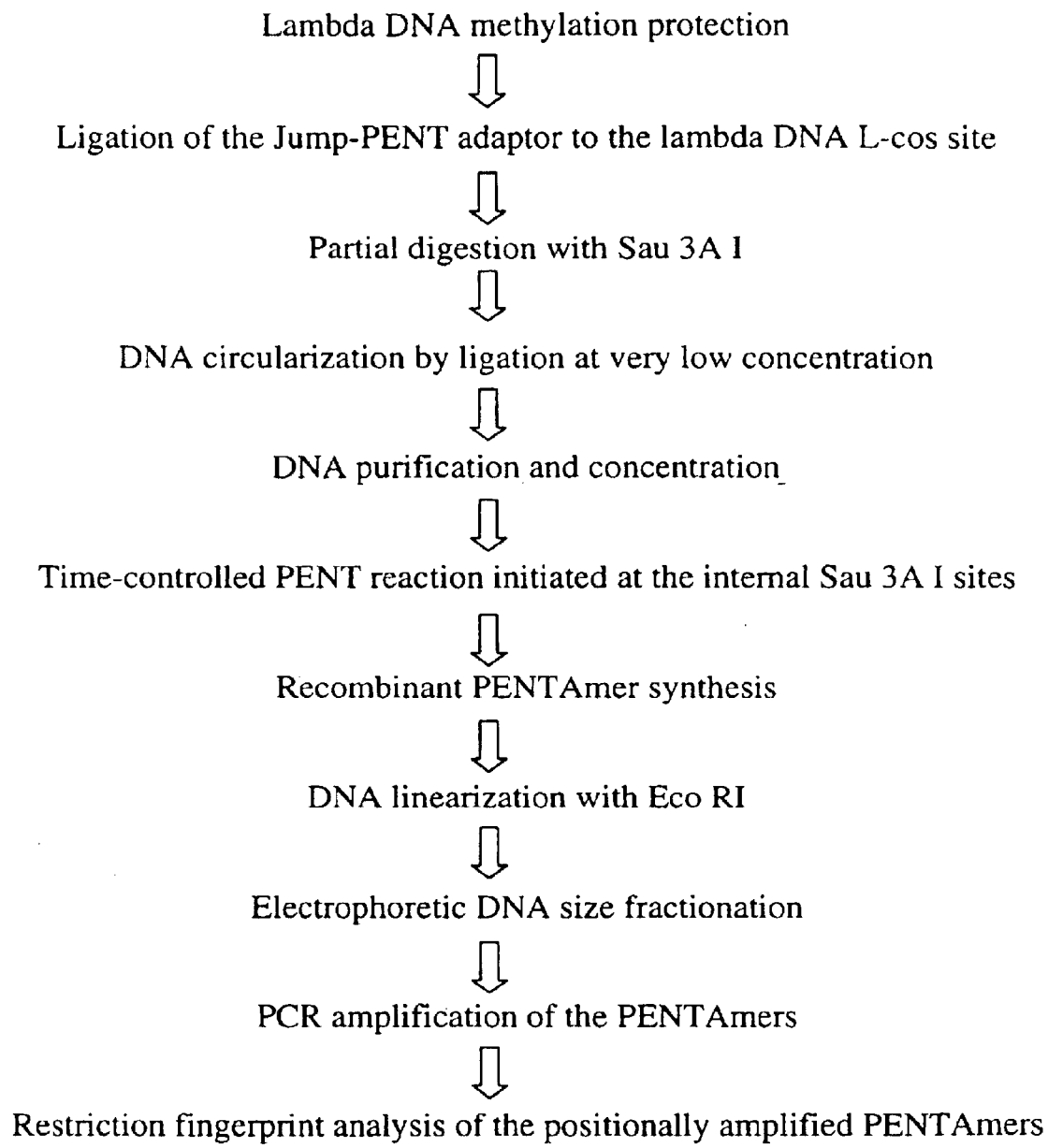
FIG. 60: Preparation of the ordered recombinant PENTAmer library from lambda DNA

Example 21
Detailed Protocol for the PENTAmer-Mediated Positional Amplification of Lambda DNA FIG. 60 shows all steps involved in the preparation, amplification and analysis of the lambda recombinant PENTAmer library.

Step 1—Lambda DNA Protection by Methylation with Eco RI-Methylase

The mixture containing 12 μg lambda DNA, 50 mM NaCl, 50 mM Tris-HCl, pH 8.0, 10 mM EDTA, 80 μM S-adenosylmethionine and 120 U of Eco RI methylase (New England BioLabs) in 150 μl volume is incubated for 6.5 h at 37° C., following by heat inactivation at 68° C. for 20 min. The methylated DNA is concentrated and then washed 3× with 0.5 ml TE-0.1 in a Microcon 100 centrifugal filter device (Amicon) by spinning at 300 g for 20 min at room temperature and recovered in 47 μl volume.

Step 2—Ligation of the Recombination Nick-Translation Adaptor RA-(L-cos) to the Lambda DNA L-cos Site The adaptor ligation is achieved in two consecutive sub steps.

2.1 Blocking Lambda DNA at the R-cos Site by Ligation of the 12-Base Blocking Oligonucleotide Complementary to the R-cos Site.

The mixture containing 23.5 μl of the washed, methylated DNA from Step 1, 20 pmol of the phosphorylated oligo 5687 I (Table 4), 20 mM Tris-HCl, pH 8.3, 25 mM KCl, 10 mM MgCl$_2$, 0.5 mM NAD, 0.1% Triton X-100 and 10 U of thermostable DNA ligase Ampligase (Epicentre Technologies) in 50 μl volume is incubated at 45° C. for 100 min after preheating at 65° C. for 5 min in the absence of Ampligase, followed by reducing temperature to 45° C. and adding ligase and inactivating by adding 2 μl 0.5 M EDTA. The ligation reaction is followed by washing the DNA 4× with 0.4 ml TE-0.1 in a Microcon 100 centrifugal filter device as described in Step 1. The DNA is recovered in 46 μl volume.

2.2 Ligation of the Recombination Nick-Translation Adaptor RA-(L-cos) to the 12-Base 5'-Overhang at the Lambda DNA L-cos Site (FIG. 61A).

The mixture containing 46 μl (200 fmol) of lambda DNA from the Step 2.1, 400 fmol of the adaptor RA-(L-cos) (FIG. 40), 20 mM Tris-HCl, pH 8.3, 25 mM KCl, 10 mM MgCl$_2$, 0.5 mM NAD, 0.1% Triton X-100 and 11 U of thermostable DNA ligase Ampligase (Epicentre Technologies) in 58 μl volume is incubated at 50° C. for 20 min, followed by incubation at 45° C. for 40 min and inactivation by adding 2 μl 0.5 M EDTA. The ligated DNA is washed twice in a Microcon 100, as described above, and recovered in a 64 μl volume.

Such ligation results in the formation of a) a covalent bond between the recessed non-protected 3'-OH group of the adaptor RA-(L-cos) and 5'-phosphate group of the L-cos 5'-overhang of lambda DNA; and b) a nick in the opposite strand (FIG. 61A).

Step 3—Partial Digestion of Lambda DNA with Sau 3A I Restriction Enzyme.

Partial digestion is performed by serial dilution method as described in Example 17. Specifically, the mixture containing 55 μl DNA from the previous step, 33 mM Tris-Acetate, pH 7.9, 66 mM K Acetate, 10 mM Mg Acetate, and 0.5 mM DTT in a total volume of 110 μl is prepared at 4° C. and divided into 5×1.5 ml Eppendorf tubes such that tube 1 contains 30 μl, tubes 2 to 4 contain 20 μl, and tube 5 contains 10 μl. Tubes are kept on ice. 2 μl of 20 times diluted Sau 3A I (Boehringer Mannheim (Indianapolis, Ind.); stock concentration 4 U/μl) are then added to tube 1 and mixed. 10 μl from tube 1 is transferred into tube 2 and mixed. The serial dilution process is continued by successively pipetting 10 μl from tube 2 to 3, 3 to 4, and 4 to 5. When finished, all five tubes contain 20 μl. All five tubes are incubated for 15 min at 37° C., and the reactions are stopped by adding 1.1 μl 200 MM EDTA followed by thermal inactivation at 68° C. for 20 min.

1 μl DNA from each tube are analyzed on 0.8% SeaKem Gold/1×TAE agarose gel (FMC BioProducts) to determine which sample has been optimally digested and will be used for further processing. On the basis of this electrophoretic analysis, tubes 4 and 5 with average size about 20 kb are chosen for processing in the next step.

Step 4—DNA Circularization by Ligation at Low Molar Concentration (FIG. 61B).

DNA circularization is performed at low concentration to favor intramolecular circularization and reduce undesirable intermolecular ligation.

The mixture containing 6 μl DNA from tube 4 and 6 μl DNA from tube 5 (above), 66 mM Tris-HCl, pH 7.5, 5 mM $MgCl_2$, 1 mM DTT, 1 mM ATP and 50 U T4 DNA ligase (Boehringer Mannheim) in the volume 1 ml is incubated at 15° C. for 18 h, followed by phenol/chloroform extraction and ethanol precipitation. Recovered DNA is washed with 70% ethanol and dissolved in 20 μl TE-0.1.

Step 4 results in a formation of junctions between the termini of the recombination nick-translation adaptors RA-(L-cos) and the internal Sau 3AI restriction sites (FIG. 61B). As a result, a nick at the adaptor/L-cos end junction (Step 2.2) becomes located near the restriction sites (nick-jumping) and can be used to initiate PENTAmer synthesis along the lambda sequences adjacent Sau 3A I restriction sites. During this process, the blocked nick at the 3'-end of the adaptor RA-(L-cos) is removed as the PENTAmer is synthesized (FIG. 61C).

Step 5—Time-Controlled PENT Reaction Initiated at the Internal Sau 3A I Sites.

The mixture containing 20 μl of circularized DNA from Step 4, 10 mM Tris-HCl, pH 8.3, 50 mM KCl, 2 mM $MgCl_2$ and 2 μl Taq DNA polymerase (30 times diluted with 1×Taq buffer from stock at 60 U/μl) in 49 μl volume is preheated at 50° C., for 5 min and then supplemented with 1 μl 2.5 mM dNTP to initiate the PENT reaction. After 5 min of incubation at 50° C. the reaction is terminated by adding 1 μl 0.5 M EDTA followed by phenol/chloroform extraction, ethanol precipitation in the presence of 20 μg of carrier yeast tRNA, washing with 70% ethanol and resuspension in TE-0.1. Additional 3 washes in Microcon 100 filter device are performed (as described in Step 1, except that the last wash was with $H_2O$) to completely eliminate the traces of nucleotides that might interfere with the next reaction. The DNA is recovered in 36 μl of $H_2O$.

Step 6—Terminal Deoxynucleotidyl Transferase (TdT)-Mediated PolyG Tailing at the Internal 3'-Ends (Nicks) of the PENT Products.

The mixture containing 36 μl of DNA from Step 5, 100 mM potassium cacodylate, pH 7.2, 2 mM $CoCl_2$, 0.2 mM DTT, 20 μM dGTP and 30 U TdT (Gibco BRL) in 50 μl volume is incubated at 37° C. for 50 min and terminated by adding 1.5 μl of 200 mM EDTA and subsequent heating at 65° C. for 20 min. After two washes in Microcon 100 filter device with TE-0.1, the DNA is recovered in 39 μl volume.

Step 7—Linearization of the Circular Recombinant DNA Molecules by Cleavage of the Recombination Nick-Translation Adaptor RA-(L-cos) Using Eco RI Restriction Endonuclease.

The mixture containing 39 μl DNA from Step 6, 50 mM Tris-HCl, pH 7.5, 100 mM NaCl, 10 mM $MgCl_2$, 1 mM DTE and 15 U Eco RI (Boehringer Mannheim; Indianapolis, Ind.) in 45 μl volume is incubated at 37° C. for 12 h, terminated with 1 μl 0.5 M EDTA and heated at 68° C. for 15 min. After 2 washes in Microcon 100 filter device with TE-0.1, the DNA is recovered in a 30 μl volume.

Step 8—Completion of Synthesis of the Recombinant PENTAmers by Ligation-Mediated Tagging at the PolyG Tails of the TdT-Treated PENT Products.

10 μl DNA from Step 7, 66 mM Tris-HCl, pH 7.5, 5 mM $MgCl_2$, 1 mM DTT, 1 mM ATP, 1 U T4 DNA ligase (Boehringer Mannheim) and nick-attaching adaptor B-3'(a) (FIG. 40) in 20 μl volume is incubated at 37° C. for 55 min, then at 40° C. for 10 min and finally at 44° C. for 15 min to assure an efficient hybridization and ligation of the adaptor to the single-stranded polyG tails. The ligation is terminated by adding 2.2 μl of 10×loading electrophoretic buffer (20% Ficoll 400, 0.1 M EDTA, pH 8.0, 1% SDS, 0.025% Bromphenol Blue, 0.025% Xylene Cyanol).

The procedure (above) was repeated using nick-attaching adaptor B-3'(b).

Step 8'—Synthesis of the Recombinant PENTAmers by Primer Extension-Mediated Tagging at the polyG Tails of the TdT-Treated PENT products.

Poly G tails at the ends of PENT products can be also extended with DNA polymerase when hybridized to single stranded oligo template with poly C terminated 3' ends.

A mixture containing 10 μl DNA from Step 7, 10 mM Tris-HCl, pH 8.3, 50 mM KCl, 83 μM dNTP, 170 nM of primer oligonucleotide 5604 I, 1 μl Taq DNA polymerase (30 times diluted with 1×Taq buffer from stock at 60 U/μl) in 30 μl volume is incubated at 50° C. for 3 min, then at 45° C. for 3 min, and finally at 40° C. for 3 min. The ligation is terminated by adding 3.3 μl of the 10×loading electrophoretic buffer (20% Ficoll 400, 0.1 M EDTA, pH 8.0, 1% SDS, 0.025% Bromphenol Blue, 0.025% Xylene Cyanol).

Step 8 (8') results in a formation of PENTAmer (FIG. 61C).

Step 9—Electrophoretic DNA Size Fractionation

Figure 62:
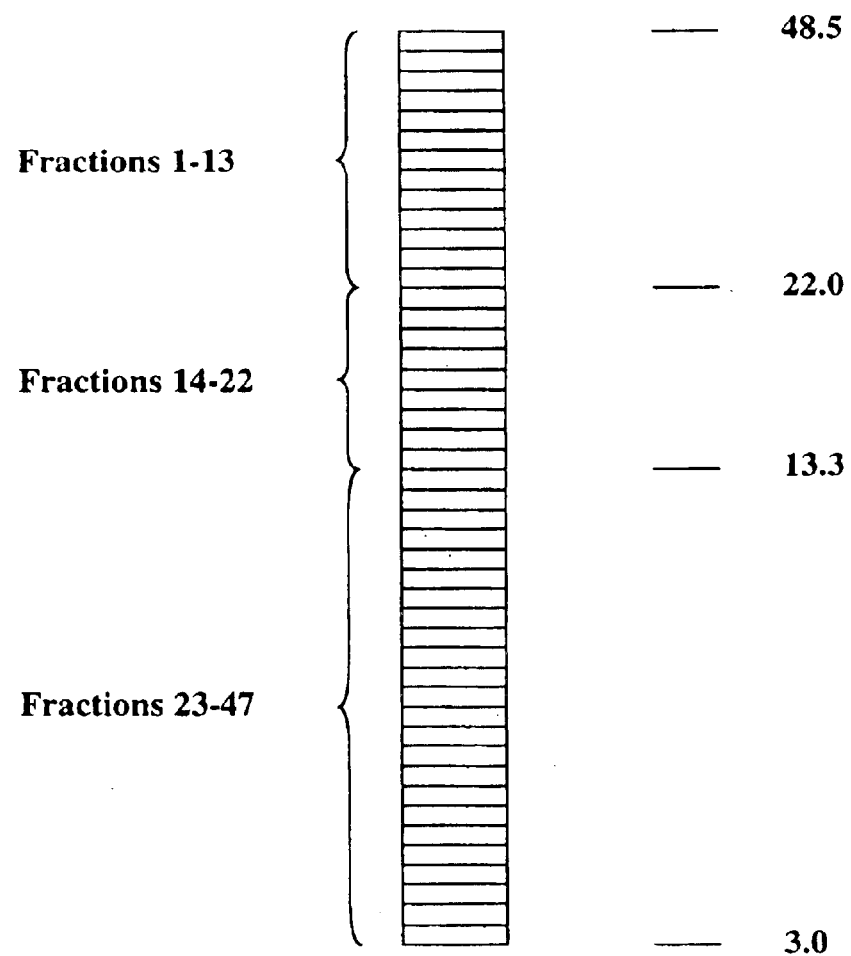
FIG. 62: Preparative agarose gel fractionation of the lambda DNA nascent PENTAmers

Nascent PENTAmers prepared at Steps 8 and 8' as well as DNA size markers are loaded on separate wells of a preparative 0.3% SeaKem Gold/1×TAE gel formed within a 1% supporting agarose frame and separated by electrophoresis at 0.6 V/cm for 30 h. Lanes with processed lambda DNA samples are excised from the gel and cut into narrow gel slices by a razor blade (FIG. 62). To establish the correlation between a fraction position on the gel and the molecular weight of DNA agarose lanes with DNA size markers (1 kb ladder, Gibco BRL and marker XV, Boehringer Mannheim; Indianapolis, Ind.) are excised from the gel, stained with EtBr and analyzed.

Example 22

PCR™ Amplification of the PENTAmers.

Forty seven agarose slices of fractionated lambda DNA preparation after ligation of down-stream nick-attaching adaptor B-3'(b) (Step 8) are subjected to further analysis. Agarose slices are washed with TE-0.1 for 16 h, melted at 95° C., and 5 μl from each fraction is mixed with 45 μl TE-0.1 in a separate tube (1/10 dilution). 48 PCR™ reactions are assembled in 0.5 ml thin wall PCR™ tubes (MJ Research). 47 mixtures contain 6 μl 1/10 diluted DNA from fractions 1–47, 3 μl 10×Advantage cDNA PCR™ Reaction Buffer (Clontech), 400 nM PCR™ primer (oligo 5603 I), 200 nM dNTP and 0.6 μl Advantage cDNA Polymerase Mix in 30 μl volume. The 48th mixture contains 6 μl non-processed lambda DNA (0.6 μg), 3 μl 10×Advantage cDNA PCR™ Reaction Buffer (Clontech), 400 nM PCR™ primer (oligo 5603 I), 200 nM dNTP and 0.6 μl Advantage cDNA Polymerase Mix in 30 μl volume (control). Cycling conditions in a DNA Engine Thermal Cycler PTC-200 (MJ Research): 10 sec at 94° C., 15 sec at 58° C., 1 min at 68° C., 34 cycles.

After PCR™, 5 μl DNA from each PCR™ tube is mixed with 0.5 μl 10×electrophoretic loading buffer (20% Ficoll 400, 0.1 M EDTA, pH 8.0, 1% SDS, 0.025% Bromphenol Blue, 0.025% Xylene Cyanol), loaded and analyzed on the 1% agarose gel (FIG. 63).

The amplified Lambda DNA PENTAmers are detected as 1 kb bands for most of the analyzed DNA fractions. The narrow size distribution shows that the PENTAmers had approximately the same lengths. Some lanes contain little amplified material, due to lack of a Sau 3A I site in certain regions of lambda DNA. Other lanes had strong signals due to the presence of several restriction sites in certain regions of lambda.

Example 23

Restriction Fingerprint Analysis of the Positionally Amplified Lambda DNA PENTAmers.

To show that 1 kb PCR products detected for most of the agarose DNA fractions represent positionally amplified PENTAmers within lambda DNA, the PCR™ products are subjected to restriction fingerprint analysis.

One set of 47 mixtures contains 12.5 µl PCR™ amplified DNA from Example 23, 50 mM Tris-HCl, pH 8.0, 10 mM MgCl$_2$, 50 mM NaCl and 3 U Mbo I (Gibco BRL) in 15 µl volume. A second set of 47 mixtures contains 12.5 µl PCR™ amplified DNA from Example 23, 50 mM Tris-HCl, pH 8.0, 10 mM MgCl$_2$, and 5 U Msp I (Gibco BRL) in 15 µl volume. Digestions are performed at 37° C. for 14 h and the tubes are mixed with 1.8 µl 10×electrophoretic loading buffer (20% Ficoll 400, 0.1 M EDTA, pH 8.0, 1% SDS, 0.025% Bromphenol Blue, 0.025% Xylene Cyanol), loaded and analyzed on a 2% NuSieve agarose gel (FMC).

FIG. 64 and FIG. 65 show the results of the fingerprint analysis. Taking into account the total number of different restriction fragments produced by Mbo I and Msp I digestion of lambda DNA (117 and 329, respectively), one can expect that most fractions should have unique restriction patterns characterized in average by 2.5 and 7 bands for Mbo I and Msp I, respectively, which is in a good agreement with the experimental data.

Figure 66:
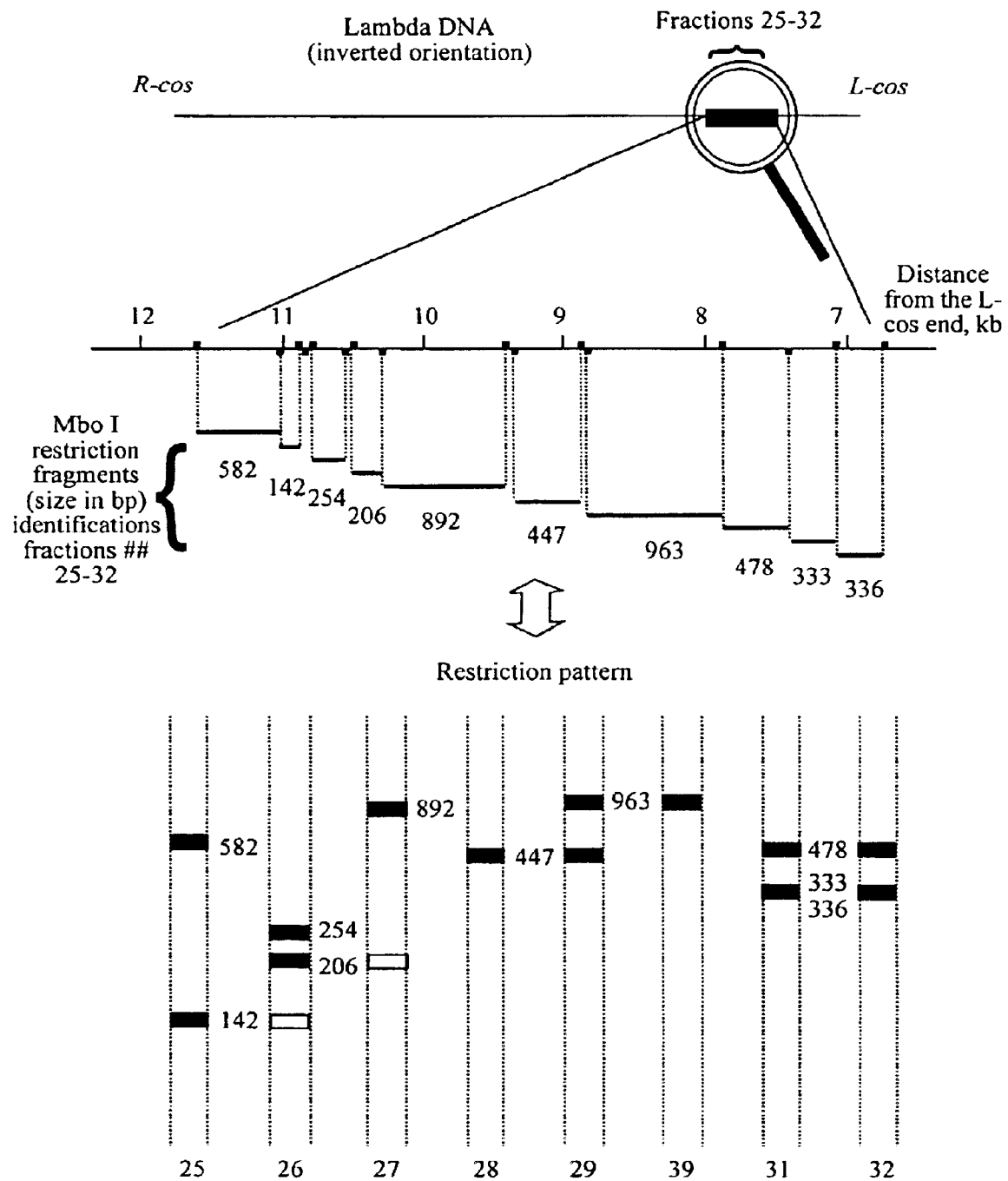
FIG. 66: Detailed Mbo I restriction fingerprint analysis of the lambda DNA PENTAmer fractions ## 25–32.
Figure 67:
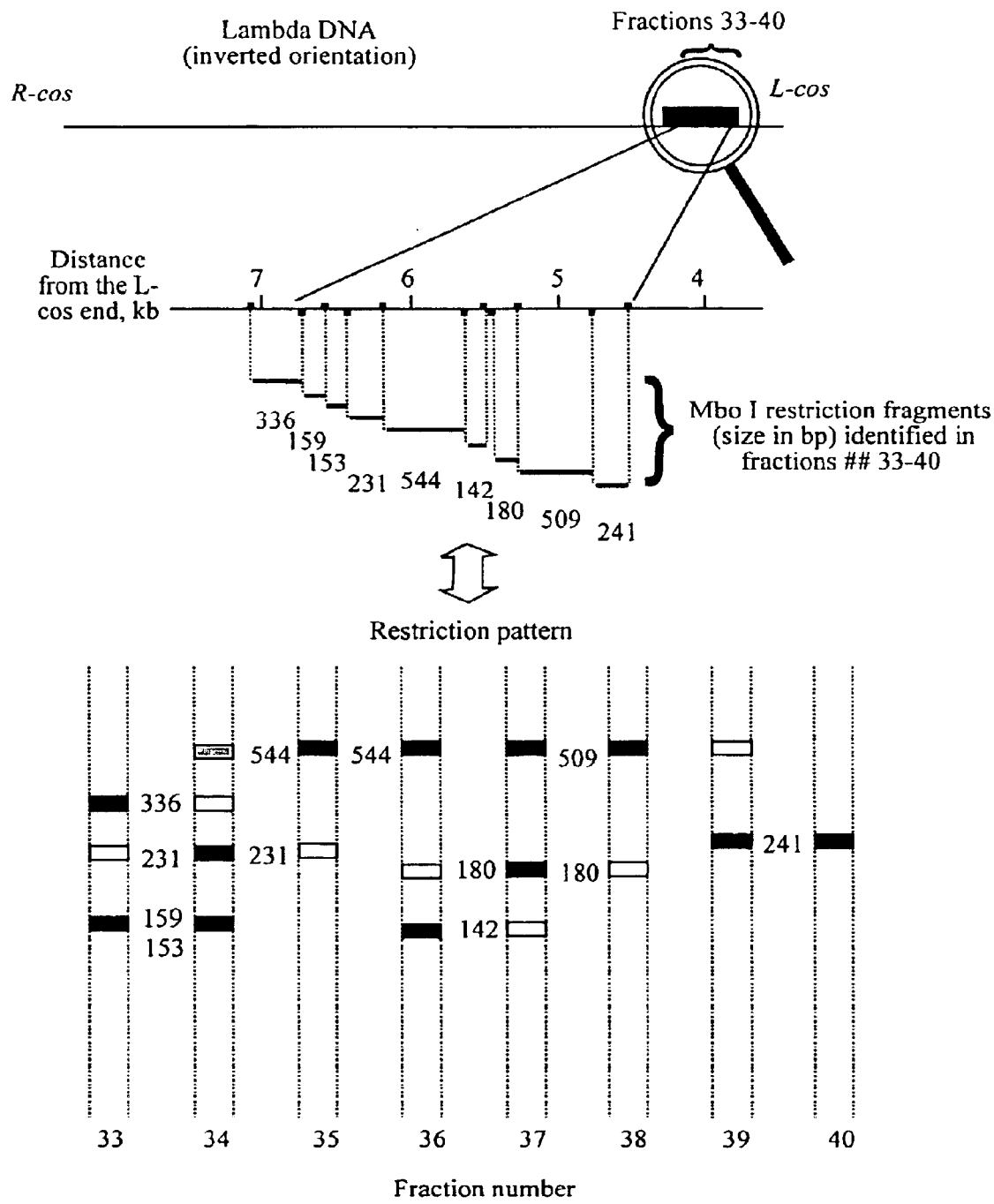
FIG. 67: Detailed Mbo I restriction fingerprint analysis of the lambda DNA PENTAmer fractions ## 33–40.

FIG. 66 and FIG. 67 show more detailed analysis of the Mbo I fingerprints of PCR™ products generated from fractions 25–32 and 33–40, respectively. Using known positions of DNA marker bands (100 bp ladder, Gibco BRL) an empirical relationship is determined between log$_{10}$ (DNA molecular weight). The migration distances of the restriction fragments in each lane were measured, and the molecular weights of all restriction fragments determined, using the empirical relationship between migration and molecular weight. The empirical molecular weights of the fragments were compared with the expected molecular weight of restriction fragments at different positions along the lambda genome. This analysis demonstrates very good correlation between the theoretically predicted and experimentally determined molecular weights within each fraction analyzed.

Example 24

Generation of Secondary PENTAmers

Secondary PENTAmers are formed by nick-translation initiated from a DNA oligomer placed at the 3' terminus of a primary PENTamer. The secondary PENTAmer permits controlled synthesis of a DNA strand complementary to the primary PENTAmer. This example uses terminal transferase to synthesize a homopolymeric stretch of guanosines at the 3' terminus of a primary PENTAmer. The guanosine homopolymer sequence then serves as an annealing site for the B1 adaptor containing a homopolymeric cytosine sequence (Table 5). Ligation of the adaptor is followed by primer extension of a DNA oligomer annealed to the B1 adaptor sequence, thereby generating a double-stranded DNA molecule the full length of the primary PENTAmer. At this point, the primary PENTAmer is competent for nick-translation in the reverse direction (i.e., from the 3' terminus to the 5' terminus of the primary PENTAmer). FIG. 3B outlines this process.

TABLE 5

Adaptor Structures

Adaptor A1 (Bam H I, Sau 3AI)
(5') P-gatctgaggttgtagaagactcggacgatacacatgcaccgtcggtgcagtcgtaatccagtcccgatctN-C7 (3')
  (3')N-C7actccaacatcttctgagcctgctatgtgtacgtggc-Biotin (5')

Adaptor A2 (Not I)
(5') P-ggcctgaggttgtagaagactcggacgatacacatgcaccg-N-C7 (3')
  (3')N-C7actccaacatcttctgagcctgctatgtgtacgtggc-Biotin (5')

Adaptor A3 (Bam HI, Sau 3AI)
(5')P-gatctgaggttgttgaagcgttuacccaautcgatuaggcaa-N-C7 (3')
  (3') N-C7actccaacaacttcgcaaaugggtuaagcuaatccgtt-Biotin (5')

Adaptor B1 (Poly N universal)
  (5') P-aagtctgcaagatcatcgcggaaggtgacaaagactcgtatcgtaaNNNNc -N-C7 (3')
(3') N-C7ttcagacgttctagtagcgccttccactgtttctgagcatagcatt-P (5')

Adaptor B2 (Poly N universal)
  (5') P-aaatcaccataccaactcgcgtcctcctgtgcatgtcgatacgtaaNNNNc -N-C7 (3')
(3')N-C7 tttagtggtgtggttgagcgcaggaggacacgtacagctatgcatt-P (5')

Adaptor B1 (Poly C universal)
  (5') P-aagtctgcaagatcatcgcggaaggtgacaaagactcgtatcgtaacccccccccccc-N-C7 (3')
(3')N-C7 ttcagacgttctagtagcgccttccactgtttctgagcatagcatt-P(5')

where

N-C7=Amino C7 Blocking group
P=5' phosphate

Adaptor 1 (BamH I, Sau3A I) in a specific embodiment is comprised of the following oligonucleotides:
(5')P-gatctgaggttgtagaagactcggacgatacacatgcaccgtcggtgcagtcgtaatccagtcccgatct-N-C7 (3') (SEQ ID NO:33); (3')N-C7-actccaacatcttc-(5') (SEQ ID NO:34); and (3')-tgagcctgctatgtgtacgtggc-Biotin (5') (SEQ ID NO:35). Adaptor 2 (NotI) in a specific embodiment is comprised of the following oligonucleotides: (5')P- ggcctgaggttgtagaagactcggacgatacacatgcaccg-N-C7 (3') (SEQ ID NO:36); (3')N-C7-actccaacatcttc-(5') (SEQ ID NO:37); and (3')-tgagcctgctatgtgtacgtggc-Biotin (5') (SEQ ID NO:38). Adaptor 3 (BamH I, Sau3A I) in a specific embodiment is comprised of the following oligonucleotides: (5')P-gatctgaggttgftgaagcgftuacccaautcgatuaggcaa-N-C7 (3') (SEQ ID NO:39); (3') N-C7-actccaacaacttc-(5') (SEQ ID NO:40); and (3')-gcaaaugggtuaagcuaatccgtt-Biotin (5') (SEQ ID NO:41). Adaptor B1 (Poly N universal) in a specific embodiment is comprised of the following oligonucleotides: (5')P-AAGTCTGCAAGATCATCGCGGAAGGTGACAAAGACTCGTATCGTAANNNNc-N-C7 (3') (SEQ ID NO:42); and (3')N-C7-ttcagacgttctagtagcgccttccactgtttctgagcatagcatt-P(5') (SEQ ID NO:43). Adaptor B2 (Poly N universal) in a specific embodiment is comprised of the following oligonucleotides: (5')P-AAATCACCATACCAACTCGCGTCCTCCTGTGCATGTCGATACGTAANNNNC-N-C7 (3') (SEQ ID NO:44); and (3')N-C7-TTTAGTGGTGTGGTTGAGCGCAGGAGGACACGTACAGCTATGCATT-P(5') (SEQ ID NO:45). Adaptor B1 (Poly C universal) in a specific embodiment is comprised of the following oligonucleotides: (5')P-AAGTCTGCAAGATCATCGCGGAAGGTGACAAAGACTCGTATCGTAACCCCCCCCCC-N-C7 (3') (SEQ ID NO:46); and (3')N-C7 TTCAGACGTTCTAGTAGCGCCTTCCACTGTTTC TGAGCATAGCATT-P(5') (SEQ ID NO:47).

For this example, the plasmid pUC19 was cut to completion with BamHI and EcoRI. The A3 adaptor (Table 5) was ligated to the BamHI site at a 2:1 ratio using T4 DNA ligase. Excess A3 adaptor was removed by washing on a microcon YM-100 (see Example 29). A primary PENTamer was generated by nick-translation from the A3 adaptor using a biotinylated DNA oligomer. The nick-translation reaction was performed for 10 minutes, resulting in approximately a 2000 nucleotide product as indicated by gel electrophoresis on a denaturing acrylamide gel. A microcon YM-100 was used to remove dNTPs and concentrate the primary PENTAmer products. Poly-guanosine was synthesized from the 3' terminus of the primary PENTAmers using terminal transferase (NEB) and 1 $\mu$M dGTP. The reaction was allowed to proceed for 15 minutes at 37° C. Products were washed using a microcon YM-100 to remove dGTP and buffer salts. The poly C universal B1 adaptor was then ligated to the guanosine homopolymer at a 5:1 ratio using Tsc DNA ligase (Roche). Ligation was performed for 2 hours at 45° C. The reaction was extracted with phenol:chloroform:isoamyl alcohol (25:24:1), and excess adaptor was removed using a microcon YM-100. The primary PENTamer products were then captured on Dynal streptavidin-conjugated magnetic beads (see bead immobilization described in Example 31). Beads were washed with 100 mM NaOH to denature double-stranded DNA and remove the complementary strand of the bead-bound primary PENTAmer. The primer extension DNA oligomer (oligomer 19, Table 6) was annealed to B1 adaptor, located at the 3' terminus of the primary PENTAmer, and extended using Taq DNA polymerase and standard PCR reaction buffer conditions for 15 minutes. Beads were washed, and the second DNA oligomer (oligomer 16, Table 6) was annealed and nick translated for 2.5, 5, and 7.5 minutes to generate secondary PENTAmers.

TABLE 6

Oligonucleotides

| Number | Sequence (5'-3') Modifications | Length (bases) and Application | |
|---|---|---|---|
| 1. | cgg tgc atg tgt atc gtc cga gt (SEQ ID NO:48) | 23 a | Adaptors A1, A2 Sequencing, end-labeling |
| 2. | ctc ctg tgc atg tcg ata cgt aac ccc ccc ccc (SEQ ID NO:49) | 33 | Amplification of poly G-tailed sequences |
| 3. | cgg tgc atg tgt atc gtc cga gt (SEQ ID NO:50) | 23 | Adaptors A1, A2 PCR primer |
| 4. | gat ctg agg ttg tag aag act cgg acg ata cac atg cac cgt cgg tgc agt cgt aat cca gtc ccg atc tc (SEQ ID NO:51) | 71 b, c | Adaptor A1 (BamH I) backbone |
| 5. | ctt cta caa cct ca (SEQ ID NO:52) | 14 c | Adaptors A1, A2 blocking primer |
| 6. | cgg tgc atg tgt atc gtc cga gt (SEQ ID NO:53) | 23 d | Adaptors A1, A2 nick-translation primer |
| 7. | ggc ctg agg ttg tag aag act cgg acg ata cac atg cac cg (SEQ ID NO:54) | 41 b, c | Adaptor A2 (Not I) backbone |
| 8. | cgg tgc atg tgt atc gtc cga gt (SEQ ID NO:55) | 23 e | Adaptors A1, A2 end-labeling |
| 9. | gat ctg agg ttg ttg aag cgt tua ccc aau tcg atu agg caa (SEQ ID NO:56) | 42 b, c | Adaptor A3 (BamH I) backbone |
| 10 | ttg cct aau cga aut ggg uaa acg (SEQ ID NO:57) | 24 d | Adaptors A3 nick-translation primer |

TABLE 6-continued

Oligonucleotides

| Number | Sequence (5'-3') Modifications | Length (bases) and Application | |
|---|---|---|---|
| 11. | ctt caa caa cct ca (SEQ ID NO:58) | 14 c | Adaptor A3 blocking primer |
| 12. | ttg cct aat cga att ggg taa acg (SEQ ID NO:59) | 24 | Adaptors A3 PCR primer |
| 13. | ttc cct aat cga att ggg taa acg (SEQ ID NO:60) ctt caa caa cct cag atc | 42 c | AdaptorA3 backbone complement block |
| 14. | tta cga tac gag tct ttg tca cct tcc (SEQ ID NO:61) gcg atg atc ttg cag act t | 46 b,c | Adaptor B1 phosphorylated strand |
| 15. | aag tct gca aga tca tcg cgg aag (SEQ ID NO:62) gtg aca aag act cgt atc gta aNNNNc | 51 c | Adaptor B1 poly N strand |
| 16. | aag tct gca aga tca tcg cgg aa (SEQ ID NO:63) | 23 | Adaptor B1 PCR primer, also used for nick-translation |
| 17. | acg ggc tag caa aat agc gct gtc (SEQ ID NO:64) c(N)g atc tga ggt tgt tga agc g | 46 c | blocking primer to prevent adaptor A3-B1 dimers formation |
| 18. | gga cag cgc tat ttt gct agc ccg t (SEQ ID NO:65) | 25 c | blocking primer to prevent adaptor A3-B1 dimers formation |
| 19. | ggt gac aaa gac tcg tat cgt aa (SEQ ID NO:66) | 23 | primer extension from B1 (poly C) |
| 20. | ctc ctg tgc atg tcg ata cgt aa (SEQ ID NO:67) | 23 | B2 proximal primer |
| 21. | aaa tca cca tac caa ctc gcg tc (SEQ ID NO:68) | 23 | B2 distal primer | a 5' Cy 5.0 labeled
b 5' phosphorylated
c 3' C7 amino blocked
d 5' biotinylated
e 5' fluorescein labeled
N random base The secondary PENTAmer products were liberated from their complementary bead-bound primary PENTAmers by washing with 100 mM NaOH. The beads were immobilized using a magnet and the solution was transferred to a fresh tube. An equal volume of 3M NaOAc, pH 5.2 was added to neutralize the base and bring the pH to approximately 5.2. Eight volumes of water and 25 volumes of ethanol were added to precipitate the secondary PENTAmers. The single-stranded DNA was pelleted at 16,000×g for 30 minutes, washed with 80% ethanol, dried, and then resuspended in water. The B2 (poly N universal) adaptor (Table 5) was ligated to the 3' end of the secondary PENTAmers at >10:1 ratio.

Figure 68:
FIG. 68: Detection of secondary PENTAmer products using PCR.

Secondary PENTAmer products were detected by using PCR with DNA oligomers complementary to the B1 (5' terminus) and B2 (3' terminus) adaptors. FIG. 68 shows agarose gel electrophoresis of two independent sets of PCR products from the 2.5, 5, and 7.5-minute nick translation reactions used in generation of the secondary PENTAmers. Lanes A and B contain DNA molecular weight markers. Lanes C, D, and E contain PCR products of secondary PENTAmers generated from 2.5, 5, and 7.5-minute nick-translation reactions, respectively. Lanes F, G, and H contain another set of 2.5, 5, and 7.5-minute products. The 2.5-minute nick translation reaction resulted in a product of approximately 400 bp. The 5-minute reaction product was slightly larger than 800 bp. The 7.5-minute reaction did not produce discrete products in either sample set.

Example 25
Activation of Recombinant Adaptors by Methylation-Sensitive Endonucleases Specific methylation within recombinant adapters can serve as a mechanism for activation of ends for recombination. Recombination adapters $RA_1$ and $RA_2$ (FIG. 69) were assembled and methylated using dam methylase. Selective digestion of the A-methylation site within the engineered GATC recognition site for endonucleases Dpn-I (cleaves methylated sites) and Mbo I (cleaves non-methylated sites) shows efficient methylation of adapters.

Lambda DNA grown under dam⁻ conditions (NEB) was digested to completion with BamHI, dephosphorylated by shrimp alkaline phosphatase (SAP), and adapters ligated (T4 DNA ligase, 15° C. 16 hrs) with a four-fold molar excess of a 1:1 mixture of $RA_1/RA_2$. Ligation reactions were heat inactivated (65° C. for 20 min.), and unligated adapters were removed by microcon filtration (Example 29). Purified Lambda fragments with adapters were either a) nick translated and subsequently Dpn-I activated for ligation-mediated recombination; or b) activated for recombination by Dpn-I digestion for recombination primed nick translation.

Adapter modified lambda fragments were nick translated (50 ng/μL DNA, 1×Perkin Elmer Taq buffer, 2 mM $MgCl_2$, 200 μM dNTPs, and 0.2 U/μL wt Taq DNA polymerase) for 4 minutes, initiating the reaction by the addition of dNTPs and stopping the reaction by addition of EDTA to 10 mM. Reactions were purified by phenol extraction and ethanol precipitation. Nick translated DNA was resuspended, and dispersed to low concentrations (1 ng/μL or 0.1 ng/μl) to maximize intramolecular recombination events in 1×thermostable ligase buffer (Roche). It was then heated to 75° C. to dissociate the protecting oligos (FIG. 70) from activated ends, exposing the complementary sequence for recombination. Thermostable ligase (Tsc ligase, Roche) was added and reactions run for 10 cycles (94° C. 1 min, 45° C. 30 min). Products were recovered by phenol extraction and ethanol precipitation for analysis of recombination.

Figure 71:
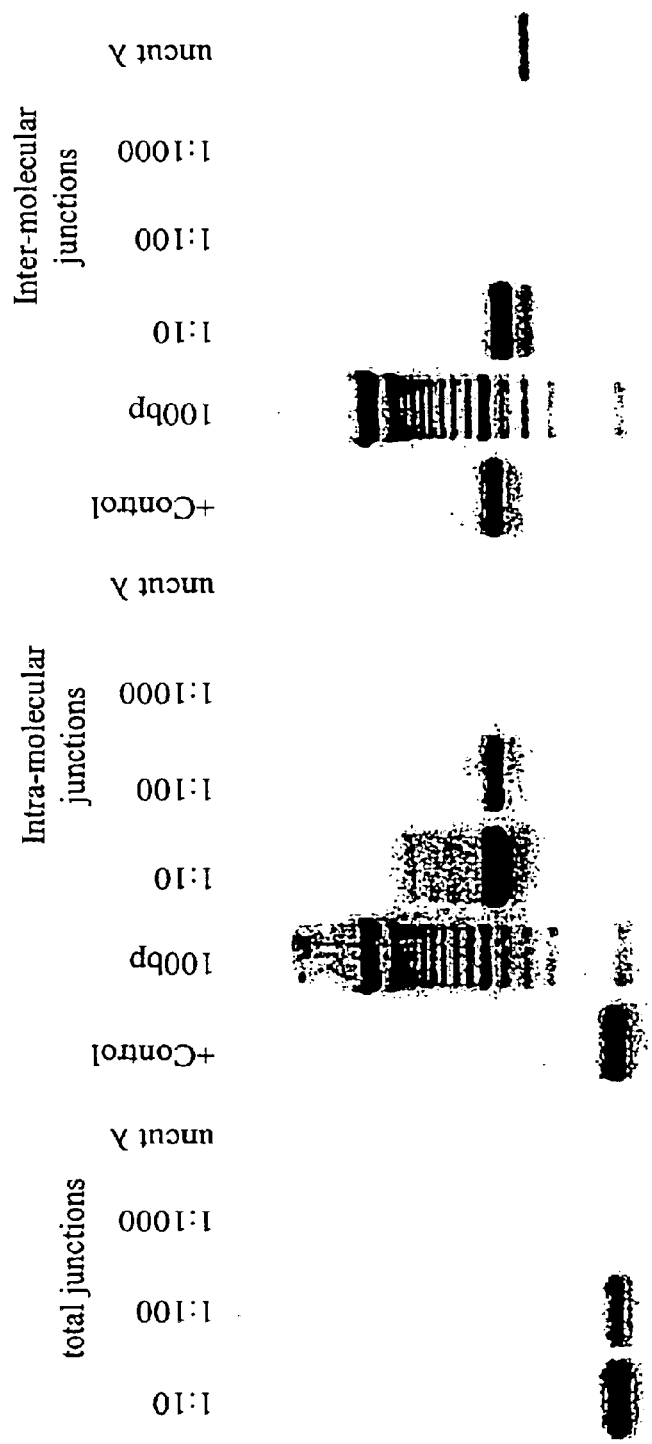
FIG. 71: Recombination efficiency from $RA_1/RA_2$ adaptors.

Recombination was assessed by junction fragment analysis of predicted lambda fragments. Oligonucleotide primers facing the BamHI fragment junctions were used to evaluate the efficiency of recombination. Amplification of a dilution series of the recombinant pool with primers from within the same fragment give the relative efficiency of intra-molecular recombination, which can be quantified and compared to selected amplification between different fragments, or intermolecular recombination. Products of amplification were size fractionated by agarose gel electrophoresis and quantified (BioRad (Hercules, Calif.) Fluor-S Imager) with values weighted for their relative occurrence in the genome. Total junction fragments are represented by PCR amplification within the recombinant junction using the designated DNA oligomers (FIG. 70, lambda recombination screening oligos). Undigested lambda DNA served as the control for primer specificity and identification of residual undigested products in the case where intermolecular recombination was tested across junctions that occur naturally in the genome. FIG. 71 demonstrates recombination efficiency from $RA^1/RA_2$ where nick translation preceded recombination as in the Example above. Normalized data shows that intra-molecular recombination approaches the theoretical maximum with DNA concentrations in the 0.1 ng/μl and 1.0 ng/μl range during recombination for this model template.

Adapter modified lambda BamHI fragments were digested with Dpn-I (Neb Dpn-I, 10 U/μg, 4 hr at 37° C.), digests were heat inactivated (80° C., 20 min) and Microcon-filtered (Example 29) to remove blocking oligos. The high molecular weight DNA recovered was diluted to low concentrations (1 ng/μl or 0.1 ng/μl) in 1×Perkin Elmer Taq buffer supplemented to 2 mM $MgCl_2$, heated (75° C.) to dissociate unligated oligos and mixed by pipetting to disperse molecules, then slowly cooled to 50° C. for optimal annealing and incubated overnight. Annealed samples were reduced to room temperature and supplemented with wt Taq DNA polymerase to 0.2 U/μl, mixed thoroughly, and returned to 50° C. for a 10 minute pre-incubation. Nick translation was initiated by addition of dNTPs to 200 μM for 4 minutes then stopped by the addition of EDTA to 10 mM. Reactions were purified by phenol extraction and ethanol precipitation for analysis of recombination.

Figure 72:
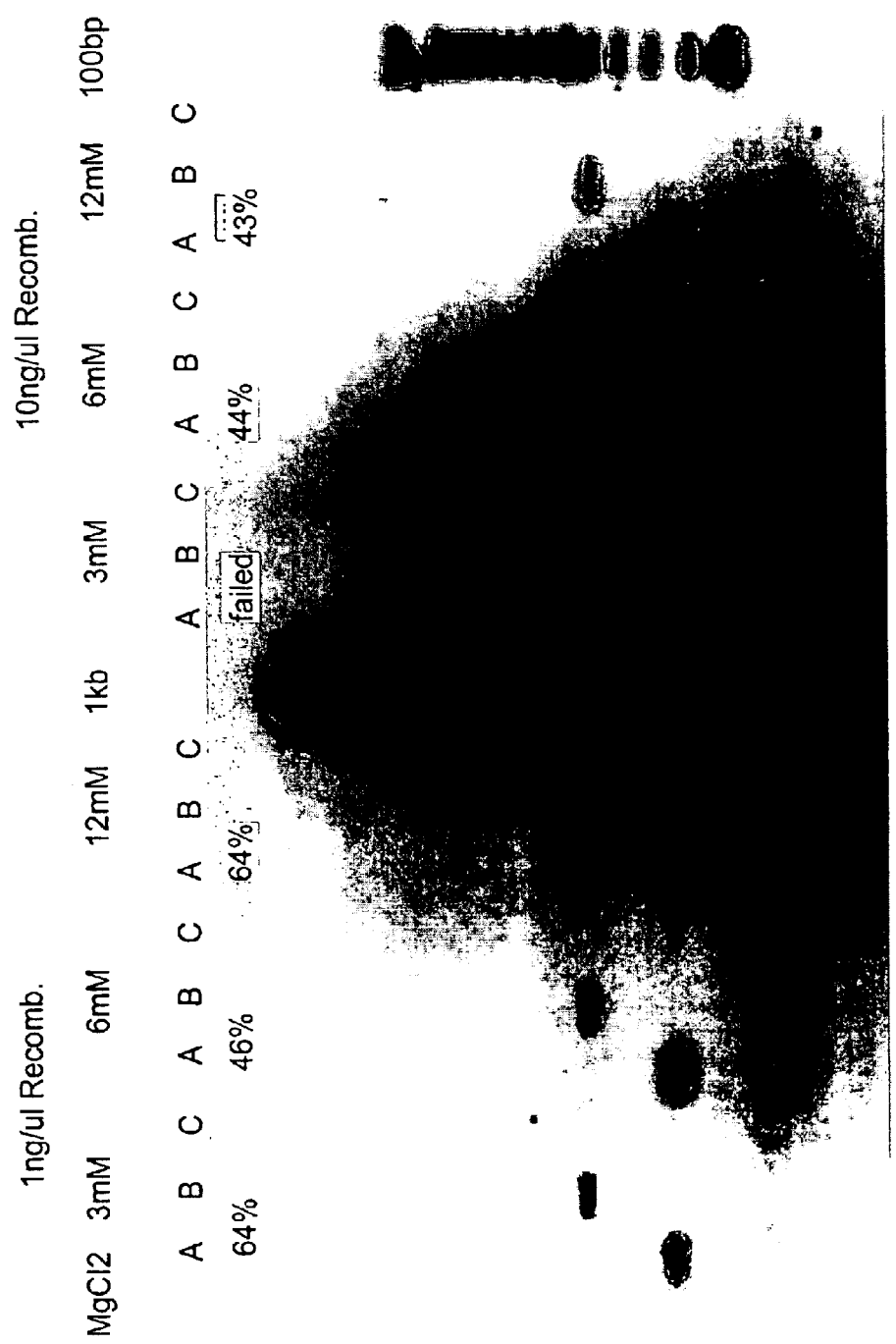
FIG. 72: Effects of $MgCl_2$ concentration on recombination efficiency.
Figure 73:
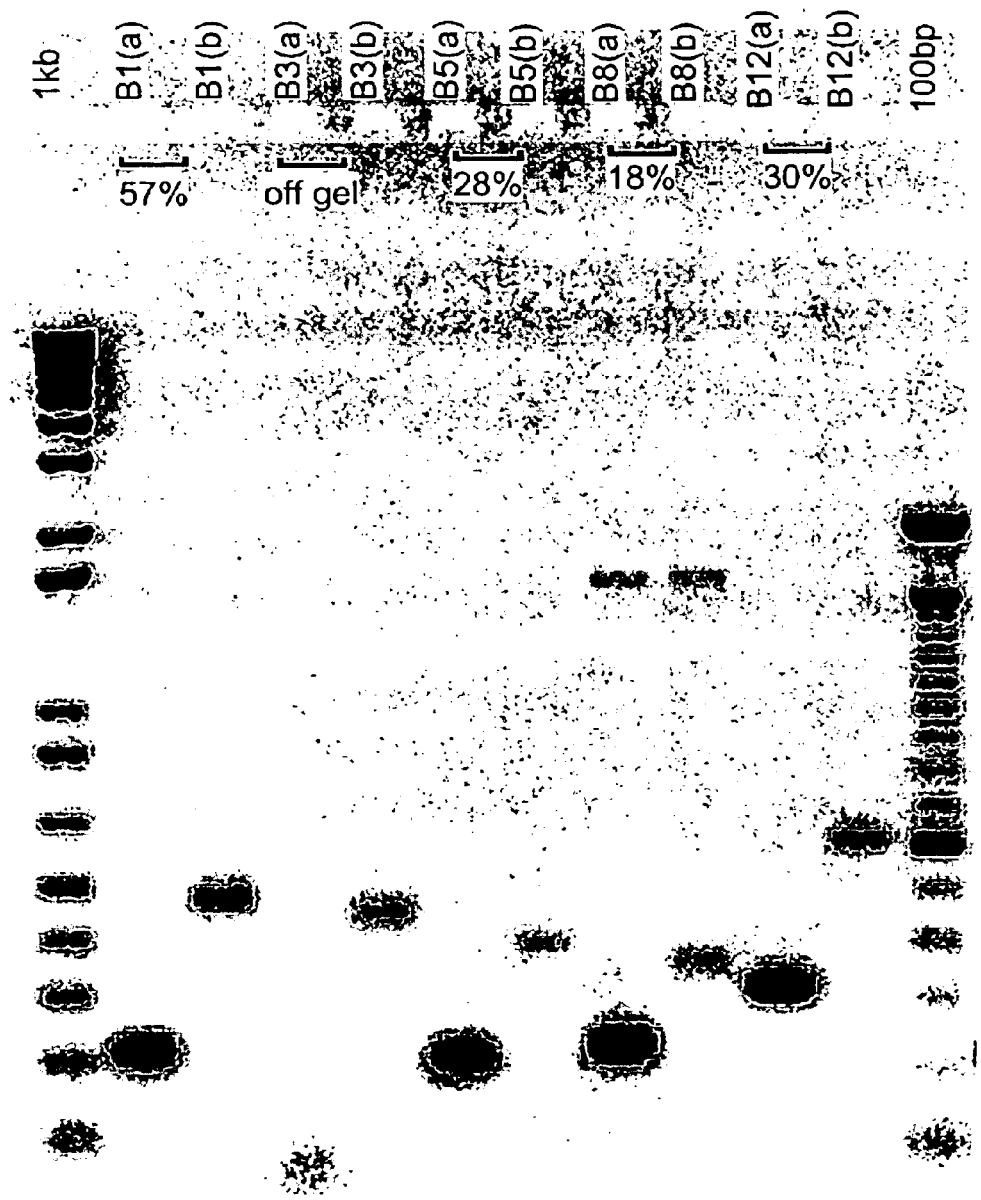
FIG. 73: Recombination efficiency with multiple kernel primer sets.

Recombination primed nick translation was applied to Lambda model templates with Dpn-I activation of $RA_1/RA_2$ prior to the annealing step giving similar results to post nick translation recombination. As this approach does not require protected adapter termini, a set of simplified recombinant adapters (Sra1/Sra2) were designed which can be directly recombined. The Sra adapters were initially tested as above with Lambda templates, and subsequently tested on total bacterial genomic preparations. A series of primer sets (B1, B3, B5, B8, B12, FIG. 71, *E. coli* recombination screening oligos) were designed to test recombination of a complete BamHI digest of *E. coli* (strain K-12, MG1655). Each set was comprised of an anchor primer (PCR) which when paired with a nest primer (NEST) amplifies the total amount of the available template in the preparation. The resulting product was compared to the product obtained using the anchor primer paired with a recombinant primer (RP). The anchor primer and recombinant primer combination amplifies the fraction of the total number of molecules that have undergone intra-molecular recombination. FIG. 72 shows an example in which the B1 primer set is used to examine the effects of $MgCl_2$ concentration on recombination efficiency expressed as a percent of the total. Primer set (A) represents the total target amplified, (B) represents the fraction which has recombined, and (C) shows the absence of product with a non-recombinant reverse primer. FIG. 73 shows all five kernel primer sets and their relative recombination efficiencies.

Example 26

Enzymatic Release of Recombinant PENTAmers, a Nicked Template Model.

Once a recombinant PENTAmer exists within the context of genomic DNA it must be released prior to the addition of terminal adapters. One method involves the conversion of the remaining nick, which has been translated outward during the timed reaction, into a double stranded break. This example describes the optimization of converting a nicked model template into their corresponding fragments.

Figure 74:
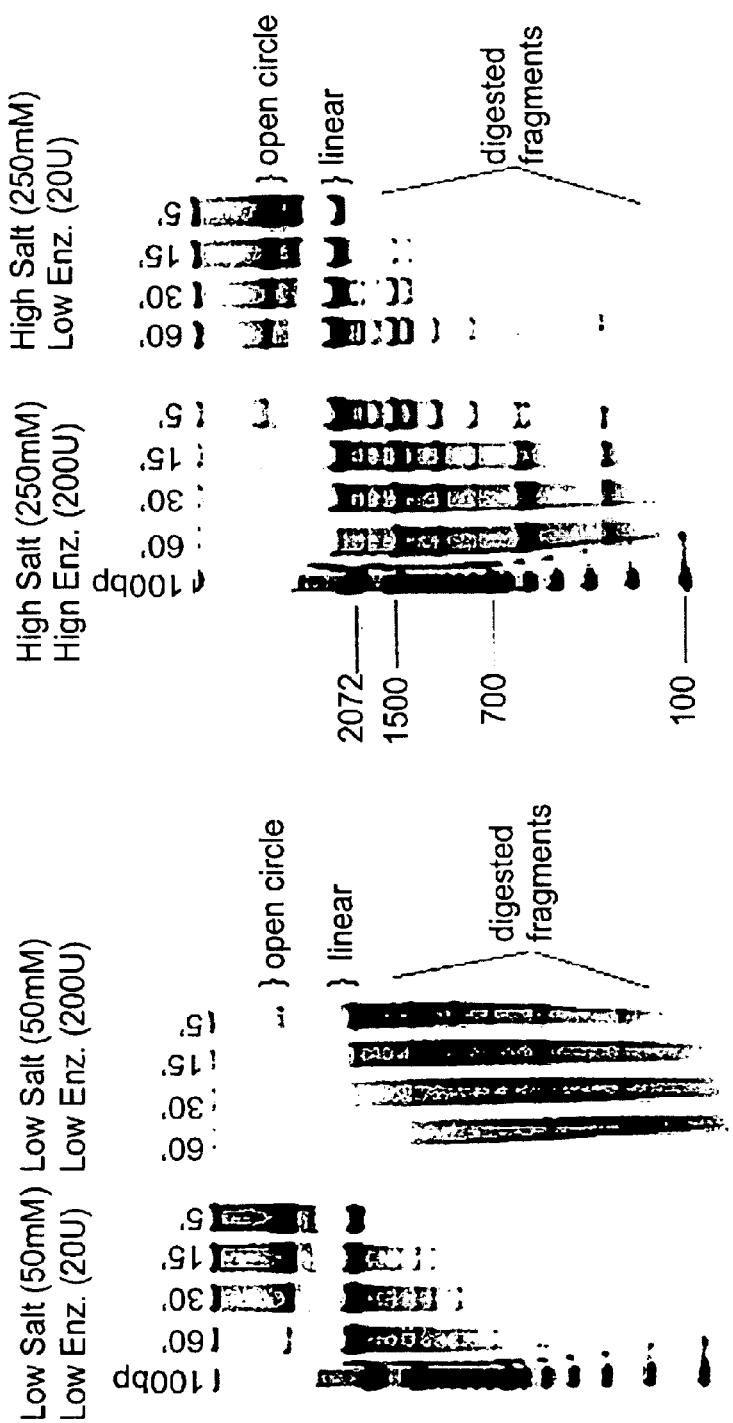
FIG. 74: Conversion of nicks to breaks through intermediate forms.
Figure 75:
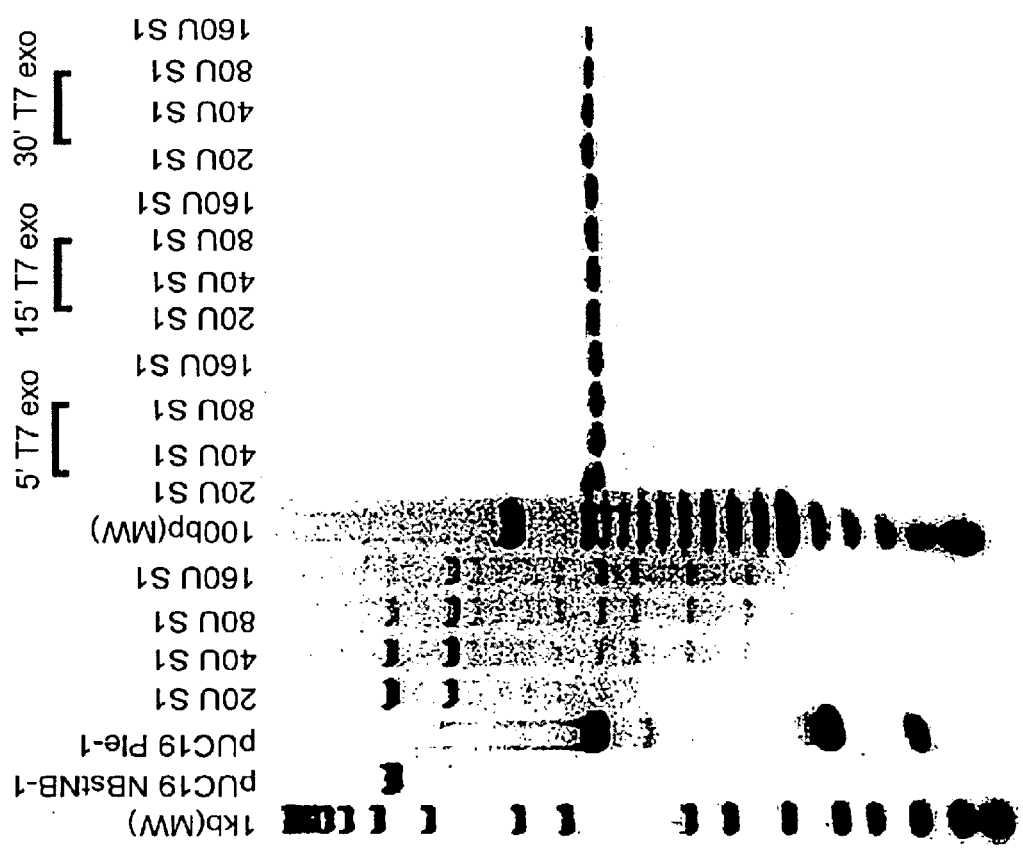
FIG. 75: Comparison of S1 digestion to T7 exonuclease/S1 digestion.
Figure 76:
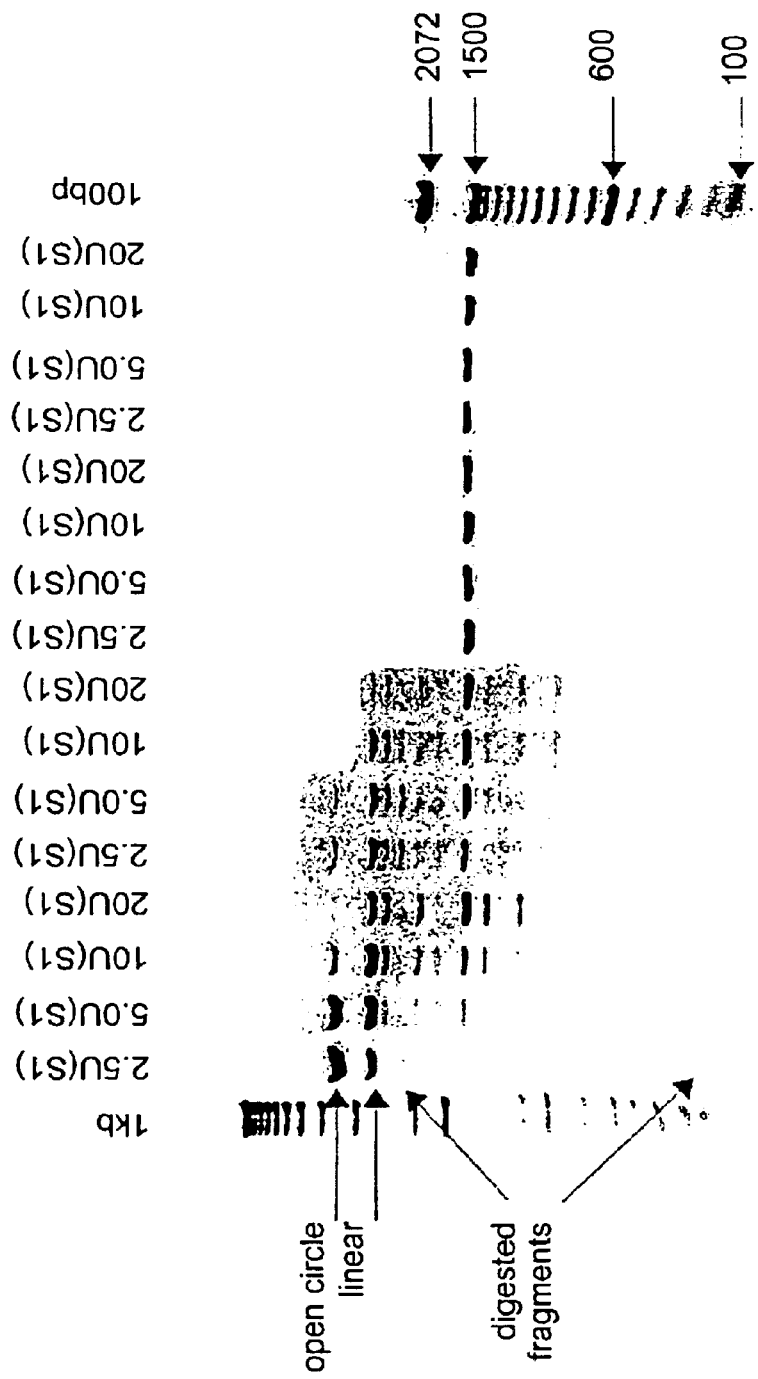
FIG. 76: Complete conversion to fragments following T7 digestion.

Nicked template was prepared utilizing the mutant restriction enzyme N. BstNBI (NEB, 10U/ug, 1 hr. 55° C.) to generate nicks within plasmid pUC19. S1 nuclease (Roche) was tested over a range of conditions to optimize the conversion of nicks to breaks and minimize the degree of non-specific cleavage. FIG. 74 shows the progressive conversion of nicks through the intermediate forms. Degradation is evident as a background of highly variable sized DNA products, most notably in samples low in salt concentration and high in enzyme concentration. S1 alone does not efficiently convert simple nicks to breaks, however a larger single stranded region can serve as an excellent template. An ideal candidate enzyme for opening the remaining nick into a gap is the T7 (gene 6) exonuclease. Nicked plasmid was subjected to a time course of T7 exonuclease treatment prior to S1 digestion. FIG. 75 demonstrates the effectiveness of this treatment in comparison to the same sample digested with S1 alone. Nicked plasmid without subsequent digest (open circle) as well as restriction digest with Ple-I, which cleaves the recognition sequence nicked by N.BstNBI, serve as controls for this assay. Since all T7 exonuclease treatments gave complete cleavage upon S1 digestion, it was of interest to titrate the T7 exonuclease enzyme required for formation of S1 accessible gaps. N.BstNBI nicked plasmid was treated with 0, 0.4, 4.0, or 40 U/μg of T7 exonuclease (NEB) for 5 minutes at room temperature. Reactions were phenol extracted and ethanol precipitated prior to treatment with 2.5, 5.0, 10, or 20 U of S1 nuclease. FIG. 76 shows the complete conversion to fragments at the 4 U/μg T7 concentration. These conditions establish a baseline for enzymatic release of PENTAmers with minimal (10 U/μg) S1 nuclease concentrations limiting the non-specific degradation associated with S1.

Example 27

Enzymatic Release of Recombinant PENTAmers Generated from Bacterial Genomic DNA

Figure 77:
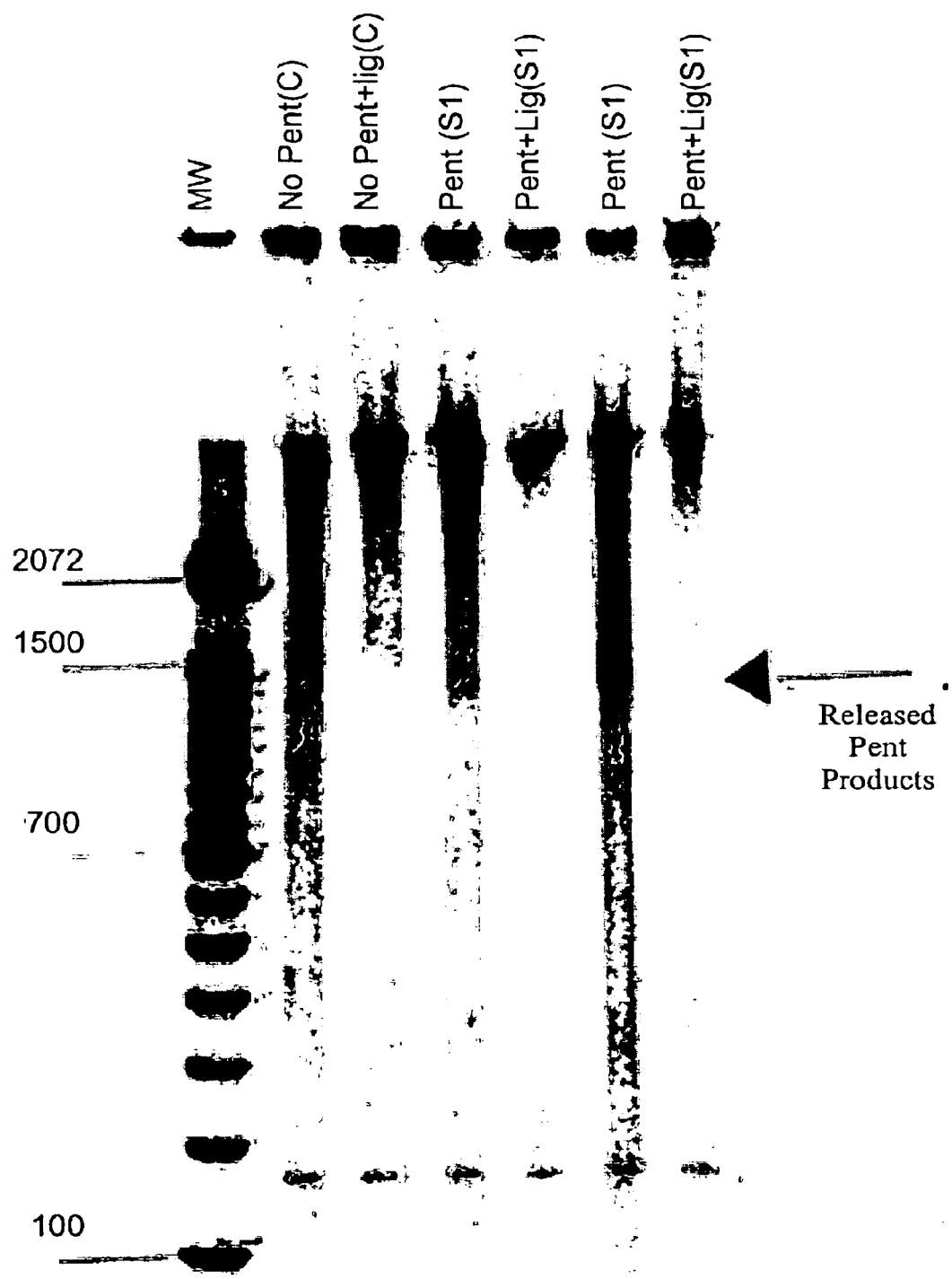
FIG. 77: Release of PENTAmers following S1 treatment.

This example describes the release of nick translation products by enzymatic methods. The conditions established in plasmid model templates were applied to primary nick translation products synthesized from adapter modified Lambda templates. Products were subjected to conditions for S1 nuclease digestion optimized on the model template (250 mM NaCl, 200 U S1, 50 mM NaOAc, 1 mM ZnOAc, pH 4.6). The primary nick translation products showed specificity through resistance to nuclease attack by prior ligation. A portion of the preparation was not nick translated and served as a negative control in which S1 treatment did not yield the release product. FIG. 77 shows a native gel of S1 released products. Ligation completely protects the sample from digestion (lanes 5 and 7) and the controls that were not nick-translated (lanes 2 and 3) confirm the origin of these products.

Figure 78:
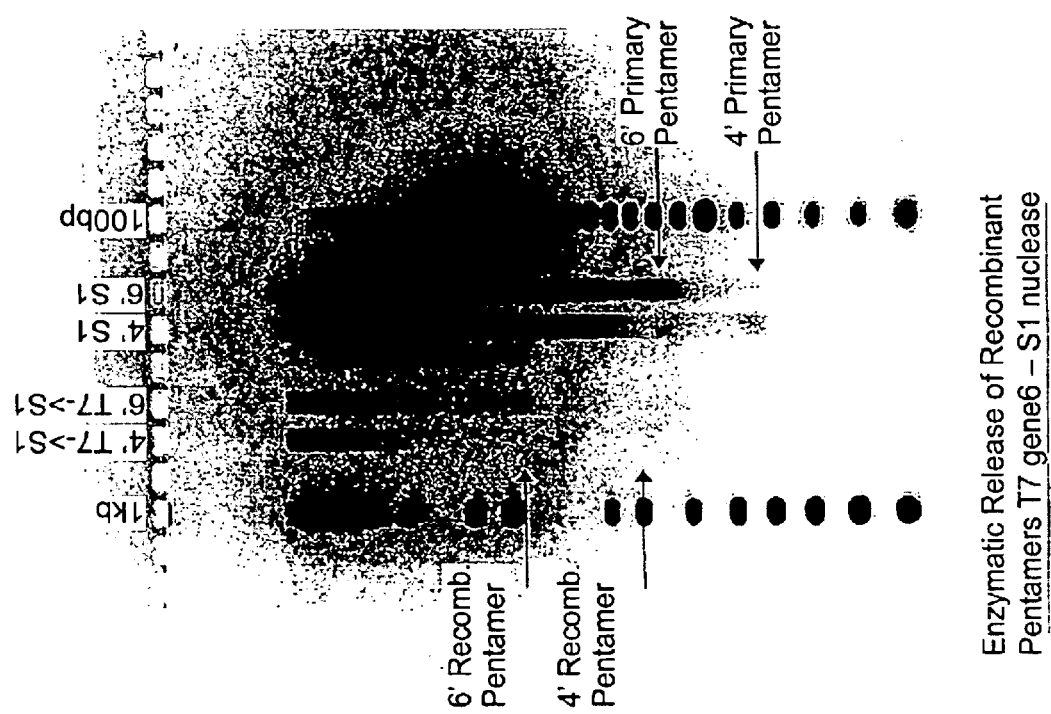
FIG. 78: Enzymatic release of recombinant PENTAmers.

As the 5'→3' exonuclease activity of T7 gene 6 would degrade primary PENTAmers from their 5' ends, further testing of the enzymatic release mechanism requires the use of recombinant PENTAmers (RPs). Recombinant PENTAmers were generated by recombination primed nick translation of BamHI cut E. coli genomic DNA with Sra1/Sra2 and recombined as described above in Example 26. Total recombined material was maximized without regard for specificity of ends by elevating DNA concentrations to 10 ng/µL during recombination. Recombined sample was nick translated for 4 or 6 minutes as described in Example 26, then subjected to S1 cleavage or T7 exonuclease digestion followed by S1 cleavage. FIG. 78 shows the size-fractionated products on a native agarose gel. In digestion with only S1 nuclease, the monomer fraction is visualized as 400 and 800 bp products. Recombinant molecules, which migrate at approximately twice the molecular weight of monomer, are not distinguishable in the background of genomic DNA. When T7 exonuclease is applied prior to S1 cleavage, much of the genomic DNA has been degraded and only the recombinant PENTAmer is observed.

Example 28

Secondary Nick Translation Release of Recombinant PENTAmer.

Figure 79:
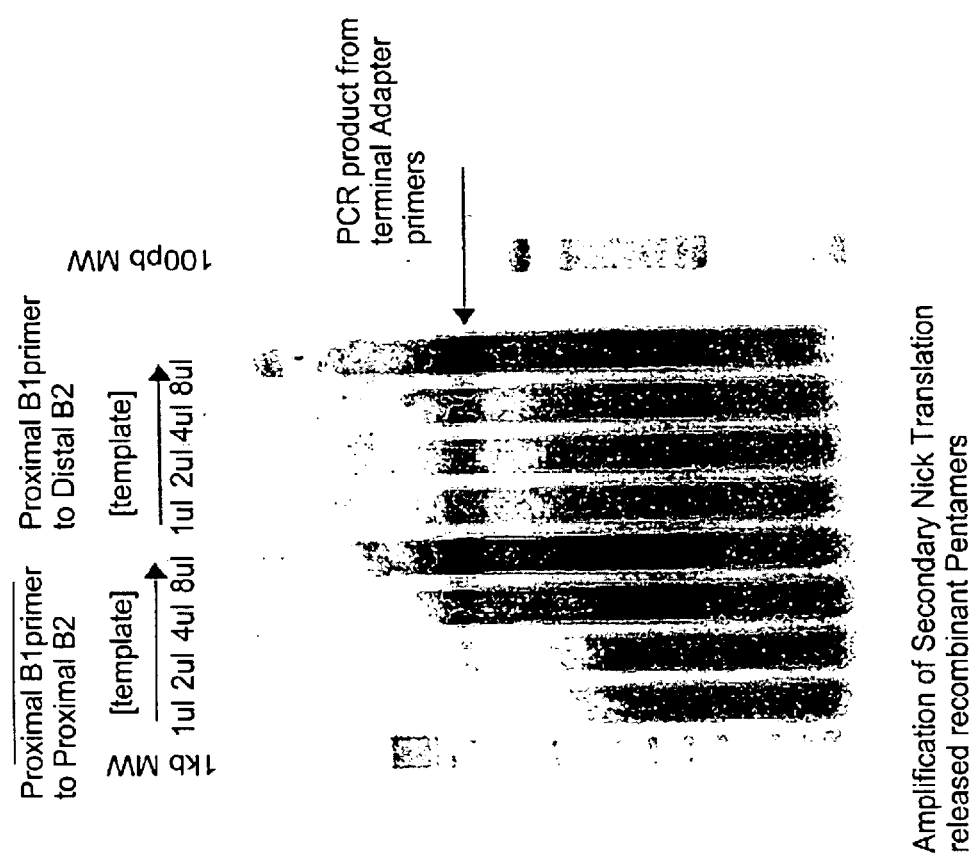
FIG. 79: Amplification of secondary nick translation released recombinant PENTAmers.

This example demonstrates an alternative to nuclease release of recombinant PENTAmers based on the example for secondary PENTAmer synthesis (Example 24). The method incorportates the following steps: terminal transferase tailing of nascent PENTAmer ends, ligation of terminal adapters, primer extension, and finally a secondary nick translation reaction to generate free recombinant PENTAmers of defined length. Recombination primed PENTAmers were generated as previously described in Example 26 at 1 ng/µL DNA concentrations and 6 mM MgCl$_2$ for recombination. After nick translation residual dNTPs were removed from the preparation by phenol extraction followed by microcon YM-100 (Millipore) filter purification (Example 30). The nascent PENTAmers were then tailed with dGTP under conditions that favor generation of short 10–15 nucleotide guanosine tails (1×NEB buffer 4, 0.25 mM CoCl$_2$, 1 µM dGTP, 0.2 U/µL terminal transferase (NEB), for 15 min. at 37° C.). Tailed products were phenol extracted and ethanol precipitated prior to terminal adapter ligation. Terminal adapters were ligated using the B1 (Poly C universal) adaptor (Table 5) with an eleven base poly-C overhang under thermostable ligase conditions (Roche) for 10 cycles (94° C. 1 min, 45° C. 30 min.). Unincorporated adapter was removed by phenol extraction and microcon filtration (Example 30). Primer extension of these templates was performed by addition of a priming oligo complementary to the proximal end of the terminal adapter. Heat denaturation (98° C. for 5 minutes) was followed by cooling to 65° C. to anneal the primer extension oligo. Bst DNA polymerase (NEB) was used to extend the primer (1×NEB thermoPol buffer, 4 U/µg BstPol, 300 µM dNTPs, 6 mM MgCl$_2$, 100 µM primer) for 30 minutes at 65° C. Bst Pol was heat inactivated (80° C., 10 minutes) and the distal adapter primer for nick translation added. This primer includes a 5' terminal biotin allowing product primed by this oligo to be captured in single stranded form on streptavidin coated magnetic beads. Reaction temperature was reduced to 50° C. for 10 minutes and nick translation was initiated by addition of wild-type Taq. The reaction was incubated for 8 minutes at 50° C. The products are denatured and bound to beads (bead immobilization described in Example 32). Adaptor was then attached to the 3' terminus by ligation (T4 DNA ligase 15° C. 16 hr) using a poly (N) guide oligo to represent the possible combinations found in the library (Table 5). Oligonucleotide primers to the 5' and 3' terminal adapters could then be used to amplify the recombinant library for further analysis. FIG. 79 shows the secondary amplification of the library. These products were T/A cloned (pCR2.1Topo, Invitrogen; Carlsbad, Calif.) and sequenced to confirm the presence of each modification and the resulting PENTAmer partners.

Example 29

Evaluation of Trapping of DNA Molecules Across Agarose Gels in One-Dimensional and Two-Dimensional Electrophoresis This example shows comparison between one-dimensional (1D) and two-dimensional (2D) Field Inversion Gel Electrophoresis (FIGE) for trapping of 2.3 kB size DNA fragment across pulsed-field grade agarose gels.

To purify full-size lambda DNA having minimal number of double stranded breaks, 6 µg of non-methylated lambda DNA (New England Biolabs; Beverly, Mass.) are heated at 75° C. in 200 µl TE buffer for 5 min and loaded in preparative well on 0.8% pulsed-field grade agarose (Bio Rad) gel. Electrophoresis is carried out in 0.5×TBE buffer on FIGE Mapper Apparatus (Bio Rad) at forward voltage of 180 V, reverse voltage of 120 V, linear switch ramps of 0.1–0.8 sec, for 16 hours at room temperature. Following staining with Sybr Gold (Molecular Probes), lambda DNA band is excised and electroeluted in 60 kD cut-off dialysis bag (Spectra/Por) in 0.5×TBE buffer at 87 V interrupted field (60 sec on, 5 sec off) for 3 hours at room temperature. Recovered DNA is concentrated in Microcon YM-100 ultrafiltration units (Millipore) at 200×g.

Figures 80A, 80B:
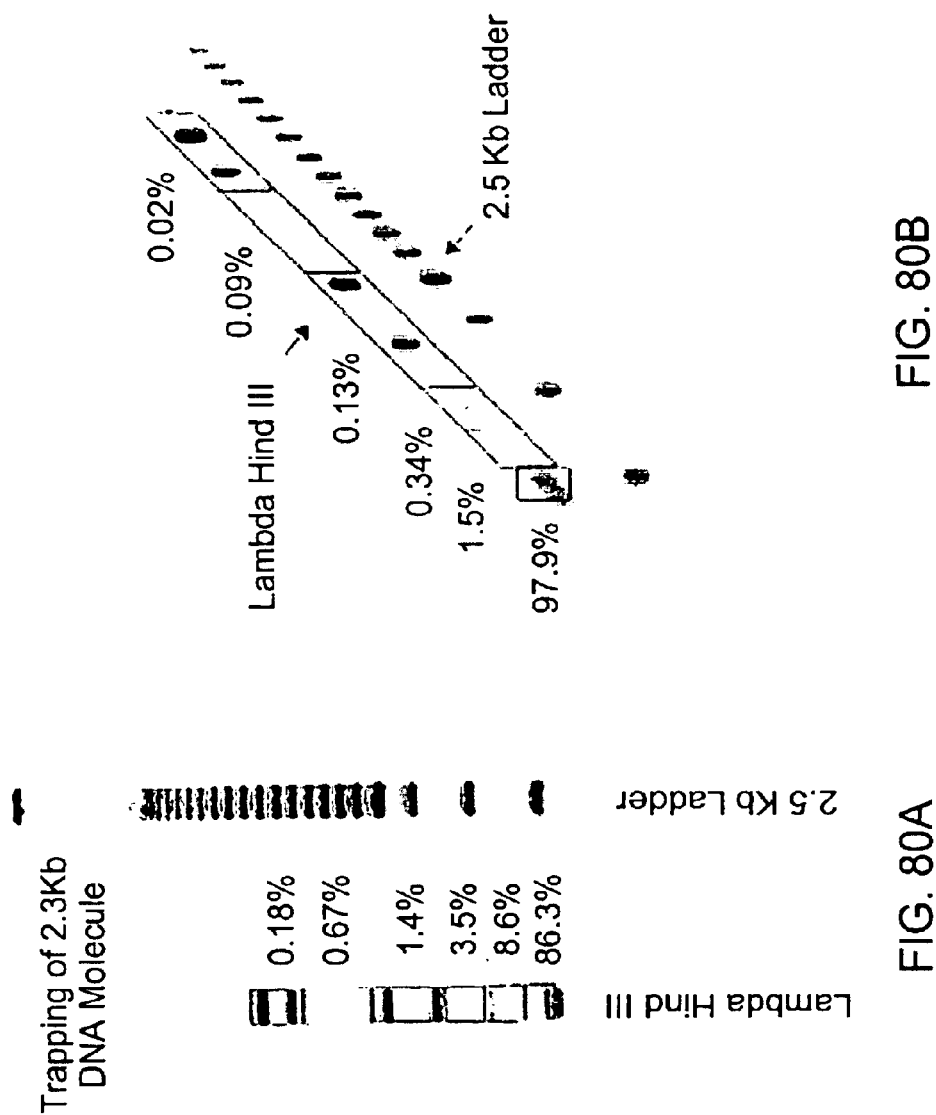
FIGS. 80A and 80B: Trapping of DNA molecules across agarose gels.

One-half microgram of purified lambda DNA is digested with 10 units of Hind III restriction endonuclease (NEB) in 50 µL volume for 3 hours at 37° C. Aliquots of digested lambda DNA (50 ng) are mixed with standard gel loading buffer and separated by 1D FIGE in 0.8% pulsed field grade agarose gel along with 2.5 Kb ladder (Bio Rad). FIG. 80A shows the result of this separation. Electrophoresis is performed in 0.5×TBE buffer on FIGE Mapper at forward voltage of 180 V, reverse voltage of 120 V, linear switch ramps of 0.1–0.8 sec, for 16 hours at room temperature. Sections of the gel are excised and directly analyzed by quantitative PCR as described bellow or a second run is carried out under the same conditions after inverting the gel at 90° resulting in diagonal separation (FIG. 80B).

After staining with Sybr Gold, sections of the gels corresponding to different size are cut out (FIGS. 80A and 80B), quantitated by mass, melted at 95° C., and serially diluted in 10 mM Tris-HCl buffer of pH 7.5. One-microliter aliquots of the prepared serial dilutions are subjected to PCR in 25 μL volume using standard PCR conditions for AdvanTaq+ (Clontech) and oligonucleotides specific for the 2.3 Kb lambda Hind III fragment. The amplified products are separated by electrophoresis in 0.5×TBE buffer on 1% garose under standard conditions, stained with Sybr Gold or EtBr and quantitated on Bio Rad Fluor S MultiImager by integrating the image pixels in specified volumes (Quantity One quantitation software, Bio Rad (Hercules, Calif.)). After normalization, dilution data are expressed as percentage of the total PCR signal.

Figure 81:
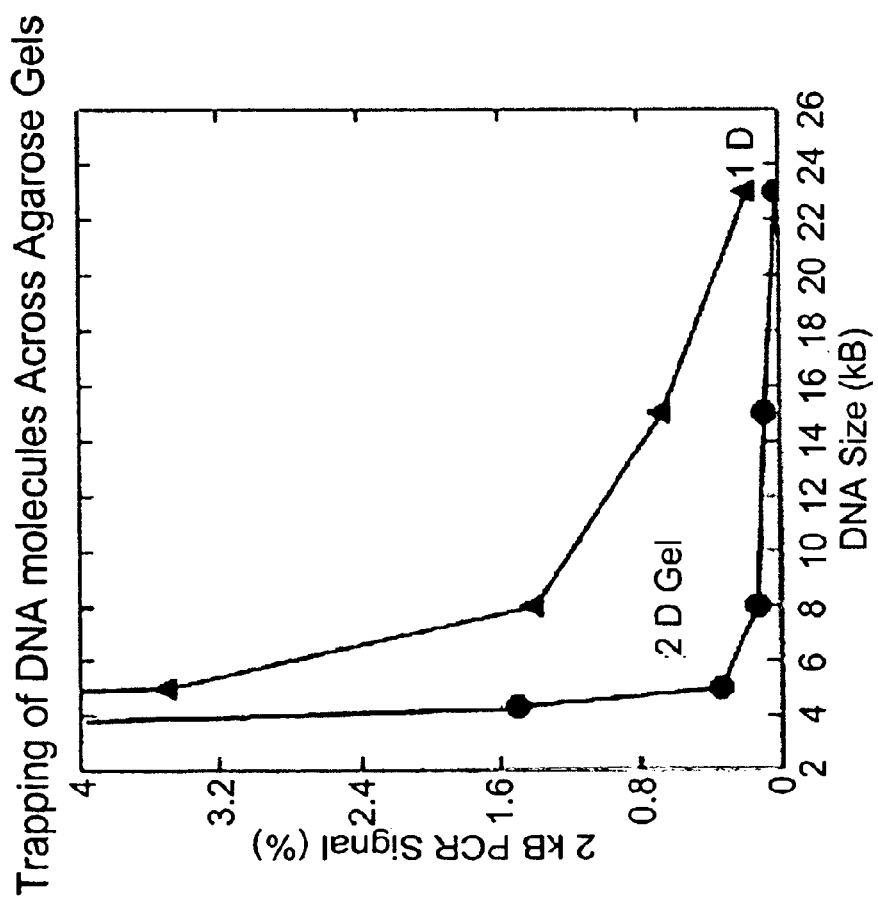
FIG. 81: Graph depicting trapping of DNA molecules across agarose 2D gels.

FIG. 81 shows average percentage distribution of trapped 2.3 Kb DNA across FIGE gel in 1D and 2D separation mode. This experiment demonstrates that 2D diagonal separation offers close to one order of magnitude better separation over 1D electrophoresis as determined by quantitating the level of cross-contamination with smaller molecules over a broad range of DNA size distribution.

Example 30

Removal of Short DNA Sequences and Taq DNA Polymerase from PENT Products by Microcon YM-100 Ultrafiltration This example shows that in the presence of moderate to high concentration of NaCl (0.2–0.625 M) and centrifugal force of 200×g double-stranded fragments of bellow 300 bp could be effectively separated from higher molecular weight DNA on Microcon YM-100 ultrafiltration units (Millipore). It also demonstrates that this procedure adequately removes Taq DNA polymerase as verified by the ability of terminal transferase to catalyze addition of polyG to model template following Microcon YM-100 purification or phenol:chloroform extraction, but not after ethanol precipitation.

Figure 82:
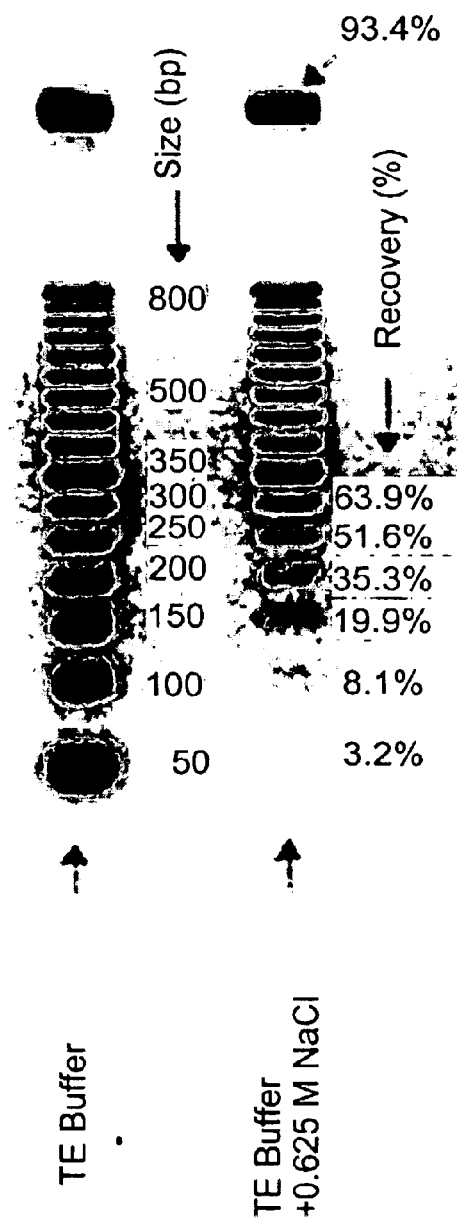
FIG. 82: Recovery of DNA fragments after Microcon YM-100 filtration.

Aliquots of 15 μg 50 bp DNA ladder (Life Technologies) in 400 μL of TE buffer or in 400 μL TE buffer supplemented with 0.5×QF buffer (Qiagen) containing 625 mM NaCl, 7.5% isopropanol, 25 mM Tris-HCl, pH 8.0, are placed in Microcon YM-100 units and centrifuged at 200×g to a volume of 100 μL. Samples are washed 2 times with 500 μL of TE buffer at 200×g, concentrated to a final volume of approximately 50 μL, and analyzed by electrophoresis on 1% agarose gel. After staining with Sybr Gold bands are quantitated on Bio Rad Fluor S MultiImager by integrating the image pixels in specified volumes. FIG. 82 shows comparison between samples filtered in just TE buffer (lane 1) or in TE buffer containing 0.5×QF buffer (lane 2). The amount of DNA in bands filtered in TE buffer is taken as 100% and the recovery of DNA across a range of DNA sizes form the sample filtered in high salt buffer is expressed in %. As shown in FIG. 82, lane 2 the cut-off limit of separation is gradual such that on average 3%, 8%, 20%, 35%, 52%, and 64% are recovered from 50 bp, 100 bp, 150 bp, 200 bp, 250 bp, and 300 bp DNA fragments, respectively. Recovery of kilobase DNA is in the range of 95%.

Figure 83:
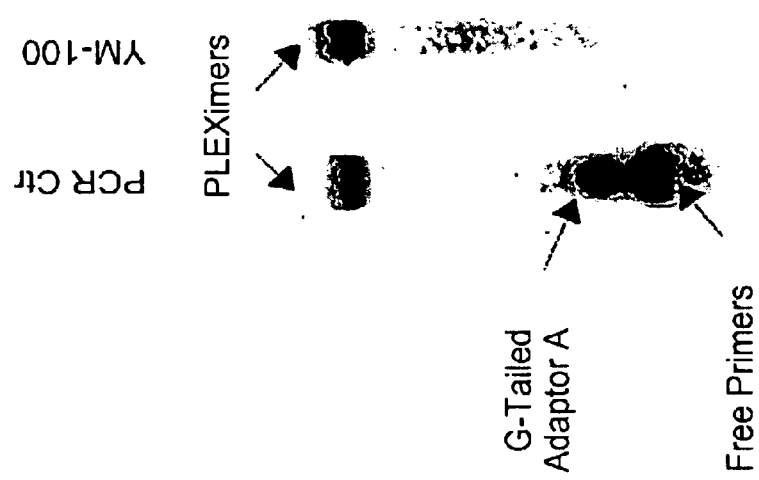
FIG. 83: Removal of free primers and G-tailed adaptor from amplified PENTAmer Not I genomic E. coli library.

Approximately 50 atomoles of primary PENTAmer library prepared from Not I digested *E. coli* genomic DNA are amplified by standard PCR with 5'-fluorescein labeled universal primer specific for adaptor $A_2$ (primer 1) and a poly C (10) primer (primer 2, see Example 4 for details in preparing the library). Thirty two PCR samples (25 μL each) are combined, mixed with ¼ vol of QF buffer (240 mM NaCl, 3% isopropanol, and 10 mM Tris-HCl, pH 8.5 final concentrations), placed in 2 Microcon YM-100 units, and centrifuged at 200×g for approximately 15 min to a volume of 100 μL each. Samples are flushed 2 times with 400 μL of TE buffer at 200×g and concentrated to a final volume of 180 μl total volume. FIG. 83 shows the products of the original PCR reaction (12 μL, lane 1) and 3 μL of the sample obtained after Microcon YM-100 filtration (lane 2) analyzed by electrophoresis on 1% agarose gel after staining with Sybr Gold on Bio Rad Fluor S MultiImager. This experiment demonstrates the complete removal of unreacted primers and small molecules corresponding to free adaptor A tailed with poly G by terminal transferase which are co-amplified as artifact during PCR (see Example 32).

Three picomoles of BamH I digested pUC19 plasmid DNA are dephosphorylated with shrimp alkaline phosphatase (SAP, Roche) and ligated to an equimolar amount of BamH I compatible nick-translation adaptor (Adaptor A1, consisting of primers 3, 4, 5) with 4 units of T4 DNA ligase (Roche) in 100 μL volume at 16° C. overnight. After purification by standard phenol-chloroform extraction and ethanol precipitation, DNA is subjected to time-controlled nick-translation with 32 units of wild-type Taq DNA polymerase in a final volume of 200 μL of 1×Perkin-Elmer PCR buffer II containing 2 mM $MgCl_2$ and 200 μM of each dNTP for 4 min at 50° C. Reaction is stopped by adding 8 μl of 0.5 M EDTA and the sample is ethanol precipitated in the presence of 20 μg tRNA as carrier. One third of the sample is kept as control, one third filtered through Microcon-YM 100 after mixing with 400 μl of 0.5×QF buffer (final concentration of 625 mM NaCl, 7.5% isopropanol, 25 mM Tris-HCl, pH 8.5) and centrifuged at 200×g to a volume of 100 μl. Sample is washed 3 times with 400 μl of TE buffer at 200×g, and concentrated to a final volume of 30 μl. The remaining one third is extracted twice with phenol-chloroform and then subjected to Microcon-YM 100 filtration as described above. One half of each sample is left as control and the other half extended by limited poly-G tailing with 15 units of terminal transferase (Roche) in the buffer recommended by the manufacturer, containing in addition 0.75 mM $CoCl_2$ and 5 μM dGTP, for 20 min at 37° C. Aliquots of each sample are normalized for amount of DNA, diluted in water and tested for tailing by terminal transferase in standard PCR using poly C (10) primer (primer 2) and primer to adaptor A1 (primer 3). Products of the PCR are analyzed on 1% agarose gel along with 1 Kb+ DNA size markers (Life Technologies) after staining with Sybr Gold on Fluor S MultiImager.

Figure 84:
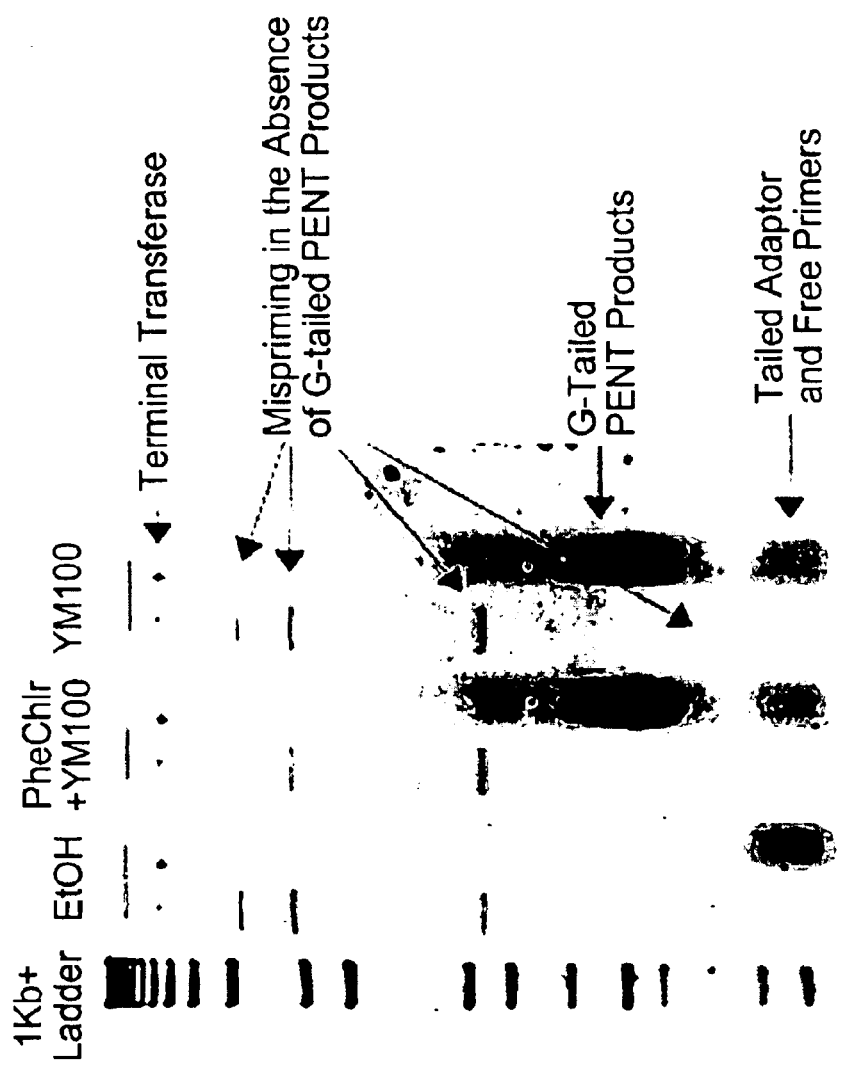
FIG. 84: Removal of inhibitory activity on terminal transferase from PENTAmer products generated from model pUC19 DNA template by Microcon YM-100 ultrafiltration.

FIG. 84 shows that unlike the sample purified only by ethanol precipitation, both Microcon YM-100 treatment and Microcon YM-100 preceded by phenol-chloroform extraction make possible tailing of PENT products by terminal transferase, presumably by removal of Taq polymerase interference. Thus, the combination of phenol-chloroform extraction followed by Microcon YM-100 purification provides the best recovery of PENT products and the most complete removal of proteins, adaptors and free oligonucleotides from kilobase DNA.

Example 31

Purification of Uniform Size DNA Molecules by Reverse Field Isodimensional Focusing (RF-IDF)

This example describes a new electrophoretic procedure used to preparatively focus and purify DNA fragments of desired size or range of sizes in agarose gels with minimum contamination of trapped small molecules.

Aliquots of 10 μg *E. coli* genomic DNA prepared by standard purification are digested in 3 tubes with 4, 2, and 1 units of Sau3AI (NEB) respectively for 20 min at 37° C. in final volume of 100 µl. Samples are combined and loaded on preparative 0.55% pulse-field grade agarose gel (Bio Rad) along with 1 Kb+ ladder (Life Technologies). Electrophoresis in forward direction is performed at 6 V/cm in interrupted mode (60 sec on, 5 sec off) for 1.5 hours. Section of the gel containing a lane of standards and a lane of the DNA sample is excised, stained with Sybr Gold and bands are visualized on Dark Reader Blue Light Transilluminator (Clare Chemical Research). The undesired DNA size impurities smaller than the cut-off threshold of 2 Kb are cut out and removed. The remaining portion of the stained slice is aligned back with the unstained gel and used as a landmark for cutting and removing of the fraction containing undesired small molecules (i.e. below 2 Kb in size). The unstained gel is then run in reverse direction in interrupted field of 6 V/cm (60 sec on, 5 sec off) for 85% of the forward time. After electrophoresis is complete, the gel is stained with Sybr Gold. The bands of interest now focused in a very sharp narrow regions are cut out and recovered from the agarose by Gel Extraction kit (Qiagen, see Example 33).

This method has efficiency of separation similar to that of two-dimensional gels, while preserving the simplicity of the traditional 1D gel electrophoresis. RF-IDF has been successfully applied for preparing size-fractionated genomic libraries of partial restriction digests as described in this example, purification of PENT products obtained by nick-translation from such libraries, and removal of adaptor sequences and adaptor dimers following PCR amplification.

Example 32

Preparation of Prototype Single Stranded Not I PENTAmer Library of E.coli MG-1655 Immobilized on Magnetic Beads and Analysis of Specific Kernel Sequences by Restriction Fingerprinting Display and Sequencing.

This example describes an optimized multi-step procedure to generate PENTAmer NotI library of E. coli immobilized on magnetic beads. Fluorescent end-labeled derivatives of the library prepared by PCR are used to display and analyze restriction fingerprint patterns on acrylamide or agarose gels or by end-labeled fragment analysis on sequencing instrument.

Genomic DNA embedded in agarose plugs is prepared by standard procedure from E. coli MG-1655 strain. After equilibrating the plugs with 1×NotI buffer (Roche) and melting the agarose at 65° C. approximately 10 µg of DNA are digested overnight at 37° C. with 20 units of Not I restriction enzyme (Roche). DNA is dephosphorylated with 5 units of shrimp alkaline phosphatase (SAP, Roche) for 15 min at 37° C. and heated for 15 min at 65° C. to inactivate SAP. Agarose is solidified at 4° C., plugs washed 5 times with 1 ml of 1×Gelase buffer (Perkin Elmer) over a period of 1 hour, melted at 65° C. for 15 min and agarose is digested with 5 units of Gelase (Perkin Elmer) at 45° C. for 2 hours.

Sample is brought to a volume of 800 µl with TE buffer containing 0.1 mM EDTA (TE-L buffer), supplemented with NaCl to a final concentration of 280 mM and split into 2 Microcon YM-100 units. Samples are centrifuged at 200×g for approximately 15 min to a volume of 100 µl, then washed twice with 400 µl of TE-L buffer at 200×g and finally concentrated to a final volume of 50 µl each.

Five micrograms of the DNA digest is mixed with 160 fmoles of pre-assembled NotI nick-translation adaptor (adaptor $A_2$—primers 5, 6 and 7). Ligation is carried out overnight at 16° C. with 1300 units of T4 ligase (NEB) in 100 µL volume. Sample is extracted with equal volume of phenol-chloroform and subjected to Microcon YM-100 filtration as described above to remove excess free adaptor.

The purified sample is subjected to nick-translation with 16 units of wild type Taq DNA polymerase (from David Engelke, University of Michigan Medical School, Department of Biological Chemistry) in 1×PCR buffer (Perkin Elmer buffer II) containing 2 mM $MgCl_2$ and 200 M of each dNTP for 5 min at 50° C. Reaction is stopped by addition of 5 µl of 0.5 M EDTA pH 8.0 and products are analyzed on 6% TBE-urea gel (Novex) after staining with Sybr Gold.

Due to steric constraints restricting binding of molecules originating from longer NotI fragments and favoring binding of PENT products derived from short NotI fragments, a heat denaturing step is introduced prior to binding of nick-translated DNA to magnetic beads. The sample is denatured by boiling at 100° C. for 5 min and cooled on ice for 3 min. Five hundred µg of streptavidin coated Dynabeads M-280 (Dynal) are prewashed with TE-L buffer and resuspended in 2×BW buffer (20 mM Tris-HCl, 2 mM EDTA, 2 M NaCl, pH 7.5). Denatured DNA is mixed with equal volume of beads in 2×BW buffer and placed on rotary shaker for 1 hr at room temperature. The beads are bound to magnet and washed with 3×100 µl each of 1×BW buffer and TE-L buffer. Non-biotinylated DNA is removed by incubating the beads in 100 µl of 0.1 N NaOH for 5 min at room temperature. Beads are neutralized by washing five times with 100 µl of TE-L buffer and then ressuspended in 50 µl of the same buffer.

Approximately 40 fmoles of library DNA corresponding to 30 µl beads are extended by limited poly-G tailing with 12 units of terminal transferase (Roche) in the buffer recommended by the manufacturer, containing in addition 0.75 mM $CoCl_2$ and 5 µM dGTP, for 20 min at 37° C. Reaction is quenched by adding 2 µl of 0.5 M EDTA and DNA cleaned by sequential washing with 2×100 µl each of TE-L buffer, 1×BW buffer, and TE-L buffer.

One µl aliquots of 10×, 50×, and 100× dilutions of poly-G extended library beads or control beads containing DNA that is not tailed with terminal transferase are used as template in standard PCR reaction with universal poly C (10) primer (primer 3) and NotI adaptor primer (primer 3) and analyzed on 1% agarose gel after Sybr Gold staining (FIG. 86A). Only two types of molecules are amplified—approximately 1 Kb band with relatively broad size distribution corresponding to library PENTAmers originating at Not I sites and having heterogeneous 3' ends and approximately 100 bp molecules, corresponding to residual free adaptor NotI which is poly G tailed and coamplified as a byproduct. As shown later, this artifact can be effectively removed by Microcon YM-100 treatment.

Figures 85A, 85B:
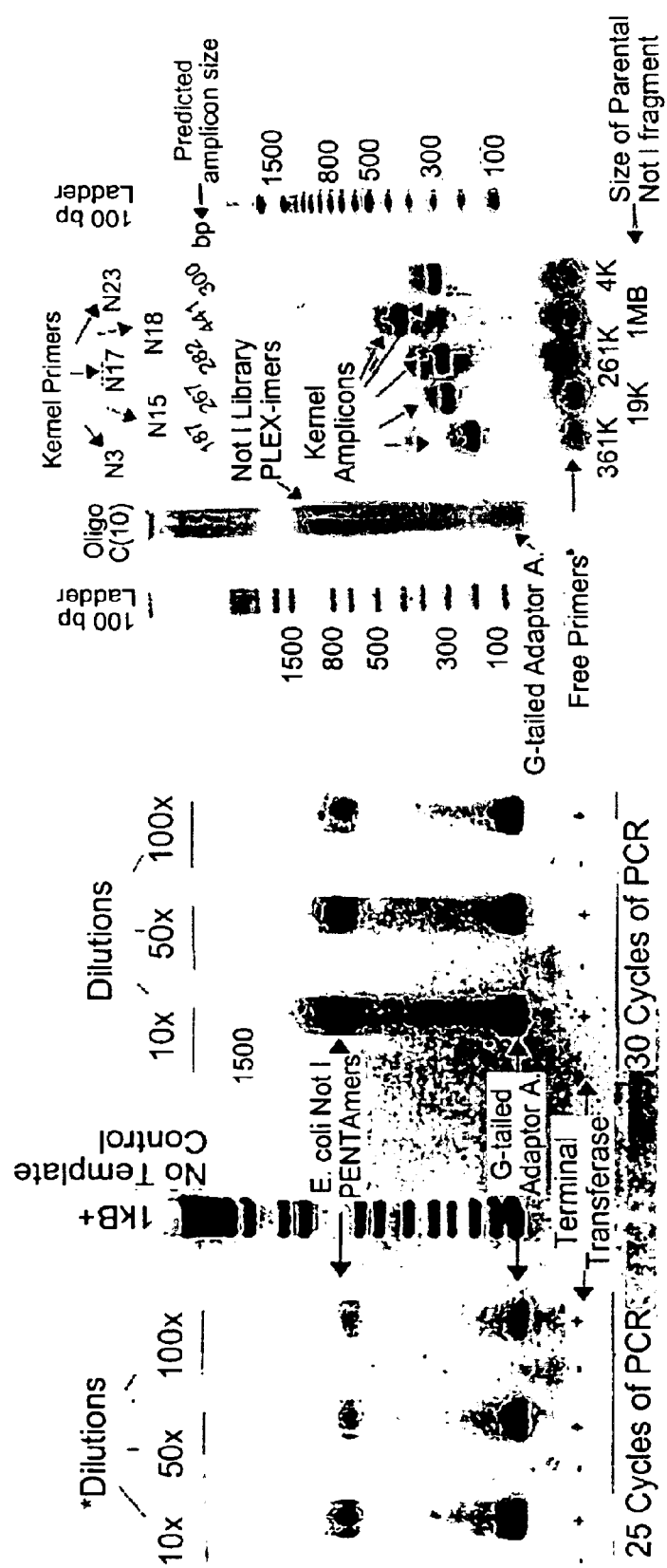
FIG. 85: PCR amplification of genomic Not I PENTAmer E. coli library and selected kernel sequences.

To test the quality and representativity of the prepared Not I PENTAmer library, specific sequences within 1 Kb from NotI sites (i.e. predicted to be within the nick-translated PENT products) are analyzed by PCR. The product of the PCR amplification from the previous step, obtained after 30 cycles of amplification of 10× diluted primary library, is purified using Qiaquick PCR purification kit (Qiagen). After appropriate dilution the sample is used as PCR template with universal Not I adaptor primer (primer 3) and a set of 5 internal primers specific for predicted PENT products originating from Not I fragments ranging from 4 kB to 1 Mb in size (FIG. 85B). This experiment demonstrates that the library is representative and all five sequences tested are present in proportional amounts in the library. The products of the PCR reactions are purified using Qiaquick PCR purification kit and subjected to dye-terminator cycle sequencing with the universal Not I adaptor primer (primer 3) using OpenGene sequencing instrument (Visible Genetics) under the manufacturer's protocol. All five sequences were confirmed to match the published database of the E. coli Genome Center at the University of Wisconsin-Madison.

Figures 87A, 87B:
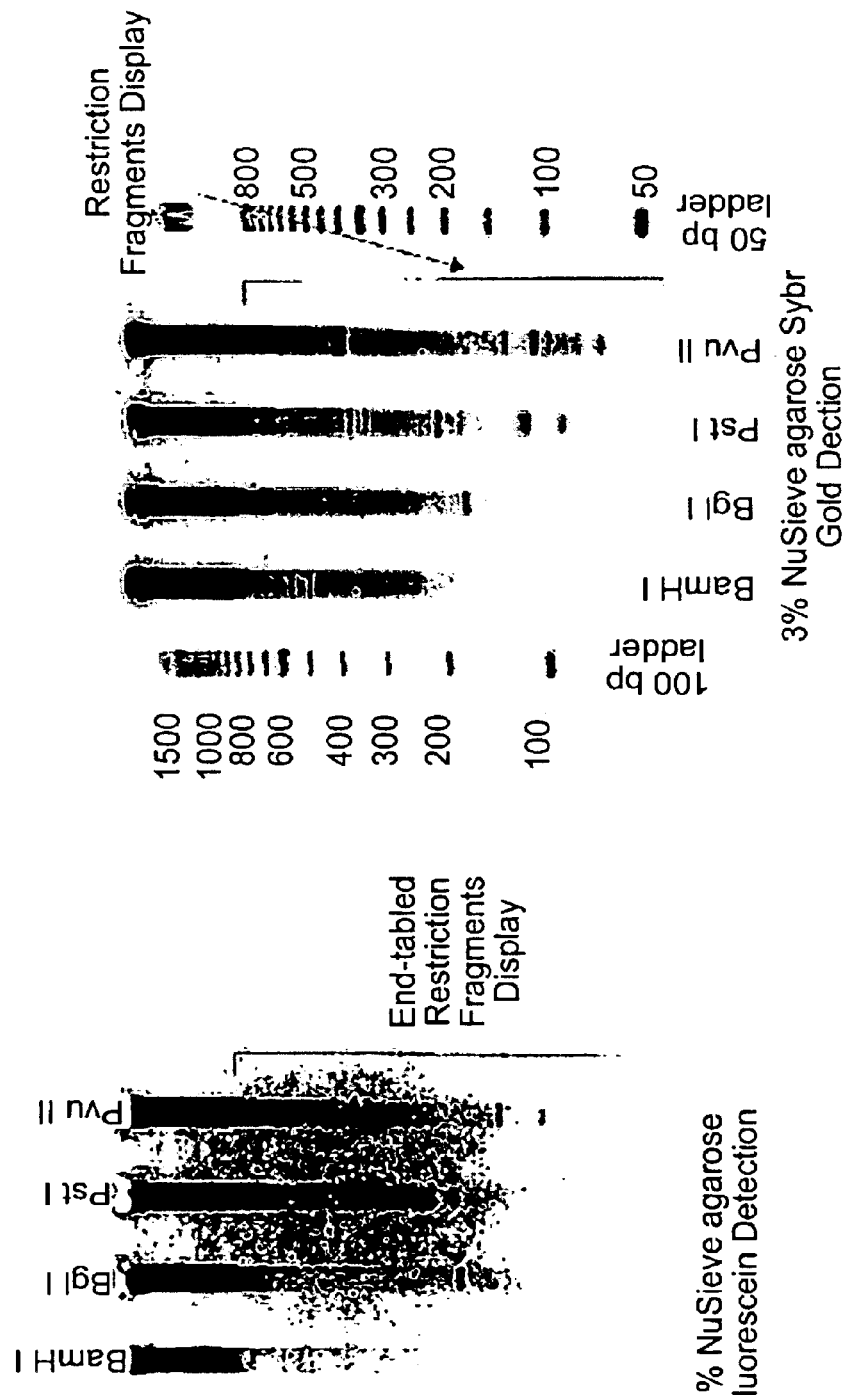
FIGS. 87A and 87B: Restriction enzyme fingerprint display of end-labeled E. coli genomic Not I PENTAmer library.

Large-scale PCR is carried out to prepare sufficient amounts of end-labeled library DNA suitable for restriction enzyme fingerprint display analysis. Approximately 50 atomoles of Not I E. coli PENTAmer library DNA per reaction is used as PCR template with poly C (10) primer (primer 2) and 5'-fluorescein labeled universal Not I adaptor primer (primer 8) in 32 individual tubes (25 μl each). The combined PCR products are purified away from artifact adaptor dimers by mixing with ¼ vol of QF buffer (240 mM NaCl, 3% isopropanol, and 10 mM Tris-HCl, pH 8.5 final concentrations) and filtration in 2 Microcon YM-100 units. Samples are centrifuged at 200×g to a volume of 100 μl, then washed 3 times with 400 μl of TE-L buffer at 200×g and concentrated to a final volume of 180 μl (see Example 30, FIG. 83). Aliquots of 500 ng of the prepared end-labeled library are digested overnight at 37° C. with 10 units of four restriction enzymes Bgl II, Pst I, Pvu II, and BamH I (NEB) in final volume of 30 μl and 250 ng of each digest are analyzed on acrylamide 4–20% gradient gel (Novex) or 3% NuSieve agarose gel (BioWitteker) along with DNA size markers. Gels are first analyzed on Fluor S MultiImager (Bio Rad) for fluorescein signal (FIG. 86A; FIG. 87A) then stained with Sybr Gold and imaged on Fluor S MultiImager (FIG. 86B; FIG. 87B). This experiment validates the presence of all predicted 46 different end-labeled sequences originating from 23 separate Not I sites in the E. coli genome.

Similar analysis of end-labeled fragments but at much higher sensitivity and at single base resolution is performed by fingerprint display of Cy-5.0 end-labeled library derivative using the fragment analysis feature of the OpenGene sequencing instrument of Visible Genetics. Labeling is carried out by PCR. Approximately 50 amoles of Not I E. coli PENTAmer library DNA per reaction is used as PCR template with universal poly C (10) primer and 5'-Cy-5.0 labeled Not I adaptor primer (primers 1 and 2) in 16 individual tubes (25 μl each). The combined PCR products are purified out of adaptor dimers by supplementing with ¼ vol of QF buffer (240 mM NaCl, 3% isopropanol, and 10 mM Tris-HCl, pH 8.5 final concentrations) and filtratered in Microcon YM-100 unit. Sample is centrifuged at 200×g to a volume of 100 μl, then washed 3 times with 400 μl of TE-L buffer at 200×g and concentrated to a final volume of 74 μl. Aliquots of 200 ng of the prepared end-labeled library are digested overnight at 37° C. with 20 units of Hha I, Msp I, and Pst I restriction enzymes (NEB) in final volume of 50 μl and samples are concentrated by standard ethanol precipitation to a volume of 5 μl. Between 20 and 40 ng of the respective digests are loaded per lane on OpenGene sequencing gel (Visible Genetics) in 1×formamide loading buffer along with DNA size markers (Amersham-Pharmacia) Table 7 shows analyses of displayed 38 end-labeled fragments obtained after digestion with Hha I.

TABLE 7

Predicted and Experimentally Determined Sizes of Hha I Restriction Fragments from Primary Genomic Not I E. coli PENTAmer Library

| Predicted Fragment Size (bp) | Calculated Fragment Size (bp) |
| --- | --- |
| 60 | 61.7 |
| 64 | 63.4 |
| 73 | 70.2 |
| 78 | 77.5 |
| 79 | 78.6 |
| 82 | 83.5 |
| 83 | 85.6 |
| 103 | 102.9 |
| 105 | 104.5 |
| 112 | 112.9 |
| 120 | 124.4 |
| 128 | 128.2 |
| 152 | 150.6 |
| 164 | 159.0 |
| 165 | 161.2 |
| 167 | 167.9 |
| 173 | 176.6 |
| 184 | 192.3 |
| 198 | 194.6 |
| 201 | 199.6 |
| 202 | 201.9 |
| 222 | 220.1 |
| 232 | 230.2 |
| 233 | 231.1 |
| 244 | 240.5 |
| 245 | 243.1 |
| 268 | 262.5 |
| 281 | 276.0 |
| 282 | 278.2 |
| 299 | 300.1 |
| 338 | 337.2 |
| 348 | 350.2 |
| 366 | 369.0 |
| 372 | 377.8 |
| 405 | 409.4 |
| 454 | 461.8 |
| 469 | 481 |
| 558 | 574.3 |

The elution times obtained after running DNA size standards are plotted as a function of size and fit to a first order linear regression equation using Dplot 95 software (USAE Waterways, correlation coefficient=0.9997). Sizes of the analyzed restriction fragments are extrapolated from the constructed plot and compared to predicted restriction pattern for the Hha I restriction enzyme for 1 Kb PENT molecules originating at Not I sites in the E. coli genome database. Discrepancy between predicted and experimental results is within 3%. This example demonstrates that the prepared primary Not I genomic PLEX-imer library is representative for all predicted sequences in the E. coli genome.

Example 33

Preparation and Analysis of PENTAmer Library from E. coli BamH I Complete Genomic Digest This example describes a protocol for preparation of primary PENTAmer library of higher complexity from E. coli genomic DNA with upstream nick-translation BamH I compatible adaptor A and downstream nick-attaching adaptor B having randomized bases at the strand used to direct ligation at the 3' end of nick-translated PENT molecules.

Genomic DNA is prepared by standard procedure from E. coli MG-1655. 10 μg of DNA aliquot is digested at 37° C. for 4 hours with 120 units of BamH I restriction enzyme (NEB) in total volume of 150 μl. The sample is split into two tubes, diluted twice with water, supplemented with 1×SAP buffer (Roche) and DNA is dephosphorylated with 10 units of SAP (Roche) for 20 min at 37° C. SAP is heat-inactivated for 15 min at 65° C. and DNA is purified by extraction with equal volume of phenol-chloroform followed by precipitation with ethanol. Digested DNA is dissolved in 50 μl of 10 mM Tris-CL pH 7.5.

The sample is mixed with 3 pmoles of pre-assembled BamH I nick-translation adaptor (Adaptor A3—primers 9, 10, and 11) and ligation is carried out overnight at 16° C. with 1200 units of T4 ligase (NEB) in 60 μl volume. To remove ligase and excess free adaptor the sample is extracted with equal volume of phenol-chloroform, supplemented with ¼ volume of QF buffer (240 mM NaCl, 3% isopropanol, and 10 mM Tris-HCl, pH 8.5 final concentrations) in a volume of 400 μl and centrifuged at 200×g to 100 μl. The sample is then washed 3 times with 400 μl of TE-L buffer at 200×g and concentrated to a volume of 80 μl.

The purified sample is subjected to nick-translation with 20 units of wild type Taq polymerase in 1×Perkin Elmer PCR buffer buffer II containing 2 mM $MgCl_2$ and 200 μM of each dNTP for 5 min at 50° C. Reaction is stopped by addition of 5 μl of 0.5 M EDTA pH 8.0 and products are analyzed on 6% TBE-urea gel (Novex) after staining with Sybr Gold.

To increase representativity of single-stranded PENT molecules bound to streptavidin beads and to prevent their reassociation with the strand used as template for nick-translation in the region of the adaptor an oligonucleotide complementary to the template strand spanning the entire adaptor sequence (primer 13) is added at a final concentration of 0.8 μM and the sample is denatured by boiling at 100° C. for 3 min and cooling on ice for 5 min. 800 μg of streptavidin coated Dynabeads M-280 (Dynal) are pre-washed with TE-L buffer and resuspended in 2×BW buffer (20 mM Tris-HCl, 2 mM EDTA, 2 M NaCl, pH 7.5). Denatured DNA is mixed with equal volume of beads in 2×BW buffer and placed on rotary shaker for 1 hr at room temperature. The beads are bound to magnet and washed with 3×100 μl each of 1×BW buffer and TE-L buffer. Non-biotinylated DNA is removed by incubating the beads in 100 μl of 0.1 N NaOH for 5 min at room temperature. Beads are neutralized by washing with 5×100 μl of TE-L buffer and then resuspended in 20 μl of water.

Adaptor $B_1$ is ligated to the single-stranded primary BamH I PENT library bound to magnetic beads. Adaptor $B_1$ consists of two oligonucleotides, one of which is 5'-phosphorylated and 3'-blocked (primer 14), and its complement that has a 3'-extension with four random bases and is also 3'-blocked primer 15). The latter oligonucleotide will anneal and direct the phosphorylated strand to single-stranded genomic PENT library molecules. The library DNA from the previous step is mixed with 40 pmoles of each adaptor B1 oligonucleotide in 1×T4 ligase buffer and 1200 units of T4 ligase (NEB) in final volume of 30 μl. Ligation is performed at room temperature for 1 hour on end-to-end rotary shaker to keep the beads in suspension. Beads are bound to magnet, washed with 2×100 μl each of 1×BW buffer and TE-L buffer and nonbiotinylated DNA molecules are removed by incubating the beads in 100 μl of 0.1 N NaOH for 5 min at room temperature. Beads are neutralized by washing with 5×100 μl of TE-L buffer, ressuspended in 100 μl of storage buffer (SB containing 0.5 M NaCl, 10 mM Tris-HCl, 10 mM EDTA, pH 7.5) and stored at 4° C.

Figure 88:
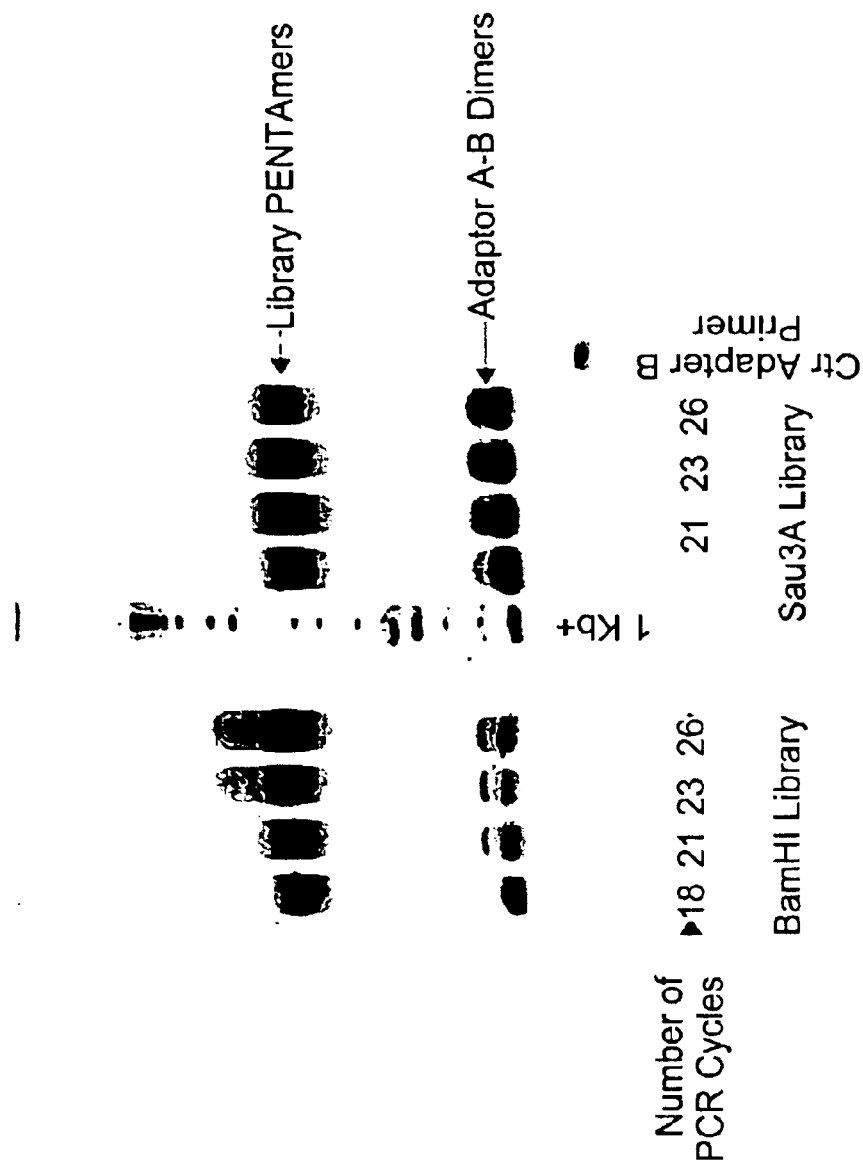
FIG. 88: PCR amplification of PENTAmer libraries prepared from human genomic DNA after partial Sau3A I or complete BamH I restriction digestion.

FIG. 88 shows analysis of selected random *E. coli* sequences in the *E. coli* genome adjacent to Bam HI sites to assess the quality and representativity of the library. One microliter of library beads diluted 10× in water are used as template in PCR reactions with universal adaptor B primer (primer 16) and 5 specific *E. coli* primers adjacent to BamH I sites. A negative control with adaptor B primer alone and a positive control with adaptor B and adaptor A primers (primers 12, 16) are also included. Aliquots of the PCR reactions are separated on 1% agarose gel and visualized on Fluor S MultiImager (Bio Rad) after staining with Sybr Gold. All five analyzed *E. coli* sequences are present in the library and are amplified as 1 Kb fragments. The sequences are confirmed by dye-terminator cycle sequencing using standard OpenGene protocol (Visible Genetics) and specific primers.

Example 34

Preparation and Analysis of PENTAmer Library from *E. coli* Sau 3AI Partial Genomic Digest This example demonstrates that a library of even higher complexity can be prepared from *E. coli* genomic DNA using partial digest with frequently cutting enzyme. This library can be potentially used for feeling gaps and de novo sequencing of genomes having the complexity of an average bacterial genome.

Aliquots of 10 μg *E. coli* genomic DNA prepared by standard purification are digested in 3 tubes with 4, 2, and 1 units of Sau3A I (NEB) respectively for 20 min at 37° C. in final volume of 100 μl. DNA fragments are size-fractionated by RF-IDF (see Example 3). Samples are combined and loaded on preparative 0.55% pulse-field grade agarose gel (Bio Rad) along with 1 Kb+ ladder (Life Technologies). Electrophoresis in forward direction is performed at 6 V/cm in interrupted mode (60 sec on, 5 sec off) for 1.5 hours. Section of the gel containing a lane of standards and a lane of the DNA sample is excised, stained with Sybr Gold and bands are visualized on Dark Reader Blue Light Transilluminator (Clare Chemical Research). The undesired DNA size impurities smaller than the cut-off threshold of 2 Kb are cut out and removed. The remaining portion of the stained slice is aligned back with the unstained gel and used as a landmark for cutting and removing of the fraction containing undesired small molecules (i.e. below 2 Kb in size). The unstained gel is then run in reverse direction in interrupted field of 6 V/cm (60 sec on, 5 sec off) for 85% of the forward time. After electrophoresis is complete the gel is stained with Sybr Gold. The bands of interest now focused in a very sharp narrow regions are cut out and recovered from the agarose by Gel Extraction kit (Qiagen) in 10 mM Tris-HCl pH 8.5.

The sample is split into two tubes, supplemented with 1×SAP buffer (Roche) and DNA is dephosphorylated with 15 units of SAP (Roche) for 20 min at 37° C. SAP is heat-inactivated for 15 min at 65° C. and DNA is purified by extraction with equal volume of phenol-chloroform and precipitation with ethanol. Digested DNA is dissolved in 100 μl of TE-L buffer.

The sample is mixed with 40 pmoles of pre-assembled BamH I nick-translation adaptor (adptor $A_3$—primers 9, 10, 11) and ligation is carried out overnight at 16° C. with 2,800 units of T4 ligase (NEB). To remove ligase and excess free adaptor the sample is extracted with equal volume of phenol-chloroform then mixed with ¼ vol of QF buffer (240 mM NaCl, 3% isopropanol, and 10 mM Tris-HCl, pH 8.5 final concentrations) in a volume of 400 μl and centrifuged at 200×g for app. 15 min to a volume of 100 μl on Microcon YM-100. The sample is then washed 3 times with 400 μl of TE-L buffer at 200×g and concentrated to a volume of 135 μl.

The purified sample is subjected to nick-translation with 38 units of wild type Taq DNA polymerase in 1×Perkin Elmer PCR buffer buffer II containing 4 mM $MgCl_2$ and 200 μM of each dNTP in final volume of 240 μl for 5 min at 50° C. Reaction is stopped by addition of 6 μl of 0.5 M EDTA pH 8.0 and products are analyzed on 6% TBE-urea gel (Novex) after staining with Sybr Gold.

The sample is supplemented with blocking oligonucleotide complementary to the nick-translation template strand adaptor sequence (primer 13) at a final concentration of 1 μM denatured by boiling at 100° C. for 3 min and cooled on ice for 5 min. 1.2 mg of streptavidin coated Dynabeads M-280 (Dynal) are prewashed with TE-L buffer and resuspended in 2×BW buffer (20 mM Tris-HCl, 2 mM EDTA, 2 M NaCl, pH 7.5). Denatured DNA is mixed with equal volume of beads in 2×BW buffer and placed on rotary shaker for 2 hr at room temperature. The beads are bound to magnet and washed with 2×100 μl each of 1×BW buffer and TE-L buffer. Non-biotinylated DNA is removed by incubating the beads in 100 μl of 0.1 N NaOH for 5 min at room temperature. Beads are washed with 100 μl of 0.1 N NaOH, neutralized by washing with 5×100 μl of TE-L buffer, and resuspended in 150 μl of TE-L buffer.

One half of the prepared library DNA is then processed for ligation with adaptor B1. To minimize formation of adaptor A-B dimers on magnetic beads the suspension (75 μl) is supplemented with 1×T4 ligase buffer (NEB) incubated with 50 pmoles of 3'-blocked oligonucleotides one of which is complementary to the biotinylated adaptor A strand and has 3'-extension of 24 bases (primer 17) to which the second oligonucleotide (primer 18) is complementary. The suspension is heated for 1 min at 60° C., cooled to room temperature and incubated for 10 min at room temperature to anneal the blocking oligonucleotides to residual adaptor A molecules bound to magnetic beads. Beads are then washed with 50 μl of 1×T4 ligase buffer and resuspended in 50 μl of the same buffer. Adaptor B1 having 3' extension of 4 randomized bases which will anneal and direct the phosphorylated strand to PENT library molecules (see Example 4) is then ligated to the library DNA. The sample from the previous step is supplemented with 40 pmoles of each adaptor B oligonucleotide (primers 14, 15) in 1×T4 ligase buffer and 4000 units of T4 ligase (NEB) in final volume of 55 μl. Ligation is performed at room temperature for 3 hours on end-to-end rotary shaker to keep the beads in suspension. Beads are bound to magnet, washed with 2×100 μl each of 1×BW buffer and TE-L buffer and nonbiotinylated DNA removed by incubating the beads in 100 μl of 0.1 N NaOH for 5 min at room temperature. Beads are washed with 100 μl of 0.1 N NaOH, neutralized by washing with 5×100 μl of TE-L buffer, resuspended in 90 μl of SB buffer and stored at 4° C.

Figure 89:
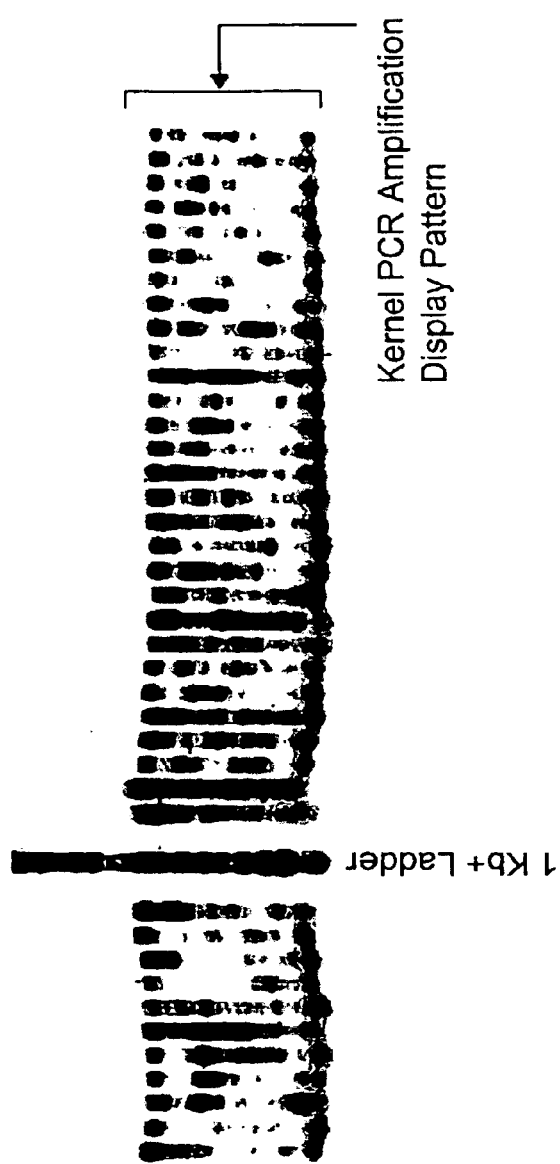
FIG. 89: PCR amplification of 40 kernel sequences from PENTAmer library prepared from E. coli genomic partial Sau3A I restriction digest.

FIG. 89 shows analysis of representivity of the PENTAmer library from E. coli Sau 3AI partial genomic digest. Forty random oligonucleotides specific for regions of the E. coli genome located approximately 100–200 bp downstream of Sau3A I restriction sites were designed to have high internal stability and low frequency of their six 3'-terminal bases matched against E. coli genomic frequency database (Oligo Primer Analysis software, Molecular Biology Insights). Magnetic beads containing library DNA are prewashed with water and 1 μl used as template for PCR amplification with 100 nM of universal adaptor B primer (primer 16) and 100 nM of each E. coli kernel primer in a final volume of 25 μl. After initial denaturing 32 cycles are carried out at 94° C. for 10 sec and 68° C. for 75 sec.

Five-microliter aliquots are separated on 1% agarose gel and visualized on Fluor S MultiImager (BioRad; Hercules, Calif.) after staining with Sybr Gold. As shown in FIG. 89, specific patterns of fragments are generated for each sequence. The bands correspond to amplified PENTAmers having the kernel sequence at different positions relative to the ligated adaptor B1. This pattern of amplification reflects the frequency of Sau3A I sites relative to a given kernel sequence and confirms the prediction for PLEX-imer libraries prepared from partially digested genomic DNA with frequently cutting restriction endonucleases.

The example demonstrates that normalized representative primary PENTAmer libraries can be prepared from E. coli genomic DNA following partial digest with frequent cutter and are potentially useful for gap feeling and de novo walking sequencing.

Example 35

Preparation and Analysis of PENTAmer Libraries from Human Genomic DNA after Complete Bam H I or Partial Sau3A I Digestion This example describes the preparation of primary human genomic PENTAmer libraries bound to magnetic beads and their amplification with universal adaptor primers.

Aliquots of 10 μg genomic DNA prepared by standard purification from fresh human lymphocytes are digested with 140 units of BamH I (NEB) for 6 hours at 37° C. or with 20 units of Sau3A I (New England Biolabs; Beverly, Mass.) for 35 min at 37° C. 20 μg of Bam H I or 50 μg of Sau3A I digested DNA are treated with 3 units/μg of SAP (Roche; Nutley, N.J.) for 20 min at 37° C. SAP is heat-inactivated for 15 min at 65° C. and DNA is purified by extraction with equal volume of phenol-chloroform and precipitation with ethanol. DNA fragments are size-fractionated by preparative RF-IDF in 0.75% pulse-field grade agarose gel (Bio Rad; Hercules, Calif.) as described in Example 3. Electrophoresis in forward direction is performed at 6 V/cm in interrupted mode (60 sec on, 5 sec off) for 2 hours. After cutting the section of the gel containing DNA molecules bellow 2 Kb, reverse field is applied at 6 V/cm (60 sec on, 5 sec off) for 1.7 hours. Bands are excised and recovered from the agarose by Gel Extraction kit Gel Extraction kit (Qiagen) in 10 mM Tris-HCl pH 8.5.

Samples are mixed with 1.2 pmoles (BamH I) or 6 pmoles (Sau3A I) of pre-assembled BamH I nick-translation adaptor (adaptor A3-primers 9, 10, 11) and after heating at 65° C. for 1 min ligation is carried out at 20° C. for 2.5 hours with 4,800 units of NEB T4 ligase (Bam H I) or 11,200 units of NEB T4 ligase (Sau3A I). To remove ligase and excess free adaptor the sample is extracted with equal volume of phenol-chloroform then mixed with ¼ vol of QF buffer (240 mM NaCl, 3% isopropanol, and 10 mM Tris-HCl, pH 8.5 final concentrations) in a volume of 400 μl and centrifuged at 200×g for approximately 15 min to a volume of 100 μL in Microcon YM-100 filtration units. The samples are washed 3 times with 400 μl of TE-L buffer at 200×g and concentrated to a volume of 65 μl (BamH I) and 120 μl (Sau3A I).

The purified samples are subjected to nick-translation with 19 units (BamH I) or 38 units (Sau3A I) of wild type Taq DNA polymerase in 1×Perkin Elmer PCR buffer buffer II containing 4 mM $MgCl_2$ and 200 μM of each dNTP in final volume of 120 μl (Bam H I) or 240 μl (Sau3A I) for 5 min at 50° C. Reactions are stopped by addition of 6 μl of 0.5 M EDTA pH 8.0 and products are analyzed on 6% TBE-urea gel (Novex) after staining with Sybr Gold.

Samples are supplemented with blocking oligonucleotide complementary to the nick-translation template strand at the region of the adaptor (primer 13) at a final concentration of 1 µM denatured by boiling at 100° C. for 3 min and cooled on ice for 5 min. 1.8 mg of streptavidin coated Dynabeads M-280 (Dynal) are prewashed with TE-L buffer and resuspended in 2×BW buffer (20 mM Tris-HCl, 2 mM EDTA, 2 M NaCl, pH 7.5). Denatured DNA samples are mixed with equal volume of beads (⅓ of the total beads with Bam H 1 and ⅔ with Sau 3A I samples) in 2×BW buffer and placed on rotary shaker for 1.5 hr at room temperature. The beads are bound to magnet and washed 2× with 100 µl each of 1×BW buffer and TE-L buffer. Non-biotinylated DNA is removed by incubating the beads in 100 µl of 0.1 N NaOH for 5 min at room temperature. Beads are washed with 100 µl of 0.1 N NaOH, neutralized by washing with 5×100 µl of TE-L buffer, and resuspended in TE-L buffer.

Prepared library DNA samples are then processed for ligation with adaptor B. To minimize formation of adaptor A-B dimers on magnetic beads the beads suspensions are supplemented with 1×T4 ligase buffer (NEB) and incubated with 50 pmoles of 3'-blocked oligonucleotides (primers 17 and 18) as described in Example 6. The suspensions are heated for 1 min at 60° C., cooled to room temperature and incubated for 10 min at room temperature to anneal the blocking oligonucleotides to residual adaptor A molecules bound to magnetic beads. Beads are then washed with 50 µl of 1×T4 ligase buffer and resuspended in 50 µl of the same buffer. Adaptor B1 having 3' extension of 4 randomized bases which will anneal and direct the phosphorylated strand to PENT library molecules is then ligated to the library DNA. The samples are supplemented with 40 pmoles (BamH I) or 80 pmoles (Sau3A I) of each adaptor B1 oligonucleotide (primers 14 and 15) in 1×T4 ligase buffer and 4000 units (BamH I) or 8000 units (Sau3A I) of T4 ligase (NEB) in final volume of 100 µl (BamH I) or 200 µl (Sau3A I). Ligation is performed at room temperature for 3.5 hours on end-to-end rotary shaker to keep the beads in suspension. Beads are bound to magnet, washed with 2×100 µl each of 1×BW buffer and TE-L buffer and non-biotinylated DNA is removed by incubating the beads in 100 µl of 0.1 N NaOH for 5 min at room temperature. Beads are washed with 100 µl of 0.1 N NaOH, neutralized by washing with 5×100 µl of TE-L buffer, resuspended in 160 µl (BamH I) or 280 µl (Sau 3A I) of SB buffer and stored at 4° C.

Figure 90:
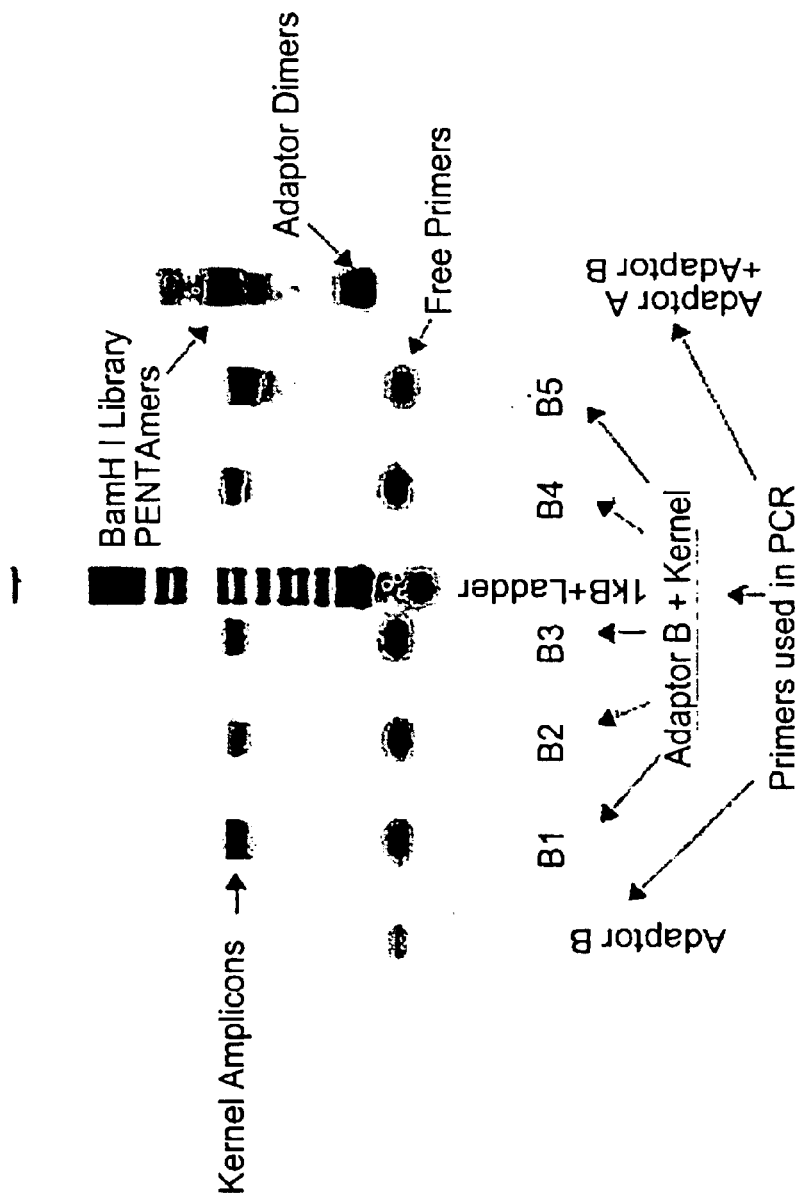
FIG. 90: PCR amplification of genomic BamH I PENTAmer E. coli library and selected kernel sequences.

FIG. 90 shows amplification of the primary PENTAmer libraries from human genomic DNA prepared by complete BamH I, or partial Sau3A I digestion. Magnetic beads containing library DNA are prewashed in water and 0.5 µl of each library used as template for PCR amplification with 100 nM of universal adaptor $A_3$ and adaptor $B_1$ primers (primers 12 and 16) in final volume of 25 µl. After initial denaturing the indicated number of cycles are carried out at 94° C. for 10 sec and 68° C. for 75 sec. Ten microliter aliquots are separated on 1% agarose gel and visualized on Fluor S MultiImager (Bio Rad; Hercules, Calif.) after staining with Sybr Gold.

This example demonstrates that primary PENTAmer libraries can be prepared from genomic DNA having the complexity of the human genome.

Example 36

Retention of Single-Stranded and Double Stranded Libraries on Streptavidin-Conjugated Magnetic Beads.

In order to test the retention of DNA on Streptavidin beads a double-stranded and single-stranded secondary BamH I library of E. coli strain K-12 were created.

Double and single-stranded secondary libraries were constructed as follows. One microliter of 12-fold diluted primary BamH I library (prepared as described in Example 33) of E. coli K-12 are used a template for each 25 µl PCR reaction. Standard PCR conditions for Advantaq+ (Clontech; Palo Alto, Calif.) are used with 0.2 µM final concentration of biotinylated Adaptor B specific primer and Adaptor A specific primer. 0.2 mM dNTP and 0.25 mM dUTP final concentration are used in each PCR reaction. A total of 16 different 25 µl PCR reactions are used. 2-step PCR cycling parameters are used: 95° C. for 1 minute, 94° C. for 10 seconds, 68° C. for 1 minute and 15 seconds, cycled for 25 rounds. This is followed by 72° C. for 1 minute and held at 4° C. The reactions are combined into one 1.5 ml tube (400 ul total) and placed in a magnet for 2 minutes. The supernatant is placed in a clean 1.5 ml tube.

In order to remove any unincorporated biotinylated primers prior to binding to Streptavidin beads, the PCR reactions are purified with Microcon YM-100 filters (Millipore). To each filter is added 100 ul of PCR reaction, 200 ul TE-L buffer (10 mM Tris pH 8.0, 0.1 mM EDTA), and 100 ul QF Buffer (Qiagen) (240 mM NaCl, 3% isopropanol, and 10 mM Tris-HCl, pH 8.5 final concentrations). The filters are spun at 200×g for 18 minutes; this is followed by 2 washes with 400 ul TE-L (200×g, 15 minutes). After elution, the volume of the combined reactions is brought up to 400 ul with TE-L. 200 ul is used for creation of the single-stranded secondary library and 200 ul is used for creation of the double-stranded secondary library.

The single-stranded secondary library bound to beads as follows. Sixty microliters of Dynal Streptavidin beads are washed twice with 100 ul 2×WB (WB: 1M Nacl, 10 mM Tris-HCl pH 7.5, 1 mM EDTA), washed once with 200 ul 1×WB, washed twice with 200 ul TE-L, and resuspended in 200 ul 2×WB. 200 ul of the purified PCR reactions are placed at 100° C. for 5 minutes, placed on ice for 5 minutes and then mixed with 200 ul of the prepared Streptavidin beads. Binding of the biotinylated PCR products to the Streptavidin beads is done by rotating the mixture at room temperature for 2.5 hours. After binding the mixture is washed once with 200 ul 2×WB, twice with 200 ul TE-L, and resuspended in 100 ul TE-L.

Removal of the non-biotinylated strand is done by resuspending the mixture in 100 µl 0.1N NaOH followed by incubation at room temperature for 2 minutes. The mixture is placed on a magnet and the supernatant is removed. The beads are resuspended once more with 100 µl 0.1N NaOH. The supernatant is again removed by placing the mixture on a magnet. Neutralization is accomplished by washing the beads 4 times with 200 ul TE-L. The single-stranded secondary library is resuspended in 40 µl ddH$_2$O.

The ends of the single-stranded library are blocked by the addition of ddATP through terminal transferase. To the 40 µl of the single-stranded library, 20 µl 5×terminal transferase buffer (Roche), 10 µl 2.5M CoCl$_2$, 10 µl 1 mM ddATP, and 20 µl Terminal Transferase (New England Biolabs) are added. The reaction is incubated at 37° C. for 30 minutes. The reaction is then washed twice with 100 µl TE-L and twice with 2×WB buffer. The single-stranded secondary library is finally resuspended in 130 ul 1×storage buffer and stored at 4° C.

The double-stranded library was bound to beads as follows. Two-hundred microliters of the purified PCR reactions is mixed with 200 µl of Dynal Streptavidin beads, prepared as above. Binding is carried out by rotating the mixture for 2.5 hours at room temperature. After binding the beads are washed twice with 200 μl 2×WB and twice with 200 μl TE-L. After washing the double-stranded secondary library is resuspended in 100 μl TE-L and stored at 4° C.

Removal of bead-bound DNA via denaturation with formamide was tested as follows. The double-stranded secondary library is washed once with 200 ul TE-L, and resuspended in 200 μl TE-L. 20 μl of the washed library is resuspended in 50 μl formamide buffer (95% formamide, 10 mM EDTA) and incubated at 95° C. for 5 minutes. The beads are placed in a magnet heated to 70° C. The supernatant is removed and 150 μl TE-L, 20 μl 3M NaAcetate, and 2 μl (20 mg/ml) Glycogen are added. The DNA is precipitated by adding 666 ul of 100% ethanol and placed at −80° C. for 1 hour. The sample is spun at 16,000×g for 30 minutes and washed 3 times with 1 ml 75% ethanol. After the sample is dried for 5 minutes in a vacu-fuge the pellet is resuspended in 100 ul TE-L (the sample is 5 fold diluted).

Serial dilutions are performed on the released DNA and untreated double-stranded secondary library from 500 to 200,000 fold. 25 μl PCR reactions are performed with 1 ul of the dilutions as template using standard Advantaq+ (Clontech; Palo Alto, Calif.) conditions. An *E. coli* K-12 specific primer and an adaptor B specific primer are used (0.2 um final concentration), this produces an approximately 1 kb PCR product. The 2-step PCR cycling parameters are used as above, but with 30 cycles. 2.5 μl of 10×loading buffer (Life Technologies; Rockville, Md.) are added to each sample and 15 μl are loaded onto a 1% TBE agarose gel under standard conditions. The gel was stained with ethidium bromide and bands were quantitated on the Bio Rad Fluor S Multiimager by integrating the image pixels in specified volumes (Quantity One software, Bio Rad; Hercules, Calif.).

Figure 91A:
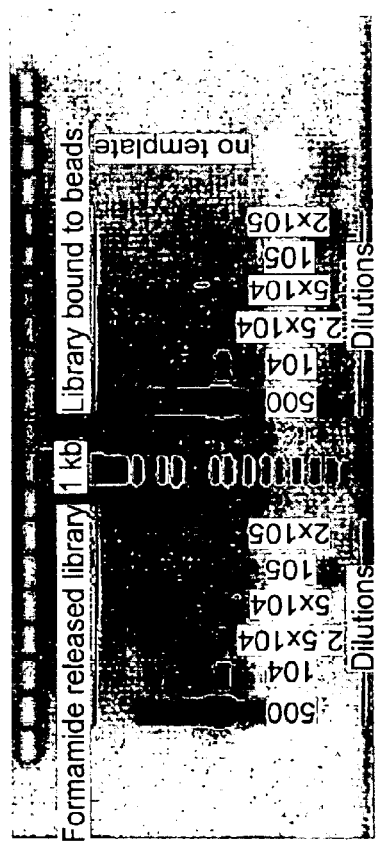
FIGS. 91A and 91B: PCR amplification of serially diluted double-stranded (91A) and double-stranded and single stranded (91B) secondary libraries.

FIG. 91A shows the PCR of the serial dilutions of the formamide released and untreated double-stranded secondary libraries. Quantitation of the band intensities (Adjusted Volumes, Quantity One software, Bio Rad), for the 500 and $10^4$ dilutions, showed that there was 25% less product in the library bound to beads compared to the formamide released library. This demonstrates that most if not all DNA is released from the streptavidin beads upon exposure to formamide. The released DNA produced more PCR product than DNA bound to streptavidin under the same conditions.

Removal of bead-bound DNA via denaturation with NaOH was tested as follows. Three samples were used: single-stranded secondary library (treated twice with NaOH), single-stranded secondary library released via formamide (treated twice with NaOH), and double stranded secondary library released via formamide (not treated with NaOH). The double-stranded library released via formamide represents the entire input of DNA prior to NaOH treatment used to make the single-stranded secondary library.

The single-stranded secondary library is washed once with 200 μl TE-L and resuspended in 200 μl TE-L. 20 μl of the library is released from the streptavidin beads via formamide as above. The released DNA is resuspended in 100 μl TE-L (the sample is 5 fold diluted). Serial dilutions from 50 to 5,000 are made for the released and unreleased single-stranded library. Serial dilutions from 1,000 to 100,000 are made for the double-stranded library. 1 μl of the serial dilutions are used as templates in 25 μl PCR reactions. The primers, PCR conditions, gel running conditions, and quantitation assays are the same as used for removal via formamide of DNA bound to Streptavidin beads test above.

Figure 91B:
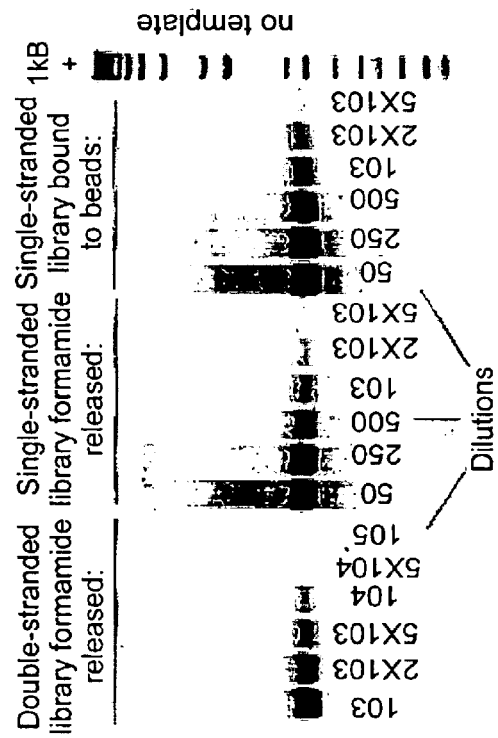

FIG. 91B shows the gel of the PCR from the serial dilutions of the various samples. The single-stranded secondary library released via formamide is similar in band intensity compared to the unreleased sample (lanes 7–12 and lanes 13–18). From the gel it is clear that there is some loss of DNA following NaOH treatment (lanes 3, 12, and 18: all 5,000 fold dilutions). Quantitation of the band intensities (Adjusted Volumes, Quantity One software, Bio Rad) was performed on each of the lanes. There are too few data points to make a very accurate estimate of loss during NaOH treatment, but by looking at the 5,000 fold dilutions among the three samples an estimate can be made. The single-stranded secondary library released from the beads is 3.5 fold less (72% loss) than the double-stranded library and the single-stranded library on the beads is 3 fold less (66% loss). If a correction is made for the double-stranded character of the library (divide by 2) then the single-stranded library is 1.8 fold less (43% loss) and the unreleased library is 1.5 fold less (32% loss). Therefore, after the 2 NaOH washes the single-stranded library has been subject to approximately a 37% loss in DNA.

Loss of DNA from sequential washing of DNA-bound beads was determined as follows. The double-stranded secondary library is subject to sequential treatments with NaOH and the supernatant is be tested by PCR to quantitate DNA loss during the washes. All non-biotinylated DNA (the second strand in the double-stranded library) should be removed with the first wash, so any product that is amplified in subsequent washes will be due to loss of DNA from the streptavidin beads as a result of the NaOH treatment.

Twenty microliters of washed double-stranded secondary library (same amount as the previous assays) are resuspended in 50 μl 0.1N NaOH and incubated at 37° C. for 3 minutes. To neutralize the supernatant, 32 μl 0.2N HCL and 5 μl 1M Tris pH 8.0 are added. 2 μl glycogen (20 mg/ml) and 267 μl 100% ethanol are added to the supernatant to precipitate the DNA. The mixture is placed at −80° C. for 1 hour. The sample is spun at 16,000-×g for 30 minutes and washed 3 times with 1 ml 75% ethanol. After the sample is dried for 5 minutes in a vacu-fuge the pellet is resuspended in 100 μl TE-L (the sample is 5 fold diluted). The double-stranded library bound to streptavidin beads is treated 5 times sequentially in this manner, and each supernatant is used in serial dilutions prior to PCR. Serial dilutions from 500 to 10,000 are performed on the first NaOH wash, the second wash is serially diluted from 50 to 1,000, and the third and fourth NaOH washes are diluted from 5 to 100. 1 μl of each dilution is used as template in a 25 μl PCR reaction The primers, PCR conditions, gel running conditions, and quantitation assays are the same as described above.

Using the data from the Adjusted Volumes of band intensities (Quantity One software, Bio Rad; Hercules, Calif.) of the various dilutions, the percentage loss of DNA from the streptavidin beads following the sequential washes with NaOH is calculated. The first wash will contain the DNA strand that is not bound to the beads and any loss. The streptavidin beads used in the subsequent washes will have bound to them the single biotinylated strand. For quantitation, the first wash is considered the total amount of DNA that will still be bound to the beads. By comparing the band intensities for the 500 fold dilutions for the first wash and the second wash, the second wash is 80% less than the first wash, which corresponds to a 20% loss in DNA. Comparing the 500-fold dilution of the first wash and the average of the 50 and 100 fold dilutions of the third and fourth washes, these washes are 87% and 88% less than the first wash respectively. This corresponds to a 12% loss in the third wash and an 11% loss in the fourth wash. If the loss of DNA from previous washes is considered in the calculations (for the third wash the total is 80% of the first wash and for the fourth wash the total is 67% of the total), the loss is 16% and 17% for the third and fourth washes respectively. Therefore, regardless of the total amount of DNA bound to the streptavidin beads there is approximately an 18% loss in DNA bound to the beads, with each subsequent exposure to NaOH.

All of the METHODS disclosed and claimed herein can be made and executed without undue experimentation in light of the present disclosure. While the compositions and methods of this invention have been described in terms of preferred embodiments, it will be apparent to those of skill in the art that variations may be applied to the METHODS and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

PUBLICATIONS

Ardrey, Electrospray Mass Spectrometry, Spectroscopy Europe, 4, 10–18, 1992.
Arnold, C. and I. J. Hodgson. 1991. Vec-torette PCR: a novel approach to genomic walking. PCR Methods Appl. 1:39–42.
Berg et al. in Automated DNA sequencing and analysis by Adams, Fields, and Venter. Academic Press (1994)
Berkenkamp et al., Science, 281:260–2, 1998
Cantor and Smith Genomics, John Wiley & Sons, Inc., N.Y., 1999.
Cheng, S. et al. (1994) Nature, 369, 684–685. long range PCR
Cormack and Somssich Gene 194 (1997) 273–276
Crain, Mass Spectrometry Reviews, 9: 505–554, 1990.
Dieffenbach and Dveksler. PCR Primer CSHL Press 1995.
Devon, R. S., Porteous, D. J., and Brookes, A. J. (1995) Nucleic Acids Res. 23, 1664–1645.
Fenn et al., J. Phys. Chem. 88, 4451–59, 1984.
Fodor, et al., Nature; 364(6437):555–6, 1995.
Forster, Ann. Phys., 2:55–75, 1948.
Freifelder, et al. Anal Biochem, 123(1):83–5, 1982
Frohman, In: PCR Protocols: A Guide To Methods And Applications, Academic Press, N.Y., 1990.
Grant, et al. Biochemistry, 35(38):12313–9, 1996.
Guilfoyle, et al. Nucleic Acids Research 25:1854–1858 (1997)
Hacia, et al., Nature Genet., 14:441–449, 1996.
Hagiwara, K. and Harris Nucleic Acids Research 24:2460–2461 (1996)
Harrison, et al., BioTechniques 22:650–653 (1997)
Higuchi et al., Biotechnology 10:413–417 1992
Hillenkamp, et al., Anal Chem., 63(24):1193A–1203A, 1991.
Holmstrom et al., Anal. Biochem. 209:278–283, 1993.
Hunkapiller, et al, Science, 254(5028):59–67. 1991
Innis, et al., PCR Protocols, Academic Press, Inc., San Diego, 1990
Jones, D. H. and S. C. Winistorfer, BioTechniques 15:894–904, 1993.
Jones, D. H. and S. C. Winistorfer, Nucleic Acids Res. 20:595–600, 1992.
Koster et al. Biomedical Environmental Mass Spectrometry, 14: 111–116, 1987.
Kwoh, et al., Proc Natl Acad Sci USA. 1986(4):1173–7, 1989.
Lee, et al., Nuc. Acids Res. 21, 3761–3766, 1993.
Liao et al, Analytical Biochemistry, 253:137–139, (1997).
Lin, et al., Analytical Biochemistry 231:449–452, 1995.
Lukyanov et al. Nucleic Acids Research 24:2194–2195 (1996).
Makarov, et al., 1997
Macrae and Brenner (1994) Genomics 24:176–178
Maniatis T, Fritsch E F and Sambrook J. (1989). Molecular cloning: A laboratory manual. Cold Spring Harbour Laboratory: Cold Spring Harbour, N.Y.
McCombie et al. Methods: Companion Methods Enzymology 3:33–40 (1991).
Methods in Enzymology, Vol. 193: "Mass Spectrometry" (McCloskey, ed.), Academic Press, New York, 1990.
Meyer, et al. Nature, 278(5702):365–7, 1979.
Nakamaye et al. Nucleic Acids Research 16:9947 (1988)
Newton, et al. Nucl. Acids Res. 21:1155–1162, 1993.
Nonisotopic DNA Probe Techniques, Academic Press, Inc., pgs. 311–352, 1992.
Ochman et al. Genetics 120:621–623 (1988).
Ohara et al., Proc. Natl Acad Sci. USA, 86:5673–5677, 1989.
Padegimas et al. Analytical Biochemistry, 260, 149–153, 1998.
Pease et al., Proc. Natl. Acad. Sci. USA, 91:5022–5026, 1994.
Primrose Principles of Genome Analysis, Second Edition, Blackwell Science, 1998.
Rasmussen et al., Anal. Biochem, 198:138–142, 1991.
Riley, J., Butler, R., Ogilvie, D., Finniear, R., Jenner, D., Powell, S., Anand, R., Smith, J. C., and Markham, A. F. (1990) Nucleic Acids Res. 18, 2887–2890
Richterich and Church, Method Enzymol., vol 218, 187–222 (1993)
Rosenthal, A., and Jones, D. S. (1990) Nucleic Acids Res. 18, 3095–3096.
Rudi et al. (1999) BioTechniques 27:1170–1177
Running et al., BioTechniques 8:276–277, 1990.
Sambrook et al., "Molecular Cloning," A Laboratory Manual, 2d Ed., Cold Spring Harbor Laboratory Press, New York, 13.7–13.9:1989.
Schram, Methods Biochem Anal., 34: 203–287 1990.
Shoemaker et al., Nature Genetics 14:450–456, 1996.
Smith et al., Anal. Chem. 62, 882–89, 1990.
Siebert et al. Nucleic Acids Res. 23, 1087–1088, 1995.
Smith, D. R. (1992) PCR Methods Appl., 2, 21–27.
Sterky et al. Journal of Biotechnology 60 (1998) 119–129
Tabor, et al., Proc Natl Acad Sci USA., 84(14):4767–71, 1987.
Unrau, P. and Deugau, K. (1994) Gene, 145, 163–169.
Vos et al., Nucleic Acids Research 23:4407–4414 (1995).
Walker et al. (1992a) PNAS 89:392–396
Walker et al. (1992b) Nuc. Acids Res. 20: 1691–1696.
Williams et al., Science, 246: 1585–87, 1989
Xu et al. Anal. Chem. Vol 69, 3595–3602, 1997
Zhang, et al. Gurr Gene 253 (2000) 145–150.

PATENTS

U.S. Pat. No. 4,942,124
U.S. Pat. No. 4,683,194
U.S. Pat. No. 4,710,465
U.S. Pat. No. 5,075,216
U.S. Pat. No. 5,143,854
U.S. Pat. No. 5,149,625
U.S. Pat. No. 5,424,186
U.S. Pat. No. 5,366,877
U.S. Pat. No. 5,547,861
U.S. Pat. No. 5,578,832
U.S. Pat. No. 5,599,668
U.S. Pat. No. 5,610,287
U.S. Pat. No. 5,837,832
U.S. Pat. No. 5,837,860
U.S. Pat. No. 5,843,651
U.S. Pat. No. 5,861,242
U.S. Pat. No. 6,027,913
U.S. Pat. No. 6,045,994
U.S. Pat. No. 6,124,120
EP 0 655 506 B1
Japanese Patent No. 59-131909
WO 88/10315
WO 89/06700
WO 90/14148
WO 96/21144
WO 98/1112
WO 98/15644
WO 99/18241
WO 00/15779
WO 00/18960
WO 00/28084
WO 00/60121

What is claimed is:

1. A method of preparing a DNA molecule having an amplifiable region comprising:
   a) obtaining a DNA sample comprising DNA molecules having regions to be amplified;
   b) attaching upstream adaptor molecules to ends of DNA molecules of the sample to provide a nick translation initiation site;
   c) subjecting the DNA molecules to nick translation comprising DNA polymerization and 5'–3' exonuclease activity to produce nick translate molecules; and
   d) attaching downstream adaptor molecules to the nick translate molecules to produce adaptor attached nick translate molecules.

2. The method of claim 1, wherein the ends of said DNA molecules are produced prior to the attachment of said upstream adaptor molecule.

3. The method of claim 2, wherein the ends of said DNA molecules are produced by at least one restriction enzyme, by an endonuclease, by mechanical shearing, by a chemical, or a combination thereof.

4. The method of claim 1, wherein said DNA polymerization step incorporates at least one modified nucleotide into said nick translate molecule.

5. The method of claim 4, wherein said modified nucleotide is an exonuclease-resistant nucleotide.

6. The method of claim 1, wherein said adaptor attached nick translate molecules are separated.

7. The method of claim 6, wherein said separation is based upon size.

8. The method of claim 1, wherein said adaptor attached nick translate molecules are denatured.

9. The method of claim 8, wherein the denatured DNA is separated.

10. The method of claim 9, wherein a single stranded adaptor attached nick translation molecule is separated from a DNA sample template strand.

11. The method of claim 1, wherein said DNA is subjected to nick translation for a specified period of time.

12. The method of claim 11, wherein the nick translation product has a predictable length.

13. The method of claim 11, wherein the nick translate molecules are substantially similar in size.

14. The method of claim 1, wherein the upstream adaptor comprises a nick translation initiation site.

15. The method of claim 1, wherein the upstream adaptor further comprises a primer binding region, a hybridization domain, a ligation domain, a detection domain, an amplification domain, a recombination domain, or a combination thereof.

16. The method of claim 1, wherein the downstream adaptor comprises a nick translation initiation site.

17. The method of claim 16, wherein said downstream adaptor further comprises a hybridization domain, a ligation domain, a detection domain, an amplification domain, a recombination domain, or a combination thereof.

18. The method of claim 1, wherein the upstream adaptor comprises at least a first and second upstream adaptor molecule construct.

19. The method of claim 1, wherein the upstream adaptor comprises a plurality of upstream adaptor molecule constructs.

20. The method of claim 18, wherein said at least a first and second upstream adaptor molecule constructs have different primer binding regions.

21. The method of claim 1, wherein the downstream adaptor comprises at least a first and second downstream adaptor molecule construct.

22. The method of claim 1, wherein the downstream adaptor comprises a plurality of downstream adaptor molecule constructs.

23. The method of claim 21, wherein the at least a first and second downstream adaptor molecule constructs have different primer binding regions.

24. The method of claim 1, further comprising amplifying adaptor attached DNA molecules.

25. The method of claim 24, wherein the amplified DNA is cloned into a vector.

26. The method of claim 24, wherein the amplified DNA is sequenced.

27. The method of claim 24, wherein the amplified DNA is separated.

28. The method of claim 1 or 24, further comprising creating a DNA library.

29. The method of claim 28, wherein the DNA library is an unordered DNA library.

30. The method of claim 28, wherein the DNA library is an ordered DNA library.

31. The method of claim 30, wherein creation of the ordered DNA library further comprises recombination.

32. The method of claim 30, wherein the ordered DNA library comprises a plurality of nick translate molecules wherein nick translation of said nick translate molecules is carried out for different periods of time.

33. The method of claim 30, wherein the ordered DNA library is further defined as a genomic ordered positional library.

34. The method of claim 24, wherein the adaptor attached nick translate molecules are amplified with primers complementary to the upstream adaptor molecule and the downstream adaptor molecule.

35. The method of claim 24, wherein the adaptor attached nick translate molecules are amplified with a first primer specific to the upstream adaptor and a second primer specific to an internal sequence of the nick translate molecule.

36. The method of claim 24, wherein the adaptor attached nick translate molecules are amplified with a first primer specific to the downstream adaptor molecule and a second primer specific to an internal sequence of the nick translate molecule.

37. The method of claim 24, wherein at least one of the primers used for amplification of the adaptor attached nick translate molecules is labeled.

38. A method of creating hybridization probes comprising preparing a labeled, amplified DNA in accordance with the method of claim 37.

39. The method of claim 1, further comprising subjecting the adaptor attached nick translate molecules to recombination.

40. The method of claim 1, wherein said downstream adaptor is attached at said nick site.

41. The method of claim 40, wherein said attachment is to the 5' strand of said nick site.

42. The method of claim 40, wherein said attachment is to the 3' strand of said nick site.

43. The method of claim 39, wherein said recombination occurs at DNA concentrations that favor intramolecular circularization and reduce undesirable intermolecular ligation.

44. The method of claim 39, wherein said recombination comprises:
   a) digesting the DNA molecule with a first sequence-specific endonuclease;
   b) ligating both strands of an adaptor molecule to the sequence-specific termini of the template molecules;

c) digesting the DNA molecules with a second sequence-specific endonuclease;
d) incubating the DNA molecules under conditions to favor intramolecular circularization and reduce undesirable intermolecular ligation;
e) concentrating the DNA molecules;
f) initiating a nick-translation reaction for a controlled time; and
g) attaching a down-stream adaptor.

45. The method of claim 39, wherein said recombination comprises:
a) methylating the DNA molecules;
b) ligating a first and second adaptor to the ends of the DNA molecule to form a recognition sequence, a single nick-translation initiation site, and a single Eco RI restriction recognition sequence within the recombination domain;
c) activating the adaptors by incubation with a restriction enzyme or nuclease;
d) incubating the DNA molecules under conditions to favor intramolecular circularization and reduce undesirable intermolecular ligation;
e) concentrating the DNA molecules;
f) initiating a nick-translation reaction for a controlled time; and
g) attaching a down-stream adaptor.

46. The method of claim 1, wherein the adaptor attached nick translate molecules are between 0.5 and 500 kB in length.

47. The method of claim 1, wherein the DNA sample is cDNA.

48. The method of claim 1, wherein the DNA sample is genomic DNA.

49. The method of claim 1, wherein the DNA sample is cloned DNA.

50. The method of claim 1, wherein the DNA sample is a BAC.

51. The method of claim 1, wherein the DNA sample is a YAC.

52. The method of claim 1, wherein the DNA sample is a cosmid.

53. The method of claim 1, wherein the DNA sample is insert clone comprising up to 500 kB.

54. A method of shotgun sequencing of DNA comprising the steps of:
a) preparing a DNA library in accordance with claim 30;
b) sequencing the library using primers specific for known loci to derive the sequence of adjacent unknown regions.

55. The method of claim 1, further comprising:
a) recombining the DNA molecules after adaptor attachment;
b) size separating the DNA molecules;
c) amplifying the DNA.

56. The method of claim 55, wherein the size separated DNA is distributed into the wells of a multi-well plate.

57. The method of claim 55, wherein the amplified DNA is sequenced.

58. The method of claim 55, wherein the amplified DNA is subsequently cloned into a vector.

59. The method of claim 1, further comprising:
a) amplifying the DNA molecules after adaptor attachment;
b) hybridizing the amplified DNA to a microarray;
c) analyzing the hybridization patterns.

60. The method of claim 1, wherein the DNA sample is modified.

61. The method of claim 60, wherein the DNA sample is methylated.

62. The method of claim 1, further comprising:
a) initiating a second nick translation reaction at the upstream adaptor comprising subjecting the DNA molecules to nick translation using a DNA polymerase having 5'-3' exonuclease activity;
b) attaching second downstream adaptor molecules to the 5' end of the molecules to produce adaptor attached nick translate molecules.

63. The method of claim 1, further comprising:
a) denaturing the adaptor attached nick translation product and separating the single stranded DNA;
b) replicating the second strand of the adaptor attached molecule to form a double stranded product;
c) subjecting the DNA molecules to nick translation using a DNA polymerase having 5'-3' exonuclease activity, to produce nick translate molecules;
d) attaching additional downstream adaptor molecules to the nick translation initiation site of the nick translate molecules to produce adaptor attached nick translate molecule molecules.

64. The method of claim 1, wherein an affinity adaptor is ligated to said DNA molecules.

65. The method of claim 64, wherein said affinity adaptor is used to separate DNA molecules.

66. The method of claim 3, wherein said restriction digestion is carried out with a frequent cutter.

67. The method of claim 3, wherein said restriction digestion is carried out with an infrequent cutter.

68. The method of claim 3, wherein said restriction digestion results in partial cleavage.

69. The method of claim 1, further comprising attaching the upstream adaptor molecule to both the proximal and distal ends of said DNA molecules to create a circular product.

70. The method of claim 69, wherein the initiation of nick translation occurs in the direction of the distal end of the nick translate molecule subjected to circularization.

71. The method of claim 69, wherein different internal regions of the nick translate molecules are exposed as distal ends.

72. The method of claim 19, wherein nick translation is carried out on a DNA sample with a plurality of upstream adaptors in a single tube.

73. The method of claim 22, wherein nick translation is carried out on a DNA sample with a plurality of downstream adaptors, in a single tube.

74. The method of claim 1, wherein the nick translation reaction proceeds through a known sequence on the DNA molecule.

75. The method of claim 74, wherein PCR primers are constructed to recognize regions within said known sequence.

76. The method of claim 75, wherein PCR amplification of nick translate products occurs using a primer specific to said known sequence and a primer specific to an attached adaptor.

77. The method of claim 1, further comprising circularizing the adaptor attached, nick translate product by:
a) incubating said adaptor attached, nick translate product with a linker oligonucleotide to form a nick site; and b) ligating the ends of said adaptor attached, nick translate product with a DNA ligase.

78. The method of claim 77, wherein said linker oligonucleotide is 20–200 bp. long.

79. The method of claim 77, wherein said linker oligonucleotide has a region complementary to the upstream adaptor and a region complementary to the downstream adaptor.

80. The method of claim 1, wherein:
   a) the DNA molecules of the DNA sample are restricted with one or more restriction enzymes;
   b) upstream adaptor molecules are attached at both ends of the restricted DNA molecules;
   c) nick translation is carried out from both upstream adaptors; and
   d) the ends of the DNA molecules are recombined.

81. The method of claim 80, further comprising separating the recombined molecules according to size.

82. The method of claim 80, wherein said restriction enzyme is a frequent cutter.

83. The method of claim 82, wherein said restriction digestion is a partial digest.

84. The method of claim 80, wherein each end of the DNA molecule is created with a different restriction enzyme.

85. The method of claim 1, wherein:
   a) the DNA molecules of the DNA sample are restricted with an infrequent cutting restriction enzyme;
   b) upstream adaptor molecules are attached at ends of the restricted DNA molecules;
   c) nick translation is carried out from the upstream adaptors;
   d) the nick translate molecules are partially restricted with a frequent cutter;
   e) internal adaptor molecules are attached at ends of the restricted DNA molecules;
   f) nick translation is carried out from the internal adaptors; and
   g) the ends of the DNA molecules are recombined.

86. The method of claim 1, wherein nucleotides integrated by nick translation are modified.

87. The method of claim 86, wherein the modified nucleotides are exonuclease resistant.

88. The method of claim 87, wherein said modified nucleotides facilitate the differentiation of the nick translate product from the template strand.

89. A method of preparing a DNA molecule having an amplifiable region comprising:
   a) obtaining a DNA sample comprising DNA molecules having regions to be amplified;
   b) attaching upstream adaptor molecules to the proximal end of DNA molecules of the sample to provide a nick translation initiation site;
   c) subjecting the DNA molecules to nick translation comprising DNA polymerization and 5'–3' exonuclease activity, for a specific time T;
   d) attaching downstream adaptor molecules to the 5' end of the degraded template strand to produce adaptor attached nick translate molecules.

90. The method of claim 89, wherein said adaptor attached nick translate molecules are amplified.

91. The method of claim 89, wherein a plurality of DNA molecules from said DNA sample are reacted for a different time T.

92. A method of preparing a DNA molecule having an amplifiable region comprising:
   a) obtaining a DNA sample comprising DNA molecules having regions to be amplified;
   b) attaching upstream adaptor molecules to the proximal end of DNA molecules of the sample to provide a nick translation initiation site;
   c) subjecting the DNA molecules to a first nick translation comprising DNA polymerization and 5'–3' exonuclease activity, for a specific time T;
   d) attaching first downstream adaptor molecules to the 3' end of the nick translate product to produce adaptor attached nick translate molecules;
   e) subjecting the DNA molecules to a second nick translation initiated from the upstream adaptor comprising DNA polymerization and 5'–3' exonuclease activity, for a specific time T; and
   f) attaching second downstream adaptor molecules to the 5' end of the degraded nick translate product.

93. The method of claim 92, wherein said adaptor attached nick translate molecules are amplified.

94. The method of claim 92, wherein a plurality of DNA molecules from said DNA sample are subjected to nick translation for a first time for a different time T.

95. The method of claim 92, wherein a plurality of DNA molecules from said DNA sample are subjected to nick translation for a second time for a different time T.

96. A method of preparing a DNA molecule having an amplifiable region comprising:
   a) obtaining a DNA sample comprising DNA molecules having regions to be amplified;
   b) attaching upstream adaptor molecules to the proximal end of DNA molecules of the sample to provide a nick translation initiation site;
   c) subjecting the DNA molecules to a first nick translation comprising DNA polymerization and 5'–3' exonuclease activity, for a specific time T;
   d) attaching a first downstream adaptor molecules to the 3' end of the nick translate product;
   e) separating the nick translate product from the template molecule;
   f) replicating the nick translate product via primer extension;
   g) subjecting the product of step f) to a second nick translation comprising DNA polymerization and 5'–3' exonuclease activity, for a specific time T; and
   h) attaching a second downstream adaptor molecules to the 3' end of the product of step g).

97. The method of claim 96, wherein said adaptor attached nick translate molecules are amplified.

98. The method of claim 96, wherein a plurality of DNA molecules from said DNA sample are subjected to nick translation for a first time for a different time T.

99. The method of claim 96, wherein a plurality of DNA molecules from said DNA sample are subjected to nick translation for a second time for a different time T.

100. A method of preparing a DNA molecule having an amplifiable region comprising:
   a) obtaining a DNA sample comprising DNA molecules having regions to be amplified;
   b) ligating an affinity adaptor to the proximal ends of said DNA molecules;
   c) subjecting the affinity adaptor attached molecules to partial cleavage;
   d) separating the affinity adaptor attached molecules;
   e) attaching upstream adaptor molecules to ends of the affinity adaptor attached molecules to provide a nick translation initiation site;

f) subjecting the affinity adaptor attached molecules to nick translation comprising DNA polymerization and 5'–3' exonuclease activity; and g) attaching downstream adaptor molecules to the nick translate molecules to produce adaptor attached nick translate molecules.

101. The method of claim 100, wherein said adaptor attached nick translate molecules are amplified.

102. The method of claim 100, wherein said polymerization incorporates modified nucleotides.

103. The method of claim 102, wherein said modified nucleotides are exonuclease resistant.

104. The method of claim 100, wherein said adaptor attached nick translate molecules are separated.

105. A method of preparing a DNA molecule having an amplifiable region comprising:
   a) obtaining a DNA sample comprising DNA molecules having regions to be amplified;
   b) attaching the first end of a recombination adaptor to one end of said DNA molecules;
   c) attaching the second end of said recombination adaptor to the opposite end of said DNA molecules;
   d) subjecting the adaptor attached molecules to nick translation comprising DNA polymerization and 5'–3' exonuclease activity; and
   e) attaching downstream adaptor molecules to the nick translate molecules to produce adaptor attached nick translate molecules.

106. The method of claim 105, wherein said adaptor attached nick translate molecules are amplified.

107. The method of claim 105, wherein said adaptor attached nick translate molecules are separated.

108. A method of preparing a DNA molecule having an amplifiable region comprising:
   a) obtaining a DNA sample comprising DNA molecules having regions to be amplified;
   b) attaching the first end of a recombination adaptor to the proximal end of said DNA molecules;
   c) partially cleaving said DNA molecules to produce cleavage products having a plurality of lengths;
   d) attaching the second end of said recombination adaptor to distal ends produced by said partial cleavage;
   e) subjecting the adaptor attached molecules to nick translation comprising DNA polymerization and 5'–3' exonuclease activity;
   f) attaching downstream adaptor molecules to the nick translate molecules to produce adaptor attached nick translate molecules; and
   g) separating said adaptor attached nick translate molecules.

109. The method of claim 108, wherein said partial cleavage is performed with a restriction enzyme.

110. The method of claim 108, wherein said partial cleavage is performed with an endonuclease.

111. The method of claim 108, wherein said partial cleavage is performed by chemical cleavage.

112. The method of claim 108, wherein said adaptor attached nick translate molecules are amplified.

113. The method of claim 108, wherein said separation is based upon size.

114. A method of preparing DNA molecules having an amplifiable region comprising:
   a) obtaining a first DNA template;
   b) attaching a first upstream adaptor molecules to said DNA template to provide a nick translation initiation site;
   c) obtaining a second DNA template;
   d) attaching a second upstream adaptor molecules to said DNA template to provide a nick translation initiation site;
   e) mixing said first and said second templates;
   f) subjecting the adaptor attached template molecules to nick translation initiated from the upstream adaptor comprising DNA polymerization and 5'–3' exonuclease activity, for a specific time T; and
   g) attaching a downstream adaptor molecules to the nick translate molecules to produce adaptor attached nick translate molecules.

115. The method of claim 114, wherein said adaptor attached nick translate molecules are amplified.

116. The method of claim 114, wherein said adaptor attached molecules are subsequently differentiated by PCR amplification employing primers specific for said first upstream adaptor and/or said second upstream adaptor.

117. A method of preparing DNA molecules having an amplifiable region comprising:
   a) obtaining a plurality of DNA templates;
   b) attaching a plurality of different first upstream adaptor molecules to said DNA templates to provide a nick translation initiation site;
   c) mixing said plurality of templates;
   d) subjecting the adaptor attached template molecules to nick translation initiated from the upstream adaptor comprising DNA polymerization and 5'–3' exonuclease activity, for a specific time T; and
   e) attaching a downstream adaptor molecules to the nick translate molecules to produce adaptor attached nick translate molecules.

118. The method of claim 117, wherein said adaptor attached nick translate molecules are amplified.

119. The method of claim 117, wherein said adaptor attached molecules are subsequently differentiated by PCR amplification employing primers specific for said first upstream adaptor or said second upstream adaptor.

120. A method of constructing a genomic library, comprising:
   a) obtaining genomic DNA;
   b) fragmenting the genome to a desired size;
   c) attaching upstream adaptor molecules to ends of the fragmented genomic DNA molecules of the sample to provide a nick translation initiation site;
   d) subjecting the DNA molecules to nick translation comprising DNA polymerization and 5'–3' exonuclease activity; and
   e) attaching downstream adaptor molecules to the nick translate molecules to produce adaptor attached nick translate molecules.

121. The method of claim 120, wherein said adaptor attached nick translate molecules are amplified.

122. The method of claim 120, wherein said nick translate molecules contain a known, kernel sequence.

123. The method of claim 120, wherein said nick translate molecules are amplified with a primer or primers specific for said kernel sequence.

124. The method of claim 120, wherein said nick translate molecules are recombined.

125. The method of claim 124, wherein said recombination comprises ligating said upstream adaptor to said downstream adaptor.

126. The method of claim 124, wherein said recombined molecule further comprises a kernel sequence.

127. The method of claim 124, wherein sequences adjacent to said kernel sequence are amplified.

128. The method of claim 120, wherein said adaptor attached nick translate molecules are inserted into a vector.

129. The method of claim 120, wherein said adaptor attached nick translate molecules are sequenced.

130. The method of claim 120, wherein said adaptor attached nick translate molecules are separated.

131. The method of claim 130, wherein said separation is based upon size.

132. The method of claim 120, wherein said upstream adaptor comprises a free 5' phosphate group.

133. The method of claim 120, wherein said adaptor attached nick translate molecule is recombined with a DNA ligase employing a linking oligonucleotide.

134. The method of claim 133, further comprising:
  a) incubating said linking oligonucleotide with said adaptor attached nick translate molecule to form a nick; and
  b) ligating the adaptor attached nick translate molecule with a DNA ligase.

135. The method of claim 134, wherein said ligase is thermostable.

136. The method of claim 134, wherein said recombination is performed under conditions to favor intramolecular circularization and reduce undesirable intermolecular ligation.

137. A method of constructing a genomic library, comprising:
  a) obtaining a genomic DNA;
  b) fragmenting the genomic DNA;
  c) attaching upstream adaptor molecules to ends of the fragmented genomic DNA molecules of the sample to provide a nick translation initiation site;
  d) subjecting the DNA molecules to nick translation comprising DNA polymerization and 5'–3' exonuclease activity, for a specific time T; and
  e) attaching downstream adaptor molecules to the nick translate molecules to produce adaptor attached nick translate molecules.

138. The method of claim 137, further comprising the step of subdividing the upstream-adaptor attached genomic DNA molecules into a plurality of reaction vessels.

139. The method of claim 137, wherein said adaptor attached nick translate molecules are amplified.

140. The method of claim 137, wherein said nick translate molecules contain a known, kernel sequence.

141. The method of claim 137, wherein said nick translate molecules are amplified with a primer or primers specific for said kernel sequence.

142. The method of claim 137, wherein said nick translate molecules are recombined.

143. The method of claim 142, wherein said recombination comprises ligating said upstream adaptor to said downstream adaptor.

144. The method of claim 142, wherein said recombined molecule further comprises a kernel sequence.

145. The method of claim 144, wherein sequences adjacent to said kernel sequence are amplified.

146. The method of claim 138, wherein said adaptor attached nick translate molecules are inserted into a vector.

147. The method of claim 138, wherein said adaptor attached nick translate molecules are sequenced.

148. The method of claim 138, wherein said adaptor attached nick translate molecules are separated.

149. The method of claim 148, wherein said separation is based upon size.

150. The method of claim 138, wherein said upstream adaptor comprises a 5' phosphate group.

151. The method of claim 138, wherein said adaptor attached nick translate molecule is recombined with a DNA ligase employing a linking oligonucleotide.

152. The method of claim 151, further comprising:
  a) incubating said linking oligonucleotide with said adaptor attached nick translate molecule to form a nick; and
  b) ligating the adaptor attached nick translate molecule to the linking oligonucleotide with a DNA ligase.

153. The method of claim 152, wherein said ligase is thermostable.

154. The method of claim 152, wherein said recombination is performed under conditions to favor intramolecular circularization and reduce undesirable intermolicular ligation.

155. The method of claim 138, wherein the specific time T varies for different reaction vessels.

156. A method of preparing an unordered DNA library comprising:
  a) obtaining a DNA sample comprising DNA molecules;
  b) cleaving said DNA molecules;
  c) attaching recombination adaptors to termini of the cleaved DNA molecules;
  d) subjecting the DNA molecules to nick translation comprising DNA polymerization and 5'–3' exonuclease activity, to produce nick translate molecules wherein said nick translation is initiated from both ends of the cleaved DNA molecules; and
  e) recombining the ends of the nick translate molecules produced by step d).

157. The method of claim 156, wherein said recombined molecules are amplified.

158. The method of claim 156, wherein said recombined molecules are sequenced.

159. The method of claim 156, wherein said recombined molecules are separated.

160. The method of claim 159, wherein said separation is based upon size.

161. A method of producing an ordered DNA library comprising:
  a) obtaining a DNA sample comprising DNA molecules;
  b) cleaving said DNA molecules;
  c) partially cleaving the cleaved DNA molecules;
  d) attaching adaptors to termini of the DNA molecules;
  e) subjecting the DNA molecules to nick translation comprising DNA polymerization and 5'–3' exonuclease activity, to produce nick translate molecules wherein said nick translation is initiated from both ends of the DNA molecules;
  f) separating the nick translate molecules; and
  g) subjecting the separated nick translate molecules to recombination.

162. A method of producing an ordered library comprising:
  a) obtaining a DNA sample comprising DNA molecules;
  b) cleaving said DNA molecules;
  c) attaching recombination adaptors to termini of the DNA molecules;
  d) subjecting the DNA molecules to nick translation comprising DNA polymerization and 5'–3' exonuclease activity, to produce nick translate molecules wherein said nick translation is initiated from both ends of the DNA molecules;

e) recombining the ends of the DNA molecules produced by step d);

f) separating the nick translate molecules according to size.

163. The method of claim 161, wherein said recombined nick translate molecules are amplified.

164. The method of claim 163, wherein nucleotide analogs are integrated during said amplification.

165. The method of claim 161, wherein said recombined nick translate molecules contain a known sequence.

166. The method of claim 165, wherein said recombined nick translate molecules are amplified with at least one primer specific for sequence within said known sequence.

167. The method of claim 166, wherein the time of primer extension is limited.

168. The method of claim 166, wherein the amplified recombined nick translate molecules are subsequently separated.

169. The method of claim 161, wherein said adaptors are covalently joined by recombination.

170. The method of claim 163, wherein said amplified recombined nick translate molecules are sequenced.

171. The method of claim 163, wherein said recombined nick translate molecules are diluted prior to amplification.

172. The method of claim 171, wherein said dilution results in a reaction mixture with only a single DNA molecule.

173. The method of claim 170, wherein said sequencing is cycle sequencing.

174. The method of claim 173, wherein said cycle sequencing employs a primer complementary to an adaptor and at least one or two base pairs adjacent to said adaptor.

175. The method of claim 170, wherein said amplified recombined nick translate molecules are cloned into a vector prior to sequencing.

176. A method of creating a DNA library, comprising:

a) obtaining a DNA sample comprising DNA molecules;

b) cleaving said DNA molecules with an infrequently-cutting restriction enzyme;

c) attaching upstream adaptor molecules to ends of said cleaved DNA molecules of the sample to provide a nick translation initiation site;

d) subjecting the DNA molecules to nick translation comprising DNA polymerization and 5'–3' exonuclease activity;

e) attaching downstream adaptor molecules to the nick translate molecules to produce adaptor attached nick translate molecules.

f) partially cleaving the adaptor attached nick translate molecules with a frequently cutting restriction enzyme;

g) attaching upstream adaptor molecules to the ends of the adaptor attached nick translate molecules produced by said partial digestion;

h) subjecting the DNA molecules to nick translation comprising DNA polymerization and 5'–3' exonuclease activity; and i) attaching downstream adaptor molecules to the nick translate molecules to produce adaptor attached nick translate molecules;

j) subjecting the product of step i) to recombination.

177. The method of claim 176, wherein said recombined molecules are separated.

178. The method of claim 176, wherein said recombined molecules are amplified.

179. The method of claim 178, wherein said amplification comprises at least one primer specific for an adaptor.

180. The method of claim 178, wherein said recombined molecules contain a known, kernel sequence.

181. The method of claim 180, wherein said amplification comprises at least one primer specific for said known, kernel sequence.

182. The method of claim 39, wherein said upstream and downstream adaptors further comprise 3' tails up to 200 bases in length.

183. The method of claim 39, wherein said upstream and downstream adaptors comprise a nick site that facilitates nick translation through an intermolecular junction.

184. A method of preparing a DNA molecule having an amplifiable region comprising:

a) obtaining a DNA sample comprising DNA molecules having regions to be amplified;

b) ligating at least a first upstream adaptor and at least a second upstream adaptor to said DNA molecules;

c) subjecting the DNA molecules to recombination under conditions to favor intramolecular circularization and reduce undesirable intermolecular ligation;

d) subjecting the recombined DNA molecules to nick translation comprising DNA polymerization and 5'–3' exonuclease activity; and e) attaching downstream adaptor molecules to the nick translate molecules to produce adaptor attached nick translate molecules.

185. The method of claim 184, wherein said adaptor attached nick translate molecules are subsequently sequenced.

186. The method of claim 1, wherein said DNA sample comprises template molecules of 1–20 kb.

187. The method of claim 1, wherein said adaptor attached nick translate molecules are distributed as an ordered microarray.

188. The method of claim 187, wherein said microarray is probed with complementary nucleic acid.

189. A method of preparing a DNA molecule having an amplifiable region comprising:

a) obtaining a DNA sample comprising DNA molecules having regions to be amplified;

b) attaching upstream adaptor molecules to ends of DNA molecules of the sample to provide a nick translation initiation site;

c) subjecting the DNA molecules to nick translation comprising DNA polymerization, to produce nick translate molecules; and d) attaching downstream adaptor molecules to the nick translate molecules to produce adaptor attached nick translate molecules.

190. The method of claim 189, wherein said adaptor attached nick translate molecules are amplified.

191. The method of claim 189, wherein said adaptor attached nick translate molecules are sequenced.

192. The method of claim 189, wherein said adaptor attached nick translate molecules are cloned into a vector.

193. The method of claim 189, wherein said adaptor attached nick translate molecules are recombined.

194. The method of claim 189, wherein said adaptor attached nick translate molecules are separated.

195. The method of claim 189, wherein said adaptor attached nick translate molecules comprise a DNA library.

196. The method of claim 1, wherein said adaptor attached nick translate molecules are assembled as a microarray, and wherein said nick translate molecules are amplified prior to said assembly.

197. The method of claim 196, wherein said microarray is assembled on a DNA chip.

198. The method of claim 197, wherein said DNA chip comprises an array of adaptor attached nick translate molecules that facilitate analysis of a patient sample to determine chromosomal mutations.

199. The method of claim 197, wherein said DNA chip comprises an array of adaptor attached nick translate molecules that facilitate diagnostic mutation analysis.

200. A method of detecting a specific DNA sequence, comprising:
 a) providing adaptor attached nick translate molecules, wherein said molecules are generated by:
   i) attaching upstream adaptor molecules to ends of DNA molecules, thereby providing a nick translation initiation site;
   ii) subjecting the DNA molecules to nick translation to produce nick translate molecules;
   iii) attaching downstream adaptor molecules to the nick translate molecules;
 b) separating the adaptor attached nick translate molecules;
 c) amplifying the adaptor attached nick translate molecules by means of sequence on the adaptor; and
 d) identifying said DNA sequence.

201. The method of claim 200, further comprising:
 a) hybridizing said adaptor attached nick translate molecules to a DNA microarray; and
 b) detecting said hybridization.

202. The method of claim 200, wherein a plurality of specific DNA sequences are detected.

203. The method of claim 200, wherein the adaptor attached nick translate molecules are from a human individual.

204. The method of claim 200, wherein the adaptor attached nick translate molecules are from a plurality of human individuals.

205. The method of claim 200, wherein the adaptor attached nick translate molecules are from a plurality of microorganisms.

206. The method of claim 1, wherein said nick translate molecules are denatured.

* * * * *